(12) United States Patent
Berman et al.

(10) Patent No.: US 7,879,872 B2
(45) Date of Patent: Feb. 1, 2011

(54) COMPOSITIONS COMPRISING MULTIPLE BIOACTIVE AGENTS, AND METHODS OF USING THE SAME

(75) Inventors: Judd M. Berman, Toronto (CA); Molly B. Schmid, Toronto (CA); John D. Mendlein, Encinitas, CA (US); Nachum Kaplan, Toronto (CA)

(73) Assignee: Affinium Pharmaceuticals, Inc., Toronto, ON (CA)

( * ) Notice: Subject to any disclaimer, the term of this patent is extended or adjusted under 35 U.S.C. 154(b) by 291 days.

(21) Appl. No.: 11/231,298

(22) Filed: Sep. 19, 2005

(65) Prior Publication Data

US 2006/0142265 A1 Jun. 29, 2006

Related U.S. Application Data

(63) Continuation-in-part of application No. PCT/IB04/001261, filed on Mar. 17, 2004.

(60) Provisional application No. 60/455,189, filed on Mar. 17, 2003, provisional application No. 60/476,970, filed on Jun. 9, 2003, provisional application No. 60/488,379, filed on Jul. 18, 2003.

(51) Int. Cl.
  *A61K 31/554* (2006.01)
  *A61K 31/517* (2006.01)
  *A61K 31/55* (2006.01)
  *A61K 31/4745* (2006.01)
  *A61K 31/496* (2006.01)

(52) U.S. Cl. .................. 514/300; 514/230.5; 546/122

(58) Field of Classification Search ............. 514/230.5, 514/232, 300, 318; 435/7.2
  See application file for complete search history.

(56) References Cited

U.S. PATENT DOCUMENTS

| | | | |
|---|---|---|---|
| 3,828,068 A | 8/1974 | Minieri | |
| 4,154,943 A | 5/1979 | Kuehne | |
| 4,977,159 A | 12/1990 | Sevrin et al. | |
| 5,614,551 A | 3/1997 | Dick et al. | |
| 5,624,941 A | 4/1997 | Barth et al. | |
| 5,932,743 A | 8/1999 | Collini et al. | |
| 5,985,867 A | 11/1999 | Rodgers et al. | |
| 5,989,832 A * | 11/1999 | Trias et al. ............. | 435/7.2 |
| 6,133,260 A | 10/2000 | Matzke et al. | |
| 6,174,878 B1 | 1/2001 | Gamache et al. | |
| 6,184,380 B1 | 2/2001 | Chiu et al. | |
| 6,187,341 B1 | 2/2001 | Johnson et al. | |
| 6,194,429 B1 | 2/2001 | Guinn et al. | |
| 6,194,441 B1 | 2/2001 | Roberts et al. | |
| 6,198,000 B1 | 3/2001 | Hawkins | |
| 6,221,859 B1 | 4/2001 | Dorso et al. | |
| 6,221,864 B1 | 4/2001 | Hirayama et al. | |
| 6,235,908 B1 | 5/2001 | Fey et al. | |
| 6,239,113 B1 | 5/2001 | Dawson et al. | |
| 6,239,141 B1 | 5/2001 | Allen et al. | |
| 6,248,363 B1 | 6/2001 | Patel et al. | |
| 6,267,985 B1 | 7/2001 | Chen et al. | |
| 6,277,836 B1 | 8/2001 | Borody et al. | |
| 6,288,239 B1 * | 9/2001 | Hollingsworth et al. ..... | 548/232 |
| 6,291,462 B1 | 9/2001 | Bartholomaeus et al. | |
| 6,294,192 B1 | 9/2001 | Patel et al. | |
| 6,303,572 B1 | 10/2001 | Rowe et al. | |
| 6,309,663 B1 | 10/2001 | Patel et al. | |
| 6,333,045 B1 | 12/2001 | Yasueda et al. | |
| 6,340,689 B1 | 1/2002 | Dubois et al. | |
| 6,346,391 B1 | 2/2002 | Oethinger et al. | |
| 6,367,985 B1 | 4/2002 | Lee et al. | |
| 6,372,752 B1 | 4/2002 | Staveski et al. | |
| 6,388,070 B1 | 5/2002 | Deshpande et al. | |
| 6,395,746 B1 | 5/2002 | Cagle et al. | |
| 6,399,629 B1 | 6/2002 | Chamberland et al. | |
| 6,406,880 B1 | 6/2002 | Thornton | |
| 6,423,341 B1 | 7/2002 | Yamaguchi et al. | |
| 6,423,741 B1 | 7/2002 | Khanuja et al. | |
| 6,428,579 B1 | 8/2002 | Valentini | |
| 6,432,444 B1 | 8/2002 | Fischetti et al. | |
| 6,436,980 B1 | 8/2002 | Leger et al. | |
| 6,441,162 B2 | 8/2002 | Yasui et al. | |
| 6,448,054 B1 | 9/2002 | Poznansky et al. | |
| 6,448,238 B1 | 9/2002 | Shoichet et al. | |
| 6,448,449 B2 | 9/2002 | Larrow | |

(Continued)

FOREIGN PATENT DOCUMENTS

| | | |
|---|---|---|
| EP | 0407200 | 1/1991 |
| HU | 210679 | 7/1993 |
| WO | WO-9518619 | 7/1995 |
| WO | WO-9600730 | 1/1996 |
| WO | WO-9748696 | 12/1997 |
| WO | WO-9857952 | 12/1998 |

(Continued)

OTHER PUBLICATIONS

Bergler, Helmut, et al., "Protein EnvM is the NADH-dependent Enoyl-ACP Reductase (FabI) of *Escherichia coli*," J. Biological Chemistry, vol. 269, No. 8, Feb. 25, 1994, pp. 5493-5496.
Grassberger, Maximilian, et al., "Preparation and Antibacterial Activities of New 1,2,3-Diazaborine Derivatives and Analogues," J. Med. Chemistry, 1984, 27, 947-953.
Heath, Richard J., et al., "A Triclosan-Resistant Bacterial Enzyme," Nature, vol. 406, Jul. 13, 2000, p. 145-146.
Heath, Richard J., et al., "Regulation of Fatty Acid Elongation and Initiation by Acyl-Acyl Carrier Protein in *Escherichia coli*," J. Biological Chemistry, vol. 271, No. 4, Jan. 26, 1996, pp. 1833-1836.
Heck, Richard F., Organic Reactions, 1982, 27, pp. 345-390.
Levy, Colin W., et al., "Molecular Basis of Triclosan Activity," Nature, vol. 398, Apr. 1, 1999, pp. 383-384.

(Continued)

*Primary Examiner*—Frederick Krass
*Assistant Examiner*—Walter E Webb
(74) *Attorney, Agent, or Firm*—Goodwin Procter LLP

(57) ABSTRACT

In part, the present invention is directed to compositions having a FabI inhibitor and at least one other bioactive agent. In another part, the present invention is directed to antibacterial compositions having a compound of formulas I-III and at least one other antibacterial agent.

4 Claims, 10 Drawing Sheets

U.S. PATENT DOCUMENTS

| | | | |
|---|---|---|---|
| 6,451,339 B2 | 9/2002 | Patel et al. | |
| 6,451,816 B1 | 9/2002 | Biedermann et al. | |
| 6,461,607 B1 | 10/2002 | Farmer | |
| 6,461,829 B1 | 10/2002 | Kahne | |
| 6,465,429 B1 | 10/2002 | Hancock et al. | |
| 6,468,964 B1 | 10/2002 | Rowe et al. | |
| 6,469,046 B1 | 10/2002 | Daines et al. | |
| 6,486,148 B2 | 11/2002 | Savage et al. | |
| 6,486,149 B2 | 11/2002 | Onodera et al. | |
| 6,486,165 B2 | 11/2002 | Zhang et al. | |
| 6,489,318 B1 | 12/2002 | Copar et al. | |
| 6,492,351 B1 | 12/2002 | Zhang et al. | |
| 6,495,158 B1 | 12/2002 | Buseman et al. | |
| 6,495,161 B1 | 12/2002 | Soon-Shiong et al. | |
| 6,495,551 B1 | 12/2002 | Betts et al. | |
| 6,497,886 B1 | 12/2002 | Breitenbach et al. | |
| 6,500,459 B1 | 12/2002 | Chhabra et al. | |
| 6,500,463 B1 | 12/2002 | van Lengerich | |
| 6,503,539 B2 | 1/2003 | Gestrelius et al. | |
| 6,503,881 B2 | 1/2003 | Krieger et al. | |
| 6,503,903 B1 | 1/2003 | Miller et al. | |
| 6,503,906 B1 | 1/2003 | Lee | |
| 6,503,908 B1 | 1/2003 | Maw et al. | |
| 6,503,953 B2 | 1/2003 | Vyden | |
| 6,503,955 B1 | 1/2003 | Dobrozsi et al. | |
| 6,509,327 B1 | 1/2003 | Cagle et al. | |
| 6,514,535 B2 | 2/2003 | Marchant | |
| 6,514,541 B2 | 2/2003 | Khanuja et al. | |
| 6,514,953 B1 | 2/2003 | Armitage et al. | |
| 6,514,962 B1 | 2/2003 | Shibatani et al. | |
| 6,514,986 B2 | 2/2003 | de Souza et al. | |
| 6,515,113 B2 | 2/2003 | Raymond et al. | |
| 6,517,827 B1 | 2/2003 | Kurtz et al. | |
| 6,518,239 B1 | 2/2003 | Kuo et al. | |
| 6,518,263 B1 | 2/2003 | Nishitani et al. | |
| 6,518,270 B1 | 2/2003 | Amin et al. | |
| 6,518,487 B1 | 2/2003 | Lowe et al. | |
| 6,521,408 B1 | 2/2003 | Kawasaki et al. | |
| 6,525,066 B2 | 2/2003 | Fukumoto et al. | |
| 6,527,759 B1 | 3/2003 | Tachibana et al. | |
| 6,528,089 B1 | 3/2003 | Kothrade et al. | |
| 6,531,126 B2 | 3/2003 | Farmer | |
| 6,531,291 B1 | 3/2003 | Kabbash et al. | |
| 6,531,465 B1 | 3/2003 | Ascher et al. | |
| 6,531,508 B1 | 3/2003 | Nomura et al. | |
| 6,531,649 B1 | 3/2003 | Mannerloef et al. | |
| 6,559,172 B1 | 5/2003 | Heerding et al. | |
| 6,573,272 B1 | 6/2003 | Miller et al. | |
| 6,673,941 B2 | 1/2004 | Heerding et al. | |
| 6,730,684 B1 | 5/2004 | Miller et al. | |
| 6,762,201 B1 | 7/2004 | Miller et al. | |
| 6,765,005 B2 | 7/2004 | Miller et al. | |
| 6,821,746 B2 | 11/2004 | DeWolf, Jr. et al. | |
| 6,846,819 B1 | 1/2005 | Miller et al. | |
| 6,951,729 B1 | 10/2005 | Dewolf, Jr. et al. | |
| 6,964,970 B2 | 11/2005 | Miller et al. | |
| 6,995,254 B1 | 2/2006 | Payne et al. | |
| 7,048,926 B2 | 5/2006 | Brandt et al. | |
| 7,049,310 B2 | 5/2006 | Burgess et al. | |
| 7,250,424 B2 * | 7/2007 | Burgess et al. | 514/300 |
| 2005/0250810 A1 | 11/2005 | Miller et al. | |
| 2006/0142265 A1 | 6/2006 | Berman et al. | |
| 2006/0183908 A1 | 8/2006 | Berman et al. | |

FOREIGN PATENT DOCUMENTS

| | | | |
|---|---|---|---|
| WO | WO 00/27628 | | 5/2000 |
| WO | WO-00/57933 A1 | | 10/2000 |
| WO | WO 01/26654 | * | 4/2001 |
| WO | WO-0126652 | | 4/2001 |
| WO | WO-0126654 | | 4/2001 |
| WO | WO-0127103 | | 4/2001 |
| WO | WO-01/41573 A1 | | 6/2001 |
| WO | WO-0148248 | | 7/2001 |
| WO | WO-01/70172 A2 | | 9/2001 |
| WO | WO 02/10332 | | 2/2002 |
| WO | WO-0242273 | | 5/2002 |
| WO | WO-0248097 | | 6/2002 |
| WO | WO-2004052890 | | 6/2004 |

OTHER PUBLICATIONS

McMurray, Laura M., et al., "Triclosan Targets Lipid Synthesis," Nature, vol. 394, Aug. 4, 1998, pp. 531-532.

Turnowsky, Friederike, et al., "envM Genes of Salmonella Typhimurium and *Escherichia coli*," J. Bacteriology, vol. 171, No. 12, Dec. 1989, pp. 6555-6565.

Ward, Walter H.J., et al., "Kinetic and Structural Characteristics of the Inhibition of Enoyl (Acyl Carrier Protein) Reductase by Triclosan," Biochemistry, 1999, vol. 38, No. 38, pp. 12514-12525.

Jossang-Yanagida, Akino, et al., "Tetrahydropyridoazepines and Tetrahydropyridoazepinones from the Corresponding Dihydroquinolones," J. Heterocyclic Chemistry, vol. 15, pp. 249-251.

Abou-Gharbia et al., "Psychotropic Agents: Synthesis and Antipysychotic Activity of Substituted B-Carbolines," J. Med. Chem., 30 (6): 1100-1115 (1987).

Ahsan et al., "Reserpine Analogue: Synthesis of B-Carboline Derivatives," J. Chem. Soc., pp. 3928-3920 (1963).

Jianxiong et al., "Synthesis and Antistaphylococcal Activity of Nematophin and Its Analogs," Bioorganic & Medicinal Chemistry Letters, Oxford, GB, 7(10): 1349-1352, (May 20, 1977) XP004136332.

Miller et al., Discovery of Aminopyridine-Based Inhibitors of Bacterial Enoyl-ACP Reductase (FABI); J. Med. Chem. 2002, vol. 45, pp. 3246-3256.

Misztal et al., "Synthesis and Pharmacologic Properties of Pyridol Derivatives of 3-Methylaminoindole 2-Methyltryptamine and Isotryptamine," Archivum Immnologiae et Therapiae Experimentalis, 24(6): 851-852 (1976).

Pachter et al., "The Chemistry of Hortiamine and 6-Methoxyhetsinine," J. Amer. Chem., 83:635-642 (1961).

Rehse et al., "Dopaminanaloge 1,2,3,4-Tetrahydro-B-Carboline," Arch. Pharm., 311(1): 11-18 (1978).

Shoji et al., "Two Novel Alkaloids from Evodia Rutaecarpa," J. Natural Products, 52(5): 1160-1162 (1989).

Database CA on STN, AN 7:66733, Rosenmund et al., "Chemistry of indole II . . . ," *Chem Ber*. 103(2): 496-509.

Database CAOLD on STN, AN CA51:10524d, Hellman et al., "N-Mannich bases (VI) condensation . . . ," *Direct Submission* (1953).

Database CAPLUS on STN, An 1977:439214. Misztal et al., "Synthesis and pharmacologic properties of pyridoyl . . . ," Arch Immuno ther Exp. 24(6): 851-862 (1976).

Himmler et al., "Synthesis and Antibacterial in Vitro Activity of Novel Analogues of Nematophin," Bioorganic & Medicinal Chemistry Letters, 8(15): 2045-2050 (Aug. 1998).

Database CAPLUS on STN, AN 1986:68547, Stuetz, et al., "Synthesis and Structure Activity . . . ," *J Med Chem*. 29(1) 112-25, (1986).

Database CAPLUS on STN, AN 1991:428908, Fuse, et al., "Preparation of cinnamamide derivatives . . . ," EP407200A1. (1991).

Database CAPLUS on STN, AN 1999; 325910 Aslanian et al., "Preparation of phenylalkylimidazoles . . . ," WO99/24406. (1999).

Stutz et al., "Synthesis and Strucure-Activity Relationships of Naftifine-Related Allylamine Antimycotics," Journal of Medicinal Chemistry, 1986, vol. 29, No. 1, 112-125.

Payne et al., Bacterial Fatty-Acid Biosynthesis: A Genomics-Driven Target For Antibacterial Drug Discovery, *Therapeutic Focus*, 2001, vol. 6, pp. 537-543.

* cited by examiner

Figure 4

| Compound B (x MIC) | | | | | | | | | | | | | |
|---|---|---|---|---|---|---|---|---|---|---|---|---|---|
| 4 | ■ | | | | | | | | | | | | |
| 2 | ■ | | | | | | | | | | | | |
| 1 | ■ | | | | | | | | | | | | |
| 0.5 | ■ | | | | | | | | | | | | |
| 0.25 | ■ | | | | | | | | | | | | |
| 0.125 | ■ | | | | | | | | | | | | |
| 0.06 | ■ | | | | | | | | | | | | |
| | ■ | ■ | ■ | ■ | ■ | ■ | ■ | ■ | ■ | ■ | ■ | | |
| | + | 0.015 | 0.03 | 0.06 | 0.125 | 0.25 | 0.5 | 1 | 2 | 4 | 8 | 16 | |
| | Compound A (x MIC) | | | | | | | | | | | | |

Figure 5

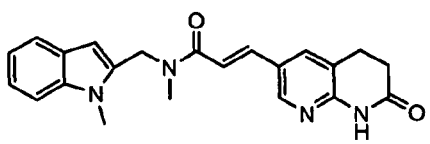

A

N-Methyl-N-(1-methyl-1H-indol-2-ylmethyl)-3-(7-oxo-5,6,7,8-tetrahydro-[1,8]naphthyridin-3-yl)-acrylamide

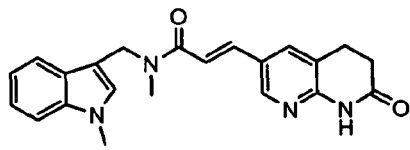

B

N-Methyl-N-(1-methyl-1H-indol-3-ylmethyl)-3-(7-oxo-5,6,7,8-tetrahydro-[1,8]naphthyridin-3-yl)-acrylamide

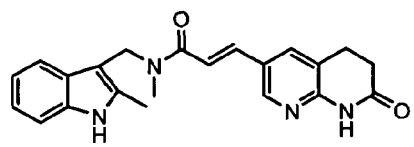

C

N-Methyl-N-(2-methyl-1H-indol-3-ylmethyl)-3-(7-oxo-5,6,7,8-tetrahydro-[1,8]naphthyridin-3-yl)-acrylamide

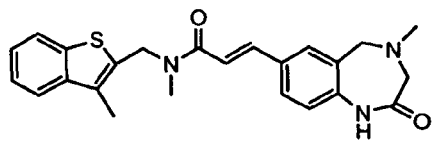

D

N-Methyl-N-(3-methyl-benzo[b]thiophen-2-ylmethyl)-3-(4-methyl-2-oxo-2,3,4,5-tetrahydro-1H-pyrido[2,3-e][1,4]diazepin-7-yl)-acrylamide

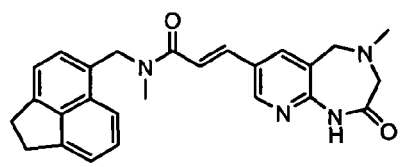

E

N-Acenaphthen-5-ylmethyl-N-methyl-3-(4-methyl-2-oxo-2,3,4,5-tetrahydro-1H-pyrido[2,3-e][1,4]diazepin-7-yl)-acrylamide

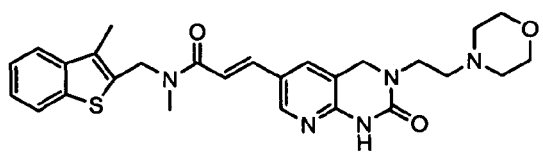

F

N-Methyl-N-(3-methyl-benzo[b]thiophen-2-ylmethyl)-3-[3-(2-morpholin-4-yl-ethyl)-2-oxo-1,2,3,4-tetrahydro-pyrido[2,3-d]pyrimidin-6-yl]-acrylamide

COMPOSITIONS COMPRISING MULTIPLE BIOACTIVE AGENTS, AND METHODS OF USING THE SAME

RELATED APPLICATION INFORMATION

This application is a continuation-in-part of PCT/IB2004/001261, filed Mar. 17, 2004, which claims priority to U.S. Provisional Patent Application Nos. 60/455,189, filed Mar. 17, 2003, 60/476,970, filed Jun. 9, 2003, and 60/488,379, filed Jul. 18, 2003. Each of these applications is incorporated herein in their entirety.

INTRODUCTION

Infections caused by or related to bacteria are a major cause of human illness worldwide, and the frequency of resistance to standard antibiotics has risen dramatically over the last decade. In particular, the extensive use of methicillin, a penicillin derivative, has led to the development of methicillin-resistant bacterial strains. Such methicillin-resistant microbes, including methicillin-resistant *Staphylococcus aureus* (MRSA) and methicillin-resistant *Staphlyococcus epidermidis* (MRSE), pose serious threats to hospitalized patients, newborns, and the elderly. Organisms resistant to methicillin are frequently resistant to multiple drug classes including cephalosporins, fluoroquinolones or glycopeptides, thus removing antibacterial agents of these classes as therapeutic options. For example, in hospital settings, MRSA is resistant to almost all antibiotics. Of the approximately 150 marketed antibiotics used today, only five are approved by the FDA for use against MRSA infections. Hence, there exists an urgent, unmet medical need and demand for new agents acting against bacterial targets.

Examples of potential bacterial targets are those enzymes involved in fatty acid biosynthesis. While the overall pathway of saturated fatty acid biosynthesis is similar in all organisms, the fatty acid synthase (FAS) systems vary considerably with respect to their structural organization. It is believed that vertebrates and yeast possess a FAS in which all the enzymatic activities are encoded on one or two polypeptide chains, respectively, and in both cases the acyl carrier protein (ACP) participates as part of the complex. In bacterial, however, it is known that each of the FAS reactions is catalyzed by a distinct, mono-functional enzyme with the ACP remaining as a discrete protein. Therefore, it may be possible to achieve selective inhibition of the bacterial system by appropriate agents that, for example, target one or more of the FAS catalyzed systems.

One such potential bacterial target is the FabI protein. FabI (previously designated EnvM) is believed to function as an enoyl-ACP reductase in the final step of the four reactions involved in each cycle of bacterial fatty acid biosynthesis. It is believed that in this pathway, the first step is catalyzed by β-ketoacyl-ACP synthase, which condenses malonyl-ACP with acetyl-CoA (FabH, synthase III). It is believed that in subsequent rounds, malonyl-ACP is condensed with the growing-chain acyl-ACP (FabB and FabF, synthases I and II, respectively). The second step in the elongation cycle is thought to be ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP. Finally, in step four, trans-2-enoyl-ACP is converted to acyl-ACP by an NADH (or NADPH)-dependent enoyl-ACP reductase (Fab I). Further rounds of this cycle, adding two carbon atoms per cycle, would eventually lead to palmitoyl-ACP (16C), where upon the cycle is stopped largely due to feedback inhibition of Fab I by palmitoyl-ACP. Thus, Fab I is believed to be a major biosynthetic enzyme and is a key regulatory point in the overall synthetic pathway of bacterial fatty acid biosynthesis.

In some bacteria it is believed that the final step of fatty acid biosyntheses is catalyzed by Fab I only, in others by FabK, an NADH and FMN dependent reductase, still others utilize both FabI and FabK.

The present invention provides, in part, compositions with FabI inhibiting properties.

SUMMARY OF INVENTION

In part, the present invention is directed towards compositions comprising a FabI inhibitor and at least one other bioactive agent, such as for example, an anti-infective agent.

For example, a composition is provided that comprises an antibacterial agent and an anti-infective agent wherein said antibacterial agent substantially inhibits Fab I. Compositions contemplated herein include those where a fractional inhibitory concentration for the combination of the antibacterial agent and the anti-infective agent is less than or equal to 4, or less than or equal to 2, as calculated against antibiotic resistant strains of bacteria, for example *Staphylococcus*. Any antibacterial agent of a composition disclose herein may inhibit FabI with a MIC of less than about 64 µg/ml. Such compositions may include those where the ratio of antibacterial agent to anti-infective agent is about 0.01:100 to about 100:0.01.

In some embodiments, the compositions of the invention further comprise a pharmaceutically acceptable carrier or excipient.

In one embodiment, the present invention relates to anti-infective compositions comprising a compound of formulas I-III, disclosed herein, and at least one other anti-infective agent.

In some embodiments, fractional amounts of the MIC of each compound are combined such that the total amount is less than about one times the MIC of either compound, and the anti-infective composition of the present invention still inhibit, for example, bacterial growth. As a non-limiting example, the anti-infective compositions of the present invention may comprise a compound of formula I at half its MIC and another anti-infective compound at a quarter of its MIC, with the combined composition inhibiting bacterial growth. Other examples using other fractional amounts can be envisioned by of ordinary skill in the art.

In one embodiment, the dosage amount of the at least one other bioactive agent in the compositions of the present invention is about half the dosage amount when the FabI inhibitor is absent. In another embodiment, the amount of the at least one other bioactive agent is less than about half of the amount in the dosage when the FabI inhibitor is absent. In another embodiment, the amount of the at least one other bioactive agent is less than about a quarter of the amount in the dosage when the FabI inhibitor is absent. In another embodiment, the amount of the at least one other bioactive agent is less than about a tenth of the amount in the dosage when the FabI inhibitor is absent.

In part, the present invention is directed towards compositions that will affect multiple species, so-called "wide spectrum" anti-bacterials. Alternatively, subject compositions that are selective for one or more bacterial or other non-mammalian species, and not for one or more mammalian species (especially human), may be identified.

In one embodiment, the dosage amount of the FabI inhibitor in the compositions of the present invention is about half the dosage amount when the at least one other bioactive agent is absent. In another embodiment, the amount of the FabI inhibitor is less than about half of the amount in the dosage when the at least one other bioactive agent is absent. In another embodiment, the amount of the FabI inhibitor is less than about a quarter of the amount in the dosage when the at least one other bioactive agent is absent. In another embodiment, the amount of the FabI inhibitor is less than about a tenth of the amount in the dosage when the at least one other bioactive agent is absent.

The subject compositions may be administered by one of a variety of means known to those of skill in the art.

In one embodiment, the anti-infective compositions of the present invention have a MIC of less than 256 µg/mL against, for example, one or more drug-resistant bacteria. In other embodiments, the anti-infective compositions of the present invention may have a MIC value of less than 128 µg/mL, or even less than 64 µg/mL.

Non-limiting examples of bacteria that the antibacterial compositions of the present invention may be used to either destroy or inhibit the growth of include a member of the genus *Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma*, and further including, but not limited to, a member of the species or group, Group A *Streptococcus*, Group B *Streptococcus*, Group C *Streptococcus*, Group D *Streptococcus*, Group G *Streptococcus, Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi, Bordetella, Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfringens, Clostridium tetani, Clostridium botulinum, Treponema pallidum, Rickettsia rickettsii, Helicobacter pylori, Escherichia coli, Propionibacterium acnes*, or *Chlamydia trachomitis*.

Non-limiting examples of illnesses caused by a bacterial infection include otitis media, conjunctivitis, pneumonia, bacteremia, meningitis, sinusitis, pleural empyema and endocarditis, and meningitis, such as for example infection of cerebrospinal fluid.

In another aspect, the subject compositions may be used to treat bacterial infections.

In certain embodiments, the present invention provides antibacterial compositions of the present invention, and methods of using the same, for the reduction and abatement of at least one of the bacteria caused disorders or conditions based on a therapeutic regimen. In certain aspects, the present invention contemplates monitoring such disorders or conditions as part of any therapeutic regimen, which may be administered over the short-term and/or long-term. These aspects of the invention may be particularly helpful in preventive care regimes. In certain embodiments, the present invention is directed to a method for formulating compositions of the present invention in a pharmaceutically acceptable excipient.

In another embodiment of the invention it will be desirable to include monitoring or diagnostic regimes or kits with subject antibacterial compositions or methods based on FabI inhibitors and at least one other bioactive agent described herein, and instructions for use of these compositions or methods. In yet another embodiment, a method of disinfecting an inanimate surface is provided comprising applying to the inanimate surface a composition of the invention.

As explained herein in greater detail, the invention will readily enable the design and implementation of trials in warm-blooded animals, including humans and mammals, necessary for easily determining or tailoring the form and dose for any composition of the present invention.

These embodiments of the present invention, other embodiments, and their features and characteristics, will be apparent from the description, drawings and claims that follow.

BRIEF DESCRIPTION OF DRAWINGS

FIG. 4 depicts a 96-well plate layout for assays of antimicrobial combinations.

FIG. 5 depicts the compounds of the antibacterial compositions of the present invention used in the combination efficacy experiments.

DETAILED DESCRIPTION

Introduction

The present invention is directed in part towards novel compositions that inhibit bacterial and/or infective enzymes and/or enzymes within infectious agents, and methods of making and using the same. In certain aspects, inhibitors and other compounds of the invention may be found by a structure-guided medicinal chemistry effort.

Figure 1:
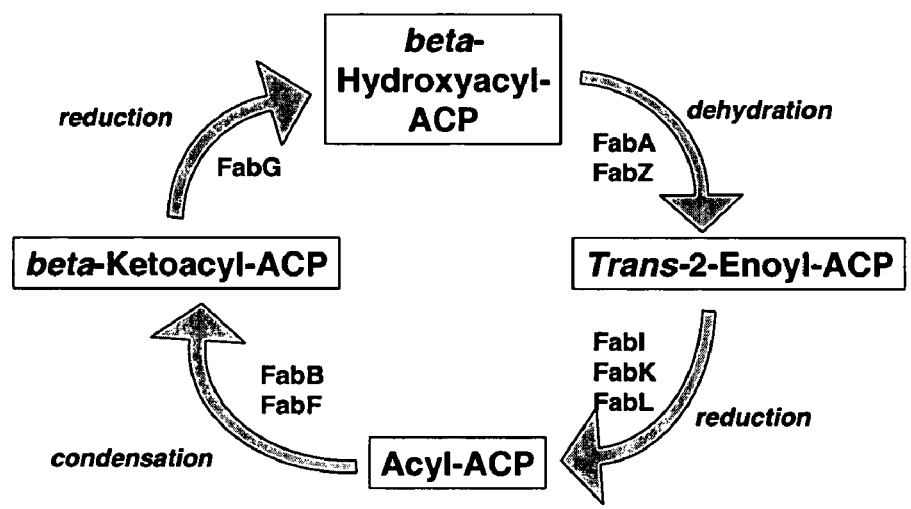
FIG. 1 depicts the bacterial fatty acid biosynthesis cycle via a Type II or dissociated fatty acid synthase system.

Bacterial fatty acid biosynthesis is believed to proceed via a Type II or dissociated fatty acid synthase system, in contrast to the mammalian Type I system. The overall process is believed to proceed in two stages—initiation and cyclical elongation. Enoyl-ACP reductase is part of the elongation cycle, in which malonyl-ACP is condensed with a growing acyl chain by β-ketoacyl-ACP synthase (FabB, FabF, FabH). The β-ketoester is reduced by β-ketoacyl-ACP reductase, which is then dehydrated to the trans-unsaturated acyl-ACP. The trans-unsaturated acyl-ACP is then reduced by enoyl-ACP reductase. (See FIG. 1).

The enoyl-ACP reductase step is believed to be accomplished by FabI in *E. coli* and other gram negative organisms and Staphylococci. In certain gram-positive organisms, FabI paralogs exist. In *Streptococcus pneumoniae*, the enzymatic step is believed to be accomplished by the FabK protein. In *B. subtilis* and *E. faecalis*, genes encoding both FabI and FabK exist. In *Mycobacterium tuberculosis* a FabI paralog termed InhA exists. Enoyl-ACP reductase is believed to be the enzymatic target of the antimicrobial product triclosan.

Figure 2:
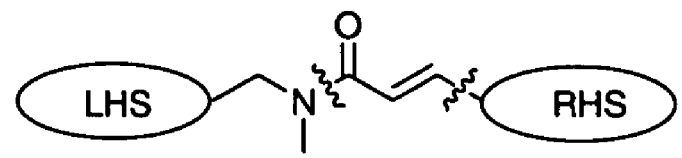
FIG. 2 depicts a simplified view of ene-amide core flanked by LHS (left-hand side) and RHS (right-hand side) moieties.
Figure 3A:
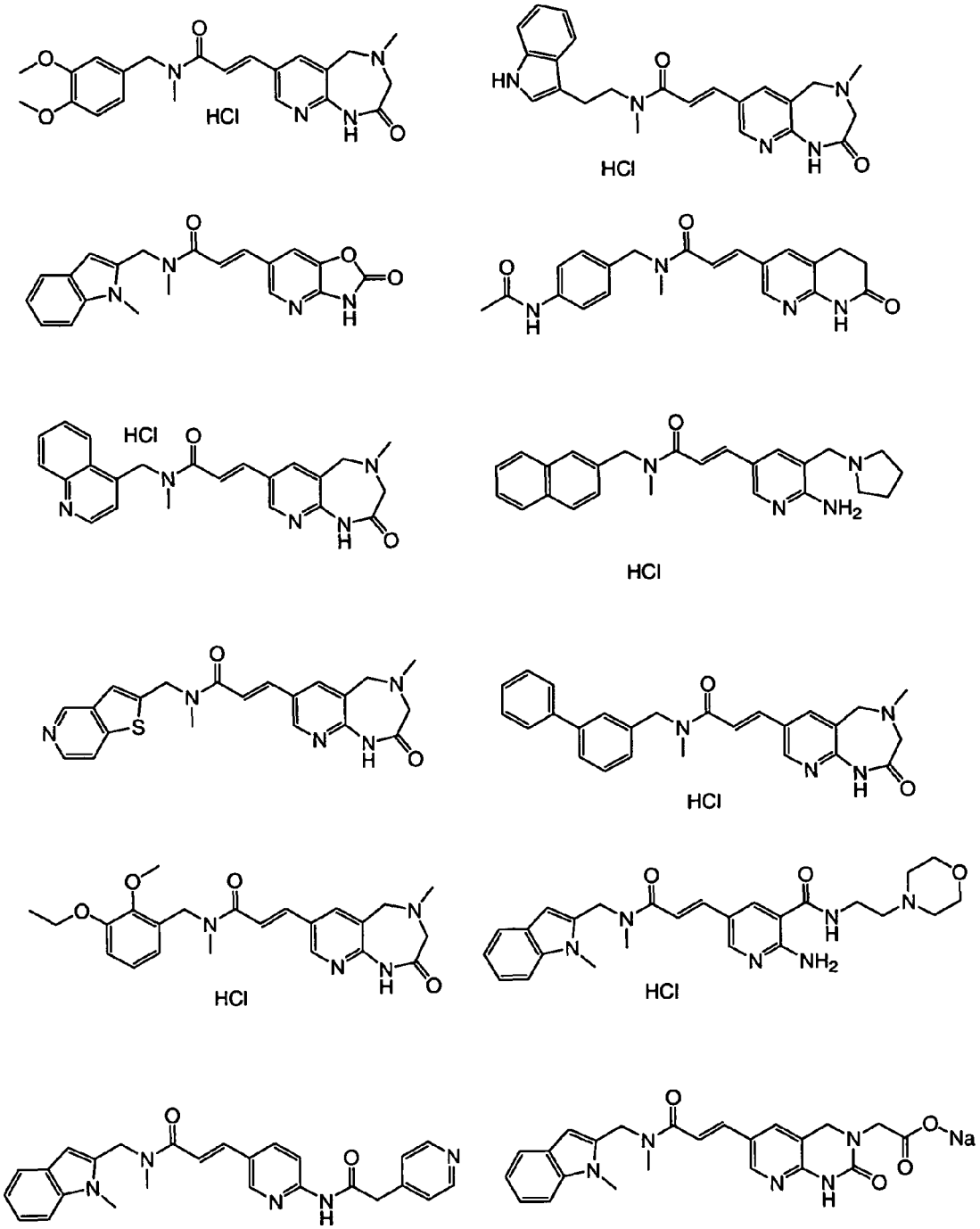
FIGS. 3*a-f* depict the structures of some of the compounds of the present invention from the representative list.
Figure 3B:
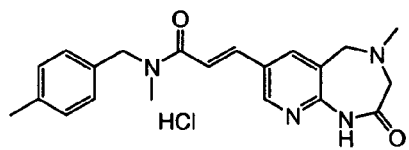
Figure 3B:
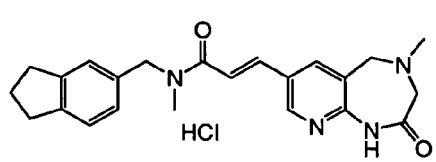
Figure 3B:
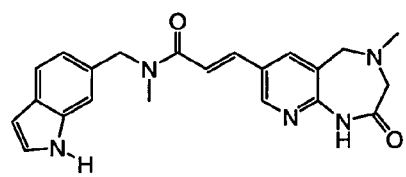
Figure 3B:
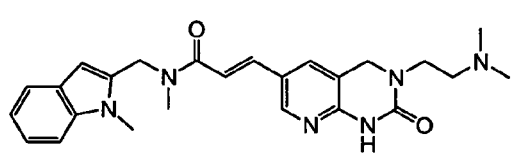
Figure 3B:
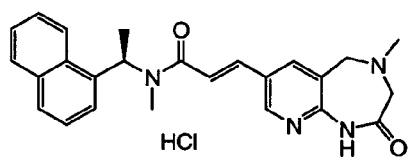
Figure 3B:
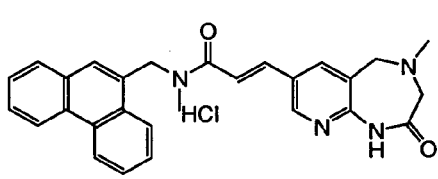
Figure 3B:
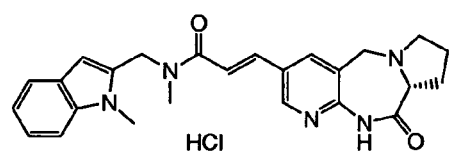
Figure 3B:
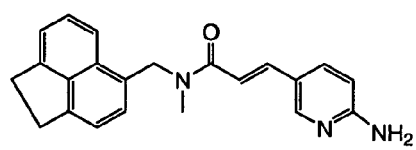
Figure 3B:
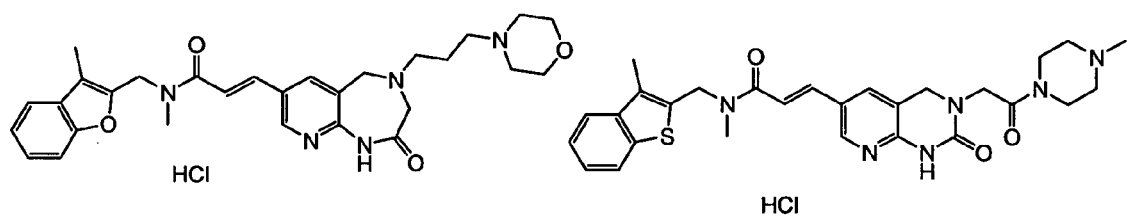
Figure 3B:
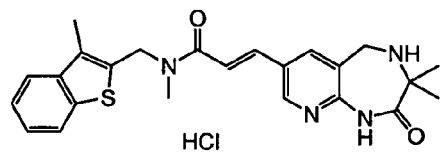
Figure 3C:
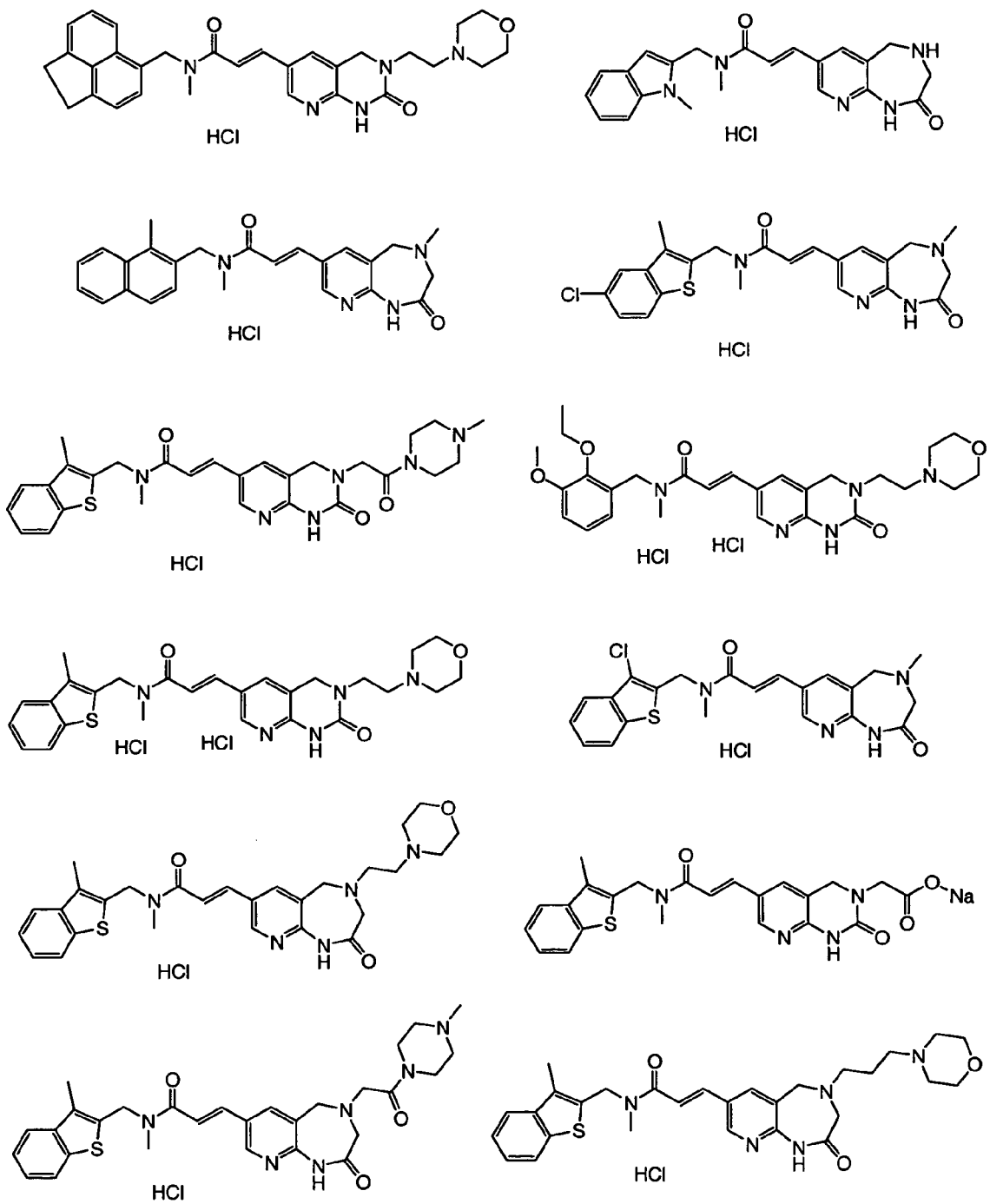
Figure 3D:
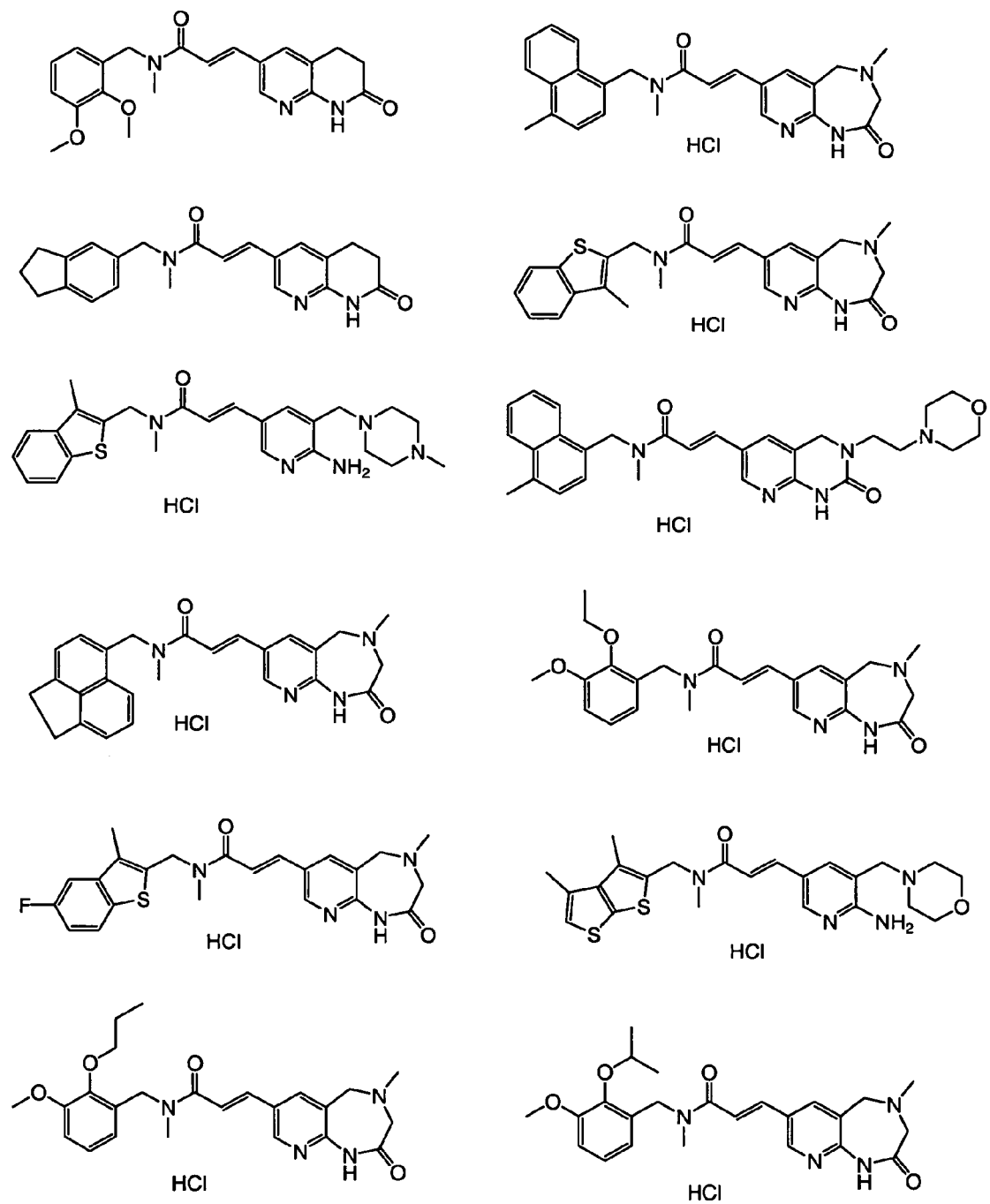
Figure 3E:
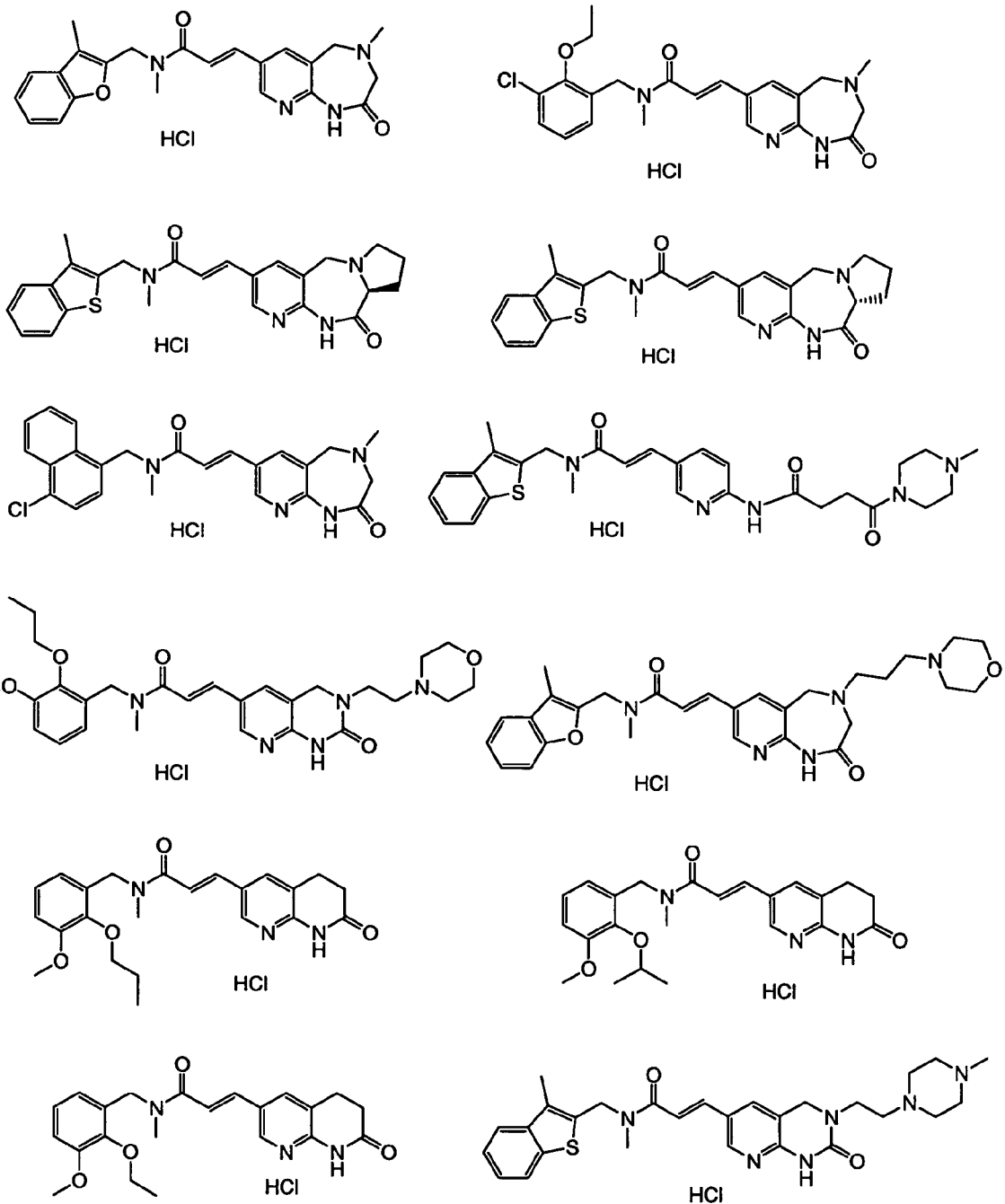
Figure 3F:
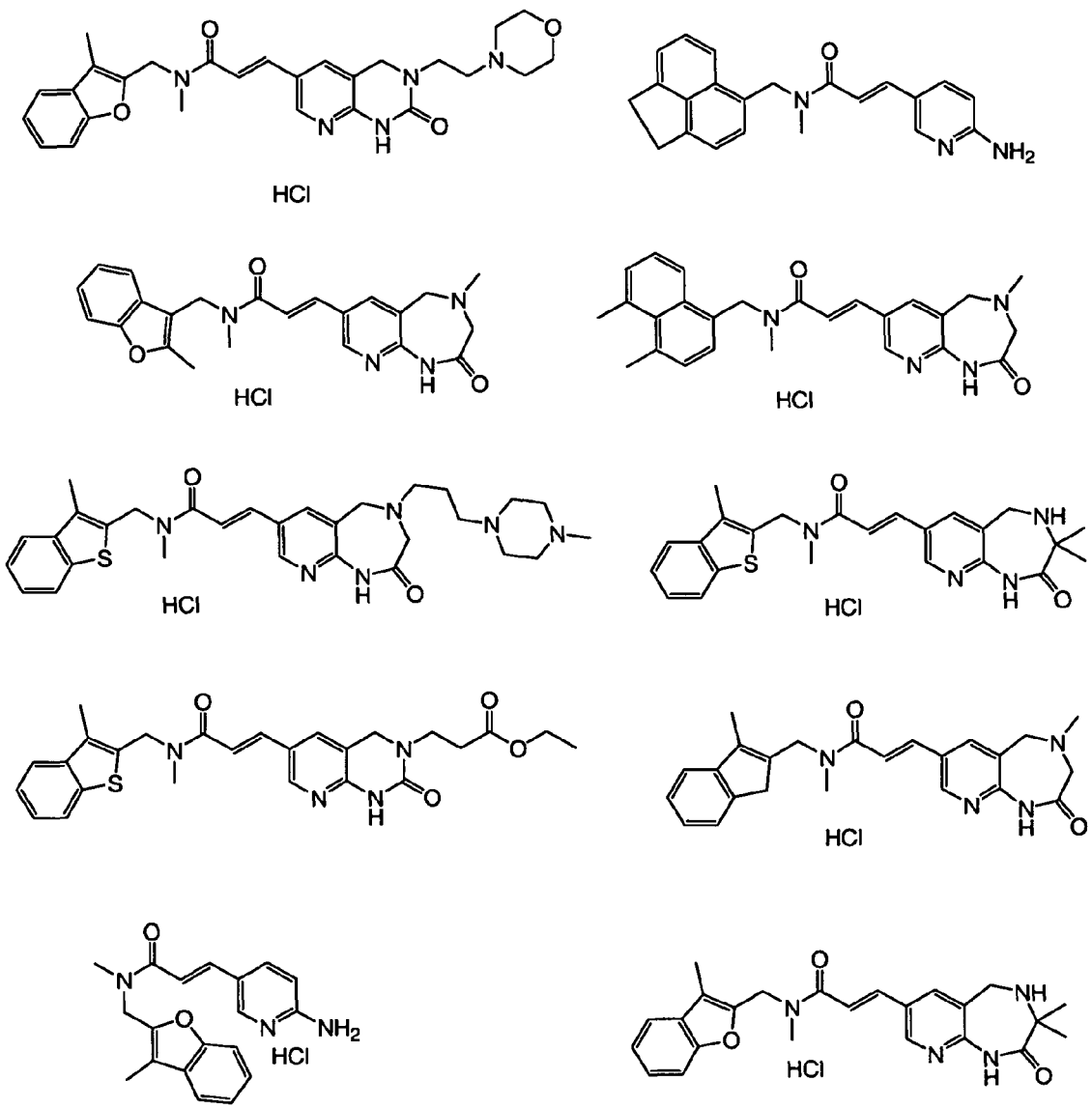

In certain embodiments, the design of new analogs having FabI inhibiting properties is based on viewing the analogs as consisting of a central acrylamide flanked by two relatively hydrophobic groups, conveniently denoted as left-hand side (LHS) and right-hand side (RHS). Schematically this is depicted in FIG. 2, where a dumbbell like structure provides one way of viewing certain of the subject compositions (the central bond disconnections that is envisioned in a retrosynthetic sense are shown with dashed lines).

The invention is also directed to compositions for treating and preventing infections, including bacterial, viral, fungal, parasitic or protozal infections. In certain aspects, the inhibitors and compounds of the invention may be used to treat bacterial infections, including infections caused by methicillin-resistant bacterial strains.

In certain embodiments, the FabI inhibitors and compounds described herein may be used alone or in combination with antibiotics, such as cephalosporins, quinolones, penicillins, macrolides and others, to treat all strains of Staphylococci, including methicillin-resistant *Staphylococcus aureus* (MRSA) and methicillin-resistant *Staphylococcus epidermis* (MRSE) strains.

Infectious diseases are an important cause of patient morbidity and mortality. Bacterial pathogens, in particular, give rise to a variety of acute and chronic conditions including skin and skin structure infections, upper and lower respiratory tract infections and urinary tract infections, and a significant incidence of life-threatening illnesses such as pneumonia and blood stream infections. Depending on the severity of illnesses, diagnosis and treatment may occur in either the community (outpatient) setting or hospital (inpatient) setting.

In the community setting, *Staphylococcus aureus* is an important causative pathogen for uncomplicated skin and skin structure infections and for mild to moderately severe upper and lower respiratory tract infections. Oral treatment of these conditions has traditionally been managed by penicillins and macrolides, and more recently by more potent agents such as broad spectrum cephalosporins, ketolides, and fluoroquinolones. However, increasing bacterial resistance, most acute among staphylococci, has rendered many therapeutic options ineffective against infection caused by resistant staphylococci. The most commonly encountered staphylococcal phenotype, classified as MRSA (methicillin-resistant *Staphylococcus aureus*) is a pathogen frequently resistant to 3 or more different classes of antimicrobials.

In the hospital environment, drug resistant staphylococci exhibit a higher prevalence than in the community and are implicated in a range of serious to life-threatening illnesses including complicated skin and skin structure infections, blood stream infections, upper and lower respiratory tract infections and disease requiring longer term therapy, e.g., endocarditis and osteomyelitis. Broad spectrum intravenous agents including cephalosporins, carbapenems, glyco- and lipopeptides, fluoroquinolones, and oxazolidinones are often utilized as therapy for hospitalized patients. Fluoroquinolones and oxazolidinones are also available as oral formulations.

The FabI inhibitors and compounds described herein may be used to treat susceptible and resistant strains of staphylococci including MRSA. Use of either an oral or an intravenous formulation of the FabI inhibitors and compounds described herein in a fixed does combination with agents used to treat infections both in the community and the hospital setting would afford the following advantages: fulfill a growing medical need for novel therapies in the treatment of staphylococcal infections; address medical and market need for an oral agent in the treatment of community based staphylococcal infections; provide and augment coverage of susceptible and resistant strains of staphylococci to currently used antimicrobials prolonging their clinical utility; provide a novel bacterial target and mechanism of action; provide no antagonism of partner antibiotic spectrum of activity; provide the decreased likelihood of resistance development; provide the decreased requirement for additional courses of antibiotics due to initial therapeutic failures; and lower overall incidence of adverse events due to multiple courses of broad spectrum antibiotics.

DEFINITIONS

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used to mean "including but not limited to". "Including" and "including but not limited to" are used interchangeably.

The term "FabI" is art-recognized and refers to bacterial enzymes believed to function as an enoyl-acyl carrier protein (ACP) reductase in the final step of the four reactions involved in each cycle of bacterial fatty acid biosynthesis. The enzyme is believed to be widely distributed in bacteria and plants.

The term "enzyme inhibitor" refers to any compound that prevents an enzyme from effectively carrying out its biochemical role(s). Therefore a "FabI inhibitor" is any compound that inhibits FabI from carrying out its biochemical role(s). The amount of inhibition of the enzyme by any such compound will vary and is described herein and elsewhere.

The term "antibiotic agent" shall mean any drug that is useful in treating, preventing, or otherwise reducing the severity of any bacterial disorder, or any complications thereof, including any of the conditions, disease, or complications arising therefrom and/or described herein. Antibiotic agents include, for example, cephalosporins, quinolones and fluoroquinolones, penicillins, penicillins and beta lactamase inhibitors, carbepenems, monobactams, macrolides and lincosamines, glycopeptides, rifampin, oxazolidonones, tetracyclines, aminoglycosides, streptogramins, sulfonamides, and the like. Other general categories of bioactive agents which may be part of a subject composition include those agents known to those of skill in the art as antibiotics and that qualify as (with defined terms being in quotation marks): "drug articles" recognized in the official United States Pharmacopoeia or official National Formulary (or any supplement thereto); "new drug" and "new animal drug" approved by the FDA of the U.S. as those terms are used in Title 21 of the United States Code; any drug that requires approval of a government entity, in the U.S. or abroad ("approved drug"); any drug that it is necessary to obtain regulatory approval so as to comply with 21 U.S.C. §355(a) ("regulatory approved drug"); any agent that is or was subject to a human drug application under 21 U.S.C. §379(g) ("human drug"). (All references to statutory code for this definition refer to such code as of the original filing date of this provisional application.) Other bioactive agents are disclosed herein, and are known to those of skill in the art. In certain embodiments, the term "bioactive agent," "antibiotic agent," or "anti-infective agent" does not include an agent that is a FabI inhibitor, so that the combinations of the present invention in certain instances will include one agent that is a FabI inhibitor and another agent that is not.

The term "synergistic" is art recognized and refers to two or more components working together so that the total effect is greater than the sum of the components. One measure of synergism for antibacterial compounds and other enzyme inhibiting compounds is described under the section *Method for Checkerboard Combination Studies*.

The term "illness" as used herein refers to any illness caused by or related to infection by an organism.

The term "bacterial illness" as used herein refers to any illness caused by or related to infection by bacteria.

The term "polynucleotide(s)" is art recognized and refers to any polyribonucleotide or polydeoxyribonucleotide that may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that comprise one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

The term "polypeptide(s)" is art recognized and refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may comprise amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may comprise many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES,* 2nd Ed., T. E. Creighton, W.H. Freeman and Company, New York (1993) and Wold, F., Posttranslational Protein Modifications: Perspectives and Prospects, pgs. 1-12 in *POSTTRANSLATIONAL COVALENT MODIFICATION OF PROTEINS*, B. C. Johnson, Ed., Academic Press, New York (1983); Seifter et al., *Meth. Enzymol.* 182:626-646 (1990) and Rattan et al., *Protein Synthesis: Posttranslational Modifications and Aging*, Ann. N.Y. Acad. Sci. 663: 48-62 (1992). Polypeptides may be branched or cyclic, with or without branching. Cyclic, branched and branched circular polypeptides may result from post-translational natural processes and may be made by entirely synthetic methods, as well.

The term "cis" is art-recognized and refers to the arrangement of two atoms or groups around a double bond such that the atoms or groups are on the same side of the double bond. Cis configurations are often labeled as (Z) configurations.

The term "trans" is art-recognized and refers to the arrangement of two atoms or groups around a double bond such that the atoms or groups are on the opposite sides of a double bond. Trans configurations are often labeled as (E) configurations.

The term "covalent bond" is art-recognized and refers to a bond between two atoms where electrons are attracted electrostatically to both nuclei of the two atoms, and the net effect of increased electron density between the nuclei counterbalances the internuclear repulsion. The term covalent bond includes coordinate bonds when the bond is with a metal ion.

The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Bioactive agents, such as for example, anti-infective agents, and Fab I inhibitors are examples of therapeutic agents.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficient amount to produce a at a reasonable benefit/risk ratio applicable to such treatment.

The terms "combinatorial library" or "library" are art-recognized and refer to a plurality of compounds, which may be termed "members," synthesized or otherwise prepared from one or more starting materials by employing either the same or different reactants or reaction conditions at each reaction in the library. There are a number of other terms of relevance to combinatorial libraries (as well as other technologies). The term "identifier tag" is art-recognized and refers to a means for recording a step in a series of reactions used in the synthesis of a chemical library. The term "immobilized" is art-recognized and, when used with respect to a species, refers to a condition in which the species is attached to a surface with an attractive force stronger than attractive forces that are present in the intended environment of use of the surface, and that act on the species. The term "solid support" is art-recognized and refers to a material which is an insoluble matrix, and may (optionally) have a rigid or semi-rigid surface. The term "linker" is art-recognized and refers to a molecule or group of molecules connecting a support, including a solid support or polymeric support, and a combinatorial library member. The term "polymeric support" is art-recognized and refers to a soluble or insoluble polymer to which a chemical moiety can be covalently bonded by reaction with a functional group of the polymeric support. The term "functional group of a polymeric support" is art-recognized and refers to a chemical moiety of a polymeric support that can react with an chemical moiety to form a polymer-supported amino ester.

The term "synthetic" is art-recognized and refers to production by in vitro chemical or enzymatic synthesis.

The term "meso compound" is art-recognized and refers to a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The term "structure-activity relationship" or "(SAR)" is art-recognized and refers to the way in which altering the molecular structure of a drug or other compound alters its interaction with a receptor, enzyme, nucleic acid or other target and the like.

The term "agonist" is art-recognized and refers to a compound that mimics the action of natural transmitter or, when the natural transmitter is not known, causes changes at the receptor complex in the absence of other receptor ligands.

The term "antagonist" is art-recognized and refers to a compound that binds to a receptor site, but does not cause any physiological changes unless another receptor ligand is present.

The term "competitive antagonist" is art-recognized and refers to a compound or that binds to a receptor site; its effects may be overcome by increased concentration of the agonist.

The term "partial agonist" is art-recognized and refers to a compound or that binds to a receptor site but does not produce the maximal effect regardless of its concentration.

The term "aliphatic" is art-recognized and refers to a linear, branched, cyclic alkane, alkene, or alkyne. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2$—. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

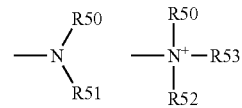

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

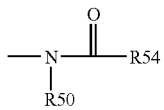

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

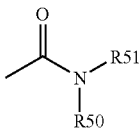

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art-recognized and includes such moieties as may be represented by the general formulas:

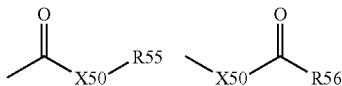

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, O—(CH$_2$)$_m$—R61, where m and R61 are described above.

The term "sulfonate" is art recognized and refers to a moiety that may be represented by the general formula:

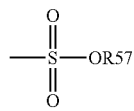

in which R57 is an electron pair, hydrogen, alkyl, cycloalkyl, or aryl.

The term "sulfate" is art recognized and includes a moiety that may be represented by the general formula:

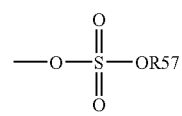

in which R57 is as defined above.

The term "sulfonamido" is art recognized and includes a moiety that may be represented by the general formula:

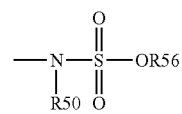

in which R50 and R56 are as defined above.

The term "sulfamoyl" is art-recognized and refers to a moiety that may be represented by the general formula:

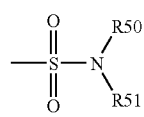

in which R50 and R51 are as defined above.

The term "sulfonyl" is art-recognized and refers to a moiety that may be represented by the general formula:

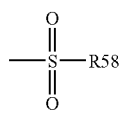

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

in which R58 is defined above.

The term "phosphoryl" is art-recognized and may in general be represented by the formula:

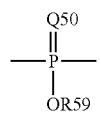

wherein Q50 represents S or O, and R59 represents hydrogen, a lower alkyl or an aryl. When used to substitute, e.g., an alkyl, the phosphoryl group of the phosphorylalkyl may be represented by the general formulas:

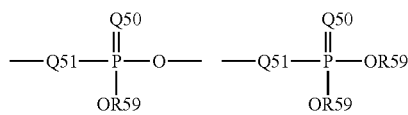

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

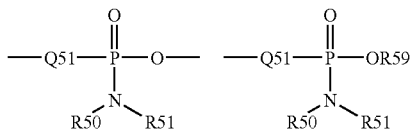

wherein Q51, R50, R51 and R59 are as defined above.

The term "phosphonamidite" is art-recognized and may be represented in the general formulas:

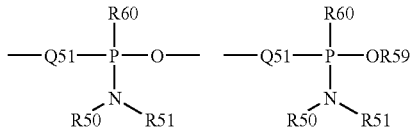

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds that may be substituted or unsubstituted.

The term "protecting group" is art-recognized and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed by Greene and Wuts in *Protective Groups in Organic Synthesis* (2$^{nd}$ ed., Wiley: New York, 1991).

The term "hydroxyl-protecting group" is art-recognized and refers to those groups intended to protect a hydrozyl group against undesirable reactions during synthetic procedures and includes, for example, benzyl or other suitable esters or ethers groups known in the art.

The term "carboxyl-protecting group" is art-recognized and refers to those groups intended to protect a carboxylic acid group, such as the C-terminus of an amino acid or peptide or an acidic or hydroxyl azepine ring substituent, against undesirable reactions during synthetic procedures and includes. Examples for protecting groups for carboxyl groups involve, for example, benzyl ester, cyclohexyl ester, 4-nitrobenzyl ester, t-butyl ester, 4-pyridylmethyl ester, and the like.

The term "amino-blocking group" is art-recognized and refers to a group which will prevent an amino group from participating in a reaction carried out on some other functional group, but which can be removed from the amine when desired. Such groups are discussed by in Ch. 7 of Greene and Wuts, cited above, and by Barton, *Protective Groups in Organic Chemistry* ch. 2 (McOmie, ed., Plenum Press, New York, 1973). Examples of suitable groups include acyl protecting groups such as, to illustrate, formyl, dansyl, acetyl, benzoyl, trifluoroacetyl, succinyl, methoxysuccinyl, benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenyl-ethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. Preferred amino-blocking groups are benzyl (—$CH_2C_6H_5$), acyl [C(O)R1] or $SiR1_3$ where R1 is $C_1$-$C_4$ alkyl, halomethyl, or 2-halo-substituted-($C_2$-$C_4$ alkoxy), aromatic urethane protecting groups as, for example, carbonylbenzyloxy (Cbz); and aliphatic urethane protecting groups such as t-butyloxycarbonyl (Boc) or 9-fluorenylmethoxycarbonyl (FMOC).

The definition of each expression, e.g. lower alkyl, m, n, p and the like, when it occurs more than once in any structure, is intended to be independent of its definition elsewhere in the same structure.

The term "electron-withdrawing group" is art-recognized, and refers to the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, March, *Advanced Organic Chemistry* 251-59 (McGraw Hill Book Company: New York, 1977). The Hammett constant values are generally negative for electron donating groups ($\sigma(P)$=–0.66 for $NH_2$) and positive for electron withdrawing groups ($\sigma(P)$=0.78 for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "amino acid" is art-recognized and refers to all compounds, whether natural or synthetic, which include both an amino functionality and an acid functionality, including amino acid analogs and derivatives.

The terms "amino acid residue" and "peptide residue" are art-recognized and refer to an amino acid or peptide molecule without the —OH of its carboxyl group.

The term "amino acid residue" further includes analogs, derivatives and congeners of any specific amino acid referred to herein, as well as C-terminal or N-terminal protected amino acid derivatives (e.g. modified with an N-terminal or C-terminal protecting group).

The names of the natural amino acids are abbreviated herein in accordance with the recommendations of IUPAC-IUB.

A "reversed" or "retro" peptide sequence as disclosed herein refers to that part of an overall sequence of covalently-bonded amino acid residues (or analogs or mimetics thereof) wherein the normal carboxyl- to amino direction of peptide bond formation in the amino acid backbone has been reversed such that, reading in the conventional left-to-right direction, the amino portion of the peptide bond precedes (rather than follows) the carbonyl portion. See, generally, Goodman et al. *Accounts of Chem. Res.* 12:423 (1979).

The reversed orientation peptides described herein include (a) those wherein one or more amino-terminal residues are converted to a reversed ("rev") orientation (thus yielding a second "carboxyl terminus" at the left-most portion of the molecule), and (b) those wherein one or more carboxyl-terminal residues are converted to a reversed ("rev") orientation (yielding a second "amino terminus" at the right-most portion of the molecule). A peptide (amide) bond cannot be formed at the interface between a normal orientation residue and a reverse orientation residue.

Therefore, certain reversed peptide compounds of the invention may be formed by utilizing an appropriate amino acid mimetic moiety to link the two adjacent portions of the sequences depicted above utilizing a reversed peptide (reversed amide) bond.

The reversed direction of bonding in such compounds will generally, in addition, require inversion of the enantiomeric configuration of the reversed amino acid residues in order to maintain a spatial orientation of side chains that is similar to that of the non-reversed peptide. The configuration of amino acids in the reversed portion of the peptides is usually (D), and the configuration of the non-reversed portion is usually (L).

Opposite or mixed configurations are acceptable when appropriate to optimize a binding activity.

The term "nucleic acid" is art-recognized and refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

The terms "gene" or "recombinant gene" are art-recognized and refer to a nucleic acid comprising an open reading frame encoding a polypeptide, including both exonic and (optionally) intronic sequences.

The term "gene construct" is art-recognized and refers to a vector, plasmid, viral genome or the like which includes an "coding sequence" for a polypeptide or which is otherwise transcribable to a biologically active RNA (e.g., antisense, decoy, ribozyme, etc), can transfect cells, in certain embodiments mammalian cells, and may cause expression of the coding sequence in cells transfected with the construct.

The term "homology" is art-recognized and refers to sequence similarity between two peptides or between two nucleic acid molecules.

The term "operably linked" is art-recognized and refers to the relationship between two nucleic acid regions, means that they are functionally related to each other.

The term "antisense" nucleic acid is art-recognized and refers to oligonucleotides which specifically hybridize (e.g., bind) under cellular conditions with a gene sequence, such as at the cellular mRNA and/or genomic DNA level, so as to inhibit expression of that gene, e.g., by inhibiting transcription and/or translation. The binding may be by conventional base pair complementarily, or, for example, in the case of binding to DNA duplexes, through specific interactions in the major groove of the double helix.

The term "host cell" is art-recognized and refers to a cell transduced with a specified transfer vector. The cell is optionally selected from in vitro cells such as those derived from cell culture, ex vivo cells, such as those derived from an organism, and in vivo cells, such as those in an organism. "Recombinant host cells" refers to cells which have been transformed or transfected with vectors constructed using recombinant DNA techniques.

The terms "recombinant protein," "heterologous protein" and "exogenous protein" are art-recognized and are used interchangeably to refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

The term "regulatory element" is art-recognized and refers to nucleotide sequences (such as DNA sequences) that induce or control transcription of protein coding sequences with which they are operably linked. Examples of regulatory elements categorized by function include initiation signals, enhancers, promoters and the like. Exemplary regulatory elements are described in Goeddel; *Methods in Enzymology* 185 (1990). In certain embodiments, transcription of a gene or other DNA is under the control of a promoter sequence (or other regulatory element) which controls the expression of a coding sequence in a cell-type in which expression is intended. A variety of promoters categorized by function are known. The term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a urogenital origin, e.g., renal cells, or cells of a neural origin, e.g., neuronal cells. The term also covers so-called "leaky" promoters, which regulate expression of a selected DNA primarily in one tissue, but cause expression in other tissues as well. The term "inducible" promoter refers to a promoter which is under environmental or developmental regulation. The term "constitutive" promoter refers to a promoter which is active under most environmental and developmental conditions.

The term "transfection" is art-recognized and refers to the introduction of a nucleic acid, e.g., an expression vector, into a recipient cell, which in certain embodiments may be by nucleic acid-mediated gene transfer. "Transformation," as used with respect to transfected nucleic acid, is an art-recognized term and refers to a process in which a cell's genotype is changed as a result of the cellular uptake of exogenous nucleic acid.

The term "transfer vector" is art-recognized and refers to a first nucleic acid molecule to which a second nucleic acid has been linked, and includes for example plasmids, cosmids or phages (as discussed in grater detail below). In certain embodiments of the present invention, the therapeutic agent is the second nucleic acid. One type of transfer vector is an episome, i.e., a nucleic acid capable of extra-chromosomal replication.

In certain embodiments, a transfer vector may be an "expression vector," which refers to a replicable DNA construct used to express DNA which encodes the desired protein and which includes a transcriptional unit comprising an assembly of (i) genetic element(s) having a regulatory role in gene expression, for example, promoters, operators, or enhancers, operatively linked to (ii) a DNA sequence encoding a desired protein which is transcribed into mRNA and translated into protein, and (iii) appropriate transcription and translation initiation and termination sequences. In certain embodiments, the therapeutic agent is the DNA sequence. The choice of promoter and other regulatory elements generally varies according to the intended host cell. In general, expression vectors of utility in recombinant DNA techniques are often in the form of "plasmids," which refer to circular double stranded DNA loops which, in their vector form are not bound to the chromosome. The invention is intended to include such other forms of expression vectors which serve equivalent functions and which become known in the art subsequently hereto.

Certain transfer vectors may contain regulatory elements for controlling transcription or translation, which may be generally derived from mammalian, microbial, viral or insect genes. The ability to replicate in a host, usually conferred by an origin of replication, and a selection gene to facilitate recognition of transformants, may additionally be incorporated.

The design of any transfer vector may depend on such factors as the choice of the host cell to be transformed and/or the type of protein desired to be expressed. Moreover, the vector's copy number, the ability to control that copy number and the expression of any other proteins encoded by the vector, such as antibiotic markers (e.g., ampicillin), may also be considered.

The term "transgenic animal" is art-recognized and refers to any animal, often a non-human mammal, a bird or an amphibian, in which one or more of the cells of the animal contain nucleic acid introduced by way of human intervention, such as by transgenic techniques well known in the art. Such nucleic acid may be referred to as a "transgene." The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. A transgene may be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene may also be present in a cell in the form of an episome. A transgene may include one or more regulatory elements and any other nucleic acid, such as introns, that may be necessary for optimal expression of a selected nucleic acid. In certain embodiments, a transgene comprises a nucleic acid sequence of interest and one or more regulatory elements for controlling transcription of the nucleotide sequence encoded by such nucleic acid sequence, e.g., the regulatory element is operably linked to a nucleic acid.

In certain embodiments, the transgene or other therapeutic agent may be a "gene therapy construct," which is an expression vector which may alter the phenotype of a cell when taken up by the cell, or a gene construct. In certain embodiments, the gene therapy construct may be a "recombinant coding sequence" which encodes a polypeptide, or is transcribable to an antisense nucleic acid, a ribozyme, or any other RNA product which alters the phenotype of the cell in which it is produced. "Recombinant gene" refers to a genetic construct including a "recombinant coding sequence."

The term "antibody" is art-recognized and refers to whole antibodies, e.g., of any isotype (IgG, IgA, IgM, IgE, etc.), and includes fragments thereof which are also specifically reactive with a vertebrate, e.g., mammalian, protein. Antibodies may be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal or other purified preparations of antibodies and recombinant antibodies.

"Human monoclonal antibodies" or "humanized" murine antibodies, as the terms are used herein, refer to murine monoclonal antibodies "humanized" by genetically recombining the nucleotide sequence encoding the murine Fv region (i.e., containing the antigen binding site) or the complementarity-determining regions thereof with the nucleotide sequence encoding at least a human constant domain region and an Fc region, e.g., in a manner similar to that disclosed in European Patent Application Publication No. 0,411,893 A3. Some additional murine residues may also be retained within the human variable region framework domains to ensure proper target site binding characteristics. In certain embodiments, humanized antibodies may decrease the immunoreactivity of the antibody or polypeptide in the host recipient, permitting an increase in the half-life and a reduction in the possibility of adverse immune reactions.

The term "small molecule" is art-recognized and refers to a composition which has a molecular weight of less than about 2000 amu, or less than about 1000 amu, and even less than about 500 amu. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides or polypeptides.

A "target" shall mean a site to which targeted constructs bind. A target may be either in vivo or in vitro. In certain embodiments, a target may be a tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatitis) and pathogenic fungi (*Candida* sp.). In still other embodiments, a target may refer to a molecular structure to which a targeting moiety binds, such as a hapten, epitope, receptor, dsDNA fragment, carbohydrate or enzyme. Additionally, a target may be a type of tissue, e.g., neuronal tissue, intestinal tissue, pancreatic tissue etc.

The term "targeting moiety" refers to any molecular structure which assists the construct in localizing to a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients, and proteins may serve as targeting moieties.

The term "modulation" is art-recognized and refers to up regulation (i.e., activation or stimulation), down regulation (i.e., inhibition or suppression) of a response, or the two in combination or apart.

The term "treating" is art-recognized and refers to curing as well as ameliorating at least one symptom of any condition or disease.

The term "prophylactic" or "therapeutic" treatment is art-recognized and refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

A "patient," "subject" or "host" to be treated by the subject method may mean either a human or non-human animal.

The term "mammal" is known in the art, and exemplary mammals include humans, primates, bovines, porcines, canines, felines, and rodents (e.g., mice and rats).

The term "bioavailable" is art-recognized and refers to a form of the subject invention that allows for it, or a portion of the amount administered, to be absorbed by, incorporated to, or otherwise physiologically available to a subject or patient to whom it is administered.

The term "pharmaceutically-acceptable salts" is art-recognized and refers to the relatively non-toxic, inorganic and organic acid addition salts of compounds, including, for example, those contained in compositions of the present invention.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes, for example, subcutaneous administration.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

As used herein, "synergy" refers to the in vitro effect of administration of a combination of an antibacterial agent such as a Fab I inhibiter, and antiinfective agent such that (1) the fractional inhibitory concentration (FIC) is less than or equal to 0.5 in an FIC assay described herein; or (2) there is at least a 100-fold (2 log.sub.10) increase in killing at 24 hours for the combination as compared with the bioactive agent alone in a time kill curve assay as described herein. An FIC of ≦0.5 is evidence of synergy. An additive response has an FIC value of >0.5 and less than or equal to 1, while an indifferent response has an FIC value of >1 and ≦2. An additive effect may still indicate that the combination of bioactive agent and cationic peptide are therapeutically useful.

Contemplated equivalents of the compositions described herein include compositions which otherwise correspond thereto, and which have the same general properties thereof (such as other compositions comprising FabI/Fab K inhibitors), wherein one or more simple variations of substituents or components are made which do not adversely affect the characteristics of the compositions of interest. In general, the components of the compositions of the present invention may be prepared by the methods illustrated in the general reaction schema as, for example, described below, or by modifications thereof, using readily available starting materials, reagents and conventional synthesis procedures. In these reactions, it is also possible to make use of variants which are in themselves known, but are not mentioned here.

FabI Inhibitors

In one embodiment, the enzyme inhibiting compositions or compounds, such as Fab I inhibiting compositions or compounds of the present invention comprise a compound depicted by formula I:

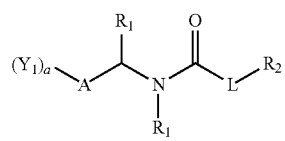

wherein, independently for each occurrence,

L is a bond, or L is alkyl, alkenyl, or cycloalkyl which may be substituted with one or more $R_1$;

A is a monocyclic ring of 4-7 atoms containing 0-2 heteroatoms, a bicyclic ring of 8-12 atoms containing 0-4 heteroatoms or a tricyclic ring of 8-12 atoms containing 0-6 heteroatoms wherein the rings are independently aliphatic, aromatic, heteroaryl or heterocyclic in nature, the heteroatoms are selected from N, S or O and the rings are optionally substituted with one or more groups selected from $C_{1-4}$ alkyl, $CH_2OH$, OR", SR", CN, $N(R")_2$, $CH_2N(R")_2$, $NO_2$, $CF_3$, $CO_2R"$, $CON(R")_2$, COR", NR"C(O)R", F, Cl, Br, I and $—S(O)_rCF_3$; wherein R" is H, alkyl or alkaryl;

$R_1$ is, independently for each occurrence, H, alkyl, cycloalkyl, aryl, or aralkyl;

$R_2$ is

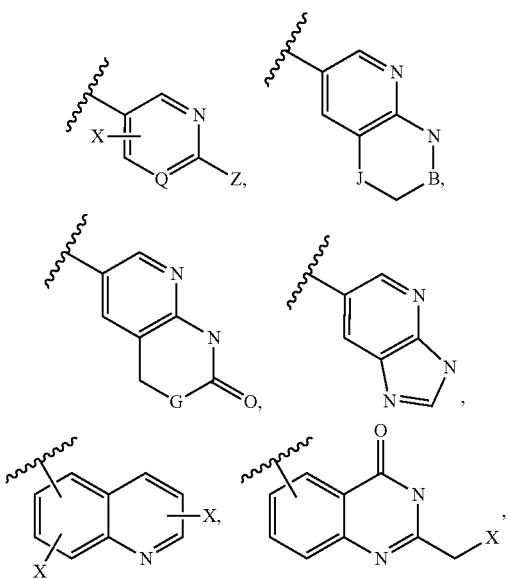

-continued

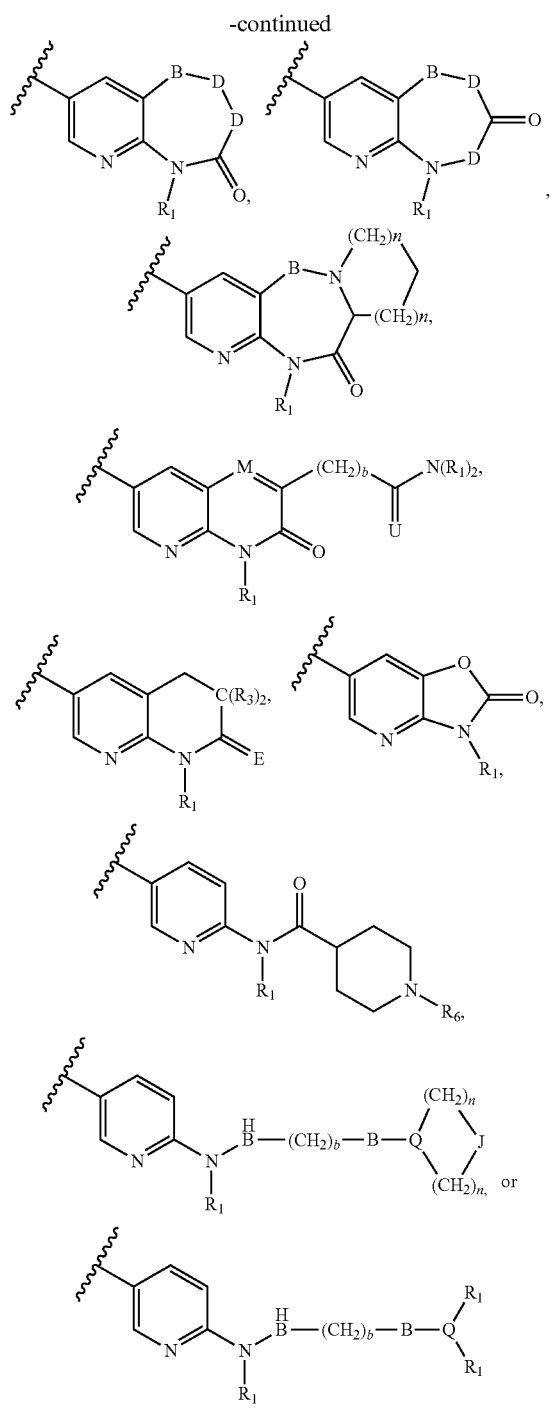

wherein, independently for each occurrence,
B is a bond, $C(R_1)_2$ or $C=O$;
E is O or S;
D is $C(R_1)_2$, $NR_1$, $C=O$,

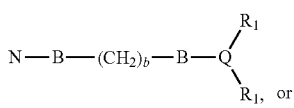

-continued

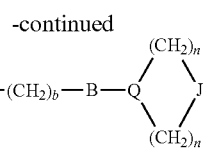

providing that the two Ds are different;
G is O, $NR_1$,

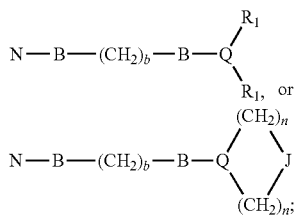

J is $NR_1$, $CH_2$, $CH_2CH_2$, or O;
M is $CR_1$ or N;
Q is N or CH;
U is O, $H_2$, or $CH_2$;
X is H, $C_{1-4}$ alkyl, $CH_2OH$, $OR_1$, $SR_1$, CN, $N(R_1)_2$, $CH_2N(R_1)_2$, $NO_2$, $CF_3$, $CO_2R_1$, $CON(R_1)_2$, $COR_1$, $NR_1C(O)R_1$, F, Cl, Br, I, $-S(O)_rCF_3$,

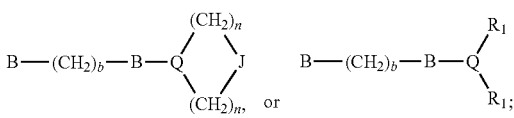

Z is H, $C_{1-4}$ alkyl, $N(R_1)_2$, $NHC(O)R_1$, $NHCH_2C(O)R_1$ or $NHC(O)CH=CHR_1$;
r is 0, 1, or 2;
$R_6$ is $C(O)OR_1$;
$R_1$ is as previously defined; and
b is an integer from 0-4;
$R_3$ is alkyl or cycloalkyl;
a is an integer from 0-4; and
$Y_1$ is

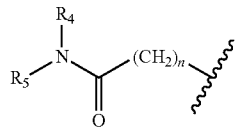

wherein,
$R_4$ is a water solubilizing group;
$R_5$ is H, alkyl, or cycloalkyl; and
n is an integer from 0 to 4, or pharmaceutically acceptable salts thereof.

In another embodiment, the enzyme inhibiting compositions of the present invention may comprise a compound depicted by formula II:

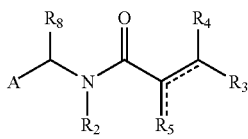
II wherein, independently for each occurrence:
A is a bicyclic or tricyclic heteroaryl ring system of 8-12 atoms, wherein said bicyclic or tricyclic heteroaryl ring system contains 1-4 heteroatoms selected from N, S, and O;
$R_2$ is alkyl or cycloalkyl;
$R_3$ is one of the following:

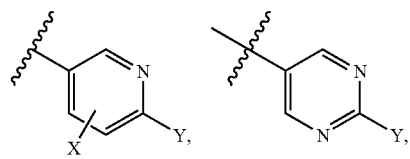

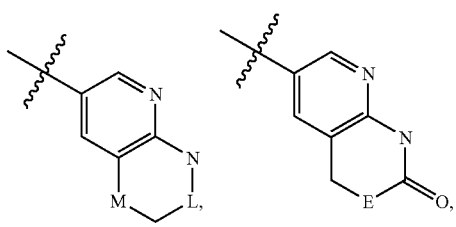

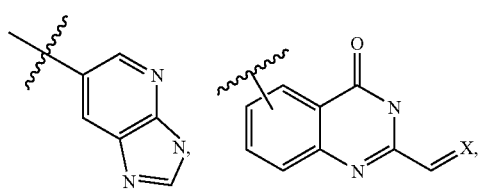

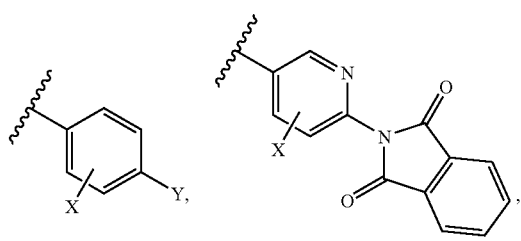

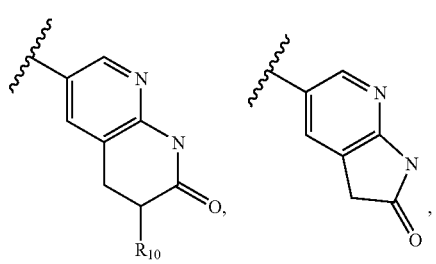

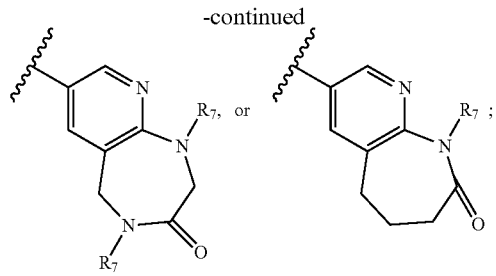

$R_4$ is H or $C_{1-4}$ alkyl;
$R_5$ is $CH_2$ when the bond to which it is attached is a double bond; or $R_5$ is H or $C_{1-4}$ alkyl when the bond to which it is attached is a single bond;
$R_7$ each independently is H, $C_{1-4}$ alkyl, —$C_{0-6}$ alkyl-Ar, —$(CH_2)_{1-3}N(R')_2$, or —$(CH_2)_{1-3}O(R')$;
$R_8$ is H or $C_{1-4}$alkyl;
$R_{10}$ is $C_{1-4}$ alkyl, $N(R')_2$, NHC(O)R', NHCH$_2$C(O)R' or NHC(O)CH=CHR'

indicates that one of two designated bonds is a double bond and the other a single bond;
Y is independently for each occurrence H, $C_{1-4}$ alkyl, $N(R')_2$, NHC(O)R', NHCH$_2$C(O)R' or NHC(O)CH=CHR';
X is H, $C_{1-4}$ alkyl, $CH_2OH$, OR', SR', CN, $N(R')_2$, CH2N$(R')_2$, $NO_2$, $CF_3$, $CO_2R'$, $CON(R')_2$, COR', NR'C(O)R', F, Cl, Br, I or —$S(O)_rCF_3$;
M is $CH_2$, —$CH_2$—$CH_2$—, or O;
L is $CH_2$ or C(O);
E is O or NR';
R' is independently for each occurrence H, $C_{1-6}$ alkyl, —$C_{0-6}$ alkyl-Het or —$C_{0-6}$ alkyl-Ar; and
r is 0, 1 or 2; or pharmaceutically acceptable salts thereof.
In certain embodiments, A may be one of the following:

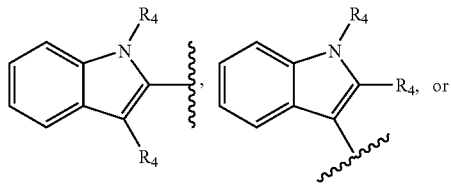

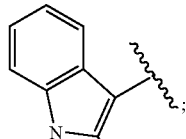

where $R_4$ is independently for each occurrence H, $C_{1-4}$alkyl, or —$N(R')_2$. In other embodiments, A is an indole moiety.
In another embodiment, the enzyme inhibiting compositions of the present invention may comprise is a compound depicted by formula III:

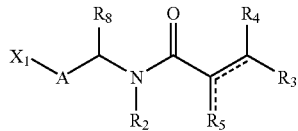

III wherein $X_1$ is

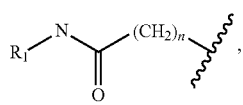

A is a bicyclic or tricyclic heteroaryl ring system of 8-12 atoms, wherein said bicyclic or tricyclic heteroaryl ring system contains 1-4 heteroatoms selected from N, S, and O;

$R_2$ is alkyl or cycloalkyl;

$R_3$ is one of the following:

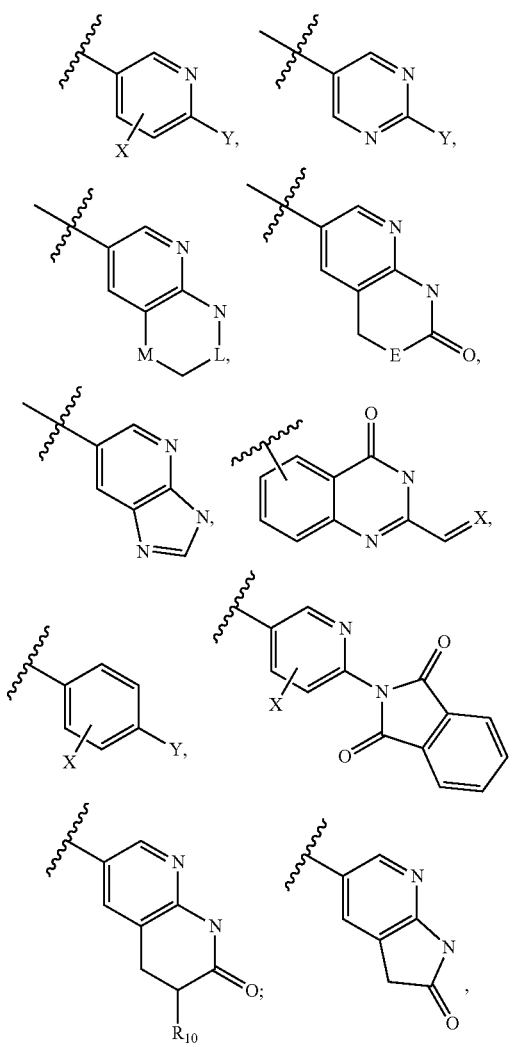

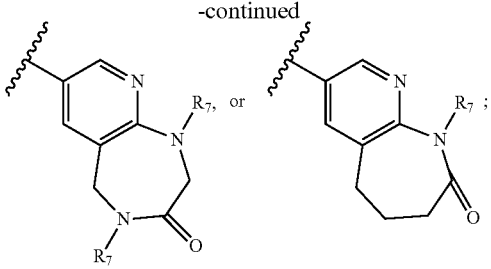

$R_4$ is H or $C_{1-4}$ alkyl;

$R_7$ each independently is H, $C_{1-4}$ alkyl, —$C_{0-6}$ alkyl-Ar, —$(CH_2)_{1-3}N(R')_2$, or —$(CH_2)_{1-3}O(R')$;

$R_8$ is H or $C_{1-4}$ alkyl;

$R_{10}$ is $C_{1-4}$ alkyl, $N(R')_2$, NHC(O)R', NHCH$_2$C(O)R' or NHC(O)CH=CHR'

indicates that one of two designated bonds is a double bond and the other a single bond;

Y is independently for each occurrence H, $C_{1-4}$ alkyl, $N(R')_2$, NHC(O)R', NHCH$_2$C(O)R' or NHC(O)CH=CHR';

X is H, $C_{1-4}$ alkyl, CH$_2$OH, OR', SR', CN, $N(R')_2$, CH2N(R')$_2$, NO$_2$, CF$_3$, CO$_2$R', CON(R')$_2$, COR', NR'C(O)R', F, Cl, Br, I or —S(O)$_r$CF$_3$;

M is CH$_2$, —CH$_2$—CH$_2$—, or O;

L is CH$_2$ or C(O);

E is O or NR';

R' is independently for each occurrence H, $C_{1-6}$ alkyl —$C_{0-6}$ alkyl-Het or —$C_{0-6}$ alkyl-Ar;

$R_1$ is a water solubilizing group;

n is an integer in the range 0 to 4;

r is 0, 1 or 2; or pharmaceutically acceptable salts thereof.

In a further embodiment, the present invention includes antibacterial compositions comprising compounds of formula I and the attendant definitions, wherein L is a $C_2$ alkenyl.

In a further embodiment, the present invention includes antibacterial compositions comprising compounds of formula I and the attendant definitions, wherein L is a $C_2$ alkenyl and $R_2$ is

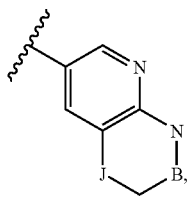

wherein B is C=O.

In a further embodiment, the present invention includes antibacterial compositions comprising compounds of formula I and the attendant definitions, wherein L is a $C_2$ alkenyl and $R_2$ is

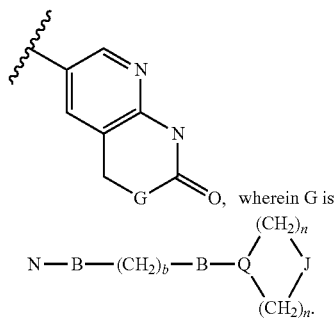

wherein G is

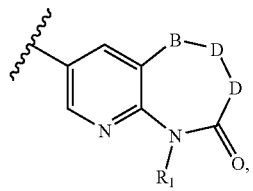

In a further embodiment, the present invention includes antibacterial compositions comprising compounds of formula I and the attendant definitions, wherein L is a $C_2$ alkenyl and $R_2$ is

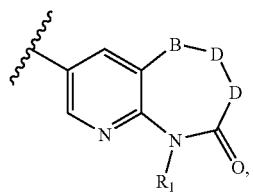

wherein $R_1$ is H.

In a further embodiment, the present invention includes antibacterial compositions comprising compounds of formula I and the attendant definitions, wherein L is a $C_2$ alkenyl and $R_2$ is

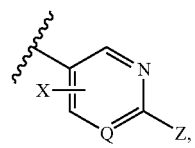

wherein $R_1$ is H and the D adjacent to B is $NR_1$.

In a further embodiment, the present invention includes antibacterial compositions comprising compounds of formula I and the attendant definitions, wherein L is a $C_2$ alkenyl and $R_2$ is

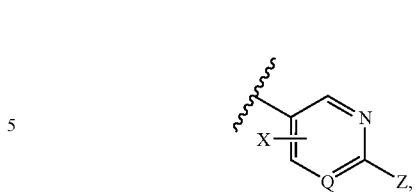

wherein Z is $N(R_1)_2$.

In a further embodiment, the present invention includes antibacterial compositions comprising compounds of formula I and the attendant definitions, wherein L is a $C_2$ alkenyl and $R_2$ is

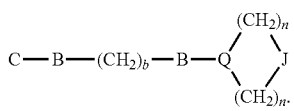

wherein Z is $N(R_1)_2$ and Q is

In a further embodiment, the present invention includes antibacterial compositions comprising compounds of formula I and the attendant definitions, wherein A is a 6 membered monocyclic aryl.

In a further embodiment, the present invention includes antibacterial compositions comprising compounds of formula I and the attendant definitions, wherein A is a 10 membered bicyclic aryl.

In a further embodiment, the present invention includes antibacterial compositions comprising compounds of formula I and the attendant definitions, wherein A is a 12 membered tricyclic aryl.

In a further embodiment, the present invention includes antibacterial compositions comprising compounds of formula I and the attendant definitions, wherein A is an 8 membered bicyclic heteroaryl.

In a further embodiment, the present invention includes antibacterial compositions comprising compounds of formula I and the attendant definitions, wherein A is a 9 membered bicyclic heteroaryl.

In a further embodiment, the present invention includes antibacterial compositions comprising compounds of formula I and the attendant definitions, wherein A comprises at least 1 heteroatom.

In a further embodiment, the present invention includes antibacterial compositions comprising compounds of formula I and the attendant definitions, wherein A comprises at least 2 heteroatoms.

In a further embodiment, the present invention includes antibacterial compositions comprising compounds of formula I and the attendant definitions, wherein A comprises at least 1 nitrogen atom.

In a further embodiment, the present invention includes antibacterial compositions comprising compounds of formula I and the attendant definitions, wherein A comprises at least 1 oxygen atom.

In a further embodiment, the present invention includes antibacterial compositions comprising compounds of formula I and the attendant definitions, wherein A comprises at least 1 sulfur atom.

In a further embodiment, the present invention includes antibacterial compositions comprising compounds of formula I and the attendant definitions, wherein A comprises at least 2 sulfur atoms.

The antibacterial compositions of the present invention comprise, but are not limited to, the following compounds:
(E)-3-(6-aminopyridin-3-yl)-N-(4,6-dichloro-1-methyl-1H-indol-2-ylmethyl)-N-methylacrylamide;

(E)-3-(2-aminopyrimidin-5-yl)-N-(2-methyl-1H-indol-3-yl-methyl)-N-methylacrylamide;
(E)-3-(6-aminopyridin-3-yl)-N-(1-ethyl-1H-indol-3-ylm-ethyl)-N-methylacrylamide;
(E)-3-(6-aminopyridin-3-yl)-N-(1-isopropyl-1H-indol-3-yl-methyl)-N-methylacrylamide;
(E)-N-methyl-N-(1-methyl-1H-indol-3-ylmethyl)-3-[6-(py-ridin-2-ylamino)pyridin-3-yl]acrylamide;
(E)-3-(6-aminopyridin-3-yl)-N-(1,4-dimethyl-1H-indol-3-ylmethyl)-N-methylacrylamide;
(E)-3-(6-aminopyridin-3-yl)-N-(3,3-dimethyl-3H-indene-1-ylmethyl)-N-methylacrylamide;
(E)-3-(2-aminopyrimidin-5-yl)-N-methyl-N-(1-methyl-1H-pyrrolo[2,3-b]pyridin-3-ylmethyl)acrylamide;
(E)-N-methyl-N-(1-methyl-1H-pyrrolo[2,3-b]pyridin-3-yl-methyl)-3-(7-oxo-5,6,7,8-tetrahydro-1,8-naphthyridin-3-yl)acrylamide;
(E)-N-methyl-N-(2-methylbenzo[b]thiophen-3-ylmethyl)-3-(7-oxo-5,6,7,8-tetrahydro-1,8-naphthyridin-3-yl)acry-lamide;
(E)-N-methyl-N-(2-methyl-1H-indol-3-ylmethyl)-3-(3-me-thyl-2-oxo-1,2,3,4-tetrahydropyrido[2,3-d]pyrimidin-6-yl)acrylamide;
(E)-3-(3H-imidazo[4,5-b]pyridin-6-yl)-N-methyl-N-(1-me-thyl-1H-indol-3-ylmethyl)acrylamide;
(E)-3-(3,4-dihydro-2H-pyrido[3,2-b]-1,4-oxazin-7-yl)-N-methyl-N-(1-methyl-1H-indol-3-ylmethyl)acrylamide;
(E)-N-(1H-indol-3-ylmethyl)-N-methyl-3-(7-oxo-5,6,7,8-tetrahydro-1,8-naphthyridin-3-yl)acrylamide;
(E)-3-(6-aminopyridin-3-yl)-N-(5-methoxy-1-methyl-1H-indol-3-ylmethyl)-N-methylacrylamide;
(E)-3-(6-aminopyridin-3-yl)-N-(4-methoxy-1-methyl-1H-indol-3-ylmethyl)-N-methylacrylamide;
(E)-3-(6-aminopyridin-3-yl)-N-(1H-indol-3-ylmethyl)-N-methylacrylamide
(E)-3-(6-aminopyridin-3-yl)-N-(7-chloro-1-methyl-1H-in-dol-3-ylmethyl)-N-methylacrylamide;
(E)-N-methyl-N-(1-methyl-1H-indol-2-ylmethyl)-3-[6-[N-(methylaminocarbonylmethyl)amino]pyridin-3-yl]acryla-mide;
(E)-3-(6-amino-5-(methoxycarbonyl)pyridin-3-yl)-N-(1-methyl-1H-indol-3-ylmethyl)-N-methylacrylamide;
(E)-N-(1-benzyl-1H-indol-3-ylmethyl)-N-methyl-3-(7-oxo-5,6,7,8-tetrahydro-1,8-naphthyridin-3-yl)acrylamide;
(E)-3-(6-aminopyridin-3-yl)-N-(7-methoxy-1-methyl-1H-indol-3-ylmethyl)-N-methylacrylamide;
(E)-N-methyl-N-(1-methyl-1H-indol-3-ylmethyl)-3-(3-me-thyl-2-oxo-1,2,3,4-tetrahydropyrido[2,3-d]pyrimidin-6-yl)acrylamide;
(E)-N-methyl-3-(7-oxo-5,6,7,8-tetrahydro-1,8-naphthyri-din-3-yl)-N-(1,2,7-trimethyl-1H-indol-3-ylmethyl)acry-lamide;
(E)-N-[1-(2-dimethylaminoethyl)-1H-indol-3-ylmethyl]-N-methyl-3-(7-oxo-5,6,7,8-tetrahydro-1,8-naphthyridin-3-yl)acrylamide;
(E)-N-(7-chloro-1-methyl-1H-indol-3-ylmethyl)-N-methyl-3-(7-oxo-5,6,7,8-tetrahydro-1,8-naphthyridin-3-yl)acry-lamide;
(E)-3-[6-amino-5-[[N-methyl-N-(2-methyl-1H-indol-3-yl-methyl)amino]carbonylethyl]pyridin-3-yl]-N-methyl-N-(2-methyl-1H-indol-3-ylmethyl)acrylamide;
(E)-N-(2,3-dihydro-1H-3a-azacyclopenta[α]indene-8-ylm-ethyl)-N-methyl-3-(7-oxo-5,6,7,8-tetrahydro-1,8-naph-thyridin-3-yl)acrylamide;
(E)-N-methyl-N-(2-methyl-1H-indol-3-ylmethyl)-3-(2-oxo-2,3-dihydro-1H-pyrrolo[2,3-b]pyridin-5-yl)acrylamide;
(E)-N-(1-ethyl-5-fluoro-1H-indol-3-ylmethyl)-N-methyl-3-(7-oxo-5,6,7,8-tetrahydro-1,8-naphthyridin-3-yl)acryla-mide;
(E)-N-(7-chloro-1H-indol-3-ylmethyl)-N-methyl-3-(7-oxo-5,6,7,8-tetrahydro-1,8-naphthyridin-3-yl)acrylamide;
(E)-3-(6-aminopyridin-3-yl)-N-(6-chloro-1-methyl-1H-in-dol-3-ylmethyl)-N-methylacrylamide;
(E)-N-(5-fluoro-1-methyl-1H-indol-3-ylmethyl)-N-methyl-3-(7-oxo-5,6,7,8-tetrahydro-1,8-naphthyridin-3-yl)acry-lamide;
(E)-N-(6-fluoro-1-methyl-1H-indol-3-ylmethyl)-N-methyl-3-(7-oxo-5,6,7,8-tetrahydro-1,8-naphthyridin-3-yl)acry-lamide;
(E)-N-(7-fluoro-1-methyl-1H-indol-3-ylmethyl)-N-methyl-3-(7-oxo-5,6,7,8-tetrahydro-1,8-naphthyridin-3-yl)acry-lamide;
(E)-3-(6-aminopyridin-3-yl)-N-(7-hydroxy-1-methyl-1H-indol-3-ylmethyl)-N-methylacrylamide;
(E)-3-(6-aminopyridin-3-yl)-N-(6-fluoro-1-methyl-1H-in-dol-3-ylmethyl)-N-methylacrylamide;
(E)-3-(6-aminopyridin-3-yl)-N-(5-chloro-1-methyl-1H-in-dol-3-ylmethyl)-N-methylacrylamide;
(E)-3-(6-aminopyridin-3-yl)-N-(4-chloro-1-methyl-1H-in-dol-3-ylmethyl)-N-methylacrylamide;
(E)-N-methyl-3-(8-oxo-6,7,8,9-tetrahydro-5H-pyrido[2,3-b]azepin-3-yl)acrylamide;
(E)-3-[6-[N-(methoxycarbonylmethyl)amino]pyridin-3-yl]-N-methyl-N-(2-methyl-1H-indol-3-ylmethyl)acrylamide;
(E)-3-[6-[N-(carboxymethyl)amino]pyridin-3-yl]-N-me-thyl-N-(2-methyl-1H-indol-3-ylmethyl)acrylamide;
(E)-N-methyl-N-(2-methyl-1H-indol-3-ylmethyl)-3-[6-[N-(methylaminocarbonylmethyl)amino]pyridin-3-yl]acryla-mide;
(E)-N-(7-chloro-1-methyl-1H-indol-3-ylmethyl)-3-[6-[N-(methoxycarbonylmethyl)amino]pyridin-3-yl]-N-methy-lacrylamide;
(E)-2,N-dimethyl-N-(2-methyl-1H-indol-3-ylmethyl)-3-(7-oxo-5,6,7,8-tetrahydro-1,8-naphthyridin-3-yl)acryla-mide;
(E)-3-[6-[N-(carboxymethyl)amino]pyridin-3-yl]-N-(7-chloro-1-methyl-1H-indol-3-ylmethyl)-N-methylacryla-mide;
(E)-N-(7-chloro-1-methyl-1H-indol-3-ylmethyl)-N-methyl-3-[6-[N-(methylaminocarbonylmethyl)amino]pyridin-3-yl]acrylamide;
(E)-3,N-dimethyl-N-(2-methyl-1H-indol-3-ylmethyl)-3-(7-oxo-5,6,7,8-tetrahydro-1,8-naphthyridin-3-yl)acryla-mide;
(E)-3-(6-aminopyridin-3-yl)-N-(4-fluoro-1-methyl-1H-in-dol-3-ylmethyl)-N-methylacrylamide;
(E)-3-(6-aminopyridin-3-yl)-N-(5-fluoro-1-methyl-1H-in-dol-3-ylmethyl)-N-methylacrylamide;
(E)-3-(6-aminopyridin-3-yl)-N-(7-fluoro-1-methyl-1H-in-dol-3-ylmethyl)-N-methylacrylamide;
(E)-3-(6-aminopyridin-3-yl)-N-(7-methoxycarbonyl-1-me-thyl-1H-indol-3-ylmethyl)-N-methylacrylamide;
(E)-3-(6-aminopyridin-3-yl)-N-(7-fluoro-1H-indol-3-ylm-ethyl)-N-methylacrylamide;
(E)-3-(6-aminopyridin-3-yl)-N-methyl-N-(1,2,7-trimethyl-1H-indol-3-ylmethyl)acrylamide;
(E)-N-methyl-N-(2-methyl-1H-indol-3-ylmethyl)-3-(8-oxo-6,7,8,9-tetrahydro-5H-pyrido[2,3-b]azepin-3-yl)acryla-mide;
(E)-3-(6-aminopyridin-3-yl)-N-(7-chloro-1H-indol-3-ylm-ethyl)-N-methylacrylamide;
(E)-3-(6-aminopyridin-3-yl)-N-(2-chloro-1-methyl-1H-in-dol-3-ylmethyl)-N-methylacrylamide;

(E)-N-(2-chloro-1-methyl-1H-indol-3-ylmethyl)-N-methyl-3-(7-oxo-5,6,7,8-tetrahydro-1,8-naphthyridin-3-yl)acrylamide;
(E)-N-(5-chloro-1-methyl-1H-indol-3-ylmethyl)-N-methyl-3-(7-oxo-5,6,7,8-tetrahydro-1,8-naphthyridin-3-yl)acrylamide;
(E)-N-(4-fluoro-1-methyl-1H-indol-3-ylmethyl)-N-methyl-3-(7-oxo-5,6,7,8-tetrahydro-1,8-naphthyridin-3-yl)acrylamide;
(E)-N-(6-chloro-1-methyl-1H-indol-3-ylmethyl)-N-methyl-3-(7-oxo-5,6,7,8-tetrahydro-1,8-naphthyridin-3-yl)acrylamide;
(E)-3-(6-aminopyridin-3-yl)-N-(4-fluoro-1H-indol-3-ylmethyl)-N-methylacrylamide;
(E)-3-(6-aminopyridin-3-yl)-N-(7-carboxy-1-methyl-1H-indol-3-ylmethyl)-N-methylacrylamide;
(E)-N-(1,7-dimethyl-1H-indol-3-ylmethyl)-N-methyl-3-(7-oxo-5,6,7,8-tetrahydro-1,8-naphthyridin-3-yl)acrylamide;
(E)-N-(1,6-dimethyl-1H-indol-3-ylmethyl)-N-methyl-3-(7-oxo-5,6,7,8-tetrahydro-1,8-naphthyridin-3-yl)acrylamide;
(E)-N-(1,4-dimethyl-1H-indol-3-ylmethyl)-N-methyl-3-(7-oxo-5,6,7,8-tetrahydro-1,8-naphthyridin-3-yl)acrylamide;
(E)-N-(3,3-dimethyl-3H-indene-1-ylmethyl)-N-methyl-3-(7-oxo-5,6,7,8-tetrahydro-1,8-naphthyridin-3-yl)acrylamide;
(E)-N-(1,5-dimethyl-1H-indol-3-ylmethyl)-N-methyl-3-(7-oxo-5,6,7,8-tetrahydro-1,8-naphthyridin-3-yl)acrylamide;
(E)-N-(7-methoxy-1-methyl-1H-indol-3-ylmethyl)-N-methyl-3-(7-oxo-5,6,7,8-tetrahydro-1,8-naphthyridin-3-yl)acrylamide;
(E)-N-(7-hydroxy-1-methyl-1H-indol-3-ylmethyl)-N-methyl-3-(7-oxo-5,6,7,8-tetrahydro-1,8-naphthyridin-3-yl)acrylamide;
N-Methyl-N-(2-methyl-1H-indol-3-ylmethyl)-3-(4-methyl-3-oxo-2,3,4,5-tetrahydro-1H-pyrido[2,3-e]-1,4-diazepin-7-yl)acrylamide;
(E)-N-[1-(2-hydroxyethyl)-1H-indol-3-ylmethyl]-N-methyl-3-(7-oxo-5,6,7,8-tetrahydro-1,8-naphthyridin-3-yl)acrylamide;
(E)-N-(4-chloro-1-methyl-1H-indol-3-ylmethyl)-N-methyl-3-(7-oxo-5,6,7,8-tetrahydro-1,8-naphthyridin-3-yl)acrylamide;
(E)-N-methyl-N-(1-methyl-1H-indol-3-ylmethyl)-3-(8-oxo-6,7,8,9-tetrahydro-5H-pyrido[2,3-b]azepin-3-yl)acrylamide;
(E)-N-(4-methoxy-1-methyl-1H-indol-3-ylmethyl)-N-methyl-3-(7-oxo-5,6,7,8-tetrahydro-1,8-naphthyridin-3-yl)acrylamide;
(E)-N-(5-methoxy-1-methyl-1H-indol-3-ylmethyl)-N-methyl-3-(7-oxo-5,6,7,8-tetrahydro-1,8-naphthyridin-3-yl)acrylamide;
(E)-N-(6-methoxy-1-methyl-1H-indol-3-ylmethyl)-N-methyl-3-(7-oxo-5,6,7,8-tetrahydro-1,8-naphthyridin-3-yl)acrylamide;
(E)-N-(naphthalen-2-ylmethyl)-N-methyl-3-(7-oxo-5,6,7,8-tetrahydro-1,8-naphthyridin-3-yl)acrylamide;
(E)-N-(quinolin-3-ylmethyl)-N-methyl-3-(7-oxo-5,6,7,8-tetrahydro-1,8-naphthyridin-3-yl)acrylamide;
(E)-N-(1-methyl-1H-indol-3-ylmethyl)-N-methyl-3-(6-amino-7-oxo-5,6,7,8-tetrahydro-1,8-naphthyridin-3-yl)acrylamide;
(E)-N-(1-ethyl-1H-indol-3-ylmethyl)-N-methyl-3-(7-oxo-5,6,7,8-tetrahydro-1,8-naphthyridin-3-yl)acrylamide;
(E)-N-(naphthalen-1-ylmethyl)-N-methyl-3-(7-oxo-5,6,7,8-tetrahydro-1,8-naphthyridin-3-yl)acrylamide;
(E)-N-(benzofuran-2-ylmethyl)-N-methyl-3-(7-oxo-5,6,7,8-tetrahydro-1,8-naphthyridin-3-yl)acrylamide;
(E)-3-(6-aminopyridin-3-yl)-N-(6-methoxycarbonyl-1-methyl-1H-indol-3-ylmethyl)-N-methylacrylamide;
(E)-N-methyl-N-(2-methyl-1H-indol-3-ylmethyl)-3-[3-(2-methoxyethyl)-2-oxo-1,2,3,4-tetrahydropyrido[2,3-d]pyrimidin-6-yl]acrylamide;
(E)-N-(1-methyl-1H-indol-3-ylmethyl)-N-methyl-3-[6-(methoxycarbonyl)-7-oxo-5,6,7,8-tetrahydro-1,8-naphthyridin-3-yl]acrylamide;
(E)-3-(6-aminopyridin-3-yl)-N-(1,3-dimethyl-1H-pyrrolo[2,3-b]pyridin-3-ylmethyl)-N-methylacrylamide;
(E)-N-(1,3-dimethyl-1H-pyrrolo[2,3-b]pyridin-3-ylmethyl)-N-methyl-3-(7-oxo-5,6,7,8-tetrahydro-1,8-naphthyridin-3-yl)acrylamide;
(E)-3-(6-aminopyridin-3-yl)-N-methyl-N-(1-methyl-1H-pyrrolo[2,3-c]pyridin-3-ylmethyl)acrylamide;
(E)-3-(6-aminopyridin-3-yl)-N-methyl-N-(1-methyl-1H-pyrrolo[3,2-c]pyridin-3-ylmethyl)acrylamide;
(E)-3-(6-aminopyridin-3-yl)-N-methyl-N-(1-methyl-1H-pyrrolo[3,2-b]pyridin-3-ylmethyl)acrylamide;
(E)-N-methyl-N-(1-methyl-1H-pyrrolo[2,3-c]pyridin-3-ylmethyl)-3-(7-oxo-5,6,7,8-tetrahydro-1,8-naphthyridin-3-yl)acrylamide;
(E)-N-methyl-N-(1-methyl-1H-pyrrolo[3,2-c]pyridin-3-ylmethyl)-3-(7-oxo-5,6,7,8-tetrahydro-1,8-naphthyridin-3-yl)acrylamide;
(E)-N-methyl-N-(1-methyl-1H-pyrrolo[3,2-b]pyridin-3-ylmethyl)-3-(7-oxo-5,6,7,8-tetrahydro-1,8-naphthyridin-3-yl)acrylamide;
(E)-3-(6-aminopyridin-3-yl)-N-(benzofuran-3-ylmethyl)-N-methylacrylamide;
(E)-3-(6-aminopyridin-3-yl)-N-methyl-N-(3-methylbenzofuran-2-ylmethyl)acrylamide;
(E)-3-(6-aminopyridin-3-yl)-N-methyl-N-(2-methylbenzofuran-3-ylmethyl)acrylamide;
(E)-N-(benzofuran-3-ylmethyl)-N-methyl-3-(7-oxo-5,6,7,8-tetrahydro-1,8-naphthyridin-3-yl)acrylamide;
(E)-N-methyl-N-(3-methylbenzofuran-2-ylmethyl)-3-(7-oxo-5,6,7,8-tetrahydro-1,8-naphthyridin-3-yl)acrylamide;
(E)-N-methyl-N-(2-methylbenzofuran-3-ylmethyl)-3-(7-oxo-5,6,7,8-tetrahydro-1,8-naphthyridin-3-yl)acrylamide;
(E)-(6-aminopyridin-3-yl)-N-methyl-N-[1-(1-methyl-1H-indol-2-yl)ethyl]acrylamide;
(E)-(6-aminopyridin-3-yl)-N-methyl-N-[1-(1-methyl-1H-indol-3-yl)ethyl]acrylamide;
(E)-N-methyl-N-[1-(1-methyl-1H-indol-2-yl)ethyl]-3-(7-oxo-5,6,7,8-tetrahydro-1,8-naphthyridin-3-yl)acrylamide;
(E)-N-methyl-N-[1-(1-methyl-1H-indol-3-yl)ethyl]-3-(7-oxo-5,6,7,8-tetrahydro-1,8-naphthyridin-3-yl)acrylamide;
(E)-N-Methyl-3-(4-methyl-2-oxo-2,3,4,5-tetrahydro-1H-pyrido[2,3-e][1,4]diazepin-7-yl)-N-(1-propyl-naphthalen-2-ylmethyl)acrylamide hydrochloride;
(E)-3-(3,3-Dimethyl-2-oxo-2,3,4,5-tetrahydro-1H-pyrido[2,3-e][1,4]diazepin-7-yl)-N-methyl-N-(3-methyl-benzo[b]thiophen-2-ylmethyl)acrylamide hydrochloride;
(E)-N-Methyl-3-(4-methyl-2-oxo-2,3,4,5-tetrahydro-1H-pyrido[2,3-e][1,4]diazepin-7-yl)-N-naphthalen-2-ylmethyl-acrylamide hydrochloide;

(E)-N-Methyl-3-(4-methyl-2-oxo-2,3,4,5-tetrahydro-1H-pyrido[2,3-e][1,4]diazepin-7-yl)-N-naphthalen-1-ylmethyl-acrylamide hydrochloride;
(E)-N-(4-Acetylamino-benzyl)-N-methyl-3-(7-oxo-5,6,7,8-tetrahydro-[1,8]naphthyridin-3-yl)acrylamide;
(E)-N-(4-Methanesulfonyl-benzyl)-N-methyl-3-(7-oxo-5,6,7,8-tetrahydro-[1,8]naphthyridin-3-yl)acrylamide;
(E)-N-(2-Methoxy-naphthalen-1-ylmethyl)-N-methyl-3-(7-oxo-5,6,7,8-tetrahydro-[1,8]naphthyridin-3-yl)acrylamide;
(E)-N-Methyl-N-(4-methyl-naphthalen-1-ylmethyl)-3-(7-oxo-5,6,7,8-tetrahydro-[1,8]naphthyridin-3-yl)acrylamide;
(E)-N-(2,3-Dimethyl-benzyl)-N-methyl-3-(7-oxo-5,6,7,8-tetrahydro-[1,8]naphthyridin-3-yl)acrylamide;
(E)-N-(4-Isopropyl-benzyl)-N-methyl-3-(7-oxo-5,6,7,8-tetrahydro-[1,8]naphthyridin-3-yl)acrylamide;
(E)-N-Indan-5ylmethyl-N-methyl-3-(7-oxo-5,6,7,8-tetrahydro-[1,8]naphthyridin-3-yl)acrylamide;
(E)-N-Indan-5ylmethyl-N-methyl-3-(4-methyl-2-oxo-2,3,4,5-tetrahydro-1H-pyrido[2,3-e][1,4]diazepin-7-yl)acrylamide hydrochloide;
(E)-N-Methyl-N-(3-methyl-benzo[b]thiophen-2-ylmethyl)-3-(4-methyl-2-oxo-2,3,4,5-tetrahydro-1H-pyrido[2,3-e][1,4]diazepin-7-yl)acrylamide hydrochloride;
(E)-N-(3,5-Dimethoxy-benzyl)-N-methyl-3-(4-methyl-2-oxo-2,3,4,5-tetrahydro-1H-pyrido[2,3-e][1,4]diazepin-7-yl)acrylamide hydrochloride;
(E)-N-[2-(1H-Indol-3-yl)-ethyl]-N-methyl-3-(4-methyl-2-oxo-2,3,4,5-tetrahydro-1H-pyrido[2,3-e][1,4]diazepin-7-yl)acrylamide hydrochloride;
(E)-N-Methyl-3-(4-methyl-2-oxo-2,3,4,5-tetrahydro-1H-pyrido[2,3-e][1,4]diazepin-7-yl)-N-(2,4,5-trimethoxy-benzyl)acrylamide hydrochloride;
(E)-N-Methyl-3-(4-methyl-2-oxo-2,3,4,5-tetrahydro-1H-pyrido[2,3-e][1,4]diazepin-7-yl)-N-phenanthren-9-ylmethyl-acrylamide hydrochloride;
(E)-N-Acenaphthen-5-ylmethyl-N-methyl-3-(4-methyl-2-oxo-2,3,4,5-tetrahydro-1H-pyrido[2,3-e][1,4]diazepin-7-yl)acrylamide hydrochloride;
(E)-N-(4-Methoxy-naphthalen-1 ylmethyl)-N-methyl-3-(4-methyl-2-oxo-2,3,4,5-tetrahydro-1H-pyrido[2,3-e][1,4]diazepin-7-yl)acrylamide hydrochloride;
(E)-N-Benzo[1,3]dioxol-5-ylmethyl-N-methyl-3-(4-methyl-2-oxo-2,3,4,5-tetrahydro-1H-pyrido[2,3-e][1,4]diazepin-7-yl)acrylamide hydrochloride;
(E)-N-(2,5-Dimethoxy-benzyl)-N-methyl-3-(4-methyl-2-oxo-2,3,4,5-tetrahydro-1H-pyrido[2,3-e][1,4]diazepin-7-yl)acrylamide hydrochloride;
(E)-N-Methyl-3-(4-methyl-2-oxo-2,3,4,5-tetrahydro-1H-pyrido[2,3-e][1,4]diazepin-7-yl)-N-quinolin-4-ylmethyl-acrylamide hydrochloride;
(E)-N-(4-Ethoxy-3-methoxy-benzyl)-N-methyl-3-(4-methyl-2-oxo-2,3,4,5-tetrahydro-1H-pyrido[2,3-e][1,4]diazepin-7-yl)acrylamide hydrochloride;
(E)-N-(2-Ethoxy-3-methoxy-benzyl)-N-methyl-3-(4-methyl-2-oxo-2,3,4,5-tetrahydro-1H-pyrido[2,3-e][1,4]diazepin-7-yl)acrylamide hydrochloride;
(E)-N-(3,4-Dimethyl-benzyl)-N-methyl-3-(4-methyl-2-oxo-2,3,4,5-tetrahydro-1H-pyrido[2,3-e][1,4]diazepin-7-yl)acrylamide hydrochloride;
(E)-N-Methyl-3-(4-methyl-2-oxo-2,3,4,5-tetrahydro-1H-pyrido[2,3-e][1,4]diazepin-7-yl)-N-(2,4,6-trimethyl-benzyl)acrylamide hydrochloride;
(E)-N-Methyl-3-(4-methyl-2-oxo-2,3,4,5-tetrahydro-1H-pyrido[2,3-e][1,4]diazepin-7-yl)-N-(2,4,5-trimethyl-benzyl)acrylamide hydrochloride;
(E)-N-Methyl-3-(4-methyl-2-oxo-2,3,4,5-tetrahydro-1H-pyrido[2,3-e][1,4]diazepin-7-yl)-N-quinolin-3-ylmethyl-acrylamide hydrochloride;
(E)-N-(3,4-Dimethoxy-benzyl)-N-methyl-3-(4-methyl-2-oxo-2,3,4,5-tetrahydro-1H-pyrido[2,3-e][1,4]diazepin-7-yl)acrylamide hydrochloride;
(E)-N-Benzofuran-2-ylmethyl-N-methyl-3-(4-methyl-2-oxo-2,3,4,5-tetrahydro-1H-pyrido[2,3-e][1,4]diazepin-7-yl)acrylamide hydrochloride;
(E)-N-Methyl-N-(2-methyl-naphthalen-1-ylmethyl)-3-(4-methyl-2-oxo-2,3,4,5-tetrahydro-1H-pyrido[2,3-e][1,4]diazepin-7-yl)acrylamide hydrochloride;
(E)-N-Biphenyl-2-ylmethyl-methyl-N-methyl-3-(4-methyl-2-oxo-2,3,4,5-tetrahydro-H-pyrido[2,3-e][1,4]diazepin-7-yl)acrylamide hydrochloride;
(E)-N-Biphenyl-3-ylmethyl-N-methyl-3-(4-methyl-2-oxo-2,3,4,5-tetrahydro-1H-pyrido[2,3-e][1,4]diazepin-7-yl)acrylamide hydrochloride;
(E)-N-(2-Ethoxy-napthalen-1-ylmethyl)-N-methyl-3-(4-methyl-2-oxo-2,3,4,5-tetrahydro-1H-pyrido[2,3-e][1,4]diazepin-7-yl)acrylamide hydrochloride;
(E)-N-(2-Ethoxy-benzyl)-N-methyl-3-(4-methyl-2-oxo-2,3,4,5-tetrahydro-1H-pyrido[2,3-e][1,4]diazepin-7-yl)acrylamide hydrochloride;
(E)-N-Methyl-3-(4-methyl-2-oxo-2,3,4,5-tetrahydro-1H-pyrido[2,3-e][1,4]diazepin-7-yl)-N-(2,3,4-trimethoxy-benzyl)acrylamide hydrochloride;
(E)-N-(2,3-Dihydro-benzo[1,4]dioxin-6ylmethyl)-N-methyl-3-(4-methyl-2-oxo-2,3,4,5-tetrahydro-1H-pyrido[2,3-e][1,4]diazepin-7-yl)acrylamide hydrochloride;
(E)-N-(2,3-Diethoxy-benzyl)-N-methyl-3-(4-methyl-2-oxo-2,3,4,5-tetrahydro-1H-pyrido[2,3-e][1,4]diazepin-7-yl)acrylamide hydrochloride;
(E)-N-(3-Ethoxy-2-methoxy-benzyl)-N-methyl-3-(4-methyl-2-oxo-2,3,4,5-tetrahydro-1H-pyrido[2,3-e][1,4]diazepin-7-yl)acrylamide hydrochloride;
(E)-N-(2-Ethoxy-3-methyl-benzyl)-N-methyl-3-(4-methyl-2-oxo-2,3,4,5-tetrahydro-H-pyrido[2,3-e][1,4]diazepin-7-yl)acrylamide hydrochloride;
(E)-N-methyl-3-(4-methyl-2-oxo-2,3,4,5-tetrahydro-1H-pyrido[2,3-e][1,4]diazepin-7-yl)-N-quinolin-5ylmethyl-acrylamide hydrochloride;
(E)-N-(3-Methoxy-2-propoxy-benzyl)-N-methyl-3-(4-methyl-2-oxo-2,3,4,5-tetrahydro-1H-pyrido[2,3-e][1,4]diazepin-7-yl)acrylamide hydrochloride;
(E)-N-(3-Methoxy-2-isopropoxy-benzyl)-N-methyl-3-(4-methyl-2-oxo-2,3,4,5-tetrahydro-1H-pyrido[2,3-e][1,4]diazepin-7-yl)acrylamide hydrochloride;
(E)-N-methyl-N-(3-methyl-benzofuran-2-ylmethyl)-3-(4-methyl-2-oxo-2,3,4,5-tetrahydro-1H-pyrido[2,3-e][1,4]diazepin-7-yl)acrylamide hydrochloride;
(E)-N-(3-Chloro-2-methoxy-benzyl)-N-methyl-3-(4-methyl-2-oxo-2,3,4,5-tetrahydro-1H-pyrido[2,3-e][1,4]diazepin-7-yl)acrylamide hydrochloride;
(E)-N-(3-Chloro-2-ethoxy-benzyl)-N-methyl-3-(4-methyl-2-oxo-2,3,4,5-tetrahydro-1H-pyrido[2,3-e][1,4]diazepin-7-yl)acrylamide hydrochloride;
(E)-N-(2,3-Dihydro-benzo[1,4]dioxin-5-ylmethyl)-N-methyl-3-(4-methyl-2-oxo-2,3,4,5-tetrahydro-1H-pyrido[2,3-e][1,4]diazepin-7-yl)acrylamide hydrochloride;
(E)-N-(4,5-Dimethyl-naphthalen-1-ylmethyl)-N-methyl-3-(4-methyl-2-oxo-2,3,4,5-tetrahydro-1H-pyrido[2,3-e][1,4]diazepin-7-yl)acrylamide hydrochloride;
(E)-N-Methyl-N-(2-methyl-benzofuran-3-ylmethyl)-3-(4-methyl-2-oxo-2,3,4,5-tetrahydro-1H-pyrido[2,3-e][1,4]diazepin-7-yl)acrylamide hydrochloride;

(E)-N-Methyl-3-(7-oxo-5,6,7,8-tetrahydro-[1,8]naphthyridin-3-yl)-N-quinolin-5-ylmethyl-acrylamide hydrochloride;

(E)-N-benzyl-N-methyl-3-(7-oxo-5,6,7,8-tetrahydro-[1,8]naphthyridin-3-yl)acrylamide;

(E)-N-methyl-N-(1-methyl-1H-indol-2-ylmethyl)-3-(4-methyl-2-oxo-2,3,4,5-tetrahydro-1H-pyrido[2,3-e][1,4]diazepin-7-yl)acrylamide hydrochloride;

(E)-(7-{2-[Methyl-(1-methyl-1H-indol-2-ylmethyl)carbamoyl]vinyl}-2-oxo-1,2,3,5-tetrahydro-pyrido[2,3-e][1,4]diazepin-4-yl)acetic acid ethyl ester hydrochloride;

(E)-N-(2,3-Dimethoxy-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-Methyl-N-(4-methyl-naphthalen-1-ylmethyl)-3-(4-methyl-2-oxo-2,3,4,5-tetrahydro-1H-pyrido[2,3-e][1,4]diazepin-7-yl)acrylamide hydrochloride;

(E)-N-(2-Methoxy-naphthalen-1-ylmethyl)-N-methyl-3-(4-methyl-2-oxo-2,3,4,5-tetrahydro-1H-pyrido[2,3-e][1,4]diazepin-7-yl)acrylamide hydrochloride;

I-(+)-(E)-N-Methyl-3-(4-methyl-2-oxo-2,3,4,5-tetrahydro-1H-pyrido[2,3-e][1,4]diazepin-7-yl)-N-(1-naphthalen-1-yl-ethyl)acrylamide hydrochloride;

(S)-(−)-(E)-N-Methyl-3-(4-methyl-2-oxo-2,3,4,5-tetrahydro-1H-pyrido[2,3-e][1,4]diazepin-7-yl)-N-(1-naphthalen-1-yl-ethyl)acrylamide hydrochloride;

(E)-N-Benzo[b]thiophen-2-ylmethyl-N-methyl-3-(4-methyl-2-oxo-2,3,4,5-tetrahydro-1H-pyrido[2,3-e][1,4]diazepin-7-yl)acrylamide hydrochloride;

(E)-N-methyl-3-(4-methyl-2-oxo-2,3,4,5-tetrahydro-1H-pyrido[2,3-e][1,4]diazepin-7-yl)-N-(3-trifluoromethyl-benzyl)acrylamide hydrochloride;

(E)-N-(2-Chloro-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-Methyl-N-(4-methyl-benzyl)-3-(4-methyl-2-oxo-2,3,4,5-tetrahydro-1H-pyrido[2,3-e][1,4]diazepin-7-yl)acrylamide hydrochloride;

(R)-(−)-(E)-N-Methyl-N-(1-methyl-1H-indol-2-ylmethyl)-3-(10-oxo-2,3,4,9,10,10$^a$-hexahydro-1H-3$^a$,8,9-triaza-benzo[f]azulen-6-yl)acrylamide hydrochloride;

(S)-(+)-(E)-N-Methyl-N-(1-methyl-1H-indol-2-ylmethyl)-3-(10-oxo-2,3,4,9,10,10$^a$-hexahydro-1H-3$^a$,8,9-triaza-benzo[f]azulen-6-yl)acrylamide hydrochloride;

(E)-3-[4-(4-Methoxy-benzyl)-2-oxo-2,3,4,5-tetrahydro-1H-pyrido[2,3-e][1,4]diazepin-7-yl]-N-methyl-N-(1-methyl-1H-indol-2-ylmethyl)acrylamide hydrochloride;

(E)-N-Methyl-N-(1-methyl-1H-indol-2-ylmethyl)-3-(2-oxo-2,3,4,5-tetrahydro-1H-pyrido[2,3-e][1,4]diazepin-7-yl)acrylamide hydrochloride;

(E)-N-Methyl-N-(3-methyl-benzo[b]thiophen-2-ylmethyl)-3-[4-(2-morpholin-4-yl-ethyl)-2-oxo-2,3,4,5-tetrahydro-1H-pyrido[2,3-e][1,4]diazepin-7-yl]acrylamide hydrochloride;

(E)-N-Methyl-N-(3-methyl-benzo[b]thiophen-2-ylmethyl)-3-{4-[2-(4-methyl-piperazin-1-yl)-2-oxo-ethyl]-2-oxo-2,3,4,5-tetrahydro-1H-pyrido[2,3-e][1,4]diazepin-7-yl}acrylamide hydrochloride;

(E)-N-Methyl-N-(3-methyl-benzo[b]thiophen-2-ylmethyl)-3-[4-(3-morpholin-4-yl-propyl)-2-oxo-2,3,4,5-tetrahydro-1H-pyrido[2,3-e][1,4]diazepin-7-yl]acrylamide hydrochloride;

(E)-N-(2-Ethoxy-3-methoxy-benzyl)-N-methyl-3-{4-[2-(4-methyl-piperazin-1-yl)-2-oxo-ethyl]-2-oxo-2,3,4,5-tetrahydro-1H-pyrido[2,3-e][1,4]diazepin-7-yl}acrylamide hydrochloride;

(S)-(+)-(E)-N-Methyl-N-(3-methyl-benzo[b]thiophen-2-ylmethyl)-3-(10-oxo-2,3,4,9,10,10$^a$-hexahydro-1H-3$^a$,8,9-triaza-benzo[f]azulen-6-yl)acrylamide hydrochloride;

(R)-(−)-(E)-N-Methyl-N-(3-methyl-benzo[b]thiophen-2-ylmethyl)-3-(10-oxo-2,3,4,9,10,10$^a$-hexahydro-1H-3$^a$,8,9-triaza-benzo[f]azulen-6-yl)acrylamide hydrochloride;

(E)-N-(4-Fluoro-naphthalen-1-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-(4-Chloro-naphthalen-1-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-Methyl-N-(3-methyl-benzofuran-2-ylmethyl)-3-[4-(3-morpholin-4-yl-propyl)-2-oxo-2,3,4,5-tetrahydro-1H-pyrido[2,3-e][1,4]diazepin-7-yl]acrylamide hydrochloride;

(E)-N-(2-Isopropoxy-3-methoxy-benzyl)-N-methyl-3-[4-(3-morpholin-4-yl-propyl)-2-oxo-2,3,4,5-tetrahydro-1H-pyrido[2,3-e][1,4]diazepin-7-yl]acrylamide hydrochloride;

(E)-N-Methyl-N-(3-methyl-benzo[b]thiophen-2-ylmethyl)-3-{4-[3-(4-methyl-piperazin-1-yl)propyl]-2-oxo-2,3,4,5-tetrahydro-1H-pyrido[2,3-e][1,4]diazepin-7-yl}acrylamide hydrochloride;

(E)-N-Methyl-N-(2-methyl-benzofuran-3-ylmethyl)-3-[4-(3-morpholin-4-yl-propyl)-2-oxo-2,3,4,5-tetrahydro-1H-pyrido[2,3-e][1,4]diazepin-7-yl]acrylamide hydrochloride;

(E)-N-(3-Chloro-benzo[b]thiophen-2-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-(5-Chloro-1-methyl-1H-indol-2-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-(1,7-Dimethyl-1H-indol-2-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-(5-Fluoro-3-methyl-benzo[b]thiophen-2-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-(5-Chloro-3-methyl-benzo[b]thiophen-2-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-3-(6-Amino-5-morpholin-4-ylmethyl-pyridin-3-yl)-N-(1,7-dimethyl-1H-indol-2-ylmethyl)-N-methyl-acrylamide hydrochloride;

(E)-3-(6-Amino-5-morpholin-4-ylmethyl-pyridin-3-yl)-N-(2-ethoxy-3-methoxy-benzyl)-N-methyl-acrylamide hydrochloride;

(E)-N-Methyl-N-(1-methyl-1H-indol-3-ylmethyl)-3-(4-methyl-2-oxo-2,3,4,5-tetrahydro-1H-pyrido[2,3-e][1,4]diazepin-7-yl)acrylamide;

(E)-7-{2-[Methyl-(1-methyl-1H-indol-3-ylmethyl)-carbamoyl]-vinyl}-2-oxo-1,2,3,5-tetrahydro-pyrido[2,3-e][1,4]diazepine-4-carboxylic acid benzyl ester;

(E)-3-(2,4-Dioxo-1,2,3,4-tetrahydro-pyrido[2,3-d]pyrimidin-6-yl)-N-methyl-N-(1-methyl-1H-indol-3-ylmethyl)acrylamide;

(E)-N-Methyl-N-(1-methyl-1H-indol-2-ylmethyl)-3-(2-oxo-2,3-dihydro-oxazolo[4,5-b]pyridin-6-yl)acrylamide;

(E)-N-Methyl-N-(1-methyl-1H-indol-3-ylmethyl)-3-(2-oxo-2,3-dihydro-oxazolo[4,5-b]pyridin-6-yl)acrylamide;

(E)-3-(6-Amino-5-{2-[methyl-(1-methyl-1H-indol-2-ylmethyl)carbamoyl]ethyl}pyridin-3-yl)-N-methyl-N-(1-methyl-1H-indol-2-ylmethyl)acrylamide;

(E)-3-(6-Amino-5-piperidin-1-ylmethyl-pyridin-3-yl)-N-methyl-N-(1-methyl-1H-indol-2-ylmethyl)acrylamide;

(E)-3-(6-Amino-5-pyrrolidin-1-ylmethyl-pyridin-3-yl)-N-methyl-N-(1-methyl-1H-indol-2-ylmethyl)acrylamide hydrochloride;

(E)-3-[6-Amino-5-(4-methyl-piperazin-1-ylmethyl)pyridin-3-yl]-N-methyl-N-(1-methyl-1H-indol-2-ylmethyl)acrylamide hydrochloride;

(E)-3-[6-Amino-5-(4-benzyl-piperidin-1-ylmethyl)pyridin-3-yl]-N-methyl-N-(1-methyl-1H-indol-2-ylmethyl)acrylamide hydrochloride;

(E)-3-(6-Amino-5-pyrrolidin-1-ylmethyl-pyridin-3-yl)-N-methyl-N-naphthalen-2-ylmethyl-acrylamide hydrochloride;

(E)-3-[6-Amino-5-(4-methyl-piperazin-1-ylmethyl)pyridin-3-yl]-N-methyl-N-(3-methyl-benzo[b]thiophen-2-ylmethyl)acrylamide hydrochloride;

(E)-3-(6-Amino-5-morpholin-4-ylmethyl-pyridin-3-yl)-N-methyl-N-(4-methyl-naphthalen-1-ylmethyl)acrylamide hydrochloride;

(E)-3-(6-Amino-5-morpholin-4-ylmethyl-pyridin-3-yl)-N-methyl-N-(3-methyl-benzo[b]thiophen-2-ylmethyl)acrylamide hydrochloride;

(E)-3-(6-Amino-5-morpholin-4-ylmethyl-pyridin-3-yl)-N-(3,4-dimethyl-thieno[2,3-b]thiophen-2-ylmethyl)-N-methyl-acrylamide hydrochloride;

(E)-3-[6-Amino-5-(4-methyl-piperazin-1-ylmethyl)pyridin-3-yl]-N-(2-ethoxy-3-methoxy-benzyl)-N-methyl-acrylamide hydrochloride;

(E)-3-[6-Amino-5-(4-methyl-piperazin-1-ylmethyl)pyridin-3-yl]-N-methyl-N-(4-methyl-naphthalen-1-ylmethyl)acrylamide hydrochloride;

(E)-3-[6-Amino-5-(4-methyl-piperazin-1-ylmethyl)pyridin-3-yl]-N-benzofuran-2-ylmethyl-N-methyl-acrylamide hydrochloride;

(E)-3-[6-Amino-5-(4-methyl-piperazin-1-ylmethyl)pyridin-3-yl]-N-(3-methoxy-2-propoxy-benzyl)-N-methyl-acrylamide hydrochloride;

(E)-3-[6-Amino-5-(4-methyl-piperazin-1-ylmethyl)pyridin-3-yl]-N-(2-ethoxy-3-methyl-benzyl)-N-methyl-acrylamide hydrochloride;

(E)-N-(3-Methoxy-2-propoxy-benzyl)-N-methyl-3-(7-oxo-5,6,7,8-tetrahydro-[1,8]naphthyridin-3-yl)acrylamide hydrochloride;

(E)-N-(2-Isopropoxy-3-methoxy-benzyl)-N-methyl-3-(7-oxo-5,6,7,8-tetrahydro-[1,8]naphthyridin-3-yl)acrylamide hydrochloride;

(E)-N-(2-Ethoxy-3-methoxy-benzyl)-N-methyl-3-(7-oxo-5,6,7,8-tetrahydro-[1,8]naphthyridin-3-yl)acrylamide hydrochloride;

(E)-3-[6-(2,5-Dioxo-pyrrolidin-1-yl)pyridin-3-yl]-N-methyl-N-(1-methyl-1H-indol-2-ylmethyl)acrylamide;

(E)-N-(5-{2-[Methyl-(1-methyl-1H-indol-2-ylmethyl)carbamoyl]vinyl}pyridin-2-yl)succinamide;

(E)-N-(5-{2-[Methyl-(1-methyl-1H-indol-2-ylmethyl)carbamoyl]vinyl}pyridin-2-yl)-4-(4-methyl-piperazin-1-yl)-4-oxo-butyramide;

(E)-N-(5-{2-[Methyl-(1-methyl-1H-indol-2-ylmethyl)carbamoyl]vinyl}pyridin-2-yl)-4-morpholin-4-yl-4-oxo-butyramide;

(E)-1-Methyl-piperidine-4-carboxylic acid (5-{2-[methyl-(1-methyl-1H-indol-2-ylmethyl)carbamoyl]vinyl}pyridin-2-yl)amide;

(E)-N-Methyl-N-(1-methyl-1H-indol-2-ylmethyl)-3-[6-(2-pyridin-4-yl-acetylamino)pyridin-3-yl]acrylamide;

(E)-1-Acetyl-piperidine-4-carboxylic acid (5-{2-[methyl-(1-methyl-1H-indol-2-ylmethyl)carbamoyl]vinyl}pyridin-2-yl)amide;

(E)-3-(6-Amino-pyridin-3-yl)-N-(2,3-dimethoxy-benzyl)-N-methyl-acrylamide;

(E)-N-(4-Acetylamino-benzyl)-3-(6-amino-pyridin-3-yl)-N-methyl-acrylamide;

(E)-3-[3-(2-Dimethylamino-ethyl)-2-oxo-1,2,3,4-tetrahydro-pyrido[2,3-d]pyrimidin-6-yl]-N-methyl-N-(1-methyl-1H-indol-2-ylmethyl)acrylamide;

(E)-N-Methyl-N-(1-methyl-1H-indol-2-ylmethyl)-3-[3-(2-morpholin-4-yl-ethyl)-2-oxo-1,2,3,4-tetrahydro-pyrido[2,3-d]pyrimidin-6-yl]acrylamide hydrochloride;

(E)-N-Methyl-N-(4-methyl-naphthalen-1-ylmethyl)-3-[3-(2-morpholin-4-yl-ethyl)-2-oxo-1,2,3,4-tetrahydro-pyrido[2,3-d]pyrimidin-6-yl]acrylamide hydrochloride;

(E)-N-Acenaphthen-5-ylmethyl-N-methyl-3-[3-(2-morpholin-4-yl-ethyl)-2-oxo-1,2,3,4-tetrahydro-pyrido[2,3-d]pyrimidin-6-yl]acrylamide hydrochloride;

(E)-N-(2-Ethoxy-3-methoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride;

(E)-N-Methyl-N-(3-methyl-benzo[b]thiophen-2-ylmethyl)-3-[3-(2-morpholin-4-yl-ethyl)-2-oxo-1,2,3,4-tetrahydro-pyrido[2,3-d]pyrimidin-6-yl]acrylamide hydrochloride;

(E)-(6-{2-[Methyl-(1-methyl-1H-indol-2-ylmethyl)carbamoyl]vinyl}-2-oxo-1,4-dihydro-2H-pyrido[2,3-d]pyrimidin-3-yl)acetic acid;

Sodium (E)-(6-{2-[methyl-(1-methyl-1H-indol-2-ylmethyl)carbamoyl]vinyl}-2-oxo-1,4-dihydro-2H-pyrido[2,3-d]pyrimidin-3-yl)acetate;

Sodium (E)-(6-{2-[methyl-(3-methyl-benzo[b]thiophen-2-ylmethyl)carbamoyl]vinyl}-2-oxo-1,4-dihydro-2H-pyrido[2,3-d]pyrimidin-3-yl)acetate;

(E)-N-Methyl-N-(1-methyl-1H-indol-2-ylmethyl)-3-{3-[2-(4-methyl-piperazin-1-yl)-2-oxo-ethyl]-2-oxo-1,2,3,4-tetrahydro-pyrido[2,3-d]pyrimidin-6-yl}acrylamide hydrochloride;

(E)-N-Methyl-N-(3-methyl-benzo[b]thiophen-2-ylmethyl)-3-{3-[2-(4-methyl-piperazin-1-yl)-2-oxo-ethyl]-2-oxo-1,2,3,4-tetrahydro-pyrido[2,3-d]pyrimidin-6-yl}acrylamide hydrochloride;

(E)-N-Methyl-N-(3-methyl-benzo[b]thiophen-2-ylmethyl)-3-{3-[2-(4-methyl-piperazin-1-yl)-2-oxo-ethyl]-2-oxo-1,2,3,4-tetrahydro-pyrido[2,3-d]pyrimidin-6-yl}acrylamide hydrochloride;

(E)-2-Amino-5-{2-[methyl-(1-methyl-1H-indol-2-ylmethyl)carbamoyl]vinyl}-N-(2-morpholin-4-yl-ethyl)nicotinamide hydrochloride;

(E)-N-(3-Methyl-benzo[b]thiophen-2-ylmethyl)-3-[3-(3-morpholin-4-yl-propyl)-2-oxo-1,2,3,4-tetrahydro-pyrido[2,3-d]pyrimidin-6-yl]acrylamide hydrochloride;

(E)-N-(2-Ethoxy-3-methoxy-benzyl)-N-methyl-3-[3-(3-morpholin-4-yl-propyl)-2-oxo-1,2,3,4-tetrahydro-pyrido[2,3-d]pyrimidin-6-yl]acrylamide hydrochloride;

(E)-N-(5-{2-[Methyl-(3-methyl-benzo[b]thiophen-2-ylmethyl)carbamoyl]vinyl}pyridin-2-yl)-4-(4-methyl-piperazin-1-yl)-4-oxo-butyramide;

(E)-N-(2,3-Diethoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride;

(E)-N-(2-Isopropoxy-3-methoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride;

(E)-N-(3-Methoxy-2-propoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride;

(E)-N-Methyl-N-(3-methyl-benzofuran-2-ylmethyl)-3-[3-(2-morpholin-4-yl-ethyl)-2-oxo-1,2,3,4-tetrahydro-pyrido[2,3-d]pyrimidin-6-yl]acrylamide hydrochloride;

(E)-N-Methyl-N-(2-methyl-benzofuran-3-ylmethyl)-3-[3-(2-morpholin-4-yl-ethyl)-2-oxo-1,2,3,4-tetrahydro-pyrido[2,3-d]pyrimidin-6-yl]acrylamide hydrochloride;

(E)-N-(3-Chloro-2-ethoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride;

(E)-N-(4-Fluoro-naphthalen-1-ylmethyl)-N-methyl-3-[3-(2-morpholin-4-yl-ethyl)-2-oxo-1,2,3,4-tetrahydro-pyrido[2,3-d]pyrimidin-6-yl]acrylamide hydrochloride;

(E)-N-(2,3-Dimethoxy-benzyl)-N-methyl-3-(7-oxo-5,6,7,8-tetrahydro-[1,8]naphthyridin-3-yl)acrylamide;

(E)-3-(6-Amino-5-morpholin-4-ylmethyl-pyridin-3-yl)-N-methyl-N-(1-methyl-1H-indol-3-ylmethyl)acrylamide;

(E)-3-(6-Amino-pyridin-3-yl)-N-methyl-N-thieno[3,2-c]pyridin-2-ylmethyl-acrylamide;

(E)-N-Methyl-3-(4-methyl-2-oxo-2,3,4,5-tetrahydro-1H-pyrido[2,3-e][1,4]diazepin-7-yl)-N-thieno[3,2-c]pyridin-2-ylmethyl-acrylamide;

(E)-N-Methyl-3-(7-oxo-5,6,7,8-tetrahydro-[1,8]naphthyridin-3-yl)-N-thieno[3,2-c]pyridin-2-ylmethyl-acrylamide;

(E)-3-(6-Amino-pyridin-3-yl)-N-(2-ethoxy-3-methoxy-benzyl)-N-methyl-acrylamide hydrochloride;

(E)-3-(6-Amino-pyridin-3-yl)-N-(2-propoxy-3-methoxy-benzyl)-N-methyl-acrylamide hydrochloride;

(E)-3-(6-amino-pyridin-3-yl)-N-(2-isopropoxy-3-methoxy-benzyl)-N-methyl-acrylamide hydrochloride;

(E)-N-Acenaphthen-5-ylmethyl-3-(6-amino-pyridin-3-yl)-N-methyl-acrylamide hydrochloride;

(E)-N-(1H-Indol-5-ylmethyl)-N-methyl-3-(4-methyl-2-oxo-2,3,4,5-tetrahydro-1H-pyrido[2,3-e][1,4]diazepin-7-yl)-acrylamide;

(E)-N-Methyl-N-(1-methylindol-5-ylmethyl)-3-(4-methyl-2-oxo-2,3,4,5-tetrahydro-1H-pyrido[2,3-e][1,4]diazepin-7-yl)-acrylamide;

(E)-N-(1H-Indol-7-ylmethyl)-N-methyl-3-(4-methyl-2-oxo-2,3,4,5-tetrahydro-1H-pyrido[2,3-e][1,4]diazepin-7-yl)-acrylamide;

(E)-N-Methyl-N-(1-methylindol-7-ylmethyl)-3-(4-methyl-2-oxo-2,3,4,5-tetrahydro-1H-pyrido[2,3-e][1,4]diazepin-7-yl)-acrylamide;

(E)-N-(1H-Indol-6-ylmethyl)-N-methyl-3-(4-methyl-2-oxo-2,3,4,5-tetrahydro-1H-pyrido[2,3-e][1,4]diazepin-7-yl)-acrylamide;

(E)-N-3-(6-Amino-pyridin-3-yl)-N-methyl-N-(2-methyl-benzofuran-3-ylmethyl)-acrylamide hydrochloride;

(E)-3-(3,3-Dimethyl-2-oxo-2,3,4,5-tetrahydro-1H-pyrido[2,3-e][1,4]diazepin-7-yl)-N-methyl-N-(3-methyl-benzofuran-2-ylmethyl)acrylamide hydrochloride;

(E)-N-Methyl-N-(3-methyl-1H-inden-2-ylmethyl)-3-(4-methyl-2-oxo-2,3,4,5-tetrahydro-1H-pyrido[2,3-e][1,4]diazepin-7-yl)acrylamide hydrochloride;

(E)-3-(6-{2-[Methyl-(3-methyl-benzo[b]thiophen-2-ylmethyl)carbamoyl]vinyl}-2-oxo-1,4-dihydro-2H-pyrido[2,3-d]pyrimidin-3-yl)propionic acid ethyl ester;

(E)-3-(6-amino-5-cyano-pyridin-3-yl)-N-methyl-N-(1-methyl-1H-indol-2-ylmethyl)-acrylamide hydrochloroide;

(E)-N-methyl-N-(1-methyl-1H-indol-2-ylmethyl)-3-(2-oxo-1,2,3,4-tetrahydro-pyrido-[2,3-b]pyrazin-7-yl)-acrylamide;

N-Methyl-N-(1-methyl-1H-indol-2-ylmethyl)-3-(7-oxo-5,6,7,8-tetrahydro-[1,8]naphthyridin-3-yl)-acrylamide;

N-Methyl-N-(1-methyl-1H-indol-3-ylmethyl)-3-(7-oxo-5,6,7,8-tetrahydro-[1,8]naphthyridin-3-yl)-acrylamide;

N-Methyl-N-(2-methyl-1H-indol-3-ylmethyl)-3-(7-oxo-5,6,7,8-tetrahydro-[1,8]naphthyridin-3-yl)-acrylamide;

N-Methyl-N-(3-methyl-benzo[b]thiophen-2-ylmethyl)-3-(4-methyl-2-oxo-2,3,4,5-tetrahydro-1H-pyrido[2,3-e][1,4]diazepin-7-yl)-acrylamide;

N-Acenaphthen-5-ylmethyl-N-methyl-3-(4-methyl-2-oxo-2,3,4,5-tetrahydro-1H-pyrido[2,3-e][1,4]diazepin-7-yl)-acrylamide; or N-Methyl-N-(3-methyl-benzo[b]thiophen-2-ylmethyl)-3-[3-(2-morpholin-4-yl-ethyl)-2-oxo-1,2,3,4-tetrahydro-pyrido[2,3-d]pyrimidin-6-yl]-acrylamide.

Also included in the antibacterial compositions of the present invention are pharmaceutically acceptable addition salts and complexes of the FabI inhibitors. In cases wherein the inhibitors may have one or more chiral centers, unless specified, the present invention comprises each unique racemic compound, as well as each unique nonracemic compound.

In cases in which the inhibitors have unsaturated carbon-carbon double bonds, both the cis (Z) and trans (E) isomers are within the scope of this invention. In cases wherein inhibitors may exist in tautomeric forms, such as keto-enol tautomers, such as

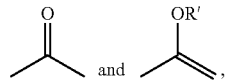

each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included in the antibiotic compounds of the present invention are prodrugs of the FabI inhibitors.

It is believed that the compositions of the present invention comprising compounds of formulas I-III are antibacterial because the compounds inhibit FabI, FabK, or both. It may be, however, that for some or all of the compounds, they inhibit other enzymes in addition or inhibit completely different enzymes. The exact mechanism by which the compositions of the present invention achieve their antibacterial properties is not meant to be limiting.

A variety of subject compounds and intermediates of them may be made by a person of ordinary skill in the art using conventional reaction techniques. Non-limiting examples of compounds and methods of making them may be found in U.S. patent application Ser. Nos. 08/790,043, 10/009,219, 10/089,019, 09/968,129, 09/968,123, 09/968,236, 09/959,172, 09/979,560, 09/980,369, 10/089,755, 10/089,739, 10/089,740, PCT Published Patent Application Nos. WO 0027628 and WO 0210332; and PCT Patent Application PCT/US03/38706.

Synthetic Routes to Compounds of Formula I

A generalized chemical approach to assembling compounds of formula I is based on viewing the analogs as consisting of a central ene-amide flanked left-hand side (LHS) and right-hand side (RHS) moieties. Schematically, this is depicted in FIG. 2. Two possible bond disconnections envisioned in a retrosynthetic sense are shown with dashed lines. Schemes I to XXXV illustrate some of the general methods that can be used in the synthesis of compounds of formula I. It will be recognized by one skilled in the art that other disconections are possible resulting in alternative modes of assembly of the compounds of the invention.

Schemes I to VIII disclose the basic chemistry involved in the synthesis of the left hand side moieties of formula I wherein the requisite LHS coupling partners are amines and the late stage chemistry involves formation of the amide linkage. The amines are typically arylalky-amines which are most conveniently prepared from commercially available arylcarbaldehydes by the action of a reducing agent such as sodium borohydride in the presence of an alkyl amine such as methyl amine (Scheme I).

Scheme I

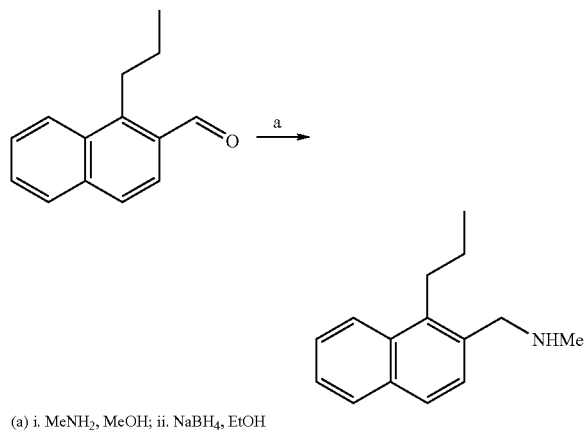

(a) i. MeNH$_2$, MeOH; ii. NaBH$_4$, EtOH

When the arylcarbaldehydes are not commercially available their synthesis can be effected by a number of general methods including the action of dimethylformamide on the lithium salt of aryl anions (Scheme IIb and IIIa).

Scheme II

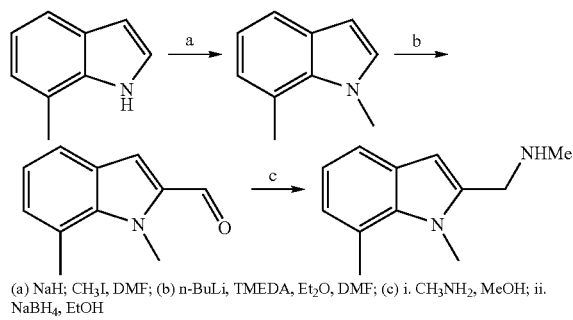

(a) NaH; CH$_3$I, DMF; (b) n-BuLi, TMEDA, Et$_2$O, DMF; (c) i. CH$_3$NH$_2$, MeOH; ii. NaBH$_4$, EtOH

Scheme III

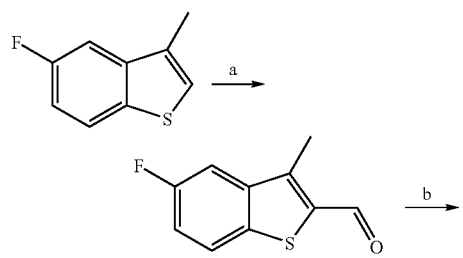

-continued

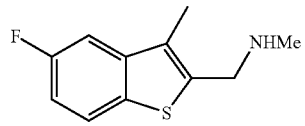

(a) n-BuLi, THF, DMF; (c) i. CH$_3$NH$_2$, MeOH; ii. NaBH$_4$, EtOH

Other methods of obtaining the desired arylcarbaldehydes include the widely employed oxidation of alcohols (Scheme Ivb) and a variety of miscellaneous methods (Scheme Va and Via).

Scheme IV

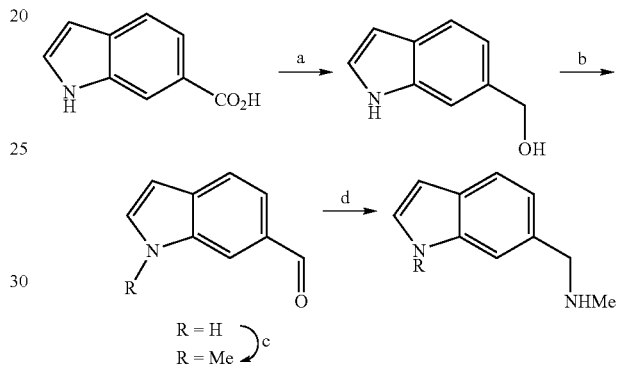

(a) LAH, THF; (b) Dess-Martine periodinane, CH$_2$Cl$_2$, DMF; (c) NaH, CH$_3$I, DMF (d) i. CH$_3$NH$_2$, MeOH; ii. NaBH$_4$, EtOH Scheme V

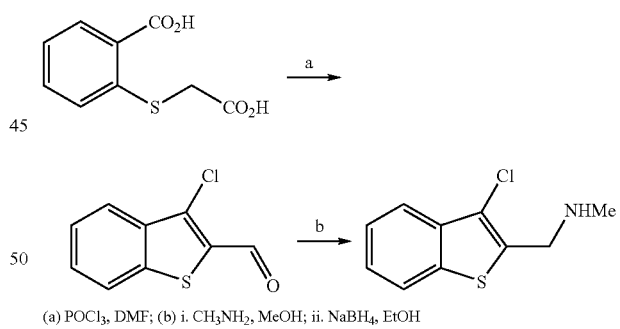

(a) POCl$_3$, DMF; (b) i. CH$_3$NH$_2$, MeOH; ii. NaBH$_4$, EtOH

Scheme VI

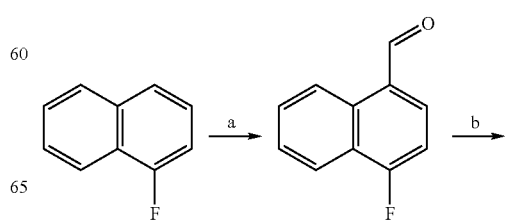

-continued

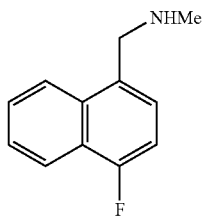

(a) CH₃OCHCl₂, SnCl₄, CH₂Cl₂; (b) i. MeNH₂, MeOH; ii. NaBH₄, EtOH

During the course of these syntheses it may be desirable to alkylate indole-like nitrogens This can be accomplished either prior to (Scheme IIa) or after formation of said carbaldehydes (Scheme Ivc) by the action of strong bases such as sodium hydride and the addition of alkylating agents such as alkyl halides. Likewise oxygen atoms appended to the aromatic systems (e.g. phenols) can be alkylated by the action of base (potassium carbonate) and an alkylhalide (Scheme VIIa).

Scheme VII

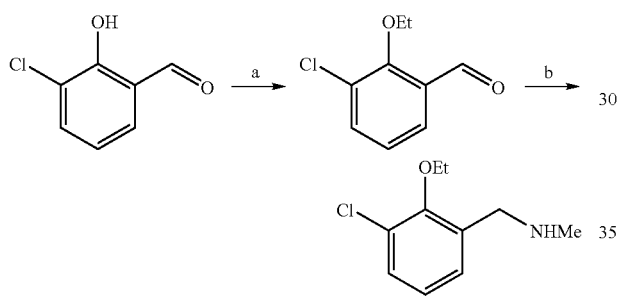

(a) Iodoethane, K₂CO₃, DMF; (b) i. MeNH₂, MeOH; ii. NaBH₄, EtOH

Yet another approach to the formation of the desired amines can be from the reduction of precursor amides (Scheme VIII)

Scheme VIII

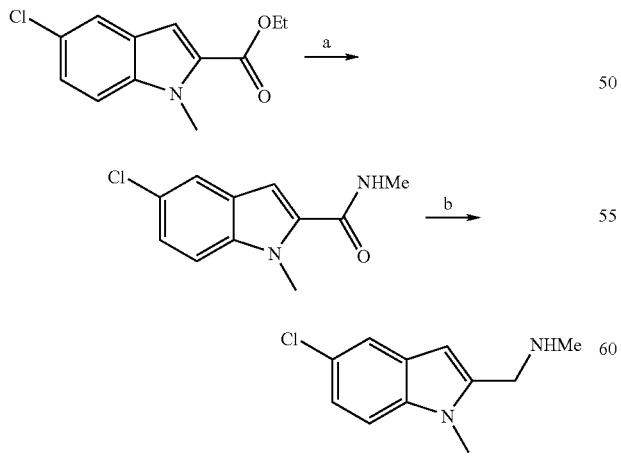

(a) CH₃Al(Cl)NHCH₃, toluene; (b) LiAlH₄, THF

Scheme IX describes the basic chemistry involved in the synthesis of the left hand side moieties of formula I wherein the requisite LHS coupling partners are ene-amides and the late stage chemistry involves formation of a carbon-carbon bond. The carbon-carbon bond formation is usually accomplished by Heck type chemistry which will be described subsequently. The ene-amide is prepared by activation of acylic acid to undergo coupling reaction (with an amine) by any one of the known methods for amide bond formation. One typically used procedure is to treat acrylic acid with a solution of a tertiary amine in DMF followed by the addition of 1-hydroxybenzotriazole hydrate and a carbodiimde such as 1-(3-dimethylaminopropyl)-3-ethyl-carbodiimide hydrochloride. The reaction mixture is then treated with the desired arylalkylamine such as methyl-(1-methyl-1H-indol-3-ylmethyl)-amine (Scheme IX).

Scheme IX

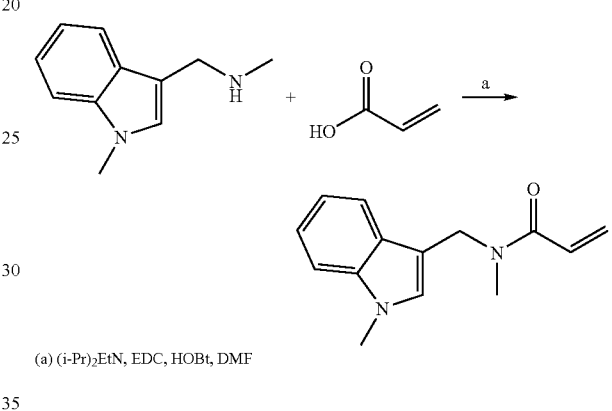

(a) (i-Pr)₂EtN, EDC, HOBt, DMF

Schemes X to XXIV disclose the basic chemistry involved in the synthesis of the right hand side moieties of formula I wherein the requisite RHS coupling partners are carboxylic acids and the late stage chemistry involves formation of the amide linkage. The carboxylic acids are typically arylalkenyl carboxylic acids whose preparation is illustrated by the schemes described below. A common starting material, 5-bromo-3-bromomethyl-pyridin-2-ylamine hydrobromide, is used in the construction of the right hand side moieties described in Schemes X-XVII. In some embodiments of the invention, this material is reacted with a commercial secondary amine (Schemes X-XII) or reacted with a secondary amine which is prepared in the manner illustrated (Schemes XIII-XIV). In either case, a tertiary base is employed. A common feature of the resultant products are compounds incorporating a pendent alkyl ester and an aminopyridine moiety which react in the presence of a base like sodium hydride to form the pyridodiazepinone bicyclic unit.

The pyridodiazepinones prepared in this manner have in common a bromine substitution in the pyridine ring. As will be seen from inspection of the Schemes X-XIV synthesis of arylalkenyl acids proceeds from intermediary bromo-pyridodiazepinones via Heck chemistry (e.g. Scheme Xc). Heck chemistry is carried out by admixture of an arylbromide with an alkylacrylate, such as tert-butylacrylate, in the presence of a palladium catalyst (Pd(OAc)₂, P(o-tol)₃) and a tertiary base such as di-(isopropyl)ethylamine in an appropriate solvent or solvents (e.g. DMF and EtCN). The desired carboxylic acid is obtained by acid-catalysed hydrolysis of the tert-butyl ester (e.g. Scheme Xd).

Scheme X

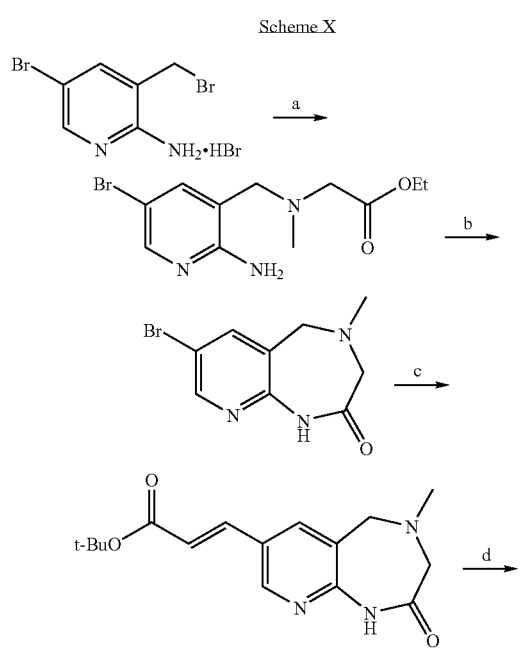

(a) sarcosine ethyl ester hydrochloride, Et$_3$N, DMF; (b) NaH, DMSO; (c) tert-butyl acrylate, Pd(OAc)$_2$, P(o-tol)$_3$, (I-Pr)$_2$EtN, EtCN, DMF; (d) i. TFA, CH$_2$Cl$_2$; ii. 4 N HCl/dioxane Scheme XI

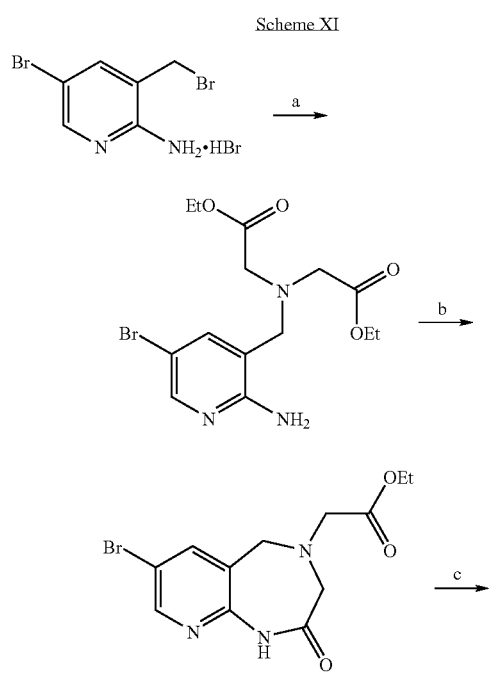

-continued

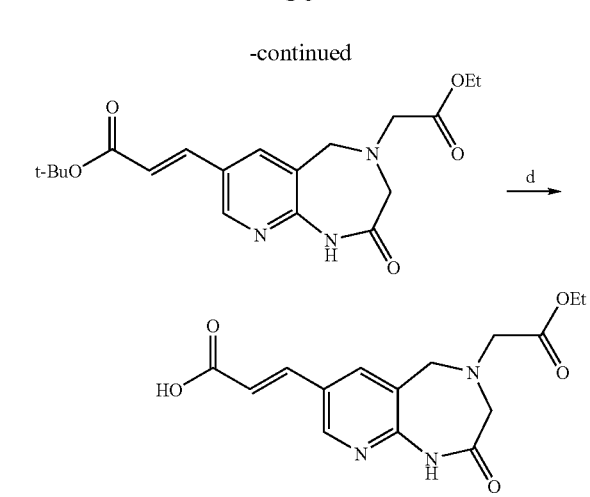

(a) diethyl iminodiacetate, Et$_3$N, CH$_3$CN; (b) NaH, DMSO; (c) tert-butyl acrylate, Pd(OAc)$_2$, P(o-tol)$_3$, (I-Pr)$_2$EtN, EtCN, DMF; (d) i. TFA, CH$_2$Cl$_2$; ii. 4 N HCl/dioxane Scheme XII

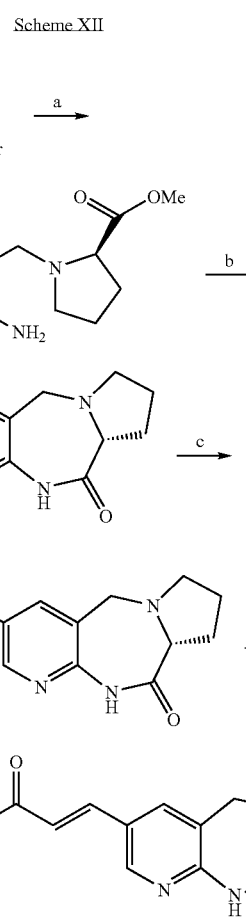

(a) D-proline methyl ester hydrochloride, Et$_3$N, DMF; (b) NaH, DMSO; (c) tert-butyl acrylate, Pd(OAc)$_2$, P(o-tol)$_3$, (I-Pr)$_2$EtN, EtCN, DMF; (d) i. TFA, CH$_2$Cl$_2$; ii. 4 N HCl/dioxane Scheme XIII

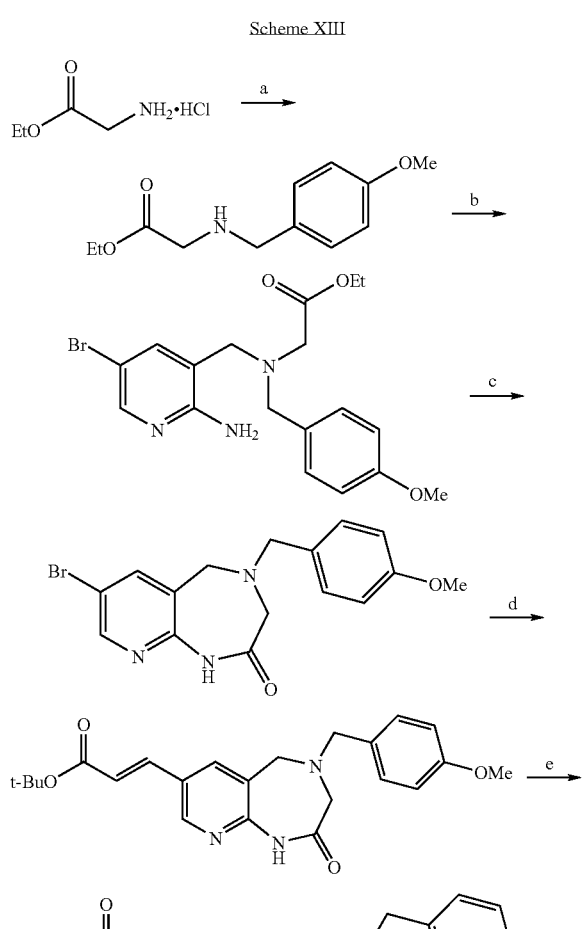

(a) p-anisaldehyde, NaBH₃CN, MeOH; (b) 5-bromo-3-bromomethyl-pyriden-2-ylamine hydrobromide, Et₃N, DMF; (c) NaH, DMSO; (d) tert-butyl acrylate, Pd(OAc)₂, P(o-tol)₃, (I-Pr)₂EtN, EtCN, DMF; (e) i. TFA, CH₂Cl₂; ii 4 N HCl/dioxane Scheme XIV

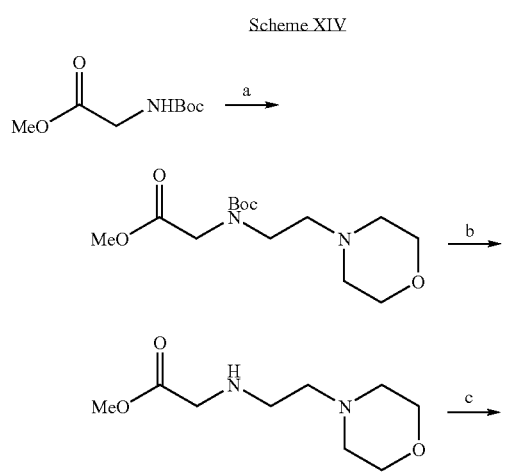

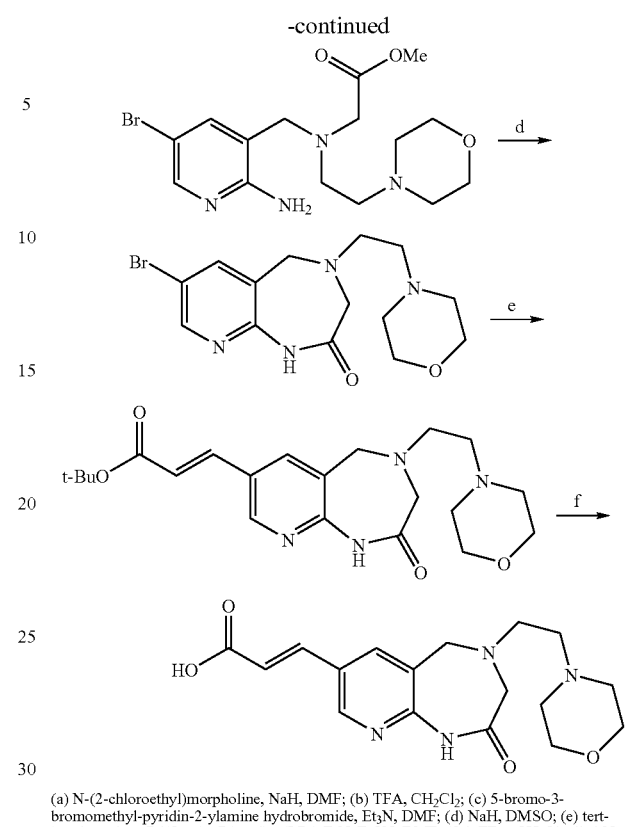

(a) N-(2-chloroethyl)morpholine, NaH, DMF; (b) TFA, CH₂Cl₂; (c) 5-bromo-3-bromomethyl-pyridin-2-ylamine hydrobromide, Et₃N, DMF; (d) NaH, DMSO; (e) tert-butyl acrylate, Pd(OAc)₂, P(o-tol)₃, (I-Pr)₂EtN, EtCN, DMF; (f) i. TFA, CH₂Cl₂; ii. 4 N HCl/dioxane Scheme XV

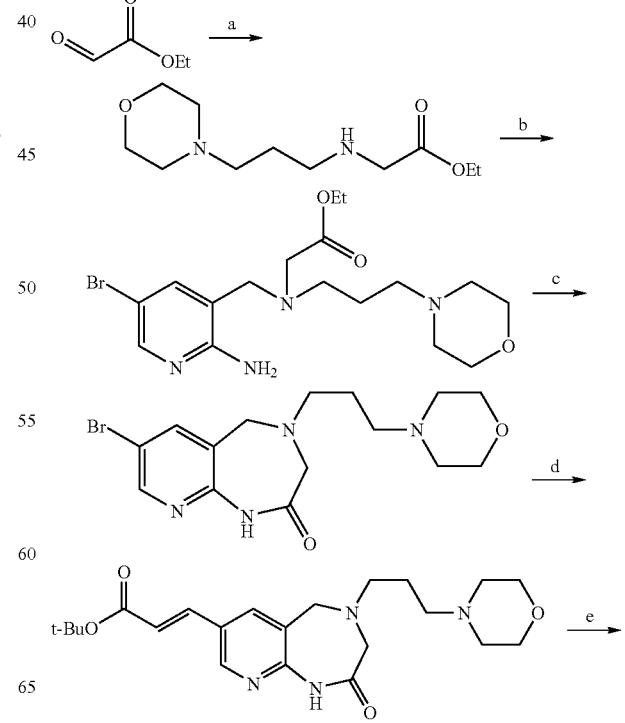

-continued

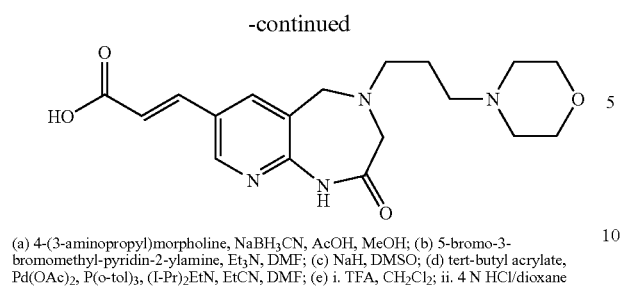

(a) 4-(3-aminopropyl)morpholine, NaBH₃CN, AcOH, MeOH; (b) 5-bromo-3-bromomethyl-pyridin-2-ylamine, Et₃N, DMF; (c) NaH, DMSO; (d) tert-butyl acrylate, Pd(OAc)₂, P(o-tol)₃, (I-Pr)₂EtN, EtCN, DMF; (e) i. TFA, CH₂Cl₂; ii. 4 N HCl/dioxane In an analogous way to the chemistry described above, 5-bromo-3-bromomethyl-pyridin-2-ylamine hydrobromide, may be reacted with primary amines (Scheme XVI, XVII, XVIII); subsequent cyclization with sodium hydride yields a pyridodiazepinone in which the nitrogen at the four position is unsubstituted. In Scheme XVI the final product represents a right hand side moiety of formula I wherein the requisite RHS coupling partners is an aryl bromide and the late stage chemistry involves formation of a carbon-carbon bond via Heck chemistry. One skilled in the art will recognize that the intermediate aryl bromides described in Schemes X-XX may also be used in late stage carbon-carbon bond forming chemistry.

Alternatively, the nitrogen at position four may be derivatized by reaction with alkylating (Scheme XVIIc) or acylating agents (Scheme XVIIIc). In the former case, further elaboration (Scheme XVIId,e) yields a derivatized bromopyridodiazepinone which is subjected to standard Heck coupling/deprotection sequence to give the desired acid. In the latter case, the CBz-protected pyridodiazepinone is similarly treated (Scheme XVIII).

Scheme XVI

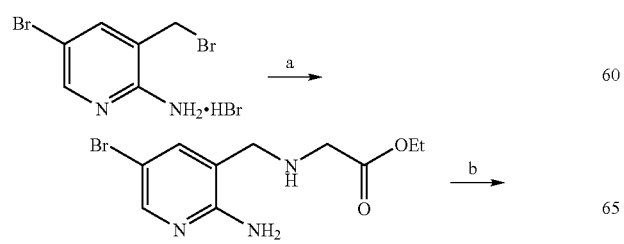

-continued

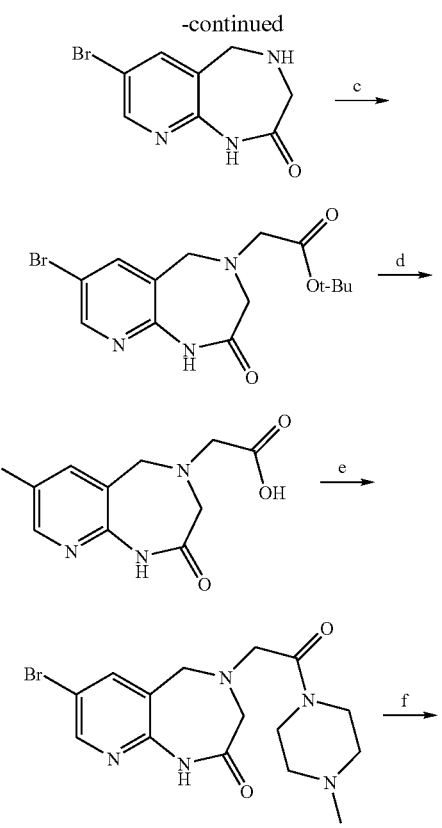

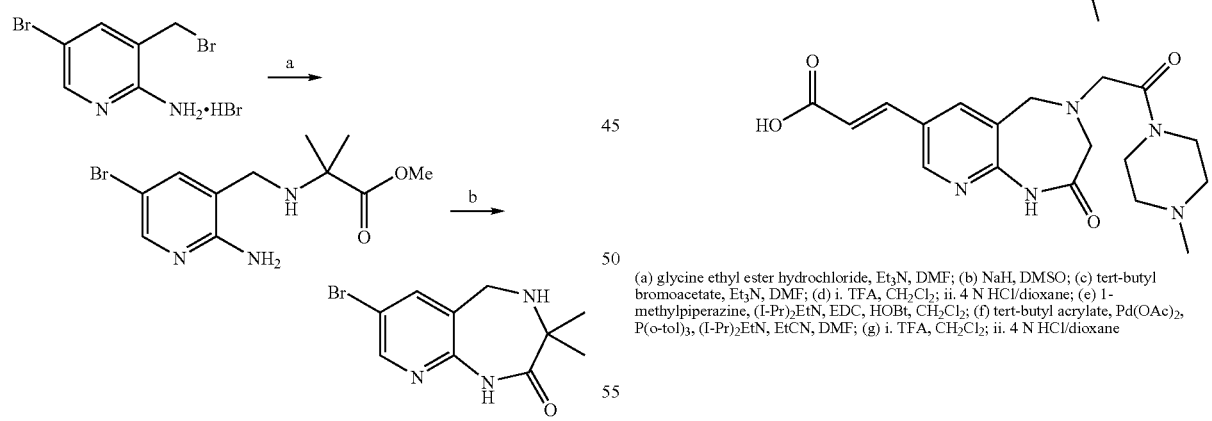

(a) glycine ethyl ester hydrochloride, Et₃N, DMF; (b) NaH, DMSO; (c) tert-butyl bromoacetate, Et₃N, DMF; (d) i. TFA, CH₂Cl₂; ii. 4 N HCl/dioxane; (e) 1-methylpiperazine, (I-Pr)₂EtN, EDC, HOBt, CH₂Cl₂; (f) tert-butyl acrylate, Pd(OAc)₂, P(o-tol)₃, (I-Pr)₂EtN, EtCN, DMF; (g) i. TFA, CH₂Cl₂; ii. 4 N HCl/dioxane Scheme XVII Scheme XVIII -continued

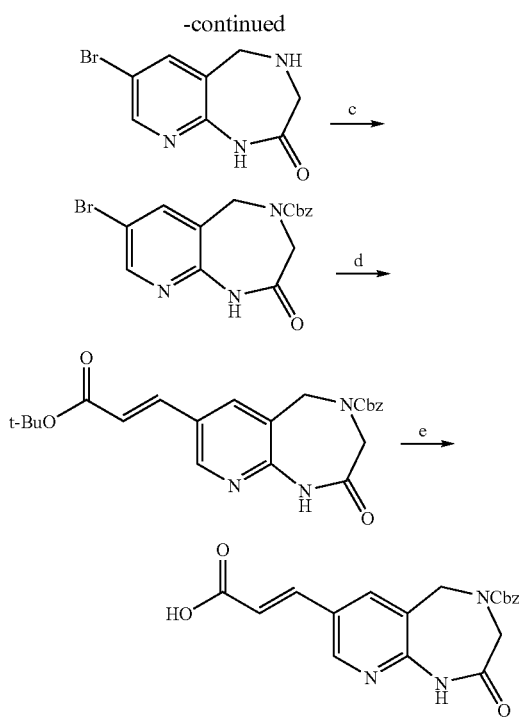

(a) glycine ethyl ester hydrochloride, Et₃N, DMF; (b) NaH, DMSO; (c) CbzCl, Et₃N, CH₂Cl₂; (d) tert-butyl acrylate, Pd(OAc)₂, P(o-tol)₃, (I-Pr)₂EtN, EtCN, DMF; (e) i. TFA, CH₂Cl₂; ii. 4 N HCl/dioxane 5-Bromo-3-bromomethyl-pyridin-2-ylamine hydrobromide, may also be reacted with cyclic secondary amines (Scheme XIX); the desired acid is obtained in the usual way.

Scheme XIX

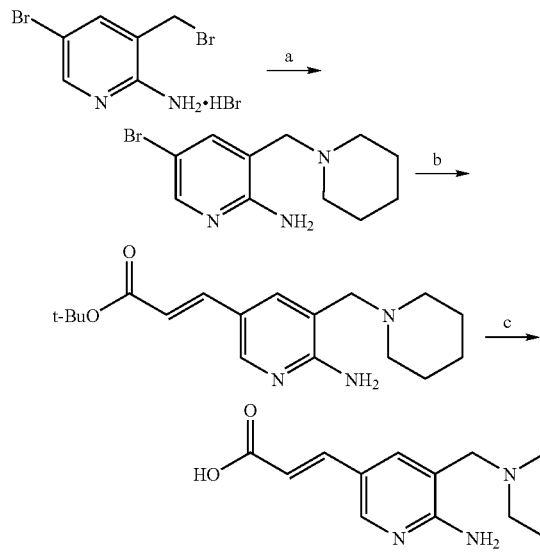

Right hand sides in which an aminopyridine ring is derivatized via an amide linkage may be realized by reaction of 2-amino-5-bromonicotinic acid hydrobromide with primary amines. Heck coupling and hyrolysis gives the desired acid (Scheme XX)

Scheme XX

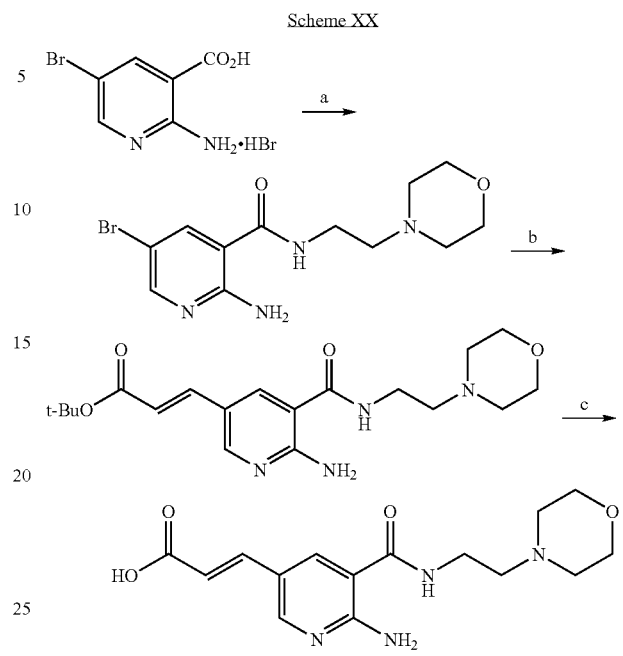

(a) 4-(2-aminoethyl)morpholine, EDC, HOBt, Et₃N, CH₂Cl₂; (b) tert-butylacrylate, DIEA, Pd(OAc)₂, P(o-tol)₃, EtCN, DMF; (c) i. TFA, CH₂Cl₂; ii. 4 N HCl/1,4-dioxane Schemes XXI-XXIV are illustrative of methods use for preparing RHS moieties wherein 3,4-dihydro-1H-pyrido[2,3-d]pyrimidin-2-ones are incorporated as RHS moieties. Schemes XXI-XXIII show preparations wherein carboxylic acids are prepared and end stage chemistry involves amide bond formation, scheme XXIV shows preparation of an aryl bromide employed in carbon-carbon bond forming end stage chemistry.

In each case an intermediate aminomethyl aminopyridine is prepared by amide bond reduction (Scheme XXI), reductive amination of aldehydes (Scheme XXII and Scheme XXIV) or, as described above in Scheme XVII, by displacement of an benzylic bromide with the desired primary amine. The latter method yields the starting material for Scheme XXIII. The subsequent step, common to all cases, is cyclization using carbonyl diimidazole to form the 3,4-dihydro-1H-pyrimidin-2-one ring. Other activated carbonyl equivalents are expected to affect a similar cyclization. In Schemes XXI-XXIII further elaboration using Heck coupling and hydrolysis gives the desired carboxylic acid RHS moieties.

Scheme XXI

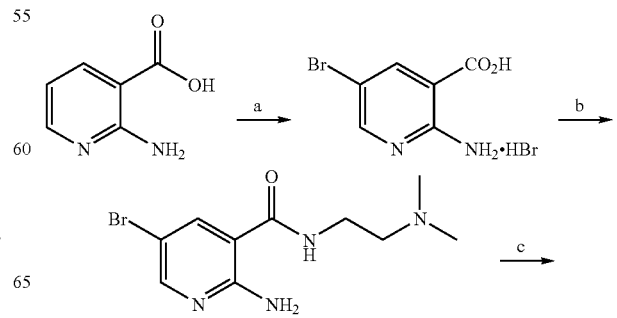

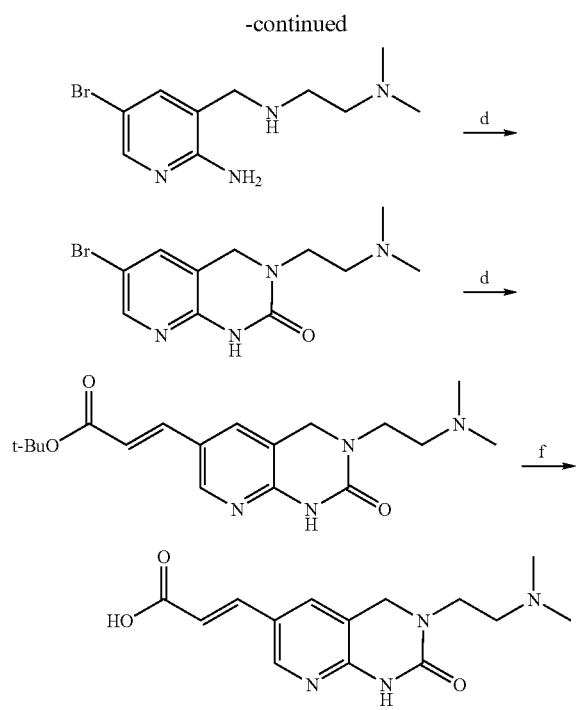

(a) Br$_2$, HOAc; (b) N, N-dimethylethylenediamine, EDC, HOBt, Et$_3$N, CH$_2$Cl$_2$; (c) i. BH$_3$; ii. HCl, MeOH; (d) CDI, 1, 4-dioxane; (e) tert-butylacrylate, DIEA, Pd(OAc)$_2$, P(o-tol)$_3$, EtCN, DMF; (f) i. TFA, CH$_2$Cl$_2$; ii. 4N HCl/dioxane Scheme XXIII

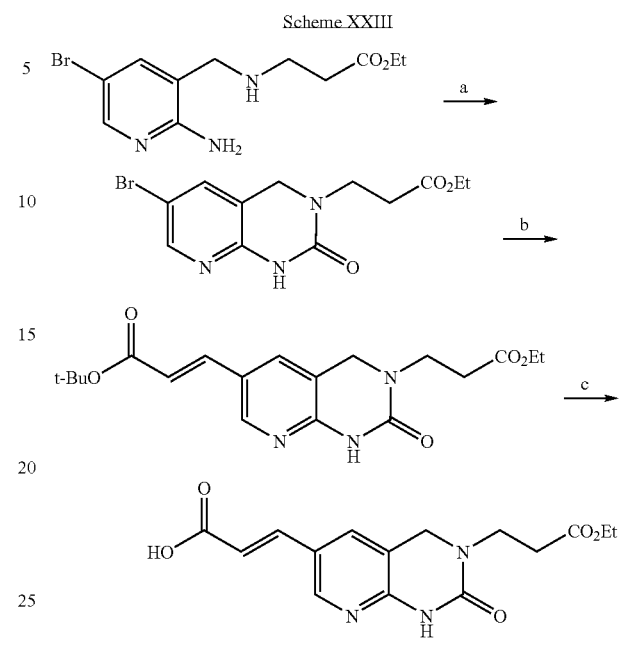

(a) CDI, 1, 4-dioxane; (b) tert-butylacrylate, DIEA, Pd(OAc)$_2$, P(o-tol)$_3$, EtCN, DMF; (c) i. TFA, CH$_2$Cl$_2$; ii. 4N HCl/dioxane.

Scheme XXII

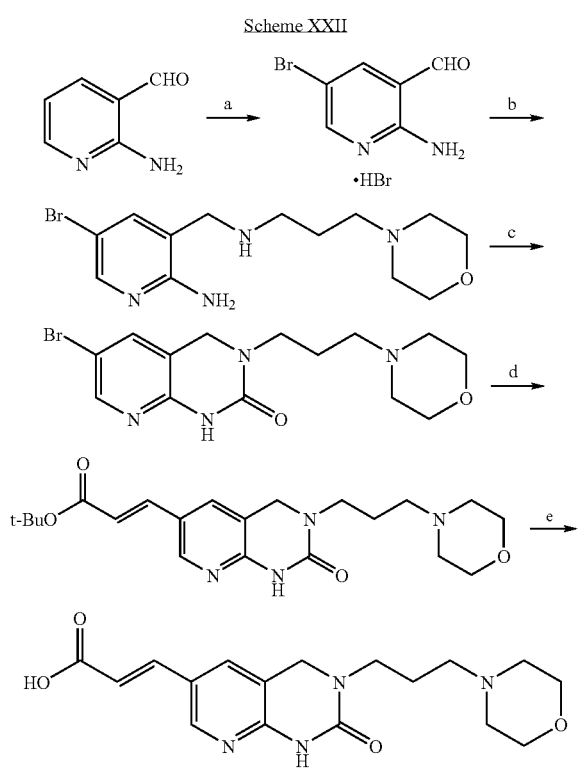

(a) Br$_2$, HOAc; (b) i. 4-(3-aminopropyl)morpholine, Et$_3$N, MeOH; ii NaBH$_4$; (c) CDI, 1, 4-dioxane; (d) tert-butylacrylate, DIEA, Pd(OAc)$_2$, P(o-tol)$_3$, EtCN, DMF; (e) i.TFA, CH$_2$Cl$_2$; ii. 4 N HCl/dioxane Scheme XXIV (a) i. Aminoacetaldehyde diethyl acetal, Et$_3$N, MgSO$_4$, MeOH; ii NaBH$_4$; (b) CDI, 1,4-dioxane Schemes XXV and XXVI are illustrative of the methods used for preparing (E)-3-(2,4-dioxo-1,2,3,4-tetrahydro-pyrido[2,3-d]pyrimidin-6-yl)-acrylic acid and (E)-3-(2-oxo-2,3-dihydro-oxazolo[4,5-b]pyridin-6-yl)-acrylic acid right hand sides respectively.

Scheme XXV

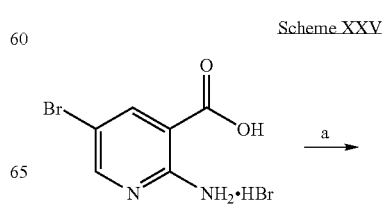

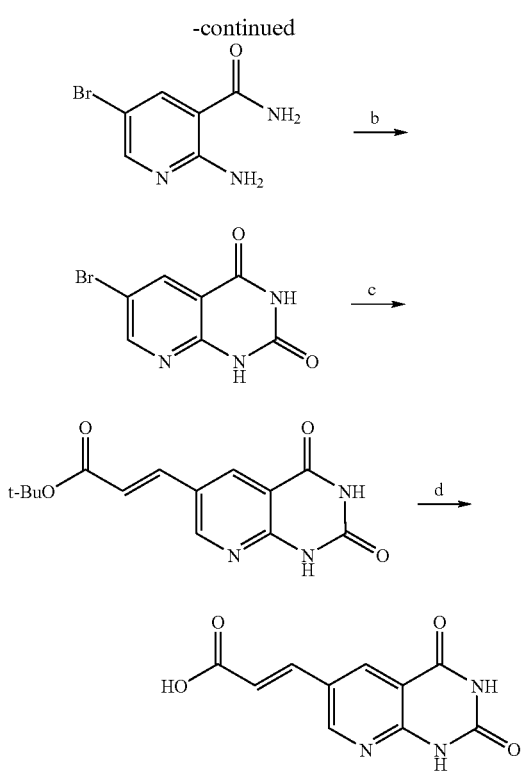

(a) (EtO)$_2$P(O)CN, NH$_4$Cl, Et$_3$N, DME; (b) oxalyl chloride, xylene; (c) Pd(OAc)$_2$, P(o-tol)$_3$, t-butyl acrylate, EtCN, DMF; (d) TFA, CH$_2$Cl$_2$ Scheme XXVI

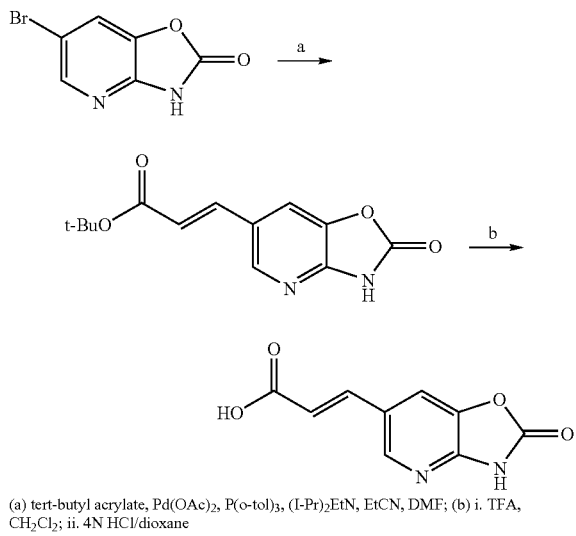

(a) tert-butyl acrylate, Pd(OAc)$_2$, P(o-tol)$_3$, (i-Pr)$_2$EtN, EtCN, DMF; (b) i. TFA, CH$_2$Cl$_2$; ii. 4N HCl/dioxane Schemes XXVII describes a specific example of a general method for assembly of compounds of formula I wherein the LHS coupling partners are amines, the RHS coupling partners are acids and the late stage chemistry involves formation of the amide linkage. There are many common methods for formation of amide linkages. In the example depicted in Scheme XXVII an acid ((E)-3-(4-methyl-2-oxo-2,3,4,5-tetrahydro-1H-pyrido[2,3-e][1,4]diazepin-7-yl)-acrylic acid) is activated by treatment with a carbodiimide (EDC) and hydroxybenzotriazole (HOBt) in the presence of a polar aprotic solvent (DMF) and reacted with a suitable amine (N-methyl-N-(1-methyl-1H-indol-3-ylmethyl)amine) in the presence of a tertiary amine base like diisopropylethylamine.

Scheme XXVII

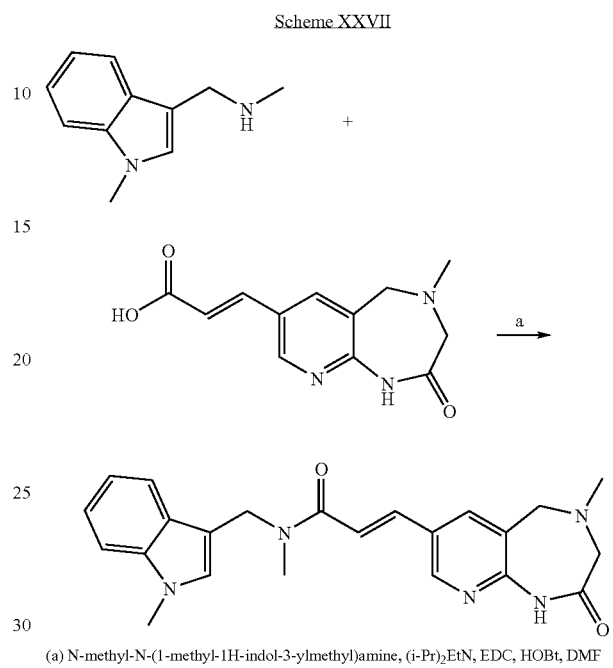

(a) N-methyl-N-(1-methyl-1H-indol-3-ylmethyl)amine, (i-Pr)$_2$EtN, EDC, HOBt, DMF An alternative method for assembling compounds of formula 1, generally referred to as Heck coupling, is depicted in Scheme XVIII. An acrylic amide such as N-methyl-N-(3-methyl-benzo[b]thiophen-2-ylmethyl)-acrylamide is treated with an aryl bromide such as 7-bromo-3,3-dimethyl-1,3,4,5-tetrahydro-pyrido[2,3-e][1,4]diazepin-2-one in the presence of a palladium catalyst (Pd(OAc)$_2$, P(o-tol)$_3$), a tertiary amine ((I-Pr)$_2$EtN) and an aprotic solvent or solvents (EtCN, DMF).

Scheme XXVIII

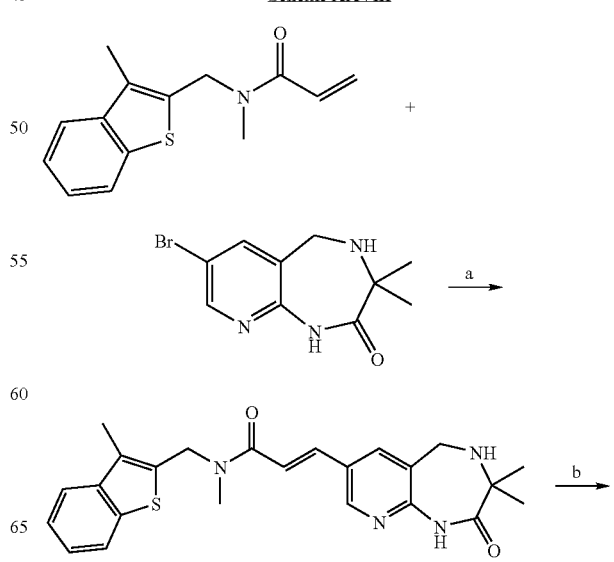

-continued

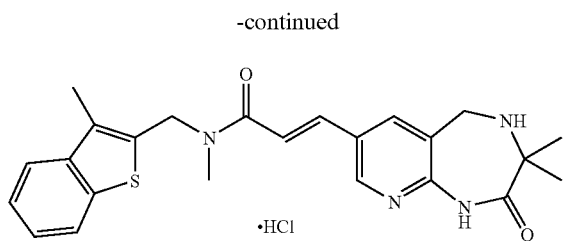

(a) α,α-dimethylglycine methyl ester hydrochloride, Et₃N, DMF; (b) NaH, DMSO; (c) N-methyl-N-(3-methyl-benzo[b]thiophen-2-ylmethyl)acrylamide, Pd(OAc)₂, P(o-tol)₃, (I-Pr)₂EtN, EtCN, DMF; (d) 1N HCl/Et₂O, CH₂Cl₂

To access certain compounds of the invention it may be necessary to perform synthetic manipulations after the right hand side and left hand side units have been assembled. Scheme XXIX for example outlines the conversion of an aminopyridine moiety to a cyclic imide followed by ring opening with ammonia.

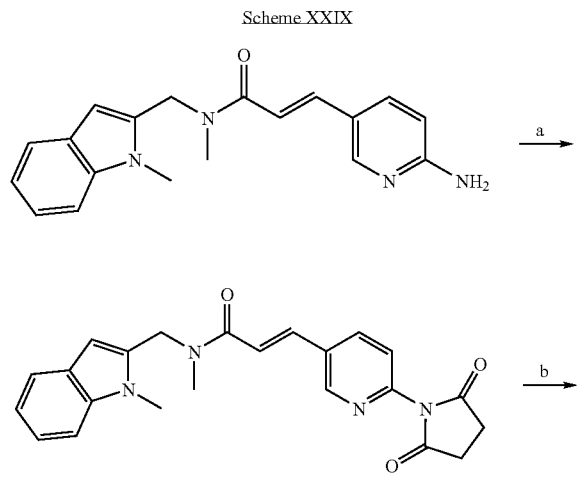

-continued (a) succinic anhydride, 1,4-dioxane; (b) NH₃, 1,4-dioxane.

Additional examples of aminopyridine derivatization are given in Schemes XXX and XXXI which describe the acylation of the amine moeity to form amide linkages.

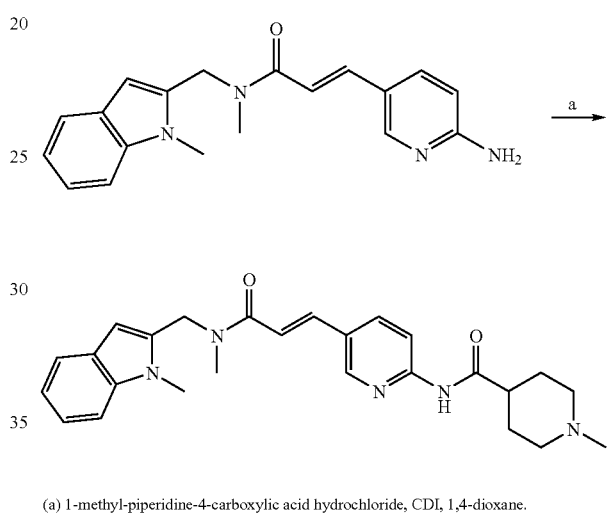

(a) 1-methyl-piperidine-4-carboxylic acid hydrochloride, CDI, 1,4-dioxane.

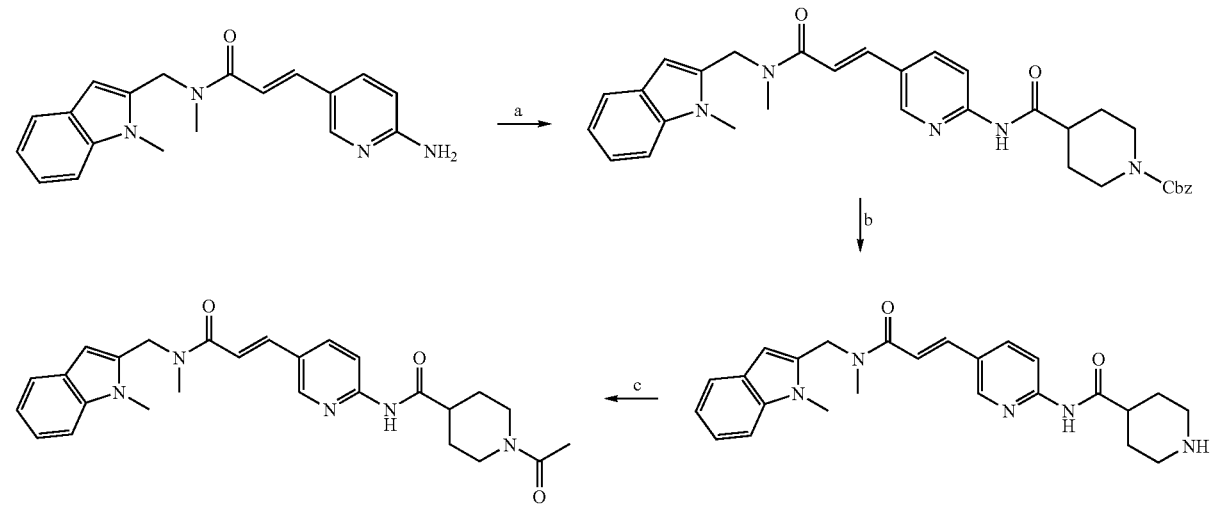

(a) [1-(carbobenzoxy)-4-piperidine]carboxylic acid, CDI, 1,4-dioxane; (b) TMSI, CH₂Cl₂; (c) Ac₂O, Et₃N, CH₂Cl₂.

In certain aspects of the invention it is desirable to have pyridodiazepinones in place on the right hand side with unsubstituted 4-position nitrogen. In these instances a suitable protecting group such as methoxybenzyl can temporarily mask the nitrogen. This protecting group may be removed in a two-step procedure by treatment with 1-chloroethyl chloroformate followed by hydrolysis of the intermediate carbamate. The hydrochloride salt may be prepared, if desired, through treatment with dilute acid (HCl) in an aprotic solvent such as ether (Scheme XXXII).

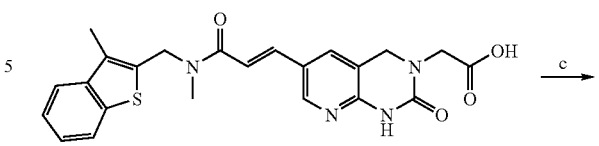
-continued

Scheme XXXII

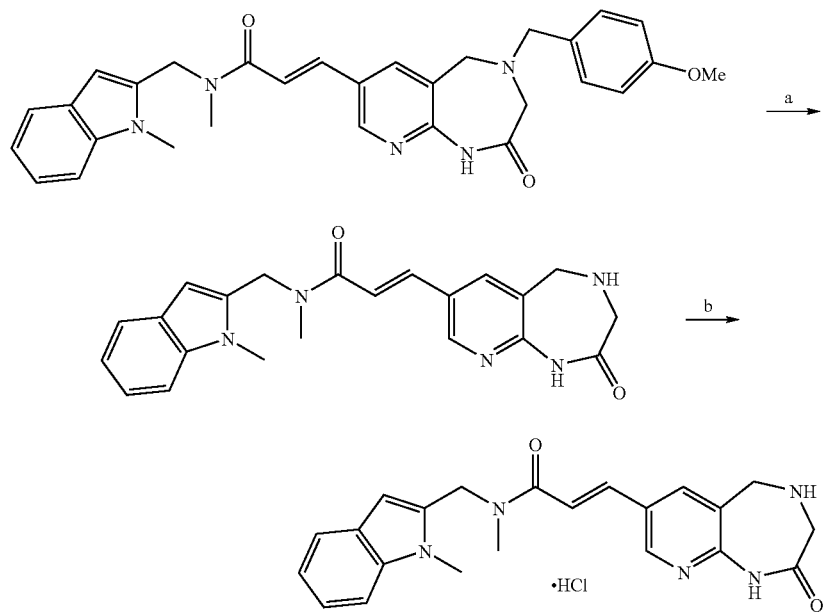

(a) i. ACE-Cl, dichloroethane; ii. MeOH; (b) 2N HCl/Et₂O, CH₂Cl₂.

Schemes XXXIII and XXXIV respectively show methods for conversion of ester and dimethylether ether groups pendent on a 3,4-dihydro-1H-pyrido[2,3-d]pyrimidin-2-one right hand side to piperidine-containing tethers. These chemical manipulations are caried out after the standard coupling reactions described above are applied (e.g. Scheme XXVII or XXVIII).

Scheme XXXIII

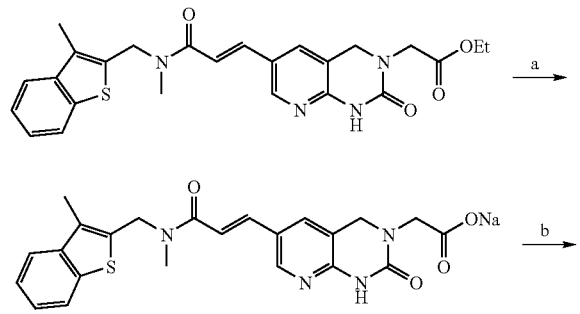

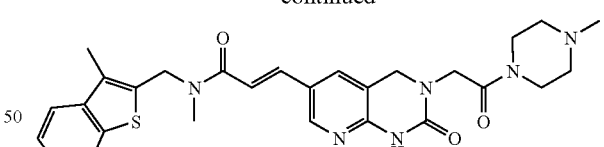
-continued (a) 1N NaOH, MeOH; b) HCl; c) i. 1-methylpiperazine, EDC, HOBt, DIEA, DMF; ii. 2N HCl/Et₂O Scheme XXXIV

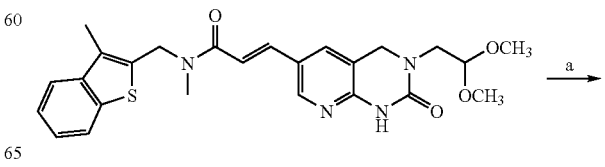

-continued

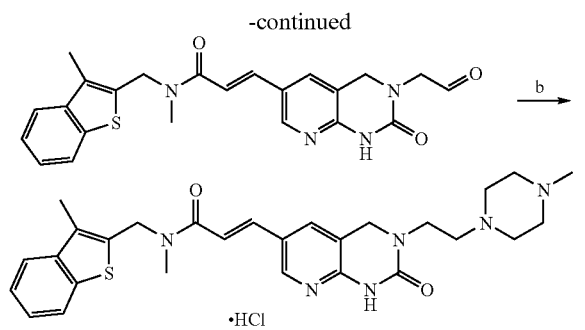

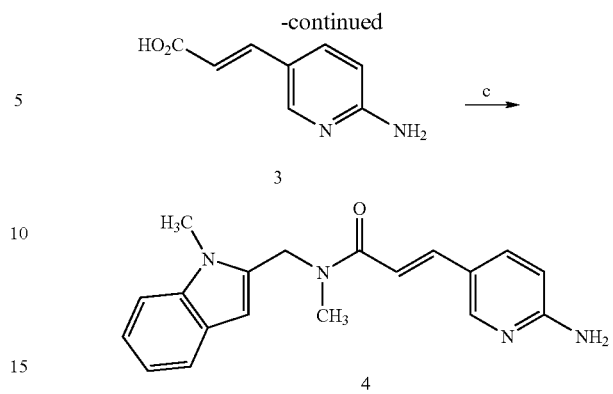

(a) TFA, H₂O, CH₂Cl₂; (b) i.1-methylpiperazine, NaBH(OAc)₃, HOAc, ClCH₂CH₂Cl; ii. 1N HCl/Et₂O, MeOH, CH₂Cl₂.

Scheme XXXV illustrates a method of compound construction falling outside the general methods described above in that a dicarboxylic acid, prepared as in Scheme XXXIVa, is reacted with two equivalents of arylmethylamine using the standard amide couping conditions.

(a) benzyl acrylate, Pd(OAc)₂, P(o-tol)₃, (i-Pr)₂NEt, propionitrile; (b) 1.0N NaOH, MeOH; (c) 1-methyl-2-(methylaminomethyl)indole, EDC, HOBt•H₂O, Et₃N, DMF.

A suitable haloaromatic derivative, for instance 2-amino-5-bromopyridine (XXXVI-1), reacts with an appropriate Scheme XXXV

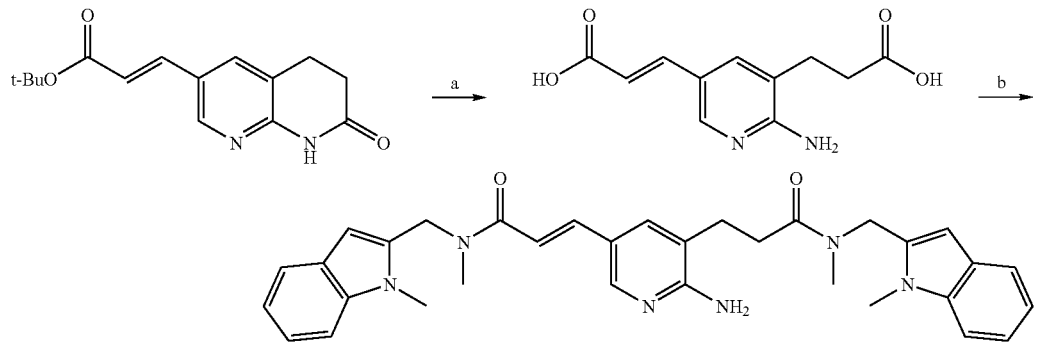

(a) i. Aq. NaOH, methanol, dioxane; (b) EDC, HOBt, DIEA, DMF, methyl-(1-methyl-1H-indol-2-ylmethyl)amine.

Synthetic Routes to Compounds of Formulas II and III

Examples of the compounds of formulas II and III in the antibacterial compositions of the present invention may be prepared by the general methods described in the Schemes hereinafter.

Scheme XXXVI

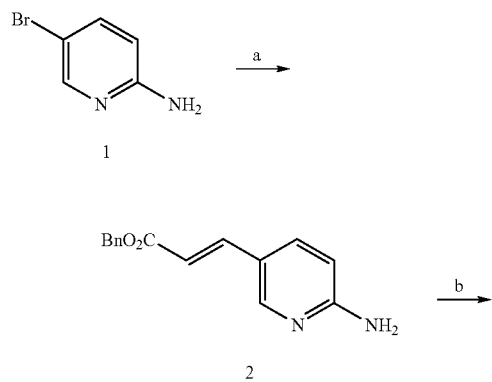

α,β-unsaturated ester, for example benzyl acrylate, in a Heck-type reaction to afford XXXVI-2. The reaction is mediated by a palladium(0) species, and generally is conducted in an inert solvent, such as CH₃CN, propionitrile, or toluene, in the presence of an appropriate acid scavenger, such as triethylamine (Et₃N) or diisopropylethylamine ((i-Pr)₂NEt). Typical sources of the palladium(0) species include palladium (II) acetate (Pd(OAc)₂) and palladium(II) chloride (PdCl₂), and oftentimes phosphine ligands, for instance triphenylphosphine (PPh₃) or tri-ortho-tolylphosphine (P(tol)₃), are included. The ethyl ester of XXXVI-2 is hydrolyzed using aqueous base, for example, LiOH in aqueous THF or NaOH in aqueous methanol or ethanol, and the intermediate carboxylate salt is acidified with a suitable acid, for instance TFA or HCl, to afford the carboxylic acid XXXVI-3. The carboxylic acid of XXXVI-3 is converted to an activated form using, for example, EDC and HOBt, or SOCl₂, and the activated form is subsequently reacted with an appropriate amine, for instance 1-methyl-2-(methylaminomethyl)indole, in a suitable solvent such as DMF, CH₂Cl₂, or CH₃CN, to afford XXXVI-4. Depending on whether acid neutralization is required, an added base, such as triethylamine (Et₃N), diisopropylethylamine ((i-Pr)₂NEt), or pyridine, may be used. Many additional methods for converting a carboxylic acid to an amide are known, and can be found in standard reference books, such as "Compendium of Organic Synthetic Methods", Vol. I-VI (published by Wiley-Interscience), or Bodansky, "The Practice of Peptide Synthesis" (published by Springer-Verlag).

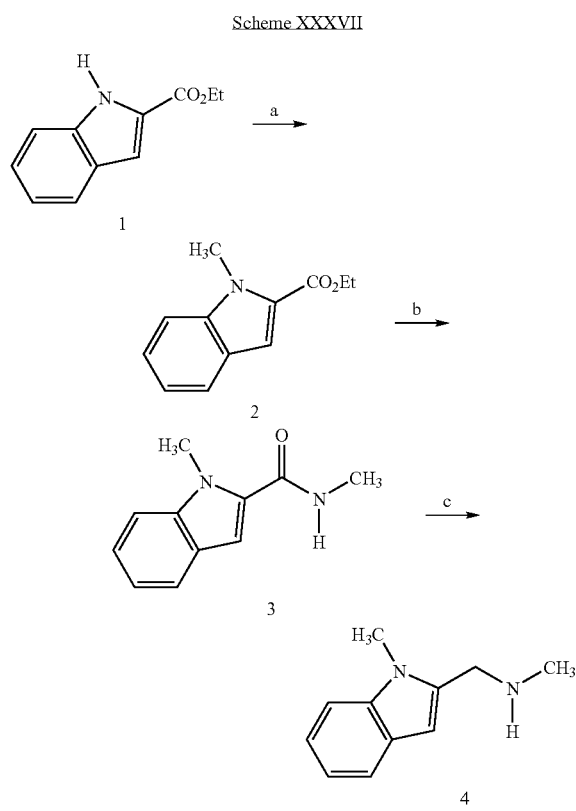

(a) NaH, MeI, DMF; (b) CH$_3$NH$_2$, H$_2$O, MeOH; (c) LiAlH$_4$, THF.

The amine coupling partners used in the present invention were prepared by established methods well-known to those of skill in the art. For example, amine XXXVII-4 is prepared by the straightforward procedure outlined in Scheme II. Commercially available ethyl indole-2-carboxylate (XXXVII-1) is deprotonated with a suitable base, generally sodium hydride (NaH), and the intermediate sodium salt is reacted with an appropriate alkylating agent, for instance methyl iodide, to afford XXXVII-2. Polar solvents such as DMF, THF, or mixtures thereof are generally preferred for this reaction. Compound XXXVII-2 can be conveniently converted to XXXVII-3 by reaction with an excess of an amine, such as methylamine, in a polar solvent, generally H$_2$O or a mixture of H$_2$O and methanol. Alternatively, the ester of XXXVII-2 can be saponified under standard conditions, typically with an alkali metal hydroxide such as LiOH, NaOH, or KOH, in an aqueous solvent, such as THF, ethanol, or methanol, and the resulting carboxylic acid can be converted to the desired amide. Typical methods for forming amides are described in Scheme I. Reduction of the amide XXXVII-3 to the amine XXXVII-4 is typically accomplished with lithium aluminum hydride (LiAlH$_4$) in refluxing THF, although many other methods can be used to reduce amides to amines. Such methods are well-known to those of skill in the art, and can be found in standard reference volumes, such as "Compendium of Organic Synthetic Methods" (published by Wiley-Interscience).

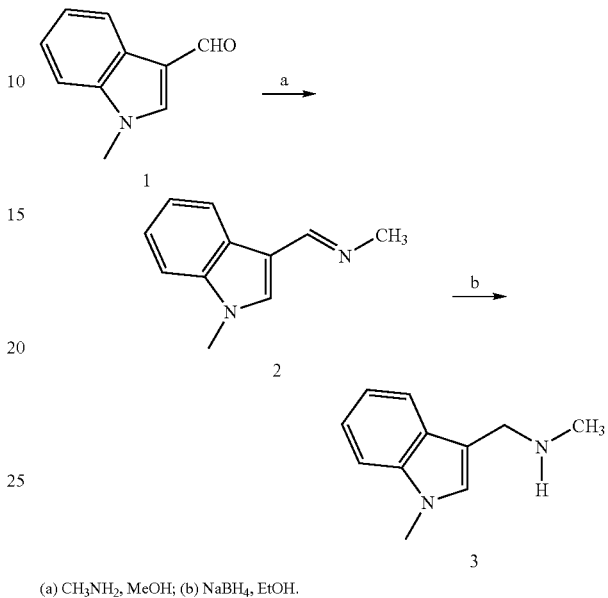

(a) CH$_3$NH$_2$, MeOH; (b) NaBH$_4$, EtOH.

The amine coupling partners used in the present invention can also be prepared by the reductive amination of an appropriate aldehyde (Scheme III). This method, which is well-known to those of skill in the art, involves the initial conversion of an aldehyde to an intermediate imine, which is subsequently reduced, oftentimes in situ, to afford the amine. For example, the commercially-available aldehyde XXXVIII-1 reacts with an appropriate amine, for instance methylamine, in a suitable solvent, typically methanol, to afford the imine XXXVIII-2. Reaction of XXXVIII-2 with a suitable reducing agent, for example sodium borohydride, sodium cyanoborohydride or sodium (triacetoxy)borohydride, gives the amine XXXVIII-3.

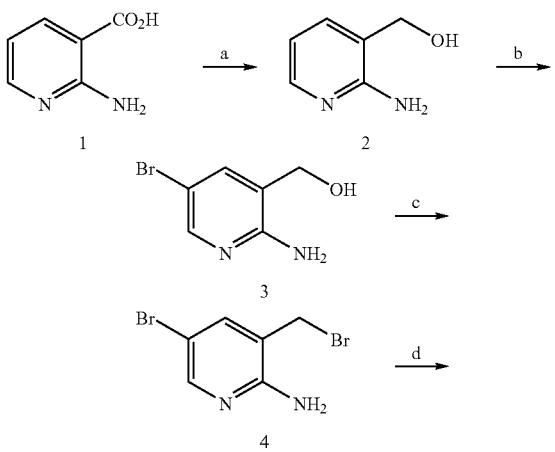

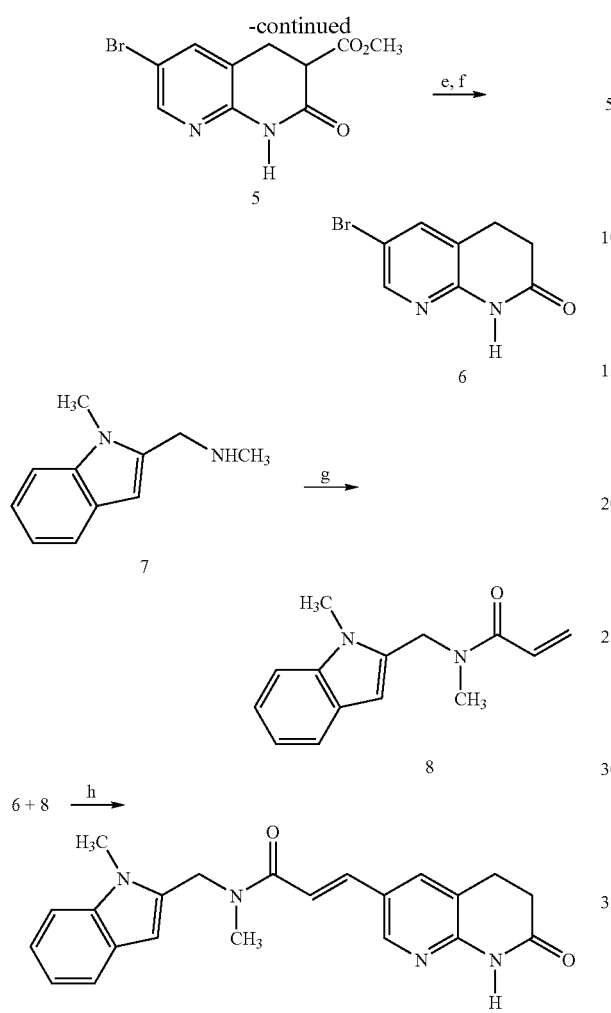

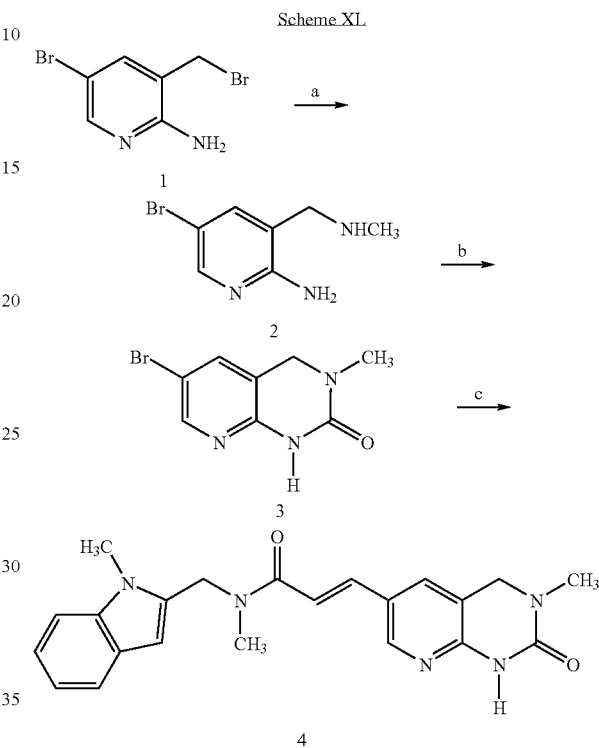

(a) CH₃NH₂, H₂O, THF; (b) (MeO)₂C=O, NaOMe, MeOH; (c) compound XXXIX-8, Pd(OAc)₂, P(o-tol)₃, (i-Pr)₂NEt, propionitrile.

(a) LiAlH₄, THF; (b) Br₂, AcOH; (c) 48% HBr; (d) (MeO₂C)₂CH₂, NaH, DMF, THF; (e) NaOH, H₂O, MeOH; (f) HCl, H₂O, MeOH; (g) acryloyl chloride, Et₃N, CH₂Cl₂; (h) Pd(OAc)₂, P(o-tol)₃, (i-Pr)₂NEt, propionitrile.

Commercially available 2-aminonicotinic acid (XXXIX-1) is reduced to alcohol XXXIX-2 under standard conditions (LiAlH₄, THF), and the aromatic ring of XXXIX-2 is brominated using, for example, bromine or N-bromosuccinimide (NBS), in a suitable solvent such as CH₂Cl₂, acetic acid (AcOH), or mixtures thereof, to afford XXXIX-3. On reaction with 48% aqueous HBr, XXXIX-3 is converted to bromide XXXIX-4, which reacts with a diester of malonic acid, for instance dimethyl malonate, under basic conditions, to afford the naphthyridone derivative XXXIX-5. Typical basic conditions include an alkali metal hydride, for instance sodium hydride, in a neutral solvent such as DMF, THF, or mixtures thereof, or an alkali metal alkoxide, such as sodium methoxide or sodium ethoxide, in an alcoholic solvent such as with methanol or ethanol. Saponification and neutralization under standard conditions affords an intermediate carboxylic acid (not shown), which is typically not isolated, but is subject to decarboxylation on gentle warming to afford the naphthyridone XXXIX-6. This compound reacts with acrylamide XXXIX-8 in a Heck-type reaction as described in Scheme I to afford XXXIX-9. Alternatively, XXXIX-6 might be converted to XXXIX-9 according to the general procedure described in Scheme I for the conversion of XXXVI-1 to XXXVI-4. The acrylamide XXXIX-8 is conveniently prepared by reaction of amine XXXIX-7 (see Scheme I) with an activated form of acrylic acid in an amide bond-forming reaction. Typical conditions for the formation of amides are described in Scheme I, and are well-known to those of skill in the art.

Benzylic bromide XL-1, prepared as described in Scheme XXXIX, reacts with an amine, for example aqueous methylamine, to afford benzylic amine XL-2. Polar solvents such as THF, DMF, DMSO, or mixture thereof, are generally preferred for this reaction. XL-2 reacts with a dialkyl carbonate, preferably dimethyl carbonate, in the presence of a suitable base, typically sodium methoxide, in an alcoholic solvent, generally methanol, to afford the cyclic urea derivative XL-3. This compound is converted to XL-4 by reaction with compound XXXIX-8 as described in Scheme XXXIX.

Scheme XLI

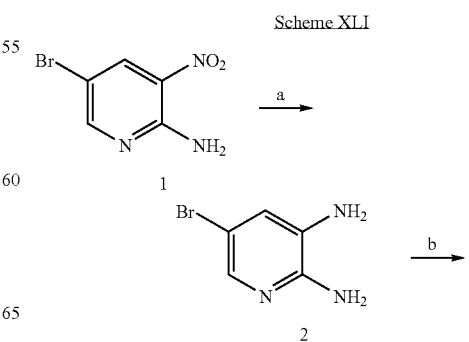

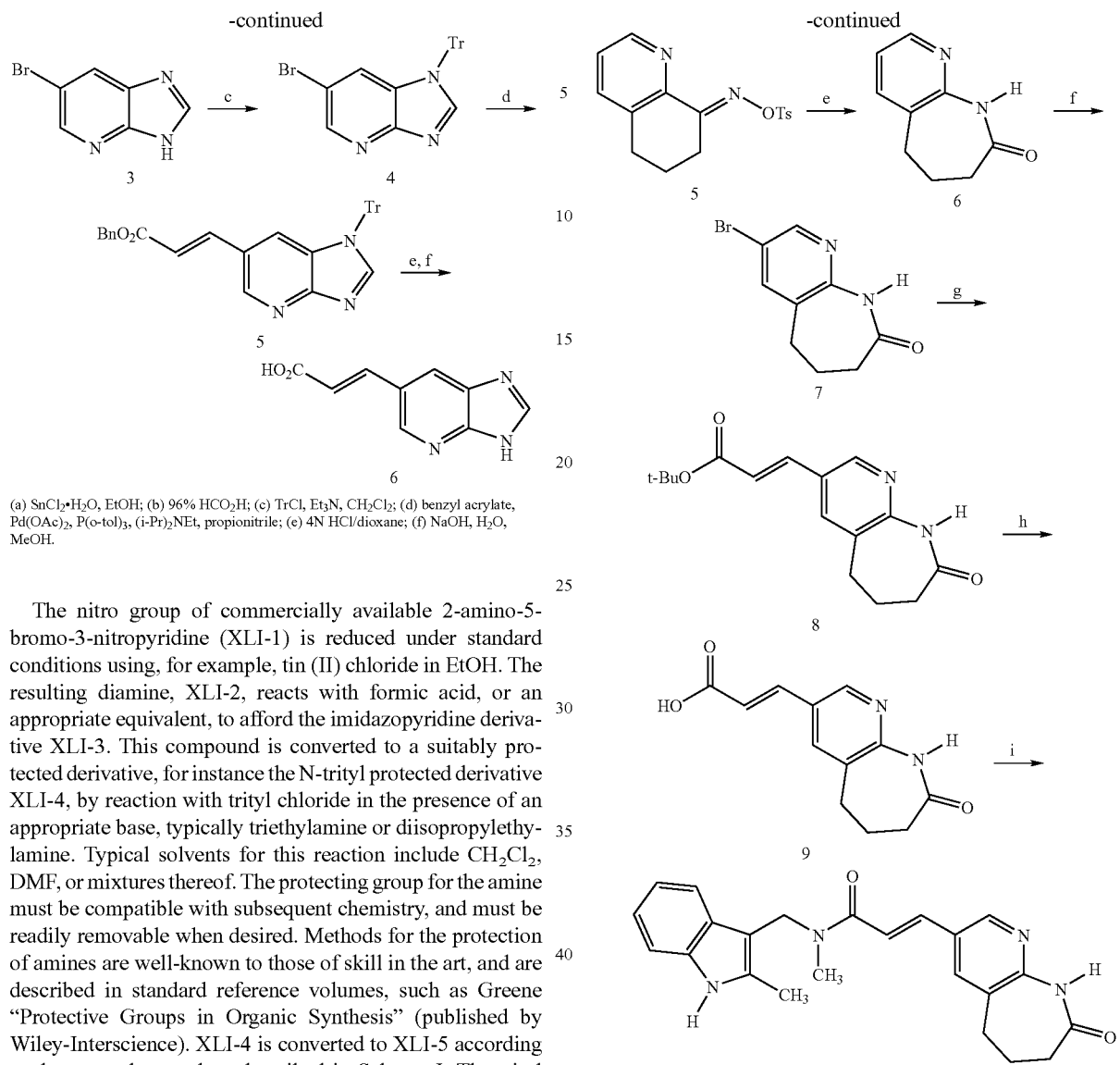

(a) SnCl₂·H₂O, EtOH; (b) 96% HCO₂H; (c) TrCl, Et₃N, CH₂Cl₂; (d) benzyl acrylate, Pd(OAc)₂, P(o-tol)₃, (i-Pr)₂NEt, propionitrile; (e) 4N HCl/dioxane; (f) NaOH, H₂O, MeOH.

The nitro group of commercially available 2-amino-5-bromo-3-nitropyridine (XLI-1) is reduced under standard conditions using, for example, tin (II) chloride in EtOH. The resulting diamine, XLI-2, reacts with formic acid, or an appropriate equivalent, to afford the imidazopyridine derivative XLI-3. This compound is converted to a suitably protected derivative, for instance the N-trityl protected derivative XLI-4, by reaction with trityl chloride in the presence of an appropriate base, typically triethylamine or diisopropylethylamine. Typical solvents for this reaction include CH₂Cl₂, DMF, or mixtures thereof. The protecting group for the amine must be compatible with subsequent chemistry, and must be readily removable when desired. Methods for the protection of amines are well-known to those of skill in the art, and are described in standard reference volumes, such as Greene "Protective Groups in Organic Synthesis" (published by Wiley-Interscience). XLI-4 is converted to XLI-5 according to the general procedure described in Scheme I. The trityl protecting group is removed under standard acidic conditions (see Greene above), and the ester is saponified as in Scheme I to afford XLI-6.

Scheme XLII

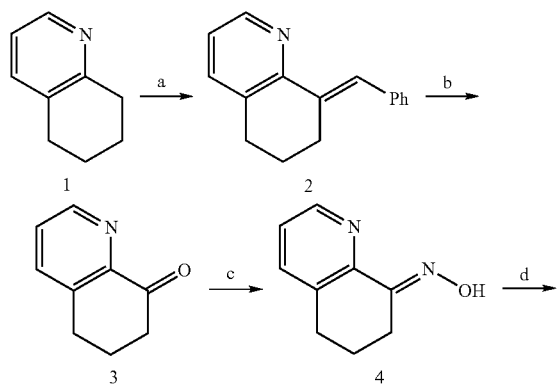

(a) PhCHO, Ac₂O; (b) O₃, CH₂Cl₂, then DMS; (c) H₂NOH·HCl, (i-Pr)₂NEt, EtOH; (d) p-TsCl, KOH, acetone, H₂O; (e) KOAc, EtOH, H₂O; (f) Br₂, CH₂Cl₂; (g) tert-butyl acrylate, Pd(OAc)₂, P(o-tol)₃, (i-Pr)₂NEt, propionitrile; (h) 4.0 N HCl/dioxane; (i) 2-methyl-3-(methylaminomethyl)indole, EDC, HOBt·H₂O, (i-Pr)₂NEt, DMF.

Commercially-available tetrahydroquinoline (XLII-1) is condensed with an appropriate aldehyde, typically benzaldehyde (PhCHO), under standard conditions to afford the olefinic derivative XLII-2. Oxidative cleavage of the exocyclic olefin affords ketone XLII-3. Generally, ozonolysis in a neutral solvent, such as methylene chloride (CH₂Cl₂), methanol (MeOH), or mixtures thereof, followed by in situ reduction of the intermediate ozonide with an appropriate reducing agent, usually dimethylsulfide, is the method of choice for this transformation. Compound XLII-3 is converted to the 7-membered lactam derivative XLII-6 as described by Jössang-Yanagida and Gansser. This procedure involves conversion of the ketone of XLII-3 to the corresponding oxime XLII-4, which is subsequently converted to the O-tosyl derivative XLII-5. A Beckmann-type rearrangement of XLII-5 affords the lactam XLII-6. Bromination of XLII-6 with a suitable brominating agent, such as bromine (Br₂) or N-bromosuccinimide (NBS), affords the bromo derivative XLII-7. Typical solvents for a bromination reaction include CH₂Cl₂, CCl₄, MeOH, AcOH, or mixtures thereof. Bromide VII-7 reacts with an appropriate α,β-unsaturated ester, for example tert-butyl acrylate, in a Heck-type reaction as described in Scheme I to afford XLII-8. The tert-butyl ester of XLII-8 is cleaved to the corresponding carboxylic acid XLII-9 under standard acidic conditions. Typical conditions for this transformation are described in standard reference volumes, such as Greene "Protective Groups in Organic Synthesis" (published by Wiley-Interscience). XLII-9 is converted to XLII-10 by the general method described in Scheme I.

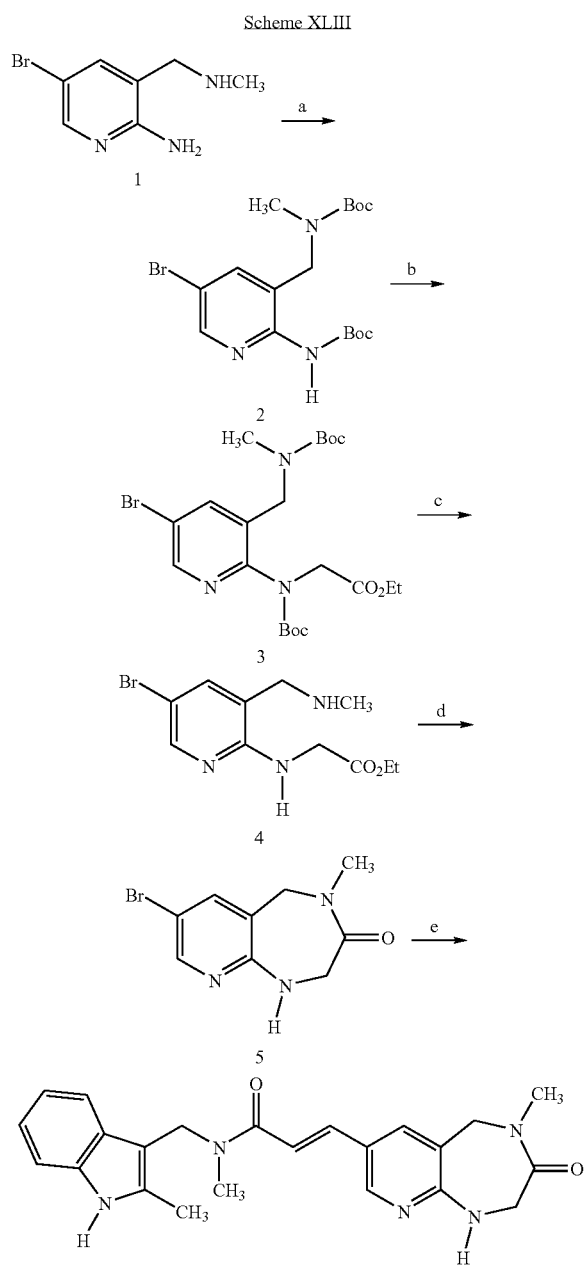

(a) (Boc)₂O, THF; (b) NaH, ethyl bromoacetate, THF; (c) TFA, CH₂Cl₂; (d) Et₃N, toluene; (e) N-methyl-N-(2-methyl-1H-indol-3-ylmethyl)acrylamide, Pd(OAc)₂, P(o-tol)₃, (i-Pr)₂NEt, propionitrile.

Compound XLIII-1, prepared as described in Scheme XL, reacts with two equivalents of an appropriate acylating agent, preferably di-tert-butyl dicarbonate, to afford XLIII-2. As discussed in Scheme XLI, the protecting group for the amines must be compatible with subsequent chemistry, and must be readily removable when desired. XLIII-2 is deprotonated with a suitable base, generally sodium hydride (NaH), and the intermediate sodium salt is reacted with an appropriate alkylating agent, for instance ethyl bromoacetate, to afford XLIII-3. Polar solvents such as DMF, THF, or mixtures thereof are generally preferred for this reaction. The Boc protecting groups are removed under standard acidic conditions (see Greene above) to afford XLIII-4, which undergoes cyclization to compound XLIII-5 on exposure to a suitable base, typically triethylamine (Et₃N) or diisopropylethylamine ((i-Pr)₂NEt). An inert solvent, such as toluene, is preferred. XLIII-5 is converted to XLIII-6 by the general method described in Scheme XXXIX.

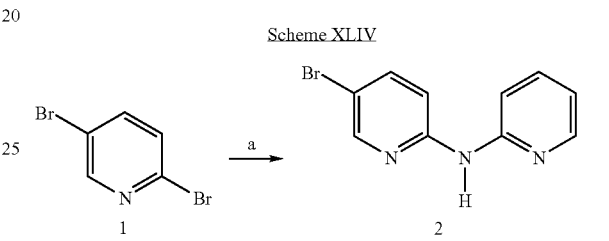

(a) 2-aminopyridine, sodium tert-butoxide, tris(dibenzylideneacetone)dipalladium(0), 1,3-bis(diphenylphosphino)propane, toluene.

Commercially available 2,5-dibromopyridine (XLIV-1) reacts with 2-aminopyridine in the presence of a suitable base, typically sodium tert-butoxide, to afford the dipyridylamine derivative XLIV-2. The reaction is mediated by a suitable palladium (0) catalyst, such as tris(dibenzylideneacetone)dipalladium(0), in the presence of an appropriate ligand, for example 1,3-bis(diphenylphosphino)propane. A neutral solvent such as toluene is preferred.

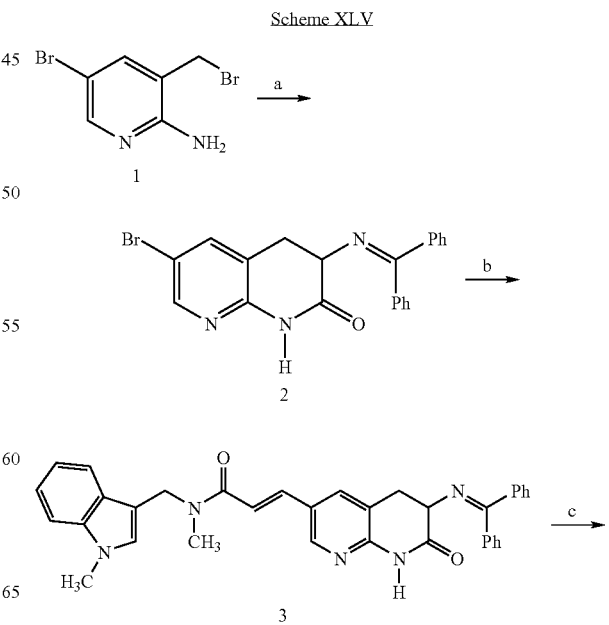

-continued

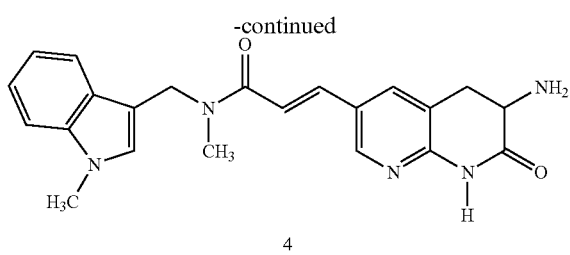

(a) N-(Diphenylmethylene)glycine ethyl ester, NaH, DMF; (b) N-methyl-N-(1-methyl-1H-indol-3-ylmethyl)acrylamide, Pd(OAc)$_2$, P(o-tol)$_3$, (i-Pr)$_2$NEt, propionitrile; (c) HCl, dioxane, H$_2$O.

Benzylic bromide XLV-1, prepared as described in Scheme XXXIX, reacts with an appropriate a-aminoester equivalent, for example N-(diphenylmethylene)glycine ethyl ester, under basic conditions, to provide XLV-2. A polar, aprotic solvent, such as DMF, THF, DME, or mixtures thereof, is generally preferred, and sodium hydride is typically the base of choice, although LDA or LiN(TMS)$_2$ might also be used. Alternatively, the reaction might be conducted in an alcoholic solvent, such as methanol or ethanol, with an alkali metal alkoxide, for example sodium methoxide or sodium ethoxide, as the base. The diphenylmethylene group is conveniently removed under acidic conditions, such as HCl in aqueous dioxane. Other conditions for the removal of a diphenylmethylene group are known to those of skill in the art, and can be found in the chemical literature or in standard reference volumes, such as Greene (see above).

It will be recognized by one skilled in the art that other methods of LHS and RHS synthesis can be employed in the preparation of said intermediates. Likewise other methods of amide and/or carbon-carbon bond formation may be used to assemble the compounds of the invention. It is also apparent that combinations of LHS and RHS other than those described above can be envisioned to prepare compounds falling within the scope of the invention as represented by formulas I-III. These possibilities are further detailed in the preparations and examples section to follow.

Acid addition salts of the compounds of formulas I-III can be prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts may be prepared by treating the parent compound with an excess of an alkaline reagent, such as a hydroxide, carbonate or alkoxide, containing the appropriate cation; or with an appropriate organic amine. Cations such as Li$^+$, Na$^+$, K$^+$, Ca$^{++}$, Mg$^{++}$ and NH$_4^+$ are some non-limiting examples of cations present in pharmaceutically acceptable salts.

Anti-Infective Agents

A second component in the compositions of the present invention may be an anti-infective agent, other than, for example, a Fab I inhibitor, such as other than a Fab I inhibitor disclosed herein. Such anti-infective agents include antibiotic or ant-bacterial agents, antivirals, anitfungals, enzyme inhibitors, antiparastic agents, and/or antiprotozoal agents.

Anti-fungal agents include, but are not limited to, terbinafine hydrochloride, nystatin, amphotericin B, griseofulvin, ketoconazole, miconazole nitrate, flucytosine, fluconazole, itraconazole, clotrimazole, benzoic acid, salicylic acid, and selenium sulfide.

Anti-viral agents include, but are not limited to, amantadine hydrochloride, rimantadin, acyclovir, famciclovir, foscarnet, ganciclovir sodium, idoxuridine, ribavirin, sorivudine, trifluridine, valacyclovir, vidarabin, didanosine, stavudine, zalcitabine, zidovudine, interferon alpha, and edoxudine.

Anti-parasitic agents include, but are not limited to, pirethrins/piperonyl butoxide, permethrin, iodoquinol, metronidazole, diethylcarbamazine citrate, piperazine, pyrantel pamoate, mebendazole, thiabendazole, praziquantel, albendazole, proguanil, quinidine gluconate injection, quinine sulfate, chloroquine phosphate, mefloquine hydrochloride, primaquine phosphate, atovaquone, co-trimoxazole (sulfamethoxazole/trimethoprim), and pentamidine isethionate.

Other non-limiting examples of bioactive agents that may be used in the compositions of the present invention include antibiotics suchs as cephalosporins, quinolones and fluoroquinolones, penicillins, penicillins and beta lactamase inhibitors, carbepenems, monobactams, macrolides and lincosamines, glycopeptides, rifampin, oxazolidonones, tetracyclines, aminoglycosides, streptogramins, sulfonamides, peptide antibiotics and derivatives such as glycopeptides and lipopeptides, oxasolidinones, streptogramins, trimethoprim-sulfomethoxazole, quinupristin-dalfopristin, lincosamides, aminoglycosides, tetracyclins, glycylcyclines, and others. Each family comprises many members.

Cephalosporins

Cephalosporins are a class of β-lactam antibiotics derived from 7-aminocephalosporanic acid (7-ACA). β-lactam antibiotics disrupt cell wall synthesis by interfering with the final crosslinking (transpeptidation) step of the peptidoglycan layer. Cephalosporins have the same mechanism of action as penicillins, but have a broader antibacterial spectrum and are resistant to β-lactamase. Cephalosporins may be commonly used when the sensitivity of the bacterium is not known or when there is a known allergy to penicillins.

Cephalosporins are further categorized by generation. Non-limiting examples of cephalosporins by generation include the following. Examples of generation I cephalosporins include cefadroxil, cefazolin, cephalexin, cephalothin, cephapirin, and cephradine. Examples of generation II cephalosporins include cefaclor, cefamandol, cefonicid, cefotetan, cefoxitin, cefprozil, ceftmetazole, cefuroxime, cefuroxime axetil, and loracarbef. Examples of generation III cephalosporins include cefdinir, ceftibuten, cefditoren, cefetamet, cefotiam HCl, cefpodoxime, cefprozil, cefuroxime (axetil), cefuroxime (sodium), cefoperazone, cefixime, cefotaxime, cefpodoxime proxetil, ceftazidime, ceftizoxime, ceftriaxone, and moxalactam. Examples of generation IV cephalosporins include cefepime and ceftobiprole.

Quinolones and Fluoroquinolones

Quinolones and fluoroquinolones are a class of broad-spectrum antibiotics that are derived from nalidixic acid. Quinolones and fluoroquinolones act bacteriocidically by inhibiting DNA replication, synthesis, and transcription by inhibiting bacterial DNA gyrases and topoisomerases.

Non-limiting examples of quinolones and fluoroquinolones include amifloxacin, cinoxacin, ciprofloxacin, enrofloxacin, enoxacin, fleroxacin, flumequine, garenoxacin, gatifloxacin, gemifloxacin, grepafloxacin, levofloxacin, lomefloxacin, moxifloxacin, nalidixic acid, norfloxacin, oxolinic acid, ofloxacin, olamufloxacin, perfloxacin, pipemidic, rosoxacin, rufloxacin, sparfloxacin, trovafloxacin, and tosufloxacin.

Penicillins

Penicillins are a class of β-lactam antibiotics derived from 6-aminopenicillanic acid (6-APA). Similar to cephalosporins, penicillins interfere with the synthesis of the bacterial cell wall by inhibiting a final crosslinking step in the peptidoglycan layer. Penicillins has a molecular formula R—$C_9H_{11}N_2O_4S$, where R is a variable side chain.

Non-limiting examples of penicillins include amoxicillin, ampicillin, bacampicillin, carbenicillin, carbenicillin indanyl, mezlocillin, piperacillin, and ticarcillin.

Penicillins and Beta Lactamase Inhibitors

Bacteria may become resistant to penicillins because some penicillins are sensitive to β-lactamase. β-lactamase is a bacterial enzyme that can hydrolyze the β-lactam bond of β-lactam antibiotics. Beta-lactamase inhibitors, including but not limited to clavulanic acid and sulbactam, irreversibly bind to and inhibit bacterial β-lactamases. Inhibition of β-lactamases prevents the hydrolysis of the β-lactam bond present in β-lactam antibiotics, such that the β-lactam antibiotic may enter the cell and disrupt bacterial cell wall synthesis.

Non-limiting examples of penicillins and beta-lactamase inhibitors include amoxicillin-clavulanic acid, ampicillin-sulbactam, benzylpenicillin, cloxacillin, dicloxacillin, methicillin, oxacillin, penicillin G (benzathine, potassium, procaine), penicillin V, piperacillin+tazobactam, ticarcillin+clavulanic acid, and nafcillin.

Carbepenems

Carbapenems are broad spectrum β-lactam antibiotics that may be used to treat both gram-positive and gram-negative bacteria.

Non-limiting examples of carbepenems include doripenem, imipenem-cilastatin, and meropenem.

Monobactams

Monobactams are monocyclic β-lactam antibiotics. Monobactams are narrow-spectrum antibiotics that may be used to treat gram-negative bacteria (e.g., *Psuedomonas*, Enterobacteriaceae).

A non-limiting example of a monobactam includes aztreonam.

Macrolides, Ketolides, and Lincosamines

Macrolides are a class of antibiotics that contain a macrolide ring, which is a large lactone ring comprising one or more deoxy sugars such as cladinose and desoamine. The lactone ring may be either 14, 15, or 16-membered. Macrolides are broad spectrum antibiotics and are commonly used to treat respiratory and soft tissue infections. Macrolides may also be used to treat patients infected with a gram-positive organism who are allergic to penicillins. Macrolides bind to 50S ribosomal subunit and disrupt protein synthesis.

Ketolides are a class of macrolide antibiotics that are derived from erythromycin. Ketolides are formed by substituting the cladinose sugar of erythromycin with a keto-group and attaching a cyclic carbamate group to the lactone ring. Ketolides inhibit protein synthesis by binding to ribosomes and are broader spectrum antibiotics compared to macrolides.

Lincosamines have similar mechanism of action to macrolides and inhibit protein synthesis by binding to the 50S subunit of the ribosome.

Non-limiting examples of macrolides and lincosamines include azithromycin, clarithromycin, clindamycin, dirithromycin, erythromycin, lincomycin, telithromycin, and troleandomycin.

Glycopeptides

Glycopeptides are a class of antibiotics that consist of glycosylated cyclic or polycyclic nonribosomal peptide. Glycopeptides inhibit the biosynthesis of the bacterial cell wall by binding to peptidoglycan precursors.

Non-limiting examples of glycopeptides include dalbavancin, oritavancin, telavancin, teicoplanin and vancomycin.

Rifamycins

Rifamycins are a class of antibiotics that bind to DNA-dependent RNA polymerase and inhibit the initiation of RNA synthesis.

Non-limiting examples of rifamycins include rifabutin, rifampin, and rifapentine.

Oxazolidonones

Oxazolidinones are a class of antibiotics that inhibits protein synthesis by binding to the 50S subunit of the ribosome to prevent translation.

A non-limiting example of oxazolidinones includes linezolid.

Tetracyclines

Tetracyclines are a class of antibiotics that inhibit cell growth by inhibiting protein synthesis, specifically translation (i.e., blocking the binding of tRNA to the 30S ribosomal subunit). Tetracyclines are broad spectrum antibiotics, but because the interaction of tetracyclines with the ribosome is weak and reversible, tetracycline is a bacteriostatic antibiotic. Resistance to tetracyclines results from one of two mechanisms: efflux or ribosomal protection. Efflux occurs when a resistance gene encodes a membrane protein that can actively pump tetracycline out of the cell. Ribosomal protection occurs when a resistance gene encodes a protein that binds to the ribosome and prevents tetracycline from binding to the ribosome.

Non-limiting examples of tetracyclines include demeclocycline, doxycycline, doxycycline hyclate, methacycline, minocycline, oxytetracycline, tetracycline, and chlortetracycline.

Aminoglycosides

Aminoglycosides are class of antibiotics containing an aminocyclitol ring and one or more amino sugars. Aminoglycosides inhibit bacterial protein synthesis by irreversibly binding to the ribosomes (e.g., the interface between the 30S and 50S subunit and additional sites on the individual subunits). Depending on where the aminoglycoside binds the ribosome, the antibiotic may prevent polysome formation or misreading of the mRNA. Aminoglycosides may be used to treat many gram-negative and gram-positive bacteria. Resistance to aminoglycosides may occur if there is a mutation in a ribosome binding site, decreased uptake of the antibiotic into the bacterial cell, or enzymatic modification (e.g., phosphorylation or acetylation) of the antibiotic.

Non-limiting examples of aminoglycosides include amikacin, amikacin sulfate, gentamicin, gentamicin sulfate, kanamycin, metilmicin, neomycin, netilmicin, streptomycin, tobramycin, and paromomycin.

Streptogramins

Streptogramins are a class of natural cyclic peptide antibiotics that inhibit bacterial growth. Streptogramins consist of at least two structurally unrelated molecules: group A streptogramins (macrolactones) and group B streptogramins (cycli hexadepsipeptides). In some embodiments, Groups A and B act synergistically to inhibit protein synthesis.

A non-limiting example of streptogramins includes quinopristin+dalfopristin.

Sulfonamides

Sulfonamides, which are also known as sulfa drugs, are a class of antibiotics derived from sulfonic acid. Sulfonamides are competitive inhibitors of para-aminobenzoic acid (PABA), a substrate of the enzyme dihyropteroate synthetase, and thus, inhibit bacterial synthesis of folic acid. Sulfonamides are bacteriostatic against a wide-spectrum of gram-positive and gram-negative bacteria.

Non-limiting examples of sulfonamides include mafenide, silver sulfadiazine, sulfacetamide, sulfadiazine, sulfamethoxazole, sulfasalazine, sulfanilamide, sulfisoxazole, trimethoprim-sulfamethoxazole, and sulfamethizole.

Others

Non-limiting examples of other antibiotic agents include bacitracin, chloramphenicol, colistemetate, fosfomycin, isoniazid, methenamine, metronidazol, mupirocin, nitrofurantoin, nitrofurazone, novobiocin, polymyxin B, spectinomycin, trimethoprim, colistin, cycloserine, capreomycin, pyrazinamide, para-aminosalicyclic acid, erythromycin ethylsuccinate+sulfisoxazole, and tigecycline.

The anti-infective agents described herein may also be used to inhibit aspartate semidlehyde dehydrogenase, deoxyuridine 5'-triphosphate nucleotidohydrolase, farnesyl disphosphate synthase, guanylate kinase, NH3-dependent NAD synthetase, hydroxymethyglutaryl-CoA reductase, peptide deformylase, peptidyl-tRNA hydrolase, phosphodiesterase, putative methylase yhhF, ribose-phosphate 3-epimerase, ribose-phosphate pryo-phosphokinase, thymidylate kinase, and xanthine phosphoribosyl transferase.

Toxicology of Compounds

Acute toxicity can be assessed using increasing doses in mice and rodents. Exploratory acute toxicity in mice and/or rats after single dose may be undertaken to begin estimation of the therapeutic window of inhibitors and to identify the potential target organis of toxicity. These studies may be combined with routine PK measurements to assure proper dosages were achieved. Generally 3-4 doses will be chosen that are estimated to span a range having no effect through to higher doses that cause major toxic, but non-lethal, effects.

Resistance Frequencies and Mechanisms of Compounds

In vitro resistance frequencies in bacteria of interest can be estimated for compounds of formula I. Experiments can determine whether resistant isolates arise when challenged to grow on solid media at 1×, 2× and 4×MIC concentrations. For example with respect to S. aureus or E. coli, the experiments may use several recent clinical isolates of methicillin-sensitive and methicillin-resistant S. aureus and a laboratory strain of E. coli with acrA efflux pump defect. In addition, experiments may use several characterized triclosan-resistant S. aureus strains. The MICs of resistant strains isolated in this manner can then be determined. Subsequent experiments can determine whether resistant strains arise after serial passage of the strains in 0.5×MIC concentrations of each lead compound.

Mechanism of resistance may be determined in S. aureus laboratory strain, RN450 and in an E. coli laboratory strain carrying an acrA efflux pump mutation. Both high dose challenge (4×MIC) and sub-MIC serial passage may be used to obtain spontaneously arising resistant isolates. If no isolates are obtained with reasonable frequencies, chemical and physical mutagenesis methods can be used to obtain resistant isolates. The fabI gene from the chromosome of resistant isolates may be PCR amplified, then may be sequenced to determine whether changes in the FabI protein caused resistance. Triplicate PCR amplifications and sequences may be performed to assure that the observed sequence changes are correct, and did not arise from PCR errors during amplification. Strains carrying resistance mutations outside of the gene of interest may be documented and saved, characterized for their effects on susceptibilities of other antibiotics as evidence of possible efflux-mediated resistance mechanisms, characterized for their ability to alter compounds characterized for their effects on the expression of the specific mRNA and FabI protein.

Cloning of S. aureus FabI

The fabI gene was cloned from the chromosomal DNA of S. aureus strain WCUH29 using the polymerase chain reaction. Amplification was performed using Taq DNA polymerase (BRL) and the following primers: 5'-CGCCTC-GAGATGTTAAATCTTGAAAACAAAACATATGTC-3' (SEQ ID NO: 1) and 5'-CGCGGATCCAATCAAGTCAG-GTTGAAATATCCA-3' (SEQ ID NO: 2) (XhoI and BamHI sites underlined). The resulting fragment was then digested with XhoI and BamHI and ligated into XhoI- and BamHI-digested expression vector pET-16b (Novagen), producing pET-His$_{10}$-fabI (His 10 disclosed as SEQ ID NO: 7). The gene sequence of fabI was confirmed by automated cycle sequencing using an Applied Biosystems model 377 machine. The untagged version of pET-fabI was constructed by digesting pET-His$_{10}$-fabI (His 10 disclosed as SEQ ID NO: 7) with NcoI and NdeI to remove a 97 by fragment encoding the His 10 tag (SEQ ID NO: 7), the factor Xa cleavage site and the first 8 amino acids of FabI, and replacing it with a linker encoding the first 8 amino acids of FabI plus a glycine residue between the initiator methionine and the lysine at position 2. This plasmid was called pET-fabI. The linker was made by annealing the following two oligonucleotides: 5'-CATGGGCTTAAATCTTGAAAACAAAACA-3' (SEQ ID NO: 3) and 5'-TATGTTTTGTTTTCAAGATT-TAAGCC-3' (SEQ ID NO: 4). The linker sequence in pET-fabI was confirmed by dideoxy sequencing. Only native FabI was used for compound evaluation. For overproduction of native FabI, plasmid pET-fabI was transformed into BL21 (DE3) (Novagen) cells, to form strain BL21(DE3):pET-fabI.

Purification of S. aureus FabI

S. aureus FabI was expressed as soluble protein to 10% of total cell protein, 400 g cells being recovered from 15 L fermentation in tryptone phosphate medium. The cells were lysed and the sample centrifuged. The resulting supernatant was filtered and purified using three consecutive chromatography columns: ion-exchange (Sourse 15Q), dye-affinity (Blue sepharose), and size exclusion chromatography columns (Superose 12). After each column the FabI containing fractions were pooled, concentrated, and checked for purity and biological activity.

Cloning/Expression Haemophilus influenzae FabI

The FabI gene was PCR amplified from Haemophilus influenzae (Q1) genomic DNA. Oligonucleotide primers were designed with unique restriction sites at both the N' and C' terminal ends of the gene to allow efficient sub-cloning into the expression vector pPROLar.

```
FORWARD PRIMER
     KpnI
5' GCGGTACCCATGCGCTTGGTTTTCTTAGAAATATTG '3

REVERSE PRIMER
     NotI
5' GCGGCCGCTTATTCTTCGCCTAATTCGCCCATTGC '3
```

PCR amplification was performed using Pfu Turbo DNA polymerase as per the instructions of the manufacturer (Stratagene). The following cycling conditions were used: 95° C. for 3 minutes followed by 30 cycles of 94° C. 1 minute, 55° C. 1 minute and 72° C. 3 minutes. A final extension at 72° C. for 5 minutes was carried out. PCR products of expected size for *Haemophilus influenzae* FabI were cloned into the PCR cloning vector TOPO TA 2.1 as per instructions of the manufacturer (Invitrogen). The fidelity of the presumptive PCR amplified *Haemophilus influenzae* FabI gene was confirmed by DNA sequencing on both strands using an ABI 377 Automative DNA Sequencer (Applied Biosystems). pPROLar was digested with KpnI and NotI restriction endonucleases using conditions as recommended by the supplier (New England Biolabs). Purification of the linear plasmid, was achieved using agarose gel purification and the Qia-quick gel purification kit as per the protocol supplied by the manufacturer (Qiagen). The *Haemophilus influenzae* FabI gene was excised from TOPO TA 2.1 by KpnI and NotI restriction endonuclease digestion and purified as above. Subsequent fragment/vector ligations were carried out using T4 DNA ligase, using conditions supplied by the manufacturer (Promega).

Transformations into *E. coli* TOP 10 competent cells are performed using the protocol as supplied by the manufacturer (Invitrogen). Verification of the resultant clones are carried out using colony PCR and restriction endonuclease digestion. Positive clones were then transformed into the expression strain *E. coli* DH5αPRO, which expresses AraC in addition to the lac repressor.

Subsequent clones are then evaluated for expression at small-scale using the conditions as recommended by the manufacturer (Clontech). Expression analysis showed overexpressed protein bands of correct size for *Haemophilus influenzae* FabI clearly visible by SDS PAGE. Protein identity was further confirmed by peptide mass fingerprinting. Further analysis by N-terminal Amino Acid sequencing of the purified protein showed that the N-terminus starts 35 residues downstream of the presumptive initiation codon. DNA sequence analysis also highlighted the presence of a ribosome binding site upstream and correctly spaced from the new initiation codon. These findings match perfectly with *E. coli* FabI and the protein is also now a similar size to other FabIs. The over-expression construct has managed to use the correct ribosome binding site and start at the correct ATG to give the correct protein.

Purification of *H. influenzae* FabI

One liter of cells containing the *H. influenzae* FabI expression construct were grown to an OD600 of 0.6. Expression was induced as described above and the cells were grown for a further 3 h and then harvested. The cell pellet was resuspended in 10 ml 50 mM Tris pH 7.5, 1 mM PMSF, 1 mM benzamidine, 1 mM DTT (buffer A) and lysed by sonication. Cell debris was removed by centrifugation. The supernatant was loaded onto a Hi-load Q (16/10) column (Pharmacia) equilibrated in buffer A. Protein was eluted over a 200 mL gradient of 0-100% buffer B, where buffer B is buffer A+1 M KCl. Fractions containing FabI were identified by SDS PAGE and by their FabI activity and pooled.

1.5 M ammonium sulfate was added to the pooled fractions and these were then loaded onto a Hi-load phenyl sepharose (16/10) column (Pharmacia) equilibrated in 50 mM Tris pH 7.5, 1 mM PMSF, 1 mM benzamidine, 1 mM DTT, 1.5 M ammonium sulfate. Proteins were eluted with a gradient of ammonium sulfate (1.5 to 0 M) over 200 mL. Fractions containing FabI were identified as above and pooled. The pooled fractions were buffer exchanged into 100 mM Tris, pH 7.5, 2 mM DTT and glycerol was then added to 50%. The protein was stored at −20° C. The identity of the protein was confirmed by N-terminal sequencing and MALDI mass spectrometry.

Cloning of *E. coli* FabI

A PCR fragment of correct size for *E. coli* FabI was PCR amplified from *E. coli* chromosomal DNA, subcloned into the TOPO TA cloning vector, and verified by colony PCR+ restriction endonuclease analysis. The presumptive *E. coli* FabI PCR fragment was subcloned into the expression vector pBluePet. The FabI clone was transformed into *E. coli* strain BL21(DE3). Small Scale expression studies show an overexpressed protein band of correct molecular weight (~28 Kda) for *E. coli* FabI clearly visible following Coomassie staining of SDS PAGE gels. DNA sequencing of the *E. coli* FabI expression constructs illustrated that no errors were apparent. N' terminal amino acid sequencing has confirmed the over-expressed protein band to be *E. coli* FabI.

Purification of *E. coli* FabI

*E. coli* FabI was expressed as soluble protein to 15% of total cell protein, 120 g cells being recovered from 3 L fermentation in shake flasks in modified terrific broth. The cells were lysed and the sample centrifuged. The resulting supernatant was filtered and purified using three consecutive chromatography columns: ion-exchange (Sourse 15Q), dye-affinity (blue sepharose), and size exclusion (superose 12). After each column the FabI containing fractions were pooled, concentrated and checked for purity and biological activity.

*S aureus* FabI Enzyme Inhibition Assay (NADH)

Assays were carried out in half-area, 96-well microtitre plates. Compounds were evaluated in 50-uL assay mixtures containing 100 mM NaADA, pH 6.5 (ADA=N-[2-acetamido]-2-iminodiacetic acid), 4% glycerol, 0.25 mM crotonoyl CoA, 1 mM NADH, and an appropriate dilution of *S. aureus* FabI. Inhibitors were typically varied over the range of 0.01-10 uM. The consumption of NADH was monitored for 20 minutes at 30° C. by following the change in absorbance at 340 nm. Initial velocities were estimated from an exponential fit of the non-linear progress curves represented by the slope of the tangent at t=0 min. $IC_{50}$'s were estimated from a fit of the initial velocities to a standard, 4-parameter model and are typically reported as the mean±S.D. of duplicate determinations. Triclosan, a commercial antibacterial agent and inhibitor of FabI, is included in all assays as a positive control. Compounds of this invention have $IC_{50}$'s from about 5.0 micromolar to about 0.05 micromolar or less.

*H. influenzae* FabI Enzyme Inhibition Assay

Assays are carried out in half-area, 96-well microtiter plates. Compounds are evaluated in 150-uL assay mixtures containing 100 mM MES, 51 mM diethanolamine, 51 mM triethanolamine, pH 6.5 (MES=2-(N-morpholino)ethanesulfonic acid), 4% glycerol, 25 uM crotonoyl-ACP, 50 uM NADH, and an appropriate dilution of *H. influenzae* FabI (approximately 20 nM). Inhibitors are typically varied over the range of 0.01-10 uM. The consumption of NADH is monitored for 20 minutes at 30° C. by following the change in absorbance at 340 nm. Initial velocities are estimated from an exponential fit of the non-linear progress curves. IC50's are estimated from a fit of the initial velocities to a standard, 4-parameter model, and are typically reported as the mean±S.D. of duplicate determinations. The apparent Ki is calculated assuming the inhibition is competitive with crotonoyl-ACP. A proprietary lead compound is currently included in all assays as a positive control.

*E. coli* FabI Enzyme Inhibition Assay

Assays were carried out in half-area, 96-well microtitre plates. Compounds were evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADH, and an appropriate dilution of *E. coli* FabI. Inhibitors were typically varied over the range of 0.01-10 uM. The consumption of NADH was monitored for 20 minutes at 30° C. by following the change in absorbance at 340 nm. Initial velocities were estimated from an exponential fit of the non-linear progress curves represented by the slope of the tangent at t=0 min. $IC_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control. Compounds of this invention may have $IC_{50}$'s from about 100.0 micromolar to about 0.05 micromolar.

Preparation and Purification of Crotonoyl-ACP

Reactions contained 5 mg/mL *E. coli* apo-ACP, 0.8 mM crotonoyl-CoA (Fluka), 10 mM $MgCl_2$, and 30 uM *S. pneumoniae* ACP synthase in 50 mM NaHEPES, pH 7.5. The mixture was gently mixed on a magnetic stirrer at 23° C. for 2 hr, and the reaction was terminated by the addition of 15 mM EDTA. The reaction mixture was filtered through a 0.2 micron filter (Millipore) and applied to a MonoQ column (Pharmacia) equilibrated with 20 mM Tris-Cl, pH 7.5. The column was washed with buffer until all non-adherent material was removed (as observed by UV detection), and the crotonoyl-ACP was eluted with a linear gradient of 0 to 400 mM NaCl.

*S. aureus* FabI Enzyme Inhibition Assay Using Crotonoyl-ACP

Assays are carried out in half-area, 96-well microtitre plates. Compounds are evaluated in 150 uL assay mixtures containing 100 mM NaADA, pH 6.5 (ADA=N-(2-acetamido)-2-iminodiacetic acid), 4% glycerol, 25 uM crotonoyl-ACP, 50 uM NADPH, and an appropriate dilution of *S. aureus* Fab I (approximately 20 nM). Inhibitors are typically varied over the range of 0.01-10 uM. The consumption of NADPH is monitored for 20 minutes at 30° C. by following the change in absorbance at 340 nm. Initial velocities are estimated from a linear fit of the progress curves. IC50's are estimated from a fit of the initial velocities to a standard, 4-parameter model (Equation 1) and are typically reported as the mean±S.D. of duplicate determinations. Compounds of this invention in this assay have $IC_{50}$'s from about 100.0 micromolar to about 0.04 micromolar. The apparent Ki is calculated from Equation 2 assuming the inhibition is competitve with crotonoyl-ACP.

$$v=\text{Range}/(1+[I]/IC50)s+\text{Background} \qquad \text{Equation 1}$$

$$Ki(app)=IC50/(1+[S]/Ks) \qquad \text{Equation 2}$$

Antimicrobial Activity Assay

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically". The compound was tested in serial two-fold dilutions ranging from 0.06 to 64 mcg/mL. A panel of 12 strains were evaluated in the assay. This panel consisted of the following laboratory strains: *Staphylococcus aureus* Oxford, *Streptococcus pneumoniae* R6, *Streptococcus pyogenes* CN10, *Enterococcus faecalis* I, *Haemophilus influenzae* Q1, *Escherichia coli* DC0, *E. coli* ESS, *E. coli* 7623 ($AcrAB^+$) *E. coli* 120 ($AcrAB^-$) *Klebsiella pneumoniae* E70, *Pseudomonas aeruginosa* K799 wt and *Candida albicans* GRI 681. The minimum inhibitory concentration (MIC) was determined as the lowest concentration of compound that inhibited visible growth. A mirror reader was used to assist in determining the MIC endpoint.

One skilled in the art would consider any antibacterial compositions of the present invention with a MIC of less than 256 µg/mL to be a potential lead composition. The antibacterial compositions used in the antimicrobial assays may have a MIC value of less than 128 µg/mL. Said compositions may have a MIC value of less than 64 µg/mL.

Method for Checkerboard Combination Studies

The combination experiments were performed and the results were interpreted using the checkerboard method as described in Eliopoulous, G. M., and R. C. Moellering, 1996, Antimicrobial combinations, p. 330-396, In V. Lorian (ed.), Antibiotics in laboratory medicine, 4th ed., The Williams & Wilkins Co., Baltimore, Md., in 96-well microtiter plates. Compound A was serially diluted along the x-axis of the test plate to a final volume of 50 µl, and compound B was serially diluted in a separate transfer plate. Dilutions in both plates were made in CAMHB (cation-adjusted Mueller Hinton broth) for Staphylococci and in CAMHB+5% sheep blood for Streptococci. Aliquots (50 µl) of Compound B were transferred to the test plate along the y-axis thereby achieving a checkerboard matrix of antimicrobial combinations (100 µl total volume) as in FIG. 4. The first column and last row (shaded in FIG. 4) contained only compound B or compound A, respectively. Plates were then inoculated with 10 µl of the test microorganism and MICs were determined according to NCCLS guidelines (see National Committee for Clinical Laboratory Standards, 2000, Methods for Dilution Antimicrobial Susceptibility Tests for Bacteria That Grow Aerobically—Fifth Edition, Approved Standard M7-A5, NCCLS, Wayne, Pa., USA.)

Data analysis was performed as follows and according to Eliopoulous, G. M., and R. C. Moellering, 1996, Antimicrobial combinations, p. 330-396, In V. Lorian (ed.), Antibiotics in laboratory medicine, 4th ed., The Williams & Wilkins Co., Baltimore, Md. First individual FIC values for each combination in a plate were calculated:

FIC(Fractional Inhibitory Concentration)=FIC*A*+FIC*B*

FICA=MICA+B/MICA i.e. the MIC of combination of compound A+compound B divided by the MIC of compound A alone.

FICB=MICB+A/MICB i.e. the MIC of combination of compound B+compound A divided by the MIC of compound B alone.

FIC values were calculated only for combinations that enabled determination of a true MIC (e.g. not > or <=values). FIC indexes were then calculated as the average of individual FIC values for each combination plate.

A summary of the FIC index values is presented below in Tables 1 and 2. Table 3 indicates combination time-kill kinetics for two bacterial strains.

TABLE 1

Summary of combination MICs with compounds of formulas I-III and other antibiotics using the checkerboard method.

| Antibiotic Strains[a] | FIC Index | | | | | | |
|---|---|---|---|---|---|---|---|
| | A | B | C | D | E | F | G |
| Vancomycin | | | | | | | |
| S. aureus 29213 | ≧0.5 ≦2 | ND | ≧0.5 ≦2 | ≧0.5 ≦2 | ≧0.5 ≦2 | ND | 1 |
| S. aureus 43300[b] | ≧0.5 ≦2 | ND | ≧0.5 ≦2 | ≧0.5 ≦2 | ≧0.5 ≦2 | ≧0.5 ≦2 | 0.75 |
| S. epidermidis 39 | <0.5 | ND | ND | <0.5 | ≧0.5 ≦2 | ND | ND |
| Rifampicin | | | | | | | |
| S. aureus 29213 | ≧0.5 ≦2 | ND | ND | ≧0.5 ≦2 | ≧0.5 ≦2 | ND | 0.8 |
| S. aureus 43300[b] | ≧0.5 ≦2 | ND | ND | ≧0.5 ≦2 | ≧0.5 ≦2 | ND | 0.75 |
| S. epidermidis 39 | <0.5 | ND | ND | ≧0.5 ≦2 | ≧0.5 ≦2 | ND | ND |
| Gentamcin | | | | | | | |
| S. aureus 29213 | ND | ND | ND | ND | ND | ND | 0.3 |
| S. aureus 43300[b] | ≧0.5 ≦2 | ND | ND | <0.5 | ND | ND | 0.4 |
| Tetracycline | | | | | | | |
| S. aureus 29213 | ≧0.5 ≦2 | ND | ND | ≧0.5 ≦2 | ND | ND | 2 |
| S. aureus 43300[b] | ND | ND | ND | ND | ND | ND | 1 |
| Ceftriaxone | | | | | | | |
| S. aureus 29213 | ≧0.5 ≦2 | ≧0.5 ≦2 | ≧0.5 ≦2 | ND | ND | ND | |
| S. aureus 43300[b] | ND | ND | ≧0.5 ≦2 | ND | ND | ND | |
| S. pneumoniae 49619 | ND | ND | ≧0.5 ≦2 | ND | ND | ND | |
| Cefuroxime | | | | | | | |
| S. aureus 29213 | ≧0.5 ≦2 | ≧0.5 ≦2 | ≧0.5 ≦2 | ND | ND | ND | 0.8 |
| S. aureus 43300[b] | ND | ND | ≧0.5 ≦2 | ND | ND | ND | 0.5 |
| S. pneumoniae 49619 | ND | ND | ≧0.5 ≦2 | ND | ND | ND | ND |
| Cefotaxime | | | | | | | |
| S. aureus 29213 | ≧0.5 ≦2 | ≧0.5 ≦2 | ≧0.5 ≦2 | ND | ND | ND | |
| S. aureus 43300[b] | ND | ND | ≧0.5 ≦2 | ND | ND | ND | |
| S. pneumoniae 49619 | ND | ND | ≧0.5 ≦2 | ND | ND | ND | |
| Linezolid | | | | | | | |
| S. aureus 29213 | ND | ND | ND | ND | ND | ND | 0.5 |
| S. aureus 43300[b] | ND | ND | ND | ND | ND | ND | 0.5 |
| Erythromycin | | | | | | | |
| S. aureus 29213 | ND | ND | ND | ND | ND | ND | 2 |
| Nafcillin | | | | | | | |
| S. aureus 29213 | ND | ND | ND | ND | ND | ND | 0.8 |
| S. aureus 43300[b] | ND | ND | ND | ND | ND | ND | 0.7 |
| Cloxacillin | | | | | | | |
| S. aureus 29213 | ND | ND | ND | ND | ND | ND | 2 |
| S. aureus 43300[b] | ND | ND | ND | ND | ND | ND | 0.75 |
| Levofloxacin | | | | | | | |
| S. aureus 29213 | ND | ND | ND | ND | ND | ND | 1 |
| S. aureus 43300[b] | ND | ND | ND | ND | ND | ND | 2 |

[a]Bacterial species are Staphylococcus aureus, Staphylococcus epidermidis and Streptococcus pneumoniae.
[b]S. aureus strain 43300 is a methicillin-resistant (MRSA) strain.
FIC index intrepretation is ≦0.5 = synergy; >0.5 ≦2 = additivity; >2 ≦4 = indifference; and >4 = antagonism.

TABLE 2

Summary of combination MIC with compound G and commercial antibiotics against clinical bacterial isolates.

| Species | Strain | Azithromycin | Ceftriaxone | Cefuroxime | Gatifloxacin FIC[a] | Levofloxacin | Meropenem | Penicillin |
|---|---|---|---|---|---|---|---|---|
| E. coli | EC_25922 | | 0.7 | | <2 | | 0.6 | |
| E. faecalis | EF_A6221420[b] | | <2 | | <2 | <2 | <2 | |
| H. influenzae | HI_49247 | <2 | | | | | | |
| P. aeruginosa | PA_27853 | | | | <2 | | <2 | |

TABLE 2-continued

Summary of combination MIC with compound G and commercial antibiotics against clinical bacterial isolates.

| Species | Strain | Azithromycin | Ceftriaxone | Cefuroxime | Gatifloxacin FIC[a] | Levofloxacin | Meropenem | Penicillin |
|---|---|---|---|---|---|---|---|---|
| S. aureus | SA_29213[b] | 0.6 | <2 | <2 | | | 1 | 0.7 |
| | SA_A6250596[b] | <2 | <2 | <2 | 1 | 1 | <2 | <2 |
| | SA_A7080336[b] | | | | 0.6 | 0.6 | | |
| S. epidermidis | SE_A7100750[b] | | 1 | | <2 | | 0.6 | |
| S. mitis | SMI_116 | | <2 | | <2 | | <2 | <2 |
| S. pneumoniae | SP_22257[b] | <2 | | | | | | |
| | SP_22425[b] | | <2 | <2 | <2 | <2 | <2 | |
| S. pyogenes | SPY_20015 | | | | <2 | | | |
| | SPY_20061[b] | | <2 | | <2 | | | |

[a]FIC index: ≦0.5 = synergy; >0.5 ≦ 2 = additivity; >2 ≦ 4 = indifference; >4 = antagonism

[b]Phenotype of indicated strain: E. faecalis strain EF_A6221420, VRE; S. aureus strain SA_29213, MSSA; S. aureus strain SA_A6250596, MRSA-MDR; S. aureus strain SA_A7080336, MRSA; S. epidermidis strain SE_A7100750, MRSE CipR; S. pneumoniae strain SP_22257, PenR EryS ClinS; S. pneumoniae strain SP_22425, PenR EryR ClinR; and S. pyogenes strain SPY_20061, EryS.

TABLE 3

Summary of combination time-kill kinetics for S. pneumoniae and E. faecalis strains.

Combination Time-kill kinetics for S. pneumoniae 22425

| Compound Combination | logCFU/ml at Time (hr): | | | | ΔlogCFU/ml (24-0 hr) |
|---|---|---|---|---|---|
| | 0 | 2 | 6 | 24 | |
| Growth Control | 5.10 | 5.68 | 7.11 | 7.55 | 2.46 |
| Compound G (0.03 ug/ml) | 5.20 | 5.63 | 7.25 | 7.61 | 2.41 |
| Compound G (1 ug/ml) | 5.12 | 5.61 | 7.18 | 7.58 | 2.45 |
| Gatifloxacin - 4 × MIC (2 ug/ml) | 5.18 | 4.26 | 2.77 | 1.70* | −3.48 |
| Gatifloxacin - 4 × MIC + Compound G (0.03 ug/ml) | 5.14 | 4.17 | 2.58 | 1.70* | −3.44 |
| Gatifloxacin - 4 × MIC + Compound G (1 ug/ml) | 5.19 | 4.23 | 2.67 | 1.70* | −3.49 |

Combination Time-kill kinetics for S. pneumoniae 22257

| Compound Combination | logCFU/ml at Time (hr): | | | | | ΔlogCFU/ml (24-0 hr) |
|---|---|---|---|---|---|---|
| | 0 | 3 | 6 | 8 | 24 | |
| Growth Control | 6.45 | 8.35 | 9.03 | 9.61 | 9.69 | 3.24 |
| Compound G (0.03 ug/ml) | 6.41 | 8.31 | 9.23 | 9.32 | 9.68 | 3.26 |
| Compound G (1 ug/ml) | 6.43 | 8.30 | 9.33 | 9.47 | 9.68 | 3.25 |
| Azithromycin - 4 × MIC (0.12 ug/ml) | 6.35 | 4.53 | 3.39 | 1.70* | 1.70* | −4.65 |
| Azithromycin - 4 × MIC + Compound G (0.03 ug/ml) | 6.41 | 4.49 | 3.47 | 1.70* | 1.70* | −4.72 |
| Azithromycin - 4 × MIC + Compound G (1 ug/ml) | 6.32 | 4.58 | 3.46 | 1.70* | 1.70* | −4.62 |
| Growth Control | 6.39 | 8.23 | 9.47 | 9.36 | 9.70 | 3.31 |
| Compound G (0.03 ug/ml) | 6.20 | 8.15 | 9.35 | 9.32 | 9.65 | 3.45 |
| Compound G (1 ug/ml) | 6.30 | 8.17 | 9.20 | 9.41 | 9.71 | 3.40 |
| Cefuroxime - 4 × MIC (8 ug/ml) | 6.39 | 1.92 | 1.70 | 1.70* | 1.70* | −4.69 |
| Cefuroxime - 4 × MIC + Compound G (0.03 ug/ml) | 6.32 | 2.00 | 1.70 | 1.70* | 1.70* | −4.62 |
| Cefuroxime - 4 × MIC + Compound G (1 ug/ml) | 6.25 | 1.92 | 1.70 | 1.70* | 1.70* | −4.55 |
| Growth Control | 6.39 | 8.23 | 9.47 | 9.36 | 9.70 | 3.31 |
| Compound G (0.03 ug/ml) | 6.20 | 8.15 | 9.35 | 9.32 | 9.65 | 3.45 |
| Compound G (1 ug/ml) | 6.30 | 8.17 | 9.20 | 9.41 | 9.71 | 3.40 |
| Cefuroxime - 4 × MIC (8 ug/ml) | 6.39 | 1.92 | 1.70 | 1.70* | 1.70* | −4.69 |
| Cefuroxime - 4 × MIC + Compound G (0.03 ug/ml) | 6.32 | 2.00 | 1.70 | 1.70* | 1.70* | −4.62 |
| Cefuroxime - 4 × MIC + Compound G (1 ug/ml) | 6.25 | 1.92 | 1.70 | 1.70* | 1.70* | −4.55 |

TABLE 3-continued

Summary of combination time-kill kinetics for *S. pneumoniae* and *E. faecalis* strains.

Combination Time-kill kinetics for *E. faecalis* A6221420

| Compound Combination | logCFU/ml at Time (hr): | | | | | ΔlogCFU/ml |
|---|---|---|---|---|---|---|
| | 0 | 2 | 4 | 8 | 24 | (24-0 hr) |
| Growth Control | 5.09 | 6.12 | 6.49 | 9.88 | 9.91 | 4.82 |
| Compound G (0.03 ug/ml) | 5.10 | 6.03 | 6.42 | 9.88 | 9.91 | 4.81 |
| Compound G (1 ug/ml) | 5.12 | 5.93 | 6.53 | 9.76 | 9.91 | 4.79 |
| Meropenem - 4 × MIC (16 ug/ml) | 5.12 | 4.31 | 3.41 | 2.67 | 1.70* | −3.43 |
| Meropenem - 4 × MIC + Compound G (0.03 ug/ml) | 5.05 | 4.24 | 3.38 | 2.64 | 1.92 | −3.13 |
| Meropenem - 4 × MIC + Compound G (1 ug/ml) | 5.07 | 4.26 | 3.34 | 2.60 | 1.82 | −3.25 |

*at lower limit of detection

Dosages

The dosage of any compositions of the present invention will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions of the present invention may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible affects on the timing of administration of the formulation, may need to be identified for any particular composition of the present invention. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions (e.g., the FabI inhibitor) because the onset and duration of effect of the different agents may be complimentary. For example, the dosage may be selected to modulate metabolism of the bacteria in such a way as to inhibit or stop growth of said bacteria or by killing said bacteria. The skilled artisan may identify this amount as provided herein as well as by using other methods known in the art.

Toxicity and therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the present invention, the therapeutically effective dose may be estimated initially from cell culture assays.

Formulation

The antibacterial compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compositions of the present invention may be formulated as eyedrops or eye ointments, for example, formulated as micronized suspensions in isotonic, pH adjusted saline, with optionally, for example a preservative, or formulated in an ointment such as petrolatum. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

The ratio between the FabI inhibitor and the at least one other antibacterial agent may vary within relatively broad ranges and will be dependent on the intended use. It is contemplated that the compositions of the present invention may comprise a ratio in the range of about 0.01:1 to 1:100 between the FabI inhibitor and the bioactive agent. In other embodiments, ratios of Fab I inhibitor to anti-infective agent by weight may range from about 1:10 to about 50:1, or from about 1:5 to about 20:1, or about 1:1 to about 15:1, e.g. about 12:1. In certain embodiments, the two or more agents in the subject compositions work synergistically.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated compositions. Such formulations may include further various antibacterial and antifungal agents, for example, paraben, chlorobutanol, phenol sorbic acid, and the like.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration. For administration by inhalation for example, compositions disclosed herein may be delivered through an aerosol spray in the form of for example, a solution, dry powder or cream.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

A pharmaceutical composition is therefore provided comprising a composition of this disclosure and a pharmaceutically acceptable carrier or excipient. Such a composition may be formulated for example, for intravenous administration, injectable administration, topical application, and/or as suppository. Compositions disclosed herein may formulated, for example, for systemic administration and/or oral administration. For example, such a composition may be formulated in tablets such that the amount of composition provided in 20 tablets, if taken together, provides a dose of at least the $ED_{50}$ but no more than ten times the $ED_{50}$. In some embodiments, the composition may be formulated for parenteral administration such that the amount of amount of antibacterial agent substantially inhibiting FabI provided in 20 cc bolus injection provides a dose of at least the $ED_{50}$ but no more that ten times the $ED_{50}$. In other embodiments, the composition may be formulated for intravenous infusion such that the amount of antibacterial agent substantially inhibiting FabI provided in one liter of intravenous injectable solution provides a dose of at least the $ED_{50}$ but no more that ten times the $ED_{50}$.

A pill is also contemplated for reducing bacterial levels in a subject with a bacteria related illness, comprising a composition of this disclosure. In some embodiments, a pill provides effective bacterial treatment for at least about 8 hours, at least about 12 hours, aat least about 24 hours, and/or at least about one week. A pack of pills in number sufficient for treatment of a bacterial illness is also contemplated, comprising a plurality of pills wherein each pill comprises a composition or a compound disclosed herein. In some embodiments, the pack contains at least 5 pills, at least 10 pills, and/or at least 20 pills.

Efficacy of Treatment

The efficacy of treatment with the subject compositions may be determined in a number of fashions known to those of skill in the art.

In one exemplary method, the median survival rate of the bacteria or bacteria median survival time or life span for treatment with a subject composition may be compared to other forms of treatment with the particular FabI inhibitor or bioactive agent contained in the subject composition, or with other bioactive agents. The decrease in median bacteria survival rate or time or life span for treatment with a subject composition as compared to treatment with another method may be 10, 25, 50, 75, 100, 150, 200, 300, 400% less or even more. The period of time for observing any such decrease may be about 3, 5, 10, 15, 390, 60 or 90 or more days. The comparison may be made against treatment with the particular FabI inhibitor or bioactive agent contained in the subject composition, or with other bioactive agents, or administration of the same or different agents by a different method, or administration as part of a different drug delivery device than a subject composition. The comparison may be made against the same or a different effective dosage of the various agents. The different regiments compared may use bacterial levels.

Alternatively, a comparison of the different treatment regimens described above may be based on the effectiveness of the treatment, using standard indicies for bacterial infections known to those of skill in the art. One method of treatment may be 10%, 20%, 30%, 50%, 75%, 100%, 150%, 200%, 300% more effective, than another method.

Alternatively, the different treatment regimens may be analyzed by comparing the therapeutic index for each of them, with treatment with a subject composition as compared to another regimen having a therapeutic index two, three, five or seven times that of, or even one, two, three or more orders of magnitude greater than, treatment with another method using the same or different FabI inhibitor, bioactive agent or combinations thereof.

Kits

This invention also provides kits for conveniently and effectively implementing the methods of this invention. Such kits comprise any subject composition, and a means for facilitating compliance with methods of this invention. Such kits may provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

The present invention also provides for kits containing at least one dose of a subject composition, and often many doses, and other materials for a treatment regimen. For example, in one embodiment, a kit of the present invention contains sufficient subject composition for from five to thirty days and optionally equipment and supplies necessary to measure one or more indices relevant to the treatment regiment. In another embodiment, kits of the present invention contain all the materials and supplies, including subject compositions, for carrying out any methods of the present invention. In still another embodiment, kits of the present invention, as described above, additionally include instructions for the use and administration of the subject compositions.

For example, a kit contemplated herein may comprise at least two compartments, wherein a first compartment comprises an Fab I inhibiting agent and a second compartment comprises a anti-infective agent, and optionally wherein a combination of the said Fab I inhibiting agent and said anti-infective agent are present in amounts that are non-antagonist. The compartments may comprise a single bottle, which together form a twin-bottle kit.

In another embodiment, the first or second compartment may be in the form of an infusion bag and the first or second compartment may be in the form of a bottle or ampoule. The first and/or the second compartment may be in the form of a syringe.

EXEMPLIFICATION

General

Proton nuclear magnetic resonance ($^1$H NMR) spectra were recorded at either 300 or 400 MHz, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Mass spectra were obtained using electrospray (ES) ionization techniques. Elemental analyses were performed by Quantitative Technologies Inc., Whitehouse, N.J. Melting points were obtained on a Thomas-Hoover melting point apparatus and are uncorrected. All temperatures are reported in degrees Celsius. Analtech Silica Gel GF and E. Merck Silica Gel 60 F-254 thin layer plates were used for thin layer chromatography. Flash chromatography was carried out on E. Merck Kieselgel 60 (230-400 mesh) silica gel. Analytical HPLC was performed on Beckman chromatography systems. Preparative HPLC was performed using Gilson chromatography systems. ODS refers to an octadecylsilyl derivatized silica gel chromatographic support. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo. General abbreviations are as follows: EDC=1-(3-dimethylaminopropyl)-3-ethylcarbodiimide hydrochloride, HOBt=1-hydroxybenzotriazole hydrate, (I-Pr)$_2$EtN=N,N-diisopropylethylamine, DMF=N,N-dimethylformamide, MeOH=methanol, EtOH=ethanol, THF=tetrahydrofuran, DMSO=dimethylsulfoxide, Et$_2$O=diethyl ether, Ar=argon, Pd(OAc)$_2$=palladium(II)acetate, P(o-tol)$_3$=tri-ortho-tolylphosphine, EtOAc=ethyl acetate, ACE-Cl=1-chloroethyl chloroformate, satd=saturated, Et$_3$N=triethylamine, TFA=trifluoroacetic acid, NaBH(OAc)$_3$=sodium triacetoxyborohydride, HOAc=acetic acid, EtCN=proprionitrile, CBzCl=benzyl chloroformate, MeCN=acetonitrile.

Preparation of intermediates for compounds of formula I and the synthesis of compounds of formula I, as described in part in Schemes I-XXXV, have been disclosed in PCT Patent Application PCT/US03/38706, filed Dec. 5, 2003, and hereby are incorporated herein in their entirety.

Preparation 1

Preparation of (E)-3-(6-aminopyridin-3-yl)acrylic acid (Method A)

a) Benzyl (E)-3-(6-aminopyridin-3-yl)acrylate

A solution of 2-amino-5-bromopyridine (2.25 g, 13.0 mmole), benzyl acrylate (3.2 g, 19.7 mmole), Pd(OAc)$_2$ (0.31 g, 1.4 mmole), tri-ortho-tolylphosphine (0.73 g, 2.4 mmole), and diisopropylethylamine (3.5 mL, 20.0 mmole) in propionitrile (50 mL) was heated at reflux overnight. The dark mixture was filtered through Celite®, and the filtrate was concentrated. Flash chromatography on silica gel (3% MeOH/CH$_2$Cl$_2$) gave the title compound (1.3 g, 39%): MS (ES) m/e 255 (M+H)$^+$.

b) (E)-3-(6-Aminopyridin-3-yl)acrylic acid

A solution of benzyl (E)-3-(6-aminopyridin-3-yl)acrylate (1.3 g, 5.1 mmole) (E)-3-(6-aminopyridin-3-yl)acrylate (1.3 g, 5.1 mmole) and 1.0 N NaOH (10 mL, 10 mmole) in MeOH was heated at reflux overnight. The solution was concentrated in vacuo, and the residue was dissolved in H$_2$O. The pH was adjusted to 6 with dilute HCl, and the solid precipitate was collected by suction filtration and dried to give the title compound (0.6 g, 72%) as a white solid: MS (ES) m/e 165 (M+H)$^+$.

Preparation 2

Preparation of (E)-3-(6-aminopyridin-3-yl)acrylic acid (Method B)

a) (E)-3-(6-Aminopyridin-3-yl)acrylic acid

Acrylic acid (23 mL, 0.33 mole) was added carefully to a solution of 2-amino-5-bromopyridine (25.92 g, 0.15 mole) and Na$_2$CO$_3$ (55.64 g, 0.53 mole) in H$_2$O (600 mL). PdCl$_2$ (0.53 g, 0.003 mole) was then added, and the mixture was heated at reflux. After 24 hr, the reaction was cooled to RT and filtered, and the filtrate was adjusted to pH 6 with aqueous HCl. Additional H$_2$O (0.5 L) was added to improve mixing, and the mixture was stirred for 1 hr. The pH was readjusted to 6, then the solid was collected by suction filtration. The filter pad was washed sequentially with H$_2$O (2×0.5 L), cold absolute EtOH (100 mL), and Et$_2$O (2×250 mL). Drying in high vacuum at elevated temperature gave the title compound (15.38 g, 62%) as a tan solid: $^1$H NMR (300 MHz, DMSO-d$_6$) δ 8.11 (d, J=2.0 Hz, 1H), 7.75 (dd, J=8.7, 2.0 Hz, 1H), 7.43 (d, J=15.8 Hz, 1H), 6.53 (s, 2H), 6.45 (d, J=8.7 Hz, 1H), 6.22 (d, J=15.8 Hz, 1H); MS (ES) m/e 165 (M+H)$^+$.

Preparation 3

Preparation of (E)-3-(2-aminopyrimidin-5-yl)acrylic acid a) Benzyl (E)-3-(2-aminopyrimidin-5-yl)acrylate According to the procedure of Preparation 1 (a), except substituting 5-bromo-2-aminopyrimidine (1.95 g, 11.2 mmole) for 2-amino-5-bromopyridine, the title compound (2.25 g, 79%) was prepared as a light orange solid: MS (ES) m/e 256 (M+H)$^+$.

b) (E)-3-(2-Aminopyrimidin-5-yl)acrylic acid

According to the procedure of Preparation 1 (b), except substituting benzyl (E)-3-(2-aminopyrimidin-5-yl)acrylate (2.93 g, 11.5 mmole) for benzyl (E)-3-(6-aminopyridin-3-yl) acrylate, the title compound (1.71 g, 90%) was prepared as an off-white solid: MS (ES) m/e 166 (M+H)$^+$.

Preparation 4

Preparation of 6-bromo-3,4-dihydro-1H-1,8-naphthyridin-2-one a) 2-Amino-3-(hydroxymethyl)pyridine Solid 2-aminonicotinic acid (199 g, 1.44 mole) was added in portions over 4 hr to 1.0 M LiAlH$_4$ in THF (3 L, 3 mole) with stirring under Argon. An ice-bath was applied to control the temperature below 30° C. After the addition was complete, the reaction was heated at reflux for 16 hr, then was cooled to 0° C. and carefully quenched by sequential addition of H$_2$O (120 mL), 15% NaOH in H$_2$O (120 mL), and H$_2$O (350 mL). The resulting thick suspension was stirred for 1 hr, then was filtered through a pad of Celite®. The filter pad was rinsed with THF (1 L), and the filtrate was concentrated to dryness to give the title compound (156 g, 87%) as a pale yellow waxy solid: MS (ES) m/e 125.1 (M+H)$^+$; $^1$H NMR (400 MHz, DMSO-d$_6$) □ 7.84 (dd, 1H), 7.37 (m, 1H), 6.53 (dd, 1H), 5.65 (br s, 2H), 5.16 (t, 1H), 4.34 (d, J=4.6 Hz, 2H).

b) 2-Amino-5-bromo-3-(hydroxymethyl)pyridine hydrobromide

To a stirred solution of 2-amino-3-(hydroxymethyl)pyridine (156 g, 1.257 mole) in HOAc (2.5 L) at ambient temperature was added bromine (64.1 mL, 1.257 mole) dropwise over 1 hr. A suspension began to form during the addition. An exotherm to 36° C. was controlled with an ice bath. After the addition, the reaction mixture was stirred at ambient temperature overnight. The yellow precipitate was filtered, washed with ether and air-dried to give the title compound (289 g, 81%): MS (ES) m/e 203.2 (M+H)$^+$; $^1$H NMR (400 MHz, DMSO-d$_6$, free base) δ 7.89 (d, J=2.3 Hz, 1H), 7.52 (s, 1H), 5.92 (br s, 2H), 5.29 (br s, 1H), 4.30 (s, 2H).

c) 2-Amino-5-bromo-3-(bromomethyl)pyridine hydrobromide

A suspension of 2-amino-5-bromo-3-(hydroxymethyl)pyridine hydrobromide (289 g, 1.02 mole) in 48% aqueous HBr (2.9 L) was heated at reflux for 12 hrs. Complete solution occurred during heating. The reaction mixture was cooled and a crystalline precipitate formed. This was filtered and washed with ethyl acetate and air dried to give the title compound (305 g, 86%).

d) Methyl (±)-6-bromo-2-oxo-1,2,3,4-tetrahydro-1H-1,8-naphthyridine-3-carboxylate To a solution of dimethyl malonate (224 g, 1.7 mole) in DMF (2 L) and THF (2 L) stirred under argon and chilled to 3° C. with an ice-acetone bath was added NaH (60% Nujol dispersion, 69.2 g, 1.7 mole) in portions over 1.5 hr. The anion solution was stirred for 15 min at ca. 5° C., then 2-amino-5-bromo-3-(bromomethyl)pyridine hydrobromide (200 g, 0.56 mole) was added in portions over 15 min. The reaction mixture was allowed to warm to ambient temperature during overnight stirring and then was heated to 80° C. for 2 hr. The reaction was then cooled and filtered and the precipitate was washed with ethyl acetate. This solid was then vigorously stirred in 2 L water for 15 min and again filtered and air-dried to give the title compound (113 g, 71%): MS (ES) m/e 286 (M+H)$^+$.

e) 6-Bromo-3,4-dihydro-1H-1,8-naphthyridin-2-one

To a suspension of methyl (±)-6-bromo-2-oxo-1,2,3,4-tetrahydro-1H-1,8-naphthyridine-3-carboxylate (170 g, 0.596 mole) in CH$_3$OH (10 L) was added 1.0 M NaOH (2.5 L). The reaction mixture was stirred and heated at reflux for 5 hrs and then cooled to ambient temperature. The suspension was acidified with 1.0 M HCl (3.0 L) and then was stirred and heated at reflux overnight. The reaction slurry was cooled and filtered and the solid was washed with water and vacuum dried to give the title compound (122 g of the hydrate, 90%) as an off-white solid, HPLC purity, 94%: MS (ES) m/e 228 (M+H)$^+$.

Preparation 5

Preparation of 6-bromo-3-methyl-3,4-dihydro-1H-pyrido[2,3-d]pyrimidin-2-one a) 2-Amino-5-bromo-3-(methylaminomethyl)pyridine A solution of 2-amino-5-bromo-3-(hydroxymethyl)pyridine (5.00 g, 24.6 mmole), from Preparation 4 (b), in 48% aqueous HBr (50 mL) was heated at reflux for 12 hrs. The reaction was concentrated and toluene was used to azeotrope the residual H$_2$O. The resulting light brown solid was placed under high vacuum overnight and used directly.

A solution of the 2-amino-3-(bromomethyl)-5-bromopyridine hydrobromide salt (prepared above) in 40% aqueous methylamine (50 mL) and THF (50 mL) was stirred at RT overnight in a pressure bottle. The reaction solution was concentrated and extracted with EtOAc (2×100 mL). The combined organic phases were washed with H$_2$O, dried over Na$_2$SO$_4$ and concentrated. Purification on silica gel afforded the title compound (4.25 g, 80%) as a yellow oil: MS (ES) m/e 217 (M+H)$^+$.

b) 6-Bromo-3-methyl-3,4-dihydro-1H-pyrido[2,3-d] pyrimidin-2-one

To a solution of 2-amino-5-bromo-3-(methylaminomethyl)pyridine (2.0 g, 9.3 mmole) in dichloroethane (50 mL) was added 1,1'-carbonyldiimidazole (1.9 g, 11.5 mmole). The reaction was heated at 50° C. overnight and concentrated. The residue was purified on silica gel (9:1 CHCl$_3$/CH$_3$OH containing 5% NH$_4$OH) to give the title compound (1.72 g, 77%) as an off-white solid: MS (ES) m/e 243 (M+H)$^+$.

Preparation 6

Preparation of (E)-3-(3H-imidazo[4,5-b]pyridin-6-yl)acrylic acid a) 5-Bromo-2,3-diaminopyridine To a suspension of 2-amino-5-bromo-3-nitropyridine (2.0 g, 9.17 mmole) in absolute EtOH (50 mL) was added SnCl$_2$ hydrate (9.3 g, 41.3 mmole), then the mixture was heated to reflux. After 3 hr the mixture was cooled to RT and concentrated. The residue was taken up in 2.0 M NaOH and extracted with EtOAc (3×). The combined organic layers were dried (MgSO$_4$), filtered, and concentrated to give the title compound (1.69 g, 98%) which was sufficiently pure for use in the next step: MS (ES) m/e 188/190 (M+H)$^+$.

b) 6-Bromo-3H-imidazo[4,5-b]pyridine

5-Bromo-2,3-diaminopyridine (1.69 g, 8.99 mmole) was taken up in 96% formic acid (50 mL) and heated to reflux. After 18 hr the mixture was cooled to RT and concentrated. The residue was taken up in H$_2$O and the pH was adjusted to 7 with 2.0 M NaOH. The title compound (1.54 g, 87%) was collected as a solid by filtration, washed with H$_2$O, and dried in vacuo: MS (ES) m/e 198/200 (M+H)$^+$.

c) 6-Bromo-4-trityl-3H-imidazo[4,5-b]pyridine

To a suspension of 6-bromo-3H-imidazo[4,5-b]pyridine (1.2 g, 6.06 mmole) in CH$_2$Cl$_2$ (30 mL) was added Et$_3$N (1.3 mL, 9.09 mmole) then trityl chloride (2.03 g, 7.27 mmole) at RT. After 72 hr the mixture was washed with H$_2$O (2×) and brine, then was dried (MgSO$_4$), filtered, and concentrated under reduced pressure to afford the title compound. This was used directly in the next step.

d) Benzyl (E)-3-(4-trityl-3H-imidazo[4,5-b]pyridin-6-yl)acrylate

A solution of 6-bromo-4-trityl-3H-imidazo[4,5-b]pyridine (from step a) (6.06 mmole), benzyl acrylate (1.18 g, 7.27 mmole), Pd(OAc)$_2$ (67 mg, 0.30 mmole), P(o-tolyl)$_3$ (183 mg, 0.6 mmole), and (i-Pr)$_2$NEt (2.64 mL, 15.15 mmole) in propionitrile (30 mL) was degassed (3×N$_2$/vacuum) then heated to reflux. After 4 hr the mixture was cooled to RT and concentrated. Flash chromatography on silica gel (30% EtOAc/hexanes) gave the title compound (1.75 g, 55% over 2 steps) as an off-white foam: $^1$H NMR (400 MHz, CDCl$_3$) δ 8.24 (d, J=2.0 Hz, 1H), 8.19 (d, J=2.0 Hz, 1H), 8.06 (s, 1H), 7.77 (d, J=16.0 Hz, 1H), 7.42-7.11 (m, 20H), 6.48 (d, J=16.0 Hz, 1H), 5.25 (s, 2H).

d) (E)-3-(3H-Imidazo[4,5-b]pyridin-6-yl)acrylic acid

Benzyl (E)-3-(4-trityl-3H-imidazo[4,5-b]pyridin-6-yl) acrylate (1.75 g, 3.35 mmole) was dissolved in 4 N HCl in dioxane (20 mL). After 1 hr the mixture was concentrated. The residue was taken up in 1:1 MeOH/H$_2$O (15 mL). 2.0 N NaOH (15 mL, 15 mmole) was added and the mixture was heated to reflux. After 18 hr the mixture was cooled to RT and concentrated to approximately ⅓ volume. The mixture was adjusted to pH 4 using 10% HCl. The solid was collected by filtration, washed with H$_2$O, and dried in vacuo to give the title compound (329 mg, 52% over 2 steps) as a white solid: $^1$H NMR (400 MHz, d$^6$-DMSO) δ 9.10 (s, 1H), 8.94 (s, 1H), 8.84 (s, 1H), 8.20 (d, J=16.0 Hz, 1H), 7.10 (d, J=16.0 Hz, 1H).

Preparation 7

Preparation of (E)-3-(3,4-dihydro-2H-pyrido[3,2-b]-1,4-oxazin-7-yl)acrylic acid a) 3,4-Dihydro-2H-pyrido[3,2-b]-1,4-oxazine To a suspension of 2H-pyrido[3,2-b]-1,4-oxazin-3(4H)-one (2.0 g, 13.3 mmole) in dry THF (40 mL) was added a solution of LiAlH$_4$ in THF (1.0 M, 26.6 mL, 26.6 mmole) slowly at 0° C. After 1 hr the mixture was quenched with 2.0 M NaOH until a solid formed. The mixture was dried (MgSO$_4$), filtered, and concentrated under reduced pressure to give the title compound (1.44 g, 79%) as a white solid which was sufficiently pure for use in the next step: MS (ES) m/e 137 (M+H)$^+$.

b) 4-(tert-Butoxycarbonyl)-3,4-dihydro-2H-pyrido[3,2-b]-1,4-oxazine

To a solution of 3,4-dihydro-2H-pyrido[3,2-b]-1,4-oxazine (1.44 g, 10.6 mmole) and di-tert-butyl dicarbonate (2.78 g, 12.7 mmole) in dry THF (50 mL) was added a solution of LiHMDS in THF (1.0 M, 12.7 mL, 12.7 mmole) dropwise at 0° C. After 30 min the mixture was quenched with saturated NH$_4$Cl and extracted with EtOAc (3×). The combined organic layers were dried (MgSO$_4$), filtered, and concentrated. Flash chromatography on silica gel (40% EtOAc/hexanes) gave the title compound (2.0 g, 80%) as a clear oil: MS (ES) m/e 237 (M+H)$^+$.

c) 4-(tert-Butoxycarbonyl)-7-bromo-3,4-dihydro-2H-pyrido[3,2-b]-1,4-oxazine

To a solution of 4-(tert-butoxycarbonyl)-3,4-dihydro-2H-pyrido[3,2-b]-1,4-oxazine (2.0 g, 8.46 mmole) in MeOH (40 mL) was added Br$_2$ (0.53 mL, 10.2 mmole) dropwise at 0° C. After 1 hr the mixture was concentrated. The residue was taken up in 1:1 Et$_2$O/hexanes and filtered. The filtrate was concentrated under reduced pressure to give the title compound (1.27 g, 48%) as an oil which solidified under vacuum: $^1$H NMR (400 MHz, CDCl$_3$) δ 8.10 (s, 1H), 7.33 (s, 1H), 4.25 (m, 2H), 3.92 (m, 2H), 1.54 (s, 9H).

d) (E)-3-[4-(tert-Butoxycarbonyl)-3,4-dihydro-2H-pyrido[3,2-b]-1,4-oxazin-7-yl]acrylic acid A solution of 4-(tert-butoxycarbonyl)-7-bromo-3,4-dihydro-2H-pyrido[3,2-b]-1,4-oxazine (1.27 g, 4.03 mmole), benzyl acrylate (785 mg, 4.84 mmole), Pd(OAc)$_2$ (45 mg, 0.20 mmole), P(o-tolyl)$_3$ (122 mg, 0.4 mmole), and (i-Pr)$_2$NEt (1.76 mL, 10.1 mmole) in propionitrile (20 mL) was degassed (3×N$_2$/vacuum) then heated to reflux. After 18 hr the mixture was cooled to RT and concentrated. Flash chromatography on silica gel (25% EtOAc/hexanes) gave the title compound (1.17 g, 73%) as a yellow oil: MS (ES) m/e 397 (M+H)$^+$.

e) (E)-3-(3,4-dihydro-2H-pyrido[3,2-b][1,4]oxazin-7-yl)acrylic acid (E)-3-[4-(tert-Butoxycarbonyl)-3,4-dihydro-2H-pyrido[3,2-b]-1,4-oxazin-7-yl]acrylic acid (1.17 g, 2.95 mmole) was dissolved in 4 N HCl in dioxane (15 mL). After 72 hr the mixture was concentrated. The residue was taken up in 1:1 MeOH/H$_2$O (20 mL). 1.0 N LiOH (15 mL, 15 mmole) was added and the mixture was heated to reflux. After 18 hr the mixture was cooled to RT and concentrated to approximately ⅓ volume. The mixture was adjusted to pH 6 using 10% HCl. The solid was collected by filtration, washed with H$_2$O and dried in vacuo to give the title compound (315 mg, 52% over 2 steps): MS (ES) m/e 207 (M+H)$^+$.

Preparation 8

Preparation of 5-bromo-2,2'-dipyridylamine

To a stirred solution of 2,5-dibromopyridine (2.4 g, 10.1 mmole) in dry toluene (75 mL) were added 2-aminopyridine (1.0 g, 10.6 mmole), tris(dibenzylideneacetone)dipalladium (0) (183 mg, 0.2 mmole), 1,3-bis(diphenylphosphino)propane (165 mg, 0.4 mmole) and sodium tert-butoxide (1.35 g, 14 mmole). The reaction was purged with Ar then heated with stirring at 70° C. After 4 h the reaction was cooled to RT, taken up in Et$_2$O (200 mL), washed with brine, dried (MgSO$_4$) and concentrated to dryness. The remaining residue was purified by flash chromatography on silica gel (0.5% (5% NH$_4$OH/ MeOH)/CHCl$_3$), triturated with hexane and dried under vacuum to give the title product (1.31 g, 52%) as a pale yellow solid: $^1$H NMR (400 MHz, CDCl$_3$) δ 9.88 (s, 1H), 8.31 (s, 1H), 8.23 (d, J=4.8 Hz, 1H), 7.83 (m, 2H), 7.67 (t, 1H), 7.62 (d, J=8.4 Hz, 1H), 6.90 (t, 1H); MS (ES) m/e 250.0 (M+H)$^+$.

Preparation 9

Preparation of
1-methyl-2-(methylaminomethyl)-1H-indole a) Ethyl 1-methyl-1H-indole-2-carboxylate NaH (60% dispersion in mineral oil, 8.02 g, 200.49 mmole) was washed with hexanes, then was suspended in dry DMF (530 mL). Solid ethyl indole-2-carboxylate (25.29 g, 133.66 mmole) was added portionwise over 5-10 min, allowing gas evolution to subside between additions. When the addition was complete, the yellow mixture was stirred for 15 min, then methyl iodide (42 mL, 668.3 mmole) was added all at once. The reaction was exothermic, and the internal temperature rose to 40-45° C. After 1 hr, the reaction was quenched with 10% NH$_4$Cl (100 mL) and concentrated on the rotavap (high vacuum). The residue was partitioned between Et$_2$O (500 mL) and H$_2$O (100 mL), and the layers were separated. The Et$_2$O layer was washed with H$_2$O (100 mL), dried (MgSO$_4$), and concentrated to leave the title compound (27.10 g, quantitative) as a light yellow solid. This was used without further purification: TLC (10% EtOAc/hexanes) Rf=0.39.

b) N,1-Dimethyl-1H-indole-2-carboxamide

A suspension of ethyl 1-methyl-1H-indole-2-carboxylate (27.10 g, 133.34 mmole) in 40% aqueous CH$_3$NH$_2$ (300 mL) and MeOH (30 mL) was stirred at RT. A solid tended to gradually creep up the walls of the flask, and was washed down periodically with MeOH. The flask was tightly stoppered to keep the material inside the flask. As the reaction proceeded, the solid dissolved, but eventually the product began to precipitate. The reaction was stirred at RT for 5 days, then was concentrated to remove approximately 200 mL of the solvent. The remaining residue was diluted with H$_2$O (300 mL), and the solid was collected by suction filtration and washed with H$_2$O. Drying at 50-60° C. in high vacuum left the title compound (23.45 g, 93%) as a faintly yellow solid: $^1$H NMR (300 MHz, CDCl$_3$) δ 7.63 (d, J=8.0 Hz, 1H), 7.27-7.43 (m, 2H), 7.10-7.20 (m, 1H), 6.80 (s, 1H), 6.10-6.30 (m, 1H), 4.06 (s, 3H), 3.01 (d, J=4.9 Hz, 3H).

c) 1-Methyl-2-(methylaminomethyl)-1H-indole

A 3-liter 3-necked roundbottom flask equipped with overhead stirring was charged with N,1-dimethyl-1H-indole-2-carboxamide (23.45 g, 124.58 mmole) and anhydrous THF (170 mL). The solution was stirred while a solution of LiAlH$_4$ in THF (1.0 M, 250 mL, 250 mmole) was added via syringe. Gas was evolved during the addition of the first 50 mL of LiAlH$_4$ solution. When the addition was complete, the resulting light yellow solution was heated at gentle reflux. After 23 hr, the reaction was cooled in ice and quenched by the sequential dropwise addition of H$_2$O (9.5 mL), 15% NaOH (9.5 mL), and H$_2$O (28.5 mL). The mixture was stirred for 15 min, then was filtered through Celite®, and the filter pad was washed thoroughly with THF. The filtrate was concentrated and the residue was flash chromatographed on silica gel (10% MeOH/CHCl$_3$ containing 0.5% conc. NH$_4$OH). The title compound (20.17 g, 93%) was obtained as a light yellow oil: $^1$H NMR (300 MHz, CDCl$_3$) δ 7.56 (d, J=7.8 Hz, 1H), 7.02-7.35 (m, 3H), 6.38 (s, 1H), 3.88 (s, 2H), 3.75 (s, 3H), 2.49 (s, 3H).

Preparation 10

Preparation of
1-methyl-3-(methylaminomethyl)-1H-indole
(Method A)

a) Methyl 1-methyl-1H-indole-3-carboxylate

NaH (60% dispersion in mineral oil, 8.56 g, 214.0 mmole) was added portionwise, allowing for gas evolution, to a solution of methyl 1H-indole-3-carboxylate (25.00 g, 142.7 mmole) in DMF (350 mL) at 0° C. When the NaH addition was complete, methyl iodide (44.4 mL, 713.5 mmole) was added at 0° C. The reaction was stirred at 0° C. for 15 minutes then at RT overnight. The reaction was diluted with water and extracted with ethyl acetate. The combined extracts were dried over K$_2$CO$_3$ and concentrated to afford the title compound (26.00 g, 96%) as an orange solid: MS (ES) m/e 190 (M+H)$^+$.

b) N,1-Dimethyl-1H-indole-3-carboxamide

A suspension of methyl 1-methyl-1H-indole-3-carboxylate (4.30 g, 22.74 mmole) in 40% aqueous CH$_3$NH$_2$ (400 mL) was stirred at RT. The flask was tightly stoppered to keep the material inside the flask. As the reaction proceeded the product began to precipitate. The reaction was stirred at RT for 3 days, then was concentrated to remove approximately 200 mL of the solvent. The remaining residue was diluted with H$_2$O (500 mL), and the solid was collected by suction filtration and washed with H$_2$O. Flash chromatography on silica gel (ethyl acetate) gave the title compound (2.4 g, 56%) as a white solid: MS (ES) m/e 189 (M+H)$^+$.

c) 1-Methyl-3-(methylaminomethyl)-1H-indole

A solution of LiAlH$_4$ in THF (1.0 M, 5.20 mL, 5.2 mmole) was slowly added via syringe to a solution of N,1-dimethyl-1H-indole-3-carboxamide (0.50 g, 2.6 mmole) in anhydrous THF (15 mL). Gas was evolved during the addition of the first 2 mL of LiAlH$_4$ solution. When the addition was complete, the resulting light yellow solution was heated at gentle reflux. After 23 hr, the reaction was cooled in ice and quenched by the sequential dropwise addition of H$_2$O (0.5 mL), 1.0 N NaOH (0.5 mL), and H$_2$O (0.5 mL). The mixture was stirred for 15 min, then was filtered through Celite®, and the filter pad was washed thoroughly with THF. The filtrate was concentrated and the residue was flash chromatographed on silica gel (10% MeOH/CHCl$_3$ containing 0.5% conc. NH$_4$OH) to afford the title compound (0.30 g, 67%) as a light yellow oil: MS (ES) m/e 175 (M+

Preparation 11

Preparation of 1-methyl-3-(methylaminomethyl)-1H-indole (Method B)

To a solution of 1-methylindole-3-carboxaldehyde (10.0 g, 62.8 mmole) in MeOH (100 mL) was added a solution of 2.0 M $CH_3NH_2$ in MeOH (126 mL, 252.0 mmole). The reaction was stirred at RT for 2 hrs, then was concentrated to a light yellow oil. This oil was dissolved in EtOH (300 mL), and $NaBH_4$ (2.38 g, 62.8 mmole) was added. After 2 hrs the reaction was concentrated to a slurry and dissolved in 1.0 N NaOH (75 mL). The aqueous solution was extracted with $Et_2O$ (2×200 mL) and the combined organic fractions were dried over $Na_2SO_4$ and concentrated. Flash chromatography on silica gel (9:1 $CHCl_3$/MeOH containing 5% $NH_4OH$) and drying in high vacuum left the title compound (10.1 g, 92%) as a faintly yellow oil: MS (ES) m/e 175 $(M+H)^+$.

Preparation 12

Preparation of 2-methyl-3-(methylaminomethyl)indole

To a solution of 2-methylindole-3-carboxaldehyde (10.00 g, 62.84 mmole) in MeOH (100 mL) was added 2 M $CH_3NH_2$ in MeOH (200 mL). After stirring for 3 hours at RT, the reaction solution was concentrated to a yellow oil which solidified under vacuum. This solid was dissolved in ethanol (350 mL) and $NaBH_4$ (2.38 g, 62.8 mmole) was added. The reaction was stirred at RT for 6 hours, then was concentrated under vacuum. The remaining residue was diluted with saturated aqueous $Na_2CO_3$ (50 mL) and extracted with EtOAc (2×200 mL). The organic phase was separated, washed with brine, and dried over $Na_2SO_4$. Flash chromatography on silica gel (9:1 $CHCl_3$/MeOH containing 5% $NH_4OH$) and drying under high vacuum gave the title compound (6.88 g, 63%) as a faintly yellow viscous solid: MS (ES) m/e 175 $(M+H)^+$.

Preparation 13

Preparation of 1,3-dimethyl-2-(methylaminomethyl)-1H-indole a) 1,3-Dimethyl-1H-indole

To a stirred solution of 3-methylindole (15.0 g, 114 mmole) in dry DMF (200 mL) was added NaH (60% dispersion in oil, 5.0 g, 125 mmole) in portions. Gas evolution was observed. The mixture was stirred for 30 min, then iodomethane (8 mL, 129 mmole) was added in one portion. The reaction became exothermic and was cooled in an ice bath. After 16 hr at RT, the reaction was concentrated under vacuum and the residue was taken up in ethyl acetate. The solution was washed with $H_2O$ then with brine, dried ($MgSO_4$), and concentrated to dryness. Purification by short path distillation under vacuum (bp 88-92° C., 0.5 mmHg) gave the title compound (16.10 g, 97%) as a pale yellow oil: $^1H$ NMR (400 MHz, $CDCl_3$) δ 7.47 (d, J=7.9 Hz, 1H), 7.35 (d, J=8.2 Hz, 1H), 7.13 (t, 1H), 7.06 (s, 1H), 7.00 (t, 1H), 3.71 (s, 3H), 2.24 (s, 3H).

b) 1,3-Dimethyl-1H-indole-2-carboxaldehyde

To a stirred solution of phosphorus oxychloride (7.0 mL, 75 mmole) in DMF (25 mL) was added dropwise a solution of 1,3-dimethylindole (12.0 g, 83 mmole) in dry DMF (6.0 mL). The reaction was stirred at RT for 2 hr then was poured onto ice. The mixture was basified with a solution of NaOH (13.2 g, 330 mmole) in $H_2O$ (44 mL), then was extracted with $Et_2O$ (2×50 mL). The combined organic layers were washed with brine, dried ($MgSO_4$), and concentrated under vacuum. Flash chromatography on silica gel (10% ethyl acetate/hexanes) gave the title compound (13.03 g, 91%) as an off-white solid: LCMS (ES) m/e 174.2 $(M+H)^+$; $^1H$ NMR (400 MHz, $CDCl_3$) δ 10.16 (s, 1H), 7.68 (d, J=8.1 Hz, 1H), 7.42 (t, 1H), 7.32 (d, J=8.5 Hz, 1H), 7.15 (t, 1H), 4.04 (s, 3H), 2.63 (s, 3H).

c) 1,3-Dimethyl-2-(methylaminomethyl)-1H-indole

To 1,3-dimethyl-1H-indole-2-carboxaldehyde (13.0 g, 75 mmole) was added a solution of 2.0 M methylamine in methanol (150 mL, 300 mmole) and HOAc (4.3 mL, 75 mmole). The solution was stirred at RT for 4 hr, then was cooled to 0° C., and sodium cyanoborohydride (5.0 g, 80 mmole) was added portionwise over 5 min. The reaction was then allowed to warm to RT. After 16 hr, the reaction was concentrated under vacuum and the residue was taken up in $Et_2O$. The solution was washed with 1.0 N NaOH then with brine, dried ($Na_2SO_4$), and concentrated to dryness. Flash chromatography on silica gel (95:5 $CHCl_3$/methanol containing 5% $NH_4OH$) gave the title compound (7.34 g, 52%) as a yellow oil: $^1H$ NMR (400 MHz, $CDCl_3$) δ 7.53 (d, J=7.8 Hz, 1H), 7.26 (d, J=7.8 Hz, 1H), 7.20 (t, 1H), 7.09 (t, 1H), 3.88 (s, 2H), 3.76 (s, 3H), 2.46 (s, 3H), 2.32 (s, 3H), 1.36 (br s, 1H).

Preparation 14

Preparation of 1-methyl-3-(methylaminomethyl)-1H-pyrrolo[2,3-b]pyridine a) 1-Methyl-1H-pyrrolo[2,3-b]pyridine

According to the procedure of Preparation 13 (a), except substituting 7-azaindole (2.28 g, 1.83 mmole) for the 3-methylindole, the title compound (1.4 g, 58%) was prepared as a yellow oil: MS (ES) m/e 133 $(M+H)^+$.

b) 1-Methyl-1H-pyrrolo[2,3-b]pyridine-3-carboxaldehyde

According to the procedure of Preparation 13 (b), except substituting 1-methyl-1H-pyrrolo[2,3-b]pyridine (0.7 g, 5.3 mmole) for the 1,3-dimethylindole, the title compound (0.4 g, 47%) was prepared as a white solid: MS (ES) m/e 161 $(M+H)^+$.

c) 1-Methyl-3-(methylaminomethyl)-1H-pyrrolo[2,3-b]pyridine

According to the procedure of Preparation 13 (c), except substituting 1-methyl-1H-pyrrolo[2,3-b]pyridine-3-carboxaldehyde (0.4 g, 2.5 mmole) for the 1,3-dimethyl-1H-indole-2-carboxaldehyde, the title compound (0.2 g, 45%) was prepared as a yellow oil: MS (ES) m/e 176 $(M+H)^+$.

Preparation 15

Preparation of 2-methyl-3-(methylaminomethyl)benzo[b]thiophene a) 2-Methylbenzo[b]thiophene-3-carboxaldehyde $SnCl_4$ (20 mL, 67 mmole) was added over 5 min to a stirred solution of 2-methylbenzo[b]thiophene (5.0 g, 33.7 mmole)

in CH$_2$Cl$_2$ (75 mL) at 0° C. under argon. After 15 minutes, dichloromethyl methyl ether (3.7 mL, 41 mmole) was added. The reaction became a yellowish colored suspension. The reaction was allowed to warm to RT and stirred for 16 h, then was poured onto ice water (200 mL). The aqueous mixture was acidified with 1.0 N HCl (100 mL) and stirred until the suspension dissolved. The organic phase was separated, dried (MgSO$_4$), and concentrated under vacuum. Purification by flash chromatography on silica gel (10% ethyl acetate/hexane) gave the title compound (5.83 g, 98%) as a white crystalline solid: $^1$H NMR (400 MHz, CDCl$_3$) δ 10.38 (s, 1H), 8.61 (d, J=8.1 Hz, 1H), 7.77 (d, J=8.0 Hz, 1H), 7.48 (t, 1H), 7.39 (t, 1H), 2.93 (s, 3H)

b) 2-Methyl-3-(methylaminomethyl)benzo[b]thiophene

According to the procedures of Preparation 1, except substituting 2-methylbenzo[b]thiophene-3-carboxaldehyde (5.0 g, 28.4 mmole) for 1-methylindole-3-carboxaldehyde, the title compound (4.89 g, 90%) was prepared as an oil which solidified in the freezer: $^1$H NMR (400 MHz, CDCl$_3$) δ7.78 (d, J=7.9 Hz, 1H), 7.75 (d, J=7.9 Hz, 1H), 7.37 (t, 1H), 7.29 (t, 1H), 3.95 (s, 2H), 2.60 (s, 3H), 2.50 (s, 3H)

Preparation 16

Preparation of 3-(methylaminomethyl)-1H-indole a) 3-(Methylaminomethyl)-1H-indole To a solution of indole-3-carboxaldehyde (5.4 g, 34.1 mmole) in MeOH (30 mL) was added a solution of 2.0 M CH$_3$NH$_2$ in MeOH (51.3 mL, 102.6 mmole). The reaction was stirred at RT overnight, then was concentrated to a light yellow oil. This oil was dissolved in EtOH (40 mL), and NaBH$_4$ (1.3 g, 34.1 mmole) was added. After 16 hrs the reaction was concentrated to a slurry and dissolved in 10% Na$_2$CO$_3$ (100 mL). The aqueous solution was extracted with EtOAc (2×200 mL) and the combined organic fractions were dried over Na$_2$SO$_4$ and concentrated. Drying in high vacuum left the title compound (5.2 g, 94%) as a faintly yellow oil: MS (ES) m/e 161 (M+H)$^+$.

Preparation 17

Preparation of 1-benzyl-3-(methylaminomethyl)-1H-indole a) 3-[N-(Benzyloxycarbonyl)-N-methylaminomethyl]-1H-indole N-(Benzyloxycarbonyloxy)succinimide (8.9 g, 35.7 mmole) was added to a solution of 3-(methylaminomethyl)-1H-indole (5.2 g, 32.5 mmole), from Preparation 16, and triethylamine (5.0 mL, 65.7 mmole) in DMF (100 mL) at RT. The reaction was stirred overnight then was concentrated in vacuo. The residue was diluted with water and the mixture was extracted with ethyl acetate. The combined extracts were dried over Na$_2$SO$_4$ and concentrated. Flash chromatography on silica gel (33% ethyl acetate/hexanes) gave the title compound (7.0 g, 74%) as an off-white solid: MS (ES) m/e 295 (M+H)$^+$.

b) 3-[N-(Benzyloxycarbonyl)-N-methylaminomethyl]-1-benzyl-1H-indole

NaH (60% dispersion in mineral oil, 0.15 g, 3.8 mmole) was added portionwise, allowing for gas evolution, to a solution of 3-[N-(benzyloxycarbonyl)-N-methylaminomethyl]-1H-indole (0.7 g, 2.5 mmole) in DMF (25 mL) at 0° C. When the NaH addition was complete, benzyl bromide (1.2 mL, 10.0 mmole) was added at 0° C. The reaction was stirred at 0° C. for 15 minutes then at RT overnight. The reaction was diluted with water and extracted with ethyl acetate. The combined extracts were dried over Na$_2$SO$_4$ and concentrated. Flash chromatography on silica gel (33% ethyl acetate/hexanes) gave the title compound (0.9 g, 93%) as an off white solid: MS (ES) m/e 385 (M+H)$^+$.

c) 1-Benzyl-3-(methylaminomethyl)-1H-indole

3-[N-(Benzyloxycarbonyl)-N-methylaminomethyl]-1-benzyl-1H-indole (0.9 g, 2.3 mmole) was added to a suspension of Pearlman's catalyst (about 0.30 g) in MeOH at RT in a Parr flask. The reaction was placed under 50 p.s.i. of H$_2$ and shaken for 5 hr. The mixture was filtered through Celite® and the filter pad was washed with MeOH. The filtrate was concentrated to afford the title compound (0.5 g, 86%) as a light yellow solid: MS (ES) m/e 251 (M+H)$^+$.

Preparation 18

Preparation of 2,3-dihydro-8-(methylaminomethyl)-1H-3a-azacyclopenta[α]indene a) 2,3-Dihydro-1H-3a-azacyclopenta[α]indene-8-carboxaldehyde According to the procedure of Preparation 13 (b), except substituting 2,3-dihydro-1H-3a-azacyclopenta[α]indene (J. Med. Chem. 1965, 8, 700; 0.24 g, 1.53 mmole) for the 1,3-dimethylindole, the title compound (0.17 g, 60%) was prepared as a yellow solid: MS (ES) m/e 186 (M+H)$^+$.

b) 2,3-Dihydro-8-(methylaminomethyl)-1H-3a-azacyclopenta[α]indene

According to the procedure of Preparation 13 (c), except substituting 2,3-dihydro-1H-3a-azacyclopenta[α]indene-8-carboxaldehyde (0.17 g, 0.92 mmole) for the 1,3-dimethyl-1H-indole-2-carboxaldehyde, the title compound (0.1 g, 54%) was prepared as a yellow oil: MS (ES) m/e 201 (M+H)$^+$.

Preparation 19

Preparation of 1,4-dimethyl-3-(methylaminomethyl)-1H-indole a) 1,4-Dimethyl-1H-indole According to the procedure of Preparation 9 (a), except substituting 4-methylindole for ethyl indole-2-carboxylate, the title compound (1.5 g, 94%) was prepared as an amber oil: MS (ES) m/e 146.2 (M+H)$^+$.

b) 1,4-Dimethyl-1H-indole-3-carboxaldehyde

According to the procedure of Preparation 9 (b), except substituting 1,4-dimethyl-1H-indole for 1,3-dimethylindole, the title compound (1.8 g, 95%) was prepared as an amber oil: MS (ES) m/e 174.2 (M+H)$^+$.

c) 1,4-Dimethyl-3-(methylaminomethyl)-1H-indole

According to the procedure of Preparation 11, except substituting 1,4-dimethyl-1H-indole-3-carboxaldehyde for 1,3-dimethyl-1H-indole-1-carboxaldehyde, the title compound (1.9 g, 99%) was prepared as an oil: MS (ES) m/e 189.0 $(M+H)^+$.

Preparation 20

Preparation of (E)-3-(2-oxo-2,3-dihydro-1H-indol-5-yl)acrylic acid hydrochloride salt a) 3,3,5-Tribromo-1,3-dihydropyrrolo[2,3-b]pyridin-2-one

To a solution of 7-azaindole (5.0 g, 42.3 mmole) in $H_2O$ (210 mL) and tert-butanol (210 mL) at RT was added $Br_2$ (27 mL, 529.0 mmole) over 20 minutes. The reaction was stirred for 12 hr at RT and concentrated to an aqueous slurry. The reaction contents were made basic with solid $NaHCO_3$ and the remaining solid was filtered and washed with $H_2O$. The filtered mass was dried under high vacuum to give the title compound (14.0 g, 89%) as a brown solid: MS (ES) m/e 370 $(M+H)^+$.

b) 5-Bromo-1,3-dihydropyrrolo[2,3-b]pyridin-2-one

To a stirred solution of 3,3,5-tribromo-1,3-dihydropyrrolo[2,3-b]pyridin-2-one (2.0 g, 5.4 mmole) in acetic acid (50 mL) at RT was added Zn metal. The reaction became exothermic and was cooled by the use of an ice bath during the initial 30 minutes. After 5 hr the reaction was filtered through Celite®, and the filter pad was washed with EtOAc. The filtrate was concentrated under vacuum and neutralized with saturated aqueous $NaHCO_3$ solution. The neutralized aqueous filtrate was then extracted with EtOAc (2×200 mL), and the combined organic extracts were dried over $Na_2SO_4$ and concentrated to a solid. The solid was washed with hexanes and dried under high vacuum to give the title compound (0.36 g, 32%): MS (ES) m/e 215 $(M+H)^+$. This was used without further purification.

c) tert-Butyl (E)-3-(2-oxo-2,3-dihydro-1H-indol-5-yl)acrylate

A solution of 5-bromo-1,3-dihydropyrrolo[2,3-b]pyridin-2-one (2.0 g, 9.49 mmole), tert-butyl acrylate (1.8 g, 14.1 mmole), $Pd(OAc)_2$ (0.32 g, 1.4 mmole), tri-ortho-tolylphosphine (0.57 g, 1.9 mmole), and diisopropylethylamine (4.9 mL, 28.2 mmole) in propionitrile (100 mL) and DMF (10 mL) was heated at reflux overnight. The dark mixture was filtered through Celite®, and the filtrate was concentrated. Flash chromatography on silica (9:1 $CHCl_3/CH_3OH$ containing 5% $NH_4OH$) gave the title compound (0.80 g, 33%) as a light yellow solid. MS (ES) m/e 261 $(M+H)^+$.

d) (E)-3-(2-Oxo-2,3-dihydro-1H-indol-5-yl)acrylic acid hydrochloride salt

To a stirred solution of tert-butyl (E)-3-(2-oxo-2,3-dihydro-1H-indol-5-yl)acrylate (0.80 g, 3.1 mmole) in $CH_2Cl_2$ (50 mL) at RT was added trifluoroacetic acid (20 mL). After 1 hr the reaction solution was concentrated and the residue was dried under vacuum. An HCl solution (20 mL, 4 M in dioxane) was added and the mixture was concentrated under vacuum. The remaining solid was triturated with diethyl ether and filtered giving the title compound (0.74 g, 33%) as a white solid: MS (ES) m/e 205 $(M+H-HCl)^+$.

Preparation 21

Preparation of 1-ethyl-3-(methylaminomethyl)-1H-indole a) 3-[N-(Benzyloxycarbonyl)-N-methylaminomethyl]-1-ethyl-1H-indole

According to the procedure of Preparation 17 (b), except substituting ethyl iodide (0.92 mL, 11.44 mmole) for the benzyl bromide, the title compound (0.90 g, 98%) was prepared as a white solid: MS (ES) m/e 323 $(M+H)^+$.

b) 1-Ethyl-3-(methylaminomethyl)-1H-indole

According to the procedure of Preparation 17 (c), except substituting 3-[N-(benzyloxycarbonyl)-N-methylaminomethyl]-1-ethyl-1H-indole (0.90 g, 2.80 mmole) for the 3-[N-(benzyloxycarbonyl)-N-methylaminomethyl]-1-benzyl-1H-indole, the title compound (0.50 g, 94%) was prepared as a white solid: MS (ES) n/e 189 $(M+H)^+$.

Preparation 22

Preparation of 1-isopropyl-3-(methylaminomethyl)-1H-indole a) 3-[N-(Benzyloxycarbonyl)-N-methylaminomethyl]-1-isopropyl-1H-indole

According to the procedure of Preparation 17 (b), except substituting isopropyl iodide (1.34 mL, 11.84 mmole) for the benzyl bromide, the title compound (0.99 g, 99%) was prepared as a white solid: MS (ES) m/e 337 $(M+H)^+$.

b) 1-ethyl-3-(methylaminomethyl)-1H-indole

According to the procedure of Preparation 17 (c), except substituting 3-[N-(Benzyloxycarbonyl)-N-methylaminomethyl]-1-isopropyl-1H-indole (0.99 g, 2.98 mmole) for the 3-[N-(Benzyloxycarbonyl)-N-methylaminomethyl]-1-benzyl-1H-indole, the title compound (0.49 g, 82%) was prepared as a white solid: MS (ES) ml/e 405 $(2M+H)^+$.

Preparation 23

Preparation of 1-acetyl-3-(methylaminomethyl)-1H-indole a) 1-Acetyl-3-(methylaminomethyl)indole

According to the procedure of Preparation 16 (a), except substituting N-acetyl-3-indole carboxaldehyde (1.33 g, 7.10 mmole), the title compound (1.40 g, 99%) was prepared as a light yellow oil: MS (ES) m/e 203 $(M+H)^+$.

Preparation 24

Preparation of N-(1H-indol-3-ylmethyl)-N-methylacrylamide a) N-(1H-indol-3-ylmethyl)-N-methylacrylamide

Acryloyl chloride (0.33 mL, 4.10 mmole) was added to a solution of 3-(methylaminomethyl)-1H-indole (0.60 g, 3.70 mmole) and $Et_3N$ (1.03 mL, 7.40 mmole) in $CH_2Cl_2$ (30 mL)

at 0° C. The reaction was held at 0° C. for ten minutes, then was stirred overnight at RT. The solution was concentrated in vacuo and the residue was diluted with water. The solution was extracted with ethyl acetate, and the combined organic extracts were washed with brine and dried over $Na_2SO_4$. The title compound (0.64 g, 80%) was obtained as a light yellow solid: MS (ES) m/e 215 (M+H)$^+$.

Preparation 25

Preparation of N-(1-benzyl-1H-indol-3-ylmethyl)-N-methylacrylamide a) N-(1-Benzyl-1H-indol-3-ylmethyl)-N-methylacrylamide According to the procedure of Preparation 24 (a), except substituting 1-benzyl-3-(methylaminomethyl)-1H-indole (1.30 g, 5.20 mmole) for of 3-(methylaminomethyl)-1H-indole, the title compound (1.40 g, 89%) was a brown solid: MS (ES) m/e 305 (M+H)$^+$.

Preparation 26

Preparation of N-[1-(2-dimethylamino)-1H-indol-3-ylmethyl]-N-methylacrylamide a) N-[1-(2-dimethylamino)-1H-indol-3-ylmethyl]-N-methylacrylamide According to the procedure of Preparation 25 (a), except substituting [1-(2-dimethylamino)]-3-(methylaminomethyl)-1H-indole (1.00 g, 2.74 mmole) for of 3-(methylaminomethyl)-1H-indole, the title compound (0.50 g, 79%) was a yellow solid: MS (ES) m/e 463 (2M+H)$^+$.

Preparation 27

Preparation of 3-bromo-5,6,7,9-tetrahydro-pyrido[2,3-b]azepin-8-one a) 8-Benzylidene-5,6,7,8-tetrahydro-quinoline Benzaldehyde (3.59 mL, 35.30 mmole) was added to a solution of 5,6,7,8-tetrahydro-quinoline (4.70 g, 35.30 mmole) in acetic anhydride (25 mL), and the solution was heated to reflux under a nitrogen atmosphere. After overnight at reflux, the reaction was concentrated in vacuo. The residue was diluted with water and extracted with ethyl acetate. The combined organic extracts were washed with brine, dried over $Na_2SO_4$, and concentrated. The residue was purified by flash chromatography on silica gel (33% EtOAc/hexanes) to give the title compound (4.50 g, 58%) as a waxy yellow solid after drying in vacuo: MS (ES) m/e 222 (M+H)$^+$.

b) 6,7-Dihydro-5H-quinolin-8-one

A solution of 8-benzylidene-5,6,7,8-tetrahydro-quinoline (4.30 g, 19.4 mmole) in $CH_2Cl_2$ (150 mL) was reacted with ozone at −78° C. for 30 minutes. Dimethyl sulfide (5 mL) was added, and the reaction was warmed to RT and stirred overnight. The mixture was concentrated in vacuo and the residue was purified by flash chromatography on silica gel (EtOAc). The title compound (2.20 g, 79%) was obtained as an off-white solid after drying in vacuo: MS (ES) m/e 148 (M+H)$^+$.

c) 6,7-Dihydro-5H-quinolin-8-one oxime

According to the reported procedure (J. Het. Chem. 1978, 15, 249-251), 6,7-dihydro-5H-quinolin-8-one was reacted with hydroxylamine hydrochloride to afford the title compound (2.40 g, 96%) as a white solid after drying in vacuo: MS (ES) m/e 163 (M+H)$^+$.

d) 6,7-Dihydro-5H-quinolin-8-one, O-toluenesulfonyloxime

According to the reported procedure (J. Het. Chem. 1978, 15, 249-251), 6,7-dihydro-5H-quinolin-8-one oxime was reacted with p-toluenesulfonyl chloride to afford the title compound (4.00 g, 85%) as a white solid after drying in vacuo: MS (ES) m/e 317 (M+H)$^+$.

e) 5,6,7,9-Tetrahydro-pyrido[2,3-b]azepin-8-one

According to the reported procedure (J. Het. Chem. 1978, 15, 249-251), 6,7-dihydro-5H-quinolin-8-one, O-toluenesulfonyloxime was reacted to afford the title compound (1.00 g, 50%) as a white solid after drying in vacuo: MS (ES) m/e 163 (M+H)$^+$.

f) 3-Bromo-5,6,7,9-tetrahydro-pyrido[2,3-b]azepin-8-one

A 10% solution of bromine (0.57 mL, 11.1 mmole) in $CH_2Cl_2$ was added dropwise over 1 hr to a solution of 5,6,7,9-tetrahydro-pyrido[2,3-b]azepin-8-one (1.20 g, 7.4 mmole) in $CH_2Cl_2$ at RT. The mixture was stirred at RT overnight, then was concentrated in vacuo. The residue was diluted with 10% $Na_2CO_3$ and extracted with EtOAc. The combined organics were dried over $Na_2SO_4$ and concentrated. Flash chromatography on silica gel (EtOAc) gave the title compound (1.00 g, 56%) as a light yellow solid after drying in vacuo: MS (ES) m/e 241/243.

Preparation 28

Preparation of 5-bromo-2-(methylaminocarbonylmethyl)aminopyridine a) 5-Bromo-2-(tert-butoxycarbonyl)aminopyridine To a solution of 2-amino-5-bromopyridine (27.56 g, 159 mmole) in THF (150 mL) was added di-tert-butyl dicarbonate (38 g, 174 mmole). The reaction was gradually heated to reflux. Vigorous gas evolution was observed initially, which subsided after approximately 10 min. After 18 hr at reflux, the reaction was concentrated to dryness. The residue was triturated with 1:1 $Et_2O$/petroleum ether, filtered and dried under vacuum to give the title compound (34.79 g, 80%) as a white solid: $^1$H NMR (400 MHz, $CDCl_3$) □ 8.49 (s, 1H), 8.37 (dd, 1H), 7.94 (d, J=9.0 Hz, 1H), 7.77 (dd, 1H), 1.57 (s, 9H).

b) 5-Bromo-2-[N-(tert-butoxycarbonyl)-N-(methoxycarbonylmethyl)amino]pyridine

To a solution of 5-bromo-2-(tert-butoxycarbonyl)aminopyridine (25.0 g, 91.5 mmole) in DMF (400 mL) was added portionwise with stirring a 60% dispersion of NaH in mineral oil (4.0 g, 100 mmole). The reaction was stirred for 15 min, then methyl bromoacetate (15 mL, 158.5 mmole) was added dropwise over 15 min. After stirring for 18 h at room temperature the reaction was concentrated to dryness. The remaining residue was taken up in EtOAc (200 mL) and $H_2O$ (200 mL) and filtered to remove insoluble material. The EtOAc phase was separated, washed with brine, dried ($Na_2SO_4$) and concentrated to dryness. Purification by flash chromatography on silica gel (10% EtOAc/Hexane) gave the title compound (16.56 g, 50%): $^1$H NMR (400 MHz, CDCl$_3$) δ 8.33 (s, 1H), 7.73 (d, J=2.5 Hz, 1H), 7.71 (d, J=2.5 Hz, 1H), 4.69 (s, 2H), 3.75 (s, 3H), 1.51 (s, 9H).

c) 5-Bromo-2-(methoxycarbonylmethyl)aminopyridine

A 50% solution of TFA in CH$_2$Cl$_2$ (200 mL) was added to 5-bromo-2-[N-(tert-butoxycarbonyl)-N-(methoxycarbonylmethyl)amino]pyridine (16.5 g, 46 mmole). After stirring for 45 min the reaction was concentrated to dryness, and the residue was diluted with 1.0 N Na$_2$CO$_3$ (300 mL). The mixture was extracted with EtOAc (300 mL), and the organic layer was washed with brine, dried (Na$_2$SO$_4$), and concentrated to dryness under vacuum. The title compound (11.32 g, 100%) was obtained as a white solid: $^1$H NMR (400 MHz, CDCl$_3$) ☐ 8.13 (d, J=2.3 Hz, 1H), 7.48 (dd, 1H), 6.40 (d, J=8.8 Hz, 1H), 4.95 (br s, 1H), 4.12 (d, J=5.5 Hz, 2H), 3.78 (s, 3H).

d) 5-Bromo-2-(methylaminocarbonylmethyl)aminopyridine

A solution of 2.0 M methylamine in MeOH (75 mL) was added to 5-bromo-2-(methoxycarbonylmethyl)aminopyridine (2.9 g, 12 mmole). The reaction was stirred for 24 h then was concentrated to dryness. The residue was triturated with 10% petroleum ether/Et$_2$O (100 mL), then was collected and dried under vacuum to give the title compound (2.96 g, 100%) as an off-white solid: MS (ES) m/e 244.2 (M+H)$^+$.

Preparation 29

Preparation of methyl 2-amino-5-bromonicotinate a) Methyl 2-aminonicotinate

Concentrated H$_2$SO$_4$ (20 mL, 360 mmole) was added dropwise over 5 minutes to a suspension of 2-aminonicotinic acid (25 g, 181 mmole) in MeOH (400 mL), and the mixture was heated at reflux; a homogeneous solution formed within 5 min. After 72 h, the reaction was cooled to room temperature and concentrated under vacuum. The residue was basified with 1.0 N Na$_2$CO$_3$ (500 mL) (Gas evolution!) and extracted with EtOAc (500 mL). The organic layer was washed with brine, dried (Na$_2$SO$_4$), and concentrated to dryness to give the title compound (19.6 g, 71%) as a white solid: $^1$H NMR (400 MHz, CDCl$_3$) ☐ 8.22 (dd, 1H), 8.13 (dd, 1H), 6.63 (dd, 1H), 6.30 (br s, 2H), 3.89 (s, 3H).

b) Methyl 2-amino-5-bromonicotinate

Bromine (0.7 mL, 14 mmole) was added dropwise to a stirred solution of methyl 2-aminonicotinate (2.0 g, 13 mmole) in HOAc (50 mL). A suspension formed within 30 min. The reaction was allowed to stir at room temperature for 2 h, then was concentrated under vacuum. The residue was triturated with 1.0 N Na$_2$CO$_3$ (50 mL) and the solid was collected by suction filtration. The solid was washed with H$_2$O (50 mL) and dried under vacuum to give the title compound (2.95 g, 98%) as a pale yellow solid: $^1$H NMR (400 MHz, CDCl$_3$) δ 8.24 (d, J=2.5 Hz, 1H), 8.23 (d, J=2.5 Hz, 1H), 6.40 (br s, 2H), 3.90 (s, 3H).

Preparation 30

Preparation of (E)-3-[6-[N-(methoxycarbonylmethyl)amino]pyridin-3-yl]acrylic acid hydrochloride salt a) tert-Butyl (E)-3-[6-[N-(methoxycarbonylmethyl)amino]pyridin-3-yl]acrylate A solution of 5-bromo-2-(methoxycarbonylmethyl)aminopyridine (4.69 g, 19.1 mmole, from Preparation 28 (c)), tert-butyl acrylate (11.2 mL, 76.5 mmole), DIEA (6.7 mL, 38.5 mmole), Pd(OAc)$_2$ (215 mg, 1 mmole), and P(o-tol)$_3$ (583 mg, 2 mmole) in propionitrile (100 mL) was purged with Ar, then was heated at reflux. After 18 h, the reaction was allowed to cool to room temperature then was concentrated to dryness. The residue was purified by flash chromatography on silica gel (40% EtOAc/hexane) to give the title compound (5.21 g, 93%) as a white solid: $^1$H NMR (400 MHz, CDCl$_3$) δ 8.19 (s, 1H), 7.62 (dd, 1H), 7.47 (d, J=16.0 Hz, 1H), 6.48 (d, J=8.7 Hz, 1H), 6.17 (d, J=15.9 Hz, 1H), 5.21 (br s, 1H), 4.20 (d, J=5.4 Hz, 2H), 3.79 (s, 3H), 1.52 (s, 1H).

b) (E)-3-[6-[N-(Methoxycarbonylmethyl)amino]pyridin-3-yl]acrylic acid hydrochloride salt A solution of 50% TFA in CH$_2$Cl$_2$ (75 mL) was added to tert-butyl (E)-3-[6-[N-(methoxycarbonylmethyl)amino]pyridin-3-yl]acrylate (5.20 g, 17.8 mmole). The reaction was stirred at room temperature for 45 min then was concentrated under vacuum. The residue was taken up in 4.0 N HCl in dioxane (75 mL), stirred for 5 min, then concentrated to dryness under vacuum. The remaining solid was triturated with 1:1 Et$_2$O/petroleum ether, filtered and dried under vacuum to give the title compound (4.87 g, 100%) as a white solid: MS (ES) m/e 237.2 (M+H)$^+$.

Preparation 31

Preparation of (E)-3-(7-oxo-5,6,7,8-tetrahydro-1,8-naphthyridin-3-yl)acrylic acid hydrochloride salt a) tert-Butyl (E)-3-(7-oxo-5,6,7,8-tetrahydro-1,8-naphthyridin-3-yl)acrylate A solution of 6-bromo-3,4-dihydro-1H-1,8-naphthyridin-2-one (12.99 g, 57 mmole), tert-butyl acrylate (34 mL, 232 mmole), DIEA (21.2 mL, 122 mmole), Pd(OAc)$_2$ (1.3 g, 5.8 mmole) and P(o-tol)$_3$ (3.5 g, 11.5 mmole) in propionitrile (200 mL) and DMF (50 mL) was purged with Ar, then was heated at reflux. After 18 h the reaction was allowed to cool to room temperature and was concentrated to dryness. The residue was purified by flash chromatography on silica gel (2-4% MeOH/CHCl$_3$). The resulting residue was triturated with 1:1 Et$_2$O/petroleum ether, collected, and dried, and the resulting material was triturated with 1:1 MeOH/H$_2$O, collected, and dried, to give the title compound (7.09 g, 45%) as an off-white solid: $^1$H NMR (400 MHz, d$_6$-DMSO) δ 10.70 (s, 1H), 8.35 (d, J=2.0 Hz, 1H), 8.04 (s, 1H), 7.50 (d, J=16.0 Hz, 1H), 6.51 (d, J=16.0 Hz, 1H), 2.89 (t, 2H), 2.53 (t, 2H), 1.48 (s, 9H); MS (ES) m/e 275.2 (M+H)$^+$.

b) (E)-3-(7-oxo-5,6,7,8-tetrahydro-1,8-naphthyridin-3-yl)acrylic acid hydrochloride salt To tert-butyl (E)-3-(7-oxo-5,6,7,8-tetrahydro-1,8-naphthyridin-3-yl)acrylate (7.0 g, 25.5 mmole) was added 1:1

TFA/CH$_2$Cl$_2$ (100 mL). The reaction was stirred for 30 min, then was concentrated under vacuum. The residue was suspended in 4 N HCl/dioxane (100 mL), triturated, and concentrated to dryness. The resulting solid was triturated with Et$_2$O, collected, and dried under vacuum to give the title compound (6.55 g, 100%) as a off-white solid: $^1$H NMR (400 MHz, d$_6$-DMSO) □ 10.72 (s, 1H), 8.35 (d, J=2.0 Hz, 1H), 8.04 (s, 1H), 7.54 (d, J=16.0 Hz, 1H), 6.51 (d, J=16.0 Hz, 1H), 2.91 (t, 2H), 2.53 (t, 2H); MS (ES) m/e 219.0 (M+H)$^+$.

Preparation 32

Preparation of N-methyl-N-(1-methyl-1H-pyrrolo[2,3-b]pyridin-ylmethyl)acrylamide A solution of acryloyl chloride (0.43 g, 5.58 mmole) in CH$_2$Cl$_2$ (10 mL) was added dropwise with stirring to a solution of 1-methyl-3-(methylaminomethyl)-1H-pyrrolo[2,3-b]pyridine (0.93 g, 5.28 mmole) and triethylamine (0.8 mL, 5.8 mmole) in CH$_2$Cl$_2$ (40 mL) at 0° C. under N$_2$. The reaction was allowed to warm to RT and stir for 1 hr, then was concentrated in vacuo. The residue was dissolved in 10% NaOH and extracted with CH$_2$Cl$_2$ (3×20 mL). The extracts were dried (MgSO$_4$), filtered, and concentrated. The residual oil was flash chromatographed on silica gel (5% MeOH/CH$_2$Cl$_2$) to give the title compound (1.0 g, 80%) as a colorless oil: MS (ES) m/e 216 (M+H)$^+$.

Preparation 33

Preparation of 7-fluoro-1-methyl-3-(methylaminomethyl)-1H-indole a) 7-Fluoro-1H-indole-3-carboxaldehyde According to the procedure of Preparation 11 (b), except substituting 7-fluoroindole (0.5 g, 3.7 mmole) for the 1,3 dimethylindole, the title compound (0.5 g, 83%) was prepared as a waxy solid: MS (ES) m/e 164 (M+H)$^+$.

b) 7-Fluoro-1-methyl-1H-indole-3-carboxaldehyde

According to the procedure of Preparation 9 (a), except substituting 7-fluoro-1H-indole-3-carboxaldehyde (0.5 g, 3.1 mmole) for the ethyl indole-2-carboxylate, the title compound (0.23 g, 43%) was prepared as a viscous oil: MS (ES) m/e 178 (M+H)$^+$.

c) 7-Fluoro-1-methyl-3-(methylaminomethyl)-1H-indole

According to the procedure of Preparation 11 (c), except substituting 7-fluoro-1-methyl-1H-indole-3-carboxaldehyde (0.23, 1.3 mmole) for the 1,3-dimethyl-1H-indole-2-carboxaldehyde, the title compound (0.18 g, 72%) was prepared as a viscous oil: MS (ES) m/e 193 (M+H)$^+$.

Preparation 34

Preparation of 6-fluoro-1-methyl-3-(methylaminomethyl)-1H-indole a) 6-Fluoro-1H-indole-3-carboxaldehyde According to the procedure of Preparation 11 (b), except substituting 6-fluoroindole (0.5 g, 3.7 mmole) for the 1,3-dimethylindole, the title compound (0.3 g, 50%) was prepared as a waxy solid: MS (ES) m/e 164 (M+H)$^+$.

b) 6-Fluoro-1-methyl-1H-indole-3-carboxaldehyde

According to the procedure of Preparation 9 (a), except substituting 6-fluoro-1H-indole-3-carboxaldehyde (0.3 g, 1.8 mmole) for the ethyl indole-2-carboxylate, the title compound (0.3 g, 94%) was prepared as a viscous oil: MS (ES) m/e 178 (M+H)$^+$.

c) 6-Fluoro-1-methyl-3-(methylaminomethyl)-1H-indole

According to the procedure of Preparation 11 (c), except substituting 6-fluoro-1-methyl-1H-indole-3-carboxaldehyde (0.3 g, 1.69 mmole) for the 1,3-dimethyl-1H-indole-2-carboxaldehyde, the title compound (0.11 g, 35%) was prepared as a viscous oil: MS (ES) m/e 193 (M+H)$^+$.

Preparation 35

Preparation of 5-fluoro-1-methyl-3-(methylaminomethyl)-1H-indole a) 5-Fluoro-1H-indole-3-carboxaldehyde According to the procedure of Preparation 11 (b), except substituting 5-fluoroindole (0.5 g, 3.7 mmole) for the 1,3-dimethylindole, the title compound (0.3 g, 50%) was prepared as a waxy solid: MS (ES) m/e 164 (M+H)$^+$.

b) 5-Fluoro-1-methyl-1H-indole-3-carboxaldehyde

According to the procedure of Preparation 9 (a), except substituting 5-fluoro-1H-indole-3-carboxaldehyde (0.3 g, 1.8 mmole) for the ethyl indole-2-carboxylate, the title compound (0.16 g, 50%) was prepared as a viscous oil: MS (ES) m/e 178 (M+H)$^+$.

c) 5-Fluoro-1-methyl-3-(methylaminomethyl)-1H-indole

According to the procedure of Preparation 11 (c), except substituting 5-fluoro-1-methyl-1H-indole-3-carboxaldehyde (0.3 g, 1.69 mmole) for the 1,3 dimethyl-1H-2-carboxaldehyde, the title compound (0.11 g, 35%) was prepared as a viscous oil: MS (ES) m/e 193 (M+H)$^+$.

Preparation 36

Preparation of 4-fluoro-1-methyl-3-(methylaminomethyl)-1H-indole a) 4-Fluoro-1H-indole-3-carboxaldehyde According to the procedure of Preparation 11 (b), except substituting 4-fluoroindole (0.5 g, 3.7 mmole) for the 1,3-dimethylindole, the title compound (0.41 g, 68%) was prepared as a waxy solid: MS (ES) m/e 164 (M+H)$^+$.

b) 4-Fluoro-1-methyl-1H-indole-3-carboxaldehyde

According to the procedure of Preparation 9 (a), except substituting 4-fluoro-1H-indole-3-carboxaldehyde (0.41 g, 2.5 mmole) for the ethyl-indole-2-carboxylate, the title compound (0.24 g, 54%) was prepared as a viscous oil: MS (ES) m/e 178 (M+H)$^+$.

c) 4-Fluoro-1-methyl-3-(methylaminomethyl)-1H-indole

According to the procedure of Preparation 11 (c), except substituting 4-fluoro-1-methyl-1H-indole-3-carboxaldehyde (0.3 g, 1.69 mmole) for the 1,3-dimethyl-1H-indole-2-carboxaldehyde, the title compound (0.2 g, 77%) was prepared as a viscous oil: MS (ES) m/e 193 (M+H)$^+$.

Preparation 37

Preparation of
(1-ethyl-5-fluoro-3-(methylaminomethyl)-1H-indole a) 5-Fluoro-1H-indole-3-carboxaldehyde According to the procedure of Preparation 11 (b), except substituting 5-fluoroindole (0.5 g, 3.7 mmole) for the 1,3-dimethylindole, the title compound (0.3 g, 50%) was prepared as a waxy solid: MS (ES) m/e 164 (M+H)$^+$.

b) 1-Ethyl-5-fluoro-1H-indole-3-carboxaldehyde

According to the procedure of Preparation 9 (a), except substituting 5-fluoro-1H-indole-3-carboxaldehyde (0.41 g, 2.5 mmole) for the ethylindole-2-carboxylate, the title compound (0.20 g, 57%) was prepared as a viscous oil: MS (ES) m/e 191 (M+H)$^+$.

c)
1-Ethyl-5-fluoro-3-(methylaminomethyl)-1H-indole

According to the procedure of Preparation 11 (c), except substituting 1-ethyl-5-fluoro-1H-indole-3-carboxaldehyde (0.2 g, 1.9 mmole) for the 1,3-dimethyl-1H-indole-2-carboxaldehyde, the title compound (0.1 g, 50%) was prepared as a viscous oil: MS (ES) m/e 207 (M+H)$^+$.

Preparation 38

Preparation of 4,6-dichloro-1-methyl-2-(methylaminomethyl)-1H-indole a) Ethyl
4,6-dichloro-1-methyl-1H-indole-2-carboxylate NaH (60% dispersion in mineral oil, 0.24 g, 6 mmole) was washed with hexanes, then was suspended in anhydrous DMF (16 mL). The mixture was cooled to 0° C., and ethyl 4,6-dichloroindole-2-carboxylate (1.03 g, 4 mmole) was added. After 2-3 min, iodomethane (1.3 mL, 20 mmole) was added, and the mixture was warmed to RT. The mixture became thick, and stirring became difficult for several minutes. After 0.5 hr, the reaction was cooled to 0° C. and quenched with 10% NH$_4$Cl (2 mL). The mixture was concentrated to dryness, and the residue was partitioned between Et$_2$O (50 mL) and H$_2$O (10 mL). The layers were separated and the organic layer was washed with H$_2$O (5 mL), dried (MgSO$_4$), and filtered, and the filter pad was washed with a little CH$_2$Cl$_2$. Concentration afforded the title compound (1.06 g, 97%) as an off-white solid: $^1$H NMR (400 MHz, CDCl$_3$) δ 7.34 (s, 1H), 7.30 (s, 1H), 7.17 (d, J=1.5 Hz, 1H), 4.39 (q, J=7.1 Hz, 2H), 4.05 (s, 3H), 1.42 (t, J=7.1 Hz, 3H); MS (ES) m/e 272 and 274 (M+H)$^+$.

b) N,1-Dimethyl-1H-indole-2-carboxamide

A suspension of ethyl 4,6-dichloro-1-methyl-1H-indole-2-carboxylate (1.06 g, 3.90 mmole) in 2.0 M CH$_3$NH$_2$/CH$_3$OH (40 mL) in a sealed pressure bottle was heated in an oil bath preset at 50° C. A homogeneous solution formed within 2.5 hr. The reaction was kept at 50° C. for 17.5 hr, during which time a solid precipitated. The mixture was cooled to RT and poured into H$_2$O (40 mL). The resulting mixture was concentrated on the rotavap to remove the methanol, and the solid was collected by suction filtration. This was washed with plenty of H$_2$O and dried in high vacuum at 45-50° C. to afford the title compound (0.99 g, 99%) as an off-white solid: $^1$H NMR (400 MHz, CDCl$_3$) δ 7.29 (s, 1H), 7.16 (d, J=1.5 Hz, 1H), 6.86 (s, 1H), 6.21 (br s, 1H), 4.02 (s, 3H), 3.02 (d, J=4.9 Hz, 3H); MS (ES) m/e 257 and 259 (M+H)$^+$.

c) 4,6-Dichloro-1-methyl-2-(methylaminomethyl)-1H-indole

A solution of 2.0 M BH$_3$.DMS in THF (3.6 mL, 7.2 mmole) was added to a solution of N,1-dimethyl-1H-indole-2-carboxamide (0.74 g, 2.88 mmole) in anhydrous THF (25 mL), and the reaction was heated at reflux. After 18 hr, the reaction was cooled to 0° C. and quenched with MeOH (5 mL). The solution was warmed to RT, stirred for 0.5 hr, then concentrated on the rotavap. The residue was re-concentrated from MeOH, then was purified by flash chromatography on silica gel (5% MeOH/CHCl$_3$ containing 0.5% conc. NH$_4$OH). The title compound (197.5 mg, 28%) was obtained as a white solid: $^1$H NMR (400 MHz, CDCl$_3$) δ 7.19 (dd, J=1.5, 0.8 Hz, 1H), 7.09 (d, J=1.5 Hz, 1H), 6.45 (s, 1H), 3.88 (s, 2H), 3.74 (s, 3H), 2.50 (s, 3H); MS (ES) m/e 212 and 214 (M+H–CH$_3$NH$_2$)$^+$.

Preparation 39

Preparation of
1,7-dimethyl-3-(methylaminomethyl)-1H-indole a) 1,7-Dimethyl-1H-indole According to the procedure of Preparation 13 (a), except substituting 7-methylindole for the 3-methylindole, the title compound (1.95 g, 90%) was obtained as a light-colored oil: MS (ES) m/e 146.2 (M+H)$^+$.

b) 1,7-Dimethyl-1H-indole-3-carboxaldehyde

According to the procedure of Preparation 13 (b), except substituting 1,7-dimethylindole for the 1,2-dimethylindole, the title compound (1.85 g, 82%) was obtained as an off white solid: MS (ES) m/e 174.2 (M+H)$^+$.

c) 1,7-Dimethyl-3-(methylaminomethyl)-1H-indole

According to the procedure of Preparation 13 (c), except substituting 1,7-dimethyl-1H-indole-3-carboxylate for the 1,3-dimethyl-1H-indole-2-carboxylate, the title compound (0.74 g, 98%) was obtained as an amber oil: MS (ES) m/e 189.2 (M+H)$^+$.

Preparation 40

Preparation of
4-methoxy-1-methyl-3-(methylaminomethyl)-1H-indole a) 4-Methoxy-1-methyl-1H-indole-3-carboxaldehyde According to the procedure of Preparation 13 (b), except substituting 1-methyl-4-methoxyindole for the 1,2-dimethylindole, the title compound (2.17 g, 93%) was obtained as an off white solid: MS (ES) m/e 190.2 (M+H)$^+$.

b)
4-Methoxy-1-methyl-3-(methylaminomethyl)-1H-indole

According to the procedure of Preparation 13 (c), except substituting 1-methyl-4-methoxy-1H-indole-3-carboxaldehyde for the 1,3-dimethyl-1H-indole-2-carboxaldehyde, the title compound (2.0 g, 95%) was obtained as a white solid: MS (ES) m/e 205.2 (M+H)+.

Preparation 41

Preparation of
5-methoxy-1-methyl-3-(methylaminomethyl)-1H-indole a) 5-Methoxy-1-methyl-1H-indole-3-carboxaldehyde According to the procedure of Preparation 13 (a), except substituting 5-methoxy-1H-indole-3-carboxaldehyde for the 3-methyl-1H-indole-3-carboxaldehyde, the title compound (0.86 g, 92%) was obtained as a light tan solid: MS (ES) m/e 190.2 (M+H)+.

b)
5-Methoxy-1-methyl-3-(methylaminomethyl)-1H-indole

According to the procedure of Preparation 13 (c), except substituting 5-methoxy-1-methyl-1H-indole-3-carboxaldehyde for the 1,3-dimethyl-1H-indole-2-carboxaldehyde, the title compound (0.85 g, 98%) was obtained as a light yellow oil: MS (ES) m/e 205.2 (M+H)+.

Preparation 42

Preparation of
7-methoxy-1-methyl-3-(methylaminomethyl)-1H-indole a) 7-Methoxy-1-methyl-1H-indole According to the procedure of Preparation 13 (a), except substituting 7-methoxyindole for 3-methylindole, the title compound (1.55 g, 96%) was obtained as a tan solid: MS (ES) m/e 162.2 (M+H)+.

b)
7-Methoxy-1-methyl-1H-indole-3-carboxaldehyde

According to the procedure of Preparation 13(b), except substituting 7-methoxy-1-methyl-1H-indole for the 1,2-dimethylindole, the title compound (1.6 g, 91%) was obtained as an off white solid: MS (ES) m/e 190.2 (M+H)+.

c)
7-Methoxy-1-methyl-3-(methylaminomethyl)-1H-indole

According to the procedure of Preparation 13(c), except substituting 7-methoxy-1-methyl-1H-indole-3-carboxaldehyde for the 1,3-dimethyl-1H-indole-2-carboxaldehyde, the title compound (1.6 g, 94%) was obtained as an amber oil: MS (ES) m/e 205.2 (M+H)+.

Preparation 43

Preparation of
7-chloro-1-methyl-3-(methylaminomethyl)-1H-indole a) 7-Chloro-1-methyl-1H-indole According to the procedure of Preparation 13 (a), except substituting 7-chloroindole for the 3-methylindole, the title compound (2.2 g, 100%) was obtained as a white solid: MS (ES) m/e 166.2 (M+H)+.

b) 7-Chloro-1-methyl-1H-indole-3-carboxaldehyde

According to the procedure of Preparation 13 (b), except substituting 7-chloro-1-methyl-1H-indole for the 1,2-dimethylindole, title compound (2.1 g, 84%) was obtained as a white solid: MS (ES) m/e 194.0 (M+H)+.

c)
7-Chloro-1-methyl-3-(methylaminomethyl)-1H-indole

According to the procedure of Preparation 13 (c), except substituting 7-chloro-1-methyl-1H-indole-3-carboxaldehyde for the 1,3-dimethyl-1H-indole-2-carboxaldehyde, the title compound (2.0 g, 93%) was obtained as an amber oil: MS (ES) m/e 209.2 (M+H)+.

Preparation 44

Preparation of
6-chloro-1-methyl-3-(methylaminomethyl)-1H-indole a) 6-Chloro-1-methyl-1H-indole According to the procedure of Preparation 13 (a), except substituting 6-chloroindole for the 3-methylindole, the title compound (2.2 g, 100%) was obtained as a white solid: MS (ES) m/e 166.2.0 (M+H)+.

b) 6-Chloro-1-methyl-1H-indole-3-carboxaldehyde

According to the procedure of Preparation 13 (b), except substituting 6-chloro-1-methyl-1H-indole for the 1,2-dimethylindole, title compound (2.2 g, 88%) was obtained as an amber oil: MS (ES) m/e 194.2 (M+H)+.

c)
6-Chloro-1-methyl-3-(methylaminomethyl)-1H-indole

According to the procedure of Preparation 13 (c), except substituting 6-chloro-1-methyl-1H-indole-3-carboxaldehyde for the 1,3-dimethyl-1H-indole-2-carboxaldehyde, the title compound (2.1 g, 93%) was obtained as an amber oil: MS (ES) m/e 209.2 (M+H)+.

Preparation 45

Preparation of
5-chloro-1-methyl-3-(methylaminomethyl)-1H-indole a) 5-Chloro-1-methyl-1H-indole According to the procedure of Preparation 13 (a), except substituting 5-chloroindole for the 3-methylindole, the title compound (2.0 g, 91%) was obtained as an amber oil: MS (ES) m/e 166.0 (M+H)+.

b) 5-Chloro-1-methyl-1H-indole-3-carboxaldehyde

According to the procedure of Preparation 13 (b), except substituting 5-chloro-1-methyl-1H-indole for the 1,2-dimethylindole, title compound (2.0 g, 83%) was obtained as an white solid: MS (ES) m/e 194.0 (M+H)+.

c)
5-Chloro-1-methyl-3-(methylaminomethyl)-1H-indole

According to the procedure of Preparation 13 (c), except substituting 5-chloro-1-methyl-1H-indole-3-carboxaldehyde for the, 3-dimethyl-1H-indole-2-carboxaldehyde, the title compound (2.1 g, 93%) was obtained as an amber oil: MS (ES) m/e 209.0 (M+H)+.

Preparation 46

Preparation of
4-chloro-1-methyl-3-(methylaminomethyl)-1H-indole a) 4-Chloro-1-methyl-1H-indole According to the procedure of Preparation 13 (a), except substituting 4-chloroindole for the 3-methylindole, the title compound (2.2 g, 100%) was obtained as an amber oil: MS (ES) m/e 166.0 (M+H)$^+$.

b) 4-Chloro-1-methyl-1H-indole-3-carboxaldehyde

According to the procedure of Preparation 13 (b), except substituting 4-chloro-1-methyl-1H-indole for the 1,2-dimethylindole, title compound (1.9 g, 76%) was obtained as an off-white solid: MS (ES) m/e 194.0 (M+H)$^+$.

c)
4-Chloro-1-methyl-3-(methylaminomethyl)-1H-indole

According to the procedure of Preparation 13 (c), except substituting 4-chloro-1-methyl-1H-indole-3-carboxaldehyde for the 1,3-dimethyl-1H-indole-2-carboxaldehyde, the title compound (1.75 g, 78%) was obtained as a yellow solid: MS (ES) m/e 209.0 (M+H)$^+$.

Preparation 47

Preparation of
1,1-dimethyl-3-(methylaminomethyl)-3H-indene a) 1,1-Dimethyl-3H-indene-3-carboxaldehyde The title compound was obtained in quantitative yield according to established literature procedures (*Chem. Pharm. Bull.* 1986, 34, 390-395; *Tet. Lett.* 1993, 34, 2979): $^1$H NMR (400 MHz, CDCl$_3$) δ10.05 (s, 1H), 8.05 (d, 2H), 7.35 (m, 4H), 1.40 (s, 6H).

b) 1,1-Dimethyl-3-(methylaminomethyl)-3H-indene

According to the procedure of Preparation 12, except substituting 1,1-dimethyl-3H-indene-3-carboxaldehyde for the 2-methylindole-3-carboxaldehyde, the title compound (3 g, 81%) was obtained as a reddish oil: MS (ES) m/e 188.2 (M+H)$^+$.

Preparation 48

Preparation of
7-hydroxy-1-methyl-3-(methylaminomethyl)-1H-indole a) 7-Benzyloxy-1-methyl-1H-indole According to the procedure of Preparation 13 (a), except substituting 7-benzyloxyindole for the 3-methylindole, the title compound (4.8 g, 100%) was obtained as an amber oil: MS (ES) m/e 238.0 (M+H)$^+$.

b)
7-Benzyloxy-1-methyl-1H-indole-3-carboxaldehyde

According to the procedure of Preparation 13 (b), except substituting 7-benzyloxy-1-methyl-1H-indole for the 1,2-dimethylindole, title compound (4.5 g, 85%) was obtained as an oil: MS (ES) m/e 266.0 (M+H)$^+$.

c) 7-Benzyloxy-1-methyl-3-(methylaminomethyl)-1H-indole

According to the procedure of Preparation 13 (c), except substituting 7-benzyloxy-1-methyl-1H-indole-3-carboxaldehyde for the 1,3-dimethyl-1H-indole-2-carboxaldehyde, the title compound (3.7 g, 88%) was obtained as an oil: MS (ES) m/e 281.2 (M+H)$^+$.

d)
7-Hydroxy-1-methyl-3-(methylaminomethyl)-1H-indole

According to the literature procedure (*J. Org. Chem.* 1978, 43, 4195-96), 7-benzyloxy-1-methyl-3-(methylaminomethyl)-1H-indole was hydrogenated to afford the title compound (300 mg, 79%) as a brown solid: MS (ES) m/e 191.2 (M+H)$^+$.

Preparation 49

Preparation of
3-(methylaminomethyl)-1,2,7-trimethyl-1H-indole a) 1,2,7-Trimethyl-1H-indole According to the procedure of Preparation 13 (a), except substituting 2,7-dimethylindole for the 3-methylindole, the title compound (960 mg, 87%) was obtained as an oil: MS (ES) m/e 160.2 (M+H)$^+$.

b) 1,2,7-Trimethylindole-3-carboxaldehyde

According to the procedure of Preparation 13 (b), except substituting 1,2,7-trimethyl-1H-indole for the 1,4-dimethylindole, the title compound (800 mg, 62%) was obtained as a light tan solid: MS (ES) m/e 188.2 (M+H)$^+$.

c)
3-(Methylaminomethyl)-1,2,7-trimethyl-1H-indole

According to the procedure of Preparation 13 (c) except substituting 1,2,7-trimethyl-1H-indole-3-carboxaldehyde for the 1,3-dimethyl-1H-indole-2-carboxaldehyde, the title compound (570 mg, 71%) was obtained as an oil which slowly crystallized: MS (ES) m/e 405.4 (2M+H)$^+$.

Preparation 50

Preparation of
7-chloro-3-(methylaminomethyl)-1H-indole a) 7-Chloro-1H-indole-3-carboxaldehyde According to the procedure of Preparation 13 (b), except substituting 7-chloroindole for the 1,2-dimethylindole, the title compound (0.48 g, 44%) was obtained as a white solid after recrystallization from hot EtOAc: MS (ES) m/e 180.0 (M+H)$^+$.

b) 7-Chloro-3-(methylaminomethyl)-1H-indole

According to the procedure of Preparation 13 (c), except substituting 7-chloro-1H-indole-3-carboxaldehyde for the 1,3-dimethyl-1H-indole-2-carboxaldehyde, the title compound (440 mg, 92%) was obtained as an off white solid: MS (ES) m/e 195.2 (M+H)$^+$.

Preparation 51

Preparation of 2-(methylaminomethyl)naphthalene

To a stirred solution of 40 wt % methylamine in H$_2$O (50 mL, 581 mmole) in THF (50 mL) at 0° C. was added 2-(bromomethyl)naphthalene (10 g, 43 mmole) in one portion. The reaction was allowed to warm to RT and stirred for 16 hr, then was then concentrated under vacuum. The residue was taken up in Et$_2$O and washed with 1.0 N NaOH then with brine, dried (Na$_2$SO$_4$), and concentrated to dryness. Purification by flash chromatography on silica gel (98:2 to 9:1 CHCl$_3$/methanol containing 5% NH$_4$OH) gave the title compound (3.95 g, 54%) as a clear oil: $^1$H NMR (400 MHz, CDCl$_3$) δ 7.85 (m, 3H), 7.79 (s, 1H), 7.49 (m, 3H), 3.94 (s, 2H), 2.53 (s, 3H).

Preparation 52

Preparation of 3-(methylaminomethyl)quinoline

A solution of 3-quinolinecarboxaldehyde (1.5 g, 10 mmole), 2.0 M CH$_3$NH$_2$/MeOH (10 mL, 20 mmole), glacial AcOH (0.6 mL, 10 mmole), and NaBH$_3$CN (0.35 g, 11 mmole) in MeOH (20 mL) was stirred at RT overnight, then was concentrated in vacuo. The residue was diluted with 5% NaOH and extracted with CH$_2$Cl$_2$. The combined organic extracts were washed with brine, dried over MgSO$_4$, and concentrated. Flash chromatography on silica gel (10% MeOH/CH$_2$Cl$_2$) gave the title compound (0.83 g, 24%) as a slightly yellow viscous oil: MS (ES) m/e 173 (M+H)$^+$.

Preparation 53

Preparation of (E)-2-methyl-3-(7-oxo-5,6,7,8-tetrahydro-1,8-naphthyridin-3-yl)acrylic acid hydrochloride salt a) tert-Butyl (E)-2-methyl-3-(7-oxo-5,6,7,8-tetrahydro-1,8-naphthyridin-3-yl)acrylate According to the procedure of Preparation 31 (a), except substituting tert-butyl methacrylate (4.7 g, 33.2 mmole) for the tert-butyl acrylate, the title compound (2.7 g, 42%) was prepared as a yellow solid: MS (ES) m/e 289 (M+H)$^+$.

b) (E)-2-methyl-3-(7-oxo-5,6,7,8-tetrahydro-1,8-naphthyridin-3-yl)acrylic acid hydrochloride salt According to the procedure of Preparation 31 (b), except substituting tert-butyl (E)-2-methyl-3-(7-oxo-5,6,7,8-tetrahydro-1,8-naphthyridin-3-yl)acrylate (2.7 g, 9.3 mmole) for the tert-butyl (E)-3-(7-oxo-5,6,7,8-tetrahydro-1,8-naphthyridin-3-yl)acrylate, the title compound (2.5 g, 99%) was prepared as a white solid: MS (ES) m/e 232 (M+H)$^+$.

Preparation 54

Preparation of (E)-3-methyl-3-(7-oxo-5,6,7,8-tetrahydro-1,8-naphthyridin-3-yl)acrylic acid hydrochloride salt a) tert-Butyl (E)-3-methyl-3-(7-oxo-5,6,7,8-tetrahydro-1,8-naphthyridin-3-yl)acrylate According to the procedure of Preparation 31 (a), except substituting tert-butyl crotonate (4.7 g, 33.2 mmole) for the tert-butyl acrylate, the title compound (3.7 g, 58%) was prepared as a yellow solid: MS (ES) m/e 289 (M+H)$^+$.

b) (E)-3-methyl-3-(7-oxo-5,6,7,8-tetrahydro-1,8-naphthyridin-3-yl)acrylic acid hydrochloride salt According to the procedure of Preparation 31 (b), except substituting tert-butyl (E)-3-methyl-3-(7-oxo-5,6,7,8-tetrahydro-1,8-naphthyridin-3-yl)acrylate (3.7 g, 12.8 mmole) for the tert-butyl (E)-3-(7-oxo-5,6,7,8-tetrahydro-1,8-naphthyridin-3-yl)acrylate, the title compound (3.4 g, 99%) was prepared as a white solid: MS (ES) m/e 232 (M+H)$^+$.

Preparation 55

Preparation of 7-bromo-4-methyl-1,2,4,5-tetrahydro-pyrido[2,3-e]-1,4-diazepin-3-one a) 5-Bromo-3-[N-(tert-butoxycarbonyl)-N-methylaminomethyl]-2-[N-(tert-butoxycarbonyl)amino]pyridine To a solution of 2-amino-5-bromo-3-(methylaminomethyl)pyridine (3.8 g, 17.6 mmole), from Preparation 5 (a), in THF was added di-tert-butyl dicarbonate (8.8 g, 40.5 mmole). The reaction was heated to reflux for 12 hr then was concentrated under vacuum. Flash chromatography on silica gel (1:1 hexanes/EtOAc) gave the title compound (6.2 g, 85%) as a white waxy solid: MS (ES) m/e 416 (M+H)$^+$.

b) 5-Bromo-2-[(ethoxycarbonyl)methylamino]-3-(methylaminomethyl)-2-[N-(tert-butoxycarbonyl)amino]pyridine bis-trifluoroacetic acid salt To a suspension of 60% NaH (0.46 g, 11.5 mmole) in THF (100 mL) at RT was added 5-bromo-3-[N-(tert-butoxycarbonyl)-N-methylaminomethyl]-2-[N-(tert-butoxycarbonyl)amino]pyridine (4.0 g, 9.61 mmole). After 30 min, ethyl bromoacetate (1.8 g, 10.6 mmole) was added. The reaction was stirred at RT for 12 hr, then was quenched with H$_2$O (5 mL) and concentrated. The residue was dissolved in EtOAc (200 mL), and the solution was washed with H$_2$O (100 mL), dried over Na$_2$SO$_4$, and concentrated under high vacuum to a light yellow solid. This was dissolved in CH$_2$Cl$_2$ (50 mL) and trifluoroacetic acid (20 mL). After 2 hr, the reaction was concentrated under vacuum and the residue was purified flash chromatography on silica gel (95:5 CHCl$_3$/CH$_3$OH). The title compound (4.1 g, 80%) was obtained as a yellow solid: MS (ES) m/e 302 (M+H)$^+$.

c) 7-Bromo-4-methyl-1,2,4,5-tetrahydropyrido[2,3-e]-1,4-diazepin-3-one

To a solution of 5-bromo-2-[(ethoxycarbonyl)methylamino]-3-(methylaminomethyl)-2-[N-(tert-butoxycarbonyl)amino]pyridine bis-trifluoroacetic acid salt (4.1 g, 7.7 mmole) in toluene was added triethylamine (3.3 mL, 23.7 mmole). The reaction was heated at reflux for 72 hr then concentrated under vacuum. Flash chromatography on silica gel (9:1 CHCl$_3$/CH$_3$OH containing 5% NH$_4$OH) gave the title compound (1.4 g, 72%) as a tan solid: MS (ES) m/e 256 (M+H)$^+$.

Preparation 56

Preparation of (E)-3-(8-oxo-6,7,8,9-tetrahydro-5H-pyrido[2,3-b]azepin-3-yl)-acrylic acid hydrochloride salt a) tert-butyl (E)-3-(8-oxo-6,7,8,9-tetrahydro-5H-pyrido[2,3-b]azepin-3-yl)acrylate A solution of 3-bromo-5,6,7,9-tetrahydro-pyrido[2,3-b]azepin-8-one (1.00 g, 4.15 mmole), tert-butyl acrylate (0.67 mL, 4.60 mmole), DIEA (1.45 mL, 8.30 mmole), Pd(OAc)$_2$ (0.09 g, 0.42 mmole) and P(o-tol)$_3$ (0.25 g, 0.85 mmole) in propionitrile (25 mL) was purged with N$_2$ and then heated at reflux overnight. The dark mixture was filtered through a pad of Celite®, and the filter pad was rinsed with acetonitrile (250 mL). The filtrate was concentrated in vacuo, and the residue was purified by flash chromatography on silica gel (ethyl acetate). The title compound (0.70 g, 58%) was obtained as a light yellow solid after drying in vacuo: MS (ES) m/e 289 (M+H)$^+$.

b) (E)-3-(8-oxo-6,7,8,9-tetrahydro-5H-pyrido[2,3-b]azepin-3-yl)-acrylic acid hydrochloride salt According to the procedure of Preparation 31 (b), except substituting tert-butyl (E)-3-(8-oxo-6,7,8,9-tetrahydro-5H-pyrido[2,3-b]azepin-3-yl)acrylate (0.70 g, 2.40 mmole) for the tert-butyl (E)-3-(7-oxo-5,6,7,8-tetrahydro-1,8-naphthyridin-3-yl)acrylate, the title compound (0.49 g, 77%) was obtained as an off-white solid after drying in vacuo: MS (ES) m/e 233 (M+H)$^+$.

Preparation 57

Preparation of 1-(2-hydroxyethyl)-3-(methylaminomethyl)-1H-indole

According to the reported literature procedure (*J. Org. Chem.* 1998, 63, 6721-6726) except substituting 3-[N-(benzyloxycarbonyl)-N-methylaminomethyl]-1H-indole (3.70 g, 12.60 mmole) for the 5-bromoindole, the title compound (4.00 g, 93%) was obtained as a yellow solid after drying in vacuo: MS (ES) m/e 338 (M+H)$^+$.

Preparation 58

Preparation of 2-chloro-1-methyl-2-(methylaminomethyl)-1H-indole a) 2-Chloro-1H-indole-3-carboxaldehyde

To DMF (30 mL) with stirring at 0° C. was added dropwise phosphorus oxychloride (10 mL, 107 mmole) over 5 minutes. The reaction was stirred for an additional 15 minutes, then oxindole (6.0 g, 45 mmole) was added portionwise over 5 min. The reaction was allowed to warm to RT and stirred for 18 h then was carefully poured into ice water (350 mL). The solution was stirred for 6 h after which time a suspension formed. The solids were filtered off, washed with cold water, pressed dry and dried under vacuum to give the title compound (6.83 g, 84%) as a yellowish solid: $^1$H NMR (400 MHz, d$_6$-DMSO) □ 10.0 (s, 1H), 8.05 (dd, 1H), 7.43 (dd, 1H), 7.23-7.31 (m, 2H); MS (ES) m/e 179.0 (M+H)$^+$.

b) 2-Chloro-1-methyl-1H-indole-3-carboxaldehyde

NaH (60% dispersion in mineral oil) (0.9 g, 22.5 mmole) was added portionwise over 5 min to a solution of 2-chloro-1H-indole-3-carboxaldehyde (3.8 g, 21.2 mmole) and iodomethane (1.5 mL, 24 mmole) in DMF (50 mL) with stirring at 0° C. The reaction was allowed to warm to RT and stir for 4 h, then was concentrated under vacuum. The remaining residue was taken up in EtOAc, and the solution was washed with water then brine, dried (MgSO$_4$), and concentrated to dryness. Trituration with 1:1 Et$_2$O/petroleum ether, filtration, and drying under vacuum gave the title compound (3.10 g, 76%) as an off-white solid: $^1$H NMR (400 MHz, CDCl$_3$) δ 10.12 (s, 1H), 8.29 (m, 1H), 7.33 (m, 3H), 3.81 (s, 3H); MS (ES) m/e 194.0 (M+H)$^+$.

c) 2-Chloro-1-methyl-2-(methylaminomethyl)-1H-indole

According to the procedure of Preparation 12, except substituting 2-chloro-1-methyl-1H-indole-3-carboxaldehyde (3.0 g, 15.5 mmole) for the 1-methylindole-3-carboxaldehyde, the title compound (2.91 g, 90%) was prepared as an oil: $^1$H NMR (400 MHz, CDCl$_3$) δ 7.60 (d, J=7.9 Hz, 1H), 7.22 (m, 2H), 7.13 (m, 1H), 3.92 (s, 2H), 3.71 (s, 3H), 2.44 (s, 3H).

Preparation 59

Preparation of 3-(benzhydrylideneamino)-6-bromo-3,4-dihydro-1H-1,8-naphthyridin-2-one NaH (60% dispersion in mineral oil, 1.2 g, 30 mmole) was added portionwise over 10 min to a solution of N-(diphenylmethylene)glycine ethyl ester (8.0 g, 30 mmole) in DMF (150 mL) with stirring under Ar at 0° C. The reaction was stirred for 15 min, then 2-amino-5-bromo-3-(bromomethyl)pyridine hydrobromide (5.0 g, 14.4 mmole) was added in one portion. The reaction was allowed to warm to RT and stir for 18 h, then was concentrated under vacuum. The remaining residue was taken up in EtOAc (150 mL), hexane (150 mL), and H$_2$O (150 mL). The resulting suspension was triturated and filtered, and the solid was dried under vacuum to give the title compound (3.27 g, 56%) as an off-white solid: $^1$H NMR (400 MHz, d$_6$-DMSO) δ 10.92 (s, 1H), 8.23 (s, 1H), 7.86 (s, 1H), 7.26-7.55 (m, 10H), 4.05 (dd, 1H), 3.10 (t, 2H); MS (ES) m/e 406.0 (M+H)$^+$.

Preparation 60

Preparation of 2-(methylaminomethyl)benzofuran

To a stirred solution of 2-benzofurancarboxaldehyde (2.22 g, 15.2 mmole) in MeOH (5 mL) was added 2 M methylamine in MeOH (15 mL), HOAc (0.86 mL, 15 mmole), and NaBH$_3$CN (1.0 g, 15.9 mmole). The reaction was stirred for 18 h at RT then concentrated under vacuum. The remaining residue was taken up in Et$_2$O, and the solution was washed with 1 N NaOH then brine, dried (Na$_2$SO$_4$), and concentrated to dryness. Purification by flash chromatography on silica gel (5% (5% NH$_4$OH in MeOH)/CHCl$_3$) gave the title compound (1.23 g, 50%) as a pale yellow oil: MS (ES) n/e 162.4 (M+H)$^+$.

Preparation 61

Preparation of methyl 1-methyl-3-(methylaminomethyl)-1H-indole-7-carboxylate a) Methyl 1-methyl-1H-indole-7-carboxylate

According to the procedure of Preparation 9 (a), except substituting methyl indole-7-carboxylate for the ethyl indole- 2-carboxylate, the title compound (2.4 g, 90%) was obtained as an oil: MS (ES) m/e 190.2 (M+H)+.

b) N-Methyl-7-methoxycarbonyl-1H-indole-3-carboxaldehyde

According to the procedure of Preparation 13 (b), except substituting methyl 1-methyl-1H-indole-7-carboxylate for the 1,3-dimethylindole, the title compound (1.8 g, 70%) was obtained as a white solid: MS (ES) m/e 218.2 (M+H)+.

c) Methyl 1-methyl-3-(methylaminomethyl)-1H-indole-7-carboxylate

According to the procedure of Preparation 12, except substituting 1-methyl-7-methoxycarbonyl-1H-indole 3-carboxaldehyde for the 2-methylindole-3-carboxaldehyde, the title compound (1.7 g, 92%) was obtained as an oil: MS (ES) m/e 233.2 (M+H)+.

Preparation 62

Preparation of methyl 1-methyl-3-(methylaminomethyl)-1H-indole-6-carboxylate a) Methyl 1-methyl-1H-indole-6-carboxylate

According to the procedure of Preparation 9 (a), except substituting methyl indole-6-carboxylate for the ethyl indole-2-carboxylate, the title compound (2.5 g, 95%) was obtained as white solid: MS (ES) m/e 190.2 (M+H)+.

b) N-Methyl-7-methoxycarbonyl-1H-indole-3-carboxaldehyde

According to the procedure of Preparation 13 (b), except substituting methyl 1-methyl-1H-indole-6-carboxylate for the 1,3-dimethylindole, the title compound (2.6 g, 98%) was obtained as a white solid: MS (ES) m/e 218.2 (M+H)+.

c) Methyl 1-methyl-3-(methylaminomethyl)-1H-indole-6-carboxylate

According to the procedure of Preparation 12, except substituting 1-methyl-7-methoxycarbonyl-1H-indole 3-carboxaldehyde for the 2-methylindole-3-carboxaldehyde, the title compound (1.9 g, 63%) was obtained as an oil: MS (ES) m/e 233.2 (M+H)+.

Preparation 63

Preparation of 6-methoxy-1-methyl-3-(methylaminomethyl)-1H-indole a) 6-Methoxy-1-methyl-1H-indole

According to the procedure of Preparation 9 (a), except substituting 6-methoxy-1H-indole for the ethyl indole-2-carboxylate, the title compound (2.3 g, 95%) was obtained as an oil: MS (ES) m/e 162.2 (M+H)+.

b) 6-Methoxy-1-methyl-1H-indole-3-carboxaldehyde

According to the procedure of Preparation 13 (b), except substituting 6-methoxy-1-methyl-1H-indole for the 1,3-dimethylindole, the title compound (2.3 g, 82%) was obtained as a tan solid: MS (ES) m/e 190.2 (M+H)+.

c) 6-Methoxy-1-methyl-3-(methylaminomethyl)-1H-indole

According to the procedure of Preparation 12, except substituting 6-methoxy-1-methyl-1H-indole-3-carboxaldehyde for the 2-methylindole-3-carboxaldehyde, the title compound (2.1 g, 87%) was obtained as an oil: MS (ES) m/e 205.2 (M+H)+.

Preparation 64

Preparation of 7-fluoro-3-(methylaminomethyl)-1H-indole a) 7-Fluoro-1H-indole-3-carboxaldehyde

According to the procedure of Preparation 13 (b), except substituting 7-fluoroindole (0.5 g, 3.7 mmole) for the 1,3-dimethylindole, the title compound (0.3 g, 55%) was prepared as a waxy solid: MS (ES) m/e 164 (M+H)+.

b) 7-Fluoro-3-(methylaminomethyl)-1H-indole

According to the procedure of Preparation 13 (c), except substituting 7-fluoro-1H-indole-3-carboxaldehyde (0.5 g, 3.1 mmole) for the 1,3-dimethyl-1H-indole-2-carboxaldehyde, the title compound (0.5 g, 90%) was prepared as a viscous oil: MS (ES) m/e 179 (M+H)+.

Preparation 65

Preparation of 4-fluoro-3-(methylaminomethyl)-1H-indole a) 4-Fluoro-1H-indole-3-carboxaldehyde

According to the procedure of Preparation 13 (b), except substituting 4-fluoroindole (0.4 g, 2.45 mmole) for the 1,3-dimethylindole, the title compound (0.31 g, 72%) was prepared as a viscous oil: MS (ES) m/e 164 (M+H)+.

b) 4-Fluoro-3-(methylaminomethyl)-1H-indole

According to the procedure of Preparation 13 (c), except substituting 4-fluoro-1H-indole-3-carboxaldehyde for the 1,3-dimethyl-1H-indole-2-carboxaldehyde, the title compound was prepared as a viscous oil: MS (ES) m/e 179 (M+H)+.

Preparation 66

Preparation of 6-bromo-3-(2-methoxyethyl)-3,4-dihydro-1H-pyrido[2,3-d]pyrimidin-2-one a) 2-Amino-5-bromo-3-[(2-methoxyethyl)aminomethyl]pyridine

2-Methoxyethylamine (1.49 mL, 17.16 mmole) was added to a solution of 2-amino-5-bromo-3-(bromomethyl)pyridine hydrobromide (1.49 g, 4.29 mmole) and DIEA (2.24 mL, 12.87 mmole) in $CH_2Cl_2$ (10 mL) at RT. The reaction was stirred overnight then was concentrated in vacuo. The residue was diluted with water and the solution was extracted with ethyl acetate. The combined organic extracts were washed with brine, dried over $Na_2SO_4$, and concentrated to afford the title compound (1.00 g, 90%) as a light brown liquid after drying in vacuo: MS (ES) m/e 260/262 (M+H)+.

b) 6-Bromo-3-(2-methoxyethyl)-3,4-dihydro-1H-pyrido[2,3-d]pyrimidin-2-one 1,1'-Carbonyldiimidazole (0.74 g, 4.60 mmole) was added to a solution of 2-amino-5-bromo-3-[(2-methoxyethyl)aminomethyl]pyridine (1.00 g, 3.80 mmole) in 1,2-dichloroethane (35 mL) at RT. The reaction was heated at 65° C. with stirring overnight, then was concentrated in vacuo. Flash chromatography on silica gel (5% MeOH/CHCl$_3$) gave title compound (0.90 g, 83%) as a yellow solid after drying in vacuo: MS (ES) m/e 286/288 (M+H)+.

Preparation 67

Preparation of Methyl-(1-propyl-naphthalen-2-ylmethyl)amine

A solution of 2.0 M methylamine in methanol (20 mL) was added to 1-propyl-naphthalene-2-carbaldehyde (0.983 g, 4.95 mmol) under N$_2$ and allowed to stir for 18 h. The solution was concentrated under reduced pressure. Then the resulting dark yellow oil was solvated in EtOH (20 mL) under N$_2$. To the solution was added NaBH$_4$ (0.187 g, 4.95 mmol) and the mixture allowed to stir for 6.5 h. The reaction was concentrated under reduced pressure, then solvated in 1 N NaOH (20 mL) and extracted with Et$_2$O (3×50 mL). The organics were combined, washed with brine (2×100 mL), dried over Na$_2$SO$_4$, filtered and concentrated to yield the title compound (0.94 g, 89%) as a yellow oil: $^1$H NMR (300 MHz, DMSO-d$_6$) δ 7.87-7.73 (m, 4H), 7.51-7.43 (m, 3H), 3.53 (m, 1H), 2.09 (s, 3H), 1.70-1.52 (m, 2H), 1.26-1.12 (m, 2H), 0.87-0.79 (m, 3H).

Preparation 68

Preparation of (4-Fluoro-naphthalen-1-ylmethyl)methylamine a) 4-Fluoro-naphthalene-1-carbaldehyde A solution of α,α-dichloromethyl methyl ether (5.9 mL, 65 mmol) in CH$_2$Cl$_2$ (30 mL) was cooled in an ice bath and then treated dropwise over 15 min with SnCl$_4$ (7.6 mL, 65 mmol). After stirring for 45 min, a solution of 1-fluoronaphthalene (5.5 mL, 50 mmol) in CH$_2$Cl$_2$ (30 mL) was added. The mixture was allowed to slowly warm to room temperature while stirring overnight. The mixture was poured in ice water (100 mL) and diluted with CH$_2$Cl$_2$ (50 mL). The layers were separated. The organic layer was diluted with CH$_2$Cl$_2$ (100 mL), washed with H$_2$O (3×50 mL), dried over Na$_2$SO$_4$, filtered, and the solvent was removed in vacuo to give the title compound (7.62 g, 87%) as a pale yellow solid: MS (ESI) m/e 175 (M+H)+.

b) (4-Fluoro-naphthalen-1-ylmethyl)methylamine

According to the procedure of Preparation 67, except substituting 4-fluoro-naphthalene-1-carbaldehyde for the 1-propyl-naphthalene-2-carbaldehyde, the title compound (3.18 g, 98%) was prepared as a golden oil: MS (ESI) m/e 190 (M+H)+.

Preparation 69

Preparation of (4-Chloro-naphthalen-1-ylmethyl)methylamine a) 4-Chloro-naphthalene-1-carbaldehyde According to the procedure of Preparation 2(a), except substituting 1-chloronaphthalene for 1-fluoronaphthalene, the title compound (5.36 g, 55%) was prepared as a pale yellow oil: MS (ESI) m/e 191 (M+H)+.

b) (4-Chloro-naphthalen-1-ylmethyl)methylamine

According to the procedure of Preparation 67, except substituting 4-chloro-naphthalene-1-carbaldehyde for the 1-propyl-naphthalene-2-carbaldehyde, the title compound (1.06 g, 60%) was prepared as a pale yellow oil: MS (ESI) m/e 206 (M+H)+.

Preparation 70

Preparation of (3-chlorobenzo[b]thiophen-2-ylmethyl)methylamine a) 3-chloro-benzo[b]thiophene-2-carbaldehyde Vilsmeier reagent was prepared via the dropwise addition of POCl$_3$ (7.9 mL, 84 mmol) into ice-cold DMF (14 mL). A solution of 2-carboxymethylsulfanyl-benzoic acid (3.0 g, 14 mmol) in DMF (15 mL) was added dropwise to the Vilsmeier reagent. The resulting mixture was warmed to room temperature and then heated to 80° C. for 3.5 h. The reaction mixture was cooled to ambient temperature. Crushed ice was added until a bright yellow precipitate appeared. The solid was isolated by filtration. Purification by flash column chromatography (silica gel, hexanes/ethyl acetate 3:2) gave the title compound (1.87 g, 68%) as a yellow powder: $^1$H NMR (300 MHz, CDCl$_3$) δ 10.36 (s, 1H), 8.03 (m, 1H), 7.86 (m, 1H), 7.59-7.53 (m, 2H).

b) (3-chlorobenzo[b]thiophen-2-ylmethyl)methylamine

To 3-chloro-benzo[b]thiophene-2-carbaldehyde (1.9 g, 9.5 mmol) was added a solution of 2 M methylamine in methanol (32 mL) and the resulting mixture was stirred overnight at room temperature. The mixture was concentrated under reduced pressure and the residue taken up in ethanol (32 mL). The solution was cooled to 0° C., NaBH$_4$ (0.54 g, 14 mmol) was added in one portion and stirring continued overnight. The mixture was concentrated under reduced pressure and the residue solvated in 1 M NaOH (200 mL). The mixture was extracted with diethyl ether (3×150 mL) and the combined organics were washed with brine (100 mL), dried over Na$_2$SO$_4$, filtered and concentrated under reduced pressure to give a yellow oil. Purification by flash column chromatography (silica gel, hexanes/ethyl acetate 1:1) gave the title compound (1.62 g, 80%) as a pale yellow oil which crystallized under vacuum: $^1$H NMR (300 MHz, CDCl$_3$) δ 7.70 (m, 2H), 7.45 (m, 2H), 4.08 (s, 2H), 2.51 (s, 3H).

Preparation 71

Preparation of (5-Chloro-1-methyl-1H-indol-2-ylmethyl)methylamine a) 5-Chloro-1-methyl-1H-indole-2-carboxylic acid methylamide To a solution of 5-chloro-1-methyl-1H-indole-2-carboxylic acid ethyl ester (1.27 g, 5.3 mmol) in toluene (10 mL) was added O,N-dimethyl-hydroxylamine (9.6 mL of a 1 M solution in toluene, 9.6 mmol). The resulting mixture was heated to reflux overnight after which the reaction was cooled to room temperature and quenched by the addition of 10% aqueous $K_2CO_3$ (50 mL). The mixture was extracted with ethyl acetate (3×200 mL). The combined organic layers were washed with brine (100 mL), dried over $Na_2SO_4$, filtered and concentrated to give the title compound (2.12 g, 96%) as a yellow solid: $^1$H NMR (300 MHz, $CDCl_3$) δ 7.59 (s, 1H), 7.27 (m, 2H), 6.73 (s, 1H), 6.13 (s, 1H), 4.03 (s, 3H), 3.01 (d, J=4.9 Hz, 3H); MS (ESI) m/e 222 (M+H)$^+$.

b) (5-Chloro-1-methyl-1H-indol-2-ylmethyl)methylamine

To an ice-cold solution of 5-chloro-1-methyl-1H-indole-2-carboxylic acid methylamide (2.12 g, 9.5 mmol) in THF (15 mL) was added lithium aluminum hydride (19 mL of a 1 M solution in THF, 19.0 mmol). Once the addition was complete, the resulting slurry was heated to reflux overnight. The mixture was cooled in an ice bath and carefully quenched by the consecutive addition of water (0.90 mL), 15% aqueous NaOH (0.90 mL) and water (2.5 mL). The resulting mixture was filtered through diatomaceous earth and the filtrate concentrated to give the title (2.00 g, quantitative) compound as an orange oil: $^1$H NMR (300 MHz, $CDCl_3$) δ 7.51 (d, J=1.8 Hz, 1H), 7.25-1.14 (m, 2H), 6.32 (s, 1H), 3.86 (s, 2H), 3.73 (d, J=4.8 Hz, 3H), 2.49 (s, 3H).

Preparation 72

Preparation of (1,7-dimethyl-1H-indol-2-ylmethyl)methylamine a) 1,7-Dimethyl-1H-indole Sodium hydride (1.15 g, 28.7 mmol, 60% in mineral oil) was rinsed with hexanes and then suspended in DMF (20 mL). To this suspension was added 7-methylindole (2.5 g, 19 mmol) portionwise. Gas evolution was allowed to subside between additions. The resulting brown mixture was stirred at room temperature for 15 min and then $CH_3I$ (2.71 g, 95.5 mmol) was added in one portion. The exothermic reaction was cooled to 30° C. and stirred for 1 h. Saturated aqueous $NH_4Cl$ (10 mL) was added and the mixture was concentrated under reduced pressure. The residue was combined with water (100 mL) and the mixture was then extracted with diethyl ether (3×100 mL). The combined organics were washed with brine, dried over $Na_2SO_4$, filtered and concentrated under reduced pressure to give the title compound (2.85 g, quantitative) as a red-pink oil which crystallized upon vacuum drying: $^1$H NMR (300 MHz, $CDCl_3$) δ 7.43 (d, J=7.6 Hz, 1H), 6.97-6.87 (m, 3H), 6.41 (d, J=3.1 Hz, 1H), 4.04 (s, 3H), 2.7 (s, 3H).

b) 1,7-Dimethyl-1H-indole-2-carbaldehyde

To a solution of 1,7-dimethylindole (2.85 g, 19.6 mmol) and TMEDA (3.3 mL, 21.6 mmol) in diethyl ether (30 mL) at −30° C. under $N_2$ was added n-butyllithium (13.5 mL of a 1.6 M solution in hexanes, 21.6 mmol) dropwise. The resulting orange solution was heated to reflux for 1 h and then DMF (4.6 mL, 58.8 mmol) was added in one portion. The solution was stirred at room temperature overnight. Saturated aqueous $NH_4Cl$ solution was added and the mixture was then extracted with ethyl acetate (3×150 mL). The combined organics were washed with water (100 mL) and brine (100 mL), dried over $Na_2SO_4$, filtered and concentrated under reduced pressure to provide an orange oil. Purification by flash column chromatography (silica gel, hexanes/ethyl acetate, 95:5) gave the title compound (1.57 g, 46%) as a yellow solid: $^1$H NMR (300 MHz, $CDCl_3$) δ 9.83 (s, 1H), 7.54 (d, J=7.8 Hz, 1H), 7.21 (s, 1H), 7.09-7.02 (m, 2H), 4.39 (s, 3H), 2.79 (s, 3H).

c) (1,7-Dimethyl-1H-indol-2-ylmethyl)methylamine

To 1,7-dimethyl-1H-indole-2-carbaldehyde (1.57 g, 9.06 mmol) was added a solution of 2 M solution of methylamine in methanol (30 mL) and the resulting mixture stirred overnight at room temperature. The mixture was concentrated under reduced pressure and the residue taken up in ethanol (30 mL). The solution was cooled to 0° C. and then $NaBH_4$ (0.34 g, 9.1 mmol) was added in one portion. The mixture was stirred overnight. Additional $NaBH_4$ (0.18 g, 4.5 mmol) was added and the mixture was again stirred overnight. The mixture was concentrated under reduced pressure and the residue combined with 1 M NaOH (200 mL). The mixture was extracted with diethyl ether (3×150 mL). The combined organics were washed with brine (100 mL), dried over $Na_2SO_4$, filtered and concentrated under reduced pressure to give the title compound as a pale yellow oil (1.60 g, 94%): $^1$H NMR (300 MHz, $CDCl_3$) δ 7.37 (d, J=7.8 Hz, 1H), 6.93-6.87 (m, 2H), 6.34 (s, 1H), 4.02 (s, 3H), 3.84 (s, 2H), 2.77 (s, 3H), 2.50 (s, 3H).

Preparation 73

Preparation of (5-Fluoro-3-methyl-benzo[b]thiophen-2-ylmethyl)methylamine a) 5-Fluoro-3-methyl-benzo[b]thiophene-2-carbaldehyde To a solution of 5-fluoro-3-methyl-benzo[b]thiophene (4.83 g, 29.1 mmol) in THF (50 mL) at −30° C. under $N_2$ was added n-butyllithium (20.0 mL of a 1.6 M solution in hexanes, 32.0 mmol) dropwise. The resulting orange solution was stirred for 1 h and then DMF (3.4 mL, 43.7 mmol) was added in one portion. The solution was warmed slowly to room temperature and stirred overnight. Saturated aqueous $NH_4Cl$ was added and the mixture was extracted with ethyl acetate (3×200 mL). The combined organics were washed with water (100 mL) and brine (100 mL), dried over $Na_2SO_4$, filtered and concentrated under reduced pressure to give the title compound (5.55 g, 97%) as a yellow solid: $^1$H NMR (300 MHz, $CDCl_3$) δ 10.32 (s, 1H), 7.80 (dd, J=9.0, 4.8 Hz, 1H), 7.53 (dd, J=9.3, 2.6 Hz, 1H), 7.31-7.24 (m, 1H), 2.76 (s, 3H).

b) (5-Fluoro-3-methyl-benzo[b]thiophen-2-ylmethyl)methylamine

To 5-fluoro-3-methyl-benzo[b]thiophene-2-carbaldehyde (5.43 g, 28.0 mmol) was added a solution of 2 M methylamine in methanol (94 mL) and the resulting mixture was stirred overnight at room temperature. The mixture was concentrated under reduced pressure and the residue taken up in ethanol (90 mL). The solution was cooled to 0° C. and then NaBH$_4$ (1.06 g, 28.0 mmol) was added in one portion. The mixture was stirred 4 hr, after which time NaBH$_4$ (0.54 g, 14.0 mmol) was added and the mixture was stirred overnight. The mixture was concentrated under reduced pressure and the residue combined with 1 M NaOH (200 mL). The mixture was extracted with diethyl ether (3×150 mL) and the combined organics were washed with brine (100 mL), dried over Na$_2$SO$_4$, filtered and concentrated under reduced pressure to the title compound (5.26 g, 90%) as a pale yellow oil: $^1$H NMR (300 MHz, CDCl$_3$) δ7.71 (dd, J=9.0, 4.8 Hz, 1H), 7.27 (dd, J=9.3, 2.6 Hz, 1H), 7.09-7.04 (m, 1H), 4.00 (s, 2H), 2.51 (s, 3H), 2.31 (s, 3H).

Preparation 74

Preparation of (5-Chloro-3-methyl-benzo[b]thiophen-2-ylmethyl)methylamine a) 5-Chloro-3-methyl-benzo[b]thiophene-2-carbaldehyde To a solution of 5-chloro-3-methyl-benzo[b]thiophene (4.98 g, 27.3 mmol) in THF (50 mL) at −40° C. was added n-butyllithium (18.7 mL of a 1.6 M solution in hexanes, 30.0 mmol) dropwise. The resulting yellow solution was stirred for 1 h and then DMF (6.3 mL, 81.9 mmol) was added in one portion. The solution was warmed slowly to room temperature and stirred overnight. Saturated aqueous NH$_4$Cl was added and the mixture was extracted with ethyl acetate (3×200 mL). The combined organics were washed with water (100 mL) and brine (100 mL), dried over Na$_2$SO$_4$, filtered and concentrated under reduced pressure to give the title compound (6.62 g, 89%) as a yellow solid: $^1$H NMR (300 MHz, CDCl$_3$) δ 10.32 (s, 1H), 7.85 (s, 1H), 7.79 (d, J=8.7 Hz, 1H), 7.46 (dd, J=8.7, 2.0 Hz, 1H), 2.74 (s, 3H).

b) (5-Chloro-3-methyl-benzo[b]thiophen-2-ylmethyl)methylamine

To 5-chloro-3-methyl-benzo[b]thiophene-2-carbaldehyde (5.10 g, 24.2 mmol) was added a solution of 2 M methylamine in methanol (81 mL) and the resulting mixture was stirred overnight at room temperature. The mixture was concentrated under reduced pressure and the residue taken up in ethanol (81 mL). The solution was cooled to 0° C., NaBH$_4$ (1.37 g, 36.3 mmol) was added in one portion, and stirring was continued overnight. The mixture was concentrated under reduced pressure and the residue was combined with 1 M NaOH (200 mL). The mixture was extracted with diethyl ether (3×150 mL). The combined organics were washed with brine (100 mL), dried over Na$_2$SO$_4$, filtered and concentrated under reduced pressure to the title compound (4.83 g, 88%) as a pale yellow oil which crystallized under vacuum: $^1$H NMR (300 MHz, CDCl$_3$) δ 7.69-7.59 (m, 2H), 7.25 (m, 1H), 3.96 (s, 2H), 2.50 (s, 3H), 2.31 (s, 3H).

Preparation 75

Preparation of (3-Methoxy-2-propoxy-benzyl)methylamine a) 3-Methoxy-2-propoxy-benzaldehyde A suspension of 2-hydroxy-3-methoxy-benzaldehyde (10.0 g, 65.6 mmol), 1-bromopropane (60 mL, 657 mmol) and K$_2$CO$_3$ (11.3 g, 82.1 mmol) in MeCN (250 mL) was heated to reflux for 12 h. The mixture was cooled to ambient temperature and the solution filtered. The filtrate was concentrated to give the title compound (12.9 g, quantitative) as light yellow oil: MS (ESI) m/e 195 (M+H)$^+$.

b) (3-Methoxy-2-propoxy-benzyl)methylamine

According to the procedure of Preparation 67, except substituting 3-methoxy-2-propoxy-benzaldehyde for 1-propyl-naphthalene-2-carbaldehyde, the title compound (13.2 g, 96%) was prepared as a light yellow oil: MS (ESI) m/e 210 (M+H)$^+$.

Preparation 76

Preparation of (2-Isopropoxy-3-methoxy-benzyl)methylamine a) 2-Isopropoxy-3-methoxy-benzaldehyde According to the procedure of Preparation 75(a), except substituting 2-iodopropane for 1-bromopropane, the title compound (6.35 g, quantitative) was prepared as light yellow oil: $^1$H NMR (300 MHz, CDCl$_3$) δ 10.5 (s, 1H), 7.42 (dd, J=6.6, 2.9 Hz, 1H), 7.16-7.08 (m, 2H), 4.63 (app septet, J=6.2 Hz, 1H), 3.89 (s, 3H), 1.33 (d, J=6.2 Hz, 6H).

b) (2-Isopropoxy-3-methoxy-benzyl)methylamine

According to the procedure of Preparation 67, except substituting 2-isopropoxy-3-methoxy-benzaldehyde for 1-propyl-naphthalene-2-carbaldehyde, the title compound (6.39 g, 93%) was prepared as a yellow oil: MS (ESI) m/e 210 (M+H)$^+$.

Preparation 77

Preparation of (2-Ethoxy-3-methyl-benzyl)methylamine a) 2-Ethoxy-3-methyl-benzaldehyde According to the procedure of Preparation 75(a), except substituting 2-hydroxy-3-methyl-benzaldehyde for 2-hydroxy-3-methoxy-benzaldehyde, and substituting iodoethane for 1-bromopropane, the title compound (10.8 g, 99%) was prepared as a brown oil: $^1$H NMR (300 MHz, CDCl$_3$) δ 10.4 (s, 1H), 7.69 (dd, J=7.6, 1.4 Hz, 1H), 7.46-7.43 (m, 1H), 7.13 (dd, J=7.6, 7.6 Hz, 1H), 4.01 (q, J=7.0 Hz, 2H), 2.34 (s, 3H), 1.46 (t, J=7.0 Hz, 3H).

b) (2-Ethoxy-3-methyl-benzyl)methylamine

According to the procedure of Preparation 67, except substituting 2-ethoxy-3-methyl-benzaldehyde for 1-propyl-naphthalene-2-carbaldehyde, the title compound (11.2 g, 95%) was prepared as a yellow oil: MS (ESI) m/e 180 (M+H)$^+$.

Preparation 78

Preparation of Methyl-naphthalen-2yl-methylamine

According to the procedure of Preparation 67, except substituting naphthalene-2-carbaldehyde for 1-propyl-naphthalene-2-carbaldehyde, the title compound (2.00 g, 91%) was prepared as a clear oil: $^1$H NMR (300 MHz, CDCl$_3$) δ 7.84-7.80 (m, 3H), 7.75 (s, 1H), 7.47-7.44 (m, 3H), 3.92 (s, 2H), 2.50 (s, 3H), 1.52 (br s, 1H).

Preparation 79

Preparation of Methyl-naphthalen-1yl-methylamine

According to the procedure of Preparation 67, except substituting naphthalene-1-carbaldehyde for 1-propyl-naphthalene-2-carbaldehyde, the title compound (2.44 g, 91%) was prepared as an orange oil: $^1$H NMR (300 MHz, CDCl$_3$) δ 8.12 (d, J=8.1 Hz, 1H), 7.86 (d, J=7.5 Hz, 1H), 7.77 (d, J=8.4 Hz, 1H), 7.54-7.40 (m, 4H), 4.20 (s, 2H), 2.55 (s, 3H), 1.50 (br s, 1H).

Preparation 80

Preparation of (4-Methanesulfonyl-benzyl)methylamine

According to the procedure of Preparation 67, except substituting 4-methanesulfonyl-benzaldehyde for 1-propyl-naphthalene-2-carbaldehyde, the title compound (1.35 g, 63%) was prepared as an off-white solid: MS (ESI) m/e 200 (M+H)$^+$.

Preparation 81

Preparation of Methyl-quinolin-5-Yl-methylamine

According to the procedure of Preparation 67, except substituting quinoline-5-carbaldehyde for 1-propyl-naphthalene-2-carbaldehyde, the title compound (1.21 g, 84%) was prepared as an orange solid: $^1$H NMR (300 MHz, DMSO-d$_6$) δ 8.90 (d, J=6.0 Hz, 1H), 8.61 (d, J=9.3 Hz, 1H), 7.91 (d, J=8.4 Hz, 1H), 7.68 (t, J=10.2 Hz, 1H), 7.57-7.51 (m, 2H), 4.08 (s, 2H), 2.34 (s, 3H), 2.13 (br s, 1H).

Preparation 82

Preparation of (2,3-Dimethylbenzyl)methylamine

According to the procedure of Preparation 67, except substituting 2,3-dimethylbenzaldehyde for 1-propyl-naphthalene-2-carbaldehyde, the title compound (1.69 g, 72%) was prepared as a yellow oil: $^1$H NMR (300 MHz, DMSO-d$_6$) δ 7.09-7.08 (m, 1H), 7.01-6.99 (m, 2H), 3.59 (s, 2H), 3.45 (br s, 1H), 2.29 (s, 3H), 2.22 (s, 3H), 2.16 (s, 3H).

Preparation 83

Preparation of (2,4,5-Trimethoxy-benzyl)methylamine

According to the procedure of Preparation 67, except substituting 2,4,5-trimethoxy-benzaldehyde for 1-propyl-naphthalene-2-carbaldehyde, the title compound (1.90 g, 88%) was prepared as a light yellow oil: $^1$H NMR (300 MHz, CDCl$_3$) δ 7.11 (s, 1H), 6.84 (s, 1H), 3.94 (s, 6H), 3.86 (s, 3H), 3.71 (s, 2H), 3.53 (br s, 1H), 2.44 (s, 3H).

Preparation 84

Preparation of Benzo[1,3]dioxol-5-ylmethyl-methylamine

According to the procedure of Preparation 67, except substituting benzo[1,3]dioxole-5-carbaldehyde for 1-propyl-naphthalene-2-carbaldehyde, the title compound (3.23 g, 97%) was prepared as a yellow oil: $^1$H NMR (300 MHz, DMSO-d$_6$) δ 6.88-6.75 (m, 3H), 5.96 (s, 2H), 3.52 (s, 2H), 2.20 (s, 3H), 1.95 (br s, 1H).

Preparation 85

Preparation of Benzo[1,3]dioxol-4-ylmethyl-methylamine

According to the procedure of Preparation 67, except substituting benzo[1,3]dioxole-4-carbaldehyde for 1-propyl-naphthalene-2-carbaldehyde, the title compound (1.79 g, 81%) was prepared as a yellow oil: $^1$H NMR (300 MHz, DMSO-d$_6$) δ 6.84-6.82 (m, 1H), 6.79-6.77 (m, 2H), 5.97 (s, 2H), 3.58 (s, 2H), 2.24 (s, 3H), 1.96 (br s, 1H).

Preparation 86

Preparation of (4-Ethoxy-3-methoxy-benzyl)methylamine

According to the procedure of Preparation 67, except substituting 4-ethoxy-3-methoxy-benzaldehyde for 1-propyl-naphthalene-2-carbaldehyde, the title compound (1.93 g, 89%) was prepared as a yellow oil: $^1$H NMR (300 MHz, DMSO-d$_6$) δ 6.90-6.76 (m, 3H), 3.97 (q, J=6.9 Hz, 2H), 3.71 (s, 3H), 3.53 (s, 2H), 2.22 (s, 3H), 2.12 (br s, 1H), 1.33-1.29 (t, J=6.9 Hz, 3H).

Preparation 87

Preparation of (2-Ethoxy-3-methoxy-benzyl)methylamine

According to the procedure of Preparation 67, except substituting 2-ethoxy-3-methoxy-benzaldehyde for 1-propyl-naphthalene-2-carbaldehyde, the title compound (2.03 g, 93%) was prepared as a yellow oil: $^1$H NMR (300 MHz, DMSO-d$_6$) δ 6.99-6.88 (m, 3H), 3.92 (q, J=6.9 Hz, 2H), 3.77 (s, 3H), 3.61 (s, 2H), 2.25 (s, 3H), 1.87 (br s, 1H), 1.26 (t, J=6.3 Hz, 3H).

Preparation 88

Preparation of (3,4-Dimethyl-benzyl)methylamine

According to the procedure of Preparation 67, except substituting 3,4-dimethyl-benzaldehyde for 1-propyl-naphthalene-2-carbaldehyde, the title compound (1.96 g, 89%) was prepared as a yellow oil: $^1$H NMR (300 MHz, DMSO-d$_6$) δ 6.92-6.80 (m, 3H), 3.71 (s, 6H), 3.55 (s, 2H), 2.23 (s, 3H), 1.94 (br s, 1H).

Preparation 89

Preparation of (2,4,5-Trimethyl-benzyl)methylamine

According to the procedure of Preparation 67, except substituting 2,4,5-trimethyl-benzaldehyde for 1-propyl-naphthalene-2-carbaldehyde, the title compound (1.48 g, 67%) was prepared as a yellow oil: $^1$H NMR (300 MHz, DMSO-d$_6$) δ 7.00 (s, 1H), 6.87 (s, 1H), 3.51 (s, 2H), 2.27 (s, 3H), 2.19 (s, 3H), 2.14 (s, 6H), 1.76 (br s, 1H).

Preparation 90

Preparation of Methyl-quinolin-3-yl-methylamine

According to the procedure of Preparation 67, except substituting quinoline-3-carbaldehyde for 1-propyl-naphthalene-2-carbaldehyde, the title compound (1.73 g, 73%) was prepared as a yellow oil: $^1$H NMR (300 MHz, DMSO-d$_6$) δ 9.29 (s, 1H), 8.60-8.58 (s, 2H), 8.09-8.04 (m, 2H), 7.85-7.79 (m, 1H), 7.69-7.64 (m, 1H), 3.52 (s, 3H), 3.33 (s, 2H).

Preparation 91

Preparation of (3,4-Dimethoxy-benzyl)methylamine

According to the procedure of Preparation 67, except substituting 3,4-dimethoxy-benzaldehyde for 1-propyl-naphthalene-2-carbaldehyde, the title compound (2.10 g, 96%) was prepared as a light yellow oil: $^1$H NMR (300 MHz, DMSO-$d_6$) δ 6.92-6.80 (m, 3H), 3.72 (d, J=4.5 Hz, 6H), 3.54 (s, 2H), 2.71 (br s, 1H), 2.23 (s, 3H).

Preparation 92

Preparation of (3,4-Dimethyl-thieno[2,3-b]thiophen-2-ylmethyl)methylamine

According to the procedure of Preparation 67, except substituting 3,4-dimethyl-thieno[2,3-b]thiophene-2-carbaldehyde for 1-propyl-naphthalene-2-carbaldehyde, the title compound (3.13 g, 97%) was prepared as a yellow oil: $^1$H NMR (300 MHz, DMSO-$d_6$) δ 7.07 (s, 1H), 3.78 (s, 2H), 2.42 (s, 3H), 2.35 (s, 3H), 2.30 (s, 3H), 2.19 (br s, 1H).

Preparation 93

Preparation of Benzofuran-2ylmethyl-methylamine

According to the procedure of Preparation 67, except substituting benzofuran-2-carbaldehyde for 1-propyl-naphthalene-2-carbaldehyde, the title compound (4.98 g, 92%) was prepared as an orange oil: $^1$H NMR (300 MHz, DMSO-$d_6$) δ 7.58-7.49 (m, 2H), 7.24-7.19 (m, 2H), 6.70 (s, 1H), 3.77 (s, 2H), 2.17 (s, 3H).

Preparation 94

Preparation of Methyl-(2-methyl-naphthalen-1-ylmethyl)amine

According to the procedure of Preparation 67, except substituting 2-methyl-naphthalene-1-carbaldehyde for 1-propyl-naphthalene-2-carbaldehyde, the title compound (1.72 g, 79%) was prepared as a yellow oil: $^1$H NMR (300 MHz, DMSO-$d_6$) δ 8.14 (d, J=8.4 Hz, 1H), 7.83 (d, J=8.3 Hz, 1H), 7.72 (d, J=8.1 Hz, 1H), 7.50-7.39 (m, 2H), 7.33 (d, J=8.3 Hz, 1H), 4.02 (s, 2H), 2.51 (s, 3H), 2.41 (s, 3H), 1.74 (br s, 1H).

Preparation 95

Preparation of Biphenyl-3-ylmethyl-methylamine

According to the procedure of Preparation 67, except substituting biphenyl-3-carbaldehyde for 1-propyl-naphthalene-2-carbaldehyde, the title compound (0.78 g, 76%) was prepared as a white solid: $^1$H NMR (300 MHz, DMSO-$d_6$) δ 7.66-7.52 (m, 2H), 7.48-7.28 (m, 7H), 3.69 (s, 2H), 2.28 (s, 3H), 2.15 (br s, 1H).

Preparation 96

Preparation of (2-Ethoxy-naphthalen-1-ylmethyl)methylamine

According to the procedure of Preparation 67, except substituting 2-ethoxy-naphthalene-1-carbaldehyde for 1-propyl-naphthalene-2-carbaldehyde, the title compound (2.02 g, 94%) was prepared as a yellow-orange oil: $^1$H NMR (300 MHz, DMSO-$d_6$) δ 8.08 (d, J=8.4 Hz, 1H), 7.85-7.82 (d, J=8.8 Hz, 2H), 7.74-7.33 (m, 3H), 4.18 (q, J=6.9 Hz, 2H), 4.06 (s, 2H), 2.31 (s, 3H), 1.62 (br s, 1H), 1.37 (t, J=6.9 Hz, 3H).

Preparation 97

Preparation of (2,3,4-Trimethoxy-benzyl)methylamine

According to the procedure of Preparation 67, except substituting 2,3,4-trimethoxy-benzaldehyde for 1-propyl-naphthalene-2-carbaldehyde, the title compound (2.17 g, quantitative) was prepared as light yellow oil: $^1$H NMR (300 MHz, DMSO-$d_6$) δ 7.99 (d, J=8.5 Hz 1H), 6.74 (d, J=8.5 Hz, 1H), 3.76 (s, 6H), 3.72 (s, 3H), 2.53 (s, 2H), 2.25 (s, 3H), 1.92 (br s, 1H).

Preparation 98

Preparation of (2,3-Dihydro-benzo[1,4]dioxin-6-ylmethyl)methylamine

According to the procedure of Preparation 67, except substituting 2,3-dihydro-benzo[1,4]dioxine-6-carbaldehyde for 1-propyl-naphthalene-2-carbaldehyde, the title compound (1.28 g, 59%) was prepared as a pale yellow oil: $^1$H NMR (300 MHz, DMSO-$d_6$) δ 6.78-6.73 (m, 3H), 4.20 (s, 4H), 3.48 (s, 2H), 2.20 (s, 3H), 1.96 (br s, 1H).

Preparation 99

Preparation of (2,3-Dihydro-benzo[1.4]dioxin-5-ylmethyl)methylamine

According to the procedure of Preparation 67, except substituting 2,3-dihydro-benzo[1,4]dioxine-5-carbaldehyde for 1-propyl-naphthalene-2-carbaldehyde. The title compound (1.97 g, 91%) was prepared as a yellow oil: $^1$H NMR (300 MHz, DMSO-$d_6$) δ 6.85-6.82 (m, 1H), 6.77-6.70 (m, 2H), 4.25-4.20 (m, 4H), 3.56 (s, 2H), 2.25 (s, 3H), 1.76 (br s, 1H).

Preparation 100

Preparation (4,5-Dimethyl-naphthalen-1-ylmethyl)methylamine

According to the procedure of Preparation 67, except substituting 4,5-dimethyl-naphthalene-1-carbaldehyde for 1-propyl-naphthalene-2-carbaldehyde, the title compound (0.88 g, 88%) was prepared as an off-white solid: $^1$H NMR (500 MHz, DMSO-$d_6$) δ 8.00 (d, J=8 Hz, 1H), 7.33-7.28 (m, 3H), 7.21 (s, 1H), 3.98 (s, 2H), 2.87 (two s, 6H), 2.33 (s, 3H), 1.96 (br s, 1H).

Preparation 101

Preparation of (2,3-Diethoxy-benzyl)methylamine

According to the procedure of Preparation 67, except substituting 2,3-diethoxy-benzaldehyde for 1-propyl-naphthalene-2-carbaldehyde, the title compound (1.81 g, 84%) was prepared as a yellow oil: $^1$H NMR (300 MHz, DMSO-$d_6$) δ 6.96-6.83 (m, 3H), 4.01 (q, J=6.9 Hz, 2H), 3.95 (q, J=6.9 Hz, 2H), 3.61 (s, 2H), 2.25 (s, 3H), 1.81 (br s, 1H), 1.33 (t, J=6.9 Hz, 3H), 1.27 (t, J=6.9 Hz, 3H).

Preparation 102

Preparation of
(3-Ethoxy-2-methoxy-benzyl)methylamine

According to the procedure of Preparation 67, except substituting 3-ethoxy-2-methoxy-benzaldehyde for 1-propyl-naphthalene-2-carbaldehyde, the title compound (1.60 g, 74%) was prepared as a yellow oil: $^1$H NMR (300 MHz, DMSO-$d_6$) δ 6.95-6.88 (m, 3H), 4.04 (q, J=6.9 Hz, 2H), 3.72 (s, 3H), 3.60 (s, 2H), 2.25 (s, 3H), 1.80 (br s, 1H), 1.34 (t, J=6.9 Hz, 3H).

Preparation 103

Preparation of
Methyl-(3-methyl-benzofuran-2-ylmethyl)amine

According to the procedure of Preparation 67, except substituting 3-methyl-benzofuran-2-carbaldehyde for 1-propyl-naphthalene-2-carbaldehyde, the title compound (2.05 g, quantitative) was prepared as a yellow oil: $^1$H NMR (300 MHz, DMSO-$d_6$) δ 7.52 (dd, J=6.7, 2.1 Hz, 1H), 7.46 (dd, J=6.5, 2.0 Hz, 1H), 7.25-7.21 (m, 2H), 3.74 (s, 2H), 2.25 (s, 3H), 2.19 (s, 3H), 2.07 (br s, 1H).

Preparation 104

Preparation of
(3-Chloro-2-methoxy-benzyl)methylamine

According to the procedure of Preparation 67, except substituting 3-chloro-2-methoxy-benzaldehyde for 1-propyl-naphthalene-2-carbaldehyde, the title compound (1.15 g, 55%) was prepared as a yellow oil: $^1$H NMR (300 MHz, DMSO-$d_6$) δ 7.37-7.33 (m, 2H), 7.11 (t, J=7.5 Hz, 1H), 3.77 (s, 3H), 3.68 (s, 2H), 2.27 (s, 3H), 2.01 (br s, 1H).

Preparation 105

Preparation of
(3-Choro-2-ethoxy-benzyl)methylamine a) 3-Chloro-2-ethoxy-benzaldehyde Iodoethane (1.54 mL, 19.2 mmol) was added to a stirring solution of 3-chloro-2-hydroxy-benzaldehyde (2.01 g, 12.8 mmol) and $K_2CO_3$ (3.90 g, 28.2 mmol) in DMF (25 mL). The mixture was heated to 50° C. and stirred for 2.5 h. The heat was removed and reaction stirred at room temperature for 18 h. The reaction was quenched with $H_2O$ (70 mL). The mixture was extracted with EtOAc (3×50 mL). The combined organics were washed with brine (2×50 mL), dried over $Na_2SO_4$, filtered and concentrated to yield the title compound (2.16 g, 91%) as a yellow oil: $^1$H NMR (300 MHz, DMSO-$d_6$) δ 10.27 (s, 1H), 7.85 (dd, J=7.8, 1.5 Hz, 1H), 7.72 (dd, J=7.8, 1.8 Hz, 1H), 7.33 (t, J=7.8 Hz, 1H), 4.14 (q, J=7.2 Hz, 2H), 1.39 (t, J=6.9 Hz, 3H).

b) (3-Chloro-2-ethoxy-benzyl)methylamine

According to the procedure of Preparation 67, except substituting 3-chloro-2-ethoxy-benzaldehyde for 1-propyl-naphthalene-2-carbaldehyde, the title compound (1.36 g, 58%) was prepared as a yellow oil: $^1$H NMR (500 MHz, DMSO-$d_6$) δ 7.36-7.33 (m, 2H), 7.14-7.08 (m, 1H), 3.93 (q, J=7.0 Hz, 2H), 3.67 (s, 2H), 2.24 (s, 3H), 2.07 (br s, 1H), 1.32 (t, J=6.9 Hz, 3H).

Preparation 106

Preparation of
Methyl-thieno[3,2-c]pyridin-2-ylmethyl-amine a) Thieno[3,2-c]pyridine-2-carbaldehyde A solution of thieno[3,2-c]pyridine (500 mg, 3.70 mmol) in anhydrous THF (10 mL) was stirred under argon and maintained at −78° C. while a solution of 1.6 M n-butyllithium in hexane (2.5 mL, 4.07 mmol) was added dropwise. The resulting wine red solution was stirred for 5 min. then DMF (573 μL, 7.4 mmol) was added. The cooling bath was removed and the reaction mixture was stirred at room temperature for 16 hr. The reaction mixture was treated with 10% aqueous HCl, made alkaline with saturated aqueous $NaHCO_3$ and extracted with $CH_2Cl_2$ (2×50 mL) The combined organic fractions were concentrated in vacuo to give an oily residue which was subjected to flash chromatography on silica gel (70% ethyl acetate:hexanes) to give the title compound as a white solid (41.5%): $^1$H-NMR (300 MHz, DMSO-$d_6$) δ 10.20 (s, 1H), 9.39 (s, 1H), 8.60 (s, 1H), 8.59 (d, J=5.5 Hz, 1H), 8.19 (d, J=5.6 Hz, 1H); MS (ES) m/e 164 (M+H)$^+$.

b) Methylthieno[3,2-c]pyridine-2-methylamine

A solution of thieno[3,2-c]pyridine-2-carbaldehyde (720 mg, 4.41 mmol) in a 2.0 M solution of methylamine in methanol (25 mL) was stirred at room temperature for 5 hours. After this time, the mixture was concentrated to dryness, dissolved in anhydrous methanol (10 mL) then cooled to 0° C. To this solution was added $NaBH_4$ (167 mg, 4.41 mmol) in one portion. The mixture was allowed to warm to room temperature and stirred at this temperature overnight. The mixture was concentrated, dissolved in $CH_2Cl_2$ (100 mL) and treated with 1.0 N NaOH (20 mL). The aqueous layer was extracted with $CH_2Cl_2$ (2×20 mL). The combined organic fractions were washed with brine, dried over $Na_2SO_4$ then concentrated to give a yellow residue which was subjected to flash chromatography on silica gel (10% 2M $NH_3$ in MeOH: $CH_2Cl_2$). The title compound was obtained as a white solid in 63.6% yield: $^1$H-NMR (300 MHz, CDCl$_3$) δ 9.01 (s, 1H), 8.45 (d, J=5.5 Hz, 1H), 7.76 (d, J=5.5 Hz, 1H), 7.29 (s, 1H), 4.10 (s, 2H), 2.54 (s, 3H); MS (ES) m/e 179 (M+H)$^+$.

Preparation 107

Preparation of (1H-Indol-5-ylmethyl)methylamine

Indole-5-carbaldehyde (1.0 g, 6.9 mmol) was dissolved in anhydrous methanol (15 mL). Methylamine (9.9 mL of 2M solution in methanol, 19.8 mmol) was added and the reaction was stirred for 3 hr. The solution was concentrated to a yellow oil and then dissolved into anhydrous methanol (20 mL). Sodium borohydride (262 mg, 6.9 mmol) was added and the mixture was stirred overnight. Water (1 mL) was added and the solution was concentrated. Sodium hydroxide (5 mL, 1N) was added and the product was extracted with ethyl acetate (3×20 mL), dried over $MgSO_4$ and concentrated to afford the title compound as a brown oil (980 mg, 91%). $^1$H NMR (200 MHz, CDCl$_3$) δ 8.60 (s, 1H), 7.56 (s, 1H), 7.35-7.15 (m, 3H), 6.55 (m, 1H), 3.85 (s, 2H), 2.49 (s, 3H).

Preparation 108

Preparation of
Methyl-(1-methylindol-5-ylmethyl)amine a) 1-Methylindole-5-carbaldehyde To a solution of indole-5-carbaldehyde (1.0 g, 6.9 mmol) in DMF (15 mL) was added sodium hydride (303 mg of 60% dispersion in oil, 7.59 mmol) in 3 portions. The mixture was stirred for 30 mins. Methyl iodide (1.96 g, 13.8 mmol) was then added and the mixture was stirred overnight. Ethyl acetate (200 mL) was added and solution was washed with $H_2O$ (3×20 mL) and brine (25 mL) dried over $MgSO_4$ and concentrated to afford N-methylindole-5-carboxaldehyde as an orange oil (1.0 g, 91%). $^1H$ NMR (200 MHz, $CDCl_3$) δ 10.05 (s, 1H), 8.09 (s, 1H), 7.90-7.80 (m, 1H), 7.35-7.15 (m, 2H), 6.85-6.80 (m, 1H), 3.95 (s, 3H).

b) Methyl-(1-methylindol-5-ylmethyl)amine

N-Methylindole-5-carbaldehyde (800 mg, 5.1 mmol) was dissolved in anhydrous methanol (15 mL). Methylamine (7.15 mL of 2M solution in methanol, 15.3 mmol) was added and the reaction was stirred for 3 hr. The solution was concentrated to a yellow oil and then dissolved into anhydrous methanol (15 mL). Sodium borohydride (194 mg, 5.1 mmol) was added and the mixture was stirred overnight. Water (1 mL) was added and the solution was concentrated to an orange oil. Sodium hydroxide (5 mL, 1N) was added and the product was extracted with ethyl acetate (3×20 mL), dried over $MgSO_4$ and concentrated to afford the title compound as an orange oil (885 mg, 100%). $^1H$ NMR (200 MHz, $CDCl_3$) δ 7.57 (s, 1H), 7.35-7.11 (m, 3H), 6.51 (d, J=2.9 Hz, 1H), 3.85 (s, 2H), 3.79 (s, 3H), 2.48 (s, 3H).

Preparation 109

Preparation of (1H-Indol-7-ylmethyl)methylamine

Indole-7-carbaldehyde (500 mg, 3.4 mmol) was dissolved in anhydrous methanol (10 mL). Methylamine (5.1 mL of 2M solution in methanol, 9.55 mmol) and the reaction was stirred for 3 hr. The solution was concentrated to a yellow oil and then dissolved into anhydrous methanol (10 mL). Sodium borohydride (131 mg, 3.45 mmol) was added and the mixture was stirred overnight. Water (1 mL) was added and the solution was concentrated. Sodium hydroxide (5 mL, 1N) was added and the indole was extracted with ethyl acetate (3×20 mL), dried over $MgSO_4$ and concentrated to afford the tide compound as a yellow oil (484 mg, 92%). $^1H$ NMR (300 MHz, $CDCl_3$) δ 7.54 (s, 1H), 7.29-7.17 (m, 2H), 7.04 (d, J=3.1 Hz, 1H), 6.44 (d, J=3.1 Hz, 1H), 3.84 (s, 2H), 2.46 (s, 3H).

Preparation 110

Preparation of
Methyl-(1-methylindol-7-ylmethyl)amine

To a solution of indole-7-carboxaldehyde (500 mg, 3.45 mmol) in DMF (8 mL) was added sodium hydride (152 mg of 60% dispersion in oil, 3.8 mmol). The mixture was stirred for 30 mins. Methyl iodide (0.98 g, 6.9 mmol) was then added and the mixture was stirred for 2 hrs. Ethyl acetate (200 mL) was added and solution was washed with $H_2O$ (3×20 mL) and brine (25 mL) dried over $MgSO_4$ and concentrated to afford N-methylindole-7-carboxaldehyde as a brown oil which was used without further purification.

The crude oil was dissolved in anhydrous methanol (10 mL). Methylamine (5.1 mL of 2M solution in methanol, 9.55 mmol) was added and the mixture was stirred for 3 hours. The solution was concentrated to a yellow oil and then dissolved into anhydrous methanol (10 mL). Sodium borohydride (131 mg, 3.45 mmol) was added and the mixture was stirred overnight. Water (1 mL) was added and the solution was concentrated to an orange oil. Sodium hydroxide (5 mL, 1N) was added and the product was extracted with ethyl acetate (3×20 mL), dried over $MgSO_4$ and concentrated to afford the title compound as a brown oil (400 mg, 68%). $^1H$ NMR (200 MHz, $CDCl_3$) δ 7.52 (dd, J=7.0, 2.0 Hz, 1H), 7.23-6.94 (m, 3H), 6.44 (d, J=3.1 Hz, 1H), 4.10 (s, 3H), 4.04 (s, 2H), 2.51 (s, 3H).

Preparation 111

Preparation of (1H-Indol-6-ylmethyl)methylamine a) (1H-Indol-6-yl)methanol

Indole-6-carboxylic acid (1.0 g, 6.2 mmol) was dissolved into anhydrous THF (20 mL) under argon. Lithium aluminum hydride (494 mg, 13 mmol) was added portionwise and the mixture was stirred overnight. The mixture was cooled to 0° C. and ethyl acetate (10 mL) was carefully added, followed by methanol (5 mL) and water (5 mL). The mixture was stirred for 30 min. and filtered through celite. The solution was concentrated and dissolved into ethyl acetate (200 mL) and washed with brine (2×20 mL), dried over $MgSO_4$ and concentrated to afford the title compound as a brown oil (880 mg, 96%). $^1H$ NMR (300 MHz, $CDCl_3$) δ 8.30 (s, 1H), 7.58 (d, J=8.1 Hz, 1H), 7.23 (d, J=1.1 Hz, 1H), 7.13-7.05 (m, 2H), 6.51-6.49 (m, 1H), 4.70 (s, 2H).

b) 1H-Indole-6-carbaldehyde

Dess-Martin periodinane (1.53 g, 2.6 mmol) was dissolved into methylene chloride (15 mL). Indol-6-yl-methanol (500 mg, 3.4 mmol) in methylene chloride (12 mL) was added and the mixture was stirred for 1 hr. Sodium hydroxide (5 mL of 1 N solution) was added and the reaction was stirred for 15 min. The organic layer was separated and washed with $H_2O$ (5 mL), brine (5 mL), dried over $MgSO_4$ and concentrated to afford the title compound as a brown solid (275 mg, 56%). $^1H$ NMR (300 MHz, DMSO-$d_6$) δ 11.7 (s, 1H), 9.98 (s, 1H), 7.97 (s, 1H), 7.70-7.65 (m, 2H), 7.52 (dd, J=8.2, 1.4 Hz, 1H), 6.57-6.5 (m, 1H).

c) (1H-Indol-6-ylmethyl)methylamine

Indole-6-carboxaldehyde (90 mg, 0.62 mmol) was dissolved in anhydrous methanol (3 mL). Methylamine (0.95 mL of 2M solution in methanol, 1.86 mmol) was added and the reaction was stirred for 3 hr. The solution was concentrated to a yellow oil and then dissolved into anhydrous methanol (3 mL). Sodium borohydride (24 mg, 0.62 mmol) was added and the mixture was stirred overnight. Water (1 mL) was added and the solution was concentrated. Sodium hydroxide (2 mL, 1N) was added and the indole was extracted with ethyl acetate (3×10 mL), dried over $MgSO_4$ and concentrated to afford the title compound as a yellow oil (98 mg, 100%). $^1H$ NMR (300 MHz, $CDCl_3$) δ 9.02 (s, 1H), 7.57 (d, J=8.1 Hz, 1H), 7.29 (s, 1H), 7.12 (d, J=3.1 Hz, 1H), 7.04 (d, J=8.1 Hz, 1H), 6.49 (d, J=2.7 Hz, 1H), 3.81 (s, 2H), 2.50 (s, 3H).

Preparation 112

Preparation of N-Methyl-N-(1-methyl-1H-indol-3-ylmethyl)acrylamide

According to the procedure of Example 1 (a), except substituting acrylic acid for the (E)-3-(4-methyl-2-oxo-2,3,4,5-tetrahydro-1H-pyrido[2,3-e][1,4]diazepin-7-yl)acrylic acid hydrochloride, and substituting methyl-(1-methyl-1H-indol-3-ylmethyl)amine for the methyl-(1-propyl-napthalen-2-ylmethyl)amine, the title compound (1.51 g, 58%) was prepared as a white solid: $^1$H NMR (300 MHz, DMSO-d$_6$) δ 7.71-7.50 (s, 1H), 7.34-7.21 (m, 2H), 7.15-6.90 (m, 2H), 6.80-6.53 (m, 1H), 6.45-6.35 (s, 1H), 5.72-5.67 (m, 1H), 4.80-4.75 (m, 2H), 3.77 (s, 3H), 3.05-2.99 (m, 3H).

Preparation 113

Preparation of N-methyl-N-(3-methyl-benzo[b]thiophen-2-ylmethyl)acrylamide

A solution of methyl-(3-methyl-benzo[b]thiophen-2-ylmethyl)amine (1.95 g, 11.4 mmol) in CH$_2$Cl$_2$ (40 mL) was treated with acryloyl chloride (1.2 mL, 14 mmol) and triethylamine (3.2 mL, 22 mmol). The mixture was stirred at room temperature for 1 h. The reaction mixture was diluted with CH$_2$Cl$_2$ (100 mL). The solution was washed with water and brine, dried over Na$_2$SO$_4$, filtered and concentrated under reduced pressure. Purification by column chromatography (silica gel, EtOAc/hexanes, 40/60) gave the title compound (2.10 g, 75%) as a pale yellow solid: MS (ESI) m/e 246 (M+H)$^+$.

Preparation 114

Preparation of (E)-3-(4-methyl-2-oxo-2,3,4,5-tetrahydro-1H-pyrido[2,3-e][1,4]diazepin-7-yl)acrylic acid a) [2-Amino-5-bromo-pyridin-3-ylmethyl)methylamino]acetic acid ethyl ester

A solution of 5-bromo-3-bromomethyl-pyridin-2-ylamine hydrobromide (1.98 g, 5.71 mmol) and sarcosine ethyl ester hydrochloride (0.90 g, 5.86 mmol) in DMF (60 mL) was treated with triethylamine (2.6 mL, 18.5 mmol). After stirring at room temperature under N$_2$ for 2 h, the cloudy mixture was diluted with H$_2$O (100 mL) and extracted with EtOAc (3×100 mL). The combined organic layers were washed with H$_2$O (3×50 mL) and brine (50 mL), dried over Na$_2$SO$_4$, filtered, and the solvent was removed in vacuo. Purification by flash column chromatography (silica gel, CH$_2$Cl$_2$/MeOH, 98:2) gave the title compound (1.37 g, 79%) as a white solid: $^1$H NMR (300 MHz, CDCl$_3$) δ 8.03 (d, J=2.3 Hz, 1H), 7.32 (d, J=2.3 Hz, 1H), 5.76 (s, 2H), 4.20 (q, J=7.1 Hz, 2H), 3.47 (s, 2H), 3.24 (s, 2H), 2.28 (s, 3H), 1.29 (t, J=7.1 Hz, 3H); MS (ESI) m/e 302 (M+H)$^+$.

b) 7-Bromo-4-methyl-1,3,4,5-tetrahydro-pyrido[2,3-e][1,4]diazepin-2-one

A solution of [2-amino-5-bromo-pyridin-3-ylmethyl)methylamino]acetic acid ethyl ester (1.37 g, 4.53 mmol) in DMSO (50 mL) was treated with NaH (0.18 g, 4.5 mmol). After stirring at room temperature under N$_2$ for 2 h, the mixture was stored in the freezer overnight. The mixture was allowed to warm to room temperature, diluted with H$_2$O (200 mL), and extracted with EtOAc (3×150 mL). The combined organic layers were washed with H$_2$O (2×50 mL) and brine (50 mL), dried over Na$_2$SO$_4$, filtered, and the solvent was removed in vacuo. Purification by flash column chromatography (silica gel, CH$_2$Cl$_2$/MeOH, 98:2) gave the title compound (0.88 g, 76%) as a white solid: $^1$H NMR (300 MHz, CDCl$_3$) δ 8.57 (s, 1H), 8.35 (d, J=2.2 Hz, 1H), 7.61 (d, J=2.1 Hz, 1H), 3.91 (s, 2H), 3.74 (s, 2H), 2.49 (s, 3H); MS (ESI) m/e 256 (M+H)$^+$.

c) (E)-3-(4-Methyl-2-oxo-2,3,4,5-tetrahydro-1H-pyrido[2,3-e][1,4]diazepin-7-yl)acrylic acid tert-butyl ester A suspension of 7-bromo-4-methyl-1,3,4,5-tetrahydro-pyrido[2,3-e][1,4]diazepin-2-one (0.63 g, 2.5 mmol) in propionitrile (10 mL) and DMF (3 mL) was de-oxygenated with Ar for 25 min. The mixture was treated with tert-butyl acrylate (1.5 mL, 10 mmol) and (i-Pr)$_2$EtN (0.9 mL, 5 mmol) and was de-oxygenated with Ar for 10 min. Pd(OAc)$_2$ (56 mg, 0.25 mmol) and P(o-tol)$_3$ (150 mg, 0.49 mmol) were added simultaneously, and the mixture was de-oxygenated a third time for 5 min. The mixture was heated to reflux for 18 h, then allowed to cool. The resulting precipitate was isolated by filtration, dissolved in CH$_2$Cl$_2$, filtered through Celite, and the solvent was removed in vacuo to give the title compound (0.60 g, 80%) as an off-white solid: $^1$H NMR (300 MHz, CDCl$_3$) δ 8.63 (s, 1H), 8.41 (d, J=2.0 Hz, 1H), 7.62 (d, J=1.7 Hz, 1H), 7.52 (d, J=16.0 Hz, 1H), 6.37 (d, J=16.0 Hz, 1H), 3.96 (s, 2H), 3.77 (s, 2H), 2.49 (s, 3H), 1.53 (s, 9H); MS (ESI) m/e 304 (M+H)$^+$.

d) (E)-3-(4-Methyl-2-oxo-2,3,4,5-tetrahydro-1H-pyrido[2,3-e][1,4]diazepin-7-yl)acrylic acid A suspension of (E)-3-(4-methyl-2-oxo-2,3,4,5-tetrahydro-1H-pyrido[2,3-e][1,4]diazepin-7-yl)acrylic acid tert-butyl ester (0.59 g, 1.9 mmol) in CH$_2$Cl$_2$ (7 mL) was treated with TFA (7 mL). After stirring at room temperature under N$_2$ for 45 min, the clear tan solution was concentrated in vacuo. The resulting oil was treated with anhydrous HCl in dioxane (10 mL, 4.0 M) and sonicated until the oil was converted to a fine off-white solid. After stirring under N$_2$ for 20 min, the solid was isolated by filtration, washed with Et$_2$O, and dried under vacuum for several hours to give the title compound (0.77 g, quantitative) as an off-white solid: $^1$H NMR (300 MHz, DMSO-d$_6$) δ 12.27 (bs, 1H), 11.28 (s, 1H), 8.78 (d, J=1.9 Hz, 1H), 8.32 (d, J=1.9 Hz, 1H), 7.65 (d, J=16.1 Hz, 1H), 6.63 (d, J=16.1 Hz, 1H), 4.32 (s, 2H), 3.82 (s, 2H), 2.89 (s, 3H); MS (ESI) m/e 248 (M+H)$^+$.

Preparation 115

Preparation of (E)-3-(4-Ethoxycarbonylmethyl-2-oxo-2,3,4,5-tetrahydro-1H-pyrido[2,3-e][1,4]diazepin-7-yl)acrylic acid hydrochloride a) [(2-Amino-5-bromo-pyridin-3-ylmethyl)ethoxycarbonylmethyl-amino]acetic acid ethyl ester A suspension of 5-bromo-3-bromomethyl-pyridin-2-ylamine hydrobromide (12.0 g, 34.6 mmol) and diethyl iminodiacetate (7.0 mL, 39.1 mmol) in CH$_3$CN (350 mL) was treated with triethylamine (10.7 mL, 76.1 mmol). After stirring at room temperature under N$_2$ for 4 h, the solvent was removed in vacuo. The resulting yellow slurry was partitioned between H$_2$O (400 mL) and EtOAc (400 mL), and the aqueous layer was extracted with EtOAc (200 mL). The combined organic layers were washed with brine (100 mL), dried over Na$_2$SO$_4$, filtered and the solvent was removed in vacuo. Purification by flash column chromatography (silica gel, CH$_2$Cl$_2$/MeOH, 99:1) gave the title compound (6.55 g, 51%) as a light tan oil: MS (ESI) m/e 374 (M+H)$^+$.

b) (7-Bromo-2-oxo-1,2,3,5-tetrahydro-pyrido[2,3-e][1,4]diazepin-4-yl)acetic acid ethyl ester A solution of [(2-amino-5-bromo-pyridin-3-ylmethyl)ethoxycarbonylmethyl-amino]-acetic acid ethyl ester (6.52 g, 17.4 mmol) in DMSO (170 mL) was treated with NaH (0.70 g, 17.5 mmol). After stirring at room temperature overnight, the mixture was diluted with H$_2$O (300 mL) and extracted with EtOAc (4×200 mL). The combined organic layers were washed with H$_2$O (3×100 mL) and brine (100 mL), dried over Na$_2$SO$_4$, filtered and the solvent was removed in vacuo to give the title compound (6.18 g, quantitative) as an off-white solid: MS (ESI) m/e 328 (M+H)$^+$.

c) (E)-3-(4-Ethoxycarbonylmethyl-2-oxo-2,3,4,5-tetrahydro-1H-pyrido[2,3-e][1,4]diazepin-7-yl)acrylic acid tert-butyl ester A suspension of (7-Bromo-2-oxo-1,2,3,5-tetrahydro-pyrido[2,3-e][1,4]diazepin-4-yl)acetic acid ethyl ester (6.18 g, 17.4 mmol) in propionitrile (70 mL) and DMF (17 mL) was de-oxygenated with Ar for 30 min. The mixture was treated with tert-butyl acrylate (10.2 mL, 69.6 mmol) and (i-Pr)$_2$EtN (6.4 mL, 37 mmol) and was then de-oxygenated with Ar for 10 min. Pd(OAc)$_2$ (0.39 g, 1.7 mmol) and P(o-tol)$_3$ (1.06 mg, 3.48 mmol) were added simultaneously, and the mixture was de-oxygenated a third time for 5 min. After heating to reflux for 14 h, the mixture was allowed to cool and then concentrated in vacuo. The resulting residue was diluted with CH$_2$Cl$_2$ and filtered through Celite. The orange filtrate was concentrated in vacuo. The resulting residue was diluted with EtOAc (200 mL) and washed with H$_2$O (100 mL). The aqueous layer was extracted with EtOAc (2×100 mL). The combined organic layers were washed with H$_2$O (2×100 mL) and brine (100 mL), dried over Na$_2$SO$_4$, filtered and the solvent was removed in vacuo. Purification by flash column chromatography (silica gel, CH$_2$Cl$_2$/MeOH, 97:3) and again by flash column chromatography (silica gel, CH$_2$Cl$_2$/MeOH, 99:1) gave the title compound (2.55 g, 39%) as an off-white solid: MS (ESI) m/e 376 (M+H)$^+$.

d) (E)-3-(4-Ethoxycarbonylmethyl-2-oxo-2,3,4,5-tetrahydro-1H-pyrido[2,3-e][1,4]diazepin-7-yl)acrylic acid hydrochloride A solution of (E)-3-(4-ethoxycarbonylmethyl-2-oxo-2,3,4,5-tetrahydro-1H-pyrido[2,3-e][1,4]diazepin-7-yl)acrylic acid tert-butyl ester (1.14 g, 3.04 mmol) in CH$_2$Cl$_2$ (8 mL) was treated with TFA (8 mL). After stirring at room temperature under N$_2$ for 45 min, the clear tan solution was concentrated in vacuo. The resulting oil was treated with anhydrous HCl in dioxane (10 mL, 4.0 M) and sonicated until the oil was converted to a fine off-white solid. The resulting mixture was diluted with Et$_2$O (100 mL) and stirred under N$_2$ for 20 min. The solid was isolated by filtration, washed with Et$_2$O, and dried under vacuum at 50° C. overnight to give the title compound (1.05 g, 88%) as an off-white solid: $^1$H NMR (300 MHz, DMSO-d$_6$) δ 10.57 (s, 1H), 8.56-8.55 (m, 1H), 8.10 (s, 1H), 6.57 (d, J=16.0 Hz, 1H), 6.57 (d, J=16.0 Hz, 1H), 4.14-4.05 (m, 3H), 3.62-3.56 (m, 6H), 1.18 (t, J=7.1 Hz, 3H); MS (ESI) m/e 320 (M+H)$^+$.

Preparation 116

Preparation of (R)-(E)-3-(10-Oxo-2,3,4,9,10,10a-hexahydro-1H-3a,8,9-triaza-benzo[f]azulen-6-yl)acrylic acid hydrochloride a) (R)-1-(2-Amino-5-bromo-pyridin-3-ylmethyl)pyrrolidine-2-carboxylic acid methyl ester A suspension of 5-bromo-3-bromomethyl-pyridin-2-ylamine hydrobromide (8.00 g, 23.1 mmol) and D-proline methyl ester hydrochloride (4.53 g, 27.4 mmol) in CH$_3$CN (100 mL) was treated with a solution of triethylamine (10.4 mL, 74.0 mmol) in CH$_3$CN (100 mL). After stirring at room temperature for 5 h, the cloudy mixture was diluted with H$_2$O (300 mL) and extracted with EtOAc (3×200 mL). The combined organic layers were washed with brine (100 mL), dried over Na$_2$SO$_4$, filtered and the solvent was removed in vacuo. Purification by flash column chromatography (silica gel, CH$_2$Cl$_2$/MeOH, 99:1 to 98:2) gave the title compound (6.55 g, 90%) as a colorless oil: MS (ESI) m/e 314 (M+H)$^+$ b) (R)-6-Bromo-1,2,3,4,9,10a-hexahydro-3a,8,9-triaza-benzo[f]azulen-10-one A solution of (R)-1-(2-amino-5-bromo-pyridin-3-ylmethyl)pyrrolidine-2-carboxylic acid methyl ester (6.52 g, 20.8 mmol) in DMSO (200 mL) was treated with NaH (60% dispersion in mineral oil, 0.83 g, 20.7 mmol). After stirring at room temperature for 3 h, the mixture was stored in the freezer for 3 d. The mixture was allowed to warm to room temperature, diluted with H$_2$O (400 mL), and extracted with EtOAc (4×200 mL). The combined organic layers were washed with H$_2$O (3×100 mL) and brine (100 mL), dried over Na$_2$SO$_4$, filtered and the solvent was removed in vacuo. Purification by flash column chromatography (silica gel, CH$_2$Cl$_2$/MeOH, 99:1) gave the title compound (3.94 g, 67%) as an off-white solid: MS (ESI) m/e 282 (M+H)$^+$.

c) (R)-(E)-3-(10-Oxo-2,3,4,9,10,10a-hexahydro-1H-3a,8,9-triaza-benzo[f]azulen-6-yl)acrylic acid tert-butyl ester A suspension of (R)-6-bromo-1,2,3,4,9,10a-hexahydro-3a,8,9-triaza-benzo[f]azulen-10-one (3.91 g, 13.8 mmol) in propionitrile (80 mL) and DMF (20 mL) was de-oxygenated with Ar for 25 min. The mixture was treated with tert-butyl acrylate (8.1 mL, 55 mmol) and (i-Pr)$_2$EtN (5.1 mL, 29 mmol) and was de-oxygenated with Ar for 15 min. Pd(OAc)$_2$ (0.31 g, 1.4 mmol) and P(o-tol)$_3$ (0.84 mg, 2.8 mmol) were added simultaneously, and the mixture was de-oxygenated a third time for 10 min. The mixture was heated to reflux overnight then allowed to cool. The resulting precipitate was isolated by filtration, dissolved in CH$_2$Cl$_2$, filtered through Celite, and the solvent was removed in vacuo to give the title compound (2.53 g, 56%) as an off-white solid: MS (ESI) m/e 330 (M+H)$^+$.

d) (R)-(E)-3-(10-Oxo-2,3,4,9,10,10a-hexahydro-1H-3a,8,9-triaza-benzo[f]azulen-6-yl)acrylic acid hydrochloride A solution of (R)-(E)-3-(10-oxo-2,3,4,9,10,10a-hexahydro-1H-3a,8,9-triaza-benzo[f]azulen-6-yl)acrylic acid tert-butyl ester (2.53 g, 7.68 mmol) in CH$_2$Cl$_2$ (15 mL) was treated with TFA (15 mL). After stirring at room temperature under N$_2$ for 45 min, the clear tan solution was concentrated in vacuo. The resulting oil was treated with anhydrous HCl (30 mL of a 4.0 M solution in dioxane, 120 mmol). The resulting mixture was sonicated for 10 min, stirred under $N_2$ for 20 min, diluted with $Et_2O$ (100 mL), sonicated for 20 min and stirred for 20 min. The solid was isolated by filtration, washed with $Et_2O$, and dried under vacuum at 50° C. overnight to give the title compound (2.66 g, quantitative) as an off-white solid: MS (ESI) m/e 274 (M+H)$^+$.

Preparation 117

Preparation of (S)-(E)-3-(10-Oxo-2,3,4,9,10,10a-hexahydro-1H-3a,8,9-triaza-benzo[f]azulen-6-yl)acrylic acid hydrochloride a) (S)-1-(2-Amino-5-bromo-pyridin-3-ylmethyl)pyrrolidine-2-carboxylic acid methyl ester A solution of 5-bromo-3-bromomethyl-pyridin-2-ylamine hydrobromide (6.00 g, 17.3 mmol) and L-proline methyl ester hydrochloride (2.88 g, 17.4 mmol) in DMF (125 mL) was treated with a solution of triethylamine (7.8 mL, 55.5 mmol) in DMF (75 mL). After stirring at room temperature under $N_2$ for 3 h, the cloudy mixture was diluted with $H_2O$ (300 mL) and extracted with EtOAc (2×300 mL). The combined organic layers were washed with $H_2O$ (2×100 mL) and brine (100 mL), dried over $Na_2SO_4$, filtered and the solvent was removed in vacuo. Purification by flash column chromatography (silica gel, $CH_2Cl_2$/MeOH, 99:1 to 98:2) gave the title compound (3.66 g, 67%) as a pale yellow oil: MS (ESI) m/e 314 (M+H)$^+$.

b) (S)-6-Bromo-1,2,3,4,9,10a-hexahydro-3a,8,9-triaza-benzo[f]azulen-10-one

A solution of (S)-1-(2-amino-5-bromo-pyridin-3-ylmethyl)pyrrolidine-2-carboxylic acid methyl ester (3.66 g, 11.6 mmol) in DMSO (120 mL) was treated with NaH (60% dispersion in mineral oil, 0.47 g, 11.7 mmol). After stirring at room temperature for 4 h, the mixture was diluted with $H_2O$ (2500 mL) and extracted with EtOAc (5×150 mL). The combined organic layers were washed with $H_2O$ (4×100 mL) and brine (100 mL), dried over $Na_2SO_4$, filtered and the solvent was removed in vacuo. Purification by flash column chromatography (silica gel, $CH_2Cl_2$/MeOH, 99:1) gave the title compound (2.75 g, 84%) as an off-white solid: MS (ESI) m/e 282 (M+H)$^+$.

c) (S)-(E)-3-(10-Oxo-2,3,4,9,10,10a-hexahydro-1H-3a,8,9-triaza-benzo[f]azulen-6-yl)acrylic acid tert-butyl ester A suspension of (S)-6-bromo-1,2,3,4,9,10a-hexahydro-3a,8,9-triaza-benzo[f]azulen-10-one (1.46 g, 5.17 mmol) in propionitrile (40 mL) and DMF (10 mL) was de-oxygenated with Ar for 30 min. The mixture was treated with tert-butyl acrylate (3.0 mL, 20 mmol) and (i-Pr)$_2$EtN (1.9 mL, 11 mmol) and was de-oxygenated with Ar for 10 min. Pd(OAc)$_2$ (0.12 g, 0.53 mmol) and P(o-tol)$_3$ (0.34 mg, 1.12 mmol) were added simultaneously, and the mixture was de-oxygenated a third time for 5 min. The mixture was heated to reflux overnight then allowed to cool. The resulting precipitate was isolated by filtration, dissolved in $CH_2Cl_2$, filtered through Celite and the solvent was removed in vacuo to give the title compound (0.68 g, 40%) as an off-white solid: MS (ESI) m/e 330 (M+H)$^+$.

d) (S)-(E)-3-(10-Oxo-2,3,4,9,10,10a-hexahydro-1H-3a,8,9-triaza-benzo[f]azulen-6-yl)acrylic acid hydrochloride A solution of (S)-(E)-3-(10-oxo-2,3,4,9,10,10a-hexahydro-1H-3a,8,9-triaza-benzo[f]azulen-6-yl)acrylic acid tert-butyl ester (0.65 g, 1.97 mmol) in $CH_2Cl_2$ (7 mL) was treated with TFA (7 mL). After stirring at room temperature for 30 min, the clear tan solution was concentrated in vacuo. The resulting oil was treated with anhydrous dioxane (20 mL of a 4.0 M solution in dioxane, 80 mmol). The resulting mixture was sonicated for 5 min, stirred under $N_2$ for 5 min and diluted with $Et_2O$. The solid was isolated by filtration, suspended in $Et_2O$, concentrated to dryness, and dried under vacuum overnight to give the title compound (0.60 g, 88%) as an off-white solid: MS (ESI) m/e 274 (M+H)$^+$.

Preparation 118

Preparation of (E)-3-[4-(4-Methoxy-benzyl)-2-oxo-2,3,4,5-tetrahydro-1H-pyrido[2,3-e][1.4]diazepin-7-yl]acrylic acid hydrochloride a) (4-Methoxy-benzylamino)acetic acid ethyl ester A suspension of glycine ethyl ester hydrochloride (10.0 g, 71.6 mmol) and NaBH$_3$CN (5.00 g, 79.6 mmol) in MeOH (60 mL) was treated dropwise over 15 min with p-anisaldehyde (11.0 mL, 90.4 mmol). After stirring at room temperature overnight, the solvent was removed in vacuo. The residue was partitioned between $CH_2Cl_2$ (200 mL) and saturated aqueous NaHCO$_3$ (300 mL). The aqueous layer was extracted with $CH_2Cl_2$ (2×200 mL) and the combined organic layers were washed with brine, dried over $Na_2SO_4$, filtered and the solvent was removed in vacuo. Purification by flash column chromatography (silica gel, hexanes/EtOAc, 90:10 to 50:50) gave the title compound (7.77 g, 49%) as a colorless liquid: MS (ESI) m/e 224 (M+H)$^+$.

b) [(2-Amino-5-bromo-pyridin-3-ylmethyl)-(4-methoxy-benzyl)amino]acetic acid ethyl ester A solution of 5-bromo-3-bromomethyl-pyridin-2-ylamine hydrobromide (11.9 g, 34.3 mmol) and (4-methoxy-benzylamino)acetic acid ethyl ester (7.70 g, 34.5 mmol) in DMF (200 mL) was treated with triethylamine (10.0 mL, 71.2 mmol). After stirring at room temperature overnight, the cloudy mixture was diluted with $H_2O$ (400 mL) and extracted with EtOAc (2×300 mL). The combined organic layers were washed with $H_2O$ (3×100 mL) and brine (100 mL), dried over $Na_2SO_4$, filtered and the solvent was removed in vacuo to give the title compound (13.0 g, 93%) as a yellow syrup: MS (ESI) m/e 408 (M+H)$^+$.

c) 7-Bromo-4-(4-methoxy-benzyl)-1,3,4,5-tetrahydro-pyrido[2,3-e][1,4]diazepin-2-one A solution of [(2-amino-5-bromo-pyridin-3-ylmethyl)-(4-methoxy-benzyl)amino]acetic acid ethyl ester (13.0 g, 31.9 mmol) in DMSO (200 mL) was treated with NaH (60% dispersion in mineral oil, 1.30 g, 32.5 mmol). After stirring at room temperature overnight, the mixture was diluted with $H_2O$ (500 mL) and a precipitate formed. The solid was isolated by filtration, washed with $H_2O$, and dried under vacuum at 50° C. for 6.5 h to give the title compound (7.16 g, 62%) as a tan powder: MS (ESI) m/e 362 (M+H)$^+$.

d) (E)-3-[4-(4-Methoxy-benzyl)-2-oxo-2,3,4,5-tetrahydro-1H-pyrido[2,3-e][1,4]diazepin-7-yl]acrylic acid tert-butyl ester A suspension of 7-bromo-4-(4-methoxy-benzyl)-1,3,4,5-tetrahydro-pyrido[2,3-e][1,4]diazepin-2-one (5.00 g, 13.8 mmol) in propionitrile (80 mL) and DMF (20 mL) was de-oxygenated with Ar for 25 min. The mixture was treated with tert-butyl acrylate (8.1 mL, 55 mmol) and (i-Pr)$_2$EtN (5.1 mL, 29 mmol) and was de-oxygenated with Ar for 15 min. Pd(OAc)$_2$ (0.32 g, 1.43 mmol) and P(o-tol)$_3$ (0.85 g, 2.79 mmol) were added simultaneously, and the mixture was de-oxygenated a third time for 5 min. The mixture was heated to reflux overnight, then allowed to cool. The resulting precipitate was isolated by filtration. Purification by flash column chromatography (silica gel, CH$_2$Cl$_2$/MeOH, 99:1) gave the title compound (3.54 g, 63%) as a white solid: MS (ESI) m/e 410 (M+H)$^+$.

e) (E)-3-[4-(4-Methoxy-benzyl)-2-oxo-2,3,4,5-tetrahydro-1H-pyrido[2,3-e][1,4]diazepin-7-yl]acrylic acid hydrochloride A suspension of (E)-3-[4-(4-methoxy-benzyl)-2-oxo-2,3,4,5-tetrahydro-1H-pyrido[2,3-e][1,4]diazepin-7-yl]acrylic acid tert-butyl ester (3.54 g, 8.65 mmol) in CH$_2$Cl$_2$ (20 mL) was treated with TFA (20 mL). After stirring at room temperature under N$_2$ for 25 min, the clear tan solution was concentrated in vacuo. The resulting residue was treated with anhydrous HCl (40 mL of a 4.0 M solution in dioxane, 160 mmol) and sonicated for 15 min. The solid was isolated by filtration, washed with Et$_2$O and dried under vacuum at 50° C. for 3 d to give the title compound (3.40 g, 92%) as a white solid: $^1$H NMR (300 MHz, DMSO-d$_6$) δ 12.38 (br s, 1H), 11.32 (s, 1H), 8.77 (s, 1H), 8.28 (s, 1H), 7.66-7.58 (m, 3H), 7.02 (d, J=8.6 Hz, 2H), 6.63 (d, J=16.1 Hz, 1H), 4.41-4.27 (m, 5H), 3.79 (s, 3H), 3.68 (s, 2H); MS (ESI) m/e 354 (M+H)$^+$.

Preparation 119

Preparation of (E)-3-[4-(2-Morpholin-4-yl-ethyl)-2-oxo-2,3,4,5-tetrahydro-1H-pyrido[2,3-e][1,4]diazepin-7-yl]acrylic acid hydrochloride a) [tert-Butoxycarbonyl-(2-morpholin-4-yl-ethyl)amino]acetic acid methyl ester A solution of N-tert-butoxycarbonyl glycine methyl ester (9.4 mL, 63.6 mmol) in DMF (250 mL) was cooled in an ice bath and treated with NaH (60% dispersion in mineral oil, 2.85 g, 71.2 mmol). After stirring at 0° C. under N$_2$ for 30 min and then at room temperature for 30 min, the mixture was cooled in an ice bath and treated with a solution of 4-(2-chloroethyl)morpholine (10.5 g, 70 mmol) in DMF (50 mL). After stirring at 0° C. for 30 min, the mixture was stirred at room temperature overnight. The mixture was diluted with H$_2$O (600 mL) and then extracted with EtOAc (5×300 mL). The combined organic layers were washed with H$_2$O (4×100 mL) and brine (100 mL), dried over Na$_2$SO$_4$, filtered and the solvent was removed in vacuo. Purification by flash column chromatography (silica gel, CH$_2$Cl$_2$/MeOH, 98:2) gave the title compound (0.79 g, 4%) as a colorless oil: MS (ESI) m/e 303 (M+H)$^+$.

b) (2-Morpholin-4-yl-ethylamino)acetic acid methyl ester

A solution of [tert-butoxycarbonyl-(2-morpholin-4-yl-ethyl)amino]acetic acid methyl ester (0.79 g, 2.61 mmol) in CH$_2$Cl$_2$ (10 mL) was treated with TFA (10 mL). After stirring at room temperature for 1 h, the solution was concentrated in vacuo. The oil was dissolved in CH$_2$Cl$_2$ (50 mL) and the resulting solution was washed with saturated aqueous NaHCO$_3$ (50 mL). The aqueous layer was extracted with CH$_2$Cl$_2$ (10×50 mL). The combined organic layers were dried over Na$_2$SO$_4$, filtered and the solvent was removed in vacuo to give the title compound (0.40 g, 76%) as a yellow oil: $^1$H NMR (300 MHz, CDCl$_3$) δ 3.69-3.74 (m, 7H), 3.45 (s, 2H), 2.69-2.73 (m, 2H), 2.45-2.52 (m, 6H), 1.84 (s, 1H).

c) [(2-Amino-5-bromo-pyridin-3-ylmethyl)-(2-morpholin-4-yl-ethyl)amino]acetic acid methyl ester A solution of (2-Morpholin-4-yl-ethylamino)acetic acid methyl ester (0.40 g, 2.0 mmol) and triethylamine (1.0 mL, 7.11 mmol) in DMF (20 mL) was treated with 5-bromo-3-bromomethyl-pyridin-2-ylamine hydrobromide (0.70 g, 2.0 mmol). After stirring at room temperature under for 7 h, the cloudy mixture was diluted with H$_2$O (50 mL) and then extracted with EtOAc (4×50 mL). The combined organic layers were washed with H$_2$O (3×50 mL) and brine (50 mL), dried over Na$_2$SO$_4$, filtered and the solvent was removed in vacuo. Purification by flash column chromatography (silica gel, CH$_2$Cl$_2$/MeOH, 98:2 to 96:4) gave the title compound (0.46 g, 60%) as a colorless oil: MS (ESI) m/e 387 (M+H)$^+$.

d) 7-Bromo-4-(2-morpholin-4-yl-ethyl)-1,3,4,5-tetrahydro-pyrido[2,3-e][1,4]diazepin-2-one A solution of [(2-amino-5-bromo-pyridin-3-ylmethyl)-(2-morpholin-4-yl-ethyl)amino]acetic acid methyl ester (0.34 g, 0.88 mmol) in DMSO (10 mL) was treated with NaH (60% dispersion in mineral oil, 35 mg, 0.88 mmol). After stirring at room temperature overnight, the mixture was diluted with H$_2$O (20 mL), and then extracted with EtOAc (4×50 mL). The combined organic layers were washed with H$_2$O (3×50 mL) and brine (50 mL), dried over Na$_2$SO$_4$, filtered and the solvent was removed in vacuo. The resulting pale yellow oil was purified by flash column chromatography (silica gel, CH$_2$Cl$_2$/MeOH, 97:3 to 90:10) to give the title compound (0.24 g, 57%) as an off-white solid: MS (ESI) m/e 355 (M+H)$^+$.

e) (E)-3-[4-(2-Morpholin-4-yl-ethyl)-2-oxo-2,3,4,5-tetrahydro-1H-pyrido[2,3-e][1,4]diazepin-7-yl]acrylic acid tert-butyl ester A suspension of 7-bromo-4-(2-morpholin-4-yl-ethyl)-1,3,4,5-tetrahydro-pyrido[2,3-e][1,4]diazepin-2-one (0.18 g, 0.52 mmol) in propionitrile (4 mL) and DMF (1 mL) was de-oxygenated with Ar for 15 min. The mixture was treated with tert-butyl acrylate (0.3 mL, 2 mmol) and (i-Pr)$_2$EtN (0.2 mL, 1 mmol) and was de-oxygenated with Ar for 10 min. Pd(OAc)$_2$ (12 mg, 0.053 mmol) and P(o-tol)$_3$ (32 mg, 0.10 mmol) were added simultaneously, and the mixture was de-oxygenated a third time for 5 min. The mixture was heated to reflux overnight, then allowed to cool. The mixture was diluted with Et$_2$O (50 mL) and the resulting solution washed with H$_2$O (20 mL). The organic layer was dried over Na$_2$SO$_4$, filtered and the solvent was removed in vacuo. Purification by flash column chromatography (silica gel, CH$_2$Cl$_2$/MeOH, 97:3) gave the title compound (92 mg, 44%) as an off-white solid: $^1$H NMR (300 MHz, DMSO-$d_6$) δ 9.51 (s, 1H), 8.52 (s, 1H), 7.61-7.49 (m, 2H), 6.36 (d, J=16.0 Hz, 1H), 4.07 (s, 2H), 3.90 (s, 2H), 3.70-3.67 (m, 4H), 2.78-2.74 (m, 2H), 2.52-2.49 (m, 6H), 1.53 (s, 9H); MS (ESI) m/e 403 (M+H)$^+$.

f) (E)-3-[4-(2-Morpholin-4-yl-ethyl)-2-oxo-2,3,4,5-tetrahydro-1H-pyrido[2,3-e][1,4]diazepin-7-yl]acrylic acid hydrochloride A solution of (E)-3-[4-(2-morpholin-4-yl-ethyl)-2-oxo-2,3,4,5-tetrahydro-1H-pyrido[2,3-e][1,4]diazepin-7-yl]acrylic acid tert-butyl ester (92 mg, 0.23 mmol) in CH$_2$Cl$_2$ (2 mL) was treated with TFA (2 mL). After stirring at room temperature for 30 min, the clear tan solution was concentrated in vacuo. The resulting oil was treated with anhydrous HCl (4 mL of a 4.0 M solution in dioxane, 16 mmol) and then sonicated for 15 min. The mixture was diluted with Et$_2$O and sonicated for 10 min. The solid was isolated by filtration, washed with Et$_2$O and dried under vacuum at 50° C. for 4.5 hr to give the title compound (0.10 g, 96%) as an off-white solid: MS (ESI) m/e 347 (M+H)$^+$.

Preparation 120

Preparation of (E)-3-{4-[2-(4-Methyl-piperazin-1-yl)-2-oxo-ethyl]-2-oxo-2,3,4,5-tetrahydro-1H-pyrido[2,3-e][1,4]diazepin-7-yl}acrylic acid hydrochloride a) [(2-Amino-5-bromo-pyridin-3-ylmethyl)amino]acetic acid ethyl ester A solution of 5-bromo-3-bromomethyl-pyridin-2-ylamine hydrobromide (6.00 g, 17.3 mmol) and glycine ethyl ester hydrochloride (2.41 g, 17.3 mmol) in DMF (200 mL) was treated with triethylamine (7.8 mL, 56 mmol). After stirring at room temperature for 3.5 h, the cloudy mixture was diluted with H$_2$O (300 mL) and then extracted with EtOAc (2×300 mL). The combined organic layers were washed with H$_2$O (3×100 mL) and brine (100 mL), dried over Na$_2$SO$_4$, filtered and the solvent was removed in vacuo. Purification by flash column chromatography (silica gel, CH$_2$Cl$_2$/MeOH, 98:2) gave the title compound (2.83 g, 57%) as a white solid: $^1$H NMR (300 MHz, CDCl$_3$) δ 8.04 (d, J=2.3 Hz, 1H), 7.36 (d, J=2.3 Hz, 1H), 5.56 (s, 2H), 4.22 (q, J=7.2 Hz, 2H), 3.71 (s, 2H), 3.38 (s, 2H), 1.73 (s, 1H), 1.30 (t, J=7.2 Hz, 3H); MS (ESI) m/e 288 (M+H)$^+$.

b) 7-Bromo-1,3,4,5-tetrahydro-pyrido[2,3-e][1,4]diazepin-2-one

A solution of [(2-amino-5-bromo-pyridin-3-ylmethyl)amino]acetic acid ethyl ester (1.79 g, 6.21 mmol) in DMSO (70 mL) was treated with NaH (60% dispersion in mineral oil, 0.25 g, 6.2 mmol). After stirring at room temperature for 27 h, the mixture was diluted with H$_2$O (300 mL), and extracted then with EtOAc (4×150 mL). The combined organic layers were washed with H$_2$O (3×50 mL) and brine (50 mL), dried over Na$_2$SO$_4$, filtered and the solvent was removed in vacuo to give the title compound (1.09 g, 72%) as an off-white solid: $^1$H NMR (300 MHz, CDCl$_3$) δ 8.26 (d, J=2.1 Hz, 1H), 8.17 (s, 1H), 7.54 (d, J=1.9 Hz, 1H), 4.03 (s, 2H), 3.93 (s, 2H), 1.85 (br s, 1H); MS (ESI) m/e 242 (M+H)$^+$.

c) (7-Bromo-2-oxo-1,2,3,5-tetrahydro-pyrido[2,3-e][1,4]diazepin-4-yl)acetic acid tert-butyl ester A solution of 7-bromo-1,3,4,5-tetrahydro-pyrido[2,3-e][1,4]diazepin-2-one (2.29 g, 9.46 mmol) in DMF (100 mL) was treated with tert-butylbromoacetate (1.7 mL, 12 mmol) and triethylamine (1.5 mL, 11 mmol). After stirring at room temperature overnight, the mixture was diluted with H$_2$O (300 mL) and then extracted with EtOAc (3×200 mL). The combined organic layers were washed with H$_2$O (3×100 mL) and brine (100 mL), dried over Na$_2$SO$_4$, filtered and the solvent was removed in vacuo. Purification by flash column chromatography (silica gel, hexanes/EtOAc, 2:1) gave the title compound (1.61 g, 48%) as a white powder: MS (ESI) t/e 356 (M+H)$^+$.

d) (7-Bromo-2-oxo-1,2,3,5-tetrahydro-pyrido[2,3-e][1,4]diazepin-4-yl)acetic acid hydrochloride A solution of (7-bromo-2-oxo-1,2,3,5-tetrahydro-pyrido[2,3-e][1,4]diazepin-4-yl)acetic acid tert-butyl ester (1.61 g, 4.52 mmol) in CH$_2$Cl$_2$ (20 mL) was treated with TFA (15 mL). After stirring at room temperature for 1 h, the solution was concentrated in vacuo. The resulting slurry was treated with anhydrous HCl (40 mL of a 4.0 M) and sonicated for 1.5 h, diluted with Et$_2$O and stirred for 1 h. The solid was isolated by filtration, washed with Et$_2$O, and dried under vacuum at 50° C. overnight to give the title compound (1.66 g, 98%) as a white solid: MS (ESI) m/e 300 (M+H)$^+$.

e) 7-Bromo-4-[2-(4-methyl-piperazin-1-yl)-2-oxo-ethyl]-1,3,4,5-tetrahydro-pyrido[2,3-e][1,4]diazepin-2-one A suspension of (7-bromo-2-oxo-1,2,3,5-tetrahydro-pyrido[2,3-e][1,4]diazepin-4-yl)acetic acid hydrochloride (1.66 g, 4.45 mmol) in CH$_2$Cl$_2$ (50 mL) was treated sequentially with (i-Pr)$_2$EtN (3.1 mL, 18 mmol), N-methyl piperazine (0.54 mL, 4.87 mmol), HOBt (0.66 g, 4.88 mmol), and EDC (0.95 g, 4.96 mmol). After stirring overnight, the mixture was diluted with CH$_2$Cl$_2$ (100 mL) and then washed with H$_2$O (100 mL). The aqueous layer was extracted with CH$_2$Cl$_2$ (4×100 mL). The combined organic layers were dried over Na$_2$SO$_4$, filtered and the solvent was removed in vacuo. Purification by flash column chromatography (silica gel, CH$_2$Cl$_2$/MeOH, 97:3 to 95:5) gave the title compound (1.42 g, 83%) as an off-white solid: MS (ESI) m/e 382 (M+H)$^+$.

f) (E)-3-{4-[2-(4-Methyl-piperazin-1-yl)-2-oxo-ethyl]-2-oxo-2,3,4,5-tetrahydro-1H-pyrido[2,3-e][1,4]diazepin-7-yl}acrylic acid tert-butyl ester A suspension of 7-Bromo-4-[2-(4-methyl-piperazin-1-yl)-2-oxo-ethyl]-1,3,4,5-tetrahydro-pyrido[2,3-e][1,4]diazepin-2-one (1.39 g, 3.64 mmol) in propionitrile (32 mL) and DMF (8 mL) was de-oxygenated with Ar for 15 min. The mixture was treated with tert-butyl acrylate (2.1 mL, 14 mmol) and (i-Pr)$_2$EtN (1.3 mL, 7.4 mmol) and then was de-oxygenated with Ar for 10 min. Pd(OAc)$_2$ (83 mg, 0.37 mmol) and P(o-tol)$_3$ (0.22 g, 0.73 mmol) were added simultaneously, and the mixture was de-oxygenated a third time for 10 min. The mixture was heated to reflux overnight, then allowed to cool. The resulting precipitate was isolated by filtration and dissolved in CH$_2$Cl$_2$. The solution was filtered through Celite and the solvent was removed in vacuo to give the title compound (1.13 g, 72%) as an off-white solid: MS (ESI) m/e 430 (M+H)$^+$.

g) (E)-3-{4-[2-(4-Methyl-piperazin-1-yl)-2-oxo-ethyl]-2-oxo-2,3,4,5-tetrahydro-1H-pyrido[2,3-e][1,4]diazepin-7-yl}acrylic acid hydrochloride A suspension of (E)-3-{4-[2-(4-Methyl-piperazin-1-yl)-2-oxo-ethyl]-2-oxo-2,3,4,5-tetrahydro-1H-pyrido[2,3-e][1,4]diazepin-7-yl}acrylic acid tert-butyl ester (1.12 g, 2.61 mmol) in CH$_2$Cl$_2$ (10 mL) was treated with TFA (10 mL). After stirring at room temperature for 35 min, the solution was concentrated in vacuo. The resulting oil was treated with anhydrous HCl (20 mL of a 4.0 M solution in dioxane, 80 mmol) and the resulting mixture was sonicated for 1 h. The mixture was diluted with Et$_2$O (50 mL) and sonicated for 10 min. The solid was isolated by filtration, washed with Et$_2$O and dried under vacuum at 50° C. for 4 h to give the title compound (1.72 g, quantitative) as an off-white solid: $^1$H NMR (500 MHz, DMSO-d$_6$) δ 11.60 (br s, 1H), 11.09 (br s, 1H), 8.82 (s, 1H), 8.47 (s, 1H), 7.66 (d, J=19.9 Hz, 1H), 6.65 (d, J=16.1 Hz, 1H), 4.43-4.40 (m, 2H), 4.31 (br s, 2H), 3.95-3.91 (m, 1H), 3.84 (br s, 2H), 3.56 (s, 4H), 3.42 (br s, 2H), 3.23-2.97 (m, 2H), 2.76 (d, J=4.1 Hz, 3H); MS (ESI) m/e 374 (M+H)$^+$.

Preparation 121

Preparation of (E)-3-[4-(3-Morpholin-4-yl-propyl)-2-oxo-2,3,4,5-tetrahydro-1H-pyrido[2,3-e][1,4]diazepin-7-yl]acrylic acid hydrochloride a) (3-Morpholin-4-yl-propylamino)acetic acid ethyl ester

A solution of 4-(3-aminopropyl)morpholine (10.0 mL, 68.4 mmol) in MeOH (180 mL) was cooled in an ice bath and treated with ethyl glyoxylate (50% solution in toluene, 20.0 mL, 98.0 mmol) and HOAc (12 mL). After stirring for 15 min, NaBH$_3$CN (4.81 g, 76.5 mmol) was added and the mixture was allowed to stir at 0° C. for 2 h. The mixture was diluted with saturated aqueous NaHCO$_3$ (500 mL) and then extracted with EtOAc (5×300 mL) followed by CH$_2$Cl$_2$ (9×200 mL). The combined CH$_2$Cl$_2$ layers were dried over Na$_2$SO$_4$, filtered and the solvent was removed in vacuo to give the title compound (7.44 g, 47%) as a colorless oil: MS (ESI) m/e 231 (M+H)$^+$.

b) [(2-Amino-5-bromo-pyridin-3-ylmethyl)-(3-morpholin-4-yl-propyl)amino]acetic acid ethyl ester A solution of 5-bromo-3-bromomethyl-pyridin-2-ylamine hydrobromide (11.2 g, 32.3 mmol) and (3-morpholin-4-yl-propylamino)acetic acid ethyl ester (7.44 g, 32.3 mmol) in DMF (200 mL) was treated with triethylamine (9.5 mL, 68 mmol). After stirring at room temperature overnight, the mixture was diluted with H$_2$O (400 mL) and then extracted with EtOAc (5×250 mL). The combined organic layers were washed with H$_2$O (2×200 mL) and brine (200 mL), dried over Na$_2$SO$_4$, filtered and the solvent was removed in vacuo to give the title compound (11.8 g, 87%) as a yellow oil: MS (ESI) m/e 415 (M+H)$^+$.

c) 7-Bromo-4-(3-morpholin-4-yl-propyl)-1,3,4,5-tetrahydro-pyrido[2,3-e][1,4]diazepin-2-one A solution of [(2-amino-5-bromo-pyridin-3-ylmethyl)-(3-morpholin-4-yl-propyl)amino]acetic acid ethyl ester (11.8 g, 28.3 mmol) in DMSO (200 mL) was treated with NaH (60% dispersion in mineral oil, 1.13 g, 28.3 mmol). After stirring at room temperature overnight, the mixture was diluted with H$_2$O (400 mL) and then extracted with EtOAc (7×250 mL). The combined organic layers were washed with H$_2$O (2×200 mL) and brine (200 mL), dried over Na$_2$SO$_4$, filtered and the solvent was removed in vacuo. Purification by flash column chromatography (silica gel, CH$_2$Cl$_2$/MeOH, 97:3 to 96:4) gave the title compound (5.76 g, 55%) as an off-white powder: MS (ESI) m/e 369 (M+H)$^+$.

d) (E)-3-[4-(3-Morpholin-4-yl-propyl)-2-oxo-2,3,4,5-tetrahydro-1H-pyrido[2,3-e][1,4]diazepin-7-yl]acrylic acid tert-butyl ester A suspension of 7-bromo-4-(3-morpholin-4-yl-propyl)-1,3,4,5-tetrahydro-pyrido[2,3-e][1,4]diazepin-2-one (5.70 g, 15.4 mmol) in propionitrile (120 mL) and DMF (30 mL) was de-oxygenated with Ar for 15 min. The mixture was treated with tert-butyl acrylate (9.0 mL, 61 mmol) and (i-Pr)$_2$EtN (5.7 mL, 33 mmol) and was de-oxygenated with Ar for 10 min. Pd(OAc)$_2$ (0.35 g, 1.6 mmol) and P(o-tol)$_3$ (0.94 g, 3.1 mmol) were added simultaneously, and the mixture was de-oxygenated a third time for 5 min. The mixture was heated to reflux overnight, then allowed to cool. The mixture was diluted with Et$_2$O (200 mL). The organic solution was filtered through Celite, washed with H$_2$O (200 mL), dried over Na$_2$SO$_4$, filtered and then concentrated in vacuo. Purification by flash column chromatography (silica gel, CH$_2$Cl$_2$/MeOH, 97:3 to 96:4) gave the title compound (3.49 g, 55%) as a tan solid: MS (ESI) m/e 417 (M+H)$^+$.

e) (E)-3-[4-(3-Morpholin-4-yl-propyl)-2-oxo-2,3,4,5-tetrahydro-1H-pyrido[2,3-e][1,4]diazepin-7-yl]acrylic acid hydrochloride A solution of (E)-3-[4-(3-Morpholin-4-yl-propyl)-2-oxo-2,3,4,5-tetrahydro-1H-pyrido[2,3-e][1,4]diazepin-7-yl]acrylic acid tert-butyl ester (2.21 g, 5.30 mmol) in CH$_2$Cl$_2$ (20 mL) was treated with TFA (20 mL). After stirring at room temperature for 30 min, the solution was concentrated in vacuo. The resulting oil was treated with anhydrous HCl (50 mL of a 4.0 M solution in dioxane, 200 mmol) and the mixture was sonicated for 1.5 h. The mixture was diluted with Et$_2$O (200 mL) and sonicated for 15 min. The solid was isolated by filtration, washed with Et$_2$O, and dried under vacuum at 50° C. for 5 h to give the title compound (3.08 g, quantitative) as an off-white solid: $^1$H NMR (500 MHz, DMSO-d$_6$) δ 11.23 (br s, 2H), 8.74 (s, 1H), 8.36 (s, 1H), 7.63 (d, J=15.9, 1H), 6.63 (d, J=16.0 Hz, 1H), 4.33 (br s, 2H), 3.90 (br s, 6H), 3.24 (m, 8H), 2.22 (br s, 2H); MS (ESI) m/e 361 (M+H)$^+$.

Preparation 122

Preparation of (E)-7-(2-carboxy-vinyl)-2-oxo-1,2,3,5-tetrahydro-pyrido[2,3-e][1,4]diazepine-4-carboxylic acid benzyl ester hydrochloride a) 7-Bromo-2-oxo-1,2,3,5-tetrahydro-pyrido[2,3-e][1,4]diazepine-4-carboxylic acid benzyl ester A suspension of 7-bromo-1,3,4,5-tetrahydro-pyrido[2,3-e][1,4]diazepin-2-one (1.08 g, 4.46 mmol) in CH$_2$Cl$_2$ (60 mL) was treated with Et$_3$N (0.80 mL, 5.7 mmol) and then cooled in an ice bath. The chilled suspension was treated dropwise with CbzCl (4.5 mmol) to give a clear solution. The ice bath was removed and the solution was allowed to stir overnight. The mixture was diluted with CH$_2$Cl$_2$ (90 mL), washed with H$_2$O (50 mL) and brine (50 mL), dried over Na$_2$SO$_4$, filtered and the solvent was removed in vacuo. Purification by flash column chromatography (silica gel, CH$_2$Cl$_2$/MeOH, 99.5:0.5 to 99:1) gave the title compound (0.52 g, 31%) as a white solid: $^1$H NMR (300 MHz, CDCl$_3$) δ 8.31-8.36 (m, 2H), 7.49-7.71 (m, 1H), 7.34-7.40 (m, 4H), 7.19-7.21 (m, 1H), 5.08-5.12 (m, 2H), 4.43-4.65 (m, 4H); MS (ESI) m/e 376 (M+H)$^+$.

b) (E)-7-(2-tert-Butoxycarbonyl-vinyl)-2-oxo-1,2,3, 5-tetrahydro-pyrido[2,3-e][1,4]diazepine-4-carboxylic acid benzyl ester A suspension of 7-bromo-2-oxo-1,2,3,5-tetrahydro-pyrido [2,3-e][1,4]diazepine-4-carboxylic acid benzyl ester (0.52 g, 1.4 mmol) in propionitrile (10 mL) and DMF (3 mL) was de-oxygenated with Ar for 20 min. The mixture was treated with tert-butyl acrylate (0.83 mL, 10 mmol) and (i-Pr)$_2$EtN (0.50 mL, 2.9 mmol) and was de-oxygenated with Ar for 10 min. Pd(OAc)$_2$ (34 mg, 0.15 mmol) and P(o-tol)$_3$ (84 mg, 0.27 mmol) were added simultaneously, and the mixture was de-oxygenated a third time for 5 min. The mixture was heated to reflux overnight, then allowed to cool. The resulting precipitate was isolated by filtration, washed with EtOAc and dissolved in CH$_2$Cl$_2$. The solution was filtered through Celite and the solvent was removed in vacuo to give the title compound (0.31 g, 53%) as an off-white solid: $^1$H NMR (300 MHz, CDCl$_3$) δ 8.49-8.57 (m, 1H), 8.30 (s, 1H), 7.43-7.73 (m, 2H), 7.33 (s, 4H), 7.17-7.18 (m, 1H), 6.21-6.40 (m, 1H), 5.05-5.11 (m, 2H), 4.46-4.68 (m, 4H), 1.54-1.57 (m, 9H); MS (ESI) m/e 424 (M+H)$^+$.

c) (E)-7-(2-Carboxy-vinyl)-2-oxo-1,2,3,5-tetrahydro-pyrido[2,3-e][1,4]diazepine-4-carboxylic acid benzyl ester hydrochloride A solution of (E)-7-(2-tert-butoxycarbonyl-vinyl)-2-oxo-1,2,3,5-tetrahydro-pyrido[2,3-e][1,4]diazepine-4-carboxylic acid benzyl ester (0.31 g, 0.73 mmol) in CH$_2$Cl$_2$ (5 mL) was treated with TFA (5 mL). After stirring at room temperature for 30 min, the clear tan solution was concentrated in vacuo. The resulting oil was treated with anhydrous HCl (10 mL of a 4.0 M solution in dioxane, 40 mmol) to give a cloudy mixture. The mixture was diluted with Et$_2$O (200 mL) to give an off-white precipitate. After stirring for 15 min, the solid was isolated by filtration, washed with Et$_2$O, and dried under vacuum for 1.5 h to give the title compound (0.27 g, 91%) as an off-white solid: $^1$H NMR (300 MHz, DMSO-d$_6$) δ 10.50-10.47 (m, 1H), 8.49 (s, 1H), 8.09-8;15 (m, 1H), 7.53-7.59 (m, 1H), 7.15-7.33 (m, 5H), 6.51-6.65 (m, 1H), 5.42 (bs, 2H), 5.05-5.08 (m, 2H), 4.63 (s, 2H), 4.43 (s, 2H); MS (ESI) m/e 368 (M+H)$^+$.

Preparation 123

Preparation of (E)-3-(2-Oxo-2,3-dihydro-oxazolo[4, 5-b]pyridine-6-yl)acrylic acid hydrochloride a) (E)-3-(2-Oxo-2,3-dihydro-oxazolo[4,5-b]pyridin-6-yl)acrylic acid tert-butyl ester A stirred solution of 6-bromo-3H-oxazolo[4,5-b]pyridin-2-one (1.00 g, 4.65 mmol), tert-butyl acrylate (2.7 mL, 18 mmol), palladium(II) acetate (104 mg, 0.465 mmol), tri-o-tolylphosphine (283 mg, 0.930 mmol), and N,N-diisopropylethylamine (1.7 mL, 9.7 mmol) in N,N-dimethylformamide (4 mL) and propionitrile (16 mL) was deoxygenated by bubbling argon through the solution for 20 min. The mixture was heated to reflux for 21 h, then allowed to cool. The mixture was concentrated in vacuo. The residue was dissolved in dichloromethane (100 mL). The solution was washed with water (2×200 mL), dried over sodium sulfate, filtered, and the solvent removed in vacuo to give a dark brown oil. Purification by flash column chromatography (silica gel, gradient from 98:2 to 94:6 CHCl$_3$/MeOH) gave the title compound (283 mg, 23%) as a brown solid: $^1$H NMR (300 MHz, CDCl$_3$) δ 8.24 (d, J=1.4 Hz, 1H), 7.64-7.55 (m, 2H), 6.37 (d, J=16.0 Hz, 1H), 1.55 (s, 9H).

b) (E)-3-(2-Oxo-2,3-dihydro-oxazolo[4,5-b]pyridin-6-yl)acrylic acid hydrochloride A solution of (E)-3-(2-oxo-2,3-dihydro-oxazolo[4,5-b]pyridine-6-yl)acrylic acid tert-butyl ester (274 mg, 1.04 mmol) in dichloromethane (5 mL) and trifluoroacetic acid (5 mL) was stirred for 30 min, then the solvents were removed in vacuo. The residue was suspended in anhydrous HCl (5 mL of a 4 M solution in 1,4-dioxane, 20 mmol) and the mixture was sonicated for 1 min. The resulting solid was collected by filtration, washed with diethyl ether and then dried in vacuo to give the title compound (194 mg, 77%) as a light brown solid: $^1$H NMR (300 MHz, DMSO-d$_6$) δ 8.31 (s, 1H), 8.13 (s, 1H), 7.63 (d, J=16.0 Hz, 1H), 6.60 (d, J=16.0 Hz, 1H).

Preparation 124

Preparation of (E)-3-[6-Amino-5-(2-carboxy-ethyl) pyridin-3-yl]acrylic acid

A solution of (E)-3-(7-oxo-5,6,7,8-tetrahydro-[1,8]naphthyridin-3-yl)acrylic acid tert-butyl ester (0.86 g, 3.0 mmol) was stirred in methanol (10 mL), dioxane (10 mL) and aq. NaOH (15 mL of a 1 N solution, 15 mmol) for 4 days. The clear solution was neutralized with aq. HCl (15 mL of a 1 N solution, 15 mmol) and stirred for 20 min. The white precipitate was collected by filtration to give (E)-3-[6-amino-5-(2-carboxy-ethyl)pyridin-3-yl]acrylic acid (0.57 g, 78%): MS (ESI) m/e 237 (M+H)$^+$.

Preparation 125

Preparation of (E)-3-(6-Amino-5-piperidin-1-ylmethyl-pyridin-3-yl)acrylic acid hydrochloride a)
5-Bromo-3-piperidin-1-ylmethyl-pyridin-2-ylamine An ice-cold suspension of 5-bromo-3-bromomethyl-pyridin-2-ylamine hydrobromide (10.0 g, 28.8 mmol) in MeCN (100 mL) was treated with piperidine (6.4 mL, 64.8 mmol). After stirring at room temperature for 3.5 h, the mixture was diluted with Et$_2$O (500 mL). The solution was filtered and then concentrated to give the title compound (4.16 g, 53%) as a pale, yellow solid: MS (ESI) m/e 270 (M+H)$^+$.

b) (E)-3-(6-Amino-5-piperidin-1-ylmethyl-pyridin-3-yl)acrylic acid tert-butyl ester A solution of 5-bromo-3-piperidin-1-ylmethyl-pyridin-2-ylamine (500 mg, 1.85 mmol), tert-butyl acrylate (0.3 mL, 2.0 mmol), (i-Pr)$_2$EtN (0.5 mL, 2.8 mmol) and P(o-tol)$_3$ (114 mg, 0.37 mmol) in EtCN (10 mL) was de-oxygenated with argon for 30 min. Pd(OAc)$_2$ (43 mg, 0.19 mmol) was added, and the mixture was de-oxygenated for 15 min. The mixture was heated to reflux for 18 h and then allowed to cool. The solvent was removed in vacuo. The residue was partitioned between EtOAc and H$_2$O. The organic layer was washed with H$_2$O and satd NaCl, dried over Na$_2$SO$_4$ and concentrated. Purification by column chromatography (silica gel, CH$_2$Cl$_2$ to 96:4 CH$_2$Cl$_2$/CH$_3$OH) gave the title compound (350 mg, 60%) as a yellow solid: MS (ESI) m/e 318 (M+H)$^+$.

c) (E)-3-(6-Amino-5-piperidin-1-ylmethyl-pyridin-3-yl)acrylic acid hydrochloride A suspension of 3-(6-amino-5-piperidin-1-ylmethyl-pyridin-3-yl)acrylic acid tert-butyl ester (250 mg, 0.79 mmol) in CH$_2$Cl$_2$ (3 mL) was treated with TFA (2 mL). After stirring at room temperature under N$_2$ for 45 min, the solution was concentrated. The resulting oil was treated with anhydrous HCl in dioxane (10 mL, 4.0 M) and then sonicated until the oil was converted to a fine off-white solid. After stirring under N$_2$ for 20 min, the solid was isolated by filtration, washed with Et$_2$O, and dried under vacuum for several hours to give the title compound (282 mg, quantitative) as an off-white solid: $^1$H NMR (300 MHz, DMSO-d$_6$) δ 10.6 (br s, 1H), 8.53 (d, J=2.1 Hz, 1H), 8.39-8.28 (m, 3H), 7.53 (d, J=15.0 Hz, 1H), 6.46 (d, J=15.0 Hz, 1H), 4.33 (s, 2H), 3.43-3.35 (m, 2H), 2.97 (s, 2H), 1.79-1.69 (m, 5H), 1.35 (s, 1H).

Preparation 126

Preparation of (E)-3-(6-Amino-5-pyrrolidin-1-ylmethyl-pyridin-3-yl)acrylic acid hydrochloride a) 5-Bromo-3-pyrrolidin-1-ylmethyl-pyridin-2-ylamine According to the procedure of Preparation 125(a), except substituting pyrrolidine for piperidine, the title compound (2.40 g, 34%) was prepared as an off-white solid: $^1$H NMR (300 MHz, CDCl$_3$) δ 8.01 (d, J=2.3 Hz, 1H), 7.34 (d, J=2.3 Hz, 1H), 5.67 (s, 2H), 3.51 (s, 2H), 2.48-2.44 (m, 4H), 1.80-1.60 (m, 4H).

b) (E)-3-(6-Amino-5-pyrrolidin-1-ylmethyl-pyridin-3-yl)acrylic acid tert-butyl ester According to the procedure of Preparation 125(b), except substituting 5-bromo-3-pyrrolidin-1-ylmethyl-pyridin-2-ylamine for 5-bromo-3-piperidin-1-ylmethyl-pyridin-2-ylamine, the title compound (1.60 g, 61%) was prepared as a light yellow solid: $^1$H NMR (300 MHz, CDCl$_3$) δ 8.08 (d, J=2.1 Hz, 1H), 7.50-7.44 (m, 2H), 6.17 (d, J=15.9 Hz, 1H), 6.00 (s, 2H), 3.56 (s, 2H), 2.49-2.45 (m, 4H), 1.81-1.76 (m, 4H), 1.52 (s, 9H).

c) (E)-3-(6-Amino-5-pyrrolidin-1-ylmethyl-pyridin-3-yl)acrylic acid hydrochloride According to the procedure of Preparation 125(c), except substituting (E)-3-(6-amino-5-pyrrolidin-1-ylmethyl-pyridin-3-yl)acrylic acid tert-butyl ester for (E)-3-(6-amino-5-piperidin-1-ylmethyl-pyridin-3-yl)acrylic acid tert-butyl ester, the title compound (1.68 g, quantitative) was prepared as an off-white solid: $^1$H NMR (300 MHz, DMSO-d$_6$) δ 11.9 (br s, 1H), 8.66-8.38 (m, 4H), 7.56 (d, J=15.9 Hz, 1H), 6.49 (d, J=15.9 Hz, 1H), 4.46 (s, 2H), 3.57-3.50 (m, 2H), 3.19-3.01 (m, 2H), 1.91-1.88 (m, 4H).

Preparation 127

Preparation of (E)-3-[6-Amino-5-(4-methyl-piperazin-1-ylmethyl)-pyridin-3-yl]acrylic acid hydrochloride a) 5-Bromo-3-(4-methyl-piperazin-1-ylmethyl)pyridin-2-ylamine According to the procedure of Preparation 125(a), except substituting 1-methylpiperizine for piperidine, the title compound (2.32 g, 30%) was prepared as a light, yellow solid: $^1$H NMR (300 MHz, CDCl$_3$) δ 8.03 (d, J=2.3 Hz, 1H), 7.32 (d, J=2.3 Hz, 1H), 5.63 (s, 2H), 3.42 (s, 2H), 2.46-2.36 (m, 8H), 2.30 (s, 3H).

b) (E)-3-[6-Amino-5-(4-methyl-piperazin-1-ylmethyl)pyridin-3-yl]acrylic acid tert-butyl ester According to the procedure of Preparation 125(b), except substituting 5-bromo-3-(4-methyl-piperazin-1-ylmethyl)pyridin-2-ylamine for 5-bromo-3-piperidin-1-ylmethyl-pyridin-2-ylamine, the title compound (1.18 g, 45%) was prepared as a yellow solid: $^1$H NMR (300 MHz, CDCl$_3$) δ 8.09 (d, J=2.2 Hz, 1H), 7.49-7.44 (m, 2H), 6.18 (d, J=15.9 Hz, 1H), 5.95 (br s, 2H), 3.47 (s, 2H), 2.38-2.59 (m, 7H), 2.96 (s, 4H), 1.52 (s, 9H).

c) (E)-3-[6-Amino-5-(4-methyl-piperazin-1-ylmethyl)pyridin-3-yl]acrylic acid hydrochloride According to the procedure of Preparation 125(c), except substituting (E)-3-[6-amino-5-(4-methyl-piperazin-1-ylmethyl)-pyridin-3-yl]acrylic acid tert-butyl ester (1.18 g, 3.55 mmol) for (E)-3-(6-amino-5-piperidin-1-ylmethyl-pyridin-3-yl)acrylic acid tert-butyl ester, the title compound (1.72 g, quantitative) was prepared as an off-white solid: $^1$H NMR (300 MHz, DMSO-d$_6$) δ 10.98 (br s, 1H), 8.61-8.34 (m, 4H), 7.53 (d, J=16.0 Hz, 1H), 6.53 (d, J=15.9 Hz, 1H), 3.81 (br s, 2H), 3.56 (s, 3H), 3.45-3.37 (m, 2H), 3.20-3.08 (m, 2H), 2.76 (s, 4H); MS (ESI) m/e 277 (M+H)$^+$.

Preparation 128

Preparation of (E)-3-[6-Amino-5-(4-benzyl-piperidin-1-ylmethyl)pyridin-3-yl]acrylic acid hydrochloride a) 3-(4-Benzyl-piperidin-1-ylmethyl)-5-bromo-pyridin-2-ylamine According to the procedure of Preparation 125(a), except substituting 4-benzylpiperidine (5.6 mL, 31.7 mmol) for piperidine and adding K$_2$CO$_3$ (19.9 g, 144 mmol) as base, the title compound (9.81 g, 95%) was prepared as a light, yellow solid: MS (ESI) m/e 36 (M+H)$^+$.

b) (E)-3-[6-Amino-5-(4-benzyl-piperidin-1-ylmethyl)pyridin-3-yl]acrylic acid tert-butyl ester According to the procedure of Preparation 125(b), except substituting 3-(4-Benzyl-piperidin-1-ylmethyl)-5-bromo-pyridin-2-ylamine for 5-bromo-3-piperidin-1-ylmethyl-pyridin-2-ylamine, the title compound (4.48 g, 80%) was prepared as a yellow solid: MS (ESI) m/e 408 (M+H)$^+$.

c) (E)-3-[6-Amino-5-(4-benzyl-piperidin-1-ylm-ethyl)pyridin-3-yl]acrylic acid hydrochloride According to the procedure of Preparation 125(c), except substituting (E)-3-[6-amino-5-(4-benzyl-piperidin-1-ylm-ethyl)pyridin-3-yl]acrylic acid tert-butyl ester for 3-(6-amino-5-piperidin-1-ylmethyl-pyridin-3-yl)acrylic acid tert-butyl ester, the title compound (5.24 g, quantitative) was prepared as an off-white solid: $^1$H NMR (300 MHz, DMSO-d$_6$) δ 10.56 (br s, 1H), 8.61-8.37 (m, 3H), 7.51 (d, J=15.9, 1H), 7.32-7.17 (m, 6H), 6.50-6.42 (m, 1H), 4.35 (br s, 2H), 3.45-3.37 (m, 2H), 3.11-2.92 (m, 2H), 1.75-1.51 (m, 6H); MS (ESI) m/e 352 (M+H)$^+$.

Preparation 129

Preparation of (E)-3-(2,4-dioxo-1,2,3,4-tetrahydro-pyrido[2,3-d]pyrimidin-6-yl)acrylic acid a) 2-Amino-5-bromo-nicotinic acid hydrobromide

Bromine (7.5 mL, 146 mmol) was added dropwise over 10 min to a suspension of 2-amino-nicotinic acid (20.0 g, 145 mmol) in glacial acetic acid (250 mL) cooled in an ice bath. After the bromine addition was complete, the mixture was stirred at ambient temperature for 2 d. The resulting light yellow solid was isolated by filtration, washed with Et$_2$O, and dried under high vacuum (40° C.) for several hours to give the title compound (40.0 g, 93%): $^1$H NMR (300 MHz, DMSO-d$_6$) δ 8.33 (d, J=2.5 Hz, 1H), 8.20 (d, J=2.5 Hz, 1H), 8.02 (bs, 3H); ESI MS m/e 217 (M+H)$^+$.

b) 2-Amino-5-bromo-nicotinamide

To an ice-cold suspension of 2-amino-5-bromo-nicotinic acid hydrobromide (5.11 g, 17.1 mmol) and ammonium chloride (9.15 g, 171 mmol) in dimethoxyethane (170 mL) was added Et$_3$N (4.8 mL, 34.2 mmol). After 10 min, diethylphosphoryl cyanide was added dropwise and the cold bath removed. After 4 h, the solution was filtered and the filtrate concentrated. The resulting residue was partitioned between EtOAc and water. The organic layer was washed with satd NaHCO$_3$ (2×) and satd NaCl, dried (Na$_2$SO$_4$) and concentrated under reduced pressure. The yellow solid was dissolved in EtOAc and then hexanes were added until precipitation occurred. The solid was collected by filtration and then triturated with EtOAc to give the title compound (1.62 g, 44%) as a yellow solid: $^1$H NMR (300 MHz, DMSO-d$_6$) δ 8.13 (s, 2H), 8.04 (bs, 1H), 7.46 (bs, 1H), 7.37 (bs, 2H).

c) 6-Bromo-1H-pyrido[2,3-d]pyrimidine-2,4-dione

Oxalyl chloride (100 mL, 1.16 mmol) was added dropwise to a suspension of 2-amino-5-bromo-nicotinamide (500 mg, 2.31 mmol) in toluene (5 mL) and the resulting mixture was heated to reflux for 4 h. The reaction mixture was cooled and the mustard-colored solid which had formed was collected by filtration. The solid was washed with a small amount of water, MeOH, and then dried under high vacuum (40° C.) overnight to give the title compound (435 mg, 77%): $^1$H NMR (300 MHz, DMSO-d$_6$) δ 11.86 (s, 1H), 11.60 (s, 1H), 8.72 (d, J=2.5 Hz, 1H), 8.35 (d, J=2.5 Hz, 1H); $^{13}$C NMR (126 MHz, DMSO-d$_6$) δ 161.4, 154.8, 151.2, 150.17, 137.8, 112.6, 111.6.

d) (E)-3-(2,4-Dioxo-1,2,3,4-tetrahydro-pyrido[2,3-d]pyrimidin-6-yl)acrylic acid tert-butyl ester A suspension of 6-bromo-1H-pyrido[2,3-d]pyrimidine-2,4-dione (430 mg, 1.59 mmol) in propionitrile (8 mL) and DMF (2 mL) was treated with tert-butyl acrylate (0.93 mL, 6.4 mmol), (i-Pr)$_2$EtN (0.6 mL, 3.3 mmol) and P(o-tol)$_3$ (100 mg, 0.32 mmol). The solution was deoxygenated with Ar for 20 min. Pd(OAc)$_2$ (36 mg, 0.16 mmol) was added and the mixture was deoxygenated with a stream of Ar for 10 min. The mixture was heated to reflux for 17 h, then allowed to cool. The resulting precipitate was isolated by filtration to give the title compound (384 mg, 83%) as a gray solid: $^1$H NMR (300 MHz, DMSO-d$_6$) δ 11.88 (s, 1H), 11.54 (s, 1H), 8.96 (d, J=2.2 Hz, 1H), 8.53 (d, J=2.2 Hz, 1H), 7.65 (d, J=16.1 Hz, 1H), 6.72 (d, J=16.1 Hz, 1H), 1.49 (s, 9H); ESI MS m/e 290 (M+H)$^+$.

e) (E)-3-(2,4-Dioxo-1,2,3,4-tetrahydro-pyrido[2,3-d]pyrimidin-6-yl)acrylic acid To a suspension of (E)-3-(2,4-dioxo-1,2,3,4-tetrahydro-pyrido[2,3-d]pyrimidin-6-yl)acrylic acid tert-butyl ester (379 mg, 1.19 mmol) in CH$_2$Cl$_2$ (10 mL) was added trifluoroacetic acid (2 mL). After 6 h, the solvent was concentrated, the resulting solid was treated with anhydrous HCl (10 mL of a 4 M solution in dioxane, 40 mmol) and the mixture was sonicated for 10 min. The mixture was diluted with Et$_2$O and the solution was filtered. The olive solid was dried under high vacuum at 45° C. overnight to give the title compound (323 mg, 91%) as the TFA salt: $^1$H NMR (300 MHz, DMSO-d$_6$) δ 11.89 (s, 1H), 11.56 (s, 1H), 8.94 (d, J=1.8 Hz, 1H), 8.53 (d, J=1.8 Hz, 1H), 7.69 (d, J=16.1 Hz, 1H), 6.72 (d, J=16.1 Hz, 1H), 4.40 (bs, 1H); ESI MS m/e 234 (C$_{10}$H$_7$N$_3$O$_4$+H)$^+$.

Preparation 130

Preparation of (E)-3-[3-(2-dimethylamino-ethyl)-2-oxo-1,2,3,4-tetrahydro-pyrido[2,3-d]-pyrimidin-6-yl]acrylic acid hydrochloride a) 2-Amino-5-bromo-N-(2-dimethylamino-ethyl)nicotinamide

To a suspension of 2-amino-5-bromo-nicotinic acid hydrobromide (4.00 g, 13.4 mmol) in CH$_2$Cl$_2$ (150 mL) was added Et$_3$N (2.79 mL, 20.1 mmol), EDC (2.70 g, 14.1 mmol), and HOBt (1.91 g, 14.1 mmol) at 0° C., and the mixture was stirred for 10 min. N,N-dimethylethylenediamine was then added, and the mixture was allowed to stir overnight at room temperature. The organic solution was washed with 2 N NaOH (2×20 mL), H$_2$O (2×20 mL) and brine, dried over Na$_2$SO$_4$ and filtered. The solvent was concentrated to give the title compound (2.70 g, 70%) as a yellow solid: MS (ESI) m/e 287 (M+H)$^+$.

b) 5-Bromo-3-[(2-dimethylamino-ethylamino)methyl]pyridin-2-ylamine

2-Amino-5-bromo-N-(2-dimethylamino-ethyl)nicotinamide (2.15 g, 7.48 mmol) was added to a BH$_3$ solution (37.5 mL of a 1 M solution in THF, 37.5 mmol), and the mixture was heated to reflux for 6 h. After cooling, the solvent was removed in vacuo. The residue was dissolved in MeOH (20 mL). Concentrated HCl (3 mL) and H$_2$O (3 mL) were added and the mixture was heated to reflux for 2 h. The solvent was then concentrated and the aqueous residue was basified to pH c) 6-Bromo-3-(2-dimethylamino-ethyl)-3,4-dihydro-1H-pyrido[2,3-d]pyrimidin-2-one A solution of 5-bromo-3-[(2-dimethylamino-ethyl)methyl]pyridin-2-ylamine (490 mg, 1.79 mmol) and 1,1'-carbonyldiimidazole (349 mg, 2.15 mmol) in 1,4-dioxane (15 mL) was heated to 80° C. for 14 h. TLC analysis indicated remaining starting material. After cooling, additional 1,1'-carbonyldiimidazole (349 mg, 2.15 mmol) and 1,4-dioxane (10 mL) were added, and the solution was heated to reflux overnight. The solvent was removed in vacuo. The residue was dissolved in $CH_2Cl_2$ (80 mL). The solution was washed with satd $NaHCO_3$, water and brine, dried over $Na_2SO_4$ and concentrated. Purification by column chromatography (silica gel, $CH_2Cl_2$/MeOH/$Et_3N$, 92:7:1) gave the title compound (270 mg, 50%) as a tan solid: $^1H$ NMR (300 MHz, DMSO-$d_6$) δ9.83 (s, 1H), 8.16 (d, J=2.1 Hz, 1H), 7.76 (s, 1H), 4.48 (s, 2H), 3.37 (t, J=6.5 Hz, 2H), 2.40 (t, J=6.5 Hz, 2H), 2.16 (s, 6H).

d) (E)-3-[3-(2-Dimethylamino-ethyl)-2-oxo-1,2,3,4-tetrahydro-pyrido[2,3-d]pyrimidin-6-yl]acrylic acid tert-butyl ester To a solution of 6-bromo-3-(2-dimethylamino-ethyl)-3,4-dihydro-1H-pyrido[2,3-d]pyrimidin-2-one (240 mg, 0.802 mmol) in propionitrile (16 mL) and DMF (4 mL) was added tert-butyl acrylate (0.46 mL, 3.2 mmol) and (i-Pr)$_2$EtN (0.28 mL, 1.6 mmol), Pd(OAc)$_2$ (18 mg, 0.080 mmol) and P(o-tol)$_3$ (49 mg, 0.16 mmol). The mixture was degassed with Ar for 15 min. The mixture was heated to reflux overnight, and then allowed to cool. The dark solution was filtered through a pad of Celite. The filtrate was concentrated. Purification by column chromatography (silica gel, $CH_2Cl_2$/MeOH/$Et_3N$, 94/5.5/0.5) gave the title compound (150 mg, 54%) as a pale-yellow solid: MS (ESI) m/e 347 (M+H)$^+$.

e) (E)-3-[3-(2-Dimethylamino-ethyl)-2-oxo-1,2,3,4-tetrahydro-pyrido[2,3-d]-pyrimidin-6-yl]acrylic acid hydrochloride A solution of (E)-3-[3-(2-dimethylamino-ethyl)-2-oxo-1,2,3,4-tetrahydro-pyrido[2,3-d]pyrimidin-6-yl]acrylic acid tert-butyl ester (145 mg, 0.419 mmol) in $CH_2Cl_2$ (4 mL) was treated with TFA (2 mL). After stirring at room temperature for 30 min, the clear tan solution was concentrated in vacuo. The resulting oil was treated with anhydrous HCl (4.0 mL of 4 M solution in dioxane, 16 mmol) and stirred until the oil was converted to a solid. The solid was isolated by filtration, washed with Et$_2$O and dried under vacuum over night to give the title compound (155 mg, quantitative) as a pale yellow solid: $^1H$ NMR (300 MHz, DMSO-$d_6$) δ 10.18 (s, 1H), 9.70 (br s, 1H), 8.36 (d, J=1.4 Hz, 1H), 7.92 (s, 1H), 7.55 (d, J=16.0 Hz, 1H), 6.48 (d, J=16.0 Hz, 1H), 4.53 (s, 2H), 4.50 (br s, 2H), 3.71 (t, J=5.6 Hz, 2H), 3.31 (t, J=5.6 Hz, 2H), 2.84 (s, 3H), 2.82 (s, 3H).

Preparation 131

Preparation of (E)-3-[3-(2-Morpholin-4-yl-ethyl)-2-oxo-1,2,3,4-tetrahydro-pyrido[2,3-d]pyrimidin-6-yl]acrylic acid hydrochloride a) 2-Amino-5-bromo-N-(2-morpholin-4-yl-ethyl) nicotinamide

According to the procedure of Preparation 130(a), except substituting 4-(2-aminoethyl)morpholine for the N,N-dimethylethylenediamine, the title compound (18 g, 82%) was prepared as a pale yellow solid: MS (ESI) m/e 329 (M+H)$^+$.

b) 5-Bromo-3-[(2-morpholin-4-yl-ethylamino)methyl]pyridin-2-ylamine

According to the procedure of Preparation 130(b), except substituting 2-amino-5-bromo-N-(2-morpholin-4-yl-ethyl) nicotinamide for 2-amino-5-bromo-N-(2-dimethylamino-ethyl)nicotinamide, the title compound (5.0 g, 35%) was prepared as a colorless oil: MS (ESI) m/e 315 (M+H)$^+$.

c) 6-Bromo-3-(2-morpholin-4-yl-ethyl)-3,4-dihydro-1H-pyrido[2,3-d]pyrimidin-2-one According to the procedure of Preparation 130(c), except substituting 5-bromo-3-[(2-morpholin-4-yl-ethylamino)methyl]pyridin-2-ylamine for 5-bromo-3-[(2-dimethylamino-ethyl)methyl]pyridin-2-ylamine, the title compound (1.1 g, 20%) was prepared as pale yellow solid: MS (ESI) m/e 341 (M+H)$^+$.

d) (E)-3-[3-(2-Morpholin-4-yl-ethyl)-2-oxo-1,2,3,4-tetrahydro-pyrido[2,3-d]pyrimidin-6-yl]acrylic acid tert-butyl ester According to the procedure of Preparation 130(d), except substituting 6-bromo-3-(2-morpholin-4-yl-ethyl)-3,4-dihydro-1H-pyrido[2,3-d]pyrimidin-2-one for 6-bromo-3-(2-dimethylamino-ethyl)-3,4-dihydro-1H-pyrido[2,3-d]pyrimidin-2-one, the title compound (0.67 g, 54%) was prepared as a white solid: MS (ES) m/e 389 (M+H)$^+$.

e) (E)-3-[3-(2-Morpholin-4-yl-ethyl)-2-oxo-1,2,3,4-tetrahydro-pyrido[2,3-d]pyrimidin-6-yl]acrylic acid hydrochloride According to the procedure of Preparation 130(e), except substituting (E)-3-[3-(2-morpholin-4-yl-ethyl)-2-oxo-1,2,3,4-tetrahydro-pyrido[2,3-d]pyrimidin-6-yl]acrylic acid tert-butyl ester for the (E)-3-[3-(2-dimethylamino-ethyl)-2-oxo-1,2,3,4-tetrahydro-pyrido[2,3-d]pyrimidin-6-yl]acrylic acid tert-butyl ester, the title compound (0.71 g, quantitative) was prepared as a white solid: $^1H$ NMR (300 MHz, DMSO-$d_6$) δ 10.64 (br s, 1H), 10.17 (br s, 1H), 8.36 (s, 1H), 7.93 (s, 1H), 7.54 (d, J=15.9 Hz, 1H), 6.49 (d, J=16.0 Hz, 1H), 5.95 (br s, 2H), 4.56 (s, 2H), 3.98-3.94 (m, 2H), 3.79-3.72 (m, 4H), 3.56-3.53 (m, 2H), 3.37-3.35 (m, 2H), 3.15-3.05 (m, 2H); MS (ESI) m/e 333 (M+H)$^+$.

Preparation 132

Preparation of (E)-3-[3-(3-Morpholin-4-yl-propyl)-2-oxo-1,2,3,4-tetrahydro-pyrido[2,3-d]pyrimidin-6-yl]acrylic acid hydrochloride a) 2-Amino-5-bromo-pyridine-3-carbaldehyde hydrobromide Bromine (1.1 mL, 20 mmol) in HOAc (20 mL) was added dropwise to a solution of 2-amino-pyridine-3-carbaldehyde (2.5 g, 20 mmol) in HOAc (50 mL) while stirring. After the addition, the mixture was allowed to stir for 2 h at room temperature. The precipitate was collected by filtration and washed with diethyl ether to afford the title compound (4.4 g, 77%) as a pale yellow solid: MS (ESI) m/e 201 (M+H)$^+$.

b) 5-Bromo-3-[(3-morpholin-4-yl-propylamino)methyl]pyridin-2-ylamine

To a solution of 2-amino-5-bromo-pyridine-3-carbaldehyde hydrobromide (4.30 g, 15.3 mmol) in MeOH (100 mL) was added triethylamine (4.3 mL, 31 mmol) and the mixture was stirred at room temperature for 10 min. The resulting suspension was treated with 4-(3-aminopropyl)morpholine (2.5 mL, 17 mmol) and the mixture was stirred for 7 h. TLC analysis indicated remaining starting material. Additional 4-(3-aminopropyl)morpholine (1.0 mL, 6.8 mmol) was added, and the mixture was allowed to stir overnight at room temperature. The mixture was cooled and then NaBH$_4$ (0.87 g, 23.0 mmol) was added in two portions. The mixture was stirred at room temperature for 4 h. The solvent was removed in vacuo. Purification by column chromatography (silica gel, CH$_2$Cl$_2$/MeOH/Et$_3$N, 97/2.5/0.5 to 85/14.5/0.5) gave the title compound (2.70 g, 54%) as a brown oil: MS (ESI) m/e 329 (M+H)$^+$.

c) 6-Bromo-3-(3-morpholin-4-yl-propyl)-3,4-dihydro-1H-pyrido[2,3-d]pyrimidin-2-one According to the procedure of Preparation 130(c), except substituting 5-bromo-3-[(3-morpholin-4-yl-propylamino)methyl]pyridin-2-ylamine for 5-bromo-3-[(2-dimethylamino-ethyl)methyl]pyridin-2-ylamine, the title compound (2.00 g, 69%) was prepared as pale yellow solid: MS (ESI) m/e 355 (M+H)$^+$.

d) (E)-3-[3-(2-Morpholin-4-yl-propyl)-2-oxo-1,2,3,4-tetrahydro-pyrido[2,3-d]pyrimidin-6-yl]acrylic acid tert-butyl ester According to the procedure of Preparation 130(d), except substituting 6-bromo-3-(3-morpholin-4-yl-propyl)-3,4-dihydro-1H-pyrido[2,3-d]pyrimidin-2-one for 6-bromo-3-(2-dimethylamino-ethyl)-3,4-dihydro-1H-pyrido[2,3-d]pyrimidin-2-one, the title compound (1.5 g, 66%) was prepared as a pale yellow solid: MS (ESI) m/e 403 (M+H)$^+$.

e) (E)-3-[3-(3-Morpholin-4-yl-propyl)-2-oxo-1,2,3,4-tetrahydro-pyrido[2,3-d]pyrimidin-6-yl]acrylic acid hydrochloride According to the procedure of Preparation 130(e), except substituting (E)-3-[3-(2-morpholin-4-yl-propyl)-2-oxo-1,2,3,4-tetrahydro-pyrido[2,3-d]pyrimidin-6-yl]acrylic acid tert-butyl ester for (E)-3-[3-(2-dimethylamino-ethyl)-2-oxo-1,2,3,4-tetrahydro-pyrido[2,3-d]pyrimidin-6-yl]acrylic acid tert-butyl ester, the title compound (1.5 g, 99%) was prepared as a yellow solid: $^1$H NMR (300 MHz, DMSO-d$_6$) δ 10.08 (s, 1H), 8.36 (d, J=1.5 Hz, 1H), 7.96 (s, 1H), 7.59-7.49 (m, 1H), 6.53-6.45 (m, 1H), 4.55-4.48 (m, 2H), 4.00-3.75 (m, 4H), 3.48-3.36 (m, 4H), 3.20-2.95 (m, 4H), 2.10-1.96 (m, 2H); MS (ESI) m/e 347 (M+H)$^+$.

Preparation 133

Preparation of (E)-3-(3-Ethoxycarbonylmethyl-2-oxo-1,2,3,4-tetrahydro-pyrido[2,3-d]pyrimidin-6-yl)acrylic acid hydrochloride a) (6-Bromo-2-oxo-1,4-dihydro-2H-pyrido[2,3-d]pyrimidin-3-yl)acetic acid ethyl ester According to the procedure of Preparation 130(c), except substituting [(2-amino-5-bromo-pyridin-3-ylmethyl)amino]acetic acid ethyl ester for 5-bromo-3-[(2-dimethylaminoethyl)methyl]pyridin-2-ylamine, the title compound (6.70 g, 67%) was prepared as a white solid: MS (ESI) m/e 314 (M+H)$^+$.

b) (E)-3-(3-Ethoxycarbonylmethyl-2-oxo-1,2,3,4-tetrahydro-pyrido[2,3-d]pyrimidin-6-yl)acrylic acid tert-butyl ester According to the procedure of Preparation 130(d), except substituting (6-bromo-2-oxo-1,4-dihydro-2H-pyrido[2,3-d]pyrimidin-3-yl)acetic acid ethyl ester for 6-bromo-3-(2-dimethylamino-ethyl)-3,4-dihydro-1H-pyrido[2,3-d]pyrimidin-2-one, the title compound (2.10 g, 76%) was prepared as a white solid: MS (ESI) m/e 362 (M+H)$^+$.

c) (E)-3-(3-Ethoxycarbonylmethyl-2-oxo-1,2,3,4-tetrahydro-pyrido[2,3-d]pyrimidin-6-yl)acrylic acid hydrochloride According to the procedure of Preparation 130(e), except substituting (E)-3-(3-ethoxycarbonylmethyl-2-oxo-1,2,3,4-tetrahydro-pyrido[2,3-d]pyrimidin-6-yl)acrylic acid tert-butyl ester for the (E)-3-[3-(2-dimethylamino-ethyl)-2-oxo-1,2,3,4-tetrahydro-pyrido[2,3-d]pyrimidin-6-yl]acrylic acid tert-butyl ester, the title compound (1.80 g, 96%) was prepared as a white solid: $^1$H NMR (300 MHz, DMSO-d$_6$) δ 10.90-9.51 (m, 2H), 8.37 (s, 1H), 7.95 (s, 1H), 7.57-7.51 (m, 1H), 6.48 (d, J=16.0 Hz, 1H), 4.53 (s, 2H), 4.18-4.11 (m, 4H), 1.21 (t, J=7.0 Hz, 3H); MS (ESI) m/e 306 (M+H)$^+$.

Preparation 134

Preparation of (E)-3-[3-(2-Ethoxycarbonyl-ethyl)-2-oxo-1,2,3,4-tetrahydro-pyrido[2,3-d]pyrimidin-6-yl]acrylic acid hydrochloride a) 3-[(2-Amino-5-bromo-pyridin-3-ylmethyl)amino]propionic acid ethyl ester A mixture of 5-bromo-3-bromomethyl-pyridin-2-ylamine hydrobromide (9.41 g, 27.1 mmol) and β-alanine ethyl ester hydrochloride (5.00 g, 32.5 mmol) in DMF (75 mL) was treated with N,N-diisopropylethylamine (16.5 mL, 94.9 mmol). After stirring at room temperature for 4 h, the cloudy mixture was diluted with CH$_2$Cl$_2$ (100 mL) and H$_2$O. The aqueous layer was extracted with CH$_2$Cl$_2$ (2×150 mL). The combined organic layers were washed with brine, dried over Na$_2$SO$_4$, filtered and the solvent removed in vacuo. Purification by column chromatography (silica gel, CH$_2$Cl$_2$/MeOH/

Et₃N, 95/4.5/0.5 to 80/19.5/0.5) gave the title compound (1.90 g, 23%) as a tan oil: MS (ESI) m/le 302 (M+H)⁺.

b) 3-(6-Bromo-2-oxo-1,4-dihydro-2H-pyrido[2,3-d]pyrimidin-3-yl)propionic acid ethyl ester According to the procedure of Preparation 130(c), except substituting 3-[(2-amino-5-bromo-pyridin-3-ylmethyl)amino]propionic acid ethyl ester for 5-bromo-3-[(2-dimethylamino-ethyl)methyl]pyridin-2-ylamine, the title compound (1.7 g, 83%) was prepared as a white solid: MS (ESI) m/e 328 (M+H)⁺.

c) (E)-3-[3-(2-Ethoxycarbonyl-ethyl)-2-oxo-1,2,3,4-tetrahydro-pyrido[2,3-d]pyrimidin-6-yl]acrylic acid tert-butyl ester According to the procedure of Preparation 130(d), except substituting 3-(6-bromo-2-oxo-1,4-dihydro-2H-pyrido[2,3-d]pyrimidin-3-yl)propionic acid ethyl ester for the 6-bromo-3-(2-dimethylamino-ethyl)-3,4-dihydro-1H-pyrido[2,3-d]pyrimidin-2-one, the title compound (0.39 g, 21%) was prepared as a white solid: MS (ESI) m/e 376 (M+H)⁺.

d) (E)-3-[3-(2-Ethoxycarbonyl-ethyl)-2-oxo-1,2,3,4-tetrahydro-pyrido[2,3-d]pyrimidin-6-yl]acrylic acid According to the procedure of Preparation 130(e), except substituting (E)-3-[3-(2-ethoxycarbonyl-ethyl)-2-oxo-1,2,3,4-tetrahydro-pyrido[2,3-d]pyrimidin-6-yl]acrylic acid tert-butyl ester for the (E)-3-[3-(2-dimethylamino-ethyl)-2-oxo-1,2,3,4-tetrahydro-pyrido[2,3-d]pyrimidin-6-yl]acrylic acid tert-butyl ester, the title compound (0.16 g, 44%) was prepared as a yellow solid: ¹H NMR (500 MHz, DMSO-d₆) δ 8.30 (d, J=1.5 Hz, 1H), 8.16 (s, 1H), 7.70-7.60 (m, 1H), 6.60-6.50 (m, 1H), 4.70 (s, 2H), 4.13 (q, J=7.0 Hz, 2H), 3.74-3.68 (t, J=6.5 Hz, 2H), 2.74-2.66 (t, J=6.5 Hz, 2H), 1.25 (t, J=5.5 Hz, 3H); MS (ESI) m/e 320 (M+H)⁺.

Preparation 135

Preparation of 6-Bromo-3-(2,2-dimethoxy-ethyl)-3,4-dihydro-1H-pyrido[2,3-d]pyrimidin-2-one a) 5-Bromo-3-[(2,2-dimethoxy-ethylamino)methyl]pyridin-2-ylamine According to the procedure of Preparation 132(b), except substituting aminoacetaldehyde diethyl acetal for the 4-(3-aminopropyl)morpholine, the title compound (1.30 g, 45%) was prepared as a yellow solid: MS (ESI) m/e 290 (M+H)⁺.

b) 6-Bromo-3-(2,2-dimethoxy-ethyl)-3,4-dihydro-1H-pyrido[2,3-d]pyrimidin-2-one

According to the procedure of Preparation 130(c), except substituting 5-bromo-3-[(2,2-dimethoxy-ethylamino)methyl]pyridin-2-ylamine for 5-bromo-3-[(2-dimethylamino-ethyl)methyl]pyridin-2-ylamine, the title compound (6.40 g, 73%) was prepared as a white solid: MS (ESI) m/e 316 (M+H)⁺.

Preparation 136

Preparation of (E)-3-{6-Amino-5-[(2-morpholin-4-yl-ethylamino)methyl]pyridin-3-yl}acrylic acid hydrochloride a) (E)-3-[6-Amino-5-(2-morpholin-4-yl-ethylcarbamoyl)pyridin-3-yl]acrylic acid tert-butyl ester According to the procedure of Preparation 130(d), except substituting 2-amino-5-bromo-N-(2-morpholin-4-yl-ethyl)nicotinamide for 6-bromo-3-(2-dimethylamino-ethyl)-3,4-dihydro-1H-pyrido[2,3-d]pyrimidin-2-one, the title compound (2.48 g, 99%) was prepared as a yellow solid: ¹H NMR (300 MHz, CDCl₃) δ 8.30 (d, J=2.4 Hz, 1H), 7.75 (d, J=2.1 Hz, 1H), 7.46 (d, J=15.9 Hz, 1H), 7.02-6.83 (m, 1H), 6.65 (br s, 2H), 6.22 (d, J=15.9, 1H), 3.77-3.69 (m, 4H), 3.56-3.50 (m, 2H), 2.62 (t, J=6.0 Hz, 2H), 2.53 (t, J=4.5 Hz, 4H), 1.53 (s, 9H); MS (ESI) m/e 377 (M+H)⁺.

b) (E)-3-[6-Amino-5-(2-morpholin-4-yl-ethylcarbamoyl)-pyridin-3-yl]acrylic acid hydrochloride According to the procedure of Preparation 130(e), except substituting (E)-3-[6-amino-5-(2-morpholin-4-yl-ethylcarbamoyl)pyridin-3-yl]acrylic acid tert-butyl ester for (E)-3-[3-(2-dimethylamino-ethyl)-2-oxo-1,2,3,4-tetrahydro-pyrido[2,3-d]pyrimidin-6-yl]acrylic acid tert-butyl ester, the title compound (2.34 g, 91%) was prepared as a white solid: MS (ESI) m/e 321 (M+H)⁺.

Preparation 137

Preparation of (E)-3-(6-Amino-5-morpholin-4-ylmethyl-pyridin-3-yl)acrylic acid hydrochloride a) 5-Bromo-3-morpholin-4-ylmethyl-pyridin-2-ylamine According to the procedure of Preparation 125(a), except substituting morpholine for piperidine, the title compound (11.5 g, 97%) was prepared as yellow foam: ¹H NMR (300 MHz, CDCl₃) δ 8.04 (d, J=2.4 Hz, 1H), 7.35 (d, J=2.3 Hz, 1H), 5.61 (s, 2H), 3.72-3.69 (m, 4H), 3.42 (s, 2H), 2.44-2.41 (m, 4H).

b) (E)-3-(6-Amino-5-morpholin-4-ylmethyl-pyridin-3-yl)acrylic acid tert-butyl ester According to the procedure of Preparation 125(b), except substituting 5-bromo-3-morpholin-4-ylmethyl-pyridin-2-ylamine for 5-bromo-3-piperidin-1-ylmethyl-pyridin-2-ylamine, the title compound (11.3 g, 84%) was prepared as a yellow solid: ¹H NMR (300 MHz, CDCl₃) δ 8.11 (d, J=2.2 Hz, 1H), 7.49-7.44 (m, 2H), 6.19 (d, J=15.9 Hz, 1H), 5.89 (s, 2H), 3.72-3.69 (m, 4H), 3.47 (s, 2H), 2.45-2.42 (m, 4H), 1.53 (s, 9H).

c) (E)-3-(6-Amino-5-morpholin-4-ylmethyl-pyridin-3-yl)acrylic acid hydrochloride According to the procedure of Preparation 125(c), except substituting (E)-3-(6-amino-5-morpholin-4-ylmethyl-pyridin-3-yl)acrylic acid tert-butyl ester for (E)-3-(6-amino-5-piperidin-1-ylmethyl-pyridin-3-yl)acrylic acid tert-butyl ester, the title compound (12.9 g, quantitative) was prepared as an off-white solid: MS (ESI) m/z 264 [M+H]⁺.

Preparation 138

Preparation of 7-Bromo-4-[3-(4-methyl-piperazin-1-yl)-propyl]-1,3,4,5-tetrahydro-pyrido[2,3-e][1,4]diazepin-2-one a) [3-(4-Methyl-piperazin-1-yl)propylamino]acetic acid ethyl ester A solution of 4-(3-aminopropyl)-1-methylpiperazine (3.1 mL, 20 mmol) in MeOH (50 mL) was cooled in an ice bath and treated with ethyl glyoxylate (50% solution in toluene, 5.6 mL, 27 mmol) and AcOH (3 mL). After stirring for 15 min, NaBH$_3$CN (1.37 g, 21.8 mmol) was added and the mixture was allowed to stir for 7 h while slowly warming to room temperature. The mixture was diluted with saturated aqueous NaHCO$_3$ (150 mL) and then extracted with EtOAc (3×100 mL) followed by CH$_2$Cl$_2$ (3×100 mL). The combined CH$_2$Cl$_2$ layers were dried over Na$_2$SO$_4$, filtered and the solvent was removed in vacuo to give the title compound (1.81 g, 38%) as a colorless oil: MS (ESI) m/e 244 (M+H)$^+$.

b) {(2-Amino-5-bromo-pyridin-3-ylmethyl)-[3-(4-methyl-piperazin-1-yl)propyl]amino}acetic acid ethyl ester A solution of [3-(4-methyl-piperazin-1-yl)propylamino] acetic acid ethyl ester (1.80 g, 7.41 mmol) and triethylamine (2.3 mL, 16.4 mmol) in DMF (50 mL) was treated with 5-bromo-3-bromomethyl-pyridin-2-ylamine hydrobromide (2.57 g, 7.41 mmol). After stirring at room temperature for 3 d, the mixture was diluted with H$_2$O (100 mL) and then extracted with EtOAc (4×100 mL). The combined organic layers were dried over Na$_2$SO$_4$, filtered and the solvent was removed in vacuo. Purification by flash column chromatography (silica gel, CH$_2$Cl$_2$/MeOH, 97:3 to 90:10) gave the title compound (0.50 g, 16%) as a colorless oil: MS (ESI) m/e 428 (M+H)$^+$.

c) 7-Bromo-4-[3-(4-methyl-piperazin-1-yl)propyl]-1,3,4,5-tetrahydro-pyrido[2,3-e][1,4]diazepin-2-one A solution of {(2-amino-5-bromo-pyridin-3-ylmethyl)-[3-(4-methyl-piperazin-1-yl)propyl]amino}acetic acid ethyl ester (0.50 g, 1.17 mmol) in DMSO (10 mL) was treated with NaH (60% dispersion in mineral oil, 47 mg, 1.17 mmol). After stirring at room temperature for 3 d, the mixture was diluted with H$_2$O (30 mL) and then extracted with EtOAc (4×50 mL). The combined organic layers were dried over Na$_2$SO$_4$, filtered and the solvent was removed in vacuo. Purification by flash column chromatography (silica gel, CH$_2$Cl$_2$/MeOH, 92:8 to 87:13) gave the title compound (0.23 g, 51%) as a white solid: MS (ESI) m/e 382 (M+H)$^+$.

Preparation 139

Preparation of 7-Bromo-3,3-dimethyl-1,3,4,5-tetrahydro-pyrido[2,3-e][1.4]diazepin-2-one a) 2-[(2-Amino-5-bromo-pyridin-3-ylmethyl)amino]-2-methylpropionic acid methyl ester A solution of 5-bromo-3-bromomethyl-pyridin-2-ylamine hydrobromide (11.0 g, 31.7 mmol) and 2-amino-2-methyl-propionic acid methyl ester (5.80 g, 49.5 mmol) in DMF (220 mL) was treated with triethylamine (9.0 mL, 18.5 mmol). After stirring at room temperature for 3 d, the mixture was diluted with H$_2$O (400 mL) and then extracted with EtOAc (4×200 mL). The combined organic layers were washed with H$_2$O (3×100 mL) and brine (100 mL), dried over Na$_2$SO$_4$, filtered and the solvent was removed in vacuo. Purification by flash column chromatography (silica gel, CH$_2$Cl$_2$/MeOH, 99:1) gave the title compound (3.87 g, 40%) as a light yellow solid: MS (ESI) m/e 302 (M+H)$^+$.

b) 7-Bromo-3,3-dimethyl-1,3,4,5-tetrahydro-pyrido[2,3-e][1,4]diazepin-2-one

A solution of 2-[(2-amino-5-bromo-pyridin-3-ylmethyl)amino]-2-methylpropionic acid methyl ester (2.63 g, 8.71 mmol) in DMSO (100 mL) was treated with NaH (60% dispersion in mineral oil, 0.35 g, 8.7 mmol). After stirring at room temperature overnight, the mixture was diluted with H$_2$O (200 mL) and then extracted with EtOAc (5×150 mL). The combined organic layers were washed with H$_2$O (3×100 mL) and brine (100 mL), dried over Na$_2$SO$_4$, filtered and the solvent was removed in vacuo. Purification by flash column chromatography (silica gel, CH$_2$Cl$_2$/MeOH, 99:1 to 98:2) gave (0.79 g, 33%) as an off-white solid: MS (ESI) m/e 270 (M+H)$^+$.

The following examples illustrate methods for preparing compounds of the antibacterial compositions of the present invention from intermediate compounds such as those described in the foregoing Preparations.

Example 1

Preparation of (E)-3-(2-aminopyrimidin-5-yl)-N-(2-methyl-1H-indol-3-ylmethyl)-N-methylacrylamide a) N-Methyl-N-(2-methyl-1H-indol-3-ylmethyl) acrylamide To a solution of 2-methyl-3-(methylaminomethyl)indole (1.5 g, 8.6 mmole) and triethylamine (1.7 g, 17.3 mmole) in CH$_2$Cl$_2$ at 5° C. under a nitrogen atmosphere was added acryloyl chloride (0.86 g, 9.48 mmole). After 1 hr the reaction solution was poured into H$_2$O (100 mL) and the layers were separated. The organic fraction was washed with H$_2$O (100 mL) followed by brine and then dried over Na$_2$SO$_4$. Concentration under vacuum gave the title compound as an orange oil which solidified under high vacuum: MS (ES) m/e 457 (2M+H)$^+$. This material was used without further purification.

b) (E)-3-(2-Aminopyrimidin-5-yl)-N-(2-methyl-1H-indol-3-ylmethyl)-N-methylacrylamide A solution of N-methyl-N-(2-methyl-1H-indol-3-ylmethyl)acrylamide (1.18 g, 6.5 mmole), 2-amino-5-bromopyrimidine (0.5 g, 2.9 mmole), Pd(OAc)$_2$ (0.11 g, 0.49 mmole), tri-ortho-tolylphosphine (0.17 g, 0.55 mmole), and diisopropylethylamine (1.5 mL, 8.6 mmole) in propionitrile (100 mL) and DMF (10 mL) was heated at reflux overnight. The dark mixture was filtered through Celite®, and the filtrate was concentrated. Flash chromatography on silica gel (9:1 CHCl$_3$/CH$_3$OH containing 5% NH$_4$OH) gave the title compound (1.2 g, 65%): MS (ES) m/e 372 (M+H)$^+$.

Example 2

Preparation of (E)-N-methyl-N-(2-methyl-1H-indol-3-ylmethyl)-3-(3-methyl-2-oxo-1,2,3,4-tetrahydropyrido[2,3-d]pyrimidin-6-yl)acrylamide According to the procedure of Example 1 (b), except substituting 6-bromo-3-methyl-3,4-dihydro-1H-pyrido[2,3-d]pyrimidin-2-one (1.2 g, 5.0 mmole) for the 2-amino-5-bromopyrimidine, the title compound (73%) was prepared as a light yellow solid: MS (ES) m/e 390 (M+H)$^+$.

Example 3

Preparation of (E)-N-methyl-N-(1-methyl-1H-indol-3-ylmethyl)-3-(3-methyl-2-oxo-1,2,3,4-tetrahydropyrido[2,3-d]pyrimidin-6-yl)acrylamide a) N-Methyl-N-(1-methyl-indol-3-ylmethyl)acrylamide According to the procedure of Example 1 (a), except substituting 1-methyl-3-(methylaminomethyl)indole for the 2-methyl-3-(methylaminomethyl)indole, the title compound (1.7 g, 99%) was prepared as an orange oil that solidified under vacuum: MS (ES) m/e 229 (M+H)$^+$. This material was used without further purification.

b) (E)-N-methyl-N-(1-methyl-1H-indol-3-ylmethyl)-3-(3-methyl-2-oxo-1,2,3,4-tetrahydropyrido[2,3-d]pyrimidin-6-yl)acrylamide According to the procedure of Preparation 1 (b), except substituting N-methyl-N-(1-methyl-indol-3-ylmethyl)acrylamide (1.7 g, 7.5 mmole) for N-methyl-N-(2-methyl-1H-indol-3-ylmethyl)acrylamide, the title compound (70%) was prepared as a light yellow solid: MS (ES) m/e 390 (M+H)$^+$.

Example 4

Preparation of (E)-N-methyl-N-(2-methyl-1H-indol-3-ylmethyl)-3-(2-oxo-2,3-dihydro-1H-pyrrolo[2,3-b]pyridin-5-yl)acrylamide To a solution of (E)-3-(2-oxo-2,3-dihydro-1H-indol-5-yl) acrylic acid hydrochloride salt (0.50 g, 2.1 mmole), hydroxybenzotriazole monohydrate (0.31 g, 2.3 mmole), diisopropylethylamine (0.80 mL, 4.6 mmole), and 2-methyl-3-(methylaminomethyl)indole (0.40 g, 2.3 mmole) in DMF (50 mL) at RT was added EDC (0.46, 2.3 mmole). After 12 hr the reaction solution was concentrated under vacuum and the residue was purified by flash chromatography on silica gel (9:1 CHCl$_3$/CH$_3$OH containing 5% NH$_4$OH) to give the title compound (0.66 g, 88%) as a light yellow solid: MS (ES) m/e 361 (M+H)$^+$.

Example 5

Preparation of (E)-3-(3H-imidazo[4,5-b]pyridin-6-yl)-N-methyl-N-(1-methyl-1H-indol-3-ylmethyl)acrylamide According to the procedure of Example 4, except substituting (E)-3-(3H-imidazo[4,5-b]pyridin-6-yl) acrylate (0.14 g, 0.74 mmole), from Preparation 6, for the (E)-3-(2-oxo-2,3-dihydro-1H-indol-5-yl)acrylic acid hydrochloride salt, and substituting 1-methyl-3-(methylaminomethyl)indole (0.14 g, 0.81 mmole) for the 2-methyl-3-(methylaminomethyl)-1H-indole, the title compound (0.23 g, 89%) was prepared as a light yellow solid: MS (ES) m/e 346 (M+H)$^+$.

Example 6

Preparation of (E)-3-(3,4-dihydro-2H-pyrido[3,2-b]-1,4-oxazin-7-yl)-N-methyl-N-(1-methyl-1H-indol-3-ylmethyl)acrylamide According to the procedure of Example 4, except substituting (E)-3-(3,4-dihydro-2H-pyrido[3,2-b][1,4]oxazin-7-yl)acrylic acid (0.11 g, 0.53 mmole), from Preparation 7, for the (E)-3-(2-oxo-2,3-dihydro-1H-indol-5-yl)acrylic acid hydrochloride salt, and substituting 1-methyl-3-(methylaminomethyl) indole (0.10 g, 0.59 mmole) for the 2-methyl-3-(methylaminomethyl)-1H-indole, the title compound (0.16 g, 82%) was prepared as a light yellow solid: MS (ES) m/e 363 (M+H)$^+$.

Example 7

Preparation of (E)-3-[6-amino-5-[[N-methyl-N-(2-methyl-1H-indol-3-ylmethyl)amino]carbonylethyl]pyridin-3-yl]-N-methyl-N-(2-methyl-1H-indol-3-ylmethyl)acrylamide a) Ethyl (E)-3-(7-oxo-5,6,7,8-tetrahydro-1,8-naphthyridin-3-yl) acrylate A solution of 6-bromo-3,4-dihydro-1H-1,8-naphthyridin-2-one (5.0 g, 21.9 mmole), from Preparation 4, ethyl acrylate (3.3 g, 32.9 mmole), Pd(OAc)$_2$ (1.1 g, 0.74 mmole), tri-orthotolylphosphine (1.3 g, 4.4 mmole), and diisopropylethylamine (11.4 mL, 65.7 mmole) in propionitrile (200 mL) and DMF (25 mL) was heated at reflux overnight. The dark mixture was filtered through Celite®, and the filtrate was concentrated. Flash chromatography on silica gel (9:1 CHCl$_3$/CH$_3$OH containing 5% NH$_4$OH) gave the title compound (3.0 g, 59%) as a light yellow solid: MS (ES) m/e 233 (M+H)$^+$.

b) (E)-3-[6-Amino-5-(2-carboxyethyl)pyridin-3-yl] acrylic acid hydrochloride salt Ethyl (E)-3-(7-oxo-5,6,7,8-tetrahydro-1,8-naphthyridin-3-yl) acrylate (1.54 g, 6.6 mmole) was dissolved in acetic acid (25 mL) and concentrated hydrochloric acid (25 mL) and the solution was heated to 100° C. After 6 hr the solution was concentrated and the residue was dried under high vacuum. The resulting solid was triturated with diethyl ether and filtered to give a 1.46 g of a mixture of (E)-3-(7-oxo-5,6,7,8-tetrahydro-1,8-naphthyridin-3-yl) acrylic acid hydrochloride salt (82%) and the title compound (18%), both as white solids: MS (ES) m/e 218 (M+H)$^+$ (major) and MS (ES) m/e 236 (M+H)$^+$ (minor). This mixture was used without further purification.

c) (E)-3-[6-Amino-5-[[N-methyl-N-(2-methyl-1H-indol-3-ylmethyl)amino]carbonylethyl]pyridin-3-yl]-N-methyl-N-(2-methyl-1H-indol-3-ylmethyl)acrylamide According to the procedure of Example 4, except substituting a mixture (1.46 g) of (E)-3-[6-amino-5-(2-carboxyethyl)pyridin-3-yl]acrylic acid hydrochloride salt and (E)-3-(7-oxo-5,6,7,8-tetrahydro-1,8-naphthyridin-3-yl) acrylic acid hydrochloride salt for the (E)-3-(2-oxo-2,3-dihydro-1H-indol-5-yl)acrylic acid hydrochloride salt, the title compound (0.47 g) was prepared as a light yellow solid: MS (ES) m/e 549 (M+H)$^+$. (E)-N-Methyl-N-(2-methyl-1H-indol-3-ylmethyl)-3-(7-oxo-5,6,7,8-tetrahydro-1,8-naphthyridin-3-yl)acrylamide (1.56 g) was also obtained as a light yellow solid: MS (ES) m/e 375 (M+H)$^+$.

Example 8

Preparation of (E)-3-(6-aminopyridin-3-yl)-N-(1-ethyl-1H-indol-3-ylmethyl)-N-methylacrylamide EDC (0.56 g, 2.93 mmole) was added to a solution of (E)-3-(6-aminopyridin-3-yl)acrylic acid (0.48 g, 2.93 mmole), 1-ethyl-3-(methylaminomethyl)-1H-indole (0.50 g. 2.66 mmole), HOBt H$_2$O (0.40 g, 2.93 mmole) and diisopropylethylamine (0.93 mL, 5.32 mmole) in DMF (30 mL) at RT. The reaction was stirred overnight then was concentrated in vacuo. The residue was diluted with water and extracted with ethyl acetate. The combined organic extracts were washed with brine and dried over Na$_2$SO$_4$. Flash chromatography on silica gel (10% MeOH/CHCl$_3$) gave title compound (0.46 g, 52%) as a yellow solid after drying in vacuo: MS (ES) m/e 335 (M+H)$^+$.

Example 9

Preparation of (E)-3-(6-aminopyridin-3-yl)-N-(1-isopropyl-1H-indol-3-ylmethyl)-N-methylacrylamide EDC (0.51 g, 2.64 mmole) was added to a solution of (E)-3-(6-aminopyridin-3-yl)acrylic acid (0.43 g, 2.64 mmole), 1-isopropyl-3-(methylaminomethyl)indole (0.49 g, 2.40 mmole), HOBt H$_2$O (0.36 g, 2.64 mmole) and diisopropylethylamine (0.84 mL 4.80 mmole) in DMF (40 mL) at RT. The reaction was stirred overnight then was concentrated in vacuo. The residue was diluted with water and extracted with ethyl acetate. The combined organic extracts were washed with brine and dried over Na$_2$SO$_4$. Flash chromatography on silica gel (10% MeOH/CHCl$_3$) gave the title compound (0.49 g, 58%) as a yellow solid after drying in vacuo: MS (ES) m/e 349 (M+H)$^+$.

Example 10

Preparation of (E)-3-(6-aminopyridin-3-yl)-N-(1H-indol-3-ylmethyl)-N-methylacrylamide EDC (1.03 g, 5.40 mmole) was added to a solution of (E)-3-(6-aminopyridin-3-yl)acrylic acid (0.89 g, 5.40 mmole), 1-acetyl-3-(methylaminomethyl)indole (1.00 g, 4.95 mmole), HOBt.H$_2$O (0.73 g., 5.40 mmole) and diisopropylethylamine (1.72 mL, 9.90 mmole) in DMF (50 mL) at RT. The reaction was stirred overnight then was concentrated in vacuo. The residue was diluted with water and extracted with ethyl acetate. The combined organic extracts were washed with brine and dried over Na$_2$SO$_4$. Flash chromatography on silica gel (5% MeOH/CHCl$_3$) gave the title compound (0.90 g, 52%) as a light yellow solid after drying in vacuo: MS (ES) m/e 307 (M+H)$^+$.

Example 11

Preparation of (E)-N-(1H-indol-3-ylmethyl)-N-methyl-3-(7-oxo-5,6,7,8-tetrahydro-1,8-naphthyridin-3-yl)acrylamide A solution of 6-bromo-3,4-dihydro-1H-1,8-naphthyridin-2-one (0.64 g, 2.80 mmole), N-(1H-indol-3-ylmethyl)-N-methylacrylamide (0.60 g, 2.80 mmole), Pd(OAc)$_2$ (0.06 g, 0.28 mmole), tri-ortho-tolylphosphine (0.17 g, 0.56 mmole) and diisopropylethylamine (0.73 mL, 4.2 mmole) in propionitrile (50 mL) was deoxygenated, then was heated to reflux under N$_2$ overnight. The dark mixture was filtered through a pad of Celite®, and the filter pad was rinsed with acetonitrile (250 mL). The filtrate was concentrated in vacuo, and the residue was purified by flash chromatography on silica gel (10% MeOH/CHCl$_3$). The title compound (0.37 g, 37%) was obtained as a light yellow solid after drying in vacuo: MS (ES) m/e 361 (M+H)$^+$.

Example 12

Preparation of (E)-N-(1-benzyl-1H-indol-3-ylmethyl)-N-methyl-3-(7-oxo-5,6,7,8-tetrahydro-1,8-naphthyridin-3-yl)acrylamide A solution of 6-bromo-3,4-dihydro-1H-1,8-naphthyridin-2-one (1.05 g, 4.60 mmole), N-(1-benzyl-1H-indol-3-ylmethyl)-N-methyl-acrylamide (1.40 g, 4.60 mmole), Pd(OAc)$_2$ (0.10 g, 0.46 mmole), tri-ortho-tolylphosphine (0.28 g, 0.92 mmole) and diisopropylethylamine (1.20 mL 6.90 mmole) in propionitrile (75 mL) was deoxygenated, then was and heated to reflux under a N$_2$ overnight. The dark mixture was filtered through a pad of Celite®, and the filter pad was rinsed with acetonitrile (300 mL). The filtrate was concentrated in vacuo, and the residue was purified by flash chromatography on silica gel (5% MeOH/CHCl$_3$). The title compound (0.70 g. 35%) was obtained as a light yellow solid after drying in vacuo: MS (ES) m/e 451 (M+H)$^+$.

Example 13

Preparation of (E)-N-[1-(2-dimethylaminoethyl)-1H-indol-3-ylmethyl]-N-methyl-3-(7-oxo-5,6,7,8-tetrahydro-1,8-naphthyridin-3-yl)acrylamide A solution of 6-bromo-3,4-dihydro-1H-1,8-naphthyridin-2-one (0.61 g, 2.70 mmole), N-[1-(2-dimethylaminoethyl)-1H-indol-3-ylmethyl]-N-methyl-acrylamide (1.00 g, 3.50 mmole), Pd(OAc)$_2$ (0.08 g, 0.35 mmole), tri-ortho-tolylphosphine (0.21 g, 0.70 mmole), and diisopropylethylamine (0.91 mL, 5.25 mmole) in propionitrile (70 mL) was deoxygenated, then was and heated to reflux under a N$_2$ overnight. The dark mixture was filtered through a pad of Celite®, and the filter pad was rinsed with acetonitrile (250 mL). The filtrate was concentrated in vacuo, and the residue was purified by flash chromatography on silica gel (10% MeOH/CHCl$_3$ containing 5% NH$_4$OH in the MeOH). The title compound (0.20 g. 13%) was obtained as a light yellow solid after drying in vacuo: MS (ES) m/e 432 (M+H)$^+$.

Example 14

Preparation of (E)-N-methyl-3-(8-oxo-6,7,8,9-tetrahydro-5H-pyrido[2,3-b]azepin-3-yl)acrylamide A solution of 3-bromo-5,6,7,9-tetrahydro-pyrido[2,3-b]azepin-8-one (0.60 g, 2.50 mmole), N-(2-methyl-1H-indol- 3-ylmethyl)-N-methylacrylamide (0.85 g, 3.75 mmole), Pd(OAc)$_2$ (0.06 g, 0.25 mmole), tri-ortho-tolylphosphine (0.15 g, 0.50 mmole) and diisopropylethylamine (0.87 mL, 5.00 mmole) in propionitrile (50 mL) was deoxygenated, then was and heated to reflux under a N$_2$ overnight. The dark mixture was filtered through a pad of Celite®, and the filter pad was rinsed with acetonitrile (200 mL). The filtrate was concentrated in vacuo, and the residue was purified by flash chromatography on silica gel (10% MeOH/CHCl$_3$). The title compound (0.35 g. 35%) was obtained as a light tan solid after drying in vacuo: MS (ES) m/e 246 (M+H)$^+$.

Example 15

Preparation of (E)-N-methyl-N-(1-methyl-1H-indol-3-ylmethyl)-3-[6-(pyridin-2-Ylamino)pyridin-3-yl]acrylamide a) N-(1-methyl-1H-indol-3-ylmethyl)-N-methylacrylamide To a stirred solution of 1-methyl-3-(methylaminomethyl)-1H-indole (1.0 g, 5.7 mmole) and Et$_3$N (0.8 mL, 5.7 mmole) in CH$_2$Cl$_2$ (50 mL) at 0° C. was added acryloyl chloride (0.47 mL, 5.8 mmole) in one portion. After stirring for 1 h the reaction was washed with cold H$_2$O and brine, then was dried (MgSO$_4$) and concentrated under vacuum. This material was used without further purification.

b) (E)-N-Methyl-N-(1-methyl-1H-indol-3-ylmethyl)-3-[6-(pyridin-2-ylamino)pyridin-3-yl]acrylamide To a solution of N-(1-methyl-1H-indol-3-ylmethyl)-N-methylacrylamide, from Example 1 (a), in propionitrile (50 mL) was added 5-bromo-2,2'-dipyridylamine (1.2 g, 4.8 mmole), DIEA (1.8 mL, 10.3 mmole), Pd(OAc)$_2$ (112 mg, 0.5 mmole), and P(o-tol)$_3$ (304 mg, 1 mmole). The reaction was purged with Ar then stirred at reflux for 16 h. After cooling to room temperature the reaction was concentrated to dryness under vacuum. Flash chromatography on silica gel (3% (5% NH$_4$OH/MeOH)/CHCl$_3$), trituration with 1:1 Et$_2$O/petroleum ether, filtration, and drying under vacuum gave the title compound (1.24 g, 65%) as an off-white solid: MS (ES) m/e 398.2 (M+H)$^+$.

Example 16

Preparation of (E)-N-methyl-N-(2-methylbenzo[b]thiophen-3-ylmethyl)-3-(7-oxo-5,6,7,8-tetrahydro-1,8-naphthyridin-3-yl)acrylamide a)
N-(Benzo[b]thiophen-3-ylmethyl)-N-methylacrylamide According to the procedure of Example 15 (a), except substituting 2-methyl-3-(methylaminomethyl)benzo[b]thiophene (1.0 g, 5.2 mmole) for 1-methyl-3-(methylaminomethyl)-1H-indole, the title compound was prepared. This was used without further purification.

b) (E)-N-Methyl-N-(2-methylbenzo[b]thiophen-3-ylmethyl)-3-(7-oxo-5,6,7,8-tetrahydro-1,8-naphthyridin-3-yl)acrylamide According to the procedure of Example 15 (b), except substituting 6-bromo-3,4-dihydro-1H-1,8-naphthyridin-2-one (1.3 g, 5.7 mmole) for the 5-bromo-2,2'-dipyridylamine, the title compound (0.849 g, 42%) was prepared as a white solid: MS (ES) m/e 392.2 (M+H)$^+$.

Example 17

Preparation of (E)-N-methyl-N-(1-methyl-1H-indol-2-ylmethyl)-3-[6-[N-(methylaminocarbonylmethyl)amino]pyridin-3-yl]acrylamide a) N-(1-methyl-1H-indol-2-ylmethyl)-N-methylacrylamide According to the procedure of Example 15 (a), except substituting 1-methyl-2-(methylaminomethyl)-1H-indole (1.2 g, 6.9 mmole) for the 1-methyl-3-(methylaminomethyl)-1H-indole, the title compound was prepared. This was used without further purification.

b) (E)-N-Methyl-N-(1-methyl-1H-indol-2-ylmethyl)-3-[6-[N-(methylaminocarbonylmethyl)amino]pyridin-3-yl]acrylamide According to the procedure of Example 15 (b), except substituting 5-bromo-2-(methylaminocarbonylmethyl)aminopyridine (1.5 g, 6.2 mmole) for the 5-bromo-2,2'-dipyridylamine, the title compound (1.7 g, 72%) was prepared as a white solid: MS (ES) m/e 392.2 (M+H)$^+$.

Example 18

Preparation of (E)-3-(6-amino-5-(methoxycarbonyl)pyridin-3-yl)-N-(1-methyl-1H-indol-3-ylmethyl)-N-methylacrylamide a) N-(1-methyl-1H-indol-2-ylmethyl)-N-methylacrylamide According to the procedure of Example 15 (a), except substituting 1-methyl-2-(methylaminomethyl)-1H-indole (1.2 g, 6.9 mmole) for the 1-methyl-3-(methylaminomethyl)-1H-indole, the title compound was prepared. This was used without further purification.

b) (E)-3-(6-Amino-5-(methoxycarbonyl)pyridin-3-yl)-N-(1-methyl-1H-indol-3-ylmethyl)-N-methylacrylamide According to the procedure of Example 15 (b), except substituting methyl 2-amino-5-bromonicotinate (1.4 g, 6.1 mmole) for the 5-bromo-2,2'-dipyridylamine, the title compound (1.78 g, 77%) was prepared as a white solid: MS (ES) m/e 379.2 (M+H)$^+$.

Example 19

Preparation of (E)-3-[6-[N-(methoxycarbonylmethyl)amino]pyridin-3-yl]-N-methyl-N-(2-methyl-1H-indol-3-ylmethyl)acrylamide To a stirred solution of (E)-3-[6-[N-(methoxycarbonylmethyl)amino]pyridin-3-yl]acrylic acid hydrochloride salt (2.0 g, 7.3 mmole) in 1:1 DMF/CH$_2$Cl$_2$ (100 mL) was added 2-methyl-3-(methylaminomethyl)indole (1.3 g, 7.5 mmole), Et$_3$N (2.1 mL, 15 mmole), and HOBt.H$_2$O (1.0 g, 7.4 mmole), followed by EDC (1.4 g, 7.3 mmole). After stirring at room temperature for 18 h the reaction was concentrated to dryness. The residue was taken up in EtOAc, and the solution was washed with H$_2$O then brine, dried (Na$_2$SO$_4$), and concentrated under vacuum. The remaining residue was purified by flash chromatography on silica gel (4% MeOH/CHCl$_3$) to give the title compound (2.08 g, 73%) as an off-white solid: MS (ES) m/e 393.2 (M+H)$^+$.

Example 20

Preparation of (E)-3-[6-[N-(carboxymethyl)amino] pyridin-3-yl]-N-methyl-N-(2-methyl-1H-indol-3-ylmethyl)acrylamide To a stirred solution of (E)-3-[6-[N-(methoxycarbonylmethyl)amino]pyridin-3-yl]-N-methyl-N-(2-methyl-1H-indol-3-ylmethyl)acrylamide (0.5 g, 1.3 mmole) in dioxane (30 mL) was added 1 N NaOH (2 mL, 2 mmole). After stirring for 18 h the reaction was neutralized with 1 N HCl (2 mL, 2 mmole) and concentrated to near dryness. The resulting suspension was diluted with H$_2$O and filtered. The solid was washed with H$_2$O and dried under vacuum to give the title compound (505 mg, 100%) as a off-white solid: MS (ES) m/e 379.2 (M+H)$^+$.

Example 21

Preparation of (E)-N-methyl-N-(2-methyl-1H-indol-3-ylmethyl)-3-[6-[N-(methylaminocarbonylmethyl) amino]pyridin-3-yl]acrylamide To (E)-3-[6-[N-(methoxycarbonylmethyl)amino]pyridin-3-yl]-N-methyl-N-(2-methyl-1H-indol-3-ylmethyl)acrylamide (0.7 g, 1.8 mmole) was added a solution of 2.0 M methylamine in MeOH (50 mL). After stirring for 72 h the reaction was concentrated to dryness. The residue was triturated with Et$_2$O, filtered, and dried under vacuum to give the title compound (0.703 g, 100%) as an off-white solid: MS (ES) m/e 392.2 (M+H)$^+$.

Example 22

Preparation of (E)-3-(2-aminopyrimidin-5-yl)-N-methyl-N-(1-methyl-1H-pyrrolo[2,3-b]pyridin-3-ylmethyl)acrylamide A solution of 2-amino-5-bromopyrimidine (0.27 g, 1.55 mmole), N-methyl-N-(1-methyl-1H-pyrrolo[2,3-b]pyridin-3-ylmethyl)acrylamide (0.5 g, 2.33 mmole), Pd(OAc)$_2$ (0.037 g, 0.163 mmole), P(o-tolyl)$_3$ (0.085 g, 0.28 mmole), and (i-Pr)$_2$NEt (0.42 mL, 2.33 mmole) in propionitrile (20 mL) was degassed then heated to reflux. After 18 hr the mixture was cooled to RT and concentrated. Flash chromatography on silica gel (10% MeOH/CH$_2$Cl$_2$) gave the title compound (0.100 g, 18%): MS (ES) m/e 363 (M+H)$^+$.

Example 23

Preparation of (E)-N-methyl-N-(1-methyl-1H-pyrrolo[2,3-b]pyridin-3-ylmethyl)-3-(7-oxo-5,6,7,8-tetrahydro-1,8-naphthyridin-3-yl)acrylamide According to the procedure of Example 22, except substituting 6-bromo-3,4-dihydro-1H-1,8-naphthyridin-2-one (0.352 g, 1.55 mmole) for the 2-amino-5-bromopyrimidine, the title compound (0.14 g, 16%) was prepared as a white powder: MS (ES) m/e 376 (M+H)$^+$.

Example 24

Preparation of (E)-N-(2,3-dihydro-1H-3a-azacyclopenta[α]indene-8-ylmethyl)-N-methyl-3-(7-oxo-5,6,7,8-tetrahydro-1,8-naphthyridin-3-yl)acrylamide EDC (0.192 g, 1.0 mmole) was added to a solution of (E)-3-(7-oxo-5,6,7,8-tetrahydro-1,8-naphthyridin-3-yl) acrylic acid hydrochloride salt (0.254 g, 1.0 mmole), 2,3-dihydro-8-(methylaminomethyl)-1H-3a-azacyclopenta[α] indene (0.2 g, 1.0 mmole), HOBt.H$_2$O (0.135 g, 1.0 mmole), and Et$_3$N (0.15 mL, 1.1 mmole) in DMF (20 mL) at RT. The reaction was stirred overnight, then was poured into H$_2$O (50 mL) and extracted with CH$_2$Cl$_2$ (2×30 mL). The combined extracts were washed with brine and dried (MgSO$_4$). Flash chromatography on silica gel (5% MeOH/CH$_2$Cl$_2$) gave the title compound (0.1 g, 25%) a yellow solid: MS (ES) m/e 401 (M+H)$^+$.

Example 25

Preparation of (E)-N-(1-ethyl-5-fluoro-1H-indol-3-ylmethyl)-N-methyl-3-(7-oxo-5,6,7,8-tetrahydro-1,8-naphthyridin-3-yl)acrylamide According to the procedure of Example 24, except substituting (1-ethyl-5-fluoro-3-(methylaminomethyl)-1H-indole (0.1 g, 0.49 mmole) for the 2,3-dihydro-8-(methylaminomethyl)-1H-3a-azacyclopenta[α]indene, the title compound (0.028 g, 15%) was prepared as a white powder: MS (ES) m/e 407 (M+H)$^+$.

Example 26

Preparation of (E)-N-(5-fluoro-1-methyl-1H-indol-3-ylmethyl)-N-methyl-3-(7-oxo-5,6,7,8-tetrahydro-1,8-naphthyridin-3-yl)acrylamide According to the procedure of Example 24, except substituting 5-fluoro-1-methyl-3-(methylaminomethyl)-1H-indole (0.13 g, 0.67 mmole) for the 2,3-dihydro-8-(methylaminomethyl)-1H-3a-azacyclopenta[α]indene, the title compound (0.1 g, 37%) was prepared as a slightly yellow crystalline solid: MS (ES) m/e 393 (M+H)$^+$.

Example 27

Preparation of (E)-N-(5-fluoro-1-methyl-1H-indol-3-ylmethyl)-N-methyl-3-(7-oxo-5,6,7,8-tetrahydro-1,8-naphthyridin-3-yl)acrylamide According to the procedure of Example 24, except substituting 6-fluoro-1-methyl-3-(methylaminomethyl)-1H-indole (0.12 g, 0.59 mmole) for the 2,3-dihydro-8-(methylaminomethyl)-1H-3a-azacyclopenta[α]indene, the title compound (0.1 g, 43%) was prepared as a white crystalline solid: MS (ES) m/e 393 (M+H)$^+$.

Example 28

Preparation of (E)-N-(7-fluoro-1-methyl-1H-indol-3-ylmethyl)-N-methyl-3-(7-oxo-5,6,7,8-tetrahydro-1,8-naphthyridin-3-yl)acrylamide According to the procedure of Example 24, except substituting 7-fluoro-1-methyl-3-(methylaminomethyl)-1H-indole (0.18 g, 0.93 mmole) for the 2,3-dihydro-8-(methylaminomethyl)-1H-3a-azacyclopenta[α]indene, the title compound (0.1 g, 27%) was prepared as a white powder: MS (ES) m/e 393 (M+H)$^+$.

Example 29

Preparation of (E)-3-(6-aminopyridin-3-yl)-N-(6-fluoro-1-methyl-1H-indol-3-ylmethyl)-N-methylacrylamide According to the procedure of Example 24, except substituting 6-fluoro-1-methyl-3-(methylaminomethyl)-1H-indole (0.11 g, 0.59 mmole) for the 2,3-dihydro-8-(methylaminomethyl)-1H-3a-azacyclopenta[α]indene, and substituting (E)-3-(6-amino-pyridin-3-yl)acrylic acid (0.098 g, 0.59 mmole) for the (E)-3-(7-oxo-5,6,7,8-tetrahydro-1,8-naphthyridin-3-yl)acrylic acid hydrochloride salt, the title compound (0.1 g, 27%) was prepared as a white powder: MS (ES) m/e 339 (M+H)$^+$.

Example 30

Preparation of (E)-3-(6-aminopyridin-3-yl)-N-(4,6-dichloro-1-methyl-1H-indol-2-ylmethyl)-N-methylacrylamide EDC (84.4 mg, 0.44 mmole) was added all at once to a solution of (E)-3-(6-amino-pyridin-3-yl)acrylic acid (65.7 mg, 0.40 mmole), 4,6-dichloro-1-methyl-2-(methylaminomethyl)-1H-indole (107.0 mg, 0.44 mmole), HOBt.H$_2$O (59.5 mg, 0.44 mmole), and Et$_3$N (0.14 mL, 1.0 mmole) in anhydrous DMF (4 mL) at RT. After 17 hr, the reaction was concentrated to dryness and the residue was re-concentrated from CHCl$_3$/xylenes (2×). Flash chromatography on silica gel (7% MeOH in 1:1 EtOAc/CHCl$_3$) gave the R$_f$ 0.44 component (10% MeOH in 1:1 EtOAc/CHCl$_3$) as a foam. This was solidified by re-concentration from MeOH/EtOAc/CHCl$_3$ several times. This material was triturated with hot EtOAc/MeOH, and the mixture was cooled to 0° C. The title compound was collected by suction filtration. The filtrate was concentrated and the residue was triturated with EtOAc to afford additional title compound. The combined desired solids were dried in high vacuum at 50-60° C. to afford the title compound (108.9 mg, 70%) as a light yellow solid: $^1$H NMR (400 MHz, CDCl$_3$) 1.8:1 mixture of amide rotamers; δ 8.08-8.20 (2×s, 1H), 7.70-7.90 (2×d, 1H), 7.57-7.70 (2×s, 1H), 7.46 (d, J=15.2 Hz, 1H), 7.18 (s, 1H), 6.97 (d, J=15.2 Hz, 1H), 6.45 and 6.15 (2×m, 4H), 5.02 and 4.82 (2×s, 2H), 3.60-3.80 (2×s, 3H), 2.99 and 3.11 (2×s, 3H); MS (ES) m/e 239 and 391 (M+H)$^+$.

Example 31

Preparation of (E)-3-(6-aminopyridin-3-yl)-N-(1,4-dimethyl-1H-indole-3-ylmethyl)-N-methylacrylamide To a stirred solution of 1,4-dimethyl-3-(methylaminomethyl)-1H-indole (188.2 mg, 1 mmole) and (E)-3-(6-aminopyridin-3-yl)acrylic acid (164 mg, 1 mmole) in dry DMF (12 mL) containing dry Et$_3$N (4 mL) was added HOBt H$_2$O (153 mg, 1 mmole) and EDC (191.8 mg, 1 mmole). The reaction was stirred overnight under argon at ambient temperature, then was concentrated in vacuo. The residue was partitioned between EtOAc and 5% NaHCO$_3$ solution, and the layers were separated. The organic layer was washed with brine, dried (MgSO$_4$), filtered, and concentrated. Flash chromatography on silica gel afforded the title compound (120 mg, 36%) as a white solid: MS (ES) m/e 335.2 (M+H)$^+$. Anal. Calcd for C$_{20}$H$_{22}$N$_4$O.0.25H$_2$O: C, 70.88; H, 6.69; N, 16.53. Found: C, 71.11; H, 6.72; N, 16.36.

Example 32

Preparation of (E)-3-(6-aminopyridin-3-yl)-N-(4-methoxy-1-methyl-1H-indol-3-ylmethyl)-N-methylacrylamide According to the procedure of Example 31, except substituting 4-methoxy-1-methyl-3-(methylaminomethyl)-1H-indole for the 1,4-dimethyl-3-(methylaminomethyl)-indole, the title compound (100 mg, 29%) was obtained as a light yellow solid: MS (ES) m/e 351.2 (M+H)$^+$. Anal. Calcd for C$_{20}$H$_{22}$N$_4$O$_2$.0.25H$_2$O: C, 67.68; H, 6.39; N, 15.79. Found: C, 67.31; H, 6.21; N, 15.97.

Example 33

Preparation of (E)-3-(6-aminopyridin-3-yl)-N-(5-methoxy-1-methyl-1H-indol-3-ylmethyl)-N-methylacrylamide According to the procedure of Example 31, except substituting 5-methoxy-1-methyl-3-(methylaminomethyl)-1H-indole for the 1,4-dimethyl-3-(methylaminomethyl)-1H-indole, the title compound (110 mg, 31%) was obtained as a light tan solid: MS (ES) m/e 351.2 (M+H)$^+$. Anal. Calcd for C$_{20}$H$_{22}$N$_4$O$_2$.0.75H$_2$O: C, 66.01; H, 6.51; N, 15.39. Found: C, 65.83; H, 6.29; N, 15.60.

Example 34

Preparation of (E)-3-(6-aminopyridin-3-yl)-N-(7-chloro-1H-indol-3-ylmethyl)-N-methylacrylamide According to the procedure of Example 31, except substituting 7-chloro-1-methyl-3-(methylaminomethyl)-1H-indole for the dimethyl-3-(methylaminomethyl)-1H-indole, the title compound (180 mg, 52%) as obtained as a yellow solid: MS (ES) m/e 355.2 (M+H)$^+$. Anal. Calcd for C$_{19}$H$_{19}$ClN$_4$O.0.25H$_2$O: C, 63.51; H, 5.47; N, 15.59. Found: C, 63.55; H, 5.32; N, 15.68.

Example 35

Preparation of (E)-3-(6-aminopyridin-3-yl)-N-(7-methoxy-1-methyl-1H-indol-3-ylmethyl)-N-methylacrylamide According to the procedure of Example 31, except substituting 7-methoxy-1-methyl-3-(methylaminomethyl)-1H-indole for the 1,4-dimethyl-3-(methylaminomethyl)-1H-indole, the title compound (140 mg, 40%) was obtained as a tan solid: MS (ES) m/e 351.2 (M+H)$^+$. Anal. Calcd for C$_{20}$H$_{22}$N$_4$O$_2$.0.5H$_2$O: C, 66.83; H, 6.45; N, 15.58. Found: C, 66.81; H, 6.41; N, 15.19.

Example 36

Preparation of (E)-3-(6-aminopyridin-3-yl)-N-(6-chloro-1H-indol-3-ylmethyl)-N-methylacrylamide According to the procedure of Example 31, except substituting 6-chloro-1-methyl-3-(methylaminomethyl)-1H-indole for the 1,4-dimethyl-3-(methylaminomethyl)-1H-indole, the title compound (176 mg, 50%) was obtained as a yellow solid: MS (ES) m/e 355.2 (M+H)$^+$. Anal. Calcd for $C_{19}H_{19}ClN_4O.0.5H_2O$: C, 62.72; H, 5.54; N, 15.40. Found: C, 62.79; H, 5.20; N, 15.85.

Example 37

Preparation of (E)-3-(6-aminopyridin-3-yl)-N-(5-chloro-1H-indol-3-ylmethyl)-N-methylacrylamide According to the procedure of Example 31, except substituting 5-chloro-1-methyl-3-(methylaminomethyl)-1H-indole for the 1,4-dimethyl-3-(methylaminomethyl)-1H-indole the title compound was obtained as a tan solid (176 mg, 54%): MS (ES) m/e 355.2 (M+H)$^+$. Anal. Calcd for $C_{19}H_{19}ClN_4O.0.25H_2O$: C, 63.51; H, 5.47; N, 15.59. Found: C, 63.63; H, 5.84; N, 15.83.

Example 38

Preparation of (E)-3-(6-aminopyridin-3-yl)-N-(4-chloro-1H-indol-3-ylmethyl)-N-methylacrylamide According to the procedure of Example 31, except substituting 4-Chloro-1-methyl-3-(methylaminomethyl)-1H-indole for the 1,4-dimethyl-3-(methylaminomethyl)-indole the title compound was obtained as a tan solid (150 mg, 42%): MS (ES) m/e 355.2 (M+H)$^+$. Anal. Calcd for $C_{19}H_{19}ClN_4O.0.25H_2O$: C, 63.51; H, 5.47; N, 15.59. Found: C, 63.33; H, 5.38; N, 15.34.

Example 39

Preparation of (E)-3-(6-aminopyridin-3-yl)-N-(3,3-dimethyl-3H-indene-1-ylmethyl)-N-methylacrylamide According to the procedure of Example 31, except substituting 1,1-dimethyl-3-(methylaminomethyl)-3H-indene for the 1,4-dimethyl-3-(methylaminomethyl-1H-indole, the title compound (43 mg, 13%) was obtained as a white solid: MS (ES) m/e 334.2 (M+H)$^+$. Anal. Calcd for $C_{21}H_{23}N_3O.0.75H_2O$: C, 72.70; H, 7.12; N, 12.11. Found: C, 72.38; H, 6.80; N, 11.69.

Example 40

Preparation of (E)-3-(6-aminopyridin-3-yl)-N-(7-hydroxy-1-methyl-1H-indol-3-ylmethyl)-N-methylacrylamide According to the procedure of Example 31, except substituting 7-hydroxy-1-methyl-3-(methylaminomethyl)-1H-indole for the 1,4-dimethyl-3-(methylaminomethyl)-1H-indole, the title compound was obtained as a tan solid (60 mg, 17.9%): MS (ES) m/e 337.2 (M+H)$^+$. Anal. Calcd for $C_{19}H_{20}N_4O_2.1.0H_2O$: C, 64.39; H, 6.26; N, 15.81. Found: C, 63.99; H, 5.78; N, 15.54.

Example 41

Preparation of (E)-N-methyl-3-(7-oxo-5,6,7,8-tetrahydro-1,8-naphthyridin-3-yl)-N-(1,2,7-trimethyl-1H-indol-3-ylmethyl)-acrylamide a) N-Methyl-N-(1,2,7-trimethyl-1H-indol-3-ylmethyl)acrylamide To a cold solution (ice bath) of 3-(methylaminomethyl)-1,2,7-trimethyl-1H-indole (570 mg, 2.8 mmole) in dry $CH_2Cl_2$ (24 mL) was added dry $Et_3N$ (0.25 mL, 2.9 mmole). The reaction was stirred in the cold under argon for 2 h then was poured into $H_2O$ (40 mL). The layers were separated, and the organic layer was washed with brine, dried ($MgSO_4$), filtered, and concentrated. The title compound (0.7 g, 97%) was obtained as a light orange solid: MS (ES) m/e 257.2 (M+H)$^+$.

b) (E)-N-Methyl-3-(7-oxo-5,6,7,8-tetrahydro-1,8-naphthyridin-3-yl)-N-(1,2,7-trimethyl-1H-indol-3-ylmethyl)-acrylamide A mixture of N-methyl-N-(1,2,7-trimethyl-1H-indol-3-ylmethyl)acrylamide (256 mg, 1 mmole) and 6-bromo-3,4-dihydro-1H-1,8-naphthyridin-2-one (227 mg, 1 mmole) in propionitrile (20 mL) was treated with DIEA (0.3 mL), $Pd(OAc)_2$ (29 mg, 0.13 mmole), and tri-o-tolylphosphine (50 mg, 0.16 mmole). The reaction was heated at reflux under argon for 10 h, then was cooled to RT and filtered through supercel. The filtrate was concentrated and the residue was purified by flash chromatography on silica gel to afford the title compound (100 mg, 25%) as an off-white solid: MS (ES) m/e 403.2 (M+H)$^+$. Anal. Calcd for $C_{24}H_{26}N_4O_2.2.75H_2O$: C, 63.77; H, 7.02; N, 12.39. Found: C, 63.81; H, 7.25; N, 11.90.

Example 42

Preparation of (E)-N-(7-chloro-1-methyl-1H-indol-3-ylmethyl)-N-methyl-3-(7-oxo-5,6,7,8-tetrahydro-1,8-naphthyridin-3-yl)-acrylamide A solution of 7-chloro-1-methyl-3-(methylaminomethyl)-1H-indole (104.3 mg, 0.5 mmole) and (E)-3-(7-oxo-5,6,7,8-tetrahydro-1,8-naphthyridin-3-yl)-acrylic acid (109.1 mg, 0.5 mmole) in dry DMF (8 mL) was treated with dry $Et_3N$ (0.2 mL), HOBt $H_2O$ (76.5 mg, 0.5 mmole) and EDC (96 mg, 0.5 mmole). The solution was stirred at RT under argon for 20 h, then was concentrated. The oily residue was dissolved in MeOH and the solution was cooled. The precipitated solid was collected, washed with cold MeOH, and dried to give the title compound (95 mg, 47%): MS (ES) m/e 409.2 (M+H)$^+$. Anal. Calcd for $C_{22}H_{21}ClN_4O_2.0.25H_2O$: C, 63.92; H, 5.24; N, 13.55. Found: C, 63.56; H, 5.14; N, 13.73.

Example 43

Preparation of (E)-N-(7-chloro-1H-indol-3-ylmethyl)-N-methyl-3-(7-oxo-5,6,7,8-tetrahydro-1,8-naphthyridin-3-yl)-acrylamide According to the procedure of Example 42, except substituting 7-chloro-3-(methylaminomethyl)-1H-indole for the 7-chloro-1-methyl-3-(methylaminomethyl)-1H-indole, the title compound (25 mg, 13%) was obtained as an off white solid after chromatography on silica gel: MS (ES) m/e 395.0 (M+H)$^+$

Example 44

Preparation of (E)-2,N-dimethyl-N-(2-methyl-1H-indol-3-ylmethyl)-3-(7-oxo-5,6,7,8-tetrahydro-1,8-naphthyridin-3-yl)acrylamide According to the procedure of Example 4, except substituting (E)-2-methyl-3-(7-oxo-5,6,7,8-tetrahydro-1,8-naphthyridin-3-yl)acrylic acid hydrochloride salt (0.50 g, 1.8 mmole) for the (E)-3-(2-oxo-2,3-dihydro-1H-indol-5-yl)acrylic acid hydrochloride salt, the title compound (0.64 g, 89%) was prepared as a light yellow solid: MS (ES) m/e 389 (M+H)$^+$.

Example 45

Preparation of (E)-3,N-dimethyl-N-(2-methyl-1H-indol-3-ylmethyl)-3-(7-oxo-5,6,7,8-tetrahydro-1,8-naphthyridin-3-yl)acrylamide According to the procedure of Example 1, except substituting (E)-3-methyl-3-(7-oxo-5,6,7,8-tetrahydro-1,8-naphthyridin-3-yl)acrylic acid hydrochloride salt (0.50 g, 1.8 mmole) for the (E)-3-(2-oxo-2,3-dihydro-1H-indol-5-yl)acrylic acid hydrochloride salt, the title compound (0.67 g, 92%) was prepared as a light yellow solid: MS (ES) m/e 389 (M+H)$^+$.

Example 46

Preparation of (E)-N-methyl-N-(2-methyl-1H-indol-3-ylmethyl)-3-(4-methyl-3-oxo-2,3,4,5-tetrahydro-1H-pyrido[2,3-e]-1,4-diazepin-7-yl)acrylamide According to the procedure of Example 162, except substituting 7-bromo-4-methyl-1,2,4,5-tetrahydropyrido[2,3-e]-1,4-diazepin-3-one (0.50 g, 1.9 mmole) for the 2-amino-5-bromopyrimidine, the title compound (0.30 g, 62%) was prepared as a light yellow solid: MS (ES) m/e 404 (M+H)$^+$.

Example 47

Preparation of (E)-N-methyl-N-(2-methyl-1H-indol-3-ylmethyl)-3-(8-oxo-6,7,8,9-tetrahydro-5H-pyrido[2,3-b]azepin-3-yl)acrylamide EDC (0.18 g, 0.96 mmole) was added to a solution of (E)-3-(8-oxo-6,7,8,9-tetrahydro-5H-pyrido[2,3-b]azepin-3-yl)acrylic acid hydrochloride salt (0.24 g, 0.87 mmole), 2-methyl-3-(methylaminomethyl)indole (0.15 g, 0.87 mmole), HOBt.H$_2$O (0.13 g., 0.96 mmole) and diisopropylethylamine (0.45 mL, 2.61 mmole) in DMF (15 mL) at RT. The reaction was stirred overnight then was concentrated in vacuo. The residue was diluted with water and extracted with ethyl acetate. The combined organic extracts were washed with brine and dried over Na$_2$SO$_4$. Preparative HPLC on a Waters C-18 ODSA column (gradient: 20-100% H$_2$O/CH$_3$CN) gave the title compound (0.13 g, 38%) as a light yellow solid after drying in vacuo: MS (ES) m/e 389 (M+H)$^+$.

Example 48

Preparation of (E)-N-[1-(2-hydroxyethyl)-1H-indol-3-ylmethyl]-N-methyl-3-(7-oxo-5,6,7,8-tetrahydro-1,8-naphthyridin-3-yl)acrylamide EDC (0.54 g, 2.80 mmole) was added to a solution of (E)-3-(7-oxo-5,6,7,8-tetrahydro-1,8-naphthyridin-3-yl)acrylic acid hydrochloride salt (0.71 g, 2.80 mmole), 1-(2-hydroxyethyl)-3-(methylaminomethyl)-1H-indole (0.52 g, 2.55 mmole), HOBt H$_2$O (0.38 g., 2.80 mmole) and diisopropylethylamine (1.11 mL, 6.40 mmole) in DMF (25 mL) at RT. The reaction was stirred overnight then was concentrated in vacuo. The residue was diluted with water and extracted with ethyl acetate. The combined organic extracts were washed with brine and dried over Na$_2$SO$_4$. Flash chromatography on silica gel (20% EtOH/EtOAc) gave title compound (0.28 g, 27%) as an off-white solid after drying in vacuo: MS (ES) m/e 405 (M+H)$^+$.

Example 49

Preparation of (E)-N-methyl-N-(1-methyl-1H-indol-3-ylmethyl)-3-(8-oxo-6,7,8,9-tetrahydro-5H-pyrido[2,3-b]azepin-3-yl)acrylamide EDC (0.06 g, 0.30 mmole) was added to a solution of (E)-3-(8-oxo-6,7,8,9-tetrahydro-5H-pyrido[2,3-b]azepin-3-yl)acrylic acid hydrochloride salt (0.07 g, 0.27 mmole), 1-methyl-3-(methylaminomethyl)-1H-indole (0.05 g, 0.27 mmole), HOBt H$_2$O (0.04 g., 0.30 mmole) and diisopropylethylamine (0.14 mL, 0.81 mmole) in DMF (15 mL) at RT. The reaction was stirred overnight then was concentrated in vacuo. The residue was diluted with water and extracted with ethyl acetate. The combined organic extracts were washed with brine and dried over Na$_2$SO$_4$. Flash chromatography on silica gel (20% EtOH/EtOAc) gave title compound (0.05 g, 48%) as an off-white solid after drying in vacuo: MS (ES) m/e 389 (M+H)$^+$.

Example 50

Preparation of (E)-N-[1-(2-hydroxyethyl)-1H-indol-3-ylmethyl]-N-methyl-3-(7-oxo-5,6,7,8-tetrahydro-1,8-naphthyridin-3-yl)acrylamide EDC (0.35 g, 1.81 mmole) was added to a solution of (E)-3-(7-oxo-5,6,7,8-tetrahydro-1,8-naphthyridin-3-yl)acrylic acid hydrochloride salt (0.42 g, 1.65 mmole), 1-ethyl-3-(methylaminomethyl)-1H-indole (0.31 g, 1.65 mmole), HOBt H$_2$O (0.24 g., 1.81 mmole) and diisopropylethylamine (0.86 mL, 4.95 mmole) in DMF (15 mL) at RT. The reaction was stirred overnight then was concentrated in vacuo. The residue was diluted with water and extracted with ethyl acetate. The combined organic extracts were washed with brine and dried over Na$_2$SO$_4$. Flash chromatography on silica gel (10% EtOH/EtOAc) gave title compound (0.39 g, 61%) as a light yellow solid after drying in vacuo: MS (ES) m/e 389 (M+H)$^+$.

Example 51

Preparation of (E)-N-(7-chloro-1-methyl-1H-indol-3-ylmethyl)-3-[6-[N-(methoxycarbonylmethyl)amino]pyridin-3-yl]-N-methylacrylamide According to the procedure of Example 19, except substituting 7-chloro-1-methyl-3-(methylaminomethyl)-1H-indole (1.4 g, 6.7 mmole) for the 2-methyl-3-(methylaminomethyl)indole, the title compound (2.38 g, 84%) was prepared as a pale yellow solid: MS (ES) m/e 427.0 (M+H)$^+$.

Example 52

Preparation of (E)-3-[6-[N-(carboxymethyl)amino]pyridin-3-yl]-N-(7-chloro-1-methyl-1H-indol-3-ylmethyl)-N-methylacrylamide According to the procedure of Example 20, except substituting (E)-N-(7-chloro-1-methyl-1H-indol-3-ylmethyl)-3-[6-[N-(methoxycarbonylmethyl)amino]pyridin-3-yl]-N-methylacrylamide (0.75 g, 1.8 mmole) for the (E)-3-[6-[N-(methoxycarbonylmethyl)amino]pyridin-3-yl]-N-methyl-N-(2-methyl-1H-indol-3-ylmethyl)acrylamide, the title compound (0.746 g, 100%) was prepared as a white solid: MS (ES) m/e 413.2 (M+H)$^+$.

Example 53

Preparation of (E)-N-(7-chloro-1-methyl-1H-indol-3-ylmethyl)-N-methyl-3-[6-[N-(methylaminocarbonylmethyl)amino]pyridin-3-yl]acrylamide According to the procedure of Example 21, except substituting (E)-N-(7-chloro-1-methyl-1H-indol-3-ylmethyl)-3-[6-[N-(methoxycarbonylmethyl)amino]pyridin-3-yl]-N-methylacrylamide (0.75 g, 1.8 mmole) for the (E)-3-[6-[N-(methoxycarbonylmethyl)amino]pyridin-3-yl]-N-methyl-N-(2-methyl-1H-indol-3-ylmethyl)acrylamide, the title compound (0.721 g, 94%) was prepared as a white solid: MS (ES) m/e 426.0 (M+H)$^+$.

Example 54

Preparation of (E)-3-(6-aminopyridin-3-yl)-N-(2-chloro-1-methyl-1H-indol-3-ylmethyl)-N-methylacrylamide According to the procedure of Example 31, except substituting 2-chloro-1-methyl-2-(methylaminomethyl)-1H-indole (0.7 g, 3.0 mmole) for the 1,4-dimethyl-3-(methylaminomethyl)-1H-indole, the title compound (0.935 g, 88%) was obtained as an off-white solid: MS (ES) m/e 355.2 (M+H)$^+$.

Example 55

Preparation of (E)-N-(2-chloro-1-methyl-1H-indol-3-ylmethyl)-N-methyl-3-(7-oxo-5,6,7,8-tetrahydro-1,8-naphthyridin-3-yl)acrylamide According to the procedure of Example 24, except substituting 2-chloro-1-methyl-2-(methylaminomethyl)-1H-indole (0.7 g, 3.0 mmole) for the 2,3-dihydro-8-(methylaminomethyl)-1H-3a-azacyclopenta[α]indene, the title compound (1.03 g, 84%) was obtained as a white solid: MS (ES) m/e 409.0 (M+H)$^+$.

Example 56

Preparation of (E)-N-(naphthalen-2-ylmethyl)-N-methyl-3-(7-oxo-5,6,7,8-tetrahydro-1,8-naphthyridin-3-yl)acrylamide According to the procedure of Example 24, except substituting 2-(methylaminomethyl)naphthalene (0.55 g, 3.2 mmole) for the 2,3-dihydro-8-(methylaminomethyl)-1H-3a-azacyclopenta[α]indene, the title compound (0.871 g, 73%) was obtained as a white solid: MS (ES) m/e 372.2 (M+H)$^+$.

Example 57

Preparation of (E)-N-(1-methyl-1H-indol-3-ylmethyl)-N-methyl-3-(6-amino-7-oxo-5,6,7,8-tetrahydro-1,8-naphthyridin-3-yl)acrylamide a) (E)-N-(1-Methyl-1H-indol-3-ylmethyl)-N-methyl-3-[6-(benzhydrylideneamino)-7-oxo-5,6,7,8-tetrahydro-1,8-naphthyridin-3-yl]acrylamide According to the procedure of Example 15, except substituting 3-(benzhydrylideneamino)-6-bromo-3,4-dihydro-1H-1,8-naphthyridin-2-one (3.5 g, 8.6 mmole) for the 5-bromo-2,2'-dipyridylamine, the title compound (3.72 g, 78%) was obtained as a pale yellow solid: MS (ES) m/e 554.4 (M+H)$^+$.

b) (E)-N-(1-Methyl-1H-indol-3-ylmethyl)-N-methyl-3-(6-amino-7-oxo-5,6,7,8-tetrahydro-1,8-naphthyridin-3-yl)acrylamide To a suspension of (E)-N-(1-methyl-1H-indol-3-ylmethyl)-N-methyl-3-[6-(benzhydrylideneamino)-7-oxo-5,6,7,8-tetrahydro-1,8-naphthyridin-3-yl]acrylamide (0.5 g, 0.9 mmole) in dioxane (15 mL) was added 1 N HCl (10 mL) with stirring at RT. After approximately 5 min the suspension cleared up then gradually reformed. After stirring for 1 h the reaction was neutralized with 1 N NaOH (10 mL) and concentrated to near dryness under vacuum. The resulting suspension was diluted with H$_2$O (20 mL) and filtered, and the solid was rinsed with cold H$_2$O and dried under vacuum. The slightly pinkish solid was triturated with Et$_2$O, filtered, and dried under vacuum to give the title compound (248 mg, 71%) as an off-white solid: MS (ES) m/e 390.4 (M+H)$^+$.

Example 58

Preparation of (E)-N-(benzofuran-2-ylmethyl)-N-methyl-3-(7-oxo-5,6,7,8-tetrahydro-1,8-naphthyridin-3-yl)acrylamide According to the procedure of Example 4, except substituting (E)-3-(7-oxo-5,6,7,8-tetrahydro-1,8-naphthyridin-3-yl)acrylic acid hydrochloride salt (1.60 g, 6.3 mmole) for the (E)-3-(2-oxo-2,3-dihydro-1H-indol-5-yl)acrylic acid hydrochloride salt, and substituting 2-(methylaminomethyl)benzofuran (1.20 g, 6.9 mmole) for the 2-methyl-3-(methylaminomethyl)indole, the title compound (2.0 g, 90%) was prepared as a tan solid: MS (ES) m/e 363 (M+H)$^+$.

Example 59

Preparation of (E)-3-(6-aminopyridin-3-yl)-N-(7-methoxycarbonyl-1-methyl-1H-indol-3-ylmethyl)-N-methylacrylamide According to the procedure of Example 31, except substituting methyl 1-methyl-3-(methylaminomethyl)-1H-indole-7-carboxylate for the 1,4-dimethyl-3-(methylaminomethyl)-1H-indole, the title compound (150 mg, 34%) was obtained, after trituration with diethyl ether, as an off-white solid: MS (ES) m/e 379.2 (M+H)$^+$. Anal. Calcd for C$_{21}$H$_{22}$N$_4$O$_3$.0.25H$_2$O: C, 65.87; H, 5.92; N, 14.63. Found: C, 66.02; H, 5.71; N, 14.29.

Example 60

Preparation of (E)-3-(aminopyridin-3-yl)-N-methyl-N-(1,2,7-trimethyl-1H-indol-3-ylmethyl)acrylamide According to the procedure of Example 31, except substituting 3-(methylaminomethyl)-1,2,7-trimethyl-1H-indole for the 1,4-dimethyl-3-(methylaminomethyl)-1H-indole, the title compound (120 mg, 29%) was obtained, after trituration with ethyl acetate, as a light yellow solid: MS (ES) m/e 349.0 $(M+H)^+$. Anal. Calcd for $C_{21}H_{24}N_4O.H_2O$: C, 68.82; H, 7.69; N, 15.29. Found: C, 68.42; H, 6.86; N, 15.61.

Example 61

Preparation of (E)-3-(6-aminopyridin-3-yl)-N-(7-chloro-1H-indol-3-ylmethyl)-N-methylacrylamide According to the procedure of Example 31, except substituting 7-chloro-3-(methylaminomethyl)-1H-indole for the 1,4-dimethyl-3-(methylaminomethyl)-1H-indole, the title compound (150 mg, 25%) was obtained, after trituration with ethyl acetate, as a light yellow solid: MS (ES) m/e 341.0 $(M+H)^+$. Anal. Calcd for $C_{18}H_{17}N_4O.0.25H_2O$: C, 62.60; H, 5.10; N, 16.22. Found: C, 62.29; H, 5.01; N, 16.32.

Example 62

Preparation of (E)-N-(5-chloro-1-methyl-1H-indol-3ylmethyl-N-methyl-3-(7-oxo-5,6,7,8-tetrahydro-1,8-naphthyridin-3-yl)acrylamide According to the procedure of Example 42, except substituting 5-chloro-1-methyl-3-(methylaminomethyl)-1H-indole for the 7-chloro-1-methyl-3-(methylaminomethyl)-1H-indole, the title compound (100 mg, 49%) was obtained as a light tan solid: MS (ES) m/e 409.0 $(M+H)^+$. Anal. Calcd for $C_{22}H_{21}ClN_4O_2.0.5H_2O$: C, 63.23; H, 5.32; N, 13.40. Found: C, 63.19; H, 5.23; N, 13.45.

Example 63

Preparation of (E)-N-(6-chloro-1-methyl-1H-indol-3-ylmethyl)-N-methyl-3-(7-oxo-5,6,7,8-tetrahydro-1,8-naphthyridin-3-yl)acrylamide According to the procedure of Example 42, except substituting 6-chloro-1-methyl-3-(methylaminomethyl)-1H-indole for the 7-chloro-1-methyl-3-(methylaminomethyl)-1H-indole, the title compound (125 mg, 61%) was obtained as a light tan solid: MS (ES) m/e 409.0 $(M+H)^+$. Anal. Calcd for $C_{22}H_{21}ClN_4O_2.0.25H_2O$: C, 63.92; H, 5.24; N, 13.55. Found: C, 63.96; H, 4.98; N, 13.66.

Example 64

Preparation of (E)-N-(1,7-dimethyl-1H-indol-3-ylmethyl)-N-methyl-3-(7-oxo-5,6,7,8-tetrahydro-1,8-naphthyridin-3-yl)acrylamide According to the procedure of Example 42, except substituting 1,7-dimethyl-3-(methylaminomethyl)-1H-indole for the 7-chloro-1-methyl-3-(methylaminomethyl)-1H-indole, the title compound (100 mg, 51%) was obtained as a white solid: MS (ES) m/e 389.2 $(M+H)^+$. Anal. Calcd for $C_{23}H_{24}N_4O_2.0.25H_2O$: C, 70.29; H, 6.28; N, 14.25. Found: C, 70.06; H, 6.23; N, 14.29

Example 65

Preparation of (E)-N-(1,6-dimethyl-1H-indol-3-ylmethyl)-N-methyl-3-(7-oxo-5,6,7,8-tetrahydro-1,8-naphthyridin-3-yl)acrylamide According to the procedure of Example 42, except substituting 1,6-dimethyl-3-(methylaminomethyl)-1H-indole for the 7-chloro-1-methyl-3-(methylaminomethyl)-1H-indole, the title compound (95 mg, 49%) was obtained as a white solid: MS (ES) m/e 389.2 $(M+H)^+$. Anal. Calcd for $C_{23}H_{24}N_4O_2.0.75H_2O$: C, 68.72; H, 6.39; N, 13.93. Found: C, 68.98; H, 6.07; N, 13.81.

Example 66

Preparation of (E)-N-(1,4-dimethyl-1H-indol-3-ylmethyl)-N-methyl-3-(7-oxo-5,6,7,8-tetrahydro-1,8-naphthyridin-3-yl)acrylamide According to the procedure of Example 42, except substituting 1,4-dimethyl-3-(methylaminomethyl)-1H-indole for the 7-chloro-1-methyl-3-(methylaminomethyl)-1H-indole, the title compound (90 mg, 46%) was obtained as a white solid: MS (ES) m/e 389.0 $(M+H)^+$. Anal. Calcd for $C_{23}H_{24}N_4O_2.0.5H_2O$: C, 69.50; H, 6.33; N, 14.10. Found: C, 69.40; H, 6.24; N, 14.20.

Example 67

Preparation of (E)-N-(1,5-dimethyl-1H-indol-3-ylmethyl)-N-methyl-3-(7-oxo-5,6,7,8-tetrahydro-1,8-naphthyridin-3-yl)acrylamide According to the procedure of Example 42, except substituting 1,5-dimethyl-3-(methylaminomethyl)-1H-indole for the 7-chloro-1-methyl-3-(methylaminomethyl)-1H-indole, the title compound (100 mg, 51%) was obtained as a white solid: MS (ES) m/e 389.2 $(M+H)^+$. Anal. Calcd for $C_{23}H_{24}N_4O_2.0.125H_2O$: C, 70.70; H, 6.25; N, 14.34. Found: C, 70.75; H, 6.15; N, 14.38.

Example 68

Preparation of (E)-N-(7-methoxy-1-methyl-1H-indol-3-ylmethyl)-N-methyl-3-(7-oxo-5,6,7,8-tetrahydro-1,8-naphthyridin-3-yl)acrylamide According to the procedure of Example 42, except substituting 7-methoxy-1-methyl-3-(methylaminomethyl)-1H-indole for the 7-chloro-1-methyl-3-(methylaminomethyl)-1H-indole, the title compound (85 mg, 42%) was obtained as an off-white solid: MS (ES) m/e 405.2 $(M+H)^+$. Anal. Calcd for $C_{23}H_{24}N_4O_3$: C, 68.30; H, 5.95; N, 13.85. Found: C, 67.95; H, 5.94; N, 13.94.

Example 69

Preparation of (E)-N-(7-hydroxy-1-methyl-1H-indol-3-ylmethyl)-N-methyl-3-(7-oxo-5,6,7,8-tetrahydro-1,8-naphthyridin-3-yl)acrylamide According to the procedure of Example 42, except substituting 7-hydroxy-1-methyl-3-(methylaminomethyl)-1H-indole for the 7-chloro-1-methyl-3-(methylaminomethyl)-1H-indole, the title compound (200 mg, 51%) was obtained as a tan solid: MS (ES) m/e 391.2 (M+H)$^+$. Anal. Calcd for C$_{22}$H$_{22}$N$_4$O$_3$.0.75H$_2$O: C, 65.41; H, 5.85; N, 13.86. Found: C, 65.25; H, 5.95; N, 13.79.

Example 70

Preparation of (E)-N-(4-chloro-1-methyl-1H-indol-3-ylmethyl)-N-methyl-3-(7-oxo-5,6,7,8-tetrahydro-1,8-naphthyridin-3-yl)acrylamide According to the procedure of Example 42, except substituting 4-chloro-1-methyl-3-(methylaminomethyl for the 7-chloro-1-methyl-3-(methylaminomethyl)-1H-indole, the title compound (100 mg, 49%) was obtained as a white solid: MS (ES) m/e 409.0 (M+H)$^+$. Anal. Calcd for C$_{22}$H$_{21}$ClN$_4$O$_2$: 0.75H$_2$O: C, 62.55; H, 5.36; N, 13.26. Found: C, 62.71; H, 5.24; N, 13.15.

Example 71

Preparation of (E)-N-(4-methoxy-1-methyl-1H-indol-3-ylmethyl)-N-methyl-3-(7-oxo-5,6,7,8-tetrahydro-1,8-naphthyridin-3-yl)acrylamide According to the procedure of Example 42, except substituting 4-methoxy-1-methyl-3-(methylaminomethyl)-1H-indole for the 7-chloro-1-methyl-3-(methylaminomethyl)-1H-indole, the title compound (65 mg, 32%) was obtained as an off-white solid: MS (ES) m/e 405.2 (M+H)$^+$. Anal. Calcd for C$_{23}$H$_{24}$N$_4$O$_3$.1.25H$_2$O: C, 64.69; H, 6.19; N, 13.33. Found: C, 64.49; H, 5.94; N, 13.76

Example 72

Preparation of (E)-N-(5-methoxy-1-methyl-1H-indol-3-ylmethyl)-N-methyl-3-(7-oxo-5,6,7,8-tetrahydro-1,8-naphthyridin-3-yl)acrylamide According to the procedure of Example 402, except substituting 5-methoxy-1-methyl-3-(methylaminomethyl)-1H-indole for the 7-chloro-1-methyl-3-(methylaminomethyl)-1H-indole, the title compound (90 mg, 44%) was obtained as an off-white solid: MS (ES) m/e 405.2 (M+H)$^+$. Anal. Calcd for C$_{23}$H$_{24}$N$_4$O$_3$.0.5H$_2$O: C, 66.81; H, 6.09; N, 13.55. Found: C, 66.67; H, 5.96; N, 13.87.

Example 73

Preparation of (E) 3-(6-aminopyridin-3-yl)-N-(7-carboxy-1-methyl-1H-indol-3-ylmethyl)-N-methylacrylamide A solution of (E)-3-(6-aminopyridin-3-yl)-N-(7-methoxycarbonyl-1-methyl-1H-indol-3-ylmethyl)-N-methylacrylamide (76 mg, 0.2 mmole) in methanol (4 mL), water (2 mL), and tetrahydrofuran (2 mL) was treated with LiOH (39 mg, 1.6 mmole), and the reaction was stirred at ambient temperature for 48 h. The mixture was filtered, and the filtrate was acidified to pH 4.0-4.5 with 1.0 N HCl. The precipitate was collected, washed with water and dried giving the title compound (25 mg, 35%) as a white solid: MS (ES) m/e 365.2 (M+H)$^+$. Anal. Calcd for C$_{20}$H$_{20}$N$_4$O$_3$.0.25H$_2$O: C, 65.11: H, 5.60; N, 15.18. Found: C, 64.83; H, 5.52; N, 15.07.

Example 74

Preparation of (E)-N-(6-methoxy-1-methyl-1H-indol-3-ylmethyl)-N-methyl-3-(7-oxo-5,6,7,8-tetrahydro-1,8-naphthyridin-3-yl)acrylamide According to the procedure of Example 42, except substituting 6-methoxy-1-methyl-3-(methylaminomethyl)-1H-indole for the 7-chloro-1-methyl-3-(methylaminomethyl)-1H-indole, the title compound (65 mg, 32%) was obtained as a yellow solid: MS (ES) m/e 405.2 (M+H)$^+$. Anal. Calcd for C$_{23}$H$_{24}$N$_4$O$_3$.H$_2$O: C, 65.38; H, 6.20; N, 13.26. Found: C, 65.36; H, 5.98; N, 13.16.

Example 75

Preparation of (E)-3-(6-aminopyridin-3-yl)-N-(6-methoxycarbonyl-1-methyl-1H-indol-3-ylmethyl)-N-methylacrylamide According to the procedure of Example 31, except substituting methyl 1-methyl-3-(methylaminomethyl)-1H-indole-6-carboxylate for the 1,4-dimethyl-3-(methylaminomethyl)-1H-indole, the title compound (168 mg, 39%) was obtained, after silica gel chromatography, as a white solid: MS (ES) m/e 379.2 (M+H)$^+$. Anal. Calcd for C$_{21}$H$_{22}$N$_4$O$_3$.0.125H$_2$O: C, 66.25; H, 5.93; N, 14.71. Found: C, 66.60; H, 6.13; N, 14.18.

Example 76

Preparation of (E)-N-(3,3-dimethyl-3H-indene-1-ylmethyl)-N-methyl-3-(7-oxo-5,6,7,8-tetrahydro-1,8-naphthyridin-3-yl)acrylamide According to the procedure of Example 42, except substituting 3,3-dimethyl-1-(methylaminomethyl)-3H-indene for the 7-chloro-1-methyl-3-(methylaminomethyl)-1H-indole, the title compound (48 mg, 12%) was obtained, after silica gel chromatography, as a tan solid: MS (ES) m/e 388.2 (M+H)$^+$. Anal. Calcd for C$_{23}$H$_{24}$N$_4$O$_3$.0.375H$_2$O: C, 73.31; H, 6.51; N, 10.66. Found: C, 72.91; H, 6.37; N, 11.16.

Example 77

Preparation of (E)-3-(6-aminopyridin-3-yl)-N-(4-fluoro-1-methyl-1H-indol-3-ylmethyl)-N-methylacrylamide According to the procedure of Example 24, except substituting 4-fluoro-1-methyl-3-(methylaminomethyl)-1H-indole (0.2 g, 1.04 mmole) for the 2,3-dihydro-8-(methylaminomethyl)-1H-3a-azacyclopenta[α]indene, and substituting (E)-3-(6-amino-pyridin-3-yl)acrylic acid (0.17 g, 1.04 mmole) for the (E)-3-(7-oxo-5,6,7,8-tetrahydro-1,8-naphthyridin-3-yl)acrylic acid hydrochloride salt, the title compound (0.11 g, 37%) was prepared as an off-white powder: MS (ES) m/e 339 (M+H)$^+$.

Example 78

Preparation of (E)-3-(6-aminopyridin-3-yl)-N-(5-fluoro-1-methyl-1H-indol-3-ylmethyl)-N-methylacrylamide According to the procedure of Example 24, except substituting 5-fluoro-1-methyl-3-(methylaminomethyl)-1H-indole (0.2 g, 1.04 mmole) for the 2,3-dihydro-8-(methylaminomethyl)-1H-3a-azacyclopenta[α]indene, and substituting (E)-3-(6-amino-pyridin-3-yl)acrylic acid (0.17 g, 1.04 mmole) for the (E)-3-(7-oxo-5,6,7,8-tetrahydro-1,8-naphthyridin-3-yl)acrylic acid hydrochloride salt, the title compound (0.14 g, 41%) was prepared as an off-white powder: MS (ES) m/e 339 (M+H)$^+$.

Example 79

Preparation of (E)-3-(6-aminopyridin-3-yl)-N-(7-fluoro-1-methyl-1H-indol-3-ylmethyl)-N-methylacrylamide According to the procedure of Example 24, except substituting 7-fluoro-1-methyl-3-(methylaminomethyl)-1H-indole (0.2 g, 1.04 mmole) for the 2,3-dihydro-8-(methylaminomethyl)-1H-3a-azacyclopenta[α]indene, and substituting (E)-3-(6-amino-pyridin-3-yl)acrylic acid (0.17 g, 1.04 mmole) for the (E)-3-(7-oxo-5,6,7,8-tetrahydro-1,8-naphthyridin-3-yl)acrylic acid hydrochloride salt, the title compound (0.1 g, 27%) was prepared as an off-white powder: MS (ES) m/e 339 (M+H)$^+$.

Example 80

Preparation of (E)-3-(6-aminopyridin-3-yl)-N-(4-fluoro-1H-indol-3-ylmethyl)-N-methylacrylamide According to the procedure of Example 24, except substituting 4-fluoro-3-(methylaminomethyl)-1H-indole (0.31 g, 1.74 mmole) for the 2,3-dihydro-8-(methylaminomethyl)-1H-3a-azacyclopenta[α]indene, and substituting (E)-3-(6-amino-pyridin-3-yl)acrylic acid (0.285 g, 1.74 mmole) for the (E)-3-(7-oxo-5,6,7,8-tetrahydro-1,8-naphthyridin-3-yl)acrylic acid hydrochloride salt, the title compound (0.2 g, 36%) was prepared as a white powder: MS (ES) m/e 325 (M+H)$^+$.

Example 81

Preparation of (E)-3-(6-aminopyridin-3-yl)-N-(7-fluoro-1H-indol-3-ylmethyl)-N-methylacrylamide According to the procedure of Example 24, except substituting 7-fluoro-3-(methylaminomethyl)-1H-indole (0.31 g, 1.74 mmole) for the 2,3-dihydro-8-(methylaminomethyl)-1H-3a-azacyclopenta[α]indene, and substituting (E)-3-(6-amino-pyridin-3-yl)acrylic acid (0.285 g, 1.74 mmole) for the (E)-3-(7-oxo-5,6,7,8-tetrahydro-1,8-naphthyridin-3-yl)acrylic acid hydrochloride salt, the title compound (0.1 g, 18%) was prepared as a white powder: MS (ES) m/e 325 (M+H)$^+$.

Example 82

Preparation of (E)-N-(4-fluoro-1-methyl-1H-indol-3-ylmethyl)-N-methyl-3-(7-oxo-5,6,7,8-tetrahydro-1,8-naphthyridin-3-yl)acrylamide According to the procedure of Example 24, except substituting 4-fluoro-1-methyl-3-(methylaminomethyl)-1H-indole (0.13 g, 0.68 mmole) for the 2,3-dihydro-8-(methylaminom-ethyl)-1H-3a-azacyclopenta[α]indene), the title compound (0.15 g, 56%) was prepared as an off-white powder: MS (ES) m/e 393 (M+H)$^+$.

Example 83

Preparation of (E)-N-(quinolin-3-ylmethyl)-N-methyl-3-(7-oxo-5,67,8-tetrahydro-1,8-naphthyridin-3-yl)acrylamide According to the procedure of Example 24, except substituting 3-(methylaminomethyl)quinoline (0.12 g, 0.67 mmole) for the 2,3-dihydro-8-(methylaminomethyl)-1H-3a-azacyclopenta[α]indene), the title compound (0.1 g, 40%) was prepared as an off-white powder: MS (ES) m/e 373 (M+H)$^+$.

Example 84

Preparation of (E)-N-(naphthalen-1-ylmethyl)-N-methyl-3-(7-oxo-56,7,8-tetrahydro-1,8-naphthyridin-3-yl)acrylamide According to the procedure of Example 24, except substituting N-methyl-1-naphthalenemethylamine hydrochloride (0.162 g, 0.95 mmole) for the 2,3-dihydro-8-(methylaminomethyl)-1H-3a-azacyclopenta[α]indene), the title compound (0.15 g, 43%) was prepared as a white powder: MS (ES) m/e 372 (M+H)$^+$.

Example 85

Preparation of (E)-N-methyl-N-(2-methyl-1H-indol-3-ylmethyl)-3-[3-(2-methoxyethyl)-2-oxo-1,2,3,4-tetrahydropyrido[2,3-d]pyrimidin-6-yl]acrylamide A solution of 6-bromo-3-(2-methoxyethyl)-3,4-dihydro-1H-pyrido[2,3-d]pyrimidin-2-one (0.86 g, 3.00 mmole), N-(2-methyl-1H-indol-3-ylmethyl)-N-methylacrylamide (see Example 1 (a), 0.68 g, 3.00 mmole), Pd(OAc)$_2$ (0.07 g, 0.30 mmole), tri-ortho-tolylphosphine (0.18 g, 0.60 mmole) and diisopropylethylamine (1.31 mL, 7.50 mmole) in propionitrile (50 mL) was deoxygenated, then was heated at reflux under N$_2$ overnight. The dark mixture was filtered through a pad of Celite®, and the filter pad was rinsed with acetonitrile (250 mL). The filtrate was concentrated in vacuo, and the residue was purified by flash chromatography on silica gel (10% EtOAc/EtOH). The title compound (0.46 g, 36%) was obtained as a light yellow solid after drying in vacuo: MS (ES) m/e 434 (M+H)$^+$.

Example 86

Preparation of (E)-N-(1-methyl-1H-indol-3-ylmethyl)-N-methyl-3-(6-methoxycarbonyl-7-oxo-5,6,7,8-tetrahydro-1,8-naphthyridin-3-yl)acrylamide According to the procedure of Example 15 (b), except substituting methyl (±)-6-bromo-2-oxo-1,2,3,4-tetrahydro-1H-1,8-naphthyridine-3-carboxylate (2.5 g, 8.8 mmole), from Preparation 4 (d), for the 5-bromo-2,2'-dipyridylamine, the title compound (1.82 g, 48%) was prepared as an off-white solid: MS (ES) m/e 433.4 (M+H)$^+$.

Example 87

Preparation of (E)-3-(6-aminopyridin-3-yl)-N-(1,3-dimethyl-1H-pyrrolo[2,3-b]pyridin-3-ylmethyl)-N-methylacrylamide The title compound is prepared following methods analogous to those described in the previous preparations and examples.

Example 88

Preparation of (E)-N-(1,3-dimethyl-1H-pyrrolo[2,3-b]pyridin-3-ylmethyl)-N-methyl-3-(7-oxo-5,6,7,8-tetrahydro-1,8-naphthyridin-3-yl)acrylamide The title compound is prepared following methods analogous to those described in the previous preparations and examples.

Example 89

Preparation of (E)-3-(6-aminopyridin-3-yl)-N-methyl-N-(1-methyl-1H-pyrrolo[2,3-c]pyridin-3-ylmethyl)acrylamide The title compound is prepared following methods analogous to those described in the previous preparations and examples.

Example 90

Preparation of (E)-3-(6-aminopyridin-3-yl)-N-methyl-N-(1-methyl-1H-pyrrolo[3,2-c]pyridin-3-ylmethyl)acrylamide The title compound is prepared following methods analogous to those described in the previous preparations and examples.

Example 91

Preparation of (E)-3-(6-aminopyridin-3-yl)-N-methyl-N-(1-methyl-1H-pyrrolo[3,2-b]pyridin-3-ylmethyl)acrylamide The title compound is prepared following methods analogous to those described in the previous preparations and examples.

Example 92

Preparation of (E)-N-methyl-N-(1-methyl-1H-pyrrolo[2,3-c]pyridin-3-ylmethyl)-3-(7-oxo-5,6,7,8-tetrahydro-1,8-naphthyridin-3-yl)acrylamide The title compound is prepared following methods analogous to those described in the previous preparations and examples.

Example 93

Preparation of (E)-N-methyl-N-(1-methyl-1H-pyrrolo[3,2-c]pyridin-3-ylmethyl)-3-(7-oxo-5,6,7,8-tetrahydro-1,8-naphthyridin-3-yl)acrylamide The title compound is prepared following methods analogous to those described in the previous preparations and examples.

Example 94

Preparation of (E)-N-methyl-N-(1-methyl-1H-pyrrolo[3,2-b]pyridin-3-ylmethyl)-3-(7-oxo-5,6,7,8-tetrahydro-1,8-naphthyridin-3-yl)acrylamide The title compound is prepared following methods analogous to those described in the previous preparations and examples.

Example 95

Preparation of (E)-3-(6-aminopyridin-3-yl)-N-(benzofuran-3-ylmethyl)-N-methylacrylamide The title compound is prepared following methods analogous to those described in the previous preparations and examples.

Example 96

Preparation of (E)-3-(6-aminopyridin-3-yl)-N-methyl-N-(3-methylbenzofuran-2-ylmethyl)acrylamide The title compound is prepared following methods analogous to those described in the previous preparations and examples.

Example 97

Preparation of (E)-3-(6-aminopyridin-3-yl)-N-methyl-N-(2-methylbenzofuran-3-ylmethyl)acrylamide The title compound is prepared following methods analogous to those described in the previous preparations and examples.

Example 98

Preparation of (E)-N-(benzofuran-3-ylmethyl)-N-methyl-3-(7-oxo-5,6,7,8-tetrahydro-1,8-naphthyridin-3-yl)acrylamide The title compound is prepared following methods analogous to those described in the previous preparations and examples.

Example 99

Preparation of (E)-N-methyl-N-(3-methylbenzofuran-2-ylmethyl)-3-(7-oxo-5,6,7,8-tetrahydro-1,8-naphthyridin-3-yl)acrylamide The title compound, compound G, is prepared following methods analogous to those described in the previous preparations and examples.

Example 100

Preparation of (E)-N-methyl-N-(2-methylbenzofuran-3-ylmethyl)-3-(7-oxo-5,6,7,8-tetrahydro-1,8-naphthyridin-3-yl)acrylamide The title compound is prepared following methods analogous to those described in the previous preparations and examples.

Example 101

Preparation of (E)-(6-aminopyridin-3-yl)-N-methyl-N-[1-(1-methyl-1H-indol-2-yl)ethyl]acrylamide The title compound is prepared following methods analogous to those described in the previous preparations and examples.

Example 102

Preparation of (E)-(6-aminopyridin-3-yl)-N-methyl-N-[1-(1-methyl-1H-indol-3-yl)ethyl]acrylamide The title compound is prepared following methods analogous to those described in the previous preparations and examples.

Example 103

Preparation of (E)-N-methyl-N-[1-(1-methyl-1H-indol-2-yl)ethyl]-3-(7-oxo-5,6,7,8-tetrahydro-1,8-naphthyridin-3-yl)acrylamide The title compound is prepared following methods analogous to those described in the previous preparations and examples.

Example 104

Preparation of (E)-N-methyl-N-[1-(1-methyl-1H-indol-3-yl)ethyl]-3-(7-oxo-5,6,7,8-tetrahydro-1,8-naphthyridin-3-yl)acrylamide The title compound is prepared following methods analogous to those described in the previous preparations and examples.

Example 105

Preparation of (E)-N-Methyl-3-(4-methyl-2-oxo-2,3,4,5-tetrahydro-1H-pyrido[2,3-e][1,4]diazepin-7-yl)-N-(1-propyl-naphthalen-2-ylmethyl)acrylamide hydrochloride a) (E)-N-Methyl-3-(4-methyl-2-oxo-2,3,4,5-tetrahydro-1H-pyrido[2,3-e][1,4]diazepin-7-yl)-N-(1-propyl-naphthalen-2-ylmethyl)acrylamide (E)-3-(4-Methyl-2-oxo-2,3,4,5-tetrahydro-1H-pyrido[2,3-e][1,4]diazepin-7-yl)acrylic acid hydrochloride (1.40 g, 1.25 mmol) was added to a solution of methyl-(1-propyl-naphthalen-2-ylmethyl)amine (0.292 g, 1.37 mmol) and diisopropylethylamine (0.65 mL, 3.75 mmol) in DMF (25 mL) followed by the addition of 1-hydroxybenzotriazole hydrate (0.185 g, 1.37 mmol) and 1-(3-dimethylaminopropyl)-3-ethylcarbodiimide hydrochloride (0.263 g, 1.37 mmol). The reaction was allowed to stir at room temperature for 18 h. The reaction was quenched with $H_2O$ (70 mL) then concentrated to a yellow oil. Purification by column chromatography (silica gel, $CH_2Cl_2$/MeOH, 99:1 to 95:5) gave the title compound (0.229 g, 41%) as a glassy orange solid and as a mixture of amide rotamers: $^1$H NMR (500 MHz, DMSO-$d_6$) δ 10.35 (s, 1H), 8.55-8.54 (m, 1H), 8.24-8.14 (m, 1H), 7.98-7.86 (m, 5H), 7.72-7.24 (m, 3H), 3.75 (s, 2H), 3.42 (s, 2H), 3.86 (s, 2H), 2.54-2.36 (m, 6H), 2.11-2.02 (m, 2H), 1.40-1.34 (m, 2H), 1.01-0.98 (m, 3H).

b) (E)-N-Methyl-3-(4-methyl-2-oxo-2,3,4,5-tetrahydro-1H-pyrido[2,3-e][1,4]diazepin-7-yl)-N-(1-propyl-naphthalen-2-ylmethyl)acrylamide hydrochloride A 2 M solution of hydrogen chloride in $Et_2O$ (0.25 ml, 0.518 mmol) was added to (E)-N-methyl-3-(4-methyl-2-oxo-2,3,4,5-tetrahydro-1H-pyrido[2,3-e][1,4]diazepin-7-yl)-N-(1-propyl-naphthalen-2-ylmethyl)acrylamide (0.229 g, 0.518 mmol) in $CH_2Cl_2$ (5 mL) via syringe. The solution was allowed to stir for 18 h during time which a precipitate fell out of the solution. The product was collected by filtration and was washed with $Et_2O$ (100 mL). The product was dried to give the title compound (0.182 g, 73%) as an orange solid and as a mixture of amide rotamers: $^1$H NMR (300 MHz, DMSO-$d_6$) δ 12.00 (br s, 1H), 11.22 (s, 1H), 8.86-8.82 (m, 1H), 8.38-8.32 (m, 1H), 7.94-7.87 (m, 4H), 7.74-7.29 (m, 5H), 6.06-5.64 (m, 1H), 4.40-4.30 (m, 2H), 3.94-3.91 (br s, 2H), 2.93-2.57 (m, 6H), 2.10-2.05 (m, 2H), 1.37-1.32 (m, 2H), 1.02-0.97 (m, 3H); MS (ESI) m/e 443 (M+H)$^+$.

Example 106

Preparation of (E)-3-(3,3-Dimethyl-2-oxo-2,3,4,5-tetrahydro-1H-pyrido[2,3-e][1,4]diazepin-7-yl)-N-methyl-N-(3-methyl-benzo[b]thiophen-2-ylmethyl)acrylamide hydrochloride a) (E)-3-(3,3-Dimethyl-2-oxo-2,3,4,5-tetrahydro-1H-pyrido[2,3-e][1,4]diazepin-7-yl)-N-methyl-N-(3-methyl-benzo[b]thiophen-2-ylmethyl)acrylamide A suspension of 7-bromo-3,3-dimethyl-1,3,4,5-tetrahydro-pyrido[2,3-e][1,4]diazepin-2-one (0.17 g, 0.63 mmol) in propionitrile (4 mL) and DMF (1 mL) was de-oxygenated with Ar for 10 min. The mixture was treated with N-methyl-N-(3-methyl-benzo[b]thiophen-2-ylmethyl)acrylamide (0.20 g, 0.81 mmol) and (i-Pr)$_2$EtN (0.24 mL, 1.3 mmol) and was de-oxygenated with Ar for 5 min. Pd(OAc)$_2$ (14 mg, 0.062 mmol) and P(o-tol)$_3$ (38 mg, 0.12 mmol) were added simultaneously, and the mixture was de-oxygenated a third time for 5 min. The mixture was heated to reflux for 4 h, then allowed to cool. The resulting precipitate was isolated by filtration, washed with EtOAc, dissolved in $CH_2Cl_2$, and the solvent was removed in vacuo. Purification by flash column chromatography (silica gel, $CH_2Cl_2$/MeOH, 98:2) gave the title compound (0.15 g, 56%) as a white solid: $^1$H NMR (300 MHz, CDCl$_3$) δ 8.97 (s, 1H), 8.45 (s, 1H), 7.77-7.65 (m, 3H), 7.53 (s, 1H), 7.40-7.29 (m, 2H), 6.98-6.84 (m, 1H), 4.94-4.89 (m, 2H), 4.02 (s, 2H), 3.15-3.10 (m, 3H), 2.43 (s, 3H), 1.70 (s, 1H), 1.49 (s, 6H); MS (ESI) m/e 435 (M+H)$^+$.

b) (E)-3-(3,3-Dimethyl-2-oxo-2,3,4,5-tetrahydro-1H-pyrido[2,3-e][1,4]diazepin-7-yl)-N-methyl-N-(3-methyl-benzo[b]thiophen-2-ylmethyl)acrylamide hydrochloride A suspension of (E)-3-(3,3-dimethyl-2-oxo-2,3,4,5-tetrahydro-1H-pyrido[2,3-e][1,4]diazepin-7-yl)-N-methyl-N-(3-methyl-benzo[b]thiophen-2-ylmethyl)acrylamide (0.15 g, 0.35 mmol) in $CH_2Cl_2$ (10 mL) was treated with anhydrous HCl in $Et_2O$ (0.35 mL, 1.0 M). After stirring for 5 min, the mixture was diluted with $Et_2O$ (50 mL) and allowed to stir for 1 h. The solid was isolated by filtration, washed with $Et_2O$, and dried under vacuum at 60° C. for 4 d to give the title compound (0.16 g, 96%) as a light yellow powder and as a mixture of amide rotamers: $^1$H NMR (300 MHz, DMSO-$d_6$) δ 10.92 (s, 1H), 10.56 (br s, 2H), 8.66-8.67 (m, 1H), 8.40 (s, 1H), 7.86-7.89 (m, 1H), 7.73-7.75 (m, 1H), 7.58-7.63 (m, 1H), 7.30-7.40 (m, 3H), 4.90-5.13 (m, 2H), 4.39-4.41 (m, 2H), 2.94-3.17 (m, 3H), 2.43 (s, 3H), 1.63 (s, 6H); MS (ESI) m/e 435 (M+H)$^+$.

Example 107

Preparation of (E)-N-Methyl-3-(4-methyl-2-oxo-2,3, 4,5-tetrahydro-1H-pyrido[2,3-e][1,4]diazepin-7-yl)- N-naphthalen-2-ylmethyl-acrylamide hydrochloride According to the procedure of Example 1, except substituting methyl-naphthalen-2-ylmethyl-amine for the methyl-(1-propyl-naphthalen-2-ylmethyl)amine, the title compound (0.397 g, quantitative) was prepared as an off-white solid and as a mixture of amide rotamers: $^1$H NMR (300 MHz, DMSO-d$_6$) δ 11.00-10.86 (br s, 1H), 11.28-11.24 (m, 1H), 8.85-8.81 (m, 1H), 8.35-8.29 (m, 1H), 7.95-7.75 (m, 4H), 7.67-7.62 (m, 1H), 7.54-7.38 (m, 4H), 5.01-4.81 (m, 2H), 4.31 (br s, 2H), 3.73 (br s, 2H), 3.17-2.97 (m, 3H), 2.91-2.87 (m, 3H); MS (ESI) m/e 401 (M+H)$^+$.

Example 108

Preparation of (E)-N-Methyl-3-(4-methyl-2-oxo-2,3, 4,5-tetrahydro-1H-pyrido[2,3-e][1,4]diazepin-7-yl)- N-naphthalen-1-ylmethyl-acrylamide hydrochloride According to the procedure of Example 1, except substituting methyl-naphthalen-1-ylmethyl-amine for the methyl-(1-propyl-naphthalen-2-ylmethyl)amine, the title compound (0.382 g, quantitative) was prepared as an off white solid and as a mixture of amide rotamers: $^1$H NMR (300 MHz, DMSO-d$_6$) δ 12.24-12.15 (br s, 1H), 11.27-11.21 (m, 1H), 8.85-8.76 (m, 1H), 8.36-8.30 (m, 1H), 8.20-7.02 (m, 9H), 5.36-5.12 (m 2H), 4.29 (br s, 2H), 3.86-3.77 (br s, 2H), 3.17-3.10 (m, 3H), 2.90-2.84 (m, 3H); MS (ESI) n/e 401 (M+H)$^+$.

Example 109

Preparation of (E)-N-(4-Acetylamino-benzyl)-N- methyl-3-(7-oxo-5,6,7,8-tetrahydro-[1,8]naphthyridin-3-yl)acrylamide According to the procedure of Example 1 (a), except substituting 4-acetamidobenzyl methyl amine for the methyl-(1-propyl-naphthalen-2-ylmethyl)amine, and substituting (E)-3-(7-oxo-5,6,7,8-tetrahydro-[1,8]naphthyridin-3yl)acrylic acid hydrochloride for (E)-3-(4-methyl-2-oxo-2,3,4,5-tetrahydro-1H-pyrido[2,3-e][1,4]diazepin-7-yl)acrylic acid hydrochloride, the title compound (0.283 g, 53%) was prepared as an off-white solid and as a mixture of amide rotamers: $^1$H NMR (300 MHz, DMSO-d$_6$) δ 10.66-10.64 (m, 1H), 9.94-9.92 (m, 1H), 8.36-8.33 (m, 1H), 8.07-8.06 (m, 1H), 7.56-7.48 (m, 3H), 7.33-7.13 (m, 3H), 4.74-4.54 (m, 2H), 3.07-2.86 (m, 5H), 2.53-2.49 (m 2H), 2.01 (s, 3H); MS (ESI) m/e 379 (M+H)$^+$.

Example 110

Preparation of (E)-N-(4-Methanesulfonyl-benzyl)-N- methyl-3-(7-oxo-5,6,7,8-tetrahydro-[1,8]naphthyridin-3-yl)acrylamide According to the procedure of Example 1 (a), except substituting (4-methanesulfonyl-benzyl)methylamine for the methyl-(1-propyl-naphthalen-2-ylmethyl)amine, and substituting (E)-3-(7-oxo-5,6,7,8-tetrahydro-[1,8]naphthyridin-3yl)acrylic acid hydrochloride for the (E)-3-(4-methyl-2-oxo-2,3,4,5-tetrahydro-1H-pyrido[2,3-e][1,4]diazepin-7-yl) acrylic acid hydrochloride, the title compound (0.400 g, 71%) was prepared as an off-white solid and as a mixture of amide rotamers: $^1$H NMR (300 MHz, DMSO-d$_6$) δ 10.6-10.65 (m, 1H), 8.38-8.34 (m, 1H), 8.10-8.04 (m, 1H), 7.95-7.89 (m, 2H), 7.57-7.46 (m, 3H), 7.28-7.23 (m, 1H), 4.96-4.72 (m, 2H), 3.20-3.16 (m, 5H), 2.94-2.84 (m, 3H) 2.56-2.49 (m, 2H); MS (APCI) m/e 400 (M+H)$^+$.

Example 111

Preparation of (E)-N-(2-Methoxy-naphthalen-1-ylmethyl)-N-methyl-3-(7-oxo-5,6,7,8-tetrahydro-[1,8] naphthyridin-3-yl)acrylamide According to the procedure of Example 1 (a), except substituting (2-methoxy-naphthalen-1-ylmethyl)methylamine for the methyl-(1-propyl-naphthalen-2-ylmethyl)amine, and substituting (E)-3-(7-oxo-5,6,7,8-tetrahydro-[1,8]naphthyridin-3yl)acrylic acid hydrochloride for the (E)-3-(4-methyl-2-oxo-2,3,4,5-tetrahydro-1H-pyrido[2,3-e][1,4]diazepin-7-yl) acrylic acid hydrochloride, the title compound (0.403 g, 71%) was prepared as an orange-brown solid and as a mixture of amide rotamers: $^1$H NMR (300 MHz, DMSO-d$_6$) δ 10.66 (s, 1H), 8.37 (s, 1H), 8.08-7.81 (m, 4H), 7.70-7.11 (m, 5H), 5.22-5.09 (m, 2H), 3.98-3.90 (m, 3H), 2.91-2.87 (m, 5H), 2.63-2.49 (m, 2H); MS (ESI) m/e 402 (M+H)$^+$.

Example 112

Preparation of (E)-N-Methyl-N-(4-methyl-naphthalen-1-ylmethyl)-3-(7-oxo-5,6,7,8-tetrahydro-[1,8] naphthyridin-3-yl)acrylamide According to the procedure of Example 1 (a), except substituting methyl-(4-methyl-naphthalen-1ylmethyl)amine for the methyl-(1-propyl-naphthalen-2-ylmethyl)amine, and substituting (E)-3-(7-oxo-5,6,7,8-tetrahydro-[1,8]naphthyridin-3yl)acrylic acid hydrochloride for the (E)-3-(4-methyl-2-oxo-2,3,4,5-tetrahydro-1H-pyrido[2,3-e][1,4]diazepin-7-yl) acrylic acid hydrochloride, the title compound (0.410 g, 76%) was prepared as an off-white solid and as a mixture of amide rotamers: $^1$H NMR (300 MHz, DMSO-d$_6$) δ 10.67-10.62 (m, 1H), 8.38-8.29 (m, 1H), 8.15-7.94 (m, 3H), 7.60-7.55 (m, 3H), 7.36-7.02 (m, 3H), 5.30-5.06 (m, 2H), 3.04-2.73 (m, 5H), 2.65-2.45 (m, 5H); MS (ESI) m/e 386 (M+H)$^+$.

Example 113

Preparation of (E)-N-(2,3-Dimethyl-benzyl)-N-methyl-3-(7-oxo-5,6,7,8-tetrahydro-[1,8]naphthyridin-3-yl)acrylamide According to the procedure of Example 1 (a), except substituting 2,3-dimethylbenzylmethyl amine for the methyl-(1-propyl-naphthalen-2-ylmethyl)amine, and substituting (E)-3-(7-oxo-5,6,7,8-tetrahydro-[1,8]naphthyridin-3yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.368 g, 75%) was prepared as an off-white solid and as a mixture of amide rotamers: $^1$H NMR (300 MHz, DMSO-d$_6$) δ 10.68-10.64 (m, 1H), 8.38-8.32 (m, 1H), 8.10-7.99 (m, 1H), 7.57-7.50 (m, 1H), 7.29-7.04 (m, 3H), 6.94-6.77 (m, 1H), 4.82-4.65 (m, 2H), 3.06-2.85 (m, 5H), 2.57-2.48 (m 2H), 2.28-2.14 (m, 6H); MS (APCI) m/e 350 (M+H)$^+$.

Example 114

Preparation of (E)-N-(4-Isopropyl-benzyl)-N-methyl-3-(7-oxo-5,6,7,8-tetrahydro-[1,8]naphthyridin-3-yl)acrylamide According to the procedure of Example 1 (a), except substituting (4-isopropyl-benzyl)methylamine for the methyl-(1-propyl-naphthalen-2-ylmethyl)amine, and substituting (E)-3-(7-oxo-5,6,7,8-tetrahydro-[1,8]naphthyridin-3yl) acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.223 g, 61%) was prepared as a light orange solid and as a mixture of amide rotamers: $^1$H NMR (300 MHz, DMSO-$d_6$) δ 10.66-10.64 (m, 1H), 8.36-8.33 (m, 1H), 8.07 (s, 1H), 7.55-7.48 (m, 1H), 7.33-7.11 (m, 5H), 4.77-4.56 (m, 2H), 3.09-2.81 (m, 6H), 2.56-2.49 (m 2H), 1.19-1.16 (m, 6H); MS (APCI) m/e 364 (M+H)$^+$.

Example 115

Preparation of (E)-N-Indan-5ylmethyl-N-methyl-3-(7-oxo-5,6,7,8-tetrahydro-[1,8]naphthyridin-3-yl) acrylamide According to the procedure of Example 1 (a), except substituting indan-5-ylmethyl-methylamine for the methyl-(1-propyl-naphthalen-2-ylmethyl)amine, and substituting (E)-3-(7-oxo-5,6,7,8-tetrahydro-[1,8]naphthyridin-3yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.232 g, 45%) was prepared as an off-white solid and as a mixture of amide rotamers: $^1$H NMR (300 MHz, DMSO-$d_6$) δ 10.66-10.64 (m, 1H), 8.36-8.33 (m, 1H), 8.07-8.06 (m, 1H), 7.54-7.49 (m, 1H), 7.33-6.89 (m, 4H), 4.75-4.56 (m, 2H), 3.07-2.72 (m, 9H), 2.53-2.49 (m, 2H), 2.04-1.94 (m 2H); MS (APCI) m/e 362 (M+H)$^+$.

Example 116

Preparation of (E)-N-Indan-5ylmethyl-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting indan-5-ylmethyl-methylamine for the methyl-(1-propyl-naphthalen-2-ylmethyl)amine, the title compound (0.060 g, 88%) was prepared as a white solid and as a mixture of amide rotamers: $^1$H NMR (300 MHz, DMSO-$d_6$) δ 12.02 (br s, 1H), 11.20 (s, 1H), 8.82-8.79 (m, 1H), 8.32-8.29 (m, 1H), 7.64-7.57 (m, 1H), 7.45-7.32 (m, 1H), 7.22-6.85 (m, 3H), 4.77-4.58 (m, 2H), 4.42 (br s, 2H), 3.80 (br s, 2H), 3.09-2.73 (m, 10H), 2.04-1.94 (m, 2H); MS (ESI) m/e 391 (M+H)$^+$.

Example 117

Preparation of (E)-N-Methyl-N-(3-methyl-benzo[b]thiophen-2-ylmethyl)-3-(4-methyl-2-oxo-2,3,4,5-tetrahydro-1H-pyrido[2,3-e][1,4]diazepin-7-yl)acrylamide hydrochloride According to the procedure of Example 1, except substituting methyl-(3-methyl-benzo[b]thiophen-2-ylmethyl) amine for the methyl-(1-propyl-naphthalen-2-ylmethyl) amine, the title compound (0.295 g, 98%) was prepared as a white solid and as a mixture of amide rotamers: $^1$H NMR (300 MHz, DMSO-$d_6$) δ 12.20 (br s, 1H), 11.22 (s, 1H), 8.83 (s, 1H), 8.34-8.31 (m, 1H), 7.89-7.86 (m, 1H), 7.75-7.72 (m, 1H), 7.65-7.31 (m, 4H), 5.13-4.90 (m, 2H), 4.29 (br s, 2H), 3.80 (br s, 2H), 3.17-2.95 (m, 3H), 2.87 (s, 3H), 2.42 (s, 3H); MS (APCI) m/e 421 (M+H)$^+$.

Example 118

Preparation of (E)-N-(3,5-Dimethoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3,5-dimethoxy-benzyl)methylamine for the methyl-(1-propyl-naphthalen-2-ylmethyl)amine, the title compound (0.307 g, quantitative) was prepared as an off-white solid and as a mixture of amide rotamers: $^1$H NMR (300 MHz, DMSO-$d_6$) δ 11.7 (br s, 1H), 10.88 (s, 1H), 8.71-8.68 (m, 1H), 8.25-8.22 (m, 1H), 7.61-7.56 (m, 1H), 7.39-7.31 (m, 1H), 6.42-6.35 (m, 3H), 4.75-4.55 (m, 2H), 4.09 (br s, 2H), 3.72-3.71 (m, 6H), 3.37 (br s, 2H), 3.11-2.89 (m, 3H), 2.73 (br s, 3H); MS (ESI) m/e 411 (M+H)$^+$.

Example 119

Preparation of (E)-N-[2-(1H-Indol-3-yl)-ethyl]-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting [2-(1H-indole-3yl)-ethyl]methylamine for the methyl-(1-propyl-naphthalen-2-ylmethyl)amine, the title compound (0.027 g, 72%) was prepared as a yellow solid and as a mixture of amide rotamers: $^1$H NMR (300 MHz, DMSO-$d_6$) δ 12.25 (br s, 1H), 11.26-11.22 (m, 1H), 10.85 (s, 1H), 8.82-8.41 (m, 1H), 8.33-7.82 (m, 1H), 7.64-6.73 (m, 7H), 4.59-4.31 (m, 4H), 3.78-3.64 (m, 3H), 3.17-2.91 (m, 7H); MS (APCI) m/e 404 (M+H)$^+$.

Example 120

Preparation of (E)-N-Methyl-3-(4-methyl-2-oxo-2,3,4,5-tetrahydro-1H-pyrido[2,3-e][1,4]diazepin-7-yl)-N-(2,4,5-trimethoxy-benzyl)acrylamide hydrochloride According to the procedure of Example 1, except substituting methyl-(2,4,5-trimethoxy-benzyl)amine for the methyl-(1-propyl-naphthalen-2-ylmethyl)amine, the title compound (0.220 g, 78%) was prepared as a light orange solid and as a mixture of amide rotamers: $^1$H NMR (300 MHz, DMSO-$d_6$) δ 11.75 (br s, 1H), 11.19 (s, 1H), 8.81-8.78 (m, 1H), 8.30-8.26 (m, 1H), 7.60-7.31 (m, 2H), 6.73-6.72 (m, 2H), 4.66-4.52 (m, 2H), 4.27 (br s, 2H), 3.79-3.64 (m, 11H), 3.09-2.86 (m, 6H); MS (ESI) m/e 441 (M+H)$^+$.

Example 121

Preparation of (E)-N-Methyl-3-(4-methyl-2-oxo-2,3,4,5-tetrahydro-1H-pyrido[2,3-e][1,4]diazepin-7-yl)-N-phenanthren-9-ylmethyl-acrylamide hydrochloride According to the procedure of Example 1, except substituting methyl-phenanthren-9-ylmethyl-amine for the methyl-(1-propyl-naphthalen-2-ylmethyl)amine, the title compound (0.511 g, 95%) was prepared as an off-white solid and as a mixture of amide rotamers: $^1$H NMR (300 MHz, DMSO-$d_6$) δ 11.99 (br s, 1H), 11.23-11.14 (m, 1H), 8.92-8.74 (m, 3H), 8.36-8.04 (m, 2H), 7.99-7.95 (m, 1H), 7.74-7.28 (m, 7H), 5.39-5.17 (m, 2H), 4.30-4.19 (m, 2H), 3.95-3.39 (m, 2H), 3.16-3.01 (m, 3H), 2.89-2.73 (m, 3H); MS (ESI) m/e 451 (M+H)$^+$.

Example 122

Preparation of (E)-N-Acenaphthen-5-ylmethyl-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting acenaphthen-5-ylmethyl-methylamine for the methyl-(1-propyl-naphthalen-2-ylmethyl)amine, the title compound (0.395 g, 91%) was prepared as a off-white solid and as a mixture of amide rotamers: $^1$H NMR (300 MHz, DMSO-$d_6$) δ 12.01 (br s, 1H), 11.19 (s, 1H), 8.82-8.76 (m, 1H), 8.32-8.22 (m, 1H), 7.81-7.63 (m, 2H), 7.55-7.14 (m, 5H), 5.25-5.03 (m, 2H), 4.28 (br s, 2H), 3.79 (m, 2H), 3.36 (br s, 4H), 3.04-2.73 (m, 6H); MS (ESI) m/e 427 (M+H)$^+$.

Example 123

Preparation of (E)-N-(4-Methoxy-naphthalen-1 ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (4-methoxy-naphthalen-1-ylmethyl)methylamine for the methyl-(1-propyl-naphthalen-2-ylmethyl)amine, the title compound (0.369 g, 87%) was prepared as an off-white solid and as a mixture of amide rotamers: $^1$H NMR (300 MHz, DMSO-$d_6$) δ 11.95 (br s, 1H), 11.22 (s, 1H), 8.83-8.76 (m, 1H), 8.32-8.02 (m, 2H), 8.10-8.00 (m, 1H), 7.69-7.32 (m, 5H), 7.11-6.95 (m, 1H), 5.25-5.03 (m, 2H), 4.29 (br s, 2H), 3.98-3.95 (m, 3H), 3.79 (m, 2H), 3.02-2.69 (m, 3H), 2.87-2.72 (m, 3H); MS (ESI) m/e 431 (M+H)$^+$.

Example 124

Preparation of (E)-N-Benzo[1,3]dioxol-5-ylmethyl-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting benzo[1,3]dioxol-5-ylmethyl-methylamine for the methyl-(1-propyl-naphthalen-2-ylmethyl)amine, the title compound (0.374 g, 91%) was prepared as an off-white solid and as a mixture of amide rotamers: $^1$H NMR (300 MHz, DMSO-$d_6$) δ 12.25 (br s, 1H), 11.23 (s, 1H), 8.81 (s, 1H), 8.32 (s, 1H), 7.62-6.57 (m, 1H), 7.46-7.31 (m, 1H), 6.93-6.71 (m, 3H), 5.99 (s, 2H), 4.72-4.52 (m, 2H), 4.29 (br s, 2H), 3.81 (br s, 2H), 3.10-2.88 (m, 6H); MS (APCI) m/e 395 (M+H)$^+$.

Example 125

Preparation of (E)-N-(2,5-Dimethoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2,5-dimethoxy-benzyl)methylamine for the methyl-(1-propyl-naphthalen-2-ylmethyl)amine, the title compound (0.396 g, 93%) was prepared as an off-white solid and as a mixture of amide rotamers: $^1$H NMR (300 MHz, DMSO-$d_6$) δ 12.05 (br s, 1H), 11.20 (m, 1H), 8.82-8.77 (m, 1H), 8.33-8.27 (m, 1H), 7.61-7.56 (m, 1H), 7.41-7.34 (m, 1H), 6.98-6.93 (m, 1H), 6.86-6.82 (m, 1H), 6.60-6.59 (m, 1H), 4.73-4.55 (m, 2H), 4.28 (br s, 2H), 3.79-3.74 (m, 5H), 3.66-3.65 (m, 3H), 3.16-2.86 (m, 6H); MS (ESI) m/e 411 (M+H)$^+$.

Example 126

Preparation of (E)-N-Methyl-3-(4-methyl-2-oxo-2,3,4,5-tetrahydro-1H-pyrido[2,3-e][1,4]diazepin-7-yl)-N-quinolin-4-ylmethyl-acrylamide hydrochloride According to the procedure of Example 1, except substituting methyl-quinolin-4-ylmethyl-amine for the methyl-(1-propyl-naphthalen-2-ylmethyl)amine, the title compound (0.259 g, 92%) was prepared as an off-white solid and as a mixture of amide rotamers: $^1$H NMR (300 MHz, DMSO-$d_6$) δ 11.22-11.14 (m, 1H), 8.98-8.94 (m, 1H), 8.84-8.74 (m, 1H), 8.37-8.16 (m, 3H), 7.93-7.88 (m, 1H), 7.78-7.73 (m, 1H), 7.69-7.63 (m, 1H), 7.48-7.21 (m, 2H), 5.50-5.24 (m, 2H), 4.30-4.19 (m, 2H), 3.81-3.74 (m, 2H), 3.27 (s, 2H), 3.06 (s, 1H), 2.87-2.80 (m, 3H); MS (ESI) m/e 402 (M+H)$^+$.

Example 127

Preparation of (E)-N-(4-Ethoxy-3-methoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (4-ethoxy-3-methoxy-benzyl)methylamine for the methyl-(1-propyl-naphthalen-2-ylmethyl)amine, the title compound (0.310 g, 95%) was prepared as an off-white solid and as a mixture of amide rotamers: $^1$H NMR (300 MHz, DMSO-$d_6$) δ 11.18 (m, 1H), 8.80-8.79 (m, 1H), 8.30-8.28 (m, 1H), 7.61-7.57 (m, 1H), 7.44-7.30 (m, 1H), 6.95-6.71 (m, 3H), 4.72-4.53 (m, 2H), 4.27 (br s, 2H), 3.99-3.92 (m, 2H), 3.79-3.72 (m, 5H), 3.08-2.72 (m, 6H), 1.33-1.26 (m, 3H); MS (ESI) m/e 425 (M+H)$^+$.

Example 128

Preparation of (E)-N-(2-Ethoxy-3-methoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2-ethoxy-3-methoxy-benzyl)methylamine for the methyl-(1-propyl-naphthalen-2-ylmethyl)amine, the title compound (0.381 g, 89%) was prepared as an off-white solid and as a mixture of amide rotamers: $^1$H NMR (300 MHz, DMSO-d$_6$) δ 12.01 (br s, 1H), 11.21 (s, 1H), 8.82-8.78 (m, 1H), 8.33-8.25 (m, 1H), 7.61-7.56 (m, 1H), 7.40-7.34 (m, 1H), 7.05-6.97 (m, 2H), 6.71-6.61 (m, 1H), 4.80-4.52 (m, 2H), 4.29 (br s, 2H), 4.0-3.94 (m, 2H), 3.79 (m, 5H), 3.11-2.87 (m, 6H), 1.31-1.25 (m, 3H); MS (ESI) m/e 425 (M+H)$^+$.

Example 129

Preparation of (E)-N-(3,4-Dimethyl-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3,4-dimethyl-benzyl)methylamine for the methyl-(1-propyl-naphthalen-2-ylmethyl)amine, the title compound (0.346 g, 91%) was prepared as an off-white solid and as a mixture of amide rotamers: $^1$H NMR (300 MHz, DMSO-d$_6$) δ 12.35 (br s, 1H), 11.23 (s, 1H), 8.82-8.79 (m, 1H), 8.34-8.30 (m, 1H), 7.62-7.57 (m, 1H), 7.44-7.32 (m, 1H), 7.14-7.08 (m, 1H), 7.02-6.92 (m, 2H), 4.74-4.55 (m, 2H), 4.28 (br s, 2H), 3.80 (m, 2H), 3.08-2.86 (m, 6H), 2.20-2.19 (m, 6H); MS (ESI) m/e 379 (M+H)$^+$.

Example 130

Preparation of (E)-N-Methyl-3-(4-methyl-2-oxo-2,3,4,5-tetrahydro-1H-pyrido[2,3-e][1,4]diazepin-7-yl)-N-(2,4,6-trimethyl-benzyl)acrylamide hydrochloride According to the procedure of Example 1, except substituting (2,4,6-trimethyl-benzyl)methylamine for the methyl-(1-propyl-naphthalen-2-ylmethyl)amine, the title compound (0.410 g, 94%) was prepared as an off-white solid and as a mixture of amide rotamers: $^1$H NMR (300 MHz, DMSO-d$_6$) δ 11.80 (br s, 1H), 11.20 (m, 1H), 8.84-8.80 (m, 1H), 8.37-8.31 (m, 1H), 7.61-7.56 (m, 1H), 7.32-7.27 (m, 1H), 6.87 (m, 2H), 4.83-4.68 (m, 2H), 4.28 (br s, 2H), 3.80 (m, 2H), 2.87-2.55 (m, 6H), 2.21-2.16 (m, 9H); MS (ESI) m/e 393 (M+H)$^+$.

Example 131

Preparation of (E)-N-Methyl-3-(4-methyl-2-oxo-2,3,4,5-tetrahydro-1H-pyrido[2,3-e][1,4]diazepin-7-yl)-N-(2,4,5-trimethyl-benzyl)acrylamide hydrochloride According to the procedure of Example 1, except substituting (2,4,5-trimethyl-benzyl)methylamine for the methyl-(1-propyl-naphthalen-2-ylmethyl)amine, the title compound (0.344 g, 95%) was prepared as an off-white solid and as a mixture of amide rotamers: $^1$H NMR (300 MHz, DMSO-d$_6$) δ 11.91 (br s, 1H), 11.25-11.22 (m, 1H), 8.83-8.78 (m, 1H), 8.34-8.24 (m, 1H), 7.63-7.57 (m, 1H), 7.40-7.32 (m, 1H), 6.97-6.95 (m, 1H), 6.85-6.73 (m, 1H), 4.73-4.57 (m, 2H), 4.30 (br s, 2H), 3.96-3.82 (m, 2H), 3.04-2.87 (m, 6H), 2.21-2.15 (m, 9H); MS (ESI) m/e 393 (M+H)$^+$.

Example 132

Preparation of (E)-N-Methyl-3-(4-methyl-2-oxo-2,3,4,5-tetrahydro-1H-pyrido[2,3-e][1,4]diazepin-7-yl)-N-quinolin-3-ylmethyl-acrylamide hydrochloride According to the procedure of Example 1, except substituting methyl-quinolin-3-ylmethyl-amine for the methyl-(1-propyl-naphthalen-2-ylmethyl)amine, the title compound (0.360 g, 92%) was prepared as an off-white solid and as a mixture of amide rotamers: $^1$H NMR (300 MHz, DMSO-d$_6$) δ 12.00 (br s, 1H), 11.23-11.20 (m, 1H), 8.92-8.89 (m, 1H), 8.83-8.80 (m, 1H), 8.34-8.24 (m, 2H), 8.08-8.03 (m, 2H), 7.80-7.78 (m, 1H), 7.69-6.61 (m, 2H), 7.52-7.36 (m, 1H), 5.09-4.86 (m, 2H), 4.30-4.25 (m, 2H), 3.81 (br s, 2H), 3.25 (s, 2H), 3.01 (s, 1H), 2.88-2.85 (m, 3H); MS (ESI) m/e 402 (M+H)$^+$.

Example 133

Preparation of (E)-N-(3,4-Dimethoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3,4-dimethoxy-benzyl)methylamine for the methyl-(1-propyl-naphthalen-2-ylmethyl)amine, the title compound (0.330 g, 92%) was prepared as a pale yellow solid and as a mixture of amide rotamers: $^1$H NMR (300 MHz, DMSO-d$_6$) δ 11.95 (br s, 1H), 11.23 (s, 1H), 8.82-8.81 (m, 1H), 8.32-8.30 (m, 1H), 7.63-7.57 (m, 1H), 7.45-7.32 (m, 1H), 6.95-6.86 (m, 2H), 6.81-6.71 (m, 1H), 4.74-4.55 (m, 2H), 4.28 (br s, 2H), 3.95-3.72 (m, 8H), 3.10-2.88 (m, 6H); MS (ESI) m/e 411 (M+H)$^+$.

Example 134

Preparation of (E)-N-Benzofuran-2-ylmethyl-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting benzofuran-2-ylmethyl-methylamine for the methyl-(1-propyl-naphthalen-2-ylmethyl)amine, the title compound (0.399 g, 93%) was prepared as an off white solid and as a mixture of amide rotamers: $^1$H NMR (300 MHz, DMSO-d$_6$) δ 11.86 (br s, 1H), 11.22 (s, 1H), 8.83 (s, 1H), 8.32 (s, 1H), 7.63-7.20 (m, 6H), 6.86-6.82 (m, 1H), 5.02-4.81 (m, 2H), 4.28 (s, 2H), 3.80 (s, 2H), 3.24-3.02 (m, 3H), 2.87 (s, 3H); MS (ESI) m/e 391 (M+H)$^+$.

Example 135

Preparation of (E)-N-Methyl-N-(2-methyl-naphthalen-1-ylmethyl)-3-(4-methyl-2-oxo-2,3,4,5-tetrahydro-1H-pyrido[2,3-e][1,4]diazepin-7-yl)acrylamide hydrochloride According to the procedure of Example 1, except substituting methyl-(2-methyl-naphthalen-1-ylmethyl)amine for the methyl-(1-propyl-naphthalen-2-ylmethyl)amine, the title compound (0.431 g, 95%) was prepared as a white solid and as a mixture of amide rotamers: $^1$H NMR (300 MHz, DMSO-d$_6$) δ 12.01 (br s, 1H), 11.24 (s, 1H), 8.93-8.83 (m, 1H), 8.44-8.32 (m, 1H), 8.10-8.07 (m, 1H), 7.92-7.82 (m, 2H), 7.71-7.66 (m, 1H), 7.49-7.28 (m, 4H), 5.30-5.18 (m, 2H), 4.29 (br s, 2H), 3.79 (br s, 2H), 2.87-2.81 (m, 6H), 2.55-2.51 (s, 3H); MS (ESI) m/e 415 (M+H)$^+$.

Example 136

Preparation of (E)-N-Biphenyl-2-ylmethyl-methyl-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting biphenyl-2-ylmethyl-methylamine for the methyl-(1-propyl-naphthalen-2-ylmethyl)amine, the title compound (0.255 g, 88%) was prepared as a white solid and as a mixture of amide rotamers: $^1$H NMR (300 MHz, DMSO-$d_6$) δ 11.95 (br s, 1H), 11.22 (s, 1H), 8.80-8.76 (m, 1H), 8.31-8.19 (m, 1H), 7.57-7.17 (m, 11H), 4.76-4.59 (m, 2H), 4.29 (br s, 2H), 3.81 (br s, 2H), 2.99-2.73 (m, 6H); MS (ESI) m/e 427 (M+H)$^+$.

Example 137

Preparation of (E)-N-Biphenyl-3-ylmethyl-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting biphenyl-3-ylmethyl-methylamine for the methyl-(1-propyl-naphthalen-2-ylmethyl)amine, the title compound (0.404 g, 85%) was prepared as an off-white solid and as a mixture of amide rotamers: $^1$H NMR (300 MHz, DMSO-$d_6$) δ 11.95 (br s, 1H), 11.22-11.21 (m, 1H), 8.82-8.81 (m, 1H), 8.32-8.30 (m, 1H), 7.65-7.21 (m, 11H), 7.92-7.82 (m, 2H), 4.92-4.71 (m, 2H), 4.28 (br s, 2H), 3.79 (br s, 2H), 2.17-2.96 (m, 3H), 2.88-2.84 (m, 3H); MS (ESI) m/e 427 (M+H)$^+$.

Example 138

Preparation of (E)-N-(2-Ethoxy-napthalen-1-ylmethyl)-N-methyl-3-(4-methyl-2-oxo-2,3,4,5-tetrahydro-1H-pyrido[2,3-e][1.4]diazepin-7-yl)acrylamide hydrochloride According to the procedure of Example 1, except substituting methyl-(2-ethoxy-naphthalen-1-ylmethyl)amine for the methyl-(1-propyl-naphthalen-2-ylmethyl)amine, the title compound (0.405 g, 90%) was prepared as a white solid and as a mixture of amide rotamers: $^1$H NMR (300 MHz, DMSO-$d_6$) δ 12.35 (br s, 1H), 11.25 (s, 1H), 8.84-8.82 (m, 1H), 8.40-8.31 (m, 1H), 8.07-8.05 (m, 1H), 7.96-7.87 (m, 2H), 7.68-7.63 (m, 1H), 7.52-7.25 (m, 4H), 5.26-5.16 (m, 2H), 4.29-4.20 (m, 4H), 4.09 (br s, 2H), 2.91-2.63 (m, 6H), 1.43-1.29 (s, 3H); MS (ESI) m/e 445 (M+H)$^+$.

Example 139

Preparation of (E)-N-(2-Ethoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2-ethoxy-benzyl)methylamine for the methyl-(1-propyl-naphthalen-2-ylmethyl)amine, the title compound (0.409 g, 87%) was prepared as a white solid and as a mixture of amide rotamers: $^1$H NMR (300 MHz, DMSO-$d_6$) δ 12.05 (br s, 1H), 11.20 (s, 1H), 8.82-8.77 (m, 1H), 8.32-8.27 (m, 1H), 7.61-7.55 (m, 1H), 7.44-7.35 (m, 1H), 7.27-7.20 (m, 1H), 7.09-6.90 (m, 3H), 4.76-4.59 (m, 2H), 4.28 (br s, 2H), 4.09-4.01 (m, 2H), 3.80 (br s, 2H), 3.16-2.85 (m, 6H), 1.37-1.27 (m, 3H); MS (ESI) m/e 395 (M+H)$^+$.

Example 140

Preparation of (E)-N-Methyl-3-(4-methyl-2-oxo-2,3,4,5-tetrahydro-1H-pyrido[2,3-e][1,4]diazepin-7-yl)-N-(2,3,4-trimethoxy-benzyl)acrylamide hydrochloride According to the procedure of Example 1, except substituting (2,3,4-trimethoxy-benzyl)methylamine for the methyl-(1-propyl-naphthalen-2-ylmethyl)amine, the title compound (0.440 g, 92%) was prepared as a white solid and as a mixture of amide rotamers: $^1$H NMR (300 MHz, DMSO-$d_6$) δ 12.25 (br s, 1H), 11.23 (s, 1H), 8.82-8.79 (m, 1H), 8.34-8.29 (m, 1H), 7.61-7.55 (m, 1H), 7.46-7.33 (m, 1H), 6.81-6.75 (m, 2H), 4.71-4.56 (m, 2H), 4.30 (br s, 2H), 3.81-3.74 (m, 11H), 3.11-2.85 (m, 6H); MS (ESI) m/e 441 (M+H)$^+$.

Example 141

Preparation of (E)-N-(2,3-Dihydro-benzo[1,4]dioxin-6ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2,3-dihydro-benzo[1,4]dioxin-6-ylmethyl)methylamine for the methyl-(1-propyl-naphthalen-2-ylmethyl)amine, the title compound (0.196 g, 93%) was prepared as a white solid and as a mixture of amide rotamers: $^1$H NMR (300 MHz, DMSO-$d_6$) δ 12.25 (br s, 1H), 11.25 (s, 1H), 8.82 (s, 1H), 8.32 (s, 1H), 7.63-7.56 (m, 1H), 7.45-7.31 (m, 1H), 6.86-6.68 (m, 3H), 4.70-4.49 (m, 2H), 4.30 (br s, 2H), 4.21 (m, 4H), 3.82 (br s, 2H), 3.09-2.87 (m, 6H); MS (APCI) m/e 409 (M+H)$^+$.

Example 142

Preparation of (E)-N-(2,3-Diethoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2,3-diethoxy-benzyl)methylamine for the methyl-(1-propyl-naphthalen-2-ylmethyl)amine, the title compound (0.331 g, 87%) was prepared as an off-white solid and as a mixture of amide rotamers: $^1$H NMR (300 MHz, DMSO-$d_6$) δ 12.49 (br s, 1H), 11.24-11.22 (m, 1H), 8.83-8.78 (m, 1H), 8.36-8.28 (m, 1H), 7.62-7.56 (m, 1H), 7.42-7.35 (m, 1H), 7.05-6.92 (m, 2H), 6.69-6.63 (m, 1H), 4.80-4.65 (m, 2H), 4.30 (br s, 2H), 4.07-3.93 (m, 4H), 3.81 (br s, 2H), 3.12-2.80 (m, 6H), 1.37-1.25 (m, 6H); MS (APCI) m/e 439 (M+H)$^+$.

Example 143

Preparation of (E)-N-(3-Ethoxy-2-methoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3-ethoxy-2-methoxy-benzyl)methylamine for the methyl-(1-propyl-naphthalen-2-ylmethyl)amine, the title compound (0.397 g, quantitative) was prepared as an off-white solid and as a mixture of amide rotamers: $^1$H NMR (300 MHz, DMSO-$d_6$) δ 12.25 (br s, 1H), 11.23-11.21 (m, 1H), 8.82-8.78 (m, 1H), 8.34-8.27 (m, 1H), 7.62-7.56 (m, 1H), 7.44-7.34 (m, 1H), 7.04-6.96 (m, 2H), 6.69-6.66 (m, 1H), 4.78-4.63 (m, 2H), 4.30 (br s, 2H), 4.09-4.02 (m, 2H), 3.82-3.76 (m, 5H), 3.12-2.86 (m, 6H), 1.38-1.32 (m, 3H); MS (ESI) m/e 425 (M+H)⁺.

Example 144

Preparation of (E)-N-(2-Ethoxy-3-methyl-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2-ethoxy-3-methyl-benzyl)methylamine for the methyl-(1-propyl-naphthalen-2-ylmethyl)amine, the title compound (0.358 g, 84%) was prepared as an off-white solid and as a mixture of amide rotamers: ¹H NMR (300 MHz, DMSO-d₆) δ 12.21 (br s, 1H), 11.23-11.21 (m, 1H), 8.82-8.78 (m, 1H), 8.34-8.25 (m, 1H), 7.63-7.56 (m, 1H), 7.41-7.35 (m, 1H), 7.16-7.11 (m, 1H), 7.05-6.87 (m, 2H), 4.82-4.67 (m, 2H), 4.30 (br s, 2H), 3.90-3.80 (m, 4H), 3.18-2.86 (m, 6H), 2.24 (s, 3H), 1.42-1.28 (m, 3H); MS (ESI) m/e 409 (M+H)⁺.

Example 145

Preparation of (E)-N-methyl-3-(4-methyl-2-oxo-2,3,4,5-tetrahydro-1H-pyrido[2,3-e][1,4]diazepin-7-yl)-N-quinolin-5ylmethyl-acrylamide hydrochloride According to the procedure of Example 1, except substituting methyl-quinolin-5-ylmethyl-amine for the methyl-(1-propyl-naphthalen-2-ylmethyl)amine, the title compound (0.399 g, quantitative) was prepared as an off-white solid and as a mixture of amide rotamers: ¹H NMR (300 MHz, DMSO-d₆) δ 12.30 (br s, 1H), 11.19-11.13 (m, 1H), 8.90-8.98 (m, 1H), 8.82-8.62 (m, 2H), 8.34-8.18 (m, 1H), 8.06-7.99 (m, 1H), 7.83-7.87 (m, 1H), 7.72-7.27 (m, 4H), 5.41-5.15 (m, 2H), 4.28-4.19 (m, 2H), 3.79-3.74 (m, 2H), 3.12-3.01 (m, 3H), 2.85-2.79 (m, 3H); MS (ESI) m/e 402 (M+H)⁺.

Example 146

Preparation of (E)-N-(3-Methoxy-2-propoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3-methoxy-2-propoxy-benzyl)methylamine for the methyl-(1-propyl-naphthalen-2-ylmethyl)amine, the title compound (0.275 g, 87%) was prepared as an off-white solid and as a mixture of amide rotamers: ¹H NMR (300 MHz, DMSO-d₆) δ 12.21 (m, 1H), 11.23-11.21 (m, 1H), 8.83-8.78 (m, 1H), 8.34-8.25 (m, 1H), 7.63-7.56 (m, 1H), 7.40-7.34 (m, 1H), 7.05-6.97 (m, 2H), 6.69-6.64 (m, 1H), 4.80-4.65 (m, 2H), 4.30 (m, 2H), 3.92-3.85 (m, 2H), 3.79 (s, 3H), 3.49 (br s, 2H), 3.12-2.86 (m, 6H), 1.75-1.68 (m, 2H), 1.01-0.94 (m, 3H); MS (ESI) m/e 439 (M+H)⁺.

Example 147

Preparation of (E)-N-(3-Methoxy-2-isopropoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3-methoxy-2-isopropoxy-benzyl)methylamine for the methyl-(1-propyl-naphthalen-2-ylmethyl)amine, the title compound (0.304 g, 85%) was prepared as an off-white solid and as a mixture of amide rotamers: ¹H NMR (300 MHz, DMSO-d₆) δ 12.20 (br s, 1H), 11.24-11.21 (m, 1H), 8.82-8.77 (m, 1H), 8.35-8.23 (m, 1H), 7.61-7.56 (m, 1H), 7.40-7.30 (m, 1H), 7.04-6.93 (m, 2H), 6.67-6.61 (m, 1H), 4.79-4.65 (m, 2H), 4.59-4.48 (m, 1H), 4.30-4.28 (br s, 2H), 3.79 (s, 3H), 3.58-3.55 (m, 2H), 3.10-2.86 (m, 6H), 1.24-1.21 (m, 6H); MS (ESI) m/e 439 (M+H)⁺.

Example 148

Preparation of (E)-N-methyl-N-(3-methyl-benzofuran-2-ylmethyl)-3-(4-methyl-2-oxo-2,3,4,5-tetrahydro-1H-pyrido[2,3-e][1,4]diazepin-7-yl)acrylamide hydrochloride According to the procedure of Example 1, except substituting methyl-(3-methyl-benzofuran-2-ylmethyl)amine for the methyl-(1-propyl-naphthalen-2-ylmethyl)amine, the title compound (0.376 g, 87%) was prepared as an off-white solid and as a mixture of amide rotamers: ¹H NMR (300 MHz, DMSO-d₆) δ 12.16 (br s, 1H), 11.23 (s, 1H), 8.85-8.82 (m, 1H), 8.33 (s, 1H), 7.63-7.22 (m, 6H), 5.01-4.81 (m, 2H), 4.30 (m, 2H), 3.58 (br s, 2H), 3.20-2.88 (m, 6H), 2.27 (m, 3H); MS (ESI) m/e 405 (M+H)⁺.

Example 149

Preparation of (E)-N-(3-Chloro-2-methoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3-chloro-2-methoxy-benzyl)methylamine for the methyl-(1-propyl-naphthalen-2-ylmethyl)amine, the title compound (0.312 g, 92%) was prepared as an off-white solid and as a mixture of amide rotamers: ¹H NMR (500 MHz, DMSO-d₆) δ 12.55 (br s, 1H), 11.21-11.19 (m, 1H), 8.82-8.79 (m, 1H), 8.35-8.28 (m, 1H), 7.61-7.57 (m, 1H), 7.45-7.31 (m, 2H), 7.19-7.11 (m, 2H), 4.87-4.70 (m, 2H), 4.30 (m, 2H), 3.82-3.77 (m, 5H), 3.17-2.86 (m, 6H); MS (ESI) m/e 415 (M+H)⁺.

Example 150

Preparation of (E)-N-(3-Chloro-2-ethoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3-chloro-2-ethoxy-benzyl)methylamine for the methyl-(1-propyl-naphthalen-2-ylmethyl)amine, the title compound (0.169 g, 91%) was prepared as a white solid and as a mixture of amide rotamers: ¹H NMR (500 MHz, DMSO-d₆) δ 12.44 (br s, 1H), 11.20-11.18 (m, 1H), 8.82-8.78 (m, 1H), 8.34-8.25 (m, 1H), 7.62-7.57 (m, 1H), 7.44-7.36 (m, 2H), 7.18-7.10 (m, 2H), 4.87-4.70 (m, 2H), 4.30 (m, 2H), 4.05-3.98 (m, 2H), 3.79-3.61 (m, 2H), 3.16-2.85 (m, 6H), 1.39-1.35 (m, 3H); MS (ESI) m/e 429 (M+H)⁺.

Example 151

Preparation of (E)-N-(2,3-Dihydro-benzo[1,4]dioxin-5-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2,3-dihydro-benzo[1,4]dioxin-5-ylmethyl)methylamine for the methyl-(1-propyl-naphthalen-2-ylmethyl)amine, the title compound (0.058 g, quantitative) was prepared as a white solid and as a mixture of amide rotamers: $^1$H NMR (300 MHz, DMSO-d$_6$) δ 12.15 (br s, 1H), 11.22-11.20 (m, 1H), 8.82-8.76 (m, 1H), 8.34-8.27 (m, 1H), 7.60-7.55 (m, 1H), 7.40-7.33 (m, 1H), 6.84-6.76 (m, 2H), 6.62-6.57 (m, 1H), 4.74-4.57 (m, 2H), 4.30-4.24 (m, 6H), 3.80 (br s, 2H), 3.16-2.87 (m, 6H); MS (ESI) m/e 409 (M+H)$^+$.

Example 152

Preparation of (E)-N-(4,5-Dimethyl-naphthalen-1-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (4,5-dimethyl-naphthalen-1-ylmethyl)methylamine for the methyl-(1-propyl-naphthalen-2-ylmethyl)amine, the title compound (0.244 g, 66%) was prepared as a white solid and as a mixture of amide rotamers: $^1$H NMR (300 MHz, DMSO-d$_6$) δ 12.08 (br s, 1H), 11.22-11.17 (m, 1H), 8.83-8.73 (m, 1H), 8.33-8.17 (m, 1H), 7.94-7.87 (m, 1H), 7.68-7.62 (m, 1H), 7.45-7.22 (m, 5H), 5.25-5.03 (m, 2H), 4.29-4.21 (m, 2H), 3.80 (br s, 2H), 3.11-3.04 (m, 3H), 2.97-2.81 (m, 9H); MS (ESI) m/e 429 (M+H)$^+$.

Example 153

Preparation of (E)-N-Methyl-N-(2-methyl-benzofuran-3-ylmethyl)-3-(4-methyl-2-oxo-2,3,4,5-tetrahydro-1H-pyrido[2,3-e][1,4]diazepin-7-yl)acrylamide hydrochloride According to the procedure of Example 1, except substituting methyl-(2-methyl-benzofuran-3-ylmethyl)amine for the methyl-(1-propyl-naphthalen-2-ylmethyl)amine, the title compound (0.213 g, 53%) was prepared as a white solid and as a mixture of amide rotamers: $^1$H NMR (300 MHz, DMSO-d$_6$) δ 12.24 (br s, 1H), 11.22 (s, 1H), 8.88-8.82 (m, 1H), 8.38-8.33 (m, 1H), 7.79-7.15 (m, 6H), 4.95-4.75 (m, 2H), 4.29 (br s, 2H), 3.80 (br s, 2H), 3.13-2.83 (m, 6H), 2.59-2.44 (m, 3H); MS (ESI) m/e 405 (M+H)$^+$.

Example 154

Preparation of (E)-N-Methyl-3-(7-oxo-5,6,7,8-tetrahydro-[1,8]naphthyridin-3-yl)-N-quinolin-5-ylmethyl-acrylamide hydrochloride According to the procedure of Example 1, except substituting methyl-quinolin-5-ylmethyl-amine for the methyl-(1-propyl-naphthalen-2-ylmethyl)amine, and substituting (E)-3-(7-oxo-5,6,7,8-tetrahydro-[1,8]naphthyridin-3-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.387 g, quantitative) was prepared as a tan solid and as a mixture of amide rotamers: $^1$H NMR (300 MHz, DMSO-d$_6$) δ 10.69-10.63 (m, 1H), 9.26-9.13 (m, 2H), 8.39-8.25 (m, 2H), 8.11-7.93 (m, 3H), 7.77-7.45 (m, 2H), 7.30-7.17 (m, 1H), 5.50-5.22 (m, 2H), 3.15-3.01 (m, 3H), 2.94-2.78 (m, 2H), 2.56-2.44 (m, 2H); MS (ESI) m/e 373 (M+H)$^+$.

Example 155

Preparation of (E)-N-benzyl-N-methyl-3-(7-oxo-5,6,7,8-tetrahydro-[1,8]naphthyridin-3-yl)acrylamide According to the procedure of Example 1 (a), except substituting benzyl-methylamine for the methyl-(1-propyl-naphthalen-2-ylmethyl)amine, and substituting (E)-3-(7-oxo-5,6,7,8-tetrahydro-[1,8]naphthyridin-3-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.462 g, 93%) was prepared as an off-white solid and as a mixture of amide rotamers: $^1$H NMR (300 MHz, DMSO-d6) δ 10.64 (s, 1H), 8.37-8.33 (m, 1H), 8.08-8.06 (m, 1H), 7.54-7.49 (m, 1H), 7.37-7.21 (m, 6H), 4.82-4.61 (m, 2H), 3.10-2.85 (m, 5H), 2.56-2.49 (m, 2H); MS (APCI) m/e 322 (M+H)$^+$.

Example 156

Preparation of (E)-N-methyl-N-(1-methyl-1H-indol-2-ylmethyl)-3-(4-methyl-2-oxo-2,3,415-tetrahydro-1H-pyrido[2,3-e][1,4]diazepin-7-yl)acrylamide hydrochloride According to the procedure of Example 1, except substituting methyl-(1-methyl-1H-indol-2-ylmethyl)amine for the methyl-(1-propyl-naphthalen-2-ylmethyl)amine, the title compound (0.27 g, 86%) was prepared as an off-white powder and as a mixture of amide rotamers: $^1$H NMR (300 MHz, DMSO-d$_6$) δ 11.96 (br s, 1H), 11.06-11.22 (m, 1H), 8.80-8.83 (m, 1H), 8.25-8.34 (m, 1H), 7.61-7.66 (m, 1H), 7.33-7.52 (m, 3H), 7.11-7.15 (m, 1H), 6.97-7.04 (m, 1H), 6.18-6.43 (m, 1H), 4.87-5.08 (m, 2H), 4.26-4.29 (m, 2H), 3.69-3.80 (m, 5H), 3.02-3.14 (m, 3H), 2.85-2.88 (m, 3H); MS (ESI) m/e 404 (M+H)$^+$.

Example 157

Preparation of (E)-(7-{2-[Methyl-(1-methyl-1H-indol-2-ylmethyl)carbamoyl]vinyl}-2-oxo-1,2,3,5-tetrahydro-pyrido[2,3-e][1,4]diazepin-4-yl)acetic acid ethyl ester hydrochloride According to the procedure of Example 1, except substituting methyl-(1-methyl-1H-indol-2-ylmethyl)amine for the methyl-(1-propyl-naphthalen-2-ylmethyl)amine, and substituting (E)-3-(4-ethoxycarbonylmethyl-2-oxo-2,3,4,5-tetrahydro-1H-pyrido[2,3-e][1,4]diazepin-7-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.22 g, 56%) was prepared as a yellow powder and as a mixture of amide rotamers: $^1$H NMR (300 MHz, DMSO-d$_6$) δ 10.53-10.54 (m, 1H), 8.56-8.59 (m, 1H), 8.09-8.16 (m, 1H), 7.28-7.61 (m, 4H), 7.10-7.15 (m, 1H), 6.99-7.04 (m, 1H), 6.19-6.42 (m, 1H), 4.86-5.06 (m, 2H), 4.00-4.14 (m, 5H), 3.62-3.72 (m, 7H), 2.99-3.12 (m, 3H), 1.12-1.20 (m, 3H); MS (ESI) m/e 476 (M+H)$^+$.

Example 158

Preparation of (E)-N-(2,3-Dimethoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2,3-dimethoxy-benzyl)methylamine for the methyl-(1-propyl-naphthalen-2-ylmethyl)amine, the title compound (0.25 g, 58%) was prepared as an off-white powder and as a mixture of amide rotamers: $^1$H NMR (300 MHz, DMSO-$d_6$) δ 11.89 (br s, 1H), 11.21 (s, 1H), 8.78-8.82 (m, 1H), 8.26-8.33 (m, 1H), 7.56-7.61 (m, 1H), 7.34-7.44 (m, 1H), 6.96-7.07 (m, 2H), 6.67-6.71 (m, 1H), 4.64-4.79 (m, 2H), 4.28 (s, 2H), 3.74-3.81 (m, 8H), 2.87-3.13 (m, 6H); MS (ESI) m/e 411 (M+H)$^+$.

Example 159

Preparation of (E)-N-Methyl-N-(4-methyl-naphthalen-1-ylmethyl)-3-(4-methyl-2-oxo-2,3,4,5-tetrahydro-1H-pyrido[2,3-e][1,4]diazepin-7-yl)acrylamide hydrochloride According to the procedure of Example 1, except substituting methyl-(4-methyl-naphthalen-1-ylmethyl)amine for the methyl-(1-propyl-naphthalen-2-ylmethyl)amine, the title compound (0.41 g, 74%) was prepared as a tan powder and as a mixture of amide rotamers: $^1$H NMR (300 MHz, DMSO-$d_6$) δ 11.82 (br s, 1H), 11.16-11.20 (m, 1H), 8.74-8.83 (m, 1H), 8.06-8.33 (m, 3H), 7.56-7.69 (m, 3H), 7.33-7.39 (m, 3H), 5.09-5.32 (m, 2H), 4.20-4.28 (m, 2H), 3.80 (s, 2H), 2.99-3.06 (m, 3H), 2.81-2.86 (m, 3H), 2.64-2.66 (m, 3H); MS (ESI) m/e 415 (M+H)$^+$.

Example 160

Preparation of (E)-N-(2-Methoxy-naphthalen-1-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2-methoxy-naphthalen-1-ylmethyl)methylamine for the methyl-(1-propyl-naphthalen-2-ylmethyl)amine, the title compound (0.41 g, 71%) was prepared as an off-white powder and as a mixture of amide rotamers: $^1$H NMR (300 MHz, DMSO-$d_6$) δ 11.88 (br s, 1H), 11.20 (s, 1H), 8.81-8.85 (m, 1H), 8.30-8.36 (m, 1H), 7.88-8.08 (m, 3H), 7.24-7.69 (m, 5H), 5.15-5.24 (m, 2H), 4.28 (s, 2H), 3.80-3.99 (m, 5H), 2.64-2.90 (m, 6H); MS (ESI) m/e 431 (M+H)$^+$.

Example 161

Preparation of (R)-(+)-(E)-N-Methyl-3-(4-methyl-2-oxo-2,3,4,5-tetrahydro-1H-pyrido[2,3-e][1,4]diazepin-7-yl)-N-(1-naphthalen-1-yl-ethyl)acrylamide hydrochloride According to the procedure of Example 1, except substituting (R)-(+)-N-methyl-1-(1-naphthyl)ethylamine for the methyl-(1-propyl-naphthalen-2-ylmethyl)amine, the title compound (0.26 g, 48%) was prepared as an off-white powder and as a mixture of amide rotamers: [α]$^{25}_D$ +92.6° (c 1.00, methanol); $^1$H NMR (300 MHz, DMSO-$d_6$) δ 12.11 (br s, 1H), 11.22 (s, 1H), 8.81-8.89 (m, 1H), 8.30-8.42 (m, 1H), 7.92-7.98 (m, 3H), 7.67-7.79 (m, 2H), 7.50-7.60 (m, 3H), 7.20-7.25 (m, 1H), 6.53-6.57 (m, 1H), 4.28 (s, 2H), 3.80 (s, 2H), 2.86-2.89 (m, 3H), 2.45-2.73 (m, 3H), 1.60-1.75 (m, 3H); MS (ESI) m/e 415 (M+H)$^+$.

Example 162

Preparation of (S)-(−)-(E)-N-Methyl-3-(4-methyl-2-oxo-2,3,4,5-tetrahydro-1H-pyrido[2,3-e][1,4]diazepin-7-yl)-N-(1-naphthalen-1-yl-ethyl)acrylamide hydrochloride According to the procedure of Example 1, except substituting (S)-(−)-N-methyl-1-(1-naphthyl)ethylamine for the methyl-(1-propyl-naphthalen-2-ylmethyl)amine, the title compound (0.34 g, 63%) was prepared as an off-white powder: [α]$^{25}_D$ −89.1° (c 1.00, methanol); $^1$H NMR (300 MHz, DMSO-$d_6$) δ 12.20 (br s, 1H), 11.21 (s, 1H), 8.88-8.81 (m, 1H), 8.41-8.30 (m, 1H), 7.98-7.92 (m, 3H), 7.72-7.67 (m, 2H), 7.59-7.50 (m, 3H), 7.25-7.19 (m, 1H), 6.57-6.51 (m, 1H), 4.28 (br s, 2H), 3.79 (br s, 2H), 2.89-2.85 (m, 3H), 2.73-2.67 (m, 3H), 1.75-1.59 (m, 3H); MS (ESI) m/e 415 (M+H)$^+$.

Example 163

Preparation of (E)-N-Benzo[b]thiophen-2-ylmethyl-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting benzo[b]thiophen-2-ylmethyl-methylamine for the methyl-(1-propyl-naphthalen-2-ylmethyl)amine, the title compound (0.40 g, 74%) was prepared as a tan powder: $^1$H NMR (300 MHz, DMSO-$d_6$) δ 11.94 (br s, 1H), 11.14 (s, 1H), 8.89-8.84 (m, 1H), 8.33-8.31 (m, 1H), 7.90-7.87 (m, 1H), 7.81-7.79 (m, 1H), 7.66-7.52 (m, 1H), 7.39-7.31 (m, 4H), 5.13-4.87 (m, 2H), 4.30 (br s, 2H), 3.81 (br s, 2H), 3.20-3.00 (m, 3H), 2.89 (s, 3H); MS (ESI) m/e 407 (M+H)$^+$.

Example 164

Preparation of (E)-N-methyl-3-(4-methyl-2-oxo-2,3,4,5-tetrahydro-1H-pyrido[2,3-e][1,4]diazepin-7-yl)-N-(3-trifluoromethyl-benzyl)acrylamide hydrochloride According to the procedure of Example 1, except substituting methyl-(3-trifluoromethyl-benzyl)amine for the methyl-(1-propyl-naphthalen-2-ylmethyl)amine, the title compound (0.39 g, 69%) was prepared as a tan powder: $^1$H NMR (300 MHz, DMSO-$d_6$) δ 12.08 (br s, 1H), 11.23 (s, 1H), 8.83-8.81 (m, 1H), 8.33-8.27 (m, 1H), 7.66-7.35 (m, 6H), 4.96-4.72 (m, 2H), 4.30 (br s, 2H), 3.80 (br s, 2H), 3.17-2.85 (m, 6H); MS (ESI) m/e 419 (M+H)$^+$.

Example 165

Preparation of (E)-N-(2-Chloro-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2-chlorobenzyl)methylamine for the methyl-(1-propyl-naphthalen-2-ylmethyl)amine, the title compound (0.38 g, 72%) was prepared as an off-white powder: $^1$H NMR (300

MHz, DMSO-d$_6$) δ 11.90 (br s, 1H), 11.23-11.91 (m, 1H), 8.83-8.78 (m, 1H), 8.34-8.24 (m, 1H), 7.63-7.32 (m, 5H), 7.20-7.16 (m, 1H), 4.92-4.71 (m, 2H), 4.30 (br s, 2H), 3.81 (br s, 2H), 3.20 (s, 2H), 2.91-2.86 (m, 4H); MS (ESI) m/e 385 (M+H)$^+$.

Example 166

Preparation of (E)-N-Methyl-N-(4-methyl-benzyl)-3-(4-methyl-2-oxo-2,3,4,5-tetrahydro-1H-pyrido[2,3-e][1,4]diazepin-7-yl)acrylamide hydrochloride According to the procedure of Example 1, except substituting N-methyl-N-(4-methylbenzyl)amine for the methyl-(1-propyl-naphthalen-2-ylmethyl)amine, the title compound (0.24 g, 48%) was prepared as tan powder: $^1$H NMR (300 MHz, DMSO-d$_6$) δ 12.25 (br s, 1H), 11.23-11.22 (m, 1H), 8.82-8.79 (m, 1H), 8.33-8.30 (m, 1H), 7.62-7.58 (m, 1H), 7.57-7.32 (m, 1H), 7.19-7.10 (m, 4H), 4.78-4.58 (m, 2H), 4.29 (br s, 2H), 3.80 (br s, 2H), 3.09-2.87 (m, 6H), 2.28 (s, 3H); MS (ESI) m/e 365 (M+H)$^+$.

Example 167

Preparation of (R)-(−)-(E)-N-Methyl-N-(1-methyl-1H-indol-2-ylmethyl)-3-(10-oxo-2,3,4,9,10,10a-hexahydro-1H-3a,8,9-triaza-benzo[f]azulen-6-yl)acrylamide hydrochloride According to the procedure of Example 1, except substituting methyl-(1-methyl-1H-indol-2-ylmethyl)amine for the methyl-(1-propyl-naphthalen-2-ylmethyl)amine, and substituting (R)-(E)-3-(10-oxo-2,3,4,9,10,10a-hexahydro-1H-3a,8,9-triaza-benzo[f]azulen-6-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.19 g, 35%) was prepared as a tan powder: [α]$^{25}_D$ −173.9° (c 1.00, methanol); $^1$H NMR (300 MHz, DMSO-d$_6$) δ 12.50 (br s, 1H), 11.27 (s, 1H), 8.83-8.74 (m, 1H), 8.32-8.25 (m, 1H), 7.65-7.60 (m, 1H), 7.51-7.32 (m, 3H), 7.15-6.96 (m, 2H), 6.43-6.18 (m, 1H), 5.07-4.86 (m, 2H), 4.47-4.21 (m, 3H), 3.79-2.88 (m, 9H), 2.09-1.88 (m, 3H); MS (ESI) m/e 430 (M+H)$^+$.

Example 168

Preparation of (S)-(+)-(E)-N-Methyl-N-(1-methyl-1H-indol-2-ylmethyl)-3-(10-oxo-2,3,4,9,10,10a-hexahydro-1H-3a,8,9-triaza-benzo[f]azulen-6-yl)acrylamide hydrochloride According to the procedure of Example 1, except substituting methyl-(1-methyl-1H-indol-2-ylmethyl)amine for the methyl-(1-propyl-naphthalen-2-ylmethyl)amine, and substituting (S)-(E)-3-(10-oxo-2,3,4,9,10,10a-hexahydro-1H-3a,8,9-triaza-benzo[f]azulen-6-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (91 mg, 23%) was prepared as a tan powder: [α]$^{25}_D$ +197.70 (c 1.00, methanol); $^1$H NMR (300 MHz, DMSO-d$_6$) δ 12.51 (br s, 1H), 11.28 (s, 1H), 8.83-8.74 (m, 1H), 8.32-8.25 (m, 1H), 7.65-7.60 (m, 1H), 7.51-7.32 (m, 3H), 7.15-6.98 (m, 2H), 6.43-6.18 (m, 1H), 5.07-4.86 (m, 2H), 4.46-4.21 (m, 3H), 3.73-3.62 (m, 4H), 3.18-2.87 (m, 5H), 2.08-1.88 (m, 3H); MS (ESI) m/e 430 (M+H)$^+$.

Example 169

Preparation of (E)-3-[4-(4-Methoxy-benzyl)-2-oxo-2,3,4,5-tetrahydro-1H-pyrido[2,3-e][1,4]diazepin-7-yl]-N-methyl-N-(1-methyl-1H-indol-2-ylmethyl)acrylamide hydrochloride According to the procedure of Example 1, except substituting methyl-(1-methyl-1H-indol-2-ylmethyl)amine for the methyl-(1-propyl-naphthalen-2-ylmethyl)amine, and substituting (E)-3-[4-(4-methoxy-benzyl)-2-oxo-2,3,4,5-tetrahydro-1H-pyrido[2,3-e][1,4]diazepin-7-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.20 g, 83%) was prepared as a tan powder: $^1$H NMR (300 MHz, DMSO-d$_6$) δ 12.07 (br s, 1H), 11.23-11.21 (m, 1H), 8.78 (s, 1H), 8.27-8.20 (m, 1H), 7.64-6.99 (m, 10H), 6.42-6.18 (m, 1H), 5.06-4.86 (m, 2H), 4.32-4.20 (m, 4H), 3.77-3.68 (m, 8H), 3.12-3.00 (m, 3H); MS (ESI) m/e 510 (M+H)$^+$.

Example 170

Preparation of (E)-N-Methyl-N-(1-methyl-1H-indol-2-ylmethyl)-3-(2-oxo-2,3,4,5-tetrahydro-1H-pyrido[2,3-e][1,4]diazepin-7-yl)acrylamide hydrochloride [AP-501382]

a) (E)-N-Methyl-N-(1-methyl-1H-indol-2-ylmethyl)-3-(2-oxo-2,3,4,5-tetrahydro-1H-pyrido[2,3-e][1,4]diazepin-7-yl)acrylamide A solution of (E)-3-[4-(4-methoxy-benzyl)-2-oxo-2,3,4,5-tetrahydro-1H-pyrido[2,3-e][1,4]diazepin-7-yl]-N-methyl-N-(1-methyl-1H-indol-2-ylmethyl)acrylamide (2.00 g, 3.92 mmol), from Example 65, in dichloroethane (80 mL) was cooled in an ice bath and treated with 1-chloroethyl chloroformate (0.47 mL, 4.31 mmol). After stirring at 0° C. under N$_2$ for 30 min and then at room temperature for 30 min, the mixture was heated to reflux for 1.5 h. The mixture was allowed to cool and then concentrated to dryness. Purification by flash column chromatography (silica gel, CH$_2$Cl$_2$/MeOH, 97:3) gave a tan solid. The solid was suspended in methanol and heated to reflux for 2 h. The mixture was allowed to cool and the solid was isolated by filtration, dissolved in CH$_2$Cl$_2$, washed with 1 N NaOH, dried over Na$_2$SO$_4$, filtered and the solvent was removed in vacuo. Purification by flash column chromatography (silica gel, CH$_2$Cl$_2$/MeOH, 97:3 to 95:5) gave the title compound (0.70 g, 49%) as an off-white solid: $^1$H NMR (300 MHz, CDCl$_3$) δ 8.38-8.33 (m, 2H), 7.72-7.67 (m, 1H), 7.60-7.57 (m, 2H), 7.32-7.20 (m, 3H), 7.14-7.09 (m, 1H), 6.90-6.80 (m, 1H), 6.49-6.38 (m, 1H), 4.93-4.78 (m, 2H), 4.08 (s, 2H), 3.95 (s, 2H), 3.71 (s, 3H), 3.13-3.07 (m, 3H); MS (ESI) m/e 390 (M+H)$^+$.

b) (E)-N-Methyl-N-(1-methyl-1H-indol-2-ylmethyl)-3-(2-oxo-2,3,4,5-tetrahydro-1H-pyrido[2,3-e][1,4]diazepin-7-yl)acrylamide hydrochloride According to the procedure of Example 1(b), except substituting (E)-N-methyl-N-(1-methyl-1H-indol-2-ylmethyl)-3-(2-oxo-2,3,4,5-tetrahydro-1H-pyrido[2,3-e][1,4]diazepin-7-yl)acrylamide for the (E)-N-methyl-3-(4-methyl-2-oxo-2,3,4,5-tetrahydro-1H-pyrido[2,3-e][1,4]diazepin-7-yl)-N-(1- propyl-naphthalen-2-ylmethyl)acrylamide, the title compound (0.14 g, 89%) was prepared as a tan solid: $^1$H NMR (300 MHz, DMSO-$d_6$) δ 11.09-11.06 (m, 1H), 9.90-9.89 (s, 2H), 8.76-8.73 (m, 1H), 8.31-8.23 (m, 1H), 7.64-7.59 (m, 1H), 7.51-7.31 (m, 3H), 7.15-7.10 (m, 1H), 7.03-6.96 (m, 1H), 6.43-6.16 (m, 1H), 5.07-4.86 (m, 2H), 4.26-4.20 (m, 2H), 3.85-3.80 (m, 2H), 3.73-3.69 (m, 3H), 3.13-3.01 (m, 3H); MS (ESI) m/e 390 (M+H)$^+$.

Example 171

Preparation of (E)-N-Methyl-N-(3-methyl-benzo[b]thiophen-2-ylmethyl)-3-[4-(2-morpholin-4-yl-ethyl)-2-oxo-2,3,4,5-tetrahydro-1H-pyrido[2,3-e][1,4]diazepin-7-yl]acrylamide hydrochloride According to the procedure of Example 1, except substituting methyl-(3-methyl-benzo[b]thiophen-2-ylmethyl)amine for the methyl-(1-propyl-naphthalen-2-ylmethyl)amine, and substituting (E)-3-[4-(2-morpholin-4-yl-ethyl)-2-oxo-2,3,4,5-tetrahydro-1H-pyrido[2,3-e][1,4]diazepin-7-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (90 mg, 74%) was prepared as a tan solid: $^1$H NMR (300 MHz, DMSO-$d_6$) δ 10.58 (br s, 2H), 8.62 (s, 1H), 8.27-8.25 (m, 1H), 7.88-7.86 (m, 1H), 7.75-7.72 (m, 1H), 7.61-7.53 (m, 1H), 7.42-7.29 (m, 3H), 5.15-4.89 (m, 2H), 4.03-3.65 (m, 12H), 3.28-3.17 (m, 4H), 3.01-2.64 (m, 3H), 2.42 (s, 3H); MS (ESI) m/e 520 (M+H)$^+$.

Example 172

Preparation of (E)-N-Methyl-N-(3-methyl-benzo[b]thiophen-2-ylmethyl)-3-{4-[2-(4-methyl-piperazin-1-yl)-2-oxo-ethyl]-2-oxo-2,3,4,5-tetrahydro-1H-pyrido[2,3-e][1,4]diazepin-7-yl}acrylamide hydrochloride According to the procedure of Example 1, except substituting methyl-(3-methyl-benzo[b]thiophen-2-ylmethyl)amine for the methyl-(1-propyl-naphthalen-2-ylmethyl)amine, and substituting (E)-3-{4-[2-(4-methyl-piperazin-1-yl)-2-oxo-ethyl]-2-oxo-2,3,4,5-tetrahydro-1H-pyrido[2,3-e][1,4]diazepin-7-yl}acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.18 g, 53%) was prepared as an off-white powder: $^1$H NMR (300 MHz, DMSO-$d_6$) δ 10.91 (br s, 1H), 10.55 (br s, 1H), 8.61 (s, 1H), 8.18 (s, 1H), 7.88-7.86 (m, 1H), 7.75-7.72 (m, 1H), 7.61-7.52 (m, 1H), 7.42-7.28 (m, 3H), 5.14-4.89 (m, 2H), 4.42-4.38 (m, 1H), 4.01 (br s, 3H), 3.65 (s, 4H), 3.39 (br s, 4H), 3.16 (s, 2H), 3.04-2.94 (m, 3H), 2.74 (br s, 3H), 2.42 (s, 3H); MS (ESI) m/e 547 (M+H)$^+$.

Example 173

Preparation of (E)-N-Methyl-N-(3-methyl-benzo[b]thiophen-2-ylmethyl)-3-[4-(3-morpholin-4-yl-propyl)-2-oxo-2,3,4,5-tetrahydro-1H-pyrido[2,3-e][1,4]diazepin-7-yl]acrylamide hydrochloride According to the procedure of Example 1, except substituting methyl-(3-methyl-benzo[b]thiophen-2-ylmethyl)amine for the methyl-(1-propyl-naphthalen-2-ylmethyl)amine, and substituting (E)-3-[4-(3-morpholin-4-yl-propyl)-2-oxo-2,3,4,5-tetrahydro-1H-pyrido[2,3-e][1,4]diazepin-7-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.20 g, 56%) was prepared as an off-white powder: $^1$H NMR (300 MHz, DMSO-$d_6$) δ 10.88 (br s, 1H), 10.48 (br s, 1H), 8.58 (s, 1H), 8.31 (s, 1H), 7.88-7.86 (m, 1H), 7.75-7.72 (m, 1H), 7.60-7.55 (m, 1H), 7.42-7.30 (m, 3H), 5.16-4.89 (m, 2H), 3.98 (br s, 2H), 3.92-3.79 (m, 4H), 3.63 (br s, 2H), 3.37-3.33 (m, 6H), 3.18-3.10 (m, 2H), 2.94 (s, 1H), 2.63 (br s, 2H), 2.42 (s, 3H), 1.92 (br s, 2H); MS (ESI) m/e 534 (M+H)$^+$.

Example 174

Preparation of (E)-N-(2-Ethoxy-3-methoxy-benzyl)-N-methyl-3-{4-[2-(4-methyl-piperazin-1-yl)-2-oxo-ethyl]-2-oxo-2,3,4,5-tetrahydro-1H-pyrido[2,3-e][1,4]diazepin-7-yl}acrylamide hydrochloride According to the procedure of Example 1, except substituting (2-ethoxy-3-methoxy-benzyl)methylamine for the methyl-(1-propyl-naphthalen-2-ylmethyl)amine, and substituting (E)-3-{4-[2-(4-methyl-piperazin-1-yl)-2-oxo-ethyl]-2-oxo-2,3,4,5-tetrahydro-1H-pyrido[2,3-e][1,4]diazepin-7-yl}acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (82 mg, 47%) was prepared as an off-white powder: $^1$H NMR (300 MHz, DMSO-$d_6$) δ 10.97 (br s, 1H), 10.67 (br s, 1H), 8.64-8.60 (m, 1H), 8.23-8.14 (m, 1H), 7.58-7.52 (m, 1H), 7.39-7.33 (m, 1H), 7.07-6.94 (m, 2H), 6.69-6.63 (m, 1H), 4.80-4.64 (m, 2H), 4.42-4.38 (m, 1H), 4.09-3.93 (m, 3H), 3.79 (s, 3H), 3.68 (br s, 2H), 3.47-3.37 (m, 8H), 3.11-2.97 (m, 5H), 2.75 (br s, 3H), 1.31-1.24 (m, 3H); MS (ESI) m/e 551 (M+H)$^+$.

Example 175

Preparation of (S)-(+)-(E)-N-Methyl-N-(3-methyl-benzo[b]thiophen-2-ylmethyl)-3-(10-oxo-2,3,4,9,10,10a-hexahydro-1H-3a,8,9-triaza-benzo[f]azulen-6-yl)acrylamide hydrochloride According to the procedure of Example 1, except substituting methyl-(3-methyl-benzo[b]thiophen-2-ylmethyl)amine for the methyl-(1-propyl-naphthalen-2-ylmethyl)amine, and substituting (S)-(E)-3-(10-oxo-2,3,4,9,10,10a-hexahydro-1H-3a,8,9-triaza-benzo[f]azulen-6-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.15 g, 62%) was prepared as a tan powder: [α]$^{25}_D$ +167.8° (c 1.05, methanol); $^1$H NMR (300 MHz, DMSO-$d_6$) δ 12.33 (br s, 1H), 11.30 (br s, 1H), 8.84 (s, 1H), 8.33 (s, 1H), 7.89-7.86 (m, 1H), 7.75-7.72 (m, 1H), 7.65-7.55 (m, 1H), 7.42-7.31 (m, 3H), 5.13-4.90 (m, 2H), 4.47-4.22 (m, 2H), 3.61 (br s, 1H), 3.42-3.39 (br s, 4H), 3.17-2.95 (m, 3H), 2.42 (s, 3H), 2.10-1.88 (2H); MS (ESI) m/e 447 (M+H)$^+$.

Example 176

Preparation of (R)-(−)-(E)-N-Methyl-N-(3-methyl-benzo[b]thiophen-2-ylmethyl)-3-(10-oxo-2,3,4,9,10,10a-hexahydro-1H-3a,8,9-triaza-benzo[f]azulen-6-yl)acrylamide hydrochloride According to the procedure of Example 1, except substituting methyl-(3-methyl-benzo[b]thiophen-2-ylmethyl)amine for the methyl-(1-propyl-naphthalen-2-ylmethyl)

amine, and substituting (R)-(E)-3-(10-oxo-2,3,4,9,10,10a-hexahydro-1H-3a,8,9-triaza-benzo[f]azulen-6-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (96 mg, 57%) was prepared as a tan powder: $[\alpha]^{25}{}_D$ –154.3° (c 1.01, methanol); $^1$H NMR (300 MHz, DMSO-d$_6$) δ 12.47 (br s, 1H), 11.29 (br s, 1H), 8.84 (s, 1H), 8.33 (s, 1H), 7.89-7.86 (m, 1H), 7.75-7.72 (m, 1H), 7.65-7.60 (m, 1H), 7.42-7.31 (m, 3H), 5.13-4.90 (m, 2H), 4.48-4.25 (m, 2H), 3.59-3.47 (m, 5H), 3.17-2.95 (m, 3H), 2.42 (s, 3H), 2.10-1.89 (m, 2H); MS (ESI) m/e 447 (M+H)$^+$.

Example 177

Preparation of (E)-N-(4-Fluoro-naphthalen-1-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (4-fluoro-naphthalen-1-ylmethyl)methylamine for the methyl-(1-propyl-naphthalen-2-ylmethyl)amine, the title compound (0.20 g, 72%) was prepared as a white powder: $^1$H NMR (500 MHz, DMSO-d$_6$) δ 12.22 (br s, 1H), 11.26-11.17 (m, 1H), 8.83-8.76 (m, 1H), 8.34-8.10 (m, 3H), 7.72-7.64 (m, 3H), 7.44-7.32 (m, 3H), 5.32-5.09 (m, 2H), 4.30 (br s, 2H), 3.85 (br s, 2H), 3.12-2.98 (m, 3H), 2.89-2.83 (m, 3H); MS (ESI) m/e 419 (M+H)$^+$.

Example 178

Preparation of (E)-N-(4-Chloro-naphthalen-1-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (4-chloro-naphthalen-1-ylmethyl)methylamine for the methyl-(1-propyl-naphthalen-2-ylmethyl)amine, the title compound (0.28 g, 48%) was prepared as a white powder: $^1$H NMR (500 MHz, DMSO-d$_6$) δ 12.29 (br s, 1H), 11.23-11.17 (m, 1H), 8.84-8.75 (m, 1H), 8.33-8.18 (m, 3H), 7.76-7.32 (m, 6H), 5.37-5.12 (m, 2H), 4.31 (br s, 2H), 3.80 (br s, 2H), 3.11-3.00 (m, 3H), 2.89-2.82 (m, 3H); MS (ESI) m/e 435 (M+H)$^+$.

Example 179

Preparation of (E)-N-Methyl-N-(3-methyl-benzofuran-2-ylmethyl)-3-[4-(3-morpholin-4-yl-propyl)-2-oxo-2,3,4,5-tetrahydro-1H-pyrido[2,3-e][1,4]diazepin-7-yl]acrylamide hydrochloride According to the procedure of Example 1, except substituting methyl-(3-methyl-benzofuran-2-ylmethyl)amine for the methyl-(1-propyl-naphthalen-2-ylmethyl)amine, and substituting (E)-3-[4-(3-morpholin-4-yl-propyl)-2-oxo-2,3,4,5-tetrahydro-1H-pyrido[2,3-e][1,4]diazepin-7-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.28 g, 78%) was prepared as an off-white powder: $^1$H NMR (300 MHz, DMSO-d$_6$) δ 10.74-10.54 (m, 2H), 8.61 (s, 1H), 8.29 (s, 1H), 7.63-7.47 (m, 3H), 7.34-7.23 (m, 3H), 5.03-4.80 (m, 2H), 4.02 (br s, 2H), 3.87-3.79 (m, 4H), 3.65 (br s, 2H), 3.48-3.38 (br s, 4H), 3.20-2.93 (m, 5H), 2.72-2.57 (br s, 2H), 2.26 (s, 3H), 1.95 (s, 2H); MS (ESI) m/e 518 (M+H)$^+$.

Example 180

Preparation of (E)-N-(2-Isopropoxy-3-methoxy-benzyl)-N-methyl-3-[4-(3-morpholin-4-yl-propyl)-2-oxo-2,3,4,5-tetrahydro-1H-pyrido[2,3-e][1,4]diazepin-7-yl]acrylamide hydrochloride According to the procedure of Example 1, except substituting (2-isopropoxy-3-methoxy-benzyl)methylamine for the methyl-(1-propyl-naphthalen-2-ylmethyl)amine, and substituting (E)-3-[4-(3-morpholin-4-yl-propyl)-2-oxo-2,3,4,5-tetrahydro-1H-pyrido[2,3-e][1,4]diazepin-7-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.17 g, 44%) was prepared as an off-white powder: $^1$H NMR (300 MHz, DMSO-d$_6$) δ 11.01 (br s, 1H), 10.66 (br s, 1H), 8.62 (br s, 1H), 8.35-8.22 (m, 1H), 7.57-7.52 (m, 1H), 7.40-7.32 (m, 1H), 7.05-6.93 (m, 2H), 6.66-6.62 (m, 1H), 4.80-4.64 (m, 2H), 4.60-4.45 (m, 1H), 4.08 (br s, 2H), 3.87-3.81 (m, 6H), 3.79 (s, 3H), 3.68 (br s, 2H), 3.50-3.38 (m, 4H), 3.21 (br s, 2H), 3.10-2.72 (m, 3H), 2.01 (br s, 2H), 1.27-1.15 (m, 6H); MS (ESI) m/e 552 (M+H)$^+$.

Example 181

Preparation of (E)-N-Methyl-N-(3-methyl-benzo[b]thiophen-2-ylmethyl)-3-{4-[3-(4-methyl-piperazin-1-yl)propyl]-2-oxo-2,3,4,5-tetrahydro-1H-pyrido[2,3-e][1,4]diazepin-7-yl}acrylamide hydrochloride According to the procedure of Example 2, except substituting 7-bromo-4-[3-(4-methyl-piperazin-1-yl)propyl]-1,3,4,5-tetrahydro-pyrido[2,3-e][1,4]diazepin-2-one for the 7-bromo-3,3-dimethyl-1,3,4,5-tetrahydro-pyrido[2,3-e][1,4]diazepin-2-one, the title compound (0.15 g, 49%) was prepared as a tan powder: $^1$H NMR (300 MHz, DMSO-d$_6$) δ 11.06 (br s, 1H), 10.64 (br s, 1H), 8.63 (s, 1H), 8.29-8.22 (m, 1H), 7.88-7.86 (m, 1H), 7.75-7.72 (m, 1H), 7.61-7.53 (m, 1H), 7.42-7.29 (m, 3H), 5.14-4.89 (m, 2H), 4.04 (br s, 2H), 3.65 (br s, 2H), 3.48-3.31 (m, 13H), 3.24-2.29 (m, 3H), 2.76 (br s, 2H), 2.42 (s, 3H), 1.89 (br s, 2H); MS (ESI) m/e 547 (M+H)$^+$.

Example 182

Preparation of (E)-N-Methyl-N-(2-methyl-benzofuran-3-ylmethyl)-3-[4-(3-morpholin-4-yl-propyl)-2-oxo-2,3,4,5-tetrahydro-1H-pyrido[2,3-e][1,4]diazepin-7-yl]acrylamide hydrochloride According to the procedure of Example 1, except substituting methyl-(2-methyl-benzofuran-3-ylmethyl)amine for the methyl-(1-propyl-naphthalen-2-ylmethyl)amine, and substituting (E)-3-[4-(3-morpholin-4-yl-propyl)-2-oxo-2,3,4,5-tetrahydro-1H-pyrido[2,3-e][1,4]diazepin-7-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.24 g, 68%) was prepared as a white powder: $^1$H NMR (300 MHz, DMSO-d$_6$) δ 10.86 (br s, 1H), 10.47 (br s, 1H), 8.54 (br s, 1H), 8.38-8.29 (m, 1H), 7.78-7.46 (m, 3H), 7.32-7.15 (m, 3H), 4.97-4.74 (m, 2H), 4.02-3.91 (m, 5H), 3.87-3.79 (m, 4H), 3.63 (br s, 2H), 3.45-3.29 (m, 4H), 3.27-3.15 (m, 4H), 3.07-2.82 (m, 3H), 1.93 (br s, 2H); MS (ESI) m/e 518 (M+H)+.

Example 183

Preparation of (E)-N-(3-Chloro-benzo[b]thiophen-2-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3-chlorobenzo[b]thiophen-2-ylmethyl)methylamine for the methyl-(1-propyl-naphthalen-2-ylmethyl)amine, the title compound (0.39 g, 88%) was prepared as an off-white powder: $^1$H NMR (300 MHz, DMSO-d$_6$) δ 12.40-11.21 (m, 2H), 8.84 (s, 1H), 8.35-8.30 (m, 1H), 8.04-8.00 (m, 1H), 7.79-7.77 (m, 1H), 7.55-7.34 (m, 4H), 5.21-4.94 (m, 2H), 4.29 (br s, 2H), 3.81 (br s, 2H), 3.24-3.00 (m, 3H), 2.88 (s, 3H); MS (ESI) m/e 441 (M+H)+.

Example 184

Preparation of (E)-N-(5-Chloro-1-methyl-1H-indol-2-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (5-chloro-1-methyl-1H-indol-2-ylmethyl)methylamine for the methyl-(1-propyl-naphthalen-2-ylmethyl)amine, the title compound (0.32 g, 43%) was prepared as an off-white powder: $^1$H NMR (300 MHz, DMSO-d$_6$) δ 12.50-11.20 (m, 2H), 8.83-8.80 (m, 1H), 8.35-8.27 (m, 1H), 7.66-7.34 (m, 4H), 7.14-7.11 (m, 1H), 6.41-6.18 (m, 1H), 5.08-4.86 (m, 2H), 4.45-4.15 (m, 2H), 3.80-3.45 (m, 5H), 3.02-2.88 (m, 3H), 2.73 (s, 3H); MS (ESI) m/e 438 (M+H)+.

Example 185

Preparation of (E)-N-(1,7-Dimethyl-1H-indol-2-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (1,7-dimethyl-1H-indol-2-ylmethyl)methylamine for the methyl-(1-propyl-naphthalen-2-ylmethyl)amine, the title compound (0.25 g, 43%) was prepared as an off-white powder: $^1$H NMR (300 MHz, DMSO-d$_6$) δ 11.85-11.12 (m, 2H), 8.78 (s, 1H), 8.31-8.21 (m, 1H), 7.65-7.60 (m, 1H), 7.38-7.27 (m, 2H), 6.88-6.82 (m, 2H), 6.39-6.11 (m, 1H), 5.03-4.83 (m, 2H), 4.24 (br s, 2H), 3.95-3.44 (m, 5H), 3.17-3.01 (m, 6H), 2.82-2.72 (m, 3H); MS (ESI) m/e 418 (M+H)+.

Example 186

Preparation of (E)-N-(5-Fluoro-3-methyl-benzo[b]thiophen-2-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (5-fluoro-3-methyl-benzo[b]thiophen-2-ylmethyl)methylamine for the methyl-(1-propyl-naphthalen-2-ylmethyl)amine, the title compound (0.33 g, 75%) was prepared as a white powder: $^1$H NMR (300 MHz, DMSO-d$_6$) δ 12.15-11.20 (m, 2H), 8.82 (s, 1H), 8.33-8.29 (m, 1H), 7.93-7.89 (m, 1H), 7.65-7.19 (m, 4H), 5.14-4.89 (m, 2H), 4.27 (br s, 2H), 3.80 (br s, 2H), 3.18-2.96 (m, 3H), 2.86 (s, 3H), 2.40 (s, 3H); MS (ESI) m/e 439 (M+H)+.

Example 187

Preparation of (E)-N-(5-Chloro-3-methyl-benzo[b]thiophen-2-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (5-chloro-3-methyl-benzo[b]thiophen-2-ylmethyl)methylamine for the methyl-(1-propyl-naphthalen-2-ylmethyl)amine, the title compound (0.39 g, 75%) was prepared as an off-white powder: $^1$H NMR (300 MHz, DMSO-d$_6$) δ 11.90-11.25 (m, 2H), 8.85 (s, 1H), 8.34-8.31 (m, 1H), 7.94-7.32 (m, 5H), 5.15-4.90 (m, 2H), 4.31 (br s, 2H), 3.83 (br s, 2H), 3.18-2.89 (m, 6H), 2.38 (s, 3H); MS (ESI) m/e 455 (M+H)+.

Example 188

Preparation of (E)-3-(6-Amino-5-morpholin-4-ylmethyl-pyridin-3-yl)-N-(1,7-dimethyl-1H-indol-2-ylmethyl)-N-methyl-acrylamide hydrochloride According to the procedure of Example 1, except substituting (1,7-dimethyl-1H-indol-2-ylmethyl)methylamine for the methyl-(1-propyl-naphthalen-2-ylmethyl)amine, and substituting (E)-3-(6-amino-5-morpholin-4-ylmethyl-pyridin-3-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.31 g, 80%) was prepared as pale yellow powder: $^1$H NMR (300 MHz, DMSO-d$_6$) δ 8.49 (s, 1H), 8.38-8.35 (m, 1H), 7.54-7.49 (m, 1H), 7.31-7.14 (m, 2H), 6.85-6.81 (m, 2H), 6.37-6.08 (m, 1H), 5.03-4.81 (m, 2H), 4.31 (br s, 2H), 3.96-3.72 (m, 7H), 3.42-2.99 (m, 10H), 2.72 (s, 3H); MS (ESI) m/e 434 (M+H)+.

Example 189

Preparation of (E)-3-(6-Amino-5-morpholin-4-ylmethyl-Pyridin-3-yl)-N-(2-ethoxy-3-methoxy-benzyl)-N-methyl-acrylamide hydrochloride According to the procedure of Example 1, except substituting (2-ethoxy-3-methoxy-benzyl)methylamine for the methyl-(1-propyl-naphthalen-2-ylmethyl)amine, and substituting (E)-3-(6-amino-5-morpholin-4-ylmethyl-pyridin-3-yl)acrylic acid hydrochloride for the (E)-3-(4-methyl-2-oxo-2,3,4,5-tetrahydro-1H-pyrido[2,3-e][1,4]diazepin-7-yl) acrylic acid hydrochloride, the title compound (0.27 g, 70%) was prepared as pale yellow powder: $^1$H NMR (300 MHz, DMSO-d$_6$) δ 8.83-8.65 (m, 1H), 8.40 (s, 1H), 7.52-7.45 (m, 1H), 7.29-7.24 (m, 1H), 7.04-6.96 (m, 2H), 6.65-6.64 (m, 1H), 4.80-4.64 (m, 2H), 4.35 (br s, 2H), 4.02-3.79 (m, 10H), 3.39-2.83 (m, 8H), 1.31-1.25 (m, 3H); MS (ESI) m/e 441 (M+H)+.

Example 190

Preparation of (E)-N-Methyl-N-(1-methyl-1H-indol-3-ylmethyl)-3-(4-methyl-2-oxo-2,3,4,5-tetrahydro-1H-pyrido[2,3-e][1,4]diazepin-7-yl)acrylamide According to the procedure of Example 1 (a), except substituting methyl-(1-methyl-1H-indol-3-ylmethyl)amine for the methyl-(1-propyl-naphthalen-2-ylmethyl)amine, the title compound (0.70 g, 75%) was prepared as an off-white powder and as a mixture of amide rotamers: $^1$H NMR (300 MHz, CDCl$_3$) δ 8.39-8.26 (m, 2H), 7.72-7.53 (m, 3H), 7.36-7.09 (m, 3H), 7.02-6.84 (m, 1H), 4.86-4.84 (m, 2H), 3.95-3.90 (m, 2H), 3.78-3.76 (m, 5H), 3.13-3.08 (m, 3H), 2.49-2.46 (m, 3H); MS (ESI) m/e 404 (M+H)$^+$.

Example 191

Preparation of (E)-7-{2-[Methyl-(1-methyl-1H-indol-3-ylmethyl)-carbamoyl]-vinyl}-2-oxo-1,2,3,5-tetrahydro-pyrido[2,3-e][1,4]diazepine-4-carboxylic acid benzyl ester According to the procedure of Example 1 (a), except substituting methyl-(1-methyl-1H-indol-3-ylmethyl)amine for the methyl-(1-propyl-naphthalen-2-ylmethyl)amine, and substituting (E)-7-(2-carboxy-vinyl)-2-oxo-1,2,3,5-tetrahydro-pyrido[2,3-e][1,4]diazepine-4-carboxylic acid benzyl ester hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.29 g, 73%) was prepared as an off-white powder and as a mixture of amide rotamers: $^1$H NMR (300 MHz, DMSO-d$_6$) δ 10.43 (s, 1H), 8.51 (s, 1H), 8.11-8.25 (m, 1H), 7.53-7.64 (m, 2H), 7.30-7.42 (m, 5H), 7.12-7.20 (m, 4H), 6.98-7.03 (m, 1H), 5.03-5.08 (m, 2H), 4.75-4.93 (m, 2H), 4.62 (s, 2H), 4.41 (s, 2H), 3.73-3.77 (m, 3H), 2.91-3.06 (m, 3H); MS (ESI) m/e 524 (M+H)$^+$.

Example 192

Preparation of (E)-3-(2,4-Dioxo-1,2,3,4-tetrahydro-pyrido[2,3-d]pyrimidin-6-yl)-N-methyl-N-(1-methyl-1H-indol-3-ylmethyl)acrylamide According to the procedure of Example 1 (a), except substituting methyl-(1-methyl-1H-indol-3-ylmethyl)amine for the methyl-(1-propyl-naphthalen-2-ylmethyl)amine, and substituting (E)-3-(2,4-dioxo-1,2,3,4-tetrahydro-pyrido[2,3-d]pyrimidin-6-yl)acrylic acid for the (E)-3-(4-methyl-2-oxo-2,3,4,5-tetrahydro-1H-pyrido[2,3-e][1,4]diazepin-7-yl) acrylic acid hydrochloride, the title compound (0.16 g, 34%) was prepared as a tan solid and as a mixture of amide rotamers; $^1$H NMR (300 MHz, DMSO-d$_6$) δ 11.84 (s, 1H), 11.53 (s, 1H), 8.91 (s, 1H), 8.73-8.66 (m, 1H), 7.78-7.30 (m, 5H), 7.17-7.12 (m, 1H), 7.03-6.98 (m, 1H), 4.96-4.73 (m, 2H), 3.76 (s, 3H), 3.07-2.90 (m, 3H); MS (ESI) m/e 390 (M+H)$^+$.

Example 193

Preparation of (E)-N-Methyl-N-(1-methyl-1H-indol-2-ylmethyl)-3-(2-oxo-2,3-dihydro-oxazolo[4,5-b]pyridin-6-yl)acrylamide According to the procedure of Example 1 (a), except substituting methyl-(1-methyl-1H-indol-2-ylmethyl)amine for the methyl-(1-propyl-naphthalen-2-ylmethyl)amine, and substituting (E)-3-(2-oxo-2,3-dihydro-oxazolo[4,5-b]pyridine-6-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.23 g, 34%) was prepared as an off-white solid and as a mixture of amide rotamers: $^1$H NMR (300 MHz, DMSO-d$_6$) δ 12.64 (br s, 1H), 8.37-8.12 (m, 2H), 7.64 (d, J=15.3 Hz, 1H), 7.51-7.26 (m, 3H), 7.17-7.07 (m, 1H), 7.04-6.94 (m, 1H), 6.42-6.17 (m, 1H), 5.06-4.85 (m, 2H), 3.73-3.68 (m, 3H), 3.12-2.99 (m, 3H); MS (ESI) m/e 363 (M+H)$^+$.

Example 194

Preparation of (E)-N-Methyl-N-(1-methyl-1H-indol-3-ylmethyl)-3-(2-oxo-2,3-dihydro-oxazolo[4,5-b]pyridin-6-yl)acrylamide According to the procedure of Example 1 (a), except substituting methyl-(1-methyl-1H-indol-3-ylmethyl)amine for the methyl-(1-propyl-naphthalen-2-ylmethyl)amine, and substituting (E)-3-(2-oxo-2,3-dihydro-oxazolo[4,5-b]pyridine-6-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.075 g, 23%) was prepared as a light brown solid: $^1$H NMR (300 MHz, CDCl$_3$) δ 8.28-8.24 (m, 1H), 7.82 (d, J=15.4 Hz, 1H), 7.71-7.49 (m, 2H), 7.37-6.87 (m, 5H), 4.88-4.86 (m, 2H), 3.78 (s, 3H), 3.16-3.12 (m, 3H); MS (ESI) m/e 363 (M+H)$^+$.

Example 195

Preparation of (E)-3-(6-Amino-5-{2-[methyl-(1-methyl-1H-indol-2-ylmethyl)carbamoyl]ethyl}pyridin-3-yl)-N-methyl-N-(1-methyl-1H-indol-2-ylmethyl)acrylamide According to the procedure of Example 1 (a), except substituting methyl-(1-methyl-1H-indol-2-ylmethyl)amine for the methyl-(1-propyl-naphthalen-2-ylmethyl)amine, and substituting (E)-3-[6-amino-5-(2-carboxy-ethyl)pyridin-3-yl]acrylic acid for the (E)-3-(4-methyl-2-oxo-2,3,4,5-tetrahydro-1H-pyrido[2,3-e][1,4]diazepin-7-yl)acrylic acid hydrochloride, the title compound (0.37 g, 28%) was prepared as an off-white powder and as a mixture of amide rotamers: $^1$H NMR (300 MHz, DMSO-d$_6$) δ 8.07 (m, 1H), 7.75-7.68 (m, 1H), 7.49-7.34 (m, 5H), 7.11-6.98 (m, 5H), 6.39-6.12 (m, 4H), 4.95-4.68 (m, 4H), 3.69 (s, 3H), 3.61 (s, 3H), 3.02-2.71 (m, 10H); MS (ESI) m/e 549 (M+H)$^+$.

Example 196

Preparation of (E)-3-(6-Amino-5-piperidin-1-ylmethyl-pyridin-3-yl)-N-methyl-N-(1-methyl-1H-indol-2-ylmethyl)acrylamide According to the procedure of Example 1 (a), except substituting (E)-3-(6-amino-5-piperidin-1-ylmethyl-pyridin-3-yl)acrylic acid hydrochloride for the (E)-3-(4-methyl-2-oxo-2,3,4,5-tetrahydro-1H-pyrido[2,3-e][1,4]diazepin-7-yl) acrylic acid hydrochloride, and substituting methyl-(1-methyl-1H-indol-2-ylmethyl)amine for the methyl-(1-propyl-naphthalen-2-ylmethyl)amine, the title compound (294 mg, 54%) was prepared as an off-white powder and as a mixture of amide rotamers: $^1$H NMR (300 MHz, DMSO-d$_6$) δ 8.12 (s, 1H), 7.78-7.68 (m, 1H), 7.49-7.38 (m, 3H), 7.14-6.97 (m, 3H), 6.63 (s, 2H), 6.41-6.18 (m, 1H), 5.02-4.83 (m, 2H), 3.72-3.67 (m, 3H), 3.39-3.34 (m, 3H), 3.09-2.96 (m, 3H), 2.29 (br s, 3H), 1.49-1.40 (m, 6H); MS (ESI) m/e 418 (M+H)$^+$.

Example 197

Preparation of (E)-3-(6-Amino-5-pyrrolidin-1-ylmethyl-pyridin-3-yl)-N-methyl-N-(1-methyl-1H-indol-2-ylmethyl)acrylamide hydrochloride According to the procedure of Example 1, except substituting (E)-3-(6-amino-5-pyrrolidin-1-ylmethyl-pyridin-3-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(1-methyl-1H-indol-2-ylmethyl)amine for the methyl-(1-propyl-naphthalen-2-ylmethyl)amine, the title compound (223 mg, 82%) was prepared as a light, yellow powder and as a mixture of amide rotamers: $^1$H NMR (300 MHz, DMSO-$d_6$) δ 10.2 (br s, 1H), 8.35 (s, 1H), 8.21 (s, 1H), 7.52-7.39 (m, 3H), 7.24-7.01 (m, 4H), 6.41-6.16 (m, 1H), 5.05-4.85 (m, 2H), 4.29 (s, 2H), 3.74-3.68 (m, 3H), 3.10-3.00 (m, 6H), 2.10-1.82 (m, 5H); MS (ESI) m/e 404 (M+H)$^+$.

Example 198

Preparation of (E)-3-[6-Amino-5-(4-methyl-piperazin-1-ylmethyl)pyridin-3-yl]-N-methyl-N-(1-methyl-1H-indol-2-ylmethyl)acrylamide hydrochloride According to the procedure of Example 1, except substituting (E)-3-[6-amino-5-(4-methyl-piperazin-1-ylmethyl)-pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(1-methyl-1H-indol-2-ylmethyl)amine for the methyl-(1-propyl-naphthalen-2-ylmethyl)amine, the title compound (136 mg, 14%) was prepared as an off-white powder and as a mixture of amide rotamers: $^1$H NMR (300 MHz, DMSO-$d_6$) δ 10.7 (br s, 1H), 8.39 (s, 1H), 8.33 (s, 1H), 8.07 (br s, 2H), 7.55-7.01 (m, 6H), 6.41-6.17 (m, 1H), 5.07-4.85 (m, 2H), 3.73-3.62 (m, 7H), 3.11-2.98 (m, 8H), 2.73 (s, 3H); MS (ESI) m/e 433 (M+H)$^+$.

Example 199

Preparation of (E)-3-[6-Amino-5-(4-benzyl-piperidin-1-ylmethyl)pyridin-3-yl]-N-methyl-N-(1-methyl-1H-indol-2-ylmethyl)acrylamide hydrochloride According to the procedure of Example 1, except substituting (E)-3-[6-amino-5-(4-benzyl-piperidin-1-ylmethyl)-pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(1-methyl-1H-indol-2-ylmethyl)amine for the methyl-(1-propyl-naphthalen-2-ylmethyl)amine, the title compound (156 mg, 30%) was prepared as an off-white powder and as a mixture of amide rotamers: $^1$H NMR (300 MHz, DMSO-$d_6$) δ 8.36-8.25 (m, 2H), 7.52-6.98 (m, 14H), 6.40-6.15 (m, 1H), 5.05-4.84 (m, 2H), 4.20 (s, 2H), 3.74-3.67 (m, 3H), 3.58-5.30 (m, 8H), 3.10-2.73 (m, 6H); MS (ESI) m/e 508 (M+H)$^+$.

Example 200

Preparation of (E)-3-(6-Amino-5-pyrrolidin-1-ylmethyl-pyridin-3-yl)-N-methyl-N-naphthalen-2-ylmethyl-acrylamide hydrochloride According to the procedure of Example 1, except substituting (E)-3-(6-amino-5-pyrrolidin-1-ylmethyl-pyridin-3-yl) acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-naphthalen-2-ylmethyl-amine for the methyl-(1-propyl-naphthalen-2-ylmethyl)amine, the title compound (51 mg, 57%) was prepared as a light, yellow solid and as a mixture of amide rotamers: $^1$H NMR (300 MHz, DMSO-$d_6$) δ 8.36-8.25 (m, 2H), 7.52-6.98 (m, 4H), 6.40-6.15 (m, 1H), 5.05-4.84 (m, 2H), 4.20 (s, 2H), 3.74-3.67 (m, 3H), 3.58-5.30 (m, 8H), 3.10-2.73 (m, 6H); MS (ESI) m/e 401 (M+H)$^+$.

Example 201

Preparation of (E)-3-[6-Amino-5-(4-methyl-piperazin-1-ylmethyl)pyridin-3-yl]-N-methyl-N-(3-methyl-benzo[b]thiophen-2-ylmethyl)acrylamide hydrochloride According to the procedure of Example 1, except substituting (E)-3-[6-amino-5-(4-methyl-piperazin-1-ylmethyl)pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(3-methyl-benzo[b]thiophen-2-ylmethyl)amine for the methyl-(1-propyl-naphthalen-2-ylmethyl)amine, the title compound (101 mg, 46%) was prepared as a light, yellow powder and as a mixture of amide rotamers: $^1$H NMR (300 MHz, DMSO-$d_6$) δ 10.6 (br s, 1H), 8.27 (s, 1H), 8.16 (s, 1H), 7.87 (d, J=7.6 Hz, 1H), 7.73 (d, J=7.1 Hz, 1H), 7.52-7.28 (m, 5H), 7.11 (d, J=15.3 Hz, 1H), 5.11-4.89 (m, 2H), 3.55 (br s, 2H), 3.37-3.23 (m, 4H), 3.14 (s, 2H), 3.10-2.92 (m, 5H), 2.72 (s, 3H), 2.42 (s, 3H); MS (ESI) m/e 450 (M+H)$^+$.

Example 202

Preparation of (E)-3-(6-Amino-5-morpholin-4-ylmethyl-pyridin-3-yl)-N-methyl-N-(4-methyl-naphthalen-1-ylmethyl)acrylamide hydrochloride According to the procedure of Example 1, except substituting (E)-3-(6-amino-5-morpholin-4-ylmethyl-pyridin-3-yl)acrylic acid hydrochloride for the (E)-3-(4-methyl-2-oxo-2,3,4,5-tetrahydro-1H-pyrido[2,3-e][1,4]diazepin-7-yl) acrylic acid hydrochloride, and substituting methyl-N-(4-methyl-naphthalen-1-ylmethyl)amine for the methyl-(1-propyl-naphthalen-2-ylmethyl)amine, the title compound (66 mg, 62%) was prepared as a pale, yellow powder and as a mixture of amide rotamers: $^1$H NMR (300 MHz, DMSO-$d_6$) δ 8.61-8.35 (m, 2H), 8.14-8.05 (m, 2H), 7.61-7.52 (m, 3H), 7.36-7.03 (m, 3H), 5.30-5.07 (m, 2H), 4.45-4.23 (m, 2H), 3.94-3.65 (m, 6H), 3.45-3.17 (m, 4H), 3.04-2.94 (m, 4H), 2.65 (s, 3H); MS (ESI) m/e 431 (M+H)$^+$.

Example 203

Preparation of (E)-3-(6-Amino-5-morpholin-4-ylmethyl-pyridin-3-yl)-N-methyl-N-(3-methyl-benzo[b]thiophen-2-ylmethyl)acrylamide hydrochloride According to the procedure of Example 1, except substituting (E)-3-(6-amino-5-morpholin-4-ylmethyl-pyridin-3-yl)acrylic acid for the (E)-3-(4-methyl-2-oxo-2,3,4,5-tetrahydro-1H-pyrido[2,3-e][1,4]diazepin-7-yl)acrylic acid hydrochloride, and substituting methyl-N-(3-methyl-benzo[b]thiophen-2-ylmethyl)amine for the methyl-(1-propyl-naphthalen-2-ylmethyl)amine, the title compound (111 mg, 67%) was prepared as a pale, yellow solid and as a mixture of amide rotamers: $^1$H NMR (300 MHz, DMSO-d$_6$) δ 8.60 (br s, 1H), 8.40 (s, 1H), 7.87 (d, J=7.4 Hz, 1H), 7.73 (d, J=6.9 Hz, 1H), 7.51 (d, J=15.3 Hz, 1H), 7.42-7.15 (m, 3H), 5.12-4.88 (m, 2H), 3.91-3.35 (m, 12H), 3.15 (s, 3H), 2.93 (s, 1H), 2.41 (s, 3H); MS (ESI) m/e 437 (M+H)$^+$;

Example 204

Preparation of (E)-3-(6-Amino-5-morpholin-4-ylmethyl-pyridin-3-yl)-N-(3,4-dimethyl-thieno[2,3-b]thiophen-2-ylmethyl)-N-methyl-acrylamide hydrochloride According the procedure of Example 1, except substituting (E)-3-(6-amino-5-morpholin-4-ylmethyl-pyridin-3-yl) acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting (3,4-dimethyl-thieno[2,3-b]thiophen-2-ylmethyl)methylamine for the methyl-(1-propyl-naphthalen-2-ylmethyl)amine, the title compound was prepared (70 mg, 13%) as a light, yellow powder and as a mixture of amide rotamers: $^1$H NMR (300 MHz, DMSO-d$_6$) δ 8.63 (s, 1H), 8.40 (s, 1H), 7.51 (d, J=15.1 Hz, 1H), 7.20-7.12 (m, 2H), 5.00-4.77 (m, 2H), 4.40-4.32 (m, 2H), 3.95-3.15 (m, 10H), 3.13 (s, 3H), 2.90 (s, 1H), 2.46 (s, 3H), 2.45 (s, 3H); MS (ESI) m/e 457 (M+H)$^+$.

Example 205

Preparation of (E)-3-[6-Amino-5-(4-methyl-piperazin-1-ylmethyl)pyridin-3-yl]-N-(2-ethoxy-3-methoxy-benzyl)-N-methyl-acrylamide hydrochloride According to the procedure of Example 1, except substituting (E)-3-[6-amino-5-(4-methyl-piperazin-1-ylmethyl)pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting (2-ethoxy-3-methoxy-benzyl)methylamine for the methyl-(1-propyl-naphthalen-2-ylmethyl)amine, the title compound (177 mg, 25%) was prepared as a pale, yellow solid and as a mixture of amide rotamers: $^1$H NMR (300 MHz, DMSO-d$_6$) δ 10.4 (s, 1H), 8.28-8.19 (m, 2H), 7.73 (s, 1H), 7.47 (d, J=15.3 Hz, 1H), 7.21 (dd, J=14.9, 5.4 Hz, 1H), 7.05-6.94 (m, 2H), 6.64 (dd, J=7.2, 7.2 Hz, 1H), 4.78-4.63 (m, 2H), 4.03-3.93 (m, 2H), 3.79 (s, 3H), 3.55-3.33 (m, 7H), 3.09-2.85 (m, 7H), 2.74 (s, 3H), 1.31-1.25 (m, 3H); MS (ESI) m/e 454 (M+H)$^+$.

Example 206

Preparation of (E)-3-[6-Amino-5-(4-methyl-piperazin-1-ylmethyl)pyridin-3-yl]-N-methyl-N-(4-methyl-naphthalen-1-ylmethyl)acrylamide hydrochloride According to the procedure of Example 1, except substituting (E)-3-[6-amino-5-(4-methyl-piperazin-1-ylmethyl)pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(4-methyl-naphthalen-1-ylmethyl)amine for the methyl-(1-propyl-naphthalen-2-ylmethyl)amine, the title compound (143 mg, 20%) was prepared as a pale, yellow solid and as a mixture of amide rotamers: $^1$H NMR (300 MHz, DMSO-d$_6$) δ 10.9 (s, 1H), 8.35-8.29 (m, 2H), 8.18-8.05 (m, 4H), 7.65-7.52 (m, 3H), 7.41-7.03 (m, 3H), 5.30-5.07 (m, 2H), 3.63-3.33 (m, 6H), 3.04-2.95 (m, 7H), 2.72-2.65 (m, 6H); MS (ESI) m/e 444 (M+H)$^+$.

Example 207

Preparation of (E)-3-[6-Amino-5-(4-methyl-piperazin-1-ylmethyl)pyridin-3-yl]-N-benzofuran-2-ylmethyl-N-methyl-acrylamide hydrochloride According to the procedure of Example 1, except substituting (E)-3-[6-amino-5-(4-methyl-piperazin-1-ylmethyl)pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting benzofuran-2-ylmethyl-methylamine for the methyl-(1-propyl-naphthalen-2-ylmethyl)amine, the title compound (158 mg, 20%) was prepared as an off-white solid and as a mixture of amide rotamers: $^1$H NMR (300 MHz, DMSO-d$_6$) δ 10.7 (s, 1H), 8.35-8.33 (m, 2H), 7.99 (br s, 2H), 7.62-7.19 (m, 6H), 6.82 (d, J=12.2 Hz, 1H), 5.01-4.80 (m, 2H), 3.62-3.25 (m, 6H), 3.22 (s, 2H), 3.10-2.92 (m, 5H), 2.73 (s, 3H); MS (ESI) m/e 420 (M+H)$^+$.

Example 208

Preparation of (E)-3-[6-Amino-5-(4-methyl-piperazin-1-ylmethyl)pyridin-3-yl]-N-(3-methoxy-2-propoxy-benzyl)-N-methyl-acrylamide hydrochloride According to the procedure of Example 1, except substituting (E)-3-[6-amino-5-(4-methyl-piperazin-1-ylmethyl)pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting (3-methoxy-2-propoxy-benzyl)methylamine for the methyl-(1-propyl-naphthalen-2-ylmethyl)amine, the title compound (50 mg, 6%) was prepared as an off-white solid and as a mixture of amide rotamers: $^1$H NMR (300 MHz, DMSO-d$_6$) δ 10.6 (br s, 1H), 8.16 (d, J=9.2 Hz, 1H), 7.86 (s, 1H), 7.43 (d, J=15.2 Hz, 1H), 7.08-6.93 (m, 3H), 6.70-6.63 (m, 3H), 4.77-4.63 (m, 2H), 3.87 (q, J=6.8 Hz, 2H), 3.79 (s, 3H), 3.48-3.31 (m, 5H), 3.09-2.86 (m, 6H), 2.72 (s, 3H), 2.44-2.35 (m, 2H), 1.71 (app sextet, J=7.0 Hz, 2H), 0.98 (t, J=7.3 Hz, 3H); MS (ESI) m/e 468 (M+H)$^+$.

Example 209

Preparation of (E)-3-[6-Amino-5-(4-methyl-piperazin-1-ylmethyl)pyridin-3-yl]-N-(2-ethoxy-3-methyl-benzyl)-N-methyl-acrylamide hydrochloride According to the procedure of Example 1, except substituting (E)-3-[6-amino-5-(4-methyl-piperazin-1-ylmethyl)pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting (3-methyl-2-ethoxy-benzyl)methylamine for the methyl-(1-propyl-naphthalen-2-ylmethyl)amine, the title compound (114 mg, 17%) was prepared as an off-white solid: $^1$H NMR (300 MHz, DMSO-d$_6$) δ 8.42 (s, 1H), 8.33 (d, J=6.0 Hz, 1H), 8.13 (br s, 2H), 7.48 (dd, J=10.0, 5.1 Hz, 1H), 7.27 (d, J=9.3 Hz, 1H), 7.13 (dd, J=10.6, 4.4 Hz, 1H), 7.04-6.97 (m, 1H), 6.90-6.87 (m, 1H), 4.81-4.66 (m, 2H), 3.87-3.81 (m, 2H), 3.63-3.36 (m, 7H), 3.10-2.85 (m, 7H), 2.72 (s, 3H), 2.24 (s, 3H), 1.35 (t, J=4.2 Hz, 3H); MS (ESI) m/e 438 (M+H)$^+$.

Example 210

Preparation of (E)-N-(3-Methoxy-2-propoxy-benzyl)-N-methyl-3-(7-oxo-5,6,7,8-tetrahydro-[1,8]naphthyridin-3-yl)acrylamide hydrochloride According to the procedure of Example 1, except substituting (E)-3-(7-oxo-5,6,7,8-tetrahydro-[1,8]naphthyridin-3-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting (3-methoxy-2-propoxy-benzyl)methylamine for the methyl-(1-propyl-naphthalen-2-ylmethyl)amine, the title compound (193 mg, 22%) was prepared as a white solid and as a mixture of amide rotamers: $^1$H NMR (300 MHz, DMSO-$d_6$) δ 10.6 (s, 1H), 8.35 (d, J=14.1 Hz, 1H), 8.09-8.01 (m, 1H), 7.50 (dd, J=15.2, 2.5 Hz, 1H), 7.24 (d, J=15.3 Hz, 1H), 7.07-6.94 (m, 2H), 6.67-6.62 (m, 1H), 5.43 (br s, 1H), 4.79-4.64 (m, 2H), 3.87 (q, J=6.9 Hz, 2H), 3.79 (s, 3H), 3.10-2.86 (m, 5H), 2.56-2.45 (m, 2H), 1.71 (app sextet, J=7.1 Hz, 2H), 0.97 (q, J=7.3 Hz, 3H); MS (ESI) m/e 410 (M+H)$^+$.

Example 211

Preparation of (E)-N-(2-Isopropoxy-3-methoxy-benzyl)-N-methyl-3-(7-oxo-5,6,7,8-tetrahydro-[1,8]naphthyridin-3-yl)acrylamide hydrochloride According to the procedure of Example 1, except substituting (E)-3-(7-oxo-5,6,7,8-tetrahydro-[1,8]naphthyridin-3-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting (2-isopropoxy-3-methoxy-benzyl)methylamine for the methyl-(1-propyl-naphthalen-2-ylmethyl)amine, the title compound (326 mg, 83%) was prepared as a white solid and as a mixture of amide rotamers: $^1$H NMR (300 MHz, DMSO-$d_6$) δ 10.6 (s, 1H), 8.36 (d, J=17.3 Hz, 1H), 8.10-7.98 (m, 1H), 7.50 (d, J=15.3 Hz, 1H), 7.28-7.17 (m, 1H), 7.05-6.93 (m, 2H), 6.63 (dd, J=7.3, 7.3 Hz, 1H), 5.77 (br s, 1H), 4.77-4.63 (m, 2H), 4.59-4.45 (m, 1H), 3.79 (s, 3H), 3.08-2.81 (m, 5H), 2.56-2.44 (m, 2H), 1.23 (t, J=5.7 Hz, 6H); MS (ESI) m/e 410 (M+H)$^+$.

Example 212

Preparation of (E)-N-(2-Ethoxy-3-methoxy-benzyl)-N-methyl-3-(7-oxo-5,6,7,8-tetrahydro-[1,8]naphthyridin-3-yl)acrylamide hydrochloride According to the procedure of Example 1, except substituting (E)-3-(7-oxo-5,6,7,8-tetrahydro-[1,8]naphthyridin-3-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting (2-ethoxy-3-methoxy-benzyl)methylamine for the methyl-(1-propyl-naphthalen-2-ylmethyl)amine, the title compound (429 mg, 88%) was prepared as an off-white solid and as a mixture of amide rotamers: $^1$H NMR (300 MHz, DMSO-$d_6$) δ 10.6 (s, 1H), 8.34 (d, J=13.2 Hz, 1H), 8.08-8.01 (m, 1H), 7.50 (dd, J=9.2, 2.0 Hz, 1H), 7.25 (dd, J=9.3, 5.5 Hz, 1H), 7.06-6.94 (m, 2H), 6.67 (dd, J=11.4, 4.7 Hz, 1H), 4.91 (br s, 1H), 4.78-4.64 (m, 2H), 4.02-3.95 (m, 2H), 3.79 (s, 3H), 3.09-2.86 (m, 5H), 2.55-2.49 (m, 2H), 1.30-1.26 (m, 3H); MS (ESI) m/e 396 (M+H)$^+$.

Example 213

Preparation of (E)-3-[6-(2,5-Dioxo-pyrrolidin-1-yl)pyridin-3-yl]-N-methyl-N-(1-methyl-1H-indol-2-ylmethyl)acrylamide A solution of 3-(6-aminopyridin-3-yl)-N-methyl-N-(1-methyl-1H-indol-2-ylmethyl)acrylamide (1.40 g, 4.37 mol) and succinic anhydride (520 mg, 5.24 mmol) in 1,4-dioxane (50 mL) was heated to reflux for 5 h. Another portion of succinic anhydride (520 mg, 5.24 mmol) was then added, and the solution was maintained at reflux overnight. The solvent was removed in vacuo. The residue was dissolved in $CH_2Cl_2$, and the solution was washed with satd $NaHCO_3$, water and brine, dried over $Na_2SO_4$, and concentrated. Purification by column chromatography (silica gel, $CH_2Cl_2$/MeOH, 98:2 to 97:3) gave the title compound (1.40 g, 76%) as an off-white solid and as a mixture of amide rotamers: mp 185-187° C.; $^1$H NMR (300 MHz, DMSO-$d_6$) δ 8.92-8.88 (m, 1H), 8.41-8.32 (m, 1H), 7.69-7.64 (m, 1H), 7.52-7.34 (m, 4H), 7.15-7.09 (m, 1H), 7.04-6.99 (m, 1H), 6.44-6.21 (m, 1H), 5.08-4.87 (m, 2H), 3.73-3.70 (m, 3H), 3.14-3.00 (m, 3H), 2.83-2.81 (m, 4H); MS (ESI) m/e 403 (M+H)$^+$.

Example 214

Preparation of (E)-N-(5-{2-[Methyl-(1-methyl-1H-indol-2-ylmethyl)carbamoyl]vinyl}pyridin-2-yl)succinamide A mixture of (E)-3-[6-(2,5-dioxo-pyrrolidin-1-yl)pyridin-3-yl]-N-methyl-N-(1-methyl-1H-indol-2-ylmethyl)acrylamide (260 mg, 0.645 mmol) and ammonia (12 mL of 0.5M solution in 1,4-dioxane, 6.0 mmol) in a sealed tube was heated to 60° C. overnight. After cooling to ambient temperature, the resulting white precipitate was collected by filtration. The resulting solid was triturated with MeOH, washed with $Et_2O$, and dried under high vacuum at 50° C. for 2 d to give the title compound (140 mg, 52%) as a white solid and as a mixture of amide rotamers: mp 225-227° C.; $^1$H NMR (300 MHz, DMSO-$d_6$) δ 10.67-10.63 (m, 1H), 8.62-8.58 (m, 1H), 8.21-8.07 (m, 2H), 7.60-7.25 (m, 5H), 7.12 (dd, J=7.7, 7.4 Hz, 1H), 7.00 (dd, J=7.3, 6.9 Hz, 1H), 6.77 (br s, 1H), 6.42-6.17 (m, 1H), 5.05-4.85 (m, 2H), 3.72-3.68 (m, 3H), 3.12-2.99 (m, 3H), 2.64-2.60 (m, 2H), 2.40-2.36 (m, 2H); MS (ESI) m/e 420 (M+H)$^+$.

Example 215

Preparation of (E)-N-(5-{2-[Methyl-(1-methyl-1H-indol-2-Ylmethyl)carbamoyl]vinyl}pyridin-2-yl)-4-(4-methyl-piperazin-1-yl)-4-oxo-butyramide According to the procedure of Example 110, except substituting 1-methylpiperazine for the ammonia, the title compound (250 mg, 77%) was prepared as a light yellow solid and as a mixture of amide rotamers, after silica gel chromatography: mp 145-147° C. dec; $^1$H NMR (300 MHz, DMSO-$d_6$) δ 10.70-10.66 (m, 1H), 8.62-8.58 (m, 1H), 8.21-8.07 (m, 2H), 7.60-7.25 (m, 4H), 7.12-7.10 (m, 1H), 7.03-6.98 (m, 1H), 6.42-6.17 (m, 1H), 5.06-4.85 (m, 2H), 3.72-3.68 (m, 3H), 3.48 (br s, 4H), 3.12-2.99 (m, 3H), 2.63-2.26 (m, 11H); MS (ESI) m/e 503 (M+H)$^+$.

Example 216

Preparation of (E)-N-(5-{2-[Methyl-(1-methyl-1H-indol-2-ylmethyl)carbamoyl]vinyl}pyridin-2-yl)-4-morpholin-4-yl-4-oxo-butyramide According to the procedure of Example 110, except substituting morpholine for the ammonia, the title compound (200 mg, 57%) was prepared as a light yellow solid and as a mixture of amide rotamers: mp 206-209° C. dec; $^1$H NMR (300 MHz, DMSO-d$_6$) δ 10.70-10.66 (m, 1H), 8.62-8.58 (m, 1H), 8.21-8.07 (m, 2H), 7.60-7.39 (m, 3H), 7.34-7.25 (m, 1H), 7.12 (dd, J=7.4, 7.2 Hz, 1H), 7.03 (dd, J=7.3, 7.2 Hz, 1H), 6.42-6.17 (m, 1H), 5.06-4.85 (m, 2H), 3.72-3.68 (m, 3H), 3.57-3.37 (m, 8H), 3.12-2.99 (m, 3H), 2.70-2.56 (m, 4H); MS (ESI) m/e 490 (M+H)$^+$.

Example 217

Preparation of (E)-1-Methyl-piperidine-4-carboxylic acid (5-{2-[methyl-(1-methyl-1H-indol-2-ylmethyl)carbamoyl]vinyl}pyridin-2-yl)amide A solution of 1-methylpiperidine-4-carboxylic acid hydrochloride (184 mg, 1.03 mmol), 1,1'-carbonyldiimidazole (167 mg, 1.03 mmol) and triethylamine (0.26 mL, 1.8 mol) in 1,4-dioxane (20 mL) was heated to reflux for 3 h. (E)-3-(6-Aminopyridin-3-yl)-N-methyl-N-(1-methyl-1H-indol-2-ylmethyl)acrylamide (300 mg, 0.936 mmol) was then added and the resulting solution was heated to reflux overnight. TLC analysis indicated remaining starting material. After cooling, additional 1-methylpiperidine-4-carboxylic acid (184 mg, 1.03 mmol) and 1,1'-carbonyldiimidazole (167 mg, 1.03 mmol) were added, and the solution was heated to reflux overnight. The solvent was removed in vacuo. The residue was dissolved in CH$_2$Cl$_2$ (100 mL), and the solution was washed with satd NaHCO$_3$, water and brine, dried over Na$_2$SO$_4$ and concentrated. Purification by column chromatography (silica gel, CH$_2$Cl$_2$/MeOH/Et$_3$N, 94:5:1 to 89:10:1) gave the title compound (330 mg, 79%) as a pale yellow solid and as a mixture of amide rotamers: mp 120-135° C. dec; $^1$H NMR (300 MHz, DMSO-d$_6$) δ 10.65-10.61 (m, 1H), 8.62-8.57 (m, 1H), 8.23-8.06 (m, 2H), 7.60-7.34 (m, 3H), 7.31-7.25 (m, 1H), 7.12 (dd, J=8.0, 7.2 Hz, 1H), 7.03-6.98 (m, 1H), 6.42-6.16 (m, 1H), 5.06-4.85 (m, 2H), 3.72-3.68 (m, 3H), 3.12-2.99 (m, 3H), 2.85-2.82 (m, 2H), 2.52-2.44 (m, 1H), 2.19 (s, 3H), 1.95-1.88 (m, 2H), 1.74-1.61 (m, 4H); MS (ESI) m/e 446 (M+H)$^+$.

Example 218

Preparation of (E)-N-Methyl-N-(1-methyl-1H-indol-2-ylmethyl)-3-[6-(2-pyridin-4-yl-acetylamino)pyridin-3-yl]acrylamide According to the procedure of Example 113, except substituting 4-pyridylacetic acid hydrochloride for the 1-methylpiperidine-4-carboxylic acid hydrochloride, the title compound (140 mg, 34%) was prepared as a light yellow solid: $^1$H NMR (300 MHz, DMSO-d$_6$) δ 11.04-10.99 (m, 1H), 8.66-8.62 (m, 1H), 8.53-8.52 (m, 2H), 8.23-8.02 (m, 2H), 7.61-7.27 (m, 6H), 7.15-7.10 (m, 1H), 7.04-6.99 (m, 1H), 6.42-6.17 (m, 1H), 5.06-4.86 (m, 2H), 3.83-3.68 (m, 5H), 3.12-3.00 (m, 3H); MS (ESI) m/e 440 (M+H)$^+$.

Example 219

Preparation of (E)-1-Acetyl-piperidine-4-carboxylic acid (5-{2-[methyl-(1-methyl-1H-indol-2-ylmethyl)carbamoyl]vinyl}pyridin-2-yl)amide a) (E)-4-(5-{2-[Methyl-(1-methyl-1H-indol-2-ylmethyl)carbamoyl]vinyl}pyridin-2-ylcarbamoyl)piperidine-1-carboxylic acid benzyl ester A solution of [1-(carbobenzoxy)-4-piperidine]carboxylic acid (250 mg, 0.950 mmol) and 1,1'-carbonyldiimidazole (162 mg, 1.00 mmol) in 1,4-dioxane (15 mL) was heated to reflux for 3 h. (E)-3-(6-Aminopyridin-3-yl)-N-methyl-N-(1-methyl-1H-indol-2-ylmethyl)acrylamide (304 mg, 0.950 mol) was then added and the resulting solution was heated to reflux overnight. TLC analysis indicated remaining starting material. After cooling, additional [1-(carbobenzoxy)-4-piperidine]carboxylic acid (250 mg, 0.950 mmol) and 1,1'-carbonyldiimidazole (162 mg, 1.00 mmol) were added, and the mixture was heated to reflux overnight. The solvent was removed in vacuo. The residue was dissolved in CH$_2$Cl$_2$ (100 mL), and the solution was washed with satd NaHCO$_3$, water and brine, dried over Na$_2$SO$_4$, and concentrated. Purification by column chromatography (silica gel, CH$_2$Cl$_2$/MeOH, 98:2 to 97:3) gave the title compound (420 mg, 78%) a white solid and as a mixture of amide rotamers: $^1$H NMR (300 MHz, CDCl$_3$) δ 8.40 (s, 1H), 8.24 (d, J=8.7 Hz, 1H), 7.97-7.88 (m, 2H), 7.72 (d, J=15.4 Hz, 1H), 7.59 (d, J=7.9 Hz, 1H), 7.36-7.20 (m, 7H), 7.11 (dd, J=7.7, 7.0 Hz, 1H), 6.89 (d, J=15.3 Hz, 1H), 6.50-6.40 (m, 1H), 5.14 (s, 2H), 4.93-4.82 (m, 2H), 4.40-4.10 (m, 2H), 3.72-3.69 (m, 3H), 3.12-3.07 (m, 3H), 2.93-2.88 (m, 2H), 2.50-2.42 (m, 1H), 2.00-1.70 (m, 4H); MS (ESI) m/e 566 (M+H)$^+$.

b) (E)-Piperidine-4-carboxylic acid (5-{2-[methyl-(1-methyl-1H-indol-2-ylmethyl) carbamoyl]vinyl}pyridin-2-yl)amide To a solution of (E)-4-(5-{2-[methyl-(1-methyl-1H-indol-2-ylmethyl)carbamoyl]vinyl}pyridin-2-ylcarbamoyl)piperidine-1-carboxylic acid benzyl ester (250 mg, 0.442 mmol) in CH$_2$Cl$_2$ (15 mL) was added trimethylsilyl iodide (0.25 mL, 1.8 mmol). The mixture was stirred at ambient temperature for 2 h, and then quenched by the addition of MeOH. The solvent was removed in vacuo. Purification by column chromatography (silica gel, CH$_2$Cl$_2$/MeOH/Et$_3$N, 94.5:5:0.5 to 89.5:10:0.5 to 74.5:35:0.5) gave the title compound (110 mg, 58%) as a white solid and as a mixture of amide rotamers: $^1$H NMR (300 MHz, DMSO-d$_6$) δ 10.59-10.55 (m, 1H), 8.62-8.57 (m, 1H), 8.19-8.09 (m, 2H), 7.60-7.25 (m, 4H), 7.18-7.09 (m, 1H), 7.12-6.98 (m, 1H), 6.42-6.17 (m, 1H), 5.06-4.85 (m, 2H), 3.72-3.68 (m, 3H), 2.99-2.94 (m, 3H), 2.60-2.42 (m, 5H), 1.70-1.65 (m, 2H), 1.50-1.45 (m, 2H).

c) (E)-1-Acetyl-piperidine-4-carboxylic acid (5-{2-[methyl-(1-methyl-1H-indol-2-ylmethyl)carbamoyl]vinyl}pyridin-2-yl)amide To a solution of (E)-piperidine-4-carboxylic acid (5-{2-[methyl-(1-methyl-1H-indol-2-ylmethyl)carbamoyl]vinyl}pyridin-2-yl)amide (80 mg, 0.18 mmol) in CH$_2$Cl$_2$ (5 mL) was added excess of triethylamine and acetic anhydride (58 mg, 0.56 mmol). The reaction mixture was stirred at ambient temperature overnight. The solvent was removed in vacuo. Purification by column chromatography (silica gel, CH$_2$Cl$_2$/MeOH/Et$_3$N, 96.5:3:0.5) gave the title compound (87 mg, 99%) as pale yellow solid and as a mixture of amide rotamers: mp=100-120° C. dec; $^1$H NMR (300 MHz, DMSO-d$_6$) δ 10.72-10.67 (m, 1H), 8.63-8.59 (m, 1H), 8.23-8.06 (m, 2H), 7.60-7.26 (m, 4H), 7.12 (dd, J=7.4, 7.3 Hz, 1H), 7.03-6.98 (m, 1H), 6.42-6.17 (m, 1H), 5.06-4.85 (m, 2H), 4.39 (d, J=11.8 Hz, 1H), 3.86 (d, J=11.6 Hz, 1H), 3.72-3.68 (m, 3H), 3.12-2.99 (m, 4H), 2.76 (m, 1H), 2.00 (s, 3H), 1.81-1.77 (m, 2H), 1.68-1.32 (m, 2H), 1.12-0.95 (m, 1H); MS (ESI) m/e 474 (M+H)$^+$.

Example 220

Preparation of (E)-3-(6-Amino-pyridin-3-yl)-N-(2,3-dimethoxy-benzyl)-N-methyl-acrylamide According to the procedure of Example 1 (a), except substituting (2,3-dimethoxy-benzyl)methyl-amine for the methyl-(1-propyl-naphthalen-2-ylmethyl)amine, and substituting (E)-3-(6-amino-pyridin-3-yl)acrylic acid for the (E)-3-(4-methyl-2-oxo-2,3,4,5-tetrahydro-1H-pyrido[2,3-e][1,4]diazepin-7-yl)acrylic acid hydrochloride, the title compound was prepared as a pale yellow solid (434 mg, 53%): $^1$H NMR (300 MHz, DMSO-d$_6$) δ 8.14 (d, J=11.3 Hz, 1H), 7.89-7.77 (m, 1H), 7.44-7.39 (m, 1H), 7.05-6.94 (m, 3H), 6.68-6.45 (m, 4H), 4.74-4.61 (m, 2H), 3.80 (s, 3H), 3.74 (s, 3H), 3.07-2.86 (m, 3H); MS (ESI) m/e 328 (M+H)$^+$.

Example 221

Preparation of (E)-N-(4-Acetylamino-benzyl)-3-(6-amino-pyridin-3-yl)-N-methyl-acrylamide According to the procedure of Example 1 (a), except substituting N-(4-methylaminomethyl-phenyl)acetamide for the methyl-(1-propyl-naphthalen-2-ylmethyl)amine, and substituting (E)-3-(6-amino-pyridin-3-yl)acrylic acid for the (E)-3-(4-methyl-2-oxo-2,3,4,5-tetrahydro-1H-pyrido[2,3-e][1,4]diazepin-7-yl)acrylic acid hydrochloride, the title compound was prepared as a pale yellow solid (200 mg, 25%): $^1$H NMR (300 MHz, DMSO-d$_6$) δ 9.93 (s, 1H), 8.15-8.13 (m, 1H), 7.86-7.79 (m, 1H), 7.54-7.39 (m, 3H), 7.15 (s, 2H), 7.03-6.93 (m, 1H), 6.46 (s, 3H), 4.70-4.53 (m, 2H), 3.04-2.87 (m, 3H), 2.02 (s, 3H); MS (ESI) m/e 325 (M+H)$^+$.

Example 222

Preparation of (E)-3-[3-(2-Dimethylamino-ethyl)-2-oxo-1,2,3,4-tetrahydro-pyrido[2,3-d]pyrimidin-6-yl]-N-methyl-N-(1-methyl-1H-indol-2-ylmethyl)acrylamide According to the procedure of Example 1 (a), except substituting (E)-3-[3-(2-dimethylamino-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(1-methyl-1H-indol-2-ylmethyl)amine for the methyl-(1-propyl-naphthalen-2-ylmethyl)amine, the title compound (40 mg, 22%) was prepared as a pale yellow solid: $^1$H NMR (300 MHz, DMSO-d$_6$) δ 9.98 (br s, 1H), 8.38-8.33 (m, 1H), 8.00-7.91 (m, 1H), 7.57-7.42 (m, 3H), 7.22-7.01 (m, 3H), 6.42-6.16 (m, 1H), 5.04-4.85 (m, 2H), 4.53-4.47 (m, 2H), 3.72-3.68 (m, 3H), 3.51-3.31 (m, 4H), 3.11-2.99 (m, 4H), 2.72-2.39 (m, 5H); MS (ESI) m/e 447 (M+H)$^+$.

Example 223

Preparation of (E)-N-Methyl-N-(1-methyl-1H-indol-2-ylmethyl)-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(1-methyl-1H-indol-2-ylmethyl)amine for the methyl-(1-propyl-naphthalen-2-ylmethyl)amine, the tide compound (355 mg, 61%) was prepared as a pale yellow solid: $^1$H NMR (300 MHz, DMSO-d$_6$) δ 10.16-9.98 (m, 2H), 8.42-8.37 (m, 1H), 8.00-7.92 (m, 1H), 7.58-7.39 (m, 3H), 7.24-6.99 (m, 3H), 6.42-6.15 (m, 1H), 5.06-4.85 (m, 2H), 4.57-4.51 (m, 2H), 4.00-3.97 (m, 2H), 3.73-3.37 (m, 11H), 3.15-2.98 (m, 5H); MS (ESI) m/e 489 (M+H)$^+$.

Example 224

Preparation of (E)-N-Methyl-N-(4-methyl-naphthalen-1-ylmethyl)-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(4-methyl-naphthalen-1-ylmethyl)amine for the methyl-(1-propyl-naphthalen-2-ylmethyl)amine, the title compound (175 mg, 50%) was prepared as a white solid: $^1$H NMR (300 MHz, DMSO-d$_6$) δ 10.50 (br s, 1H), 10.14-10.09 (m, 1H), 8.41-8.30 (m, 1H), 8.16-7.85 (m, 3H), 7.69-7.53 (m, 3H), 7.40-7.01 (m, 3H), 5.37-4.85 (m, 4H), 4.65-4.46 (m, 2H), 3.99-3.93 (m, 2H), 3.78-3.31 (m, 6H), 3.20-2.98 (m, 5H), 2.65-2.63 (m, 3H); MS (ESI) m/e 500 (M+H)$^+$.

Example 225

Preparation of (E)-N-Acenaphthen-5-ylmethyl-N-methyl-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting acenaphthen-5-ylmethyl-methylamine for the methyl-(1-propyl-naphthalen-2-ylmethyl)amine, the title compound (175 mg, 43%) was prepared as a pale yellow solid: $^1$H NMR (300 MHz, DMSO-d$_6$) δ 10.15-10.11 (m, 2H), 8.41-8.33 (m, 1H), 7.98-7.96 (m, 1H), 7.88-7.74 (m, 1H), 7.60-7.44 (m, 2H), 7.38-7.12 (m, 4H), 5.23-5.01 (m, 2H), 4.55-4.46 (m, 2H), 4.00-3.96 (m, 2H), 3.86-3.36 (m, 10H), 3.12-2.89 (m, 7H); MS (ESI) m/e 512 (M+H)$^+$.

Example 226

Preparation of (E)-N-(2-Ethoxy-3-methoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting (2-ethoxy-3-methoxy-benzyl)methylamine for the methyl-(1-propyl-naphthalen-2-ylmethyl)amine, the title compound (155 mg, 37%) was prepared as a off-white solid: $^1$H NMR (300 MHz, DMSO-d$_6$) δ 10.15-10.13 (m, 2H), 8.40-8.35 (m, 1H), 8.00-7.92 (m, 1H), 7.54-7.42 (m, 1H), 7.25-7.20 (m, 1H), 7.13-6.68 (m, 2H), 6.66-6.61 (m, 1H), 5.11 (br s, 1H), 4.78-4.63 (m, 2H), 4.57-4.52 (m, 2H), 4.01-3.95 (m, 4H), 3.82-3.58 (m, 9H), 3.37-3.35 (m, 2H), 3.20-2.86 (m, 5H), 1.28-1.18 (m, 3H); MS (ESI) m/e 510 (M+H)$^+$.

Example 227

Preparation of (E)-N-Methyl-N-(3-methyl-benzo[b]thiophen-2-ylmethyl)-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(3-methyl-benzo[b]thiophen-2-ylmethyl)amine for the methyl-(1-propyl-naphthalen-2-ylmethyl)amine, the title compound (140 mg, 33%) was prepared as a off-white solid: $^1$H NMR (300 MHz, DMSO-d$_6$) δ 10.45 (br s, 1H), 10.14 (s, 1H), 8.41-8.39 (m, 1H), 8.01 (s, 1H), 7.88-7.86 (m, 1H), 7.74-7.73 (m, 1H), 7.56-7.53 (m, 1H), 7.41-7.18 (m, 3H), 6.31 (br s, 1H), 5.11-4.88 (m, 2H), 4.57-4.55 (m, 2H), 3.99-3.96 (m, 2H), 3.75-3.71 (m, 4H), 3.57-3.55 (m, 2H), 3.39-3.37 (m, 2H), 3.15-2.94 (m, 5H), 2.42 (s, 3H); MS (ESI) m/e 506 (M+H)$^+$.

Example 228

Preparation of (E)-(6-{2-[Methyl-(1-methyl-1H-indol-2-ylmethyl)carbamoyl]vinyl}-2-oxo-1,4-dihydro-2H-pyrido[2,3-d]pyrimidin-3-yl)acetic acid a) (E)-(6-{2-[Methyl-(1-methyl-1H-indol-2-ylmethyl)carbamoyl]vinyl}-2-oxo-1,4-dihydro-2H-pyrido[2,3-d]pyrimidin-3-yl)acetic acid ethyl ester According to the procedure of Example 1 (a), except substituting (E)-3-(3-ethoxycarbonylmethyl-2-oxo-1,2,3,4-tetrahydro-pyrido[2,3-d]pyrimidin-6-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(1-methyl-1H-indol-2-ylmethyl)amine for the methyl-(1-propyl-naphthalen-2-ylmethyl)amine, the title compound (1.20 g, 89%) was prepared as a tan solid and as a mixture of amide rotamers: $^1$H NMR (300 MHz, CDCl$_3$) δ 8.34-8.28 (m, 1H), 7.66-7.34 (m, 2H), 7.60-7.53 (m, 2H), 7.33-7.21 (m, 2H), 7.11 (t, J=7.5 Hz, 1H), 6.83 (d, J=15.0 Hz, 1H), 6.50-6.40 (m, 1H), 4.93-4.30 (m, 2H), 4.59-4.52 (m, 2H), 4.27-4.19 (m, 4H), 3.71 (s, 3H), 3.13-3.06 (m, 3H), 1.30 (t, J=7.2 Hz, 3H); MS (ESI) m/e 462 (M+H)$^+$.

b) (E)-(6-{2-[Methyl-(1-methyl-1H-indol-2-ylmethyl)carbamoyl]vinyl}-2-oxo-1,4-dihydro-2H-pyrido[2,3-d]pyrimidin-3-yl)acetic acid A suspension of (E)-(6-{2-[methyl-(1-methyl-1H-indol-2-ylmethyl)carbamoyl]vinyl}-2-oxo-1,4-dihydro-2H-pyrido[2,3-d]pyrimidin-3-yl)acetic acid ethyl ester (0.40 g, 0.87 mmol) in methanol (30 mL) was treated with 1N NaOH (10 mL, 10 mmol). The mixture was heated at reflux for 2 h. After cooling, the methanol was evaporated. The residue was diluted with H$_2$O (15 mL) and neutralized to pH 6 with 2N HCl. The solid was collected by filtration, and triturated subsequently with a mixture CH$_3$CN/H$_2$O (9:1, v/v), diethyl ether, and methanol to give the title compound (180 mg, 48%) as a tan solid: $^1$H NMR (300 MHz, DMSO-d$_6$) δ 12.78 (s, 1H), 10.09-10.06 (m, 1H), 8.39-8.36 (m, 1H), 8.01-7.92 (m, 1H), 7.57-7.39 (m, 3H), 7.26-6.69 (m, 3H), 6.42-6.18 (m, 1H), 5.04-4.85 (m, 2H), 4.53-4.48 (m, 2H), 4.05-4.01 (m, 2H), 3.72-3.68 (m, 3H), 3.11-2.99 (m, 3H); MS (ESI) m/e 434 (M+H)$^+$.

Example 229

Preparation of Sodium (E)-(6-{2-[methyl-(1-methyl-1H-indol-2-ylmethyl)carbamoyl]vinyl}-2-oxo-1,4-dihydro-2H-pyrido[2,3-d]pyrimidin-3-yl)acetate A suspension of (E)-(6-{2-[methyl-(1-methyl-1H-indol-2-ylmethyl)carbamoyl]vinyl}-2-oxo, 1,4-dihydro-2H-pyrido[2,3-d]pyrimidin-3-yl)acetic acid ethyl ester (0.19 g, 0.40 mmol) in methanol (20 mL) was treated with 1N NaOH (0.80 mL, 0.80 mmol). The mixture was heated at reflux for 2 h. After cooling, the solid was collected by filtration to give the title compound (140 mg, 77%) as an off-white solid: $^1$H NMR (300 MHz, DMSO-d$_6$+D$_2$O) δ 8.30-8.25 (m, 1H), 7.97-7.86 (m, 1H), 7.55-7.42 (m, 3H), 7.17-7.05 (m, 3H), 6.46-6.22 (m, 1H), 5.03-4.86 (m, 2H), 4.55 (s, 1H), 4.48 (s, 1H), 3.76-3.67 (m, 5H), 3.13-3.05 (m, 3H); MS (ESI) m/e 434 (M+H)$^+$.

Example 230

Preparation of Sodium (E)-(6-{2-[methyl-(3-methyl-benzo[b]thiophen-2-ylmethyl)carbamoyl]vinyl}-2-oxo-1,4-dihydro-2H-pyrido[2,3-d]pyrimidin-3-yl)acetate a) (E)-(6-{2-[Methyl-(3-methyl-benzo[b]thiophen-2-ylmethyl)carbamoyl]vinyl}-2-oxo-1,4-dihydro-2H-pyrido[2,3-d]pyrimidin-3-yl)acetic acid ethyl ester According to the procedure of Example 1 (a), except substituting (E)-3-(3-ethoxycarbonylmethyl-2-oxo-1,2,3,4-tetrahydro-pyrido[2,3-d]pyrimidin-6-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(3-methyl-benzo[b]thiophen-2-ylmethyl)amine for the methyl-(1-propyl-naphthalen-2-ylmethyl)amine, the title compound (380 mg, 59%)

was prepared as a tan solid and as a mixture of amide rotomers: ¹H NMR (300 MHz, DMSO-d₆) δ 10.15 (s, 1H), 8.40 (s, 1H), 8.01 (s, 1H), 7.87 (d, J=7.5 Hz, 1H), 7.43 (d, J=7.8 Hz, 1H), 7.64 (d, J=15.3 Hz, 1H), 7.42-7.16 (m, 3H), 5.11-4.88 (m, 2H), 4.53 (s, 2H), 4.18-4.11 (m, 4H), 3.14-2.93 (m, 3H), 2.42 (s, 3H), 1.21 (t, J=6.9 Hz, 3H); MS (ESI) m/e 479 (M+H)⁺.

b) Sodium (E)-(6-{2-[methyl-(3-methyl-benzo[b]thiophen-2-ylmethyl)carbamoyl]vinyl}-2-oxo-1,4-dihydro-2H-pyrido[2,3-d]pyrimidin-3-yl)acetate According to the procedure of Example 125, except substituting (E)-(6-{2-[methyl-(3-methyl-benzo[b]thiophen-2-ylmethyl)carbamoyl]vinyl}-2-oxo-1,4-dihydro-2H-pyrido[2,3-d]pyrimidin-3-yl)acetic acid ethyl ester for the (E)-(6-{2-[methyl-(1-methyl-1H-indol-2-ylmethyl)carbamoyl]vinyl}-2-oxo-1,4-dihydro-2H-pyrido[2,3-d]pyrimidin-3-yl) acetic acid ethyl ester, the title compound (300 mg, 85%) was prepared as a white solid: ¹H NMR (300 MHz, DMSO-d₆+D₂O) δ 8.29-8.28 (m, 1H), 7.95-7.84 (m, 2H), 7.77 (d, J=4.8 Hz, 1H), 7.53-7.49 (m, 1H), 7.46-7.43 (m, 1H), 7.40-7.37 (m, 1H), 7.22-7.09 (m, 1H), 5.07-4.89 (m, 2H), 4.55-4.53 (m, 2H), 3.78-3.77 (m, 2H), 3.17-3.01 (m, 3H), 2.42 (s, 3H); MS (ESI) m/e 451 (M+H)⁺.

Example 231

Preparation of (E)-N-Methyl-N-(1-methyl-1H-indol-2-ylmethyl)-3-{3-[2-(4-methyl-piperazin-1-yl)-2-oxo-ethyl]-2-oxo-1,2,3,4-tetrahydro-pyrido[2,3-d]pyrimidin-6-yl}acrylamide hydrochloride According to the procedure of Example 1, except substituting (E)-(6-{2-[methyl-(1-methyl-1H-indol-2-ylmethyl)carbamoyl]vinyl}-2-oxo-1,4-dihydro-2H-pyrido[2,3-d]pyrimidin-3-yl)acetic acid for the (E)-3-(4-methyl-2-oxo-2,3,4,5-tetrahydro-1H-pyrido[2,3-e][1,4]diazepin-7-yl)acrylic acid hydrochloride, and substituting 1-methylpiperazine for the methyl-(1-propyl-naphthalen-2-ylmethyl)amine, the title compound (173 mg, 43%) was prepared as a off-white solid: ¹H NMR (300 MHz, DMSO-d₆) □ 10.78 (br s, 1H), 10.07-10.03 (m, 1H), 8.41-8.37 (m, 1H), 7.98-7.90 (m, 1H), 7.57-7.39 (m, 3H), 7.25-6.99 (m, 3H), 6.42-6.17 (m, 1H), 5.04-4.85 (m, 2H), 4.46-4.03 (m, 5H), 3.72-3.68 (m, 3H), 3.44-3.41 (m, 3H), 3.11-2.91 (m, 7H), 2.78 (s, 3H); MS (ESI) m/e 516 (M+H)⁺.

Example 232

Preparation of (E)-N-Methyl-N-(3-methyl-benzo[b]thiophen-2-ylmethyl)-3-{3-[2-(4-methyl-piperazin-1-yl)-2-oxo-ethyl]-2-oxo-1,2,3,4-tetrahydro-pyrido[2,3-d]pyrimidin-6-yl}acrylamide hydrochloride a) (E)-(6-{2-[Methyl-(3-methyl-benzo[b]thiophen-2-ylmethyl)carbamoyl]vinyl}-2-oxo-1,4-dihydro-2H-pyrido[2,3-d]pyrimidin-3-yl)acetic acid According to the procedure of Example 124 (b), except substituting (E)-(6-{2-[methyl-(3-methyl-benzo[b]thiophen-2-ylmethyl)carbamoyl]vinyl}-2-oxo-1,4-dihydro-2H-pyrido[2,3-d]pyrimidin-3-yl)acetic acid ethyl ester for the (E)-(6-{2-[methyl-(1-methyl-1H-indol-2-ylmethyl)carbamoyl]vinyl}-2-oxo-1,4-dihydro-2H-pyrido[2,3-d]pyrimidin-3-yl) acetic acid ethyl ester, the title compound (720 mg, 89%) was prepared as a light yellow solid and as a mixture of amide rotomers: ¹H NMR (300 MHz, DMSO-d₆) δ 10.78 (br s, 1H), 10.08 (s, 1H), 8.39 (s, 1H), 8.01 (s, 1H), 7.88 (d, J=7.5 Hz, 1H), 7.74 (d, J=7.4 Hz, 1H), 7.56-7.16 (m, 4H), 5.11-4.88 (m, 2H), 4.52 (s, 2H), 4.04 (s, 2H), 3.14-2.93 (m, 3H), 2.42 (s, 3H); MS (ESI) m/e 451 (M+H)⁺.

b) (E)-N-Methyl-N-(3-methyl-benzo[b]thiophen-2-ylmethyl)-3-{3-[2-(4-methyl-piperazin-1-yl)-2-oxo-ethyl]-2-oxo-1,2,3,4-tetrahydro-pyrido[2,3-d]pyrimidin-6-yl}acrylamide hydrochloride According to the procedure of Example 1, except substituting (E)-(6-{2-[methyl-(3-methyl-benzo[b]thiophen-2-ylmethyl)carbamoyl]vinyl}-2-oxo-1,4-dihydro-2H-pyrido[2,3-d]pyrimidin-3-yl)acetic acid for the (E)-3-(4-methyl-2-oxo-2,3,4,5-tetrahydro-1H-pyrido[2,3-e][1,4]diazepin-7-yl) acrylic acid, and substituting 1-methylpiperazine for the methyl-(1-propyl-naphthalen-2-ylmethyl)amine, the title compound (44 mg, 9%) was prepared as a pale-yellow solid, after purification by preparative HPLC: ¹H NMR (300 MHz, DMSO-d₆) δ 10.60 (br s, 1H), 10.06 (s, 1H), 8.40 (s, 1H), 7.98 (s, 1H), 7.87 (d, J=7.5 Hz, 1H), 7.73 (d, J=8.0 Hz, 1H), 7.56-7.51 (m, 1H), 7.42-7.15 (m, 3H), 5.11-4.88 (m, 2H), 4.46-4.38 (m, 4H), 4.22-4.04 (m, 2H), 3.61-3.42 (m, 4H), 3.17-2.73 (m, 8H), 2.42 (s, 3H); MS (ESI) m/e 533 (M+H)⁺.

Example 233

Preparation of (E)-N-Methyl-N-(3-methyl-benzo[b]thiophen-2-ylmethyl)-3-{3-[2-(4-methyl-piperazin-1-yl)-2-oxo-ethyl]-2-oxo-1,2,3,4-tetrahydro-pyrido[2,3-d]pyrimidin-6-yl}acrylamide hydrochloride a) (E)-3-[3-(2,2-Dimethoxy-ethyl)-2-oxo-1,2,3,4-tetrahydro-pyrido[2,3-d]pyrimidin-6-yl]-N-methyl-N-(3-methyl-benzo[b]thiophen-2-ylmethyl)acrylamide According to the procedure of Example 2, except substituting 6-bromo-3-(2,2-dimethoxy-ethyl)-3,4-dihydro-1H-pyrido[2,3-d]pyrimidin-2-one for the 7-bromo-3,3-dimethyl-1,3,4,5-tetrahydro-pyrido[2,3-e][1,4]diazepin-2-one, the title compound (490 mg, 60%) was prepared as a white solid and as a mixture of amide rotomers: ¹H NMR (300 MHz, CDCl₃) δ 8.33 (br s, 1H), 8.07-8.02 (m, 1H), 7.78-7.76 (m, 1H), 7.71-7.67 (m, 2H), 7.52-7.48 (m, 1H), 7.38-7.22 (m, 2H), 6.89-6.80 (m, 1H), 4.95-4.88 (m, 2H), 4.61-4.58 (m, 3H), 3.52-3.51 (m, 2H), 3.44 (s, 6H), 3.15-3.11 (m, 3H), 2.44 (s, 3H); MS (ESI) m/e 481 (M+H)⁺.

b) (E)-N-Methyl-N-(3-methyl-benzo[b]thiophen-2-ylmethyl)-3-[2-oxo-3-(2-oxo-ethyl)-1,2,3,4-tetrahydro-pyrido[2,3-d]pyrimidin-6-yl]acrylamide A suspension of (E)-3-[3-(2,2-dimethoxy-ethyl)-2-oxo-1,2,3,4-tetrahydro-pyrido[2,3-d]pyrimidin-6-yl]-N-methyl-N-(3-methyl-benzo[b]thiophen-2-ylmethyl)acrylamide (450 mg, 0.937 mmol) in CH₂Cl₂ (20 mL) was treated with TFA (1 mL) and H₂O (1 mL). The reaction was allowed to stir overnight at room temperature. The solution was washed with saturated NaHCO₃ (2×15 mL). The aqueous solutions were extracted with CH₂Cl₂ (40 mL). The combined CH₂Cl₂ solutions were washed with brine, dried over Na₂SO₄, and concentrated to give the title compound (440 mg, 99%) as a white solid and as amide rotomers: ¹H NMR (300 MHz, DMSO-d₆) δ 10.15 (s, 1H), 9.54 (s, 1H), 8.40 (s, 1H), 8.02 (s, 1H), 7.87 (d, J=7.5 Hz, 1H), 7.73 (d, J=7.8 Hz, 1H), 7.53-7.31 (m, 4H), 5.11-4.88 (m, 2H), 4.51 (s, 2H), 4.18 (s, 2H), 3.15-2.93 (m, 3H), 2.42 (s, 3H); MS (ESI) m/e 435 (M+H)⁺.

c) (E)-N-Methyl-N-(3-methyl-benzo[b]thiophen-2-ylmethyl)-3-{3-[2-(4-methyl-piperazin-1-yl)-ethyl]-2-oxo-1,2,3,4-tetrahydro-pyrido[2,3-d]pyrimidin-6-yl}acrylamide hydrochloride To a suspension of (E)-N-methyl-N-(3-methyl-benzo[b]thiophen-2-ylmethyl)-3-[2-oxo-3-(2-oxo-ethyl)-1,2,3,4-tetrahydro-pyrido[2,3-d]pyrimidin-6-yl]acrylamide (410 mg, 0.945 mmol) in dichloroethane (25 mL) was added 1-methylpiperazine (0.16 mL, 1.4 mmol) and a few drops of HOAc, followed by the addition of NaBH(OAc)₃ (320 mg, 1.51 mmol). The reaction mixture was allowed to stir over night at room temperature. The resulting precipitate was collected by filtration to give a white solid. Purification by column chromatography (silica gel, CH₂Cl₂/MeOH/Et₃N, 90/9.5/0.5 to 85/14.5/0.5) afforded the free base (400 mg, 82%) of the title compound. The free base was dissolved in a mixture of CH₂Cl₂/MeOH (8 mL/0.7 mL). To this was added 1N HCl in diethyl ether (0.48 mL, 0.48 mmol), and the mixture was stirred at room temperature for 30 min. The resulting precipitate was collected by filtration to give the title compound (190 mg, 72%) as a white solid: ¹H NMR (300 MHz, DMSO-d₆) δ 11.95-10.90 (m, 1H), 10.07 (s, 1H), 8.40 (s, 1H), 7.99 (s, 1H), 7.87 (d, J=4.5 Hz, 1H), 7.73 (d, J=4.5 Hz, 1H), 7.54 (d, J=9.3 Hz, 1H), 7.41-7.17 (m, 3H), 5.11-4.88 (m, 2H), 4.58-4.56 (m, 2H), 3.93-3.29 (m, 11H), 3.17 (s, 3H), 2.94-2.80 (m, 4H), 2.42 (s, 3H); MS (ESI) m/e 519 (M+H)⁺.

Example 234

Preparation of (E)-2-Amino-5-{2-[methyl-(1-methyl-1H-indol-2-ylmethyl)carbamoyl]vinyl}-N-(2-morpholin-4-yl-ethyl)nicotinamide hydrochloride According to the procedure of Example 1, except substituting 3-[6-amino-5-(2-morpholin-4-yl-ethylcarbamoyl)pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and methyl-(1-methyl-1H-indol-2-ylmethyl)amine for the methyl-(1-propyl-naphthalen-2-ylmethyl)amine, the title compound (170 mg, 23%) was prepared as a pale yellow solid: ¹H NMR (300 MHz, DMSO-d₆) δ 10.87-10.61 (m, 1H), 9.69-9.66 (m, 1H), 9.40-9.28 (m, 1H), 8.70-8.31 (m, 3H), 7.95-7.39 (m, 4H), 7.15-6.97 (m, 2H), 6.40-6.08 (m, 1H), 5.27-4.85 (m, 2H), 3.94-3.55 (m, 12H), 3.20-2.96 (m, 6H); MS (ESI) m/e 477 (M+H)⁺.

Example 235

Preparation of (E)-N-(3-Methyl-benzo[b]thiophen-2-ylmethyl)-3-[3-(3-morpholin-4-yl-propyl)-2-oxo-1,2,3,4-tetrahydro-pyrido[2,3-d]pyrimidin-6-yl]acrylamide hydrochloride According to the procedure of Example 1, except substituting methyl-(3-methyl-benzo[b]thiophen-2-ylmethyl)amine for the methyl-(1-propyl-naphthalen-2-ylmethyl)amine, and substituting (E)-3-[3-(3-morpholin-4-yl-propyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (0.86 g, 86%) was prepared as an off-white solid: ¹H NMR (500 MHz, DMSO-d₆) δ 10.96 (br s, 1H), 10.01 (br s, 1H), 8.39 (s, 1H), 8.01 (d, J=7.0 Hz, 1H), 7.86 (d, J=7.5 Hz, 1H), 7.73 (d, J=7.0 Hz, 1H), 7.58-7.51 (m, 1H), 7.40 (t, J=7.5 Hz, 1H), 7.32 (t, J=7.5 Hz, 1H), 7.21-7.12 (m, 1H), 5.16-4.63 (m, 2H), 4.51-4.49 (m, 2H), 3.94-3.92 (m 2H), 3.80-3.75 (m, 2H), 3.43-3.36 (m, 5H), 3.14-2.93 (m, 6H), 2.41 (s, 3H), 1.96-2.09 (m, 2H); MS (ESI) m/e 520 (M+H)⁺.

Example 236

Preparation of (E)-N-(2-Ethoxy-3-methoxy-benzyl)-N-methyl-3-[3-(3-morpholin-4-yl-propyl)-2-oxo-1,2,3,4-tetrahydro-pyrido[2,3-d]pyrimidin-6-yl]acrylamide hydrochloride According to the procedure of Example 1, except substituting (2-ethoxy-3-methoxy-benzyl)methylamine for the methyl-(1-propyl-naphthalen-2-ylmethyl)amine, and substituting (E)-3-[3-(3-morpholin-4-yl-propyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (0.67 g, 62%) was prepared as an off-white solid: ¹H NMR (500 MHz, DMSO-d₆) δ 11.16 (br s, 1H), 9.97 (d, J=11 Hz, 1H), 8.40-8.30 (m, 1H), 8.02-7.91 (m, 1H), 7.53-7.46 (m, 1H), 7.24-7.18 (m, 1H), 7.09-6.93 (m, 2H), 6.71-6.63 (m, 1H), 4.79-4.62 (m, 2H), 4.55-4.40 (m, 2H), 4.21-3.85 (m, 2H), 3.80-3.75 (m, 6H), 3.45-3.37 (m, 4H), 3.09-2.86 (m, 8H), 2.08-1.97 (m, 2H), 1.30-1.26 (m, 3H); MS (ESI) m/e 524 (M+H)⁺.

Example 237

Preparation of (E)-N-(5-{2-[Methyl-(3-methyl-benzo[b]thiophen-2-ylmethyl) carbamoyl]vinyl}pyridin-2-yl)-4-(4-methyl-piperazin-1-yl)-4-oxo-butyramide a) (E)-3-(6-Amino-pyridin-3-yl)-N-methyl-N-(3-methyl-benzo[b]thiophen-2-ylmethyl)acrylamide According to the procedure of Example 1, except substituting methyl-(3-methyl-benzo[b]thiophen-2-ylmethyl) amine for the methyl-(1-propyl-naphthalen-2-ylmethyl) amine, and substituting (E)-3-(6-amino-pyridin-3-yl)acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (2.2 g, 73%) was prepared as a yellow solid: ¹H NMR (300 MHz, DMSO-d₆) 8.21 (s, 1H), 2.81-2.75 (m, 1H), 2.71-2.59 (m, 3H), 7.41-7.25 (m, 2H), 6.85-6.65 (m, 1H), 6.50-6.41 (m, 1H), 5.01-4.81 (m, 2H), 4.78-4.61 (m, 2H), 3.12 (s, 3H), 2.41 (s, 3H); MS (ESI) m/e 338 (M+H)⁺.

b) (E)-3-[6-(2,5-Dioxo-pyrrolidin-1-yl)pyridin-3-yl]-N-methyl-N-(3-methyl-benzo[b]thiophen-2-ylmethyl)acrylamide According to the procedure of Example 109, except substituting (E)-3-(6-amino-pyridin-3-yl)-N-methyl-N-(3-methyl-benzo[b]thiophen-2-ylmethyl)acrylamide (2.2 g, 6.6 mmol) for the (E)-3-(6-aminopyridin-3-yl)-N-methyl-N-(1-methyl-1H-indol-2-ylmethyl)acrylamide, and succinic anhydride (0.80 g, 8.0 mmol) in 1,4-dioxane (119 mL) was heated to reflux for 15 h overnight. The title compound (1.7 g, 61%) was prepared as a yellow oil: ¹H NMR (300 MHz, DMSO-d₆) δ 8.78 (s, 1H), 8.01-7.91 (m, 1H), 7.80-7.72 (m, 2H), 7.70-7.63 (m, 1H), 7.43-7.39 (m, 3H), 7.01-6.92 (m, 1H), 5.01-

4.85 (m, 2H), 3.21-3.10 (m, 3H), 2.90-2.85 (m, 4H), 2.44 (s, 3H); MS (ESI) m/e 420 (M+H)$^+$ c) (E)-N-(5-{2-[Methyl-(3-methyl-benzo[b]thiophen-2-ylmethyl)carbamoyl]vinyl}pyridin-2-yl)-4(4-methyl-piperazin-1-yl)-4-oxo-butyramide According to the procedure of Example 110 except substituting 3-[6-(2,5-dioxo-pyrrolidin-1-yl)pyridin-3-yl]-N-methyl-N-(3-methyl-benzo[b]thiophen-2-ylmethyl)acrylamide for the (E)-3-[6-(2,5-dioxo-pyrrolidin-1-yl)-pyridin-3-yl]-N-methyl-N-(1-methyl-1H-indol-2-ylmethyl)acrylamide, and substituting 1-methylpiperazine for the ammonia, the title compound (0.53 g, 51%) was prepared as a light yellow solid: $^1$H NMR 300 MHz, DMSO-d$_6$) δ 10.71 (br s, 1H), 8.74-8.61 (m, 1H), 8.22-8.15 (m, 1H), 8.13-8.05 (m, 1H), 7.91-7.85 (m, 1H), 7.78-7.71 (m, 1H), 7.60-7.50 (m, 1H), 7.39-7.33 (m, 3H), 5.15-4.88 (m, 2H), 3.75-3.61 (m, 2H), 3.38-3.28 (m, 3H), 3.19-3.10 (m, 2H), 3.05-2.75 (m, 4H), 2.71-2.51 (m, 7H), 2.41 (s, 3H); MS (ESI) m/e 520 (M+H)$^+$.

Example 238

Preparation of (E)-N-(2,3-Diethoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting 2,3-diethoxy-benzyl-methylamine for the methyl-(1-propyl-naphthalen-2-ylmethyl)amine, and substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (0.18 g, 56%) was prepared as an off-white solid: $^1$H NMR (300 MHz, DMSO-d$_6$) δ 10.63-10.49 (m, 1H), 10.14-10.12 (m, 1H), 8.41-8.31 (m, 1H), 8.03-7.91 (m, 1H), 7.52-7.45 (m, 1H), 7.38-7.19 (m, 1H), 7.03-6.90 (m, 2H), 6.70-6.51 (m, 1H), 4.63-4.51 (m, 4H), 4.02-3.91 (m, 6H), 3.81-3.68 (m, 4H), 3.60-3.50 (m, 2H), 3.40-3.28 (m, 2H), 3.20-2.85 (m, 5H), 1.40-1.31 (m, 6H); MS (ESI) m/e 524 (M+H)$^+$.

Example 239

Preparation of (E)-N-(2-Isopropoxy-3-methoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting 2-isopropoxy-3-methoxy-benzyl-methylamine for the methyl-(1-propyl-naphthalen-2-ylmethyl)amine, and substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (0.15 g, 47%) was prepared as an off-white solid: $^1$H NMR (500 MHz, DMSO-d$_6$) δ 10.41-10.21 (m, 1H), 10.13 (br s, 1H), 8.41-8.31 (m, 1H), 8.01-7.93 (m, 1H), 7.51-7.43 (m, 1H), 7.31-7.11 (m, 1H), 7.01-6.91 (m, 2H), 6.70-6.59 (m, 1H), 4.76-4.52 (m, 5H), 4.11-3.85 (m, 7H), 3.84-3.60 (m, 3H), 3.59-3.51 (m, 2H), 3.40-3.31 (m, 2H), 3.07-2.86 (m, 4H), 1.23 (m, 6H); MS (ESI) m/e 524 (M+H)$^+$.

Example 240

Preparation of (E)-N-(3-Methoxy-2-propoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting 3-methoxy-2-propoxy-benzyl-methylamine for the methyl-(1-propyl-naphthalen-2-ylmethyl)amine, and substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (0.10 g, 35%) was prepared as an off-white solid: $^1$H NMR (300 MHz, DMSO-d$_6$) δ 10.68 (br s, 1H), 10.13 (m, 1H), 8.40-8.30 (m, 1H), 8.01-7.90 (m, 1H), 7.60-7.42 (m, 1H), 7.29-7.15 (m, 1H), 7.01-6.90 (m, 2H), 6.70-6.60 (m, 1H), 4.80-4.51 (m, 4H), 4.02-3.70 (m, 10H), 3.60-3.50 (m, 2H), 3.42-3.30 (m, 2H), 3.20-2.87 (m, 6H), 1.74-1.67 (m, 2H), 1.00-0.91 (m, 3H); MS (ESI) m/e 524 (M+H)$^+$.

Example 241

Preparation of (E)-N-Methyl-N-(3-methyl-benzofuran-2-ylmethyl)-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting methyl-(3-methyl-benzofuran-2-ylmethyl)amine for the methyl-(1-propyl-naphthalen-2-ylmethyl)amine, and substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (0.26 g, 91%) was prepared as an off-white solid: $^1$H NMR (500 MHz, DMSO-d$_6$) δ 10.75 (br s, 1H), 10.11 (s, 1H), 8.39 (d, J=7.5 Hz, 1H), 7.99 (t, J=9.0 Hz, 1H), 7.59-7.47 (m, 3H), 7.29-7.17 (m, 3H), 5.01-4.57 (m, 4H), 3.97-3.95 (m, 2H), 3.81-3.71 (m, 4H), 3.60-3.51 (m, 2H), 3.41-3.31 (m, 2H), 3.21-2.91 (m, 5H), 2.26 (s, 3H); MS (ESI) m/e 490 (M+H)$^+$.

Example 242

Preparation of (E)-N-Methyl-N-(2-methyl-benzofuran-3-ylmethyl)-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting methyl-(2-methyl-benzofuran-3-ylmethyl)amine for the methyl-(1-propyl-naphthalen-2-ylmethyl)amine, and substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (0.17 g, 82%) was prepared as an off-white solid: $^1$H NMR (500 MHz, DMSO-d$_6$) δ 10.70-10.59 (m, 1H), 10.13 (s, 1H), 8.41-8.35 (m, 1H), 8.10-7.99 (m, 1H), 7.58-7.46 (m, 3H), 7.22-7.15 (m, 3H), 5.31-4.93 (m, 2H), 4.72-4.52 (m, 3H), 4.01-3.91 (m, 2H), 3.81-3.71 (m, 4H), 3.60-3.50 (m, 2H), 3.39-3.30 (m, 2H), 3.19-3.01 (m, 4H), 2.51 (s, 3H); MS (ESI) m/e 490 M+H)+.

Example 243

Preparation of (E)-N-(3-Chloro-2-ethoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting 3-chloro-2-ethoxy-benzyl-methylamine for the methyl-(1-propyl-naphthalen-2-ylmethyl)amine, and substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (0.15 g, 60%) was prepared as an off-white solid: $^1$H NMR (500 MHz, DMSO-d$_6$) δ 10.82-10.69 (m, 1H), 10.11-10.09 (m, 1H), 8.41-8.33 (m, 1H), 8.01-7.91 (m, 1H), 7.58-7.48 (m, 1H), 7.47-7.36 (m, 1H), 7.28-7.01 (m, 3H), 4.86-4.68 (m, 2H), 4.60-4.51 (m, 2H), 4.07-3.91 (m, 4H), 3.82-3.71 (m, 4H), 3.59-3.49 (m, 2H), 3.40-3.30 (m, 2H), 3.13-2.88 (m, 4H), 1.38 (t, J=7.0 Hz, 3H); MS (ESI) m/e 514 (M+H)+.

Example 244

Preparation of (E)-N-(4-Fluoro-naphthalen-1-ylmethyl)-N-methyl-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting 4-fluoro-naphthalen-1-ylmethyl-methylamine for the methyl-(1-propyl-naphthalen-2-ylmethyl)amine, and substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (0.13 g, 43%) was prepared as an off-white solid: $^1$H NMR (500 MHz, DMSO-d$_6$) δ 10.64-10.51 (m, 1H), 10.12 (m, 1H), 8.45-8.30 (m, 1H), 8.22-8.07 (m, 2H), 8.03-7.86 (m, 1H), 7.78-7.62 (m, 2H), 7.63-7.51 (m, 1H), 7.43 (t, J=7.5 Hz, 1H), 7.32 (t, J=8.6 Hz, 1H), 7.21-7.12 (m, 1H), 5.03-5.02 (m, 2H), 4.57-4.42 (m, 2H), 4.01-3.91 (m, 2H), 3.80-3.63 (m, 4H), 3.53-3.43 (m, 2H), 3.40-3.25 (m, 2H), 3.09-2.96 (m, 5H); MS (ESI) m/e 504 (M+H)+.

Example 245

Preparation of (E)-N-(2,3-Dimethoxy-benzyl)-N-methyl-3-(7-oxo-5,6,7,8-tetrahydro-[1.8]naphthyridin-3-yl)acrylamide According to the procedure of Example 1 (a), except substituting (2,3-dimethoxy-benzyl)methylamine for the methyl-(1-propyl-naphthalen-2-ylmethyl)amine, and substituting (E)-3-(7-oxo-5,6,7,8-tetrahydro-[1,8]naphthyridin-3-yl)acrylic acid hydrochloride for the (E)-3-(4-methyl-2-oxo-2,3,4,5-tetrahydro-1H-pyrido[2,3-e][1,4]diazepin-7-yl) acrylic acid hydrochloride, the title compound (0.362 g, 61%) was prepared as an orange solid and as a mixture of amide rotamers: $^1$H NMR (300 MHz, DMSO-d$_6$) δ 10.67-10.64 (m, 1H), 8.36-8.32 (m, 1H), 8.09-8.02 (m, 1H), 7.52-7.47 (m, 1H), 7.31-7.22 (m, 1H), 7.08-6.95 (m, 2H), 6.69-6.64 (m, 1H), 4.78-4.62 (m, 2H), 3.80 (s, 3H), 3.73 (s, 3H), 3.01-2.85 (m, 5H), 2.56-2.49 (m, 2H); MS (ESI) m/e 382 (M+H)+.

Example 246

Preparation of (E)-3-(6-Amino-5-morpholin-4-ylmethyl-pyridin-3-yl)-N-methyl-N-(1-methyl-1H-indol-3-ylmethyl)acrylamide According to the procedure of Example 2(a), except substituting N-methyl-N-(1-methyl-1H-indol-3-ylmethyl)acrylamide for the N-methyl-N-(3-methyl-benzo[b]thiophen-2-ylmethyl)acrylamide, and substituting 5-bromo-3-morpholin-4-ylmethyl-pyridin-2-ylamine for the 7-bromo-3,3-dimethyl-1,3,4,5-tetrahydro-pyrido[2,3-e][1,4]diazepin-2-one, the title compound (510 mg, 38%) was prepared as an off-white powder: $^1$H NMR (300 MHz, DMSO-d$_6$) δ 8.13 (s, 1H), 7.78 (s, 1H), 7.63-6.91 (m, 7H), 6.51 (s, 2H), 4.89-4.72 (m, 2H), 3.76 (s, 3H), 3.57 (br s, 4H), 3.42-3.34 (m, 2H), 3.02-2.90 (m, 3H), 2.33 (br s, 4H); MS (ESI) m/e 420 (M+H)+.

Example 247

Preparation of (E)-3-(6-Amino-pyridin-3-yl)-N-methyl-N-thieno[3,2-c]pyridin-2-ylmethyl-acrylamide EDC hydrochloride (118 mg, 0.62 mmol) was added to a solution of methyl-thieno[3,2-c]pyridine-2-ylmethyl-amine (100 mg, 0.56 mmol), (E)-3-(6-amino-pyridin-3-yl)acrylic acid (101 mg, 0.62 mmol), HOBt H$_2$O (83 mg, 0.62 mmol) and triethylamine (235 µL, 1.68 mmol) in anhydrous DMF (5 mL). The mixture was stirred at room temperature overnight then diluted with H$_2$O (10 mL) and extracted with CH$_2$Cl$_2$ (3×50 mL). The combined organic fractions were dried over MgSO$_4$, filtered and evaporated to give a yellow residue which was subjected to flash chromatography on silica gel (10% MeOH: CH$_2$Cl$_2$) to yield the title compound (61.0%). $^1$H-NMR (300 MHz, CDCl$_3$) δ 9.04 (s, 1H), 8.45 (d, J=5.3 Hz, 1H), 8.26 (s, 1H), 7.76-7.67 (m, 3H), 7.32 (d, J=15.0 Hz, 1H), 6.76 (d, J=15.2 Hz, 1H), 6.53 (d, J=8.3 Hz, 1H), 4.95 (s, 2H), 4.76 (br s, 2H), 3.22 (s, 3H); MS (ES) m/e 325.1 (M+H)+.

Example 248

Preparation of (E)-N-Methyl-3-(4-methyl-2-oxo-2,3,4,5-tetrahydro-1H-pyrido[2,3-e][1,4]diazepin-7-yl)-N-thieno[3,2-c]pyridin-2-ylmethyl-acrylamide EDC hydrochloride (118 mg, 0.62 mmol) was added to a solution of methyl-thieno[3,2-c]priding-2-ylmethyl-amine (100 mg, 0.56 mmol), (E)-3-(4-methyl-2-oxo-2,3,4,5-tetrahydro-1H-pyrido[2,3-e][1,4]diazepin-7-yl)acrylic acid dihydrochloride (198 mg, 0.62 mmol), HOBt.H$_2$O (83 mg, 0.62 mmol) and triethylamine (470 µL, 3.37 mmol) in anhydrous DMF (7 mL). The mixture was stirred at room temperature overnight; subsequent dilution with H$_2$O (10 mL) resulted in formation of a precipitate. The precipitate was filtered then subjected to flash chromatography on silca gel (10% MeOH:CH$_2$Cl$_2$) to yield the title compound (57.0%). $^1$H-NMR (300 MHz, DMSO-d$_6$) a 1:1.8 mixture of amide rotamers δ 10.38 (s, 1H), 9.07 (s, 1H), 8.57 (d, J=2.0 Hz, 1H), 8.39 (d, J=5.6 Hz, 1H), 8.17 (s, 1H), 8.00 (m, 1H), 7.62-7.44 (m, 2H), 7.30 (d, J=15.5 Hz, 1H), 5.19 and 4.91 (2×s, 2H), 3.80 (br s, 2H), 3.45 (br s, 2H), 3.22 and 3.00 (2×s, 3H), 2.38 (s, 3H); MS (ES) m/e 408.4 (M+H)+.

Example 249

Preparation of (E)-N-Methyl-3-(7-oxo-5,6,7,8-tetrahydro-[1,8]naphthyridin-3-yl)-N-thieno[3,2-c]pyridin-2-ylmethyl-acrylamide According to the procedure for preparation of Example 144, except substituting (E)-3-(4-methyl-2-oxo-2,3,4,5-tetrahydro-1H-pyrido[2,3-e][1,4]diazepin-7-yl)acrylic acid dihydrochloride for (E)-3-(7-oxo-5,6,7,8-tetrahydro-[1,8] naphthyridin-3-yl)acrylic acid (246 mg, 0.62 mmol), the title compound (18.3%) was obtained as a white solid after purification by flash chromatography on silica gel (10% MeOH: $CH_2Cl_2$). $^1$H-NMR (300 MHz, DMSO-$d_6$) a 1:1.8 mixture of amide rotamers δ 11.05 and 10.67 (2×s, 1H), 9.07 (s, 1H), 8.43-8.38 (m, 2H), 8.12 (d, J=11.7 Hz, 1H), 7.99-7.98 (m, 1H), 7.60-7.20 (m, 3H), 5.17 and 4.90 (2×s, 2H), 3.19 and 3.00 (2×s, 3H), 2.95-2.90 (m, 2H), 2.57-2.51 (m, 2H); MS (ES) m/e 379.4 (M+H)$^+$.

Example 250

Preparation of (E)-3-(6-Amino-pyridin-3-yl)-N-(2-ethoxy-3-methoxy-benzyl)-N-methyl acrylamide hydrochloride EDC (231 mg, 1.2 mmol) was added to a solution of (E)-3-(6-amino-pyridin-3-yl)acrylic acid (164 mg, 1.0 mmol), (2-ethoxy-3-methoxy-benzyl)methylamine (215 mg, 1.1 mmol), HOBt $H_2O$ (149 mg, 1.1 mmol) and DIPEA (525 µL, 3.0 mmol) in dry DMF (10 mL). After 18 hr of stirring, the mixture was diluted with water (60 mL) and extracted with EtOAc (2×20 mL). The organic layer was washed with brine (2×30 mL), dried and evaporated. Flash chromatography (silica 1-3% MeOH in $CH_2Cl_2$) furnished pure free base which was dissolved in $CH_2Cl_2$ (10 mL). After addition of HCl (1.5 mL, 1M in ether), the solvents were evaporated and the residue was washed with ether and dried to afford the title compound (172 mg, 46%). $^1$H NMR (300 MHz, DMSO-$d_6$) δ 8.28 (m, 3H), 7.48 and 7.45 (rotamers, 2d, J=15.4 Hz, 1H), 7.25 and 7.23 (rotamers, 2d, J=15.4 Hz, 1H), 7.00 (m, 3H), 6.62 (m, 1H), 4.78 and 4.63 (rotamers, 2s, 2H), 3.98 (m, 2H), 3.79 (s, 3H), 3.08 and 2.84 (rotamers, 2s, 3H), 1.28 (m, 3H). MS (ESI) m/e 342 (M+H)$^+$.

Example 251

Preparation of (E)-3-(6-Amino-pyridin-3-yl)-N-(2-propoxy-3-methoxy-benzyl)-N-methyl-acrylamide hydrochloride EDC (231 mg, 1.2 mmol) was added to a solution of (E)-3-(6-amino-pyridin-3-yl)acrylic acid (164 mg, 1.0 mmol), (2-propoxy-3-methoxy-benzyl)methylamine (230 mg, 1.1 mmol), HOBt $H_2O$ (149 mg, 1.1 mmol) and DIPEA (525 µL, 3.0 mmol) in dry DMF (10 mL). After 18 hr of stirring, the mixture was diluted with water (60 mL) and extracted with EtOAc (2×20 mL). The organic layer was washed with brine (2×30 mL), dried and evaporated. Flash chromatography (silica 1-3% MeOH in $CH_2Cl_2$) furnished pure free base which was dissolved in $CH_2Cl_2$ (10 mL). After addition of HCl (1.5 mL, 1M in ether), the solvents were evaporated; the residue was washed with ether and dried to afford the title compound (185 mg, 47%). $^1$H NMR (300 MHz, DMSO-$d_6$) δ 8.16 (m, 3H), 7.48 and 7.45 (rotamers, 2d, J=15.4 Hz, 1H), 7.23 (d, J=15.4 Hz, 1H), 7.00 (m, 3H), 6.61 (m, 1H), 4.78 and 4.63 (rotamers, 2s, 2H), 3.87 (m, 2H), 3.79 (s, 3H), 3.09 and 2.85 (rotamers, 2s, 3H), 1.71 (m, 2H), 0.97 (m, 3H). MS (ESI) m/e 356 (M+H)$^+$.

Example 252

Preparation of (E)-3-(6-amino-pyridin-3-yl)-N-(2-isopropoxy-3-methoxy-benzyl)-N-methyl-acrylamide hydrochloride EDC (231 mg, 1.2 mmol) was added to a solution of (E)-3-(6-amino-pyridin-3-yl)acrylic acid (164 mg, 1.0 mmol), (2-isopropoxy-3-methoxy-benzyl)methylamine (230 mg, 1.1 mmol), HOBt $H_2O$ (149 mg, 1.1 mmol) and DIPEA (525 µL, 3.0 mmol) in dry DMF (10 mL). After 18 hr of stirring, the mixture was diluted with water (60 mL) and extracted with EtOAc (2×20 mL). The organic layer was washed with brine (2×30 mL), dried and evaporated. Flash chromatography (silica 1-3% MeOH in $CH_2Cl_2$) of the residue furnished pure free base which was dissolved in $CH_2Cl_2$ (10 mL). After addition of HCl (1.5 mL, 1M in ether) the solvents were evaporated; the residue was washed with ether and dried to afford the title compound (180 mg, 46%). $^1$H NMR (300 MHz, DMSO-$d_6$) δ 8.31 (m, 3H), 7.46 and 7.45 (rotamers, 2d, J=15.4 Hz, 1H), 7.23 and 7.17 (rotamers, 2d, J=15.4 Hz, 1H), 6.99 (m, 3H), 6.62 (m, 1H), 4.76 and 4.63 (rotamers, 2s, 2H), 4.51 (m, 1H), 3.79 (s, 3H), 3.06 and 2.85 (rotamers, 2s, 3H), 1.22 (d, J=6.1 Hz, 3H) 1.21 (d, J=6.1 Hz, 3H). MS (ESI) m/e 356 (M+H)$^+$.

Example 253

Preparation of (E)-3-(6-amino-pyridin-3-yl)-N-methyl-N-(3-methyl-benzofuran-2-ylmethyl)acrylamide hydrochloride EDC (231 mg, 1.2 mmol) was added to a solution of (E)-3-(6-amino-pyridin-3-yl)acrylic acid (164 mg, 1.0 mmol), methyl-(3-methyl-benzofuran-2-ylmethyl)amine (193 mg, 1.1 mmol), HOBt.$H_2O$ (149 mg, 1.1 mmol) and DIPEA (525 µL, 3.0 mmol) in dry DMF (10 mL). After 18 hr of stirring, the mixture was diluted with water (60 mL) and extracted with EtOAc (2×20 mL). The oraganic layer was washed with brine (2×30 mL), dried and evaporated. Flash chromatography (silica 1-3% MeOH in $CH_2Cl_2$) of the residue furnished pure free base which was dissolved in $CH_2Cl_2$ (10 mL). After addition of HCl (1.5 mL, 1M in ether), the solvents were evaporated, washed with ether and dried to afford the title compound (195 mg, 54%). $^1$H NMR (300 MHz, DMSO-$d_6$) δ 8.36 (m, 3H), 7.50 (m, 3H), 7.25 (m, 3H), 7.02 (m, 1H), 4.98 and 4.79 (rotamers, 2s, 2H), 3.17 and 2.92 (rotamers, 2s, 3H), 2.26 (s, 3H). MS (ESI) m/e 322 (M+H)$^+$.

Example 254

Preparation of (E)-N-Acenaphthen-5-ylmethyl-3-(6-amino-pyridin-3-yl)-N-methyl-acrylamide hydrochloride To a solution of acenaphthen-5-ylmethyl-methylamine (216 mg, 1.1 mmol), (E)-3-(6-amino-pyridin-3-yl)acrylic acid (164 mg, 1 mmol), HOBt (148 mg, 1.1 mmol) and diisopropylethylamine (0.8 mL, 4.4 mmol) in DMF (20 mL) was added EDC hydrochloride (210 mg, 1.1 mmol). The mixture was stirred overnight at room temperature. Water (100 mL) was added and the solution stirred for 1 hour. The precipitate was collected by filtration. The yellow solid was preabsorded onto silica gel and purified by column chromatography (95:5 $CH_2Cl_2$/MeOH). The residue was dissolved into methylene chloride followed by addition of 1M HCl/ether. The precipitate was collected by filtration to afford (E)-N-acenaphthen-5-ylmethyl-3-(6-amino-pyridin-3-yl)-N-methyl-acrylamide hydrochloride (120 mg, 32%) as a white solid and as a mixture of amide rotamers. $^1$H NMR (300 MHz, DMSO-$d_6$) δ 8.44-8.28 (m, 3H), 7.84-7.72 (m, 1H), 7.59-7.12 (m, 6H), 7.07-6.92 (m, 1H), 5.15-5.02 (2×s, 2H), 3.35-3.15 (bs, 2H), 3.18 (s, 4H), 3.07-2.90 (2×s, 3H); ESI MS m/z 344 $[C_{22}H_{21}N_3O+H]^+$.

Example 255

Preparation of (E)-N-(1H-Indol-5-ylmethyl)-N-methyl-3-(4-methyl-2-oxo-2,3,4,5-tetrahydro-1H-pyrido[2,3-e][1,4]diazepin-7-yl)acrylamide To a solution of (1H-indol-5-ylmethyl)methylamine (143 mg, 0.9 mmol), (E)-3-(4-methyl-2-oxo-2,3,4,5-tetrahydro-1H-pyrido[2,3-e][1,4]diazepin-7-yl)acrylic acid dihydrochloride (250 mg, 0.8 mmol), HOBt (121 mg, 0.9 mmol) and diisopropylethylamine (0.61 mL, 3.6 mmol) in DMF (25 mL) was added EDC hydrochloride (172 mg, 0.9 mmol). The mixture was stirred overnight at room temperature. Water (100 mL) was added and the solution was stirred for 1 hr. The precipitate was collected by filtration. The yellow solid was preabsorded onto silica gel and purified by column chromatography (95:5 $CH_2Cl_2$/MeOH) to afford (E)-N-(1H-indol-5-ylmethyl)-N-methyl-3-(4-methyl-2-oxo-2,3,4,5-tetrahydro-1H-pyrido[2,3-e][1,4]diazepin-7-yl)acrylamide (195 mg, 63%) as a white solid and as a mixture of amide rotamers. $^1$H NMR (300 MHz, DMSO-$d_6$) δ 11.07 (d, J=7.6 Hz, 1H), 10.37 (m, 1H), 8.52 (dd, J=7.0, 1.9 Hz, 1H), 8.15 (d, J=2.0 Hz, 1H), 7.59-7.26 (m, 5H), 7.07-6.92 (m, 1H), 6.38 (d, J=1.9 Hz, 1H), 4.66-4.85 (2×s, 2H), 3.74-3.77 (m, 2H), 3.42-3.38 (m, 2H), 3.08-2.90 (2×s, 3H), 2.37-2.32 (2×s, 3H); ESI MS m/z 390 $[C_{22}H_{23}N_5O_2+H]^+$.

Example 256

Preparation of (E)-N-Methyl-N-(1-methylindol-5-ylmethyl)-3-(4-methyl-2-oxo-2,3,4,5-tetrahydro-1H-pyrido[2,3-e][1,4]diazepin-7-yl)acrylamide To a solution of (methyl-(1-methyl-1H-indol-5-ylmethyl) amine (103 mg, 0.6 mmol), (E)-3-(4-methyl-2-oxo-2,3,4,5-tetrahydro-1H-pyrido[2,3-e][1,4]diazepin-7-yl)acrylic acid dihydrochloride (160 mg, 0.5 mmol), HOBt (81 mg, 0.5 mmol) and diisopropylethylamine (0.41 mL, 2 mmol) in DMF (12 mL) was added EDC hydrochloride (114 mg, 0.6 mmol). The mixture was stirred overnight at room temperature. Water (75 mL) was added and the solution stirred for 1 hr. The precipitate was collected by filtration. The yellow solid was preabsorded onto silica gel and purified by column chromatography (95:5 $CH_2Cl_2$/MeOH) to give a yellow oil. Diethyl ether (100 mL) was added and the mixture was sonicated. The ether layer was decanted to afford (E)-N-methyl-N-(1-methylindol-5-ylmethyl)-3-(4-methyl-2-oxo-2,3,4,5-tetrahydro-1H-pyrido[2,3-e][1,4]diazepin-7-yl)acrylamide (158 mg, 78%) as a white solid and as a mixture of amide rotamers. $^1$H NMR (300 MHz, DMSO-$d_6$) δ 10.33 (d, J=4.3 Hz, 1H), 8.51 (d, J=6.1 Hz, 1H), 8.13 (s, 1H), 7.59-7.25 (m, 5H), 7.09-7.02 (m, 1H), 6.37 (s 1H), 4.67-4.86 (2×s, 2H), 3.72-3.79 (m, 5H), 3.42-3.38 (m, 2H), 3.06-2.87 (2×s, 3H), 2.37-2.33 (2×s, 3H); ESI MS m/z 404 $[C_{23}H_{25}N_5O_2+H]^+$.

Example 257

Preparation of (E)-N-(1H-Indol-7-ylmethyl)-N-methyl-3-(4-methyl-2-oxo-2,3,4,5-tetrahydro-1H-pyrido[2,3-e][1,4]diazepin-7-yl)acrylamide To a solution of (1H-indol-7-ylmethyl)methylamine (103 mg, 0.6 mmol), (E)-3-(4-methyl-2-oxo-2,3,4,5-tetrahydro-1H-pyrido[2,3-e][1,4]diazepin-7-yl)acrylic acid dihydrochloride (160 mg, 0.5 mmol), HOBt (81 mg, 0.5 mmol) and diisopropylethylamine (0.41 mL, 2 mmol) in DMF (12 mL) was added EDC hydrochloride (114 mg, 0.6 mmol). The mixture was stirred overnight at room temperature. Water (75 mL) was added and the solution stirred for 1 hr. The precipitate was collected by filtration and triturated with hexanes to afford (E)-N-(1H-indol-7-ylmethyl)-N-methyl-3-(4-methyl-2-oxo-2,3,4,5-tetrahydro-1H-pyrido[2,3-e][1,4]diazepin-7-yl)acrylamide (155 mg, 79%) as a white solid and as a mixture of amide rotamers. $^1$H NMR (300 MHz, DMSO-$d_6$) δ 10.78-11.23 (m, 1H), 10.34-10.30 (m, 1H), 8.54-8.45 (m, 1H), 8.14-8.00 (m, 1H), 7.64-7.27 (m, 4H), 6.99-6.75 (m, 2H), 6.47-6.45 (m, 1H), 5.10-4.82 (2×s, 2H), 3.79-3.71 (2×s, 2H), 3.42-3.38 (m, 2H), 3.15-2.95 (2×s, 3H), 2.36-2.31 (2×s, 3H); ESI MS m/z 390 $[C_{22}H_{23}N_5O_2+H]^+$

Example 258

Preparation of (E)-N-Methyl-N-(1-methylindol-7-ylmethyl)-3-(4-methyl-2-oxo-2,3,4,5-tetrahydro-1H-pyrido[2,3-e][1,4]diazepin-7-yl)acrylamide To a solution of (methyl-(1-methyl-1H-indol-7-ylmethyl) amine (103 mg, 0.6 mmol), (E)-3-(4-methyl-2-oxo-2,3,4,5-tetrahydro-1H-pyrido[2,3-e][1,4]diazepin-7-yl)acrylic acid dihydrochloride (160 mg, 0.5 mmol), HOBt (81 mg, 0.5 mmol) and diisopropylethylamine (0.41 mL, 2 mmol) in DMF (12 mL) was added EDC hydrochloride (114 mg, 0.6 mmol). The mixture was stirred overnight at room temperature. Water (75 mL) was added and the solution stirred for 1 hr. The precipitate was collected by filtration and triturated with hexanes to afford (E)-N-methyl-N-(1-methylindol-7-yl-methyl)-3-(4-methyl-2-oxo-2,3,4,5-tetrahydro-1H-pyrido[2,3-e][1,4]diazepin-7-yl)acrylamide (100 mg, 50%) as a white solid and as a mixture of amide rotamers. $^1$H NMR (300 MHz, DMSO-$d_6$) δ 10.33 (m, 1H), 8.54-8.47 (m, 1H), 8.16-7.97 (m, 1H), 7.62-7.19 (m, 4H), 6.92-6.97 (m, 1H), 6.78-6.58 (m, 1H), 6.39 (d, J=3.1 Hz, 1H) 5.48-5.19 (2×s, 2H), 3.99-4.11 (2×s, 3H), 3.79-3.70 (2×s, 2H), 3.42-3.36 (m, 2H), 3.30-3.13 (2×s, 3H), 2.36-2.30 (2×s, 3H); ESI MS m/z 404 $[C_{23}H_{25}N_5O_2+H]^+$.

Example 259

Preparation of (E)-N-(1H-Indol-6-ylmethyl)-N-methyl-3-(4-methyl-2-oxo-2,3,4,5-tetrahydro-1H-pyrido[2,3-e][1,4]diazepin-7-yl)acrylamide To a solution of (1H-indol-6-ylmethyl)methylamine (98 mg, 0.6 mmol), (E)-3-(4-methyl-2-oxo-2,3,4,5-tetrahydro-1H-pyrido[2,3-e][1,4]diazepin-7-yl)acrylic acid dihydrochloride (160 mg, 0.5 mmol) HOBt (81 mg, 0.5 mmol) and diisopropylethylamine (0.41 mL, 2 mmol) in DMF (12 mL) was added EDC hydrochloride (114 mg, 0.6 mmol). The mixture was stirred overnight at room temperature. Water (75 mL) was added and the solution stirred for 1 hr. The precipitate was collected by filtration and triturated with hexanes to afford (E)-N-(1H-indol-6-ylmethyl)-N-methyl-3-(4-methyl-2-oxo-2,3,4,5-tetrahydro-1H-pyrido[2,3-e][1,4]diazepin-7-yl)acrylamide (89 mg, 37%) as a white solid and as a mixture of amide rotomers. $^1$H NMR (300 MHz, DMSO-d$_6$) δ 11.03-11.01 (m, 1H), 10.33-10.30 (m, 1H), 8.52 (d, J=7.6 Hz, 1H), 8.13 (d, J=2.4 Hz, 1H), 7.60-7.22 (m, 5H), 6.92-6.86 (m, 1H), 6.37 (s, 1H), 4.88-4.68 (2×s, 2H), 3.78-3.74 (m, 2H), 3.42-3.38 (m, 2H), 3.08-2.89 (2×s, 3H), 2.36-2.33 (2×s, 3H); ESI MS m/z 390 [C$_{22}$H$_{23}$N$_5$O$_2$+H]$^+$.

Example 260

(E)-N-3-(6-Amino-pyridin-3-yl)-N-methyl-N-(2-methyl-benzofuran-3-ylmethyl)-acrylamide hydrochloride To a solution of methyl-(2-methylbenzofuran-3-ylmethyl)-amine (176 mg, 1.0 mmol), 3-(6-amino-pyridin-3-yl)-acrylic acid (150 mg, 0.91 mmol), HOBt (135 mg, 1.0 mmol) and diisopropylethylamine (0.46 mL, 2.7 mmol) in DMF (10 mL) was added EDC (209 mg, 1.1 mmol). The yellow solution was stirred overnight at room temperature. The reaction mixture was cooled to 0° C. then treated with H$_2$O (40 mL) to form a precipitate. The precipitate was filtered, washed with H$_2$O (20 mL) then with a 10% EtOAc:hexanes solution (10 mL). The solid was dissolved in a 10% MeOH:CH$_2$Cl$_2$ solution (20 mL), cooled to 0° C. then treated with 2 mL of a 1.0 M HCl in Et$_2$O. After stirring for 10 minutes, the yellow solution was concentrated to dryness then triturated with Et$_2$O (20 mL). The title compound was collected and dried under vacuo to yield the title compound (76.9%) as a mixture of amide rotamers. $^1$H NMR (300 MHz, DMSO-d$_6$) δ 8.41-8.33 (m, 3H), 7.58-7.02 (m, 6H), 4.93 and 4.74 (2×s, 2H), 3.05 and 2.82 (2×s, 3H), 2.53 and 2.48 (2×s, 3H); MS (ESI) m/e 322 (M+H)$^+$.

Example 261

Preparation of (E)-3-(3,3-Dimethyl-2-oxo-2,3,4,5-tetrahydro-1H-pyrido[2,3-e][1.4]diazepin-7-yl)-N-methyl-N-(3-methyl-benzofuran-2-ylmethyl)acrylamide hydrochloride a) N-Methyl-N-(3-methyl-benzofuran-2-ylmethyl) acrylamide According to the procedure of Preparation 65, except substituting methyl-(3-methyl-benzofuran-2-ylmethyl)amine for the methyl-(3-methyl-benzo[b]thiophen-2-ylmethyl) amine, the title compound (0.95 g, 73%) was prepared as an white solid: $^1$H NMR (300 MHz, CDCl$_3$) δ 7.50-7.47 (m, 1H), 7.42-7.39 (m, 1H), 7.30-7.17 (m, 2H), 6.90-6.55 (m, 1H), 6.41-6.35 (m, 1H), 5.79-5.70 (m, 1H), 4.78-4.64 (m, 2H), 3.14-3.02 (m, 3H), 2.29-2.62 (m, 3H).

b) (E)-3-(3,3-Dimethyl-2-oxo-2,3,4,5-tetrahydro-1H-pyrido[2,3-e][1,4]diazepin-7-yl)-N-methyl-N-(3-methyl-benzofuran-2-ylmethyl)acrylamide According to the procedure of Example 2, except substituting N-methyl-N-(3-methyl-benzofuran-2-ylmethyl)acrylamide for the N-methyl-N-(3-methyl-benzo[b]thiophen-2-ylmethyl)acrylamide, the title compound (0.25 g, 60%) was prepared as a white solid and as a mixture of amide rotamers: $^1$H NMR (300 MHz, DMSO-d$_6$) δ 10.92 (s, 1H), 10.55 (br s, 2H), 8.68-8.65 (m, 1H), 8.39 (s, 1H), 7.60-7.24 (m, 6H), 5.01-4.81 (m, 2H), 4.40 (s, 2H), 3.20-2.93 (m, 3H), 2.27 (s, 3H), 1.63 (s, 6H); MS (ESI) m/e 419 (M+H)$^+$.

Example 262

Preparation of (E)-N-Methyl-N-(3-methyl-1H-inden-2-ylmethyl)-3-(4-methyl-2-oxo-2,3,4,5-tetrahydro-1H-pyrido[2,3-e][1,4]diazepin-7-yl)acrylamide hydrochloride According to the procedure of Example 1, except substituting methyl-(3-methyl-1H-inden-2ylmethyl)amine (0.237 g, 1.37 mmol) for methyl-(1-propyl-naphthalen-2ylmethyl) amine, the title compound (0.303 g, 60%) was prepared as light yellow solid and as a mixture of amide rotamers: $^1$H NMR (300 MHz, DMSO-d$_6$) δ 12.32 (br s, 1H), 11.21 (br s, 1H), 8.82-8.81 (m, 1H), 8.34 (s, 1H), 7.61-7.25 (m, 5H), 7.17-7.12 (m, 1H), 4.67-4.51 (m, 2H), 4.29 (br s, 2H), 3.80 (br s, 2H), 3.28-3.26 (m, 2H), 3.12-2.87 (m, 6H), 2.16-2.14 (m, 3H); MS (ESI) m/e 403 (M+H)$^+$.

Example 263

Preparation of (E)-3-(6-{2-[Methyl-(3-methyl-benzo[b]thiophen-2-ylmethyl)carbamoyl]vinyl}-2-oxo-1,4-dihydro-2H-pyrido[2,3-d]pyrimidin-3-yl)propionic acid ethyl ester According to the procedure of Example 2, except substituting 3-(6-bromo-2-oxo-1,4-dihydro-2H-pyrido[2,3-d]pyrimidin-3-yl)propionic acid ethyl ester for the 7-bromo-3,3-dimethyl-1,3,4,5-tetrahydro-pyrido[2,3-e][1,4]diazepin-2-one, the title compound (0.40 g, 38%) quantitative) was prepared as an off-white solid and as a mixture of amide rotamers: $^1$H NMR (300 MHz, DMSO-d$_6$) δ 9.97 (s, 1H), 8.36 (s, 1H), 8.00 (s, 1H), 7.87 (d, J=7.5 Hz, 1H), 7.73 (d, J=7.8 Hz, 1H), 7.55-7.50 (m, 1H), 7.41-7.31 (m, 3H), 7.19-7.14 (m, 1H), 5.10-4.88 (m, 2H), 4.50 (s, 2H), 4.08-4.01 (m, 2H), 3.55-3.46 (m, 2H), 3.15-2.93 (m, 3H), 2.62-2.58 (t, J=6.6 Hz, 2H), 2.41 (s, 3H), 1.23-1.03 (m, 3H); MS (ESI) m/e 493 (M+H)$^+$.

Example 264

Preparation of (E)-3-(6-amino-5-cyano-pyridin-3-yl)-N-methyl-N-(1-methyl-1H-indol-2-ylmethyl)-acrylamide hydrochloroide a) 2-amino-5-bromo-nicotinonitrile Bromine (1.1 mL, 21 mmol) in AcOH (3 mL) was added dropwise to a solution of 2-amino-nicotinonitrile (1.00 g, 8.4 mmol) in AcOH (20 mL) at 10° C. The orange mixture was stirred for 22 hours at ambient temperature then diluted with ether (100 mL). The resultant precipitated salt was filtered, washed with ether and dried on air. The precipitate was suspended in water (100 mL), neutralized with 1N NaOH, filtered, washed with water and dried on air to give 1.29 g (78%) title compound. $^1$H NMR (300 MHz, DMSO-d$_6$) δ 8.27 (d, J=2.5 Hz, 1H), 8.14 (d, J=2.5 Hz, 1H), 7.13 (s, br, 2H). MS (ESI) m/e: 197.9655 (M+H)$^+$.

b) N-methyl-N-(1-methyl-1H-indol-2-ylmethyl)-acrylamide

Acryloyl chloride (5.13 mL, 63.1 mmol) was added dropwise to a stirred $CH_2Cl_2$ (100 mL) solution of methyl-(1-methyl-1H-indol-2-ylmethyl)-amine (10.0 g, 57.4 mmol) and triethylamine (12 mL, 86.1 mmol) at −78° C. The reaction mixture was warmed to −30° C. over 30 min and quenched with water. The reaction mixture was diluted with $CH_2Cl_2$ (100 mL), washed with dilute $NaHCO_3$, HCl and water, dried and evaporated to afford 9.91 g (76%) title compound. $^1H$ NMR (300 MHz, DMSO-$d_6$) δ 7.44 (m, 2H), 7.12 (t, J=7.2 Hz, 1H), 7.00 (t, J=7.2 Hz, 1H), 6.81 (dd, J=7.4 and 16.7 Hz, 1H), 6.40 and 6.14 (rotamers, 2s, 1H), 6.20 (dd, J=2.5 and 16.7 Hz, 1H), 5.7 (m, 1H), 4.90 and 4.80 (rotamers, 2s, 2H), 3.68 and 3.66 (rotamers, 2s, 3H), 3.00 and 2.96 (rotamers, 2s, 3H). MS (ESI) m/e: 229.1 $(M+H)^+$.

c) (E)-3-(6-amino-5-cyano-pyridin-3-yl)-N-methyl-N-(1-methyl-1H-indol-2-ylmethyl)-acryl-amide hydrochloride A propionitrile (15 mL) solution of 2-amino-5-bromonicotinonitrile (198 mg, 1 mmol), N-methyl-N-(1-methyl-1H-indol-2-ylmethyl)-acrylamide (457 mg, 2 mmol) and diisopropyl-ethylamine (523 μL, 3 mmol) was purged with Argon for 10 min. $Pd(OAc)_2$ (23 mg, 0.1 mmol) and $P(o-Tol)_3$ (61 mg, 0.2 mmol) was added and the Argon purge was repeated. The mixture was heated to 100° C. and stirred for 6 hr under Argon. Upon cooling, solvents were removed under vacuo and the residue was purified by Flash chromatography (silica, 2% MeOH in $CH_2Cl_2$). The purified free base was converted to its HCl salt by addition of HCl (1 mL, 1 mmol, 1M in ether). The salt was washed with ether and dried to afford 162 mg (43%) of the title compound. $^1H$ NMR (300 MHz, DMSO-$d_6$) δ 8.50 (m, 2H), 7.55-6.95 (m, 4H), 6.40 and 6.17 (rotamers, 2s, 1H), 5.03 and 4.83 (rotamers, 2s, 2H), 3.71 and 3.67 (rotamers, 2s, 3H), 3.09 and 2.96 (rotamers, 2s, 3H). MS (ESI) m/e: 346.1662 $(M+H)^+$.

Example 265

Preparation of (E)-N-methyl-N-(1-methyl-1H-indol-2-ylmethyl)-3-(2-oxo-12,3,4-tetrahydro-pyrido-[2,3-b]pyrazin-7-yl)-acrylamide a) 7-bromo-3,4-dihydro-1H-pyrido[2,3-b]pyrazin-2-one

A mixture of 5-bromo-2,3-diaminopyridine (11.64 g, 61.9 mmol) and glyoxylic acid monohydrate (22.80 g, 247.7 mmol) in MeOH (200 mL) was stirred for 62 hours. The precipitate was filtered, washed with MeOH and dried at 110° C. to give 12.60 g (90%) of a regioisomeric mixture of the condensation products. The mixture (4.52 g, 20 mmol) was suspended in DME (300 mL) and, after addition of $NaBH(OAc)_3$ (11.87 g, 56 mmol), it was stirred for 88 hours at 60° C. Upon cooling, EtOAc (500 mL) and water (300 mL) was added and the pH was adjusted to 8.0 with 2N NaOH. The aqueous phase was separated and extracted with EtOAc (2×200 mL). The combined organic phases were washed with water and brine, dried and evaporated. The residue was stirred with $CH_2Cl_2$ (50 mL) for 24 hr then filtered. The solid cake was stirred with EtOAc (100 mL) at 75° C. for 14 hours, filtered and dried to afford the title compound (2.35 g, 52%). $^1H$ NMR (300 MHz, DMSO-$d_6$) δ 10.47 (s, br, 1H), 7.65 (d, J=2.2 Hz, 1H), 7.01 (t, J=2.2 Hz, 1H), 6.99 (s, br, 1H), 3.93 (d, J=1.5 Hz, 2H). MS (ESI) m/e: 227.9764 $(M+H)^+$.

b) 7-bromo-2-oxo-2,3-dihydro-1H-pyrido[2,3-b]pyrazine-4-carboxylic acid tert-butyl ester $Boc_2O$ (3.23 g, 14.8 mmol) was added to a stirred MeCN (120 mL) suspension containing 7-bromo-3,4-dihydro-1H-pyrido[2,3-b]pyrazin-2-one (2.25 g, 9.85 mmol), triethylamine (4.12 mL, 29.6 mmol) and N,N-dimethylaminopyridine (120 mg, 1 mmol). After 24 hr stirring, additional $Boc_2O$ (3.23 g, 14.8 mmol) was added and the stirring was continued for 2 days. The solvent was removed in vacuo and the residue was purified by Flash Chromatography (silica, 1-2% MeOH in $CH_2Cl_2$) to afford the title compound (499 mg, 16%). $^1H$ NMR (300 MHz, DMSO-$d_6$) δ 10.82 (s, br, 1H), 8.16 (d, J=2.3 Hz, 1H), 7.45 (t, J=2.3 Hz, 1H), 4.30 (s, 2H), 1.44 (s, 9H). MS (ESI) m/e: 328.0 $(M+H)^+$, 272.0 $(M-tert-Bu)^+$.

c) (E)-7-{2-[methyl-(1-methyl-1H-indol-2-ylmethyl)-carbamoyl]-vinyl}-2-oxo-2,3-dihydro-1H-pyrido[2,3-b]pyrazine-4-carboxylic acid tert-butyl ester A solution of 7-bromo-2-oxo-2,3-dihydro-1H-pyrido[2,3-b]pyrazine-4-carboxylic acid tert-butyl ester (494 mg, 1.5 mmol) in propionitrile (12 mL) was treated with N-methyl-N-(1-methyl-1H-indol-2-ylmethyl)-acrylamide (685 mg, 3 mmol) and diisopropylethylamine (788 μL, 4.5 mmol) and purged with Argon for 10 min. $Pd(OAc)_2$ (34 mg, 0.15 mmol) and $P(o-Tol)_3$ (92 mg, 0.3 mmol) was added and the Argon purge was repeated. The mixture was heated to 100° C. and stirred for 6 hours under Argon. Upon cooling, solvent was removed and the residue was purified by Flash chromatography (silica, 1-3% MeOH in $CH_2Cl_2$) to afford the title compound (480 mg, 67%). $^1H$ NMR (300 MHz, DMSO-$d_6$) δ 10.81 and 10.73 (rotamers, 2s, br, 1H), 8.46 and 8.41 (rotamers, 2s, 1H), 7.58 (d, J=15.4 Hz, 1H), 7.51 (m, 3H), 7.23 (d, J=15.4 Hz, 1H), 7.11 (m, 1H), 7.03 (m, 1H), 6.45 and 6.20 (rotamers, 2s, 1H), 5.06 and 4.87 (rotamers, 2s, 2H), 4.32 and 4.28 (rotamers, 2s, 2H), 3.74 and 3.71 (rotamers, 2s, 3H), 3.16 and 3.05 (rotamers, 2s, 3H), 1.44 and 1.42 (rotamers, 2s, 9H). MS (ESI) m/e: 476.2 $(M+H)^+$, 420.2 $(M-tert-Bu)^+$.

d) (E)-N-methyl-N-(1-methyl-1H-indol-2-ylmethyl)-3-(2-oxo-1,2,3,4-tetrahydro-pyrido[2,3-b]pyrazin-7-yl)-acrylamide Trifluoroacetic acid (0.5 mL) was added to a solution of (E)-7-{2-[methyl-(1-methyl-1H-indol-2-ylmethyl)-carbamoyl]-vinyl}-2-oxo-2,3-dihydro-1H-pyrido[2,3-b]pyrazine-4-carboxylic acid tert-butyl ester in $CH_2Cl_2$ (1 mL) at 10° C. After stirring 1 hr, volatiles were removed in vacuo and the resulting residue was dissolved in EtOAc (2 mL). Upon addition of dilute NaOH, a precipitate formed. The solid was collected by filtration, washed with water (100 mL), MeOH (50 mL), EtOAc (50 mL) and $CH_2Cl_2$ (50 mL) to afford the title compound (170 mg). $^1H$ NMR (300 MHz, DMSO-$d_6$) δ 10.42 and 10.33 (rotamers, 2s, br, 1H), 7.90 (m, 1H), 7.45 (m, 3H), 7.22 (m, 1H), 7.12 (m, 1H), 6.83 (d, J=15.4 Hz, 1H), 6.42 and 6.17 (rotamers, 2s, 1H), 4.98 and 4.84 (rotamers, 2s, 2H), 3.99 and 3.95 (rotamers, 2s, 2H), 3.72 and 3.68 (rotamers, 2s, 3H), 3.07 and 3.00 (rotamers, 2s, 3H). MS (ESI) m/e: 376 $(M+H)^+$.

Example 266

Preparation of (E)-3-(3,3-Dimethyl-2-oxo-2,3,4,5-tetrahydro-1H-pyrido[2,3-e][1,4]diazepin-7-yl)-N-methyl-N-(2-ethoxy-3-trifluoromethoxybenzyl)acrylamide hydrochloride a) 2-Hydroxy-3-trifluoromethoxybenzaldehyde

A solution of 2-trifluoromethoxyphenol (5.13 g, 28.8 mmol) in anhydrous acetonitrile (150 mL) in oven-dried glassware was treated with triethylamine (15.0 mL, 108 mmol) and $MgCl_2$ (4.11 g, 43.2 mmol) which had been dried under vacuum with heat. Paraformaldehyde (5.18 g, 172 mmol), which had been dried under vacuum with $P_2O_5$, was added and the solution was heated to reflux. After 5 days, the reaction was quenched with 1 N HCl (200 mL) and the mixture was extracted using $Et_2O$ (2×100 mL). The combined organics were washed with brine (2×150 mL), dried ($Na_2SO_4$) and concentrated to a yellow solid. Purification by column chromatography (silica gel, 98:2 to 95:5 hexanes/EtOAc) gave the title compound (2.45 g, 41%) as a yellow powder: $^1$H NMR (300 MHz, DMSO-$d_6$) δ 10.24 (s, 1H), 7.75-7.65 (m, 2H), 7.08 (t, J=7.9 Hz, 1H).

b) 2-Ethoxy-3-trifluoromethoxybenzaldehyde

To a solution of 2-hydroxy-3-trifluoromethoxybenzaldehyde (1.00 g, 4.82 mmol) in DMF (10 mL), was added $K_2CO_3$ (1.46 g, 10.6 mmol) followed by iodoethane (0.57 mL, 7.24 mmol) and the mixture was heated to 37° C. for 6 h. The reaction was quenched by the addition of $H_2O$ (40 mL) and the mixture was extracted with EtOAc (3×100 mL). The combined organics were washed with brine (2×100 mL), dried ($Na_2SO_4$) and concentrated to yield the title compound (1.17 g, quant.) as an orange oil: $^1$H NMR (300 MHz, DMSO-$d_6$) δ 10.31 (s, 1H), 7.77 (m, 2H), 7.38 (t, J=8.1 Hz, 1H), 4.19 (q, J=6.9 Hz, 2H), 1.36 (t, J=6.9 Hz, 3H).

c) (2-Ethoxy-3-trifluoromethoxybenzyl)methylamine

A solution of methylamine (20 mL of a 2.0 M solution if MeOH, 40 mmol) was added to 2-ethoxy-3-trifluoromethoxybenzaldehyde (1.17 g, 4.95 mmol) under $N_2$ and the solution was stirred for 18 h. The solution was concentrated under reduced pressure. The resulting clear oil was dissolved in EtOH (20 mL) and treated with $NaBH_4$ (0.187 g, 4.95 mmol). After stirring for 5.5 h, the reaction mixture was concentrated under reduced pressure, then dissolved in 1 N NaOH (20 mL) and extracted with $Et_2O$ (3×50 mL). The combined organics were collected, washed with brine (2×100 mL), dried ($Na_2SO_4$) and concentrated to yield the title compound (0.72 g, 58%) as a clear oil: $^1$H NMR (500 MHz, DMSO-$d_6$) δ 7.40 (dd, J=7.7, 1.55 Hz, 1H), 7.25 (d, J=9.5 Hz, 1H), 7.16 (t, J=7.7 Hz, 1H), 3.97 (t, J=7.0 Hz, 2H), 3.68 (s, 2H), 2.28 (s, 3H), 2.02 (br s, 1H), 1.35-1.30 (m, 3H).

d) N-(2-Ethoxy-3-trifluoromethoxybenzyl)-N-methylacrylamide

To a solution of (2-ethoxy-3-trifluoromethoxybenzyl)methylamine (0.720 g, 2.08 mmol) in $CH_2Cl_2$ (25 mL), was added acryloyl chloride (0.25 mL, 3.15 mmol) drop-wise. After stirring for five minutes, triethylamine (0.43 mL, 3.15 mmol) was added. The solution was allowed to stir under $N_2$ for 3 h. The solution was diluted with $CH_2Cl_2$ (30 mL) and then washed with $H_2O$ (3×50 mL) and brine (2×100 mL), dried ($Na_2SO_4$) and concentrated to yield the title compound (0.746 g, 86%) as a yellow oil and as a mixture of amide rotamers: $^1$H NMR (500 MHz, CDCl$_3$) δ 7.21-7.02 (m, 3H), 6.67-6.50 (m, 1H), 6.41-6.36 (m, 1H), 5.75-5.58 (m, 1H), 4.75-4.65 (m, 2H), 4.14-4.05 (m, 2H), 3.03-2.99 (m, 3H), 1.43-141 (m, 3H).

e) (E)-3-(3,3-Dimethyl-2-oxo-2,3,4,5-tetrahydro-1H-pyrido[2,3-e][1,4]diazepin-7-yl)-N-methyl-N-(2-ethoxy-3-trifluoromethoxybenzyl)acrylamide A solution of N-(2-ethoxy-3-trifluoromethoxybenzyl)-N-methylacrylamide (0.447 g, 1.47 mmol) in propionitrile (5 mL) and DMF (1 mL) was deoxygenated with Ar for 20 min and then treated with diisopropylethylamine (0.40 mL, 2.3 mmol) and 7-bromo-3,3-dimethyl-1,3,4,5-tetrahydro-pyrido[2,3-e][1,4]diazepin-2-one (0.300 g, 1.11 mmol). The solution was deoxygenated with Ar for 20 minutes. Pd(OAc)$_2$ (0.024 g, 0.111 mmol) and P(o-tol)$_3$ (0.067 g, 0.222 mmol) were added and the solution deoxygenated with Ar for 20 min. The mixture was heated to reflux for 18 h then, allowed to cool. The mixture was diluted with EtOAc (30 mL) and was washed with $H_2O$ (3×50 mL) and brine (2×50 mL), dried ($Na_2SO_4$) and concentrated to a yellow-orange solid. Purification by column chromatography (silica gel, $CH_2Cl_2$/MeOH, 100 to 98:2) gave the title compound (0.25 g, 31%) as an off-white solid and as a mixture of amide rotamers: $^1$H NMR (300 MHz, DMSO-$d_6$) δ 9.80-9.78 (m, 1H), 8.40-8.37 (m, 1H), 8.01-7.93 (m, 1H), 7.56-7.49 (m, 1H), 7.36-7.09 (m, 4H), 4.87-4.68 (m, 2H), 4.06-3.83 (m, 4H), 3.31-2.88 (m, 4H), 1.36-1.29 (m, 9H).

f) (E)-3-(3,3-Dimethyl-2-oxo-2,3,4,5-tetrahydro-1H-pyrido[2,3-e][1,4]diazepin-7-yl)-N-methyl-N-(2-ethoxy-3-trifluoromethoxybenzyl)acrylamide hydrochloride A stirring solution of (E)-3-(3,3-dimethyl-2-oxo-2,3,4,5-tetrahydro-1H-pyrido[2,3-e][1,4]diazepin-7-yl)-N-methyl-N-(2-ethoxy-3-trifluoromethoxybenzyl)acrylamide (0.172 g, 0.349 mmol) in $CH_2Cl_2$ (4 mL) under $N_2$ was treated with anhydrous HCl (0.17 mL of a 2 M solution in diethyl ether, 0.34 mmol). After stirring for 18 h, the resulting solid was collected by filtration, washed with $Et_2O$ (100 mL) and dried to yield the title compound (0.11 g, 62%) as an off white solid and as a mixture of amide rotamers: $^1$H NMR (300 MHz, DMSO-$d_6$) δ 10.94 (br s, 1H), 10.38 (br s, 2H), 8.67-8.64 (m, 1H), 8.38-8.30 (m, 1H), 7.62-7.54 (m, 1H), 7.41-7.10 (m, 4H), 4.89-4.70 (m, 2H), 4.41-4.36 (m, 2H), 4.06-4.00 (m, 2H), 3.17-2.87 (m, 3H), 1.61-1.59 (m, 6H), 1.37-1.31 (m, 3H); MS (ESI) m/e 493 (M+H)$^+$.

Example 267

Preparation of (E)-3-(3,3-Dimethyl-2-oxo-2,3,4,5-tetrahydro-1H-pyrido[2,3-e][1,4]diazepin-7-yl)-N-methyl-N-(2-propoxy-3-trifluoromethoxybenzyl) acrylamide hydrochloride a) 2-Hydroxy-3-trifluoromethoxybenzaldehyde

A solution of 2-trifluoromethoxyphenol (5.13 g, 28.8 mmol) in anhydrous acetonitrile (150 mL) in oven-dried glassware was treated with triethylamine (15.0 mL, 108 mmol) and $MgCl_2$ (4.11 g, 43.2 mmol) which had been dried under vacuum with heating. Paraformaldehyde (5.18 g, 172 mmol), which had been dried under vacuum with $P_2O_5$, was then added and the solution was heated to reflux. After 5 days, the reaction was quenched with 1 N HCl (200 mL). The mixture was extracted using Et$_2$O (2×100 mL). The combined organics were washed with brine (2×150 mL), dried (Na$_2$SO$_4$) and concentrated to a yellow solid. Purification by column chromatography (silica gel, 98:2 to 95:5 hexanes/EtOAc) gave the title compound (2.45 g, 41%) as a yellow powder: $^1$H NMR (300 MHz, DMSO-d$_6$) δ 10.24 (s, 1H), 7.75-7.65 (m, 2H), 7.08 (t, J=7.9 Hz, 1H).

b) 2-Propoxy-3-trifluoromethoxybenzaldehyde

To a solution of 2-hydroxy-3-trifluoromethoxybenzaldehyde (1.00 g, 4.82 mmol) in DMF (10 mL) was added K$_2$CO$_3$ (1.46 g, 10.6 mmol) followed by 1-bromopropane (0.65 mL, 7.2 mmol). The solution was heated to 37° C. for 6 h. The reaction was quenched with H$_2$O (40 mL) and the mixture was extracted with EtOAc (3×50 mL). The combined organics were washed with brine (2×100 mL), dried (Na$_2$SO$_4$) and concentrated to yield the title compound (1.15 g, 96%) as a yellow oil: $^1$H NMR (300 MHz, DMSO-d$_6$) δ 10.30 (s, 1H), 7.77 (d, J=8.0 Hz, 2H), 7.38 (t, J=7.9 Hz, 1H), 4.09 (t, J=6.4 Hz, 2H), 1.81-1.72 (m, 2H), 1.01 (t, J=7.4 Hz, 3H).

c) Methyl-(2-propoxy-3-trifluoromethoxybenzyl)amine

A solution of methylamine (19 mL of a 2.0 M solution in MeOH, 38 mmol) was added to 2-propoxy-3-trifluoromethoxybenzaldehyde (1.15 g, 4.60 mmol). The mixture was stirred for 18 h. The solution was concentrated under reduced pressure. The resulting clear oil was dissolved in EtOH (19 mL) and treated with NaBH$_4$ (0.174 g, 4.60 mmol). After stirring for 5.5 h, the reaction mixture was concentrated under reduced pressure, then dissolved in 1 N NaOH (19 mL). The mixture was extracted with Et$_2$O (3×50 mL). The organics were collected, washed with brine (2×100 mL), dried (Na$_2$SO$_4$) and concentrated to yield the title compound (0.89 g, 73%) as an orange oil: $^1$H NMR (300 MHz, DMSO-d$_6$) δ 7.41 (dd, J=7.7, 1.6 Hz, 1H), 7.25 (dd, J=6.7, 1.3 Hz, 1H), 7.16 (t, J=7.7 Hz, 1H), 3.87 (t, J=6.3 Hz, 2H), 3.68 (s, 2H), 2.27 (s, 3H), 2.07 (br s, 1H), 1.74 (q, J=6.4 Hz, 2H), 1.02 (t, J=3.1 Hz, 3H).

d) N-Methyl-N-(2-propoxy-3-trifluoromethoxybenzyl)acrylamide

To a solution of methyl-(2-propoxy-3-trifluoromethoxybenzyl)amine (0.890 g, 3.35 mmol) in CH$_2$Cl$_2$ (30 mL) was added acryloyl chloride (0.30 mL, 3.6 mmol) drop-wise. After stirring for five minutes, triethylamine (0.51 mL, 3.6 mmol) was added. The solution was allowed to stir under N$_2$ for 3 h. The solution was diluted with CH$_2$Cl$_2$ (30 mL), washed with H$_2$O (3×50 mL) and brine (2×50 mL), dried (Na$_2$SO$_4$) filtered and concentrated to yield the title compound (0.95 g, 90%) as a yellow oil and as a mixture of amide rotamers: $^1$H NMR (500 MHz, CDCl$_3$) δ 7.21-7.00 (m, 3H), 6.67-6.48 (m, 1H), 6.41-6.36 (m, 1H), 5.76-5.66 (m, 1H), 4.75-4.65 (m, 2H), 3.99-3.93 (m, 2H), 3.03 (s, 3H), 1.83-1.78 (m, 2H), 1.07-1.03 (m, 3H).

e) (E)-3-(3,3-Dimethyl-2-oxo-2,3,4,5-tetrahydro-1H-pyrido[2,3-e][1,4]diazepin-7-yl)-N-methyl-N-(2-propoxy-3-trifluoromethoxybenzyl)acrylamide A solution of N-methyl-N-(2-propoxy-3-trifluoromethoxybenzyl)acrylamide (0.468 g, 1.47 mmol) in propi-onitrile (5 mL) and DMF (1 mL) was deoxygenated with Ar for 20 min. The solution was treated sequentially with diisopropylethylamine (0.40 mL, 2.3 mmol) and 7-bromo-3,3-dimethyl-1,3,4,5-tetrahydro-pyrido[2,3-e][1,4]diazepin-2-one (0.300 g, 1.11 mmol). The solution was deoxygenated with Ar for 20 min. Pd(OAc)$_2$ (0.024 g, 0.111 mmol) and P(o-tol)$_3$ (0.067 g, 0.222 mmol) were added and the solution was deoxygenated with Ar for 20 minutes. The mixture was heated to reflux for 18 h, then allowed to cool. The mixture was diluted with EtOAc (30 mL) and then washed with H$_2$O (3×50 mL) and brine (2×100 mL), dried (Na$_2$SO$_4$) and concentrated to a yellow-orange solid. Purification by column chromatography (silica gel, CH$_2$Cl$_2$/MeOH, 100 to 98:2) gave the title compound (0.25 g, 31%) as an off-white solid and as a mixture of amide rotamers: $^1$H NMR (300 MHz, DMSO-d$_6$) δ 9.80-9.78 (m, 1H), 8.41-8.36 (m, 1H), 8.01-7.92 (m, 1H), 7.56-7.49 (m, 1H), 7.36-7.08 (m, 4H), 4.87-4.69 (m, 2H), 3.96-3.83 (m, 4H), 3.16-2.88 (m, 4H), 1.78-1.71 (m, 2H), 1.31-1.29 (m, 6H), 1.03-0.98 (m, 3H); MS (ESI) m/e 507 (M+H)$^+$.

f) (E)-3-(3,3-Dimethyl-2-oxo-2,3,4,5-tetrahydro-1H-pyrido[2,3-e][1,4]diazepin-7-yl)-N-methyl-N-(2-propoxy-3-trifluoromethoxybenzyl)acrylamide hydrochloride A stirring solution of (E)-3-(3,3-dimethyl-2-oxo-2,3,4,5-tetrahydro-1H-pyrido[2,3-e][1,4]diazepin-7-yl)-N-methyl-N-(2-propoxy-3-trifluoromethoxybenzyl)acrylamide (0.255 g, 0.503 mmol) in CH$_2$Cl$_2$ (5 mL) under N$_2$, was treated with anhydrous HCl (0.25 mL of a 2 M solution in diethyl ether, 0.5 mmol). After stirring for 18 h, the resulting solid was collected by filtration and washed with Et$_2$O (150 mL). The solid was dried under vacuum to yield the target compound (0.21 g, 82%) as an off white solid and as a mixture of amide rotamers: $^1$H NMR (300 MHz, DMSO-d$_6$) δ 10.93-10.91 (m, 1H), 10.51 (br s, 2H), 8.66-8.64 (m, 1H), 8.40-8.32 (m, 1H), 7.63-7.54 (m, 1H), 7.40-7.09 (m, 4H), 4.89-4.70 (m, 2H), 4.41-4.36 (m, 2H), 3.96-3.90 (m, 2H), 3.18-2.87 (m, 3H), 1.79-1.70 (m, 2H), 1.63-1.61 (m, 6H), 1.09-0.97 (m, 3H); MS (ESI) m/e 507 (M+H)$^+$.

Example 268

Preparation of (E)-N-(3-Chloro-2-ethoxybenzyl)-N-methyl-3-(7-oxo-5,6,7,8-tetrahydro-[1,8]naphthyridin-3-yl)acrylamide a) 3-Chloro-2-isopropoxybenzoic acid isopropyl ester 2-Iodopropane (1.73 mL, 17.3 mmol) was added to a stirring solution of 3-chloro-2-hydroxybenzoic acid (2.00 g, 11.5 mmol) and K$_2$CO$_3$ (3.52 g, 25.4 mmol) in DMF (25 mL) under N$_2$. After stirring at 70° C. for 18 h, additional 2-iodopropane (1.73 mL, 17.3 mmol) was added. The solution was allowed to stir for an additional 48 h. The reaction was quenched with H$_2$O (70 mL) and the mixture was extracted with Et$_2$O (2×100 mL). The combined organics were washed with brine (100 mL), dried (Na$_2$SO$_4$) and concentrated to yield the title compound (2.29 g, 77%) as a clear oil: $^1$H NMR (300 MHz, DMSO-d$_6$) δ 7.68 (dd, J=8.1, 1.8 Hz, 1H), 7.58

(dd, J=7.8, 1.8 Hz, 1H), 7.20 (t, J=7.8 Hz, 1H), 5.16-5.50 (m, 1H), 4.39-4.30 (m, 1H), 1.29 (d, J=7.2 Hz, 6H), 1.22 (d, J=6.0 Hz, 6H).

b) (3-Chloro-2-isopropoxyphenyl)methanol

Diisobutylaluminum lithium hydride (26.8 mL of a 1.0 M in hexanes, 26.8 mmol) was added dropwise to a solution of 3-chloro-2-isopropoxybenzoic acid isopropyl ester (2.29 g, 8.94 mmol) in THF (20 mL) under $N_2$ at 0° C. After the addition was complete, the ice bath was removed, the solution warmed to ambient temperature, and the reaction mixture stirred for 5 d. The reaction was cooled to 0° C. and quenched using 1N HCl (100 mL) until all the solids dissolved. The solution was extracted with $Et_2O$ (3×50 mL). The combined organics were washed with brine (2×100 mL), dried ($Na_2SO_4$) and concentrated to yield the title compound (1.60 g, 89%) as an off-white solid: $^1$H NMR (500 MHz, DMSO-$d_6$) δ 7.41 (d, J=4.5 Hz, 1H), 7.33 (dd, J=8.0, 1.5 Hz, 1H), 7.11 (t, J=8.0 Hz, 1H), 5.19 (t, J=5.7 Hz, 1H), 4.53 (d, J=5.5 Hz, 1H), 4.44-4.36 (m, 1H), 1.24 (d, J=6.1 Hz, 6H).

c) 3-Chloro-2-isopropoxybenzaldehyde $MnO_2$ (4.86 g, 56.0 mmol) was added to a stirring solution of (3-chloro-2-isopropoxyphenyl)methanol (1.60 g, 8.00 mmol) in benzene (75 mL), under $N_2$. After stirring for 48 h, the solution was filtered over diatomaceous earth, the pad was rinsed with $CH_2Cl_2$ (100 mL), and the solution was concentrated to a yellow oil. Purification by column chromatography (silica gel hexanes/EtOAc, 98:2) gave the title compound (0.50 g, 31%) as a clear oil: $^1$H NMR (300 MHz, DMSO-$d_6$) δ 10.28 (s, 1H), 7.84 (dd, J=7.8, 1.5 Hz, 1H), 7.72 (dd, J=7.8, 1.5 Hz, 1H), 7.31 (t, J=8.1 Hz, 1H), 4.53-4.48 (m, 1H), 1.32 (d, J=6.0 Hz, 6H).

d) (3-chloro-2-isopropoxybenzyl)methylamine

Methylamine (10.3 mL of a 2.0 M solution in MeOH, 20.6 mmol) was added to 3-chloro-2-isopropoxybenzaldehyde (0.500 g, 2.52 mmol) and the mixture was stirred for 72 h. The solution was concentrated under reduced pressure. The resulting light yellow oil was dissolved in EtOH (10.3 mL) and treated with $NaBH_4$ (0.095 g, 2.52 mmol). After stirring for 18 h, the reaction mixture was concentrated under reduced pressure, dissolved in 1 N NaOH (20 mL) and extracted with $Et_2O$ (3×50 mL). The combined organics were washed with brine (2×75 mL), dried ($Na_2SO_4$) and concentrated to give the title compound (0.50 g, 93%) as a yellow oil: $^1$H NMR (300 MHz, DMSO-$d_6$) δ 7.40-7.31 (m, 2H), 7.08 (t, J=7.8 Hz, 1H), 4.42 (q, J=6.1 Hz, 1H), 3.66 (s, 2H), 2.25 (s, 3H), 2.02 (br s, 1H), 1.25 (d, J=6.1 Hz, 6H).

e) (E)-N-(3-Chloro-2-ethoxybenzyl)-N-methyl-3-(7-oxo-5,6,7,8-tetrahydro-[1,8]naphthyridin-3-yl)acrylamide A stirring solution of (3-chloro-2-isopropoxybenzyl)methylamine (0.229 g, 1.07 mmol) and diisopropylethylamine (0.51 mL, 2.9 mmol) in DMF (20 mL) under $N_2$ was treated sequentially with (E)-3-(7-oxo-5,6,7,8-tetrahydro-[1,8]naphthyridin-3-yl)acrylic acid hydrochloride (0.250 g, 0.980 mmol), 1-hydroxybenzotriazole hydrate (0.144 g, 1.07 mmol) and 1-(3-dimethylaminopropyl)-3-ethylcarbodiimide hydrochloride (0.205 g, 1.07 mmol). After stirring for 18 h, the reaction mixture was diluted with $H_2O$ (30 mL). The resulting solids were collected by filtration and washed with $Et_2O$ (100 mL), suspended in MeOH (30 mL) and sonicated for 30 minutes. The solids were then collected by filtration, washed with MeOH and dried to yield the title compound (0.085 g, 21%) as a white solid and as a mixture of amide rotamers: $^1$H NMR (300 MHz, DMSO-$d_6$) δ 10.67-10.64 (m, 1H), 8.37-8.32 (m, 1H), 8.09-7.91 (m, 1H), 7.53-7.48 (m, 1H), 7.42-7.37 (m, 1H), 7.28-7.02 (m, 3H), 4.83-4.68 (m, 2H), 4.53-4.45 (m, 1H), 2.94-2.85 (m, 5H), 2.56-2.49 (m, 2H), 1.33-1.28 (m, 6H); MS (ESI) m/e 414 (M+H)$^+$.

Example 269

Preparation of (E)-N-(3-Chloro-2-propoxybenzyl)-3-(3,3-dimethyl-2-oxo-2,3,4,5-tetrahydro-1H-pyrido[2,3-e][1,4]diazepin-7-yl)-N-methylacrylamide hydrochloride a) 3-Chloro-2-propoxybenzoic acid propyl ester To a solution of 3-chlorosalicylic acid (3.42 g, 19.8 mmol) in DMF (45 mL) was added $K_2CO_3$ (6.02 g, 43.5 mmol) followed by 1-bromopropane (5.39 mL, 59.4 mmol). The mixture was heated to 30° C. After 18 h, additional 1-bromopropane (1.79 mL, 19.6 mmol) was added to ensure the dialkylated product. After stirring for an additional 48 h, the reaction was quenched with $H_2O$ (75 mL) and the mixture was extracted with $Et_2O$ (3×100 mL). The combined organics were washed with brine (2×100 mL), dried ($Na_2SO_4$) and concentrated to yield the title compound (2.62 g, 51%) as a yellow oil: $^1$H NMR (300 MHz, DMSO-$d_6$) δ 7.71 (dd, J=7.9, 1.5 Hz, 1H), 7.64 (dd, J=7.8, 1.6 Hz, 1H), 7.24 (t, J=7.8 Hz, 1H), 4.22 (t, J=6.6 Hz, 2H), 3.92 (t, J=6.5 Hz, 2H), 1.78-1.67 (m, 4H), 1.01-0.93 (m, 6H).

b) (3-Chloro-2-propoxyphenyl)methanol

Diisobutylaluminum lithium hydride (30.7 mL of a 1.0 M in hexanes, 30.7 mmol) was added dropwise to an ice-cold solution of 3-chloro-2-propoxybenzoic acid propyl ester (2.63 g, 10.2 mmol) in THF (20 mL). After the addition was complete, the ice bath was removed and the mixture stirred at ambient temperature for 18 h. The reaction was cooled to 0° C. and HCl (1N, 100 mL) was added until all the resulting solids returned to solution. The solution was extracted with $Et_2O$ (3×100 mL). The combined organics were washed with brine (2×100 mL), dried ($Na_2SO_4$) filtered and concentrated to yield the title compound (1.12 g, 56%) as a light yellow oil: $^1$H NMR (500 MHz, DMSO-$d_6$) δ 7.40-7.33 (m, 2H), 7.13 (t, J=7.7 Hz, 1H), 5.22 (t, J=5.6 Hz, 1H), 5.56 (d, J=5.6 Hz, 2H), 3.84 (t, J=6.4 Hz, 2H), 1.76-1.71 (m, 2H), 1.01 (t, J=7.3 Hz, 3H).

c) 3-Chloro-2-propoxybenzaldehyde $MnO_2$ (3.40 g, 39.2 mmol) was added to a stirring solution of (3-chloro-2-propoxyphenyl)methanol (1.12 g, 5.60 mmol) in benzene (54 mL) under $N_2$. After stirring for 48 h, the solution was filtered over diatomaceous earth, the pad rinsed with $CH_2Cl_2$ (100 mL), and the solution concentrated to a clear oil. Purification by column chromatography (silica gel, hexanes/EtOAc, 98:2) gave the title compound (0.42 g, 38%) as a clear oil: $^1$H NMR (300 MHz, DMSO-$d_6$) δ 10.27 (s, 1H), 7.85 (d, J=1.6 Hz, 1H), 7.73 (d, J=1.6 Hz, 1H), 7.32 (t, J=7.8 Hz, 1H), 4.04 (t, J=6.4 Hz, 2H), 1.85-1.78 (m, 2H), 1.03 (t, J=7.3 Hz, 3H).

d) (3-Chloro-2-propoxybenzyl)methylamine

A solution of methylamine (8.5 mL of a 2.0 M solution in MeOH, 17 mmol) was added to 3-chloro-2-propoxybenzaldehyde (0.425 g, 2.14 mmol) and the mixture was stirred for 72 h. The solution was concentrated under reduced pressure. The resulting clear oil was dissolved in EtOH (8.5 mL) and treated with $NaBH_4$ (0.080 g, 2.1 mmol). After stirring for 18 h, the reaction mixture was concentrated under reduced pressure and then dissolved in 1 N NaOH (10 mL). The mixture was extracted with $Et_2O$ (3×50 mL). The combined organics were washed with brine (2×100 mL), dried ($Na_2SO_4$) and concentrated to yield the title compound (0.441 g, 96%) as a light yellow oil: $^1H$ NMR (300 MHz, DMSO-$d_6$) δ 7.37-7.31 (m, 2H), 7.08 (t, J=7.7 Hz, 1H), 3.85 (t, J=6.4 Hz, 2H), 3.67 (s, 2H), 2.26 (s, 3H), 2.04 (br s, 1H), 1.82-1.70 (m, 2H), 1.02 (t, J=7.3 Hz, 3H).

d) N-(3-Chloro-2-propoxybenzyl)-N-methylacrylamide

To a solution of (3-chloro-2-propoxybenzyl)methylamine (0.435 g, 2.04 mmol) in $CH_2Cl_2$ (18 mL) was added acryloyl chloride (0.18 mL, 2.24 mmol) drop-wise. After stirring for five minutes, triethylamine (0.531 mL, 2.24 mmol) was added. The solution was stirred under $N_2$ for 18 h. The solution was diluted with $CH_2Cl_2$ (30 mL) and then washed with $H_2O$ (3×50 mL) and brine (2×100 mL), dried over $Na_2SO_4$, filtered and concentrated to yield the title compound (0.48 g, 89%) as a light yellow oil and as a mixture of amide rotamers: $^1H$ NMR (500 MHz, $CDCl_3$) δ 7.31-7.26 (m, 1H), 7.10-6.98 (m, 2H), 6.63-6.37 (m, 2H), 5.77-5.73 (m, 1H), 4.76-4.65 (m, 2H), 3.94-3.89 (m, 2H), 3.01 (s, 3H), 1.89-1.82 (m, 2H), 1.11-1.05 (m, 3H).

e) (E)-N-(3-Chloro-2-propoxybenzyl)-3-(3,3-dimethyl-2-oxo-2,3,4,5-tetrahydro-1H-pyrido[2,3-e][1,4]diazepin-7-yl)-N-methylacrylamide A solution of N-(3-chloro-2-propoxybenzyl)-N-methylacrylamide (0.392 g, 1.47 mmol) in propionitrile (5 mL) and DMF (1 mL) was deoxygenated with Ar for 20 min. The solution was treated with diisopropylethylamine (0.40 mL, 2.33 mmol) and 7-bromo-3,3-dimethyl-1,3,4,5-tetrahydro-pyrido[2,3-e][1,4]diazepin-2-one (0.300 g, 1.11 mmol). The solution was deoxygenated with Ar for 20 min. $Pd(OAc)_2$ (0.024 g, 0.111 mmol) and $P(o-tol)_3$ (0.067 g, 0.222 mmol) were then added and the solution was deoxygenated again with Ar for 20 min. The mixture was heated to reflux for 18 h, then allowed to cool. The mixture was diluted with EtOAc (30 mL) and was washed with $H_2O$ (3×50 mL). The organic layer was washed with brine (1×100 mL), dried ($Na_2SO_4$) and concentrated to an orange oil. Purification by column chromatography (silica gel, $CH_2Cl_2$/MeOH, 100 to 98:2) gave the title compound (0.30 g, 59%) as a light yellow solid and as a mixture of amide rotamers: $^1H$ NMR (300 MHz, DMSO-$d_6$) δ 9.80-9.78 (m, 1H), 8.40-8.37 (m, 1H), 8.01-7.92 (m, 1H), 7.54-7.49 (m, 1H), 7.41-7.25 (m, 2H), 7.15-7.05 (m, 2H), 4.86-4.68 (m, 2H), 3.91-3.84 (m, 4H), 3.14-2.95 (m, 4H), 1.83-1.76 (m, 2H), 1.31-1.29 (m, 6H), 1.05-0.99 (m, 3H).

f) (E)-N-(3-Chloro-2-propoxybenzyl)-3-(3,3-dimethyl-2-oxo-2,3,4,5-tetrahydro-1H-pyrido[2,3-e][1,4]diazepin-7-yl)-N-methylacrylamide hydrochloride A stirring solution of (E)-N-(3-chloro-2-propoxybenzyl)-3-(3,3-dimethyl-2-oxo-2,3,4,5-tetrahydro-1H-pyrido[2,3-e][1,4]diazepin-7-yl)-N-methylacrylamide (0.300 g, 0.656 mmol) in $CH_2Cl_2$ (7 mL) under $N_2$ was treated with anhydrous HCl (0.32 mL of a 2 M solution in diethyl ether, 0.64 mmol) After stirring for 7 h, the resulting solid was collected by filtration, washed with $Et_2O$ (100 mL) and then dried to yield the target compound (0.25 g, 79%) as an off white solid and as a mixture of amide rotamers: $^1H$ NMR (300 MHz, DMSO-$d_6$) δ 10.93 (br s, 1H), 10.38 (br s, 2H), 8.66-8.63 (m, 1H), 8.37-8.28 (m, 1H), 7.62-7.54 (m, 1H), 7.44-7.32 (m, 2H), 7.19-7.02 (m, 2H), 4.87-4.69 (m, 2H), 4.41-4.37 (m, 2H), 3.94-3.87 (m, 2H), 3.16-2.89 (m, 3H), 1.83-1.76 (m, 2H), 1.61-1.59 (m, 6H), 1.05-0.99 (m, 3H); MS (APCI) m/e 457 $(M+H)^+$.

Example 270

Preparation of (E)-N-(2-Isobutoxy-3-methoxybenzyl)-N-methyl-3-(7-oxo-5,6,7,8-tetrahydro-[1,8]naphthyridin-3-yl)acrylamide a) 2-Isobutoxy-3-methoxybenzaldehyde

A solution of 2-hydroxy-3-methoxybenzaldehyde (4.00 g, 26.2 mmol) in DMF (50 mL) was treated with $K_2CO_3$ (8.00 g, 57.9 mmol) followed by iodoisobutane (4.53 mL, 39.4 mmol). The resulting slurry was stirred for at ambient temperature for 18 h. Additional DMF (70 mL) was added to help aid stirring, and the mixture was heated to 40° C. for 18 h. Additional iodoisobutane (2.26 mL, 19.7 mmol) was added and the mixture was stirred at ambient temperature for 48 h. The reaction was quenched with $H_2O$ (100 mL) and the mixture was extracted with EtOAc (3×100 mL). The combined organics were washed with $H_2O$ (2×100 mL) and brine (2×100 mL), dried ($Na_2SO_4$) and concentrated to an orange oil. Purification by column chromatography (silica gel, hexanes/EtOAc, 90:10) gave the title compound (2.46 g, 62%) as a clear oil: $^1H$ NMR (300 MHz, DMSO-$d_6$) δ 10.34 (s, 1H), 7.36 (dd, J=7.9, 1.7 Hz, 1H), 7.27 (dd, J=7.8, 1.7 Hz, 1H), 7.19 (dt, J=7.8, 0.6 Hz, 1H), 3.85 (m, 5H), 2.09-2.00 (m, 1H), 0.99 (d, J=6.7 Hz, 6H).

b) (2-Isobutoxy-3-methoxybenzyl)methylamine

A solution of methylamine (64 mL of a 2.0 M solution in MeOH, 128 mmol) was added to 2-isobutoxy-3-methoxybenzaldehyde (2.45 g, 11.9 mmol) and the solution was stirred for 18 h. The solution was concentrated under reduced pressure. The resulting clear oil was dissolved in EtOH (64 mL) and treated with $NaBH_4$ (0.616 g, 16.3 mmol). After stirring for 7 h, the mixture was concentrated under reduced pressure and then dissolved in 1 N NaOH (57 mL). The mixture was extracted with $Et_2O$ (3×75 mL). The combined organics were washed with brine (2×100 mL), dried ($Na_2SO_4$) and concentrated to yield the title compound (2.43 g, 91%) as a light yellow oil: $^1H$ NMR (300 MHz, DMSO-$d_6$) δ 7.01-6.88 (m, 3H), 3.76 (s, 3H), 3.63 (t, J=6.4 Hz, 3H), 2.25 (s, 3H), 2.00-1.93 (m, 1H), 1.84 (br s, 1H), 0.98 (d, J=6.6 Hz, 6H).

c) N-(2-Isobutoxy-3-methoxybenzyl)-N-methylacrylamide

To a solution of (2-isobutoxy-3-methoxybenzyl)methylamine (2.00 g, 8.96 mmol) in $CH_2Cl_2$ (80 mL) was added acryloyl chloride (0.85 mL, 9.8 mmol) drop-wise. After stirring for five minutes, triethylamine (1.37 mL, 9.86 mmol) was added. The solution was stirred for 6 hours. The solution was diluted with $CH_2Cl_2$ (30 mL) and then washed with $H_2O$ (3×100 mL) and brine (2×100 mL), dried ($Na_2SO_4$) and concentrated to yield the title compound (2.30 g, 92%) as a light yellow oil and as a mixture of amide rotamers: $^1H$ NMR (500 MHz, DMSO-$d_6$) δ 7.06-6.93 (m, 2H), 6.85-6.62 (m, 1H), 6.57-6.53 (m, 1H), 6.17-6.13 (m, 1H), 5.73-5.63 (m, 1H), 4.64-4.58 (m, 2H), 3.79-3.78 (m, 3H), 3.69-3.66 (m, 2H), 2.95-2.87 (m, 3H), 2.01-1.98 (m, 1H), 0.99-0.97 (m, 6H).

d) (E)-N-(2-Isobutoxy-3-methoxybenzyl)-N-methyl-3-(7-oxo-5,6,7,8-tetrahydro-[1,8]naphthyridin-3-yl)acrylamide A solution of N-(2-isobutoxy-3-methoxybenzyl)-N-methyl-acrylamide (0.475 g, 1.71 mmol) in propionitrile (6 mL) and DMF (1.2 mL) was deoxygenated with Ar for 20 min. The solution was treated with diisopropylethylamine (0.48 mL, 2.77 mmol) and 6-bromo-3,4-dihydro-1H-[1,8]naphthyridin-2-one (0.300 g, 1.32 mmol). The solution was deoxygenated with Ar for 20 min. Pd(OAc)$_2$ (0.029 g, 0.13 mmol) and P(o-tol)$_3$ (0.080 g, 0.26 mmol) were then added and the mixture was deoxygenated with Ar for 20 min. The mixture was heated to reflux for 18 h. Upon cooling, a precipitate formed. The solids were collected by filtration and washed with water. Purification by column chromatography (silica gel, $CH_2Cl_2$/MeOH 9:1) gave an orange solid. The solid was dissolved in $CH_2Cl_2$ and the solution was diluted with hexanes. The resulting precipitate was collected by filtration, washed with $Et_2O$ (50 mL) and dried to yield the title compound (0.18 g, 32%) as an off-white solid and as a mixture of amide rotamers: $^1H$ NMR (300 MHz, DMSO-$d_6$) δ 10.66-10.64 (m, 1H), 8.36-8.32 (m, 1H), 8.09-8.00 (m, 1H), 7.53-7.47 (m, 1H), 7.27-7.20 (m, 1H), 7.04-7.96 (m, 2H), 6.66-6.60 (m, 1H), 4.79-4.64 (m, 2H), 3.79 (s, 3H), 3.72-3.67 (m, 2H), 3.10-2.85 (m, 5H), 2.56-2.49 (m, 2H), 2.03-1.97 (m, 1H), 1.00-0.97 (m, 6H); MS (ESI) m/e 424 (M+H)$^+$.

Example 271

Preparation of (E)-N-(3-Isopropyl-2-propoxybenzyl)-N-methyl-3-(7-oxo-5,6,7,8-tetrahydro-[1,8]naphthyridin-3-yl)acrylamide a) 3-Isopropyl-2-propoxybenzoic acid propyl ester

1-Bromopropane (7.55 mL, 83.1 mmol) was added to a stirring solution of 2-hydroxy-3-isopropylbenzoic acid (5.00 g, 27.7 mmol) and $K_2CO_3$ (11.48 g, 83.1 mmol) in DMF (60 mL). After stirring at 30° C. for 18 h, the reaction was quenched with $H_2O$ (100 mL) and the mixture extracted with EtOAc (3×100 mL). The combined organics were washed with brine (3×200 mL), dried ($Na_2SO_4$) and concentrated to a clear oil. Purification by column chromatography (silica gel, hexanes/EtOAc, 100 to 95:5) gave the title compound (3.96 g, 54%) as a clear oil: $^1H$ NMR (300 MHz, CDCl$_3$) δ 7.60 (dd, J=7.6, 1.7 Hz, 1H), 7.41 (dd, J=7.7, 1.7 Hz, 1H), 7.10 (t, J=7.7 Hz, 1H), 4.26 (t, J=6.7 Hz, 2H), 3.83 (t, J=6.7 Hz, 2H), 3.46-3.37 (m, 1H), 1.87-1.75 (m, 4H), 1.22 (d, J=6.9 Hz, 6H), 1.06-0.99 (m, 6H).

b) (3-Isopropyl-2-propoxyphenyl)methanol

Diisobutylaluminum lithium hydride (40.8 mL of a 1.0 M in hexanes, 40.8 mmol) was added dropwise to an ice-cold solution of 3-isopropyl-2-propoxybenzoic acid propyl ester (3.60 g, 13.6 mmol) in THF (30 mL). After the addition was complete, the ice bath was removed and the reaction mixture was stirred at ambient temperature for 18 h. The reaction was cooled to 0° C. and HCl (1N, 180 mL) was added until all the resulting solids returned to solution. The mixture was extracted with EtOAc (3×150 mL). The combined organics were washed with brine (2×200 mL), dried ($Na_2SO_4$) and concentrated to yield the title compound (2.76 g, 97%) as a yellow oil: $^1H$ NMR (300 MHz, DMSO-$d_6$) δ 7.25 (d, J=6.3 Hz, 1H), 7.17 (d, J=5.9 Hz, 1H), 7.10 (t, J=7.5 Hz, 1H), 5.02 (t, J=5.6 Hz, 1H), 4.52 (d, J=5.5 Hz, 2H), 3.68 (t, J=6.4 Hz, 2H), 3.32-3.25 (m, 1H), 1.77-1.70 (m, 2H), 1.16 (d, J=6.9, 6H), 1.02 (t, J=7.3 Hz, 3H).

c) 3-Isopropyl-2-propoxybenzaldehyde

MnO$_2$ (6.88 g, 79.2 mmol) was added to a stirring solution of (3-isopropyl-2-propoxyphenyl)methanol (2.75 g, 13.2 mmol) in benzene (130 mL) under $N_2$. After stirring for 48 h, the solution was filtered over diatomaceous earth, the pad rinsed with $CH_2Cl_2$ (200 mL) and the solution concentrated to a yellow oil. Purification by column chromatography (silica gel, hexanes/EtOAc, 100 to 98:2) gave the title compound (1.49 g, 54%) as a light yellow oil: $^1H$ NMR (300 MHz, DMSO-$d_6$) δ 10.26 (s, 1H), 7.67 (dd, J=7.6, 1.7 Hz, 1H), 7.59 (dd, J=7.6, 1.7 Hz, 1H), 7.28 (t, J=7.6 Hz, 1H), 3.87 (t, J=6.4 Hz, 2H), 3.35-3.30 (m, 2H), 1.85-1.78 (m, 2H), 1.21 (t, J=6.9 Hz, 7H), 1.03 (t, J=7.3 Hz, 3H).

d) (3-Isopropyl-2-propoxybenzyl)methylamine

A solution of methylamine (30 mL of a 2.0 M solution in MeOH, 60 mmol) was added to 3-isopropyl-2-propoxybenzaldehyde (1.49 g, 7.22 mmol) and the mixture was stirred for 72 h. The solution was concentrated under reduced pressure. The resulting dark yellow oil was dissolved in EtOH (30 mL) and treated with NaBH$_4$ (0.273 g, 7.22 mmol). After 18 h, the reaction mixture was concentrated under reduced pressure and dissolved in 1 N NaOH (30 mL). The mixture was extracted with $Et_2O$ (3×75 mL). The combined organics were dried ($Na_2SO_4$) and concentrated to yield the title compound (1.52 g, 95%) as an orange oil: $^1H$ NMR (300 MHz, DMSO-$d_6$) δ 7.21-7.14 (m, 2H), 7.04 (t, J=7.5 Hz, 1H), 3.70 (t, J=6.3 Hz, 2H), 3.63 (s, 2H), 3.32-3.23 (m, 1H), 2.28 (s, 3H), 1.78 (br s, 1H), 1.76-1.71 (m, 2H), 1.16 (d, J=6.9 Hz, 6H), 1.03 (t, J=7.3 Hz, 3H).

e) (E)-N-(3-Isopropyl-2-propoxybenzyl)-N-methyl-3-(7-oxo-5,6,7,8-tetrahydro-[1,8]naphthyridin-3-yl)acrylamide A solution of (3-isopropyl-2-propoxybenzyl)methylamine (0.238 g, 1.07 mmol) and diisopropyl-ethylamine (0.51 mL, 2.9 mmol) in DMF (20 mL) under $N_2$ was treated sequentially with (E)-3-(7-oxo-5,6,7,8-tetrahydro-[1,8]naphthyridin-3-yl)acrylic acid hydrochloride (0.250 g, 0.981 mmol), 1-hydroxybenzotriazole hydrate (0.144 g, 1.07 mmol) and 1-(3-dimethylaminopropyl)-3-ethylcarbodiimide hydrochloride (0.205 g, 1.07 mmol). After stirring for 18 h, the reaction mixture was diluted with $H_2O$ (30 mL). The resulting solids were collected by filtration and when washed with $Et_2O$ (50 mL) were unexpectedly dissolved. The filtrate was extracted with EtOAc (3×50 mL). The combined organics were washed with brine (2×100 mL), dried (Na$_2$SO$_4$) and concentrated to a light yellow solid. Purification by column chromatography (silica gel, CH$_2$Cl$_2$/MeOH, 100 to 99.5:0.5) gave the title compound (0.26 g, 63%) as a white solid and as a mixture of amide rotamers: $^1$H NMR (500 MHz, DMSO-d$_6$) δ 10.64-10.62 (m, 1H), 8.37-8.31 (m, 1H), 8.09-7.98 (m, 1H), 7.52-7.49 (m, 1H), 7.28-7.19 (m, 2H), 7.10-7.06 (m, 1H), 6.89-6.87 (m, 1H), 4.80-4.66 (m, 2H), 3.76-3.70 (m, 2H), 3.31-3.26 (m, 1H), 3.12-2.85 (m, 5H), 2.55-2.49 (m, 2H), 1.82-1.76 (m, 2H), 1.19-1.17 (m, 6H), 1.05-1.02 (m, 3H); MS (ESI) m/e 422 (M+H)$^+$.

Example 272

Preparation of (E)-N-(2-Ethoxy-3-isopropylbenzyl)-N-methyl-3-(7-oxo-5,6,7,8-tetrahydro-[1,8]naphthyridin-3-yl)acrylamide a) Preparation of 2-Ethoxy-3-isopropylbenzoic acid propyl ester Iodoethane (6.64 mL, 83.1 mmol) was added to a stirring solution of 2-hydroxy-3-isopropylbenzoic acid (5.00 g, 27.7 mmol) and K$_2$CO$_3$ (11.48 g, 83.1 mmol) in DMF (60 mL). After stirring at 30° C. for 18 h, the reaction was quenched with H$_2$O (100 mL) and the mixture was extracted with EtOAc (3×100 mL). The combined organics were washed with brine (3×250 mL), dried (Na$_2$SO$_4$) and concentrated to a clear oil. Purification by column chromatography (silica gel, hexanes/EtOAc, 100 to 98:2) gave the title compound (4.54 g, 69%) as an orange oil: $^1$H NMR (300 MHz, CDCl$_3$) δ 7.60 (dd, J=7.6, 1.7 Hz, 1H), 7.41 (dd, J=7.7, 1.7 Hz, 1H), 7.11 (t, J=7.7 Hz, 1H), 4.37 (q, J=7.1 Hz, 2H), 3.95 (q, J=7.0 Hz, 2H), 3.43-3.39 (m, 1H), 1.45-1.39 (m, 6H), 1.22 (d, J=6.9 Hz, 6H).

b) Preparation of (2-Ethoxy-3-isopropylphenyl)methanol

Diisobutylaluminum lithium hydride (55.0 mL of a 1.0 M in hexanes, 55.0 mmol) was added drop-wise to an ice-cold solution of 2-ethoxy-3-isopropylbenzoic acid propyl ester (4.34 g, 18.3 mmol) in THF (40 mL). After the addition was complete, the ice bath was removed and reaction mixture was stirred for 18 h. The reaction was cooled to 0° C. and HCl (1N, 275 mL) was added until all the resulting solids returned to solution. The mixture was extracted with EtOAc (3×150 mL). The combined organics were washed with brine (2×200 mL), dried (Na$_2$SO$_4$) and concentrated to yield the title compound (3.73 g, quantitative) as a light yellow oil: $^1$H NMR (300 MHz, DMSO-d$_6$) δ 7.24 (d, J=5.7 Hz, 1H), 7.16 (d, J=1.7 Hz, 1H), 7.07 (t, J=7.5 Hz, 1H), 5.02 (t, J=5.6 Hz, 1H), 4.52 (d, J=5.6 Hz, 2H), 3.77 (q, J=7.0 Hz, 2H), 3.32-3.25 (m, 1H), 1.33 (t, J=6.9 Hz, 3H), 1.16 (d, J=6.9 Hz, 6H).

c) 2-Ethoxy-3-isopropyl-benzaldehyde

MnO$_2$ (9.49 g, 109 mmol) was added to a stirring solution of (2-ethoxy-3-isopropylphenyl)methanol (3.54 g, 18.2 mmol) in benzene (175 mL) under N$_2$. After stirring for 48 h, the solution was filtered over diatomaceous earth and the pad rinsed with CH$_2$Cl$_2$ (200 mL), and the solution was concentrated to a clear oil. Purification by column chromatography (silica gel, hexanes/EtOAc, 100 to 98:2) gave the title compound (1.49 g, 42%) as a light yellow oil: $^1$H NMR (300 MHz, DMSO-d$_6$) δ 10.26 (s, 1H), 7.67 (dd, J=7.6, 1.7 Hz, 1H), 7.59 (dd, J=7.6, 1.7 Hz, 1H), 7.28 (t, J=7.6 Hz, 1H), 3.97 (q, J=6.9 Hz, 2H), 3.32-3.30 (m, 1H), 1.39 (t, J=6.9 Hz, 3H), 1.21 (d, J=6.9 Hz, 6H).

d) (2-Ethoxy-3-isopropylbenzyl)methylamine

A solution of methylamine (30 mL of a 2.0 M solution, 60 mmol) was added to 2-ethoxy-3-isopropylbenzaldehyde (1.49 g, 7.75 mmol) and the mixture was stirred for 72 h. The solution was concentrated under reduced pressure. The residue was dissolved in EtOH (30 mL) and treated with NaBH$_4$ (0.293 g, 7.75 mmol). After stirring for 18 h, the reaction mixture was concentrated under reduced pressure and then dissolved in 1 N NaOH (30 mL). The mixture was extracted with Et$_2$O (3×50 mL). The combined organics were collected, washed with brine (2×100 mL), dried (Na$_2$SO$_4$) and concentrated to yield the title compound (1.51 g, 94%) as a light yellow oil: $^1$H NMR (300 MHz, DMSO-d$_6$) δ 7.21-7.13 (m, 2H), 7.04 (t, J=7.5 Hz, 1H), 3.79 (q, J=7.0 Hz, 2H), 3.63 (s, 2H), 3.28-3.23 (m, 1H), 2.29 (s, 3H), 1.93 (br s, 1H), 1.35 (t, J=3.8 Hz, 3H), 1.16 (d, J=6.9 Hz, 6H).

e) (E)-N-(2-Ethoxy-3-isopropylbenzyl)-N-methyl-3-(7-oxo-5,6,7,8-tetrahydro-[1,8]naphthyridin-3-yl)acrylamide A solution of (2-ethoxy-3-isopropylbenzyl)methylamine (0.223 g, 1.07 mmol) and diisopropyl-ethylamine (0.51 mL, 2.94 mmol) in DMF (20 mL) was treated sequentially with (E)-3-(7-oxo-5,6,7,8-tetrahydro-[1,8]naphthyridin-3-yl) acrylic acid hydrochloride (0.250 g, 0.981 mmol), 1-hydroxybenzotriazole hydrate (0.144 g, 1.07 mmol) and 1-(3-dimethylaminopropyl)-3-ethylcarbodiimide hydrochloride (0.205 g, 1.07 mmol). After stirring for 18 h, the reaction mixture was diluted with H$_2$O (30 mL). The resulting solids were collected by filtration, and when washed with Et$_2$O (50 mL), unexpectedly dissolved. The filtrate was extracted with EtOAc (3×50 mL). The combined organics were washed with brine (2×100 mL), dried over Na$_2$SO$_4$, filtered and concentrated to a light orange solid. Purification by column chromatography (silica gel, CH$_2$Cl$_2$/MeOH, 100 to 99.5:0.5) gave the title compound (0.20 g, 52%) as a white solid and as a mixture of amide rotamers: $^1$H NMR (500 MHz, DMSO-d$_6$) δ 10.64-10.61 (m, 1H), 8.37-8.31 (m, 1H), 8.09-7.99 (m, 1H), 7.52-7.49 (m, 1H), 7.28-7.20 (m, 2H), 7.11-7.05 (m, 1H), 6.89-6.86 (m, 1H), 4.81-4.66 (m, 2H), 3.86-3.79 (m, 2H), 3.28-3.25 (m, 1H), 3.11-2.85 (m, 5H), 2.55-2.49 (m, 2H), 1.39-1.35 (m, 3H), 1.19-1.17 (m, 6H); MS (ESI) m/e 408 (M+H)$^+$.

Example 273

Preparation of (E)-3-(3,3-Dimethyl-2-oxo-2,3,4,5-tetrahydro-1H-pyrido[2,3-e][1,4]diazepin-7-yl)-N-(3-isopropyl-2-propoxybenzyl)-N-methylacrylamide hydrochloride a) N-(3-Isopropyl-2-propoxybenzyl)-N-methylacrylamide To a solution of (3-isopropyl-2-propoxybenzyl)methylamine (1.00 g, 4.51 mmol) in CH$_2$Cl$_2$ (40 mL) was added acryloyl chloride (0.43 mL, 4.96 mmol) drop-wise. After stirring for five minutes, triethylamine (0.69 mL, 4.96 mmol) was added and the solution was stirred for 5 hours. The solution was diluted with CH$_2$Cl$_2$ (50 mL), washed with H$_2$O (3×50 mL) and brine (2×100 mL), dried (Na$_2$SO$_4$) and concentrated to yield the title compound (1.10 g, 88%) as a light yellow oil and a mixture of amide rotamers: $^1$H NMR (300 MHz, DMSO-d$_6$) δ 7.23-7.19 (m, 1H), 7.10-7.06 (m, 1H), 6.86-6.80 (m, 2H), 6.20-6.13 (m, 1H), 5.61-5.79 (m, 1H), 4.68-4.61 (m, 2H), 3.71-3.67 (m, 2H), 3.34-3.26 (m, 1H), 3.01-2.88 (m, 3H), 1.78-1.76 (m, 2H), 1.19-1.17 (m, 6H), 1.06-1.00 (m, 3H).

b) (E)-3-(3,3-Dimethyl-2-oxo-2,3,4,5-tetrahydro-1H-pyrido[2,3-e][1,4]diazepin-7-yl)-N-(3-isopropyl-2-propoxybenzyl)-N-methylacrylamide A solution of N-(3-isopropyl-2-propoxybenzyl)-N-methylacrylamide (0.397 g, 1.47 mmol) in propionitrile (5 mL) and DMF (1 mL) was deoxygenated with Ar for 20 min. The solution was treated with diisopropylethylamine (0.40 mL, 2.33 mmol) and 7-bromo-3,3-dimethyl-1,3,4,5-tetrahydro-pyrido[2,3-e][1,4]diazepin-2-one (0.300 g, 1.11 mmol). The solution was deoxygenated with Ar for 20 min. Pd(OAc)$_2$ (0.024 g, 0.111 mmol) and P(o-tol)$_3$ (0.067 g, 0.222 mmol) were then added and the mixture deoxygenated with Ar for 20 min. The mixture was heated to reflux for 18 h, then allowed to cool. The solution was diluted with EtOAc (30 mL) and H$_2$O (50 mL). The aqueous layer was extracted with EtOAc (3×50 mL). The combined organics were washed with brine (2×100 mL), dried over Na$_2$SO$_4$, filtered and concentrated to an orange oil. Purification by column chromatography (silica gel, CH$_2$Cl$_2$/MeOH, 100 to 95:5) gave the title compound (0.16 g, 31%) as an off-white solid and as a mixture of amide rotamers: $^1$H NMR (300 MHz, DMSO-d$_6$) δ 9.80-9.77 (m, 1H), 8.40-8.35 (m, 1H), 8.01-7.91 (m, 1H), 7.55-7.48 (m, 1H), 7.31-7.20 (m, 2H), 7.10-7.03 (m, 1H), 6.88-6.85 (m, 1H), 4.81-4.66 (m, 2H), 3.90-3.83 (m, 2H), 3.77-3.69 (m, 2H), 3.32-3.25 (m, 1H), 3.12-2.90 (m, 4H), 1.81-1.77 (m, 2H), 1.31-1.28 (m, 6H), 1.19-1.17 (m, 6H), 1.06-1.01 (3H).

c) (E)-3-(3,3-Dimethyl-2-oxo-2,3,4,5-tetrahydro-1H-pyrido[2,3-e][1,4]diazepin-7-yl)-N-(3-isopropyl-2-propoxybenzyl)-N-methylacrylamide hydrochloride A stirring solution of (E)-3-(3,3-dimethyl-2-oxo-2,3,4,5-tetrahydro-1H-pyrido[2,3-e][1,4]diazepin-7-yl)-N-(3-isopropyl-2-propoxybenzyl)-N-methylacrylamide (0.164 g, 0.352 mmol) in CH$_2$Cl$_2$ (4 mL) under N$_2$ was treated with anhydrous HCl (0.17 mL of a 2.0 M solution in diethyl ether, 0.34 mmol) After stirring for 18 h, the resulting solid was collected by filtration, washed with Et$_2$O (100 mL) and dried to yield the title compound (0.12 g, 71%) as an off white solid and as a mixture of amide rotamers: $^1$H NMR (300 MHz, DMSO-d$_6$) δ 10.95 (br s, 1H), 10.25 (br s, 2H), 8.67-8.63 (m, 1H), 8.36-8.26 (m, 1H), 7.62-7.54 (m, 1H), 7.39-7.31 (m, 1H), 7.26-7.20 (m, 1H), 7.13-7.05 (m, 1H), 6.90-6.84 (m, 1H), 4.82-4.67 (m, 2H), 4.41-4.36 (m, 2H), 3.77-3.69 (m, 2H), 3.30-3.25 (m, 1H), 3.16-2.89 (m, 3H), 1.82-1.75 (m, 2H), 1.60-1.58 (m, 6H), 1.23-1.13 (m, 6H), 1.06-1.01 (m, 3H); MS (ESI) m/e 465 (M+H)$^+$.

Example 274

Preparation of (E)-N-(3-Isopropyl-2-propoxybenzyl)-N-methyl-3-(2-oxo-2,3,4,5-tetrahydro-1H-pyrido[2,3-e][1,4]diazepin-7-yl)acrylamide a) (E)-N-(3-Isopropyl-2-propoxybenzyl)-N-methyl-3-(2-oxo-2,3,4,5-tetrahydro-1H-pyrido[2,3-e][1,4]diazepin-7-yl)acrylamide A solution of N-(3-isopropyl-2-propoxybenzyl)-N-methylacrylamide (0.385 g, 1.40 mmol) in propionitrile (5 mL) and DMF (1 mL) was deoxygenated with Ar for 20 min. The solution was treated with diisopropylethylamine (0.39 mL, 2.25 mmol) and 7-bromo-1,3,4,5-tetrahydro-pyrido[2,3-e][1,4]diazepin-2-one (0.300 g, 1.07 mmol). The solution was deoxygenated with Ar for 20 min. Pd(OAc)$_2$ (0.024 g, 0.10 mmol) and P(o-tol)$_3$ (0.065 g, 0.21 mmol) were then added and the solution deoxygenated with Ar for 20 min. The solution was heated to reflux for 18 h, then allowed to cool. The solution was diluted with H$_2$O (30 mL) and the mixture was washed with EtOAc (3×50 mL). The combined organics were washed with brine (2×100 mL), dried (Na$_2$SO$_4$) and concentrated. Purification by column chromatography (silica gel, CH$_2$Cl$_2$/MeOH, 100 to 95:5) gave the title compound (0.15 g, 33%) as an off-white solid and as a mixture of amide rotamers: $^1$H NMR (300 MHz, DMSO-d$_6$) δ 10.08-10.05 (m, 1H), 8.45-8.39 (m, 1H), 8.03-7.93 (m, 1H), 7.55-7.49 (m, 1H), 7.32-7.20 (m, 2H), 7.13-7.04 (m, 1H), 6.88-6.86 (m, 1H), 4.81-4.66 (m, 2H), 3.91-3.86 (m, 2H), 3.76-3.69 (m, 2H), 3.63-3.60 (m, 2H), 3.30-3.25 (m, 1H), 3.12-2.90 (m, 4H), 1.83-1.75 (m, 2H), 1.24-1.17 (m, 6H), 1.06-1.01 (m, 3H).

b) (E)-N-(3-Isopropyl-2-propoxybenzyl)-N-methyl-3-(2-oxo-2,3,4,5-tetrahydro-1H-pyrido[2,3-e][1,4]diazepin-7-yl)acrylamide hydrochloride A stirring solution of (E)-N-(3-isopropyl-2-propoxybenzyl)-3-(3,3-dimethyl-2-oxo-2,3,4,5-tetrahydro-1H-pyrido[2,3-e][1,4]diazepin-7-yl)-N-methylacrylamide (0.158 g, 0.362 mmol) in CH$_2$Cl$_2$ (4 mL) under N$_2$ was treated with anhydrous HCl (0.18 mL of a 2.0 M solution in diethyl ether, 0.36 mmol) After stirring for 18 h, the resulting solid was collected by filtration, washed with Et$_2$O (100 mL) and dried to yield the title compound (0.15 g, 91%) as an off white solid and as a mixture of amide rotamers: $^1$H NMR (300 MHz, DMSO-d$_6$) δ 11.10-11.07 (m, 1H), 10.07 (br s, 2H), 8.77-8.72 (m, 1H), 8.33-8.24 (m, 1H), 7.63-7.55 (m, 1H), 7.40-7.31 (m, 1H), 7.26-7.21 (m, 1H), 7.13-7.05 (m, 1H), 6.90-6.83 (m, 1H), 4.83-4.67 (m, 2H), 4.28-4.22 (m, 2H), 3.85-3.69 (m, 4H), 3.30-3.25 (m, 1H), 3.14-2.89 (m, 3H), 1.81-1.75 (m, 2H), 1.20-1.17 (m, 6H), 1.06-1.01 (m, 3H); MS (ESI) m/e 437 (M+H)$^+$.

Example 275

Preparation of (S)-(+)-(E)-N-Methyl-N-(3-methylbenzofuran-2-ylmethyl)-3-(10-oxo-2,3,4,9,10,10a-hexahydro-1H-3a,8,9-triazabenzo[f]azulen-6-yl)acrylamide hydrochloride a) (S)-(E)-N-Methyl-N-(3-methylbenzofuran-2-ylmethyl)-3-(10-oxo-2,3,4,9,10,10a-hexahydro-1H-3a,8,9-triazabenzo[f]azulen-6-yl)acrylamide A solution of N-methyl-N-(3-methylbenzofuran-2-ylmethyl)acrylamide (0.210 g, 0.920 mmol) in propionitrile (3 mL) and DMF (0.65 mL) was deoxygenated with Ar for 20 min. The solution was treated with diisopropylethylamine (0.24 mL, 1.4 mmol) and (S)-6-bromo-1,2,3,4,9,10a-hexahydro-3a,8,9-triazabenzo[f]azulen-10-one (0.200 g, 0.708 mmol). The solution was deoxygenated with Ar for 20 min. Pd(OAc)$_2$ (0.015 g, 0.070 mmol) and P(o-tol)$_3$ (0.067 g, 0.14 mmol) were then added and the solution was deoxygenated with Ar for 20 min. The solution was heated to reflux for 18 h, then allowed to cool. The solution was diluted with CH$_2$Cl$_2$ (50 mL) and was washed with H$_2$O (3×100 mL). The combined organics were washed with brine (2×100 mL), dried (Na$_2$SO$_4$) and concentrated. Purification by column chromatography (silica gel, CH$_2$Cl$_2$/MeOH, 98:2) gave the title compound (0.25 g, 77%) as a glassy yellow solid and as a mixture of amide rotamers: $^1$H NMR (300 MHz, CDCl$_3$) δ 8.74 (s, 1H), 8.60-8.50 (m, 1H), 7.75-7.67 (m, 2H), 7.49-7.48 (m, 1H), 7.42-7.40 (m, 1H), 7.28-7.16 (m, 3H), 4.83-4.71 (m, 2H), 3.99-3.82 (m, 2H), 3.59-2.57 (m, 1H), 3.23-3.08 (m, 3H), 2.89-2.86 (m, 2H), 2.53-2.44 (m, 1H), 2.31-2.30 (m, 3H), 2.04-1.68 (m, 3H).

b) (S)-(+)-(E)-N-Methyl-N-(3-methylbenzofuran-2-ylmethyl)-3-(10-oxo-2,3,4,9,10,10a-hexahydro-1H-3a,8,9-triazabenzo[f]azulen-6-yl)acrylamide hydrochloride A stirring solution of (S)-(E)-N-methyl-N-(3-methylbenzofuran-2-ylmethyl)-3-(10-oxo-2,3,4,9,10,10a-hexahydro-1H-3a,8,9-triazabenzo[f]azulen-6-yl)acrylamide (0.235 g, 0.545 mmol) in CH$_2$Cl$_2$ (5 mL) under N$_2$ was treated with anhydrous HCl (0.27 mL of a 2.0 M solution in diethyl ether, 0.54 mmol) After stirring for 18 h, the resulting solid was collected by filtration, washed with Et$_2$O (100 mL) and dried to yield the title compound (0.22 g, 89%) as a yellow solid and as a mixture of amide rotamers: $^1$H NMR (300 MHz, DMSO-d$_6$) δ 12.15 (br s, 1H), 11.30 (br s, 1H), 8.87-8.83 (m, 1H), 8.36-8.31 (m, 1H), 7.63-7.55 (m, 2H), 7.50-7.48 (m, 1H), 7.35-7.22 (m, 3H), 5.07-4.95 (m, 2H), 4.47-4.26 (m, 3H), 3.63 (br s, 2H), 3.20-2.93 (m, 3H), 2.27 (s, 4H), 2.10 (br s, 1H), 1.88 (m, 2H); $[α]^{25}_D$ +66.30 (c 0.90, methanol); MS (ESI) m/e 431 (M+H)$^+$.

Example 276

Preparation of (R)-(−)-(E)-N-Methyl-N-(3-methylbenzofuran-2-ylmethyl)-3-(10-oxo-2,3,4,9,10,10a-hexahydro-1H-3a,8,9-triazabenzo[f]azulen-6-yl)acrylamide hydrochloride a) (R)-(E)-N-Methyl-N-(3-methylbenzofuran-2-ylmethyl)-3-(10-oxo-2,3,4,9,10,10a-hexahydro-1H-3a,8,9-triazabenzo[f]azulen-6-yl)acrylamide A solution of methyl-(3-methylbenzofuran-2-ylmethyl)amine (0.166 g, 0.953 mmol) and diisopropylethylamine (0.45 mL, 2.59 mmol) in DMF (20 mL) under N$_2$ was treated sequentially with (R)-6-bromo-1,2,3,4,9,10a-hexahydro-3a,8,9-triazabenzo[f]azulen-10-one (0.300 g, 0.866 mmol), 1-hydroxybenzotriazole hydrate (0.128 g, 0.953 mmol) and 1-(3-dimethylaminopropyl)-3-ethylcarbodiimide hydrochloride (0.182 g, 0.953 mmol). After stirring for 18 h, the reaction mixture was diluted with H$_2$O (30 mL). The resulting solids were collected by filtration, washed with Et$_2$O and dried to give the title compound (0.93 g, 31%) as a white solid and as a mixture of amide rotamers: $^1$H NMR (300 MHz, DMSO-d$_6$) δ 10.38 (s, 1H), 8.59-8.56 (m, 1H), 8.23-8.21 (m, 1H), 7.58-7.21 (m, 6H), 5.00-4.79 (m, 2H), 3.96-3.92 (m, 1H), 3.55-3.47 (m, 2H), 3.19-2.84 (m, 4H), 2.61-2.59 (m, 1H), 2.26 (m, 4H), 1.76-1.74 (m, 3H).

b) (R)-(−)-(E)-N-Methyl-N-(3-methylbenzofuran-2-ylmethyl)-3-(10-oxo-2,3,4,9,10,10a-hexahydro-1H-3a,8,9-triazabenzo[f]azulen-6-yl)acrylamide hydrochloride A stirring solution of (R)-(E)-N-methyl-N-(3-methylbenzofuran-2-ylmethyl)-3-(10-oxo-2,3,4,9,10,10a-hexahydro-1H-3a,8,9-triazabenzo[f]azulen-6-yl)acrylamide (0.090 g, 0.20 mmol) in CH$_2$Cl$_2$ (3 mL) under N$_2$ was treated with anhydrous HCl (0.10 mL of a 2.0 M solution in diethyl ether, 0.20 mmol) After stirring for 18 h, the resulting solid was collected by filtration, washed with Et$_2$O (50 mL) and dried to yield the target compound (0.066 g, 67%) as an off white solid and as a mixture of amide rotamers: $^1$H NMR (300 MHz, DMSO-d$_6$) δ 12.31 (br s, 1H), 11.29 (br s, 1H), 8.85-8.83 (m, 1H), 8.33-8.31 (m, 1H), 7.62-7.56 (m, 2H), 7.451-7.48 (m, 1H), 7.35-7.22 (m, 3H), 5.07-4.81 (m, 2H), 4.51-4.16 (m, 3H), 3.58 (br s, 3H), 3.20-2.94 (m, 3H), 2.27 (m, 3H), 2.10-1.89 (m, 3H); $[α]^{25}_D$ −52.4° (c 0.86, methanol); MS (ESI) m/e 431 (M+H)$^+$.

Example 277

Preparation of (E)-3-(3,3-Dimethyl-2-oxo-2,3,4,5-tetrahydro-1H-pyrido[2,3-e][1,4]diazepin-7-yl)-N-(2-isobutoxy-3-methoxybenzyl)-N-methylacrylamide hydrochloride a) (E)-3-(3,3-Dimethyl-2-oxo-2,3,4,5-tetrahydro-1H-pyrido[2,3-e][1,4]diazepin-7-yl)-N-(2-isobutoxy-3-methoxybenzyl)-N-methylacrylamide A solution of N-(2-isobutoxy-3-methoxybenzyl)-N-methylacrylamide (0.407 g, 1.47 mmol) in propionitrile (5 mL) and DMF (1 mL) was deoxygenated with Ar for 20 min. The solution was treated with diisopropylethylamine (0.40 mL, 2.33 mmol) and 7-bromo-3,3-dimethyl-1,3,4,5-tetrahydropyrido[2,3-e][1,4]diazepin-2-one (0.300 g, 1.11 mmol). The solution was deoxygenated with Ar for 20 min. Pd(OAc)$_2$ (0.024 g, 0.11 mmol) and P(o-tol)$_3$ (0.067 g, 0.22 mmol) were then added and the solution was deoxygenated with Ar for 20 min. The solution was heated to reflux for 18 h, then allowed to cool. The solution was diluted with EtOAc (30 mL) and was washed with H$_2$O (3×50 mL). The organic layer was washed with brine (2×50 mL), dried (Na$_2$SO$_4$) and concentrated to an orange oil. Purification by column chromatography (silica gel, CH$_2$Cl$_2$/MeOH, 100 to 98:2) gave the title compound (0.19 g, 32%) as an off-white solid and as a mixture of amide rotamers: $^1$H NMR (300 MHz, DMSO-d$_6$) δ 9.79-9.77 (m, 1H), 8.40-8.35 (m, 1H), 8.00-7.92 (m, 1H), 7.54-7.48 (m, 1H), 7.29-7.22 (m, 1H), 7.04-6.96 (m, 2H), 6.66-6.63 (m, 1H), 4.79-4.64 (m, 2H), 3.89-3.83 (m, 2H), 3.79 (s, 3H), 3.72-3.67 (m, 2H), 3.11-2.87 (m, 4H), 2.04-1.99 (m, 1H), 1.31-1.29 (m, 6H), 1.00-0.97 (m, 6H).

b) (E)-3-(3,3-Dimethyl-2-oxo-2,3,4,5-tetrahydro-1H-pyrido[2,3-e][1,4]diazepin-7-yl)-N-(2-isobutoxy-3-methoxybenzyl)-N-methylacrylamide hydrochloride A stirring solution of (E)-3-(3,3-dimethyl-2-oxo-2,3,4,5-tetrahydro-1H-pyrido[2,3-e][1,4]diazepin-7-yl)-N-(2-isobutoxy-3-methoxybenzyl)-N-methylacrylamide (0.196 g, 0.426 mmol) in CH$_2$Cl$_2$ (4 mL) under N$_2$ was treated with anhydrous HCl (0.21 mL of a 2.0 M solution in diethyl ether, 0.42 mmol) After stirring for 7 h, the resulting solid was collected by filtration, washed with Et$_2$O (100 mL) and dried to yield the title compound (0.10 g, 47%) as an off white solid and as a mixture of amide rotamers: $^1$H NMR (300 MHz, DMSO-d$_6$) δ 10.93-10.92 (m, 1H), 10.51 (br s, 2H), 8.66-8.62 (m, 1H), 8.40-8.32 (m, 1H), 7.60-7.53 (m, 1H), 7.38-7.33 (m, 1H), 7.05-6.94 (m, 2H), 6.68-6.61 (m, 1H), 4.80-4.65 (m, 2H), 4.42-4.37 (m, 2H), 3.79 (s, 3H), 3.72-3.68 (m, 2H), 3.12-2.86 (m, 3H), 2.04-1.97 (m, 1H), 1.63-1.61 (m, 6H), 1.00-0.97 (m, 6H); MS (ESI) m/e 467 (M+H)$^+$.

Example 278

Preparation of (E)-3-(6-amino-pyridin-3-yl)-N-(3-chloro-4-fluoro-benzo[b]thiophen-2-ylmethyl)-N-methylacrylamide hydrochloride a) 3-chloro-4-fluoro-benzo[b]thiophene-2-carbonyl chloride

A mixture of 3-(2-fluoro-phenyl)acrylic acid (15.0 g, 90.3 mmol), $SOCl_2$ (40 mL, 542 mmol) and pyridine (0.72 mL, 9.00 mmol) in chlorobenzene (90 mL) was heated to reflux for 3 d. The mixture was cooled to room temperature and concentrated. The residue was triturated with hexanes to give the title compound (5.46 g, 26%) as a yellow solid: $^1$H NMR (500 MHz, $CDCl_3$) δ 7.63 (dd, J=8.2, 0.8 Hz, 1H), 7.56 (ddd, J=8.0, 8.0, 4.5 Hz, 1H), 7.16 (ddd, J=11.2, 7.9, 0.8 Hz, 1H).

b) (3-chloro-4-fluoro-benzo[b]thiophen-2-yl)methanol

To an ice-cold suspension of 3-chloro-4-fluoro-benzo[b]thiophene-2-carbonyl chloride (5.46 g, 23.6 mmol) in THF (120 mL) was added lithium aluminum hydride (11.8 mL of a 1.0 M solution in THF, 11.8 mmol) dropwise. The mixture was stirred for 2 h then quenched with NaOH (0.35 N solution in $H_2O$). The mixture was diluted with $Et_2O$ and the solution filtered. The filtrate was dried ($Na_2SO_4$) and concentrated. Purification by flash column chromatography (silica gel, hexanes/EtOAc, 8:2) gave the title compound (4.52 g, 96%) as an off-white solid: $^1$H NMR (300 MHz, $CDCl_3$) δ 7.57 (d, J=8.1 Hz, 1H), 7.31 (ddd, J=8.0, 8.0, 4.7 Hz, 1H), 7.06 (dd, J=11.3, 8.0 Hz, 1H), 4.97 (d, J=6.2 Hz, 2H), 2.04 (t, J=6.2 Hz, 1H).

c) 3-chloro-4-fluoro-benzo[b]thiophene-2-carbaldehyde

A suspension of (3-chloro-4-fluoro-benzo[b]thiophen-2-yl)methanol (1.00 g, 4.63 mmol) and $MnO_2$ (3.10 g, 35.2 mmol) in benzene (50 mL) was stirred at room temperature overnight. The solution was filtered through diatamaceous earth and the was filtrate was concentrated to give the title compound (880 mg, 87%) as an off-white solid: $^1$H NMR (500 MHz, $CDCl_3$) δ 10.32 (s, 1H), 7.63 (dd, J=8.2, 0.4 Hz, 1H), 7.50 (ddd, J=8.1, 8.1, 4.7 Hz, 1H), 7.13 (ddd, J=11.0, 7.9, 0.4 Hz, 1H).

d) (3-chloro-4-fluoro-benzo[b]thiophen-2-ylmethyl)methylamine

A solution of 3-chloro-4-fluoro-benzo[b]thiophene-2-carbaldehyde (880 mg, 4.04 mmol) in $CH_3NH_2$ (20 mL of a 2.0 M solution in MeOH, 40 mmol) was stirred at room temperature overnight. The mixture was concentrated. The residue was dissolved in EtOH (30 mL), and after cooling in an ice bath, $NaBH_4$ (153 mg, 4.04 mmol) was added. The mixture was slowly warmed to room temperature and then stirred overnight. The mixture was concentrated. The residue was taken up in NaOH (30 mL) and the mixture was extracted with $Et_2O$ (3×). The combined organics were washed with satd NaCl, dried ($Na_2SO_4$) and concentrated. Purification by column chromatography (silica gel, 95:5 $CH_2Cl_2$/MeOH) gave the title compound (443 mg, 48%) as a yellow oil: $^1$H NMR (300 MHz, $CDCl_3$) δ 7.54 (dd, J=8.0, 0.6 Hz, 1H), 7.27 (ddd, J=8.0, 8.0, 4.6 Hz, 1H), 7.03 (ddd, J=11.4, 8.0, 0.6 Hz, 1H), 4.05 (s, 2H), 2.53 (s, 3H), 1.55 (s, 1H).

e) (E)-3-(6-amino-pyridin-3-yl)-N-(3-chloro-4-fluoro-benzo[b]thiophen-2-ylmethyl)-N-methylacrylamide To a solution of 3-(6-amino-pyridin-3-yl)acrylic acid trifluoroacetic acid salt (487 mg, 1.75 mmol) in DMF (10 mL) was added 3-chloro-4-fluoro-benzo[b]thiophen-2-ylmethyl)methylamine (440 mg, 1.92 mmol), EDC (368 mg, 1.92 mmol), HOBt (260 mg, 1.92 mmol), and DIEA (1.0 mL, 6.1 mmol). The mixture was stirred at room temperature overnight. The mixture was diluted with $H_2O$ and the solid was collected by filtration. Purification by semi-preparative HPLC (Phenomenex Luna C18(2) 10μ, 250×21 mm, $CH_3CN/H_2O$/0.05% TFA) gave a solid. The solid was partitioned between EtOAc and satd $NaHCO_3$. The organic layer was concentrated to give the title compound (257 mg, 39%) as a white solid: MS (ESI) m/e 376 (M+H)$^+$.

f) (E)-3-(6-amino-pyridin-3-yl)-N-(3-chloro-4-fluoro-benzo[b]thiophen-2-ylmethyl)-N-methylacrylamide hydrochloride A solution of (E)-3-(6-amino-pyridin-3-yl)-N-(3-chloro-4-fluoro-benzo[b]thiophen-2-ylmethyl)-N-methylacrylamide (257 mg, 0.68 mmol) in $CH_2Cl_2$ (10 mL) was treated with anhydrous HCl (0.68 mL of a 1.0 M solution in $Et_2O$, 0.68 mmol). The mixture was stirred overnight at room temperature and then diluted with $Et_2O$. The resulting solid was collected by filtration and then dried under vacuum at 50° C. for 2 d to give the title compound (282 mg, 98%) as an off-white solid and as a mixture of amide rotamers: $^1$H NMR (300 MHz, DMSO-$d_6$) δ 8.43-8.33 (m, 4H), 7.87-7.82 (m, 1H), 7.55-7.20 (m, 4H), 7.04-7.00 (m, 1H), 5.15-4.88 (m, 2H), 3.54 (br s, 1H), 3.22-2.97 (m, 3H); MS (ESI) m/e 376 (M+H)+.

Example 279

Preparation of (E)-3-(6-amino-pyridin-3-yl)-N-(3-chloro-7-fluoro-benzo[b]thiophen-2-ylmethyl)-N-methylacryl amide hydrochloride a) 3-chloro-7-fluoro-benzo[b]thiophene-2-carbonyl chloride

A mixture of 3-(3-fluoro-phenyl)acrylic acid (10.2 g, 61.4 mmol), $SOCl_2$ (22 mL, 301 mmol) and pyridine (0.50 mL, 6.00 mmol) in chlorobenzene (60 mL) was heated to reflux for 3 d. The mixture was cooled to room temperature and concentrated. The residue was triturated with hexanes to give the title compound (7.81 g, 55%) as a yellow solid and as a 6:1 mixture of the 5-fluoro and 7-fluoro isomers. The mixture was used directly in the next step without further purification.

b) (3-chloro-7-fluoro-benzo[b]thiophen-2-yl)methanol

To an ice-cold suspension of a 6:1 mixture of 3-chloro-5-fluoro-benzo[b]thiophene-2-carbonyl chloride and 3-chloro-7-fluoro-benzo[b]thiophene-2-carbonyl chloride (5.46 g, 23.6 mmol) in THF (120 mL) was added lithium aluminum hydride (11.8 mL of a 1.0 M solution in THF, 11.8 mmol) dropwise. The mixture was stirred for 4 h then quenched with NaOH (0.35 N solution in $H_2O$). The mixture was diluted with $Et_2O$ and the solution filtered. The filtrate was dried ($Na_2SO_4$) and concentrated. Purification by flash column chromatography (silica gel, hexanes/EtOAc, 9:1 to hexanes/

EtOAc 8:2) gave the title compound (600 mg, 4% (2 steps), 7-fluoro isomer) as a light, yellow solid: $^1$H NMR (300 MHz, CDCl$_3$) δ 7.59 (d, J=8.0 Hz, 1H), 7.41 (ddd, J=8.0, 8.0, 4.9 Hz, 1H), 7.10 (dd, J=9.1, 9.1 Hz, 1H), 5.00 (d, J=6.2 Hz, 2H), 2.04 (t, J=6.5 Hz, 1H).

c)
3-chloro-7-fluoro-benzo[b]thiophene-2-carbaldehyde

A suspension of (3-chloro-7-fluoro-benzo[b]thiophen-2-yl)methanol (600 g, 2.78 mmol) and MnO$_2$ (1.69 g, 19.5 mmol) in benzene (25 mL) was stirred at room temperature for 2 d. The solution was filtered through diatomaceous earth and the filtrate concentrated to give the title compound (610 mg, quantitative) as a light, yellow solid: $^1$H NMR (300 MHz, CDCl$_3$) δ 10.35 (s, 1H), 7.83 (d, J=8.1 Hz, 1H), 7.51 (ddd, J=8.0, 8.0, 4.8 Hz, 1H), 7.32-7.26 (m, 1H).

d) (3-chloro-7-fluoro-benzo[b]thiophen-2-ylmethyl)methylamine

A solution of 3-chloro-7-fluoro-benzo[b]thiophene-2-carbaldehyde (610 mg, 2.78 mmol) in CH$_3$NH$_2$ (20 mL of a 2.0 M solution in MeOH, 40 mmol) was stirred at room temperature overnight. The mixture was concentrated. The residue was dissolved in EtOH (20 mL), and after cooling in an ice bath, NaBH$_4$ (159 mg, 4.20 mmol) was added. The mixture was slowly warmed to room temperature and then stirred overnight. The mixture was concentrated. The residue was taken up in NaOH (20 mL) and the mixture extracted with Et$_2$O (3×). The combined organics were washed with satd NaCl, dried (Na$_2$SO$_4$) and concentrated. Purification by column chromatography (silica gel, 95:5 CH$_2$Cl$_2$/MeOH) gave the title compound (460 g, 70%) as a brown oil: $^1$H NMR (300 MHz, CDCl$_3$) δ 7.56 (d, J=8.0 Hz, 1H), 7.38 (ddd, J=7.9, 7.9, 4.9 Hz, 1H), 7.06 (dd, J=8.8, 8.8 Hz, 1H), 4.09 (s, 2H), 2.53 (s, 3H), 1.55 (s, 1H).

e) (E)-3-(6-amino-pyridin-3-yl)-N-(3-chloro-7-fluoro-benzo[b]thiophen-2-ylmethyl)-N-methylacrylamide To a solution of 3-(6-amino-pyridin-3-yl)acrylic acid trifluoroacetic acid salt (509 mg, 1.83 mmol) in DMF (15 mL) was added 3-chloro-7-fluoro-benzo[b]thiophen-2-ylmethyl)methylamine (460 mg, 2.01 mmol), EDC (385 mg, 2.01 mmol), HOBt (272 mg, 2.01 mmol) and DIEA (0.9 mL, 5.5 mmol). The mixture was stirred at room temperature overnight. The mixture was diluted with H$_2$O and the solid collected by filtration. Purification by semi-preparative HPLC (Phenomenex Luna C18(2) 10μ, 250 21.20 mm, CH$_3$CN/H$_2$O/0.05% TFA) gave a solid. The solid was partitioned between EtOAc and satd NaHCO$_3$. The organic layer was concentrated to give to give a pale yellow solid. The solid was dissolved in a minimum amount of hot MeCN. The precipitate was collected by filtration to give the title compound (105 mg, 15%) as a white solid: MS (ESI) m/e 376 (M+H)$^+$.

f) (E)-3-(6-amino-pyridin-3-yl)-N-(3-chloro-7-fluoro-benzo[b]thiophen-2-ylmethyl)-N-methylacrylamide hydrochloride A suspension of (E)-3-(6-amino-pyridin-3-yl)-N-(3-chloro-7-fluoro-benzo[b]thiophen-2-ylmethyl)-N-methylacrylamide (105 mg, 0.28 mmol) in CH$_2$Cl$_2$ (10 mL) was treated with anhydrous HCl (0.28 mL of a 1.0 M solution in Et$_2$O, 0.28 mmol) and then the mixture was stirred at room temperature overnight. The mixture was diluted with Et$_2$O. The resulting solid was collected by filtration and dried under vacuum at 50° C. overnight to give the title compound (111 mg, 96%) as an off-white solid and as a mixture of amide rotamers: $^1$H NMR (300 MHz, DMSO-d$_6$) δ 8.43-8.33 (m, 4H), 7.67-7.52 (m, 3H), 7.41-7.35 (m, 1H), 7.25-7.19 (m, 1H), 7.04-7.01 (m, 1H), 5.21-4.92 (m, 2H), 3.63 (br s, 1H), 3.23-2.98 (m, 3H); MS (ESI) m/e 376 (M+H)$^+$.

Example 280

Preparation of (E)-6-{2-[methyl-(3-methyl-benzo[b]thiophen-2-ylmethyl)-carbamoyl]-vinyl}-2-oxo-1,2-dihydro-[1,8]naphthyridine-3-carboxylic acid sodium salt a) 6-Bromo-2-oxo-1,2-dihydro-[1,8]naphthyridine-3-carboxylic acid ethyl ester A mixture of 2-amino-5-bromo-pyridine-3-carbaldehyde (4.00 g, 14.2 mmol), diethyl malonate (21.6 mL, 142 mmol) and piperidine (7.00 mL, 71.0 mmol) in EtOH (70 mL) was heated to reflux overnight. The mixture was cooled to room temperature and the solid was collected by filtration to give the title compound (2.41 g, 57%) as an off-white solid: $^1$H NMR (300 MHz, CDCl$_3$) δ 12.65 (s, 1H), 8.70 (d, J=2.4 Hz, 1H), 8.56 (d, J=2.4 Hz, 1H), 8.45 (s, 1H), 4.29 (q, J=7.1 Hz, 2H), 1.30 (t, J=7.1 Hz, 3H).

b) (E)-6-{2-[methyl-(3-methyl-benzo[b]thiophen-2-ylmethyl)carbamoyl]vinyl}-2-oxo-1,2-dihydro-[1,8]naphthyridine-3-carboxylic acid ethyl ester A suspension of N-methyl-N-(3-methyl-benzo[b]thiophen-2-ylmethyl)acrylamide (500 mg, 2.04 mmol), 6-bromo-2-oxo-1,2-dihydro-[1,8]naphthyridine-3-carboxylic acid ethyl ester (665 mg, 2.24 mmol), (o-tol)$_3$P (135 mg, 0.44 mmol) and DIEA (0.4 mL, 2.45 mmol) in EtCN (10 mL) and DMF (10 mL) was deoxygenated with argon for 30 min. Pd(OAc)$_2$ (50 mg, 0.22 mmol) was added, the mixture was deoxygenated with argon for 20 min and then heated to reflux overnight. The mixture was cooled to room temperature and concentrated. The residue was partitioned between CH$_2$Cl$_2$ and H$_2$O. The organic layer was washed with satd NaCl, dried (Na$_2$SO$_4$) and concentrated. Purification by column chromatography (silica gel, 89:10:1 CH$_2$Cl$_2$/MeOH/conc NH$_4$OH) gave the title compound (530 mg, 56%) as a yellow solid and as a mixture of amide rotamers: $^1$H NMR (300 MHz, DMSO-d$_6$) δ 12.63 (s, 1H), 8.98 (d, J=2.1 Hz, 1H), 8.67 (s, 1H), 8.44-8.42 (m, 1H), 7.88 (d, J=7.6 Hz, 1H), 7.75-7.52 (m, 2H), 7.43-7.31 (m, 3H), 5.14-4.91 (m, 2H), 4.32-4.25 (m, 2H), 3.18-2.96 (m, 3H), 2.43 (s, 3H), 1.33-1.27 (m, 3H); MS (ESI) m/e 462 (M+H)$^+$.

c) (E)-6-{2-[methyl-(3-methyl-benzo[b]thiophen-2-ylmethyl)carbamoyl]vinyl}-2-oxo-1,2-dihydro-[1,8]naphthyridine-3-carboxylic acid sodium salt To a suspension of (E)-6-{2-[methyl-(3-methyl-benzo[b]thiophen-2-ylmethyl)carbamoyl]vinyl}-2-oxo-1,2-dihydro-[1,8]naphthyridine-3-carboxylic acid ethyl ester (349 mg, 0.76 mmol) in MeOH (10 mL) and CH$_2$Cl$_2$ (5 mL) was added NaOH (1.53 mL of a 0.995 M solution in H$_2$O, 1.53 mmol) dropwise. The mixture was stirred at room temperature overnight. The solid was collected by filtration and then dried under vacuum at 50° C. for 2 d. Trituration with 5:1 MeCN/H$_2$O gave the title compound (85 mg, 25%) as an off-white solid and as a mixture of amide rotamers: $^1$H NMR (300 MHz, DMSO-d$_6$+TFA-d) δ 9.15 (s, 1H), 8.85 (s, 2H), 7.88 (d, J=7.5 Hz, 1H), 7.76-7.58 (m, 2H), 7.46-7.34 (m, 3H), 5.15-4.92 (m, 2H), 3.20-2.98 (m, 3H), 2.44 (s, 3H); MS (ESI) m/e 434 (M−Na+2H)$^+$.

Example 281

Preparation of (E)-spiro[2-oxo-2,3,4,5-tetrahydro-1H-pyrido[2,3-e][1,4]diazepin-3,1'-cyclopentane]-7-yl-N-(3-methyl-benzofuran-2-ylmethyl)-N-methylacrylamide hydrochloride a) 1-[(2-amino-5-bromo-pyridin-3-ylmethyl)amino]cyclopentanecarboxylic acid methyl ester To an ice-cold suspension of 5-bromo-3-bromomethyl-pyridin-2-ylamine hydrobromide (8.64 g, 24.9 mmol) and 1-amino-cyclopentanecarboxylic acid methyl ester (3.56 g, 24.9 mmol) in DMF (100 mL) was added Et$_3$N (5.30 mL, 37.4 mmol) slowly. The mixture was stirred for 2 h and then diluted with H$_2$O. The solid was collected by filtration to give the title compound (3.55 g, 43%) as a yellow solid: $^1$H NMR (300 MHz, CDCl$_3$) δ 8.02 (d, J=2.3 Hz, 1H), 7.37 (d, J=2.3 Hz, 1H), 5.49 (s, 2H), 3.76 (s, 3H), 3.52 (s, 2H), 2.12-2.05 (m, 2H), 1.79 (br s, 7H).

b) spiro[7-bromo-2-oxo-2,3,4,5-tetrahydro-1H-pyrido[2,3-e][1,4]diazepin-3,1'-cyclopentane]

A solution of 1-[(2-amino-5-bromo-pyridin-3-ylmethyl)amino]cyclopentanecarboxylic acid methyl ester (3.45 g, 10.5 mmol) in DMSO (100 mL) was treated with NaH (60% dispersion in mineral oil, 420 mg, 10.5 mmol) and stirred at room temperature for 2 d. The mixture was diluted with H$_2$O and the solid was collected by filtration. The solid was triturated with CHCl$_3$/MeOH to give the title compound (1.79 g, 58%) as an off-white solid: $^1$H NMR (300 MHz, CDCl$_3$) δ 8.23 (d, J=2.3 Hz, 1H), 8.13 (br s, 1H), 7.51 (d, J=2.0 Hz, 1H), 3.92 (s, 2H), 2.31-2.22 (m, 2H), 1.86-1.73 (m, 7H).

c) (E)-spiro[2-oxo-2,3,4,5-tetrahydro-1H-pyrido[2,3-e][1,4]diazepin-3,1'-cyclopentane]-7-yl-N-(3-methyl-benzofuran-2-ylmethyl)-N-methylacrylamide A mixture of spiro[7-bromo-2-oxo-2,3,4,5-tetrahydro-1H-pyrido[2,3-e][1,4]diazepin-3,1'-cyclopentane] (456 mg, 1.54 mmol), N-methyl-N-(3-methyl-benzofuran-2-ylmethyl)acrylamide (320 mg, 1.40 mmol), (o-tol)$_3$P (137 mg, 0.45 mmol) and DIEA (0.35 mL, 2.10 mmol) in DMF (10 mL) was deoxygenated with argon for 30 min. Pd(OAc)$_2$ (50 mg, 0.22 mmol) was added, the mixture was deoxygenated with argon again and then heated to 100° C. overnight. The mixture was cooled to room temperature and partitioned between CH$_2$Cl$_2$/H$_2$O. The organic layer was washed with H$_2$O and satd NaCl, dried (Na$_2$SO$_4$) and concentrated. Purification by column chromatography (silica gel, 95:5 CH$_2$Cl$_2$/MeOH) gave a light yellow solid. The solid was suspended in MeOH and the mixture sonicated. The solid was collected by filtration to give the title compound (354 mg, 57%) as an off-white solid and as a mixture of amide rotamers: $^1$H NMR (300 MHz, CDCl$_3$) δ 8.84 (m, 1H), 8.45-8.42 (m, 1H), 7.66 (d, J=15.4 Hz, 1H), 7.55-7.48 (m, 2H), 7.41 (d, J=8.0 Hz, 1H), 7.28-7.21 (m, 2H), 7.15-6.84 (m, 1H), 4.83-4.72 (m, 2H), 3.96 (s, 2H), 3.23-3.09 (m, 3H), 2.33-2.25 (m, 5H), 1.84-1.74 (m, 7H).

d) (E)-spiro[2-oxo-2,3,4,5-tetrahydro-1H-pyrido[2,3-e][1,4]diazepin-3,1'-cyclopentane]-7-yl-N-(3-methyl-benzofuran-2-ylmethyl)-N-methylacrylamide hydrochloride A suspension of (E)-spiro[2-oxo-2,3,4,5-tetrahydro-1H-pyrido[2,3-e][1,4]diazepin-3,1'-cyclopentane]-7-yl-N-(3-methyl-benzofuran-2-ylmethyl)-N-methylacrylamide (354 mg, 0.80 mmol) in CH$_2$Cl$_2$ (15 mL) was treated with anhydrous HCl (0.80 mL of a 1.0 M solution in Et$_2$O, 0.80 mmol) and the mixture was stirred at room temperature overnight. The mixture was diluted with Et$_2$O and then the solid was collected by filtration to give the title compound (305 mg, 80%) as an off-white solid and as a mixture of amide rotamers: $^1$H NMR (300 MHz, DMSO-d$_6$) δ 11.02 (s, 1H), 10.6 (s, 2H), 8.73 (d, J=8.6 Hz, 1H), 8.38 (s, 1H), 7.66-7.22 (m, 6H), 5.02-4.81 (m, 2H), 4.29 (s, 2H), 3.21-2.93 (m, 3H), 2.27 (s, 3H), 2.20-2.16 (m, 2H), 1.90-1.76 (m, 4H), 1.62-1.60 (2H); MS (ESI) m/e 445 (M+H)$^+$.

Example 282

Preparation of (E)-spiro[2-oxo-2,3,4,5-tetrahydro-1H-pyrido[2,3-e][1,4]diazepin-3,1'-cyclopentane]-7-yl-N-(3-methoxy-2-propoxybenzyl)-N-methylacrylamide hydrochloride a) (E)-spiro[2-oxo-2,3,4,5-tetrahydro-1H-pyrido[2,3-e][1,4]diazepin-3,1'-cyclopentane]-7-yl-N-(3-methoxy-2-propoxybenzyl)-N-methylacrylamide A mixture of spiro[7-bromo-2-oxo-2,3,4,5-tetrahydro-1H-pyrido[2,3-e][1,4]diazepin-3,1'-cyclopentane] (450 mg, 1.52 mmol), N-(3-methoxy-2-propoxybenzyl)-N-methylacrylamide (400 mg, 1.52 mmol), (o-tol)$_3$P (131 mg, 0.43 mmol) and DIEA (0.30 mL, 1.82 mmol) in DMF (10 mL) was deoxygenated with argon for 30 min. Pd(OAc)$_2$ (50 mg, 0.22 mmol) was added, the mixture was deoxygenated with argon and then heated to 100° C. overnight. The mixture was cooled to room temperature and partitioned between CH$_2$Cl$_2$/H$_2$O. The organic layer was washed with H$_2$O and satd NaCl, dried (Na$_2$SO$_4$) and concentrated. Purification by column chromatography (silica gel, CH$_2$Cl$_2$ to 96:4 CH$_2$Cl$_2$/MeOH) gave a light yellow solid. The solid was suspended in MeOH and the mixture sonicated. The solid was collected by filtration to give the title compound (333 mg, 46%) as an off-white solid and as a mixture of amide rotamers: $^1$H NMR (300 MHz, DMSO-d$_6$) δ 8.40-8.28 (m, 2H), 7.69-7.61 (m, 1H), 7.54-7.46 (m, 1H), 7.07-6.71 (m, 4H), 4.81-7.41 (m, 2H), 4.00-3.86 (m, 7H), 3.09 (s, 3H), 2.33-2.26 (m, 2H), 1.84-1.67 (m, 9H), 1.04 (t, J=7.4 Hz, 3H).

b) (E)-spiro[2-oxo-2,3,4,5-tetrahydro-1H-pyrido[2,3-e][1,4]diazepin-3,1'-cyclopentane]-7-yl-N-(3-methoxy-2-propoxybenzyl)-N-methylacrylamide hydrochloride A suspension of (E)-spiro[2-oxo-2,3,4,5-tetrahydro-1H-pyrido[2,3-e][1,4]diazepin-3,1'-cyclopentane]-7-yl-N-(3-methoxy-2-propoxybenzyl)-N-methylacrylamide hydrochloride (333 mg, 0.70 mmol) in CH$_2$Cl$_2$ (10 mL) was treated with anhydrous HCl (0.70 mL of a 1.0 M solution in Et$_2$O, 0.70 mmol) and the mixture was stirred at room temperature overnight. The mixture was diluted with Et$_2$O. The resulting solid was collected by filtration and dried under vacuum at 50° C. overnight to give the title compound (293 mg, 81%) as an off-white solid and as a mixture of amide rotamers: $^1$H NMR (300 MHz, DMSO-d$_6$) δ 11.00 (s, 1H), 10.58 (s, 2H), 8.71 (d, J=12.0 Hz, 1H), 8.38-8.31 (m, 1H), 7.08-7.54 (m, 1H), 7.41-7.35 (m, 1H), 7.08-6.95 (m, 2H), 6.69-6.63 (m, 1H), 4.81-4.65 (m, 2H), 4.29-4.26 (m, 2H), 3.92-3.85 (m, 2H), 3.80 (s, 3H), 3.12-2.87 (m, 3H), 2.21-2.10 (m, 2H), 1.90-1.58 (m, 8H), 1.01-0.94 (m, 3H); MS (ESI) n/e 479 (M+H)$^+$.

Example 283

Preparation of (E)-N-(3-ethyl-benzofuran-2-ylmethyl)-N-methyl-3-(2-oxo-2,3,4,5-tetrahydro-1H-pyrido[2,3,-e][1,4]diazepin-7-yl)acrylamide hydrochloride a) 1-But-2-enyloxy-iodobenzene An ice-cold solution of 2-iodophenol (10.0 g, 45.4 mmol) in DMF (100 mL) was added dropwise to a solution of NaH (2.16 g, 90.8 mmol) in DMF at 0° C. Crotylbromide (7.97 g, 59.0 mmol) was then added. The mixture was warmed to room temperature and stirred overnight. The reaction was quenched with water (50 mL) and the mixture was extracted with CH$_2$Cl$_2$ (3×). The combined organics were washed with brine and dried over Na$_2$SO$_4$ to give the title compound (12.2 g, 99%) as a yellow oil: $^1$H NMR (500 MHz, DMSO-d$_6$) δ 7.76 (dd, J=7.8, 1.5 Hz, 1H), 7.27-7.22 (m, 1H), 6.80 (dd, J=8.4, 1.2 Hz, 1H), 6.70-6.65 (m, 1H), 5.95-5.80 (m, 1H), 5.75-5.65 (m, 1H), 4.55-4.45 (m, 2H), 1.76-1.70 (m, 3H); ESI MS m/z 275 (M+H)$^+$.

b) 3-Ethyl-benzofuran

To a solution of 1-but-2-enyloxy-iodobenzene (7.60 g, 27.7 mmol) in DMF (46 mL) was added n-Bu$_4$NCl (8.46 g, 30.4 mmol), Pd(OAc)$_2$ (0.338 g, 1.30 mmol), Na$_2$CO$_3$ (6.01 g, 56.7 mmol) and NaOAc (2.77 g, 27.0 mmol). The mixture was heated to reflux under nitrogen atmosphere overnight. The mixture was diluted with EtOAc and washed with water. The combined organics were washed with brine and dried over Na$_2$SO$_4$. Purification by column chromatography (silica gel, hexanes) gave the title compound (1.74 g, 43%) as a yellow oil: $^1$H NMR (300 MHz, DMSO-d$_6$) δ 7.75 (s, 1H), 7.63-7.61 (m, 1H), 7.55 (t, J=6.6 Hz, 1H), 7.34-7.23 (m, 2H), 2.71-2.63 (m, 2H), 1.28 (t, J=7.5 Hz, 3H); ESI MS m/z 147 (M+H)$^+$.

c) 3-Ethyl-bezofuran-2-carbadehyde

To a solution of 3-ethyl-benzofuran (1.6 g, 11 mmol) in THF (30 mL) cooled to −40° C. was added n-butyllithium (10.8 mL of a 2.5 M solution in hexane, 27.2 mmol). The mixture was stirred for 15 minutes then DMF (2.78 g, 38.1 mmol) was added. The mixture slowly warmed to room temperature and was stirred overnight under nitrogen atmosphere. The reaction was quenched with saturated NH$_4$Cl and the resulting mixture was extracted with EtOAc (3×). The combined organics were washed with water and brine, dried and concentrated. Purification by column chromatography (silica gel, hexane/EtOAc, 5:1) gave the title compound (1.24 g, 65%) as a yellow oil: $^1$H NMR (500 MHz, DMSO-d$_6$) δ 9.98 (s, 1H), 6.88-6.65 (m, 1H), 6.54 (d, J=0.5 Hz, 2H), 6.41-6.20 (m, 1H), 2.11 (d, J=7.5 Hz, 2H), 0.375 (t, J=7.5 Hz, 3H); ESI MS m/z 175 (M+H)$^+$.

d) (3-Ethyl-benzofuran-2-ylmethyl)methylamine

3-Ethyl-benzofuran-2-carbaldehyde (1.16 g, 6.65 mmol) was added to a solution of methylamine (26 mL of a 2M solution in MeOH, 52 mmol) and the resulting mixture was stirred overnight. The mixture was concentrated under reduced pressure. The residue was taken up in ethanol (20 mL) and then cooled in an ice-bath. NaBH$_4$ (370 mg, 9.90 mmol) was added in one portion. The mixture was concentrated under reduced pressure and the residue taken up in 1 M NaOH. The mixture was extracted with Et$_2$O (3×). The combined organics were washed with brine, dried and concentrated under reduced pressure to give the title compound (1.12 g, 89%) as a yellow oil: $^1$H NMR (300 MHz, DMSO-d$_6$) δ 7.58 (dd, J=8.4, 6.6 Hz, 1H), 7.46 (d, J=7.2 Hz, 1H), 7.30-7.25 (m, 2H), 3.75 (s, 2H), 2.68 (t, J=7.5 Hz, 2H), 2.26 (s, 3H), 2.05 (br s, 1H), 1.21 (t, J=7.5 Hz, 3H); ESI MS m/z 190 (M+H)$^+$.

e) (E)-N-(3-ethyl-benzofuran-2-ylmethyl)-N-methyl-3-(2-oxo-2,3,4,5-tetrahydro-1H-pyrido[2,3,-e][1,4]diazepin-7-yl)acrylamide A solution of (3-ethyl-benzofuran-2-ylmethyl)methylamine (185 mg, 0.979 mmol) and (i-Pr)$_2$EtN (0.427 mL, 2.44 mmol) in DMF (25 mL) was treated successively with 3-(2-oxo-2,3,4,5-tetrahydro-1H-pyrido[2,3-e][1,4]diazepin-7-yl)acrylic acid hydrochloride (250 mg, 0.816 mmol), HOBt (115 mg, 0.856 mmol), and EDC (316 mg, 2.44 mmol). After stirring overnight at room temperature, the mixture was diluted with water and then extracted with EtOAc (3×). The combined organics were washed with brine and dried, filtered and concentrated in vacuo. Purification by column chromatography (silica gel, CH$_2$Cl$_2$/CH$_3$OH, 40:2 to 35:2) gave the title compound (125 mg, 37%) as a yellow solid: ESI MS m/z 405 (M+H)$^+$.

f) (E)-N-(3-ethyl-benzofuran-2-ylmethyl)-N-methyl-3-(2-oxo-2,3,4,5-tetrahydro-1H-pyrido[2,3,-e][1,4]diazepin-7-yl)acrylamide hydrochloride A suspension of (E)-N-(3-ethyl-benzofuran-2-ylmethyl)-N-methyl-3-(2-oxo-2,3,4,5-tetrahydro-1H-pyrido[2,3,-e][1,4]diazepin-7-yl)acrylamide (100 mg, 0.247 mmol) in CH$_2$Cl$_2$ (3 mL) and CH$_3$OH (0.5 mL) was treated with anhydrous HCl (0.123 mL of a 2M solution in Et$_2$O, 0.247 mmol). After stirring for 1 h, the mixture was diluted with Et$_2$O (3 mL) and stirred for 10 minutes. The solid was isolated by filtration, washed with Et$_2$O and dried under vacuum at 50° C. overnight to give the title compound (81.0 mg, 81%) as an off-white solid and as a mixture of amide rotamers: $^1$H NMR (500 MHz, DMSO-d$_6$) δ 10.0 (br s, 2H), 8.82-8.75 (m, 1H), 8.33-8.27 (m, 1H), 7.68-7.55 (m, 3H), 7.50 (t, J=7.5 Hz, 1H), 7.33-7.24 (m, 3H), 5.01-4.81 (m, 2H), 4.26 (s, 2H), 3.84 (s, 2H), 3.20-2.92 (m, 3H), 2.78-2.74 (m, 2H), 1.23-1.19 (m, 3H); ESI MS m/z 405 (M+H)$^+$.

Example 284

Preparation of (E)-3-(3,3-Dimethyl-2-oxo-2,3,4,5-tetrahydro 1H-pyrido[2,3-e][1,4]dizepin-7-yl)-N-methyl-N-(3-propyl-benzofuran-2-ylmethyl)acrylamide hydrochloride a) 1-Iodo-2-pent-2-enyloxy-benzene An ice-cold solution of 2-iodophenol (6.00 g, 272 mmol) in DMF (100 mL) was added dropwise to a solution of NaH (1.30 g, 54.4 mmol) in DMF. 1-Bromo-pent-2-ene (4.87 g, 327 mmol) was then added. The mixture slowly warmed to room temperature overnight. The reaction was quenched with water (50 mL) and the mixture was extracted with CH$_2$Cl$_2$ (3×). The combined organics were washed with brine and dried over Na$_2$SO$_4$ to give the title compound (8.50 g, 99%) as a yellow oil: $^1$H NMR (300 MHz, DMSO-d$_6$) δ 7.75 (dd, J=7.5, 1.2, Hz, 1H), 7.36-7.30 (m, 1H), 6.98 (d, J=8.1 Hz, 1H), 6.76-6.71 (m, 1H), 6.01-5.89 (m, 1H), 5.67 (t, J=5.7 Hz, 1H), 4.54 (d, J=5.7 Hz, 2H), 2.08 (t, J=7.5 Hz, 2H), 0.98 (t, J=7.5 Hz, 3H).

b) 3-Propyl-benzofuran

To a solution of 1-but-2-enyloxy-iodobenzene (4.00 g, 13.8 mmol) in DMF (46 mL) was added n-Bu$_4$NCl (5.36 g. 19.3 mmol), Pd(OAc)$_2$ (0.168 g, 0.690 mmol), Na$_2$CO$_3$ (2.99 g, 28.2 mmol) and NaOAc (1.13 g, 13.8 mmol). The mixture was heated to reflux under nitrogen atmosphere overnight. The mixture was diluted with EtOAc and washed with water. The aqueous layer was extracted with EtOAc (3×). The combined organics were washed with brine and dried over Na$_2$SO$_4$. Purification by column chromatography (silica gel, hexanes) gave the title compound (1.79 g, 81%) as a yellow oil: $^1$H NMR (300 MHz, DMSO-d$_6$) δ 7.75 (s, 1H), 7.63-7.60 (m, 1H), 7.54 (d, J=7.5 Hz, 1H), 7.33-7.22 (m, 2H), 2.64-2.59 (m, 2H), 1.72-1.64 (m, 2H), 0.96 (t, J=7.2 Hz, 3H); ESI MS m/z 161 (M+H)$^+$.

c) 3-Propyl-bezofuran-2-carbadehyde

To a solution of 3-propyl-benzofuran (1.79 g, 11.1 mmol) in THF (30 mL) at −30° C. under N$_2$ was added n-butyllithium (11 mL of a 2.5 M solution in hexane, 27.5 mmol) dropwise. The mixture was stirred for 15 minutes then DMF (2.83 g, 38.8 mmol) was added. The mixture was slowly warmed to room temperature overnight. The reaction was quenched with saturated NH$_4$Cl and the resulting mixture was extracted with EtOAc (3×). The combined organics were washed with water and brine, and then dried over Na$_2$SO$_4$. Purification by column chromatography (silica gel, hexanes/EtOAc, 5:1) gave the title compound (1.45 g, 70%) as a yellow oil: $^1$H NMR (300 MHz, DMSO-d$_6$) δ 10.0 (s, 1H), 7.93-7.90 (m, 1H), 7.70 (t, J=8.4 Hz, 1H), 7.62-7.56 (m, 1H), 7.42-7.37 (m, 1H), 3.10 (t, J=7.2 Hz, 2H), 1.77-1.65 (m, 2H), 1.00-0.92 (m, 3H); ESI MS m/z 189 (M+H)$^+$.

d) Methyl-(3-propyl-benzofuran-2-ylmethyl)amine

To 3-propyl-benzofuran-2-carbaldehyde (1.36 g, 72.2 mmol) was added methylamine (29 mL of a 2 M solution in methanol, 58 mmol). The resulting mixture was stirred overnight at room temperature under nitrogen. The mixture was concentrated under reduced pressure. The residue was taken up in ethanol (20 mL) and the solution was cooled in an ice-bath. NaBH$_4$ (490 mg, 10.8 mmol) was added in one portion. The mixture was concentrated under reduced pressure and the residue taken up in 1 M NaOH. The mixture was extracted with Et$_2$O (3×). The combined organics were washed, dried (Na$_2$SO$_4$), filtered and concentrated under reduced pressure to give the title compound (1.68 g, 99%) as a yellow oil: $^1$H NMR (300 MHz, DMSO-d$_6$) δ 7.60-7.54 (m, 1H), 7.49 (dd, J=7.2, 1.2 Hz, 1H), 7.25-7.20 (m, 2H), 3.76 (s, 2H), 2.65 (t, J=7.2 Hz, 2H), 2.30 (d, J=9.3 Hz, 3H), 1.99 (s, 1H), 1.66-1.58 (m, 2H), 0.94-0.86 (m, 3H); ESI MS m/z 204 (M+H)$^+$.

e) N-Methyl-N-(3-propyl-benzofuran-2-ylmethyl) acrylamide

A solution of methyl-(3-propyl-benzofuran-2-ylmethyl) amine (1.10 g, 5.41 mmol) in CH$_2$Cl$_2$ (40 mL) was treated with acryloyl chloride (0.45 mL, 5.68 mmol) and triethylamine (1.5 mL, 10.8 mmol). The mixture was stirred at room temperature for 2 h. The solution was washed with water and brine, dried (Na$_2$SO$_4$), filtered and concentrated under reduced pressure to give the title compound (1.46 g, 99%) as a yellow solid: $^1$H NMR (300 MHz, DMSO-d$_6$) δ 7.59 (d, J=5.4 Hz, 1H), 7.49 (d, J=7.5 Hz, 1H), 7.28-7.15 (m, 2H), 6.89-6.70 (m, 1H), 6.20 (t, J=2.4 Hz, 1H), 5.75 (t, J=4.5 Hz, 1H), 4.83-4.71 (m, 2H), 3.33-3.07 (m, 2H), 2.87-2.67 (m, 3H), 1.65-1.58 (m, 2H), 0.95-0.88 (m, 3H); ESI MS m/z 258 (M+H)$^+$.

f) (E)-3-(3,3-Dimethyl-2-oxo-2,3,4,5-tetrahydro 1H-pyrido[2,3-e][1,4]dizepin-7-yl)-N-methyl-N-(3-propyl-benzofuran-2-ylmethyl)acrylamide To 7-bromo-3,3-dimethyl-1,3,4,5-tetrahydro-pyrido[2,3-e][1,4]diazepin-2-one (400 mg, 1.48 mmol) in propionitrile (40 mL) and DMF (10 mL) was added N-methyl-N-(3-propyl-benzofuran-2-ylmethyl)acrylamide (410 mg, 1.63 mmol), (i-Pr)$_2$EtN (0.51 mL, 2.96 mmol), Pd(OAc)$_2$ (332 mg, 0.148 mmol) and P(o-tol)$_3$ (90.1 mg, 0.296 mmol), and the mixture was de-oxygenated with argon for 15 min. The mixture was heated to reflux overnight, allowed to cool and then filtered. The filtrate was concentrated and the residue was dissolved in CH$_2$Cl$_2$ (150 mL). The organic solution was washed with water and brine, dried and the solvent was removed in vacuo. Purification by column chromatography (silica gel, CH$_2$Cl$_2$/MeOH, 20:1) gave the title compound (87.0 mg, 11%) as an off-white solid: MS m/z 447 (M+H)$^+$.

g) (E)-3-(3,3-Dimethyl-2-oxo-2,3,4,5-tetrahydro 1H-pyrido[2,3-e][1,4]diazepin-7-yl)-N-methyl-N-(3-propyl-benzofuran-2-ylmethyl)acrylamide hydrochloride A suspension of (E)-3-(3,3-dimethyl-2-oxo-2,3,4,5-tetrahydro 1H-pyrido[2,3-e][1,4]diazepin-7-yl)-N-methyl-N-(3-propyl-benzofuran-2-ylmethyl)acrylamide (84.0 mg, 0.188 mmol) in CH$_2$Cl$_2$ (3 mL) was treated with anhydrous HCl (0.094 mL of a 2 M solution in Et$_2$O, 0.188 mmol). After stirring for 1 h, the mixture was diluted with Et$_2$O (5 mL) and then stirred for 10 min. The solid was isolated by filtration, washed with Et$_2$O, and dried under vacuum at 50° C. overnight to give the title compound (65.0 mg, 72%) as an off-white solid and as a mixture of amide rotamers: $^1$H NMR (300 MHz, DMSO-d$_6$) δ 10.9 (s, 1H), 10.3 (br s, 2H) 8.71-8.65 (m, 1H), 8.37 (s, 1H), 7.60-7.48 (m, 3H), 7.34-7.20 (m, 3H), 5.01-4.81 (m, 2H), 4.41 (s, 2H), 3.20-2.90 (m, 3H), 2.73 (t, J=7.2 Hz, 2H), 1.70-1.61 (m, 8H), 0.93 (t, J=7.5 Hz, 3H); ESI MS m/z 447 (M+H)$^+$.

Example 285

Preparation of (E)-3-(3,3-dimethyl-2-oxo-2,3,4,5-tetrahydro-1H-pyrido[2,3-e][1,4]diazepin-7-yl)-N-(3-ethyl-benzofuran-2-ylmethyl)-N-methylacrylamide hydrochloride a) N-(3-ethyl-benzofuran-2-ylmethyl)-N-methylacrylamide

A solution of N-(3-ethyl-benzofuran-2-ylmethyl)methylamine (860 mg, 4.54 mmol) in CH$_2$Cl$_2$ (32 mL) was treated with acryloyl chloride (0.38 mL, 4.77 mmol) and triethylamine (1.3 mL, 9.08 mmol). The mixture was stirred at room temperature for 2 h. The solution was washed with water and brine, dried (Na$_2$SO$_4$), filtered and concentrated under reduced pressure to give the title compound (1.10 g, 99%) as a yellow solid: $^1$H NMR (300 MHz, CDCl$_3$) δ 7.55 (dd, J=6.9, 1.8 Hz, 1H), 7.41 (d, J=7.5 Hz, 1H), 7.28-7.20 (m, 2H), 6.59 (t, J=6.6 Hz, 1H), 6.45-6.32 (m, 1H), 5.75-5.70 (m, 1H), 4.78-4.63 (m, 2H), 3.15-3.01 (m, 3H), 2.82-2.70 (m, 2H), 1.35-1.23 (m, 3H); ESI MS m/z 244 (M+H)$^+$.

b) (E)-3-(3,3-dimethyl-2-oxo-2,3,4,5-tetrahydro-1H-pyrido[2,3-e][1,4]diazepin-7-yl)-N-(3-ethyl-benzofuran-2-ylmethyl)-N-methylacrylamide To 7-bromo-3,3-dimethyl-1,3,4,5-tetrahydro-pyrido[2,3-e][1,4]diazepin-2-one (400 mg, 1.48 mmol) in propionitrile (40 mL) and DMF (10 mL) was added N-(3-ethyl-benzofuran-2-ylmethyl)-N-methylacrylamide (410 mg, 1.62 mmol), (i-Pr)$_2$EtN (0.51 mL, 2.96 mmol), Pd(OAc)$_2$ (332 mg, 0.148 mmol) and P(o-tol)$_3$ (90.1 mg, 0.296 mmol), and the mixture was de-oxygenated with argon for 15 min. The mixture was heated to reflux overnight, allowed to cool and then filtered. The filtrate was concentrated and the residue was dissolved in CH$_2$Cl$_2$ (150 mL). The organic solution was washed with water and brine, dried (Na$_2$SO$_4$) and the solvent was removed in vacuo. Purification by column chromatography (silica gel, CH$_2$Cl$_2$/MeOH, 20:1) gave the title compound (130 mg, 20%) as an off-white solid: MS m/z 433 (M+H)$^+$.

c) (E)-3-(3,3-dimethyl-2-oxo-2,3,4,5-tetrahydro-1H-pyrido[2,3-e][1,4]diazepin-7-yl)-N-(3-ethyl-benzofuran-2-ylmethyl)-N-methylacrylamide hydrochloride A suspension of (E)-3-(3,3-dimethyl-2-oxo-2,3,4,5-tetrahydro-1H-pyrido[2,3-e][1,4]diazepin-7-yl)-N-(3-ethyl-benzofuran-2-ylmethyl)-N-methylacrylamide (59.0 mg, 0.136 mmol) in CH$_2$Cl$_2$ (4 mL) and CH$_3$OH (0.3 mL) was treated with anhydrous HCl (0.068 mL of a 2 M solution in Et$_2$O, 0.136 mmol). After stirring for 1 h, the mixture was diluted with Et$_2$O (5 mL) and stirred for 10 minutes. The solid was isolated by filtration, washed with Et$_2$O, and dried under vacuum at 50° C. overnight to give the title compound (63.0 mg, 99%) as an off-white solid and as a mixture of amide rotamers: $^1$H NMR (500 MHz, DMSO-d$_6$) δ 10.9 (s, 1H), 10.5 (br s, 2H) 8.71-8.60 (m, 1H), 8.39 (d, J=8.0 Hz, 1H), 7.65-7.50 (m, 3H), 7.35-7.20 (m, 3H), 4.80-5.01 (m, 2H), 4.40 (s, 2H), 3.20-2.90 (m, 3H), 2.77 (d, J=7.0 Hz, 2H), 1.62 (s, 6H), 1.22 (t, J=7.0 Hz, 3H); ESI MS m/z 433 (M+H)$^+$.

Example 286

Preparation of (E)-3-(3,3-Dimethyl-2-oxo-2,3,4,5-tetrahydro-1H-pyrido[2,3-e][1,4]diazepin-7-yl)-N-methyl-N-(3-methylbenzofuran-2-ylmethyl)acrylamide hydrochloride a) (E)-3-(3,3-Dimethyl-2-oxo-2,3,4,5-tetrahydro-1H-pyrido[2,3-e][1,4]diazepin-7-yl)-N-methyl-N-(3-methylbenzofuran-2-ylmethyl)acrylamide A suspension of 7-bromo-3,3-dimethyl-1,3,4,5-tetrahydro-pyrido[2,3-e][1,4]diazepin-2-one (0.27 g, 1.0 mmol) and N-methyl-N-(3-methylbenzofuran-2-ylmethyl)acrylamide (0.31 g, 1.4 mmol) in propionitrile (5 mL) and DMF (1.3 mL) was de-oxygenated with Ar for 10 min. The mixture was treated with (i-Pr)$_2$EtN (0.37 mL, 2.1 mmol) and was de-oxygenated with Ar for 10 min. Pd(OAc)$_2$ (22 mg, 0.098 mmol) and P(o-tol)$_3$ (61 mg, 0.20 mmol) were added simultaneously, and the mixture was de-oxygenated a third time for 5 min. The mixture was heated to reflux overnight, then allowed to cool. The resulting precipitate was isolated by filtration, washed with EtOAc, dissolved in CH$_2$Cl$_2$/MeOH (1:1) and the solvent was removed in vacuo. Purification by flash column chromatography (silica gel, CH$_2$Cl$_2$/MeOH, 97:3) gave the title compound (0.25 g, 60%) as a white solid: MS (ESI) m/e 419 (M+H)$^+$.

b) (E)-3-(3,3-Dimethyl-2-oxo-2,3,4,5-tetrahydro-1H-pyrido[2,3-e][1,4]diazepin-7-yl)-N-methyl-N-(3-methylbenzofuran-2-ylmethyl)acrylamide hydrochloride A suspension of (E)-3-(3,3-dimethyl-2-oxo-2,3,4,5-tetrahydro-1H-pyrido[2,3-e][1,4]diazepin-7-yl)-N-methyl-N-(3-methylbenzofuran-2-ylmethyl)acrylamide (0.20 g, 0.48 mmol) in CH$_2$Cl$_2$ (10 mL) was treated with anhydrous HCl (0.48 mL of a 1.0 M solution in Et$_2$O, 0.48 mmol). After stirring for 45 min, the mixture was diluted with Et$_2$O (50 mL) and stirred for 3 h. The solid was isolated by filtration, washed with Et$_2$O, and dried under vacuum at 50° C. overnight to give the title compound (0.21 g, 97%) as a white powder and as a mixture of amide rotamers: $^1$H NMR (300 MHz, DMSO-d$_6$) δ 10.92 (s, 1H), 10.55 (br s, 2H), 8.68-8.65 (m, 1H), 8.39 (s, 1H), 7.60-7.22 (m, 6H), 5.01-4.81 (m, 2H), 4.40 (s, 2H), 3.20-2.93 (m, 3H), 2.27 (s, 3H), 1.63 (s, 6H); MS (ESI) m/e 419 (M+H)$^+$.

Example 287

Preparation of (E)-3-(3,3-Dimethyl-2-oxo-2,3,4,5-tetrahydro-1H-pyrido[2,3-e][1,4]diazepin-7-yl)-N-(3-methoxy-2-propoxybenzyl)-N-methylacrylamide hydrochloride a)
N-(3-Methoxy-2-propoxybenzyl)-N-methylacrylamide A solution of (3-methoxy-2-propoxybenzyl)methylamine (1.00 g, 4.78 mmol) in CH$_2$Cl$_2$ (40 mL) was treated with acryloyl chloride (0.42 mL, 5.2 mmol) followed by Et$_3$N (0.74 mL, 5.3 mmol). After stirring for 1.5 h, the solution was diluted with CH$_2$Cl$_2$ (50 mL) and washed with saturated aqueous NaHCO$_3$ (50 mL). The aqueous layer was extracted with CH$_2$Cl$_2$ (50 mL). The combined organic layers were dried over Na$_2$SO$_4$, filtered and concentrated to give the title compound (1.11 g, 88%) as a tan oil and as a mixture of amide rotamers: $^1$H NMR (300 MHz, CDCl$_3$) δ 7.06-6.94 (m, 2H), 6.85-6.70 (m, 1H), 6.65-6.58 (m, 1H), 6.18-6.13 (m, 1H), 5.73-5.63 (m, 1H), 4.64-4.58 (m, 2H), 3.89-3.84 (m, 2H), 3.79-3.78 (m, 3H), 2.99-2.86 (m, 3H), 1.73-1.66 (m, 2H), 0.97 (t, J=7.4 Hz, 3H).

b) (E)-3-(3,3-Dimethyl-2-oxo-2,3,4,5-tetrahydro-1H-pyrido[2,3-e][1,4]diazepin-7-yl)-N-(3-methoxy-2-propoxybenzyl)-N-methylacrylamide A suspension of 7-bromo-3,3-dimethyl-1,3,4,5-tetrahydro-pyrido[2,3-e][1,4]diazepin-2-one (0.30 g, 1.1 mmol) and N-(3-methoxy-2-propoxybenzyl)-N-methylacrylamide (0.35 g, 1.3 mmol) in propionitrile (5 mL) and DMF (1.3 mL) was de-oxygenated with Ar for 5 min. The mixture was treated with (i-Pr)$_2$EtN (0.41 mL, 2.4 mmol) and was de-oxygenated with Ar for 10 min. Pd(OAc)$_2$ (25 mg, 0.11 mmol) and P(o-tol)$_3$ (69 mg, 0.23 mmol) were added simultaneously, and the mixture was de-oxygenated a third time for 5 min. The mixture was heated to reflux overnight, then allowed to cool. The mixture was diluted with Et$_2$O (50 mL) and EtOAc (25 mL), washed with H$_2$O (25 mL), dried over Na$_2$SO$_4$, filtered and concentrated to an orange residue. Purification by flash column chromatography (silica gel, CH$_2$Cl$_2$/MeOH, 98:2 to 97:3) gave the title compound (0.30 g, 60%) as an off-white solid: MS (ESI) m/e 453 (M+H)$^+$.

c) (E)-3-(3,3-Dimethyl-2-oxo-2,3,4,5-tetrahydro-1H-pyrido[2,3-e][1,4]diazepin-7-yl)-N-(3-methoxy-2-propoxybenzyl)-N-methylacrylamide hydrochloride A suspension of (E)-3-(3,3-dimethyl-2-oxo-2,3,4,5-tetrahydro-1H-pyrido[2,3-e][1,4]diazepin-7-yl)-N-(3-methoxy-2-propoxybenzyl)-N-methylacrylamide (0.19 g, 0.42 mmol) in CH$_2$Cl$_2$ (5 mL) was treated with anhydrous HCl (0.42 mL of a 1.0 M solution in Et$_2$O, 0.42 mmol). After stirring for 1 h, the mixture was diluted with Et$_2$O (50 mL) and allowed to stir for 3 h. The solid was isolated by filtration, washed with Et$_2$O and dried under vacuum at 50° C. for 3 d to give the title compound (0.17 g, 84%) as an off-white powder and as a mixture of amide rotamers: $^1$H NMR (300 MHz, DMSO-d$_6$) δ 10.94-10.92 (m, 1H), 10.47 (br s, 2H), 8.67-8.62 (m, 1H), 8.39-8.32 (m, 1H), 7.60-7.53 (m, 1H), 7.39-7.33 (m, 1H), 7.05-6.95 (m, 2H), 6.69-6.62 (m, 1H), 4.80-4.65 (m, 2H), 4.42-4.38 (m, 2H), 3.92-3.85 (m, 2H), 3.80 (s, 3H), 3.12-2.86 (m, 3H), 1.75-1.67 (m, 2H), 1.63-1.61 (m, 6H), 1.01-0.94 (m, 3H); MS (ESI) m/e 453 (M+H)$^+$.

Example 288

Preparation of (E)-3-(3,3-Dimethyl-2-oxo-2,3,4,5-tetrahydro-1H-pyrido[2,3-e][1,4]diazepin-7-yl)-N-methyl-N-(1-methyl-1H-indol-2-ylmethyl)acrylamide hydrochloride a) N-Methyl-N-(1-methyl-1H-indol-2-ylmethyl)acrylamide A solution of methyl-(1-methyl-1H-indol-2-ylmethyl)amine (2.00 g, 11.5 mmol) in CH$_2$Cl$_2$ (100 mL) was treated with acryloyl chloride (1.03 mL, 12.7 mmol) followed by Et$_3$N (1.8 mL, 13 mmol). After stirring for 2 h, the solution was diluted with CH$_2$Cl$_2$ (100 mL) and washed with saturated aqueous NaHCO$_3$ (200 mL). The aqueous layer was extracted with CH$_2$Cl$_2$ (200 mL). The combined organic layers were dried over Na$_2$SO$_4$, filtered and concentrated to an orange oil. Purification by flash column chromatography (silica gel, CH$_2$Cl$_2$/MeOH, 99.5:0.5 to 99:1) gave the title compound (2.10 g, 80%) as a tan oil: $^1$H NMR (300 MHz, CDCl$_3$) δ 7.59-7.56 (m, 1H), 7.32-7.19 (m, 2H), 7.13-7.08 (m, 1H), 6.66-6.57 (m, 1H), 6.47-6.38 (m, 2H), 5.78-5.74 (m, 1H), 4.88-4.74 (m, 2H), 3.69 (s, 3H), 3.06-2.97 (m, 3H); MS (ESI) m/e 229 (M+H)$^+$.

b) (E)-3-(3,3-Dimethyl-2-oxo-2,3,4,5-tetrahydro-1H-pyrido[2,3-e][1,4]diazepin-7-yl)-N-methyl-N-(1-methyl-1H-indol-2-ylmethyl)acrylamide A suspension of 7-bromo-3,3-dimethyl-1,3,4,5-tetrahydro-pyrido[2,3-e][1,4]diazepin-2-one (0.30 g, 1.1 mmol) and N-methyl-N-(1-methyl-1H-indol-2-ylmethyl)acrylamide (0.35 g, 1.3 mmol) in propionitrile (5 mL) and DMF (1.3 mL) was de-oxygenated with Ar for 10 min. The mixture was treated with (i-Pr)$_2$EtN (0.41 mL, 2.4 mmol) and was de-oxygenated with Ar for 5 min. Pd(OAc)$_2$ (25 mg, 0.11 mmol) and P(o-tol)$_3$ (70 mg, 0.23 mmol) were added simultaneously, and the mixture was de-oxygenated a third time for 5 min. The mixture was heated to reflux overnight, then allowed to cool. The mixture was diluted with EtOAc (100 mL), washed with H$_2$O (50 mL), dried over Na$_2$SO$_4$, filtered and concentrated to an orange residue. Purification by flash column chromatography (silica gel, CH$_2$Cl$_2$/MeOH, 98:2 to 97:3) gave the title compound (0.24 g, 51%) as a light pink solid: MS (ESI) m/e 418 (M+H)$^+$.

c) (E)-3-(3,3-Dimethyl-2-oxo-2,3,4,5-tetrahydro-1H-pyrido[2,3-e][1,4]diazepin-7-yl)-N-methyl-N-(1-methyl-1H-indol-2-ylmethyl)acrylamide hydrochloride A suspension of (E)-3-(3,3-dimethyl-2-oxo-2,3,4,5-tetrahydro-1H-pyrido[2,3-e][1,4]diazepin-7-yl)-N-methyl-N-(1-methyl-1H-indol-2-ylmethyl)acrylamide (0.15 g, 0.36 mmol) in CH$_2$Cl$_2$ (5 mL) was treated with anhydrous HCl (0.36 mL of a 1.0 M solution in Et$_2$O, 0.36 mmol). After stirring for 10 min, the mixture was diluted with Et$_2$O (50 mL) and then stirred for 1.5 h. The solid was isolated by filtration, washed with Et$_2$O, and dried under vacuum at 50° C. for 3 d to give the title compound (0.14 g, 83%) as a tan powder and as a mixture of amide rotamers: $^1$H NMR (500 MHz, DMSO-d$_6$) δ 10.90-10.87 (m, 1H), 10.54 (br s, 2H), 8.66-8.63 (m, 1H), 8.39-8.33 (s, 1H), 7.62-7.59 (m, 1H), 7.51-7.32 (m, 3H), 7.14-7.11 (m, 1H), 7.03-6.99 (m, 1H), 6.43-6.19 (m, 1H), 5.07-4.86 (m, 2H), 4.40-4.35 (m, 2H), 3.74-3.69 (m, 3H), 3.13-3.00 (m, 3H), 1.63-1.59 (m, 6H); MS (ESI) n/e 418 (M+H)$^+$.

Example 289

Preparation of (E)-N-Methyl-N-(3-methylbenzofuran-2-ylmethyl)-3-(2-oxo-2,3,4,5-tetrahydro-1H-pyrido[2,3-e][1,4]diazepin-7-yl)acrylamide hydrochloride a) 7-Bromo-1,3,4,5-tetrahydropyrido[2,3-e][1,4]diazepin-2-one hydrochloride A solution of 7-bromo-4-(4-methoxybenzyl)-1,3,4,5-tetrahydropyrido[2,3-e][1,4]diazepin-2-one (3.37 g, 9.30 mmol) in dichloroethane (180 mL) was cooled in an ice bath and treated with ACE-Cl (1.1 mL, 10 mmol). After stirring at 0° C. under N$_2$ for 30 min and then at room temperature for 30 min, the mixture was heated to reflux for 1 h. The mixture was allowed to cool and then concentrated to dryness. Purification by flash column chromatography (silica gel, CH$_2$Cl$_2$/MeOH, 99:1) gave a white solid. A portion of the solid (1.02 g, 2.93 mmol) was suspended in methanol (50 mL) and heated to reflux for 3 h. The mixture was allowed to cool and the solid was isolated by filtration, washed with MeOH and dried under vacuum at 50° C. overnight to give the title compound (0.66 g, 46%) as a white solid: $^1$H NMR (300 MHz, DMSO-d$_6$) δ 11.05 (s, 1H), 10.30 (br s, 2H), 8.57 (d, J=2.3 Hz, 1H), 8.15 (d, J=2.3 Hz, 1H), 4.24 (s, 2H), 3.79 (s, 2H); MS (ESI) m/e 242 (M+H)$^+$.

b) (E)-N-Methyl-N-(3-methylbenzofuran-2-ylmethyl)-3-(2-oxo-2,3,4,5-tetrahydro-1H-pyrido[2,3-e][1,4]diazepin-7-yl)acrylamide A suspension of 7-bromo-1,3,4,5-tetrahydropyrido[2,3-e][1,4]diazepin-2-one hydrochloride (0.29 g, 1.0 mmol) and N-methyl-N-(3-methylbenzofuran-2-ylmethyl)acrylamide (0.29 g, 1.3 mmol) in propionitrile (5 mL) and DMF (1.3 mL) was de-oxygenated with Ar for 10 min. The mixture was treated with (i-Pr)$_2$EtN (0.56 mL, 3.2 mmol) and was de-oxygenated with Ar for 5 min. Pd(OAc)$_2$ (24 mg, 0.11 mmol) and P(o-tol)$_3$ (64 mg, 0.21 mmol) were added simultaneously, and the mixture was de-oxygenated a third time for 5 min. The mixture was heated to reflux overnight, then allowed to cool. The resulting precipitate was isolated by filtration, dissolved in CH$_2$Cl$_2$/MeOH and the solvent was removed in vacuo. Purification by flash column chromatography (silica gel, CH$_2$Cl$_2$/MeOH, 98:2 to 96:4) gave the title compound (0.18 g, 47%) as a white solid: MS (ESI) m/e 391 (M+H)$^+$.

c) (E)-N-Methyl-N-(3-methylbenzofuran-2-ylmethyl)-3-(2-oxo-2,3,4,5-tetrahydro-1H-pyrido[2,3-e][1,4]diazepin-7-yl)acrylamide hydrochloride A suspension of (E)-N-Methyl-N-(3-methylbenzofuran-2-ylmethyl)-3-(2-oxo-2,3,4,5-tetrahydro-1H-pyrido[2,3-e][1,4]diazepin-7-yl)acrylamide (0.16 g, 0.40 mmol) in CH$_2$Cl$_2$ (10 mL) was treated with anhydrous HCl (0.40 mL of a 1.0 M solution in Et$_2$O, 0.40 mmol). After stirring for 45 min, the mixture was diluted with Et$_2$O (50 mL) and then stiffed for 1 h. The solid was isolated by filtration, washed with Et$_2$O, and dried under vacuum at 50° C. for 3 d to give the title compound (0.15 g, 90%) as a white powder and as a mixture of amide rotamers: $^1$H NMR (300 MHz, DMSO-d$_6$) δ 11.09 (s, 1H), 10.12 (br s, 2H), 8.79-8.76 (m, 1H), 8.33-8.31 (s, 1H), 7.60-7.24 (m, 6H), 5.01-4.81 (m, 2H), 4.26 (s, 2H), 3.85 (s, 2H), 3.20-2.93 (m, 3H), 2.27 (s, 3H); MS (ESI) m/e 391 (M+H)$^+$.

Example 290

Preparation of (E)-3-(2,2-Dimethyl-3-oxo-3,4-dihydro-2H-pyrido[3,2-b][1,4]oxazin-7-yl)-N-methyl-N-(3-methylbenzofuran-2-ylmethyl)acrylamide a) 7-Bromo-2,2-dimethyl-4H-pyrido[3,2-b][1,4]oxazin-3-one To a mixture of 2-amino-5-bromopyridin-3-ol (0.500 g, 2.64 mmol) and K$_2$CO$_3$ (1.09 g, 7.93 mmol) in acetone (11.0 mL) was added ethyl bromoisobutyrate (0.50 mL, 3.4 mmol). The solution was stirred under N$_2$ for 18 h and then heated to reflux. After 18 h, the solution was cooled and concentrated. The light-pink, sweet-smelling solid was dissolved in CH$_2$Cl$_2$ (50 mL) and MeOH (5 mL). The solution was diluted with H$_2$O (150 mL) and then washed with CH$_2$Cl$_2$ (3×75 mL). The combined organic layers were washed with brine (2×100 mL), dried (Na$_2$SO$_4$) and concentrated to yield the title compound (0.57 g, 84%) as an off-white solid: $^1$H NMR (300 MHz, DMSO-d$_6$) δ 11.39 (s, 1H), 8.03 (d, J=1.2 Hz, 1H), 7.66 (d, 0.9 Hz, 1H), 1.43 (s, 6H).

b) (E)-3-(2,2-Dimethyl-3-oxo-3,4-dihydro-2H-pyrido[3,2-b][1,4]oxazin-7-yl)-N-methyl-N-(3-methylbenzofuran-2-ylmethyl)acrylamide A solution of N-methyl-N-(3-methylbenzofuran-2-ylmethyl)acrylamide (0.231 g, 1.01 mmol) in propionitrile (4 mL) and DMF (0.8 mL) was deoxygenated with Ar for 20 min. The solution was treated with diisopropylethylamine (0.28 mL, 1.64 mmol) and 7-bromo-2,2-dimethyl-4H-pyrido[3,2-b][1,4]oxazin-3-one (0.200 g, 0.775 mmol). The solution was deoxygenated with Ar for 20 min. Pd(OAc)$_2$ (0.017 g, 0.078 mmol) and P(o-tol)$_3$ (0.047 g, 0.15 mmol) were then added and the solution was deoxygenated again with Ar for 10 min. The mixture was heated to reflux for 18 h, then allowed to cool. The mixture was diluted with H$_2$O (100 mL). The resulting solids were collected by filtration and washed with Et$_2$O (50 mL). Residual palladium was removed by silica gel plug (silica gel, 95:5, CH$_2$Cl$_2$/MeOH) the resulting solution concentrated to reveal a light orange solid. The solid was triturated with Et$_2$O and dried to give the title compound (0.14 g, 46%) as a light pink solid and as a mixture of amide rotamers: $^1$H NMR (300 MHz, DMSO-d$_6$) δ 11.41 (s, 1H), 8.20-8.19 (m, 1H), 7.97-7.93 (m, 1H), 7.57-7.48 (m, 3H), 7.28-7.23 (m, 3H), 5.00-4.78 (m, 2H), 3.17-2.92 (m, 3H), 2.62 (s, 3H), 1.44 (m, 6H); MS (ESI) m/e 406 (M+H)$^+$.

Example 291

Preparation of (E)-3-(2,2-Dimethyl-3,4-dihydro-2H-pyrido[3,2-b][1,4]oxazin-7-yl)-N-methyl-N-(3-methyl-benzofuran-2-ylmethyl)-acrylamide hydrochloride a) 7-Bromo-2,2-dimethyl-3,4-dihydro-2H-pyrido[3,2-b][1,4]oxazine To a solution of 7-bromo-2,2-dimethyl-4H-pyrido[3,2-b][1,4]oxazin-3-one (0.360 g, 1.39 mmol) in THF (8.9 mL) at 0° C. was added BH$_3$ (8.43 mL of a 1.0 M solution in THF, 8.43 mmol). The solution was heated to reflux. After 18 h, the solution was cooled to 0° C. and the reaction quenched with MeOH (15 mL). The mixture was concentrated and the resulting off-white solid was dissolved in MeOH (15 mL) and NaOH (10 mL of a 1 N solution). The mixture was heated at reflux to 4 h. The MeOH was removed under reduced pressure. The resulting precipitate was collected by filtration and washed with H$_2$O (10 mL). The white solid was dried to give the title compound (0.260 g, 76%) as white needles: $^1$H NMR (300 MHz, DMSO-d$_6$) δ 7.62 (d, J=2.1 Hz, 1H), 7.10 (d, J=1.5 Hz, 1H), 7.03 (br s, 1H), 3.14 (d, J=2.4 Hz, 2H), 1.25 (s, 6H); MS (ESI) m/e 243 (M+H)$^+$.

b) (E)-3-(2,2-Dimethyl-3,4-dihydro-2H-pyrido[3,2-b][1,4]oxazin-7-yl)-N-methyl-N-(3-methylbenzofuran-2-ylmethyl)acrylamide A solution of N-methyl-N-(3-methylbenzofuran-2-ylmethyl)acrylamide (0.190 g, 0.637 mmol) in propionitrile (3 mL) and DMF (0.6 mL) was deoxygenated with Ar for 20 min. The solution was treated with diisopropylethylamine (0.23 mL, 1.33 mmol) and 7-bromo-2,2-dimethyl-3,4-dihydro-2H-pyrido[3,2-b][1,4]oxazine (0.154 g, 0.828 mmol). The solution was deoxygenated with Ar for 20 min. Pd(OAc)$_2$ (0.014 g, 0.063 mmol) and P(o-tol)$_3$ (0.038 g, 0.12 mmol) were then added and the solution was deoxygenated again with Ar for 10 min. The mixture was heated to reflux for 2 h, then allowed to cool. The mixture was diluted with H$_2$O (200 mL) and the solution was washed with EtOAc (3×50 mL). The combined organic layers were washed with brine (2×30 mL), dried (Na$_2$SO$_4$) and concentrated to give a dark green oil. Column chromatography (silica gel, CH$_2$Cl$_2$/MeOH, 100 to 98:2) gave the title compound (0.14 g, 59%) as a light yellow solid and as a mixture of amide rotamers: $^1$H NMR (500 MHz, DMSO-d$_6$) δ 7.79 (s, 1H), 7.56-7.54 (m, 1H), 7.51-7.47 (m, 2H), 7.41-7.38 (m, 1H), 7.32 (br s, 1H), 7.29-6.93 (m, 3H), 4.95-4.76 (m, 2H), 3.19 (m, 2H), 3.14-2.90 (m, 3H), 2.25 (s, 3H), 1.26 (s, 6H); MS (ESI) m/e 392 (M+H)$^+$.

c) (E)-3-(2,2-Dimethyl-3,4-dihydro-2H-pyrido[3,2-b][1,4]oxazin-7-yl)-N-methyl-N-(3-methylbenzofuran-2-ylmethyl)acrylamide hydrogen chloride A stirring solution of (E)-3-(2,2-dimethyl-3,4-dihydro-2H-pyrido[3,2-b][1,4]oxazin-7-yl)-N-methyl-N-(3-methylbenzofuran-2-ylmethyl)acrylamide (0.147 g, 0.375 mmol) in $CH_2Cl_2$ (4 mL) under $N_2$ was treated with anhydrous HCl (0.18 mL of a 2 M solution in diethyl ether, 0.37 mmol). After stirring for 6 h, the resulting solids were collected by filtration, washed with $Et_2O$ (50 mL) and dried to yield the title compound (0.14 g, 88%) as an off-white solid and as a mixture of amide rotamers: $^1$H NMR (300 MHz, DMSO-$d_6$) δ 8.69 (br s, 1H), 8.00-7.94 (m, 2H), 7.57-7.55 (m, 1H), 7.49-7.44 (m, 2H), 7.30-7.14 (m, 3H), 4.99-4.77 (m, 2H), 3.37 (br s, 2H), 3.15-2.90 (m, 3H), 2.25 (s, 3H), 1.32 (s, 6H); MS (ESI) m/e 392 (M+H)$^+$.

Example 292

Preparation of (E)-3-(3,4-Dihydro-2H-pyrido[3,2-b][1,4]oxazin-7-yl)-N-methyl-N-(3-methylbenzofuran-2-ylmethyl)acrylamide hydrochloride a) 3,4-Dihydro-2H-pyrido[3,2-b][1,4]oxazine

To an ice-cold solution of 4H-pyrido[3,2-b][1,4]oxazin-3-one (5.00 g, 33.3 mmol) in THF (40 mL) was added lithium aluminum hydride (66.6 mL of a 1.0 M solution in THF, 66.6 mmol). Following the addition, the solution was heated to reflux. After 18 h, the solution was cooled to 0° C. and quenched the reaction with $H_2O$ (4 mL) followed by NaOH (4 mL, 15%) and $H_2O$ (10 mL). The resulting slurry was filtered over Celite and the filtrate concentrated to give the title compound (3.87 g, 85%) as a blue-gray powder: $^1$H NMR (500 MHz, DMSO-$d_6$) δ 7.53 (dd, J=4.5, 1.0 Hz, 1H), 6.90-6.89 (m, 1H), 6.61 (br s, 1H), 6.44 (dd, J=8.0, 3.0 Hz, 1H), 4.08 (t, J=4.5 Hz, 2H), 3.39-3.36 (m, 2H); MS (ESI) m/e 137 (M+H)$^+$.

b) 7-Bromo-2,2-dimethyl-3,4-dihydro-2H-pyrido[3,2-b][1,4]oxazine hydrogen bromide To an ice-cold solution of 3,4-dihydro-2H-pyrido[3,2-b][1,4]oxazine (3.86 g, 28.3 mmol) in acetic acid (71.7 mL) was added $Br_2$ (1.83 mL, 35.6 mmol). The mixture was stirred for 3 h at 0° C. then warmed to ambient temperature. After 2 h, the resulting solids were collected by filtration and washed with EtOAc (400 mL). The solids were dried to give the title compound (6.31 g, 60%) as a dark orange powder: $^1$H NMR (300 MHz, DMSO-$d_6$) δ 12.25 (br s, 1H), 7.77 (t, J=1.8 Hz, 1H), 7.45 (t, J=2.1 Hz, 1H), 4.20 (t, J=4.6 Hz, 2H), 3.48 (t, J=4.6 Hz, 2H); MS (ESI) m/e 215 (M+H)$^+$.

c) (E)-3-(3,4-Dihydro-2H-pyrido[3,2-b][1,4]oxazin-7-yl)-N-methyl-N-(3-methylbenzofuran-2-ylmethyl)acrylamide A solution of N-methyl-N-(3-methylbenzofuran-2-ylmethyl)acrylamide (0.190 g, 0.637 mmol) in propionitrile (3 mL) and DMF (0.6 mL) was deoxygenated with Ar for 20 min. The solution was treated with diisopropylethylamine (0.34 mL, 1.97 mmol) and 7-bromo-2,2-dimethyl-3,4-dihydro-2H-pyrido[3,2-b][1,4]oxazine (0.188 g, 0.828 mmol). The solution was deoxygenated with Ar for 20 min. Pd(OAc)$_2$ (0.014 g, 0.078 mmol) and P(o-tol)$_3$ (0.038 g, 0.15 mmol) were then added and the solution was deoxygenated again with Ar for 20 min. The mixture was heated to reflux for 2 h, then allowed to cool. The mixture was diluted with $H_2O$ (200 mL) and the resulting solution was washed with EtOAc (3×50 mL). The combined organic layers were washed with brine (2×30 mL), dried (Na$_2$SO$_4$) and concentrated to a dark green oil. Column chromatography (silica gel, CH$_2$Cl$_2$/MeOH, 100 to 98:2) gave the title compound (0.12 g, 52%) as a light yellow solid and as a mixture of amide rotamers: $^1$H NMR (300 MHz, DMSO-$d_6$) δ 7.83 (br s, 1H), 7.62-7.60 (m, 1H), 7.56-7.51 (m, 2H), 7.48-7.41 (m, 1H), 7.38-7.69 (m, 4H), 5.01-4.95 (m, 2H), 4.03 (s, 2H), 3.48 (s, 2H), 3.06-2.90 (m, 3H), 2.18 (s, 3H); MS (ESI) m/e 364 (M+H)$^+$.

d) (E)-3-(3,4-Dihydro-2H-pyrido[3,2-b][1,4]oxazin-7-yl)-N-methyl-N-(3-methylbenzofuran-2-ylmethyl)acrylamide hydrogen chloride A stirring solution of (E)-3-(3,4-dihydro-2H-pyrido[3,2-b][1,4]oxazin-7-yl)-N-methyl-N-(3-methylbenzofuran-2-ylmethyl)acrylamide (0.121 g, 0.332 mmol) in CH$_2$Cl$_2$ (4 mL) under N$_2$ was treated with anhydrous HCl (0.16 mL of a 2 M solution in diethyl ether, 0.33 mmol). After stirring for 72 h, the resulting solids were collected by filtration, washed with Et$_2$O (50 mL) and dried to yield the title compound (0.094 g, 71%) as an off-white solid and as a mixture of amide rotamers: $^1$H NMR (300 MHz, DMSO-$d_6$) δ 8.74 (br s, 1H), 7.97-7.93 (m, 2H), 7.57-7.55 (m, 1H), 7.49-7.77 (m, 2H), 7.30-7.13 (m, 3H), 4.99-4.77 (m, 2H), 4.25 (br s, 2H), 3.57 (m, 2H), 3.16-2.91 (m, 3H), 2.25 (s, 3H); MS (ESI) m/e 364 (M+H)$^+$.

Example 293

Preparation of (E)-N-(2-Ethoxy-3-isopropylbenzyl)-N-methyl-3-(2-oxo-2,3,4,5-tetrahydro-1H-pyrido[2,3-e][1,4]diazepin-7-yl)-acrylamide hydrochloride a) N-(3-Chloro-2-propoxybenzyl)-N-methylacrylamide

To a solution of (2-ethoxy-3-isopropylbenzyl)methylamine (1.00 g, 4.82 mmol) in CH$_2$Cl$_2$ (40 mL) was added acryloyl chloride (0.46 mL, 5.3 mmol) drop-wise. After stirring for five minutes, triethylamine (0.74 mL, 5.3 mmol) was added. The solution was stirred under N$_2$ for 5 hours. The solution was diluted with CH$_2$Cl$_2$ (50 mL) and then washed with H$_2$O (3×50 mL) and brine (2×100 mL), dried over Na$_2$SO$_4$, filtered and concentrated to yield the title compound (1.15 g, 92%) as a clear oil and as a mixture of amide rotamers: $^1$H NMR (300 MHz, DMSO-$d_6$) δ 7.25-7.19 (m, 1H), 7.13-7.03 (m, 1H), 6.89-6.67 (m, 2H), 6.20-6.12 (m, 1H), 5.79-5.53 (m, 1H), 4.68-4.60 (m, 2H), 3.81-3.76 (m, 2H), 3.28-3.23 (m, 1H), 3.01-2.87 (m, 3H), 1.38-1.33 (m, 3H), 1.19-1.16 (m, 6H); MS (ESI) m/e 262 (M+H)$^+$.

b) (E)-N-(2-Ethoxy-3-isopropylbenzyl)-3-[4-(4-methoxybenzyl)-2-oxo-2,3,4,5-tetrahydro-1H-pyrido[2,3-e][1,4]diazepin-7-yl]-N-methylacrylamide A solution of N-(2-ethoxy-3-isopropylbenzyl)-N-methylacrylamide (0.281 g, 1.07 mmol) in propionitrile (4 mL) and DMF (0.8 mL) was deoxygenated with Ar for 20 min. The solution was treated with diisopropylethylamine (0.30 mL, 1.73 mmol) and 7-bromo-4-(4-methoxy-benzyl)-1,3,4,5-tetrahydro-pyrido[2,3-e][1,4]diazepin-2-one (0.300 g, 0.828 mmol). The solution was deoxygenated with Ar for 20 min. Pd(OAc)$_2$ (0.018 g, 0.082 mmol) and P(o-tol)$_3$ (0.050 g, 0.16 mmol) were then added and the solution was deoxygenated again with Ar for 10 min. The mixture was heated to reflux for 1.5 h, then allowed to cool. The mixture was diluted with H₂O (100 mL) and then was washed with EtOAc (3×50 mL). The organic layer was washed with brine (2×100 mL), dried (Na₂SO₄) and concentrated to an orange oil. Purification by column chromatography (silica gel, CH₂Cl₂ to CH₂Cl₂/MeOH, 100 to 99.5:0.5) gave the title compound (0.20 g, 44%) as a light yellow solid and as a mixture of amide rotamers: ¹H NMR (300 MHz, DMSO-d₆) δ 10.43-10.41 (m, 1H), 8.55-8.49 (m, 1H), 8.10-8.01 (m, 1H), 7.55-7.50 (m, 1H), 7.35-7.17 (m, 4H), 7.12-7.04 (m, 1H), 6.91-6.85 (m, 3H), 4.80-4.66 (m, 2H), 3.83-3.70 (m, 7H), 3.65-3.62 (m, 2H), 3.41-3.38 (m, 2H), 3.29-3.90 (m, 1H), 2.56-2.51 (m, 3H), 1.39-1.37 (m, 3H), 1.25-1.11 (m, 6H); MS (ESI) m/e 543 (M+H)⁺.

c) (E)-N-(2-Ethoxy-3-isopropylbenzyl)-N-methyl-3-(2-oxo-2,3,4,5-tetrahydro-1H-pyrido[2,3-e][1,4]diazepin-7-yl)acrylamide hydrochloride A suspension of N-(2-ethoxy-3-isopropylbenzyl)-3-[4-(4-methoxybenzyl)-2-oxo-2,3,4,5-tetrahydro-1H-pyrido[2,3-e][1,4]diazepin-7-yl]-N-methylacrylamide (0.200 g, 0.369 mmol) in dichloroethane (8.0 mL) was cooled in an ice bath and treated with 1-chloroethyl chloroformate (0.044 mL, 0.40 mmol). After stirring at 0° C. under N₂ for 30 min and then at room temperature for 30 min, the mixture was heated to reflux for 2 h. The mixture was allowed to cool and then concentrated to dryness. Purification by flash column chromatography (silica gel, CH₂Cl₂ to CH₂Cl₂/MeOH, 100 to 99.5:0.5) gave a white solid (0.128 g, 0.241 mmol). The solid was dissolved in methanol (4 mL) and heated to reflux for 6.5 h. The mixture was allowed to cool and the resulting solid was isolated by filtration, washed with MeOH and Et₂O and dried to give the title compound (1.28 g, 46%) as a white powder and as a mixture of amide rotamers: ¹H NMR (300 MHz, DMSO-d₆) δ 11.08-11.06 (m, 1H), 9.96 (br s, 2H), 8.77-8.71 (m, 1H), 8.32-8.23 (m, 1H), 7.63-7.55 (m, 1H), 7.40-7.32 (m, 1H), 7.26-7.21 (m, 1H), 7.13-7.04 (m, 1H), 6.91-6.84 (m, 1H), 4.83-4.67 (m, 2H), 4.27-4.22 (m, 2H), 3.88-3.78 (m, 4H), 3.29-2.25 (m, 1H), 3.13-2.89 (m, 3H), 1.40-1.35 (m, 3H), 1.19-1.17 (m, 6H); MS (ESI) m/e 423 (M+H)⁺.

Example 294

Preparation of (E)-N-(2-Isobutoxy-3-methoxybenzyl)-N-methyl-3-(2-oxo-2,3,4,5-tetrahydro-1H-pyrido[2,3-e][1,4]diazepin-7-yl)acrylamide hydrochloride a) (E)-N-(2-Isobutoxy-3-methoxybenzyl)-N-methyl-3-(2-oxo-2,3,4,5-tetrahydro-1H-pyrido[2,3-e][1,4]diazepin-7-yl)acrylamide A solution of N-(2-isobutoxy-3-methoxybenzyl)-N-methylacrylamide (0.387 g, 1.40 mmol) in propionitrile (5 mL) and DMF (1 mL) was deoxygenated with Ar for 20 min. Then treated with diisopropylethylamine (0.39 mL, 2.25 mmol) and 7-bromo-1,3,4,5-tetrahydro-pyrido[2,3-e][1,4]diazepin-2-one (0.300 g, 1.07 mmol). The solution was deoxygenated with Ar for 20 min. Then Pd(OAc)₂ (0.024 g, 0.10 mmol) and P(o-tol)₃ (0.065 g, 0.21 mmol) were added and the solution deoxygenated with Ar for 20 min. The solution was heated to reflux for 18 h, then allowed to cool. The solution was diluted with H₂O (30 mL) and was washed with EtOAc (3×50 mL). The organics were washed with brine (2×100 mL), dried over Na₂SO₄, filtered and concentrated to an orange-brown semisolid. Purification by column chromatography (silica gel, CH₂Cl₂ to CH₂Cl₂/MeOH, 100 to 95:5) gave the title compound (0.10 g, 23%) as an yellow-orange solid and as a mixture of amide rotamers: ¹H NMR (300 MHz, DMSO-d₆) δ 10.08-10.06 (m, 1H), 8.44-8.39 (m, 1H), 8.02-7.95 (m, 1H), 7.53-7.48 (m, 1H), 7.30-7.25 (m, 1H), 7.04-6.93 (m, 2H), 6.66-6.41 (m, 1H), 4.79-4.64 (m, 2H), 3.91-3.87 (m, 2H), 3.79 (s, 3H), 3.71-3.61 (m, 4H), 3.11-2.87 (m, 4H), 2.03-1.99 (m, 1H), 1.00-0.97 (m, 6H); MS (ESI) m/e 439 (M+H)⁺.

b) (E)-N-(2-Isobutoxy-3-methoxybenzyl)-N-methyl-3-(2-oxo-2,3,4,5-tetrahydro-1H-pyrido[2,3-e][1,4]diazepin-7-yl)acrylamide hydrochloride A stirring solution of (E)-N-(2-isobutoxy-3-methoxybenzyl)-N-methyl-3-(2-oxo-2,3,4,5-tetrahydro-1H-pyrido[2,3-e][1,4]diazepin-7-yl)acrylamide (0.108 g, 0.246 mmol) in CH₂Cl₂ (3 mL) under N₂ was treated with HCl (0.12 mL of a 2.0 M solution in diethyl ether, 24 mmol). After stirring for 18 h, the resulting solid was collected by filtration and washed with Et₂O (100 mL) and dried. The solid was dissolved in CH₂Cl₂ (2 mL) and layered with hexanes (5 mL). The resulting solids were collected by filtration, washed with Et₂O (50 mL) and dried to yield the target compound (0.052 g, 45%) as a tan solid and as a mixture of amide rotamers: ¹H NMR (300 MHz, DMSO-d₆) δ 11.09-11.07 (m, 1H), 10.03 (br s, 2H), 8.77-8.71 (m, 1H), 8.31-8.24 (m, 1H), 7.62-7.54 (m, 1H), 7.38-7.31 (m, 1H), 7.05-6.59 (m, 2H), 6.68-6.59 (m, 1H), 4.81-4.65 (m, 2H), 4.27-4.23 (m, 2H), 3.85-3.82 (m, 2H), 3.79 (s, 3H), 3.72-3.68 (m, 2H), 3.12-2.88 (m, 3H), 2.06-1.97 (m, 1H), 1.00-0.98 (m, 6H); MS (ESI) m/e 439 (M+H)⁺.

Example 295

Preparation of (E)-3-[6-Amino-5-(1-hydroxy-1-methyl-ethyl)-pyridin-3-yl]-N-methyl-N-(3-methyl-benzofuran-2-ylmethyl)-acrylamide a) 2-(2-Amino-5-bromo-pyridin-3-yl)-propan-2-ol A solution of 2-Amino-5-bromo-nicotinic acid methyl ester (2.89 g, 13.5 mmol) in anhydrous THF (50 mL) was cooled to 0° C., then treated with a slow dropwise addition of 3.0 M methyl magnesium chloride in THF (20.85 mL, 62.5 mmol) over 30 min. The resulting solution was warmed to room temperature and stirred for 20 h. The reaction was then cooled to 0° C. and quenched with saturated NH₄Cl solution (10 mL). The solution was then diluted with water (100 mL) and extracted with ethyl acetate (2×100 mL). The combined organic fractions were washed with H₂O (100 mL), brine (100 mL), dried over MgSO₄ then concentrated to give a yellow residue. This residue was subjected to flash chromatography on silica gel using 50% ethyl acetate:hexanes to give the title compound as a yellow crystalline solid. Yield: 2.74 g (95%); ¹H NMR (300 MHz, DMSO-d₆) δ 7.89 (s, 1H), 7.40 (s, 1H), 6.27 (br s, 2H), 5.49 (s, 1H), 1.46 (s, 6H); ESI MS m/z 231 (100%); 233 (100%)[C₈H₁₁N₂OBr+H]⁺ b) (E)-3-[6-Amino-5-(1-hydroxy-1-methyl-ethyl)-pyridin-3-yl]-acrylic acid tert-butyl ester A suspension of 2-(2-Amino-5-bromo-pyridin-3-yl)-propan-2-ol (200 mg, 0.86 mmol), tert-butyl acrylate (628 μL, 4.3 mmol) and (i-Pr)₂EtN (452 μL, 2.6 mmol) in DMF (10 mL) was de-oxygenated with Ar for 30 min. The mixture was treated with Pd(OAc)₂ (19.4 mg, 0.09 mmol) and P(o-tol)₃ (51.7 mg, 0.18 mmol) then heated to 110° C. for 20 h. The hot mixture was filtered through a pad of celite. The filtrate was diluted with H$_2$O (100 mL) then extracted with ethyl acetate (2×100 mL). The combined organic fractions were dried over MgSO$_4$, and subjected to flash chromatography on silica gel using 50% ethyl acetate:hexanes. The appropriate fractions were collected and concentrated to yield a yellow crystalline solid. Yield: 153 mg (64%); $^1$H NMR (300 MHz, DMSO-d$_6$) δ 8.09 (d, J=2.1 Hz, 1H), 7.65 (d, J=2.4 Hz, 1H), 7.45 (d, J=15.8 Hz, 1H), 6.69 (s, 2H), 6.32 (d, J=15.8 Hz, 1H), 5.53 (s, 1H), 1.52 (s, 6H), 1.48 (s, 9H); ESI MS m/z 279 [C$_{15}$H$_{22}$N$_2$O$_3$+H]$^+$ c) (E)-3-[6-Amino-5-(1-hydroxy-1-methyl-ethyl)-pyridin-3-yl]-acrylic acid hydrochloride A suspension of (E)-3-[6-Amino-5-(1-hydroxy-1-methyl-ethyl)-pyridin-3-yl]-acrylic acid tert-butyl ester (0.13 g, 0.47 mmol) in CH$_2$Cl$_2$ (6 mL) was treated with TFA (6 mL). After stirring at room temperature for 2 h, the solution was concentrated in vacuo. The resulting oil was treated with anhydrous HCl in dioxane (3 mL, 4.0 M) and sonicated until the oil was converted to a fine off-white solid. After stirring for 20 min, the suspension was concentrated. The solid was washed with Et$_2$O, isolated by filtration and dried under vacuum. Yield: 0.11 g (92%); $^1$H NMR (300 MHz, DMSO-d$_6$) δ 8.29 (d, J=1.5 Hz, 1H), 8.23 (br, s, 2H), 8.13 (d, J=1.8 Hz, 1H), 7.52 (d, J=16.1 Hz, 1H), 6.65 (d, J=16.1 Hz, 1H), 4.29 (s, 1H), 1.56 (s, 6H); ESI MS m/z 223 [C$_{11}$H$_{10}$N$_2$O$_4$+H]$^+$ d) (E)-3-[6-Amino-5-(1-hydroxy-1-methyl-ethyl)-pyridin-3-yl]-N-methyl-N-(3-methyl-benzofuran-2-ylmethyl)-acrylamide EDC (98 mg, 0.51 mmol) was added to a suspension of 3-[6-Amino-5-(1-hydroxy-1-methyl-ethyl)-pyridin-3-yl]-acrylic acid hydrochloride (110 mg, 0.43 mmol), HOBt (63 mg, 0.47 mmol), methyl-(3-methyl-benzofuran-2-ylmethyl)-amine (110 mg, 0.47 mmol) and (i-Pr)$_2$EtN (0.36 mL, 2.1 mmol) in DMF (7 mL). The mixture was allowed to stir overnight at 40° C. The mixture was cooled to 0° C. and diluted with H$_2$O (60 mL) with rapid stirring. Only a small amount of precipitate was formed, therefore the product was extracted using EtOAc (2×50 mL), the combined organic layers washed with brine (60 mL), dried over MgSO$_4$ and dried under high vacuum. The solid was then subjected to flash chromatography on silica gel using 10% methanol:dichloromethane. Yield: 77.6 mg (48%); $^1$H NMR (300 MHz, DMSO-d$_6$) δ 8.13 (s, 1H), 7.70 (s, 1H), 7.58 (d, J=7.9 Hz, 1H), 7.50 (d, J=7.6 Hz, 1H), 7.44 (s, 1H), 7.23-7.32 (m, 2H), 6.98 (d, J=17.7 Hz, 1H), 6.59 (s, 2H), 5.51 (s, 1H), 5.00 and 4.80 (2×s, 2H), 3.20 and 2.99 (2×s, 3H), 2.28 (s, 3H), 1.54 (s, 6H); ESI MS m/z 380.2 [C$_{22}$H$_{25}$N$_3$O$_3$+H]$^+$ Example 296

Preparation of (E)-3-[6-Amino-5-(1-hydroxy-1-methyl-ethyl)-pyridin-3-yl]-N-methyl-N-(1-methyl-1H-indol-2-ylmethyl)-acrylamide EDC (0.13 g, 0.70 mmol) was added to a suspension of (E)-3-[6-Amino-5-(1-hydroxy-1-methyl-ethyl)-pyridin-3-yl]-acrylic acid hydrochloride (0.15 g, 0.58 mmol), HOBt (0.09 g, 0.64 mmol), Methyl-(1-methyl-1H-indol-2-ylmethyl)-amine (0.11 g, 0.64 mmol) and (i-Pr)$_2$EtN (0.49 mL, 2.9 mmol) in DMF (8 mL). The mixture was allowed to stir overnight at 35° C. The mixture was cooled to 0° C. and diluted with H$_2$O (60 mL) with rapid stirring. The resulting precipitate was filtered, washed with H$_2$O (20 mL) then dried under high vacuum. The solid was then triturated with Et$_2$O, and the resultant white solid was collected, to yield 36 mg of product. An extraction on the original filtrate was done using EtOAc (2×75 mL) and the combined organic layers were washed with brine (100 mL), dried over MgSO$_4$, and concentrated in vacuo. The resulting off-white solid was subjected to flash chromatography on silica gel using 10% methanol:dichloromethane. Yield: 138 mg (79.5%); $^1$H NMR (300 MHz, DMSO-d$_6$) δ 8.14 (s, 1H), 7.68 (s, 1H), 7.52-7.40 (m, 3H), 7.15-6.98 (m, 3H), 6.58 (s, 2H), 6.41 and 6.25 (2×s, 1H), 5.49 (s, 1H), 5.04 and 4.85 (2×s, 2H), 3.69 (s, 3H), 3.10 and 2.98 (2×s, 3H), 1.53 (s, 6H); ESI MS m/z 379 [C$_{22}$H$_{26}$N$_4$O$_2$+H]$^+$ Example 297

Preparation of (E)-3-[6-Amino-5-(1-hydroxy-1-methyl-ethyl)-pyridin-3-yl]-N-methyl-N-(2-methyl-benzofuran-3-ylmethyl)-acrylamide EDC (0.13 g, 0.70 mmol) was added to a suspension of (E)-3-[6-Amino-5-(1-hydroxy-1-methyl-ethyl)-pyridin-3-yl]-acrylic acid hydrochloride (0.15 g, 0.58 mmol), HOBt (0.09 g, 0.64 mmol), methyl-(2-methyl-benzofuran-3-ylmethyl)-amine (0.11 g, 0.64 mmol) and (i-Pr)$_2$EtN (0.60 mL, 2.48 mmol) in DMF (6 mL). The mixture was allowed to stir overnight at room temperature. The mixture was cooled to 0° C. and diluted with H$_2$O (15 mL) with rapid stirring. The resulting precipitate was filtered, washed with H$_2$O (20 mL) then dried under high vacuum. The solid was then triturated with Et$_2$O, and the resultant beige solid was collected, to yield 160 mg (73%) of product. $^1$H NMR (300 MHz, DMSO-d$_6$) δ 8.14 (s, 1H), 7.67-7.47 (m, 4H), 7.26-6.99 (m, 3H), 6.58 (s, 2H), 5.49 (s, 1H), 4.80 and 4.74 (2×s, 2H), 3.04 and 2.85 (2×s, 3H), 2.52 (s, 3H), 1.53 (s, 6H); ESI MS m/z 380 [C$_{22}$H$_{25}$N$_3$O$_3$+H]$^+$ Example 298

Preparation of (E)-3-(6-amino-pyridin-3-yl)-N-(3-cyano-1H-indol-2-ylmethyl)-N-methyl-acrylamide a) 1-diethoxymethyl-1H-indole-3-carbonitrile 1H-Indole-3-carbonitrile (5.07 g, 35.7 mmol) was heated with triethylorthoformate (60 mL) in a pressure vessel at 160° C. for 3 d. Upon cooling, the solvent was evaporated and the residue was submitted to chromatography (20% ether in hexanes) to afford the title compound (7.46 g, 86%). NMR (300 MHz, CDCl$_3$, δ): 7.92 (s, 1H), 7.76 (m, 1H), 7.62 (m, 1H), 7.32 (m, 2H), 6.23 (s, 1H), 3.63 (m, 4H), 1.23 (t, J=7.2 Hz, 6H).

b) 1-diethoxymethyl-2-formyl-1H-indole-3-carbonitrile tert-Butyl lithium (18.1 mL, 31 mmol, 1.7M in pentane) was added to a THF (100 mL) solution of 1-diethoxymethyl-1H-indole-3-carbonitrile (6.83 g, 28 mmol) at −78° C. The mixture was warmed to 10° C., stirred for 30 min at this temperature, cooled to −78° C. and heated with DMF (20 mL). The mixture was warmed to 10° C., stirred for 30 min at this temperature, cooled to −78° C. and quenched with a saturated aqueous solution of NaHCO$_3$. The resulting mixture was treated with ether (200 mL); the organic layer was washed with water and brine, dried and evaporated to dryness. NMR (300 MHz, CDCl$_3$, δ): 10.24 (s, 1H), 8.10 (d, J=7.7 Hz, 1H), 7.91 (d, J=7.7 Hz, 1H), 7.53 (t, J=7.7 Hz, 1H), 7.43 (t, J=7.5 Hz, 1H), 7.34 (s, 1H), 3.80 (m, 2H), 3.52 (m, 2H), 1.26 (t, J=6.4 Hz, 1H).

c) 2-formyl-1H-indole-3-carbonitrile

Hydrochloric acid (4 mL, 20%) was added to a THF (100 mL) solution of 1-diethoxymethyl-2-formyl-1H-indole-3-carbonitrile (5.33 g, 19.57 mmol) at 0° C. The mixture was stirred at 20° C. for 41 h then treated with 5% aqueous $K_2CO_3$ (25 mL). The reaction mixture was concentrated to 50 mL and treated with methylene chloride (200 mL). The organic layer was washed with water, dried and evaporated to afford the title compound (2.81 g, 84%). $^1$H NMR (300 MHz, DMSO-$d_6$, δ): 13.20 (s, br, 1H), 10.02 (s, 1H), 7.82 (d, J=8.0 Hz, 1H), 7.63 (d, J=7.7 Hz, 1H), 7.51 (t, J=7.1 Hz, 1H), 7.37 (t, J=7.5 Hz, 1H).

d) 2-methylaminomethyl-1H-indole-3-carbonitrile

Methylamine (6.2 mL, 49.4 mmol, 33% in EtOH) was added to a MeOH (50 mL) solution of 2-formyl-1H-indole-3-carbonitrile (2.80 g, 16.5 mmol) at 0° C. Upon stirring for 5 h at 0° C., $NaBH_4$ (740 mg, 19.8 mmol) was added to the solution and the stirring was continued for 16 h. The mixture was diluted with water, extracted with methylene chloride; the organic layer was dried and evaporated. The crude residue was subjected to chromatography (1-5% MeOH in methylene chloride). The desired fractions were collected and concentrated; the residue was recrystallized from a methylene chloride/hexane mixture to afford the title compound (2.30 g, 75%). $^1$H NMR (300 MHz, DMSO-$d_6$, δ): 7.54 (m, 1H), 7.48 (m 1H), 7.21 (m, 2H), 3.93 (s, 2H), 2.31 (s, 3H). MS (ESI): m/e 186 (M+H)$^+$.

e) 3-(6-amino-pyridin-3-yl)-N-(3-cyano-1H-indol-2-ylmethyl)-N-methyl-acrylamide

EDC (250 mg, 1.3 mmol) was added to a solution of (E)-3-(6-Amino-pyridin-3-yl)-acrylic acid (172 mg, 1.05 mmol), 2-methylaminomethyl-1H-indole-3-carbonitrile (186 mg, 1.0 mmol), HOBt $H_2O$ (135 mg, 1.0 mmol) and DIPEA (510 μL, 3.0 mmol) in dry DMF (4 mL). After 3 d of stirring, the mixture was diluted with water (50 mL) at 10° C. The resulting precipitate was filtered, washed with water and dried to afford the title compound (277 mg, 84%). $^1$H NMR (300 MHz, DMSO-$d_6$, δ): 12.1 (m, 1H), 8.16 (s, 1H), 7.84 (s, 1H), 7.5 (m, 3H), 7.2 (m, 2H), 6.97 (m, 1H), 6.44 (s, 2H), 5.08 and 4.88 (rotamers, 2s, 2H), 3.22 and 2.96 (rotamers, 2s, 3H). MS (ESI): m/e 332 (M+H)$^+$.

Example 299

Preparation of (E)-N-(3-cyano-1H-indol-2-ylmethyl)-N-methyl-3-(7-oxo-5,6,7,8-tetrahydro-[1,8]naphthyridin-3-yl)-acrylamide EDC (250 mg, 1.3 mmol) was added to a solution of 3-(7-Oxo-5,6,7,8-tetrahydro-[1,8]naphthyridin-3-yl)-acrylic acid hydrochloride (267 mg, 1.05 mmol), 2-methylaminomethyl-1H-indole-3-carbonitrile (186 mg, 1.0 mmol), HOBt $H_2O$ (135 mg, 1.0 mmol) and DIPEA (510 μL, 3.0 mmol) in dry DMF (4 mL). After 3 days of stirring, the mixture was diluted with water (50 mL) at 10° C. The precipitate was filtered, washed with water and dried. The solid was stirred in MeOH (10 mL), filtered and dried to afford 239 mg (62%) title compound. $^1$H NMR (300 MHz, DMSO-$d_6$, δ): 12.28 and 12.09 (rotamers, 2s, 1H), 10.66 (s, 1H), 8.37 (s, 1H), 8.11 and 8.05 (rotamers, 2s, 1H), 7.52 (m, 3H), 7.22 (m, 3H), 5.13 and 4.90 (rotamers, 2s, 2H), 3.27 and 2.97 (rotamers, 2s, 3H), 2.92 (m, 2H), 2.55 (m, 2H). MS (ESI): nm/e 386 (M+H)$^+$.

Example 300

Preparation of (E)-N-Methyl-N-(3-methyl-benzofuran-2-ylmethyl)-3-(3-oxo-2,3,4,5-tetrahydro-1H-pyrido[2,3-e][1,4]diazepin-7-yl)-acrylamide hydrochloride a) (3-Cyanopyridin-2-ylamino)-acetic acid ethyl ester 2-Chloro-3-cyanopyridine (10.0 g, 72 mmol) was dissolved into anhydrous DMSO (200 ml). Glycine ethyl ester hydrochloride (11 g, 79 mmol) and sodium carbonate (4.5 g, 42 mmol) were added and the mixture was stirred for 10 min under argon. Potassium fluoride (4.2 g, 72 mmol) was added and the mixture was heated to 120° C. for 48 h. The mixture was cooled to room temperature and added to water (400 mL). The crude product was extracted with $CH_2Cl_2$ (4×100 mL), dried over $MgSO_4$ and concentrated to an orange solid which was purified by silica gel ($CH_2Cl_2$) to give an orange solid (7.5 g, 51%). $^1$H NMR (300 MHz, $CDCl_3$) δ 8.27 (dd, J=5.0, 2.0 Hz, 1H), 7.69 (dd, J=7.6, 2.0 Hz, 1H), 6.66 (dd, J=7.6, 5.0 Hz, 1H), 5.70 (bs, 1H), 4.21-4.28 (m, 4H), 1.29 (t, J=7.2 Hz, 3H); ESI MS m/z 206 [$C_{10}H_{11}N_3O_2$+H]$^+$.

b) (3-Formylpyridin-2-ylamino)acetic acid ethyl ester (3-Cyanopyridin-2-ylamino)acetic acid ethyl ester (2.6 g, 12.6 mmol) was dissolved into a 1:1:2 mixture of $H_2O$/$CH_3COOH$/pyridine (75 mL) under argon. Sodium hypophosphite (5.0 g) and Raney nickel (2.0 g) were added and the mixture was stirred at room temperature for 3 h. The slurry was filtered through a bed of celite and the filter cake was washed with water. Concentrated $NH_4OH$ was added to the filtrate until pH 10 was reached. The solution was extracted with ethyl acetate (4×50 mL). The organic phase was washed with brine (50 mL), dried over $MgSO_4$ and concentrated. The product was purified by silica gel chromatography ($CH_2Cl_2$/EtOAc 9:1) to give the title compound as a clear yellow oil (2.16 g, 83%). $^1$H NMR (300 MHz, $CDCl_3$) δ 9.86 (s, 1H), 8.69 (bs, 1H), 8.31 (dd, J=4.8, 1.9 Hz, 1H), 7.79 (dd, J=7.6, 2.0 Hz, 1H), 6.72 (dd, J=7.6, 4.8 Hz, 1H), 4.32 (d, J=5.5 Hz, 2H), 4.24 (q, J=7.0 Hz, 2H), 1.29 (t, J=7.2 Hz, 3H).

c) 1,2,4,5-Tetrahydro-pyrido[2,3-e][1,4]diazepin-3-one

Raney nickel (3 g) was added to anhydrous methanol (50 mL) under argon and washed with anhydrous methanol (4×50 mL). (3-Cyanopyridin-2-ylamino)-acetic acid ethyl ester (3.35 g, 16.3 mmol) was dissolved in methanol (50 mL) and added to the Raney nickel slurry. The reaction vessel was purged with argon for 10 min. Sodium methoxide solution (16.3 mmol, 3.75 mL) was added and the argon purge was repeated (5 min). The reaction flask was charged with $H_2$ and stirred at room temperature for 48 h. Dilute HCl (16.3 mL of a 1 M solution) was added and the flask was purged with argon for 30 min. The slurry was filtered through celite and the filter cake was washed with 1:1 methanol/water. The filtrate was concentrated and extracted with ethyl acetate (4×100 mL), dried over $MgSO_4$ and concentrated to afford the title compound as a beige solid (850 mg, 30%). ¹H NMR (300 MHz, DMSO-d₆) δ 8.07 (t, J=5.2 Hz, 1H), 7.82 (dd, J=4.9, 1.5 Hz, 1H), 7.21 (dd, J=7.1, 1.6 Hz, 1H), 6.69 (t, J=5.0 Hz, 1H), 6.43 (dd, J=7.2, 5.0 Hz, 1H), 4.24 (d, J=5.9 Hz, 2H), 3.91 (d, J=5.1 Hz, 2H).

d) 7-Bromo-1,2,4,5-tetrahydro-pyrido[2,3-e][1,4]diazepin-3-one 1,2,4,5-Tetrahydro-pyrido[2,3-e][1,4]diazepin-3-one (164 mg, 1.0 mmol) was dissolved into acetic acid (1 mL). Bromine (160 mg, 1.0 mmol) was added dropwise at room temperature and the solution was stirred overnight. Hexane (5 mL) was added and the orange precipitate was filtered and dried in vacuo. The title compound was isolated as an orange solid (190 mg, 78%). ¹H NMR (300 MHz, DMSO-d₆) δ 8.26 (t, J=5.7 Hz, 1H), 8.06 (d, J=2.1 Hz, 1H), 7.81 (d, J=2.1 Hz, 1H), 4.35 (d, J=5.7 Hz, 2H), 4.08 (s, 2H).

e) 3-(3-Oxo-2,3,4,5-tetrahydro-1H-pyrido[2,3-e][1,4]diazepin-7-yl)-acrylic acid tert-butyl ester 7-Bromo-1,2,4,5-tetrahydro-pyrido[2,3-e][1,4]diazepin-3-one (145 mg, 0.6 mmol) and tert-butyl acrylate (307 mg, 2.4 mmol) were dissolved in DMF (3 mL) and the reaction vessel was purged with argon for 5 min. Tri-σ-tolylphosphine (37 mg, 0.12 mmol) and palladium acetate (14 mg, 0.06 mmol) were added and the solution was degassed with argon. Diisopropylethylamine (0.23 mL, 1.32 mmol) was added and the solution was degassed with argon, sealed and heated to 90° C. for 16 h. The reaction was cooled to room temperature and filtered through a bed of celite. The filter cake was washed with ethyl acetate (50 mL) and the filtrate was washed with H₂O (5 mL) and brine (5 mL), dried over MgSO₄ and concentrated to a brown oil. The oil was subjected to silica gel chromatography (5% MeOH./CH₂Cl₂ to 10% MeOH/CH₂Cl₂) to yield the title compound as a yellow solid (96 mg, 52%). ¹H NMR (300 MHz, DMSO-d₆) δ 8.18 (t, J=5.7 Hz, 1H), 8.07 (d, J=2.1 Hz, 1H), 7.37 (d, J=15.8 Hz, 1H), 7.35 (t, J=5.3 Hz, 1H), 6.24 (d, J=15.8 Hz, 1H), 4.28 (d, J=5.7 Hz, 2H), 3.98 (d, J=5.1 Hz, 2H), 1.45 (s, 9H); ESI MS m/z 290 [$C_{15}H_{19}N_3O_3$+H]⁺.

f) 3-(3-Oxo-2,3,4,5-tetrahydro-1H-pyrido[2,3-e][1,4]diazepin-7-yl)-acrylic acid 3-(3-Oxo-2,3,4,5-tetrahydro-1H-pyrido[2,3-e][1,4]diazepin-7-yl)-acrylic acid tert-butyl ester (96 mg, 0.31 mmol) was dissolved into 1:1 CH₂Cl₂/TFA (2 mL) and stirred at room temperature for 30 min. The solvents were removed in vacuo to afford the title compound as a brown solid (44 mg, 61%) and as a mixture of amide rotamers. ¹H NMR (300 MHz, DMSO-d₆) δ 8.18 (t, J=5.7 Hz, 1H), 8.07 (d, J=2.1 Hz, 1H), 7.37 (d, J=15.8 Hz, 1H), 7.35 (t, J=5.3 Hz, 1H), 6.24 (d, J=15.8 Hz, 1H), 4.28 (d, J=5.7 Hz, 2H), 3.98 (d, J=5.1 Hz, 2H), 1.45 (s, 9H).

g) (E)-N-Methyl-N-(3-methyl-benzofuran-2-ylmethyl)-3-(3-oxo-2,3,4,5-tetrahydro-1H-pyrido[2,3-e][1,4]diazepin-7-yl)-acrylamide hydrochloride EDC (0.05 g, 0.27 mmol) was added to a suspension of 3-(3-Oxo-2,3,4,5-tetrahydro-1H-pyrido[2,3-e][1,4]diazepin-7-yl)-acrylic acid (51 mg, 0.22 mmol), HOBt (0.03 g, 0.24 mmol), methyl-(3-methyl-benzofuran-2-ylmethyl)-amine (53 mg, 0.3 mmol), and (i-Pr)₂EtN (0.22 mL, 1.32 mmol) in DMF (5 mL). The mixture was allowed to stir overnight at 40° C. The mixture was cooled to 0° C. and diluted with H₂O (15 mL) with rapid stirring. The resulting precipitate was filtered, washed with H₂O (5 mL) then dried under high vacuum. The solid was then subjected to flash chromatography on silica gel using 5% methanol:dichloromethane. To yield the product as free base fractions containing product are combined and concentrated to dryness.

To obtain the hydrochloride salt, fractions containing product were combined and treated with 1.25 mL of 2.0 M HCl in Et₂O. The resulting suspension was concentrated, triturated with Et₂O (12 mL) then filtered to give the title compound as a beige solid (59 mg, 63%). ¹H NMR (300 MHz, DMSO-d₆) δ 8.42 (bs, 1H), 8.23 (bs, 2H), 7.57-7.43 (m, 4H), 7.30-7.08 (m, 3H), 4.97-4.78 (m, 2H), 4.41-4.39 (m, 2H), 4.19 (s, 2H), 2.88-2.72 (m, 3H), 2.25 (s, 3H); ESI MS m/z 391 [$C_{22}H_{22}N_4O_3$+H]⁺.

Example 301

Preparation of (E)-N-(1,2-Dimethyl-1H-indol-3-ylmethyl)-N-methyl-3-(3-oxo-2,3,4,5-tetrahydro-1H-pyrido[2,3-e][1,4]diazepin-7-yl)-acrylamide According to the method of example 35g, 3-(3-Oxo-2,3,4,5-tetrahydro-1H-pyrido[2,3-e][1,4]diazepin-7-yl)-acrylic acid (100 mg, 0.43 mmol) and methyl-(2-methyl-1H-indol-3-ylmethyl)-amine (91 mg, 0.52 mmol) were coupled to yield the title compound as a brown solid (55 mg, 33%) and as a mixture of amide rotomers. ¹H NMR (300 MHz, DMSO-d₆) δ 11.03-10.87 (m, 1H), 8.18-8.10 (m, 2H), 7.80-7.72 (m, 1H), 7.53-7.40 (m, 2H), 7.33-7.24 (m, 2H), 7.02-6.86 (m, 2H), 4.84-4.71 (m, 2H), 4.28-4.08 (m, 2H), 3.98-3.82 (s, 2H), 2.92-2.72 (m, 3H), 2.40-2.37 (s, 3H); ESI MS m/z 390 [$C_{22}H_{23}N_5O_2$+H]⁺.

Example 302

Preparation of (E)-N-Methyl-N-(2-methyl-benzofuran-3-ylmethyl)-3-(4-methyl-3-oxo-2,3,4,5-tetrahydro-1H-pyrido[2,3-e][1,4]diazepin-7-yl)-acrylamide hydrochloride a) 7-Bromo-4-methyl-1,2,4,5-tetrahydro-pyrido[2,3-e][1,4]diazepin-3-one (3-Cyanopyridin-2-ylamino)-acetic acid ethyl ester (2.16 g, 10.4 mmol) was dissolved in anhydrous methanol (25 mL) under argon. Methylamine (33% solution in ethanol, 3.9 mL, 31.2 mmol) was added and the solution was stirred 3 h. The solvent was removed in vacuo and the residue was dissolved into anhydrous methanol (25 mL). Sodium borohydride (400 mg, 10.5 mmol) was added and the mixture was stirred overnight at room temperature. The solvent was removed in vacuo and the residue was treated with saturated NaHCO₃ solution (25 mL); the aqueous mixture was extracted with ethyl acetate (3×25 mL). The organic phase was washed with brine (10 mL), dried over MgSO₄ and concentrated to a green solid (1.2 g, 65%). The solid was dissolved in acetic acid (12 mL) and bromine (1.03 g, 6.8 mmol) was added dropwise. The reaction was stirred at room temperature for 72 h and treated with diethyl ether (50 mL). The resulting orange precipitate was collected by filtration and purified by silica gel chromatography (5% MeOH/CH₂Cl₂) to afford the title compound as a yellow solid (310 mg, 18%). ¹H NMR (300 MHz, CD₃OD) δ 7.91 (d, J=2.3 Hz, 1H), 7.52 (d, J=2.3 Hz, 1H), 4.62 (s, 2H), 4.21 (s, 2H), 3.07 (s, 3H).

b) 3-(4-Methyl-3-oxo-2,3,4,5-tetrahydro-1H-pyrido [2,3-e][1,4]diazepin-7-yl)-acrylic acid tert-butyl ester According to the procedure of Example 35e 7-bromo-4-methyl-1,2,4,5-tetrahydro-pyrido[2,3-e][1,4]diazepin-3-one (310 mg, 1.22 mmol) was converted via Heck coupling to the title compound which was isolated as a brown oil (220 mg, 60%). $^1$H NMR (300 MHz, DMSO-d$_6$) δ 8.08 (d, J=1.8 Hz, 1H), 7.77 (d, J=2.1 Hz, 1H), 7.44 (t, J=4.8 Hz, 1H), 7.37 (d, J=16.1 Hz, 1H), 6.24 (d, J=15.7 Hz, 1H), 4.54 (s, 2H), 4.09 (d, J=5.5 Hz, 2H), 2.72 (s, 3H), 1.45 (s, 9H).

c) 3-(4-Methyl-3-oxo-2,3,4,5-tetrahydro-1H-pyrido [2,3-e][1,4]diazepin-7-yl)-acrylic acid According to the procedure of Example 35f, 3-(4-methyl-3-oxo-2,3,4,5-tetrahydro-1H-pyrido[2,3-e][1,4]diazepin-7-yl)-acrylic acid tert-butyl ester (220 mg, 0.72 mmol) was converted to the title compound which was isolated as a brown solid (quantitative).

d) (E)-N-Methyl-N-(2-methyl-benzofuran-3-ylmethyl)-3-(4-methyl-3-oxo-2,3,4,5-tetrahydro-1H-pyrido[2,3-e][1,4]diazepin-7-yl)-acrylamide hydrochloride According to the method of example 35g, 3-(4-Methyl-3-oxo-2,3,4,5-tetrahydro-1H-pyrido[2,3-e][1,4]diazepin-7-yl)-acrylic acid (69 mg, 0.28 mmol) and methyl-(2-methyl-benzofuran-3-ylmethyl)amine (60 mg, 0.34 mmol) were coupled to yield the title compound as a solid (52 mg, 42%) and as a mixture of amide rotomers. $^1$H NMR (300 MHz, DMSO-d$_6$) δ8.75 (bs, 1H), 8.33-8.26 (m, 2H), 7.54-7.44 (m, 3H), 7.22-7.10 (m, 3H), 4.90-4.66 (m, 4H), 4.11 (s, 2H), 3.02-2.72 (m, 9H); ESI MS m/z 405 [C$_{23}$H$_{24}$N$_4$O$_3$+H]$^+$.

Example 303

Preparation of (E)-N-Methyl-N-(3-methyl-benzofuran-2-ylmethyl)-3-(4-methyl-3-oxo-2,3,4,5-tetrahydro-1H-pyrido[2,3-e][1,4]diazepin-7-yl)-acrylamide hydrochloride According to the method of Example 35g 3-(4-methyl-3-oxo-2,3,4,5-tetrahydro-1H-pyrido[2,3-e][1,4]diazepin-7-yl)-acrylic acid (190 mg, 0.4 mmol) and methyl-(3-methyl-benzofuran-2-ylmethyl)-amine (88 mg, 0.5 mmol) were coupled to yield the title compound as a solid (100 mg, 56%) and as a mixture of amide rotomers. $^1$H NMR (300 MHz, DMSO-d$_6$) δ8.61 (bs, 1H), 8.30-8.24 (m, 2H), 7.59-7.44 (m, 3H), 7.30-7.08 (m, 3H), 4.97-4.67 (m, 4H), 4.31 (s, 2H), 3.17-2.89 (m, 6H), 2.25 (s, 3H); ESI MS m/z 405 [C$_{23}$H$_{24}$N$_4$O$_3$+H]$^+$.

Example 304

Preparation of (E)-N-(3-Methoxy-2-propoxy-benzyl)-N-methyl-3-(4-methyl-3-oxo-2,3,4,5-tetrahydro-1H-pyrido[2,3-e][1,4]diazepin-7-yl)-acrylamide According to the method of example 35g, 3-(4-methyl-3-oxo-2,3,4,5-tetrahydro-1H-pyrido[2,3-e][1,4]diazepin-7-yl)-acrylic acid (100 mg, 0.21 mmol) and (3-methoxy-2-propoxy-benzyl)methylamine (63 mg, 0.3 mmol) were coupled to yield the title compound as a solid (43 mg, 48%) and as a mixture of amide rotomers. $^1$H NMR (300 MHz, DMSO-d$_6$) δ8.55 (bs, 1H), 8.30-8.20 (m, 2H), 7.49-7.42 (m, 1H), 7.19-7.15 (m, 1H), 7.08-6.90 (m, 2H), 6.63 (t, J=7.2 Hz, 1H), 4.76-4.63 (m, 4H), 4.30 (s, 2H), 3.90-3.84 (m, 2H), 3.78 (s, 3H), 3.09-2.83 (m, 6H), 1.62-1.72 (m, 2H), 0.99-0.95 (m, 3H); ESI MS m/z 439 [C$_{24}$H$_{30}$N$_4$O$_4$+H]$^+$.

Example 305

Preparation of (E)-N-Methyl-N-(2-methyl-1H-indol-3-ylmethyl)-3-(4-methyl-3-oxo-2,3,4,5-tetrahydro-1H-pyrido[2,3-e][1,4]diazepin-7-yl)-acrylamide According to the method of example 35g, 3-(4-methyl-3-oxo-2,3,4,5-tetrahydro-1H-pyrido[2,3-e][1,4]diazepin-7-yl)-acrylic acid (69 mg, 0.28 mmol) and methyl-(2-methyl-1H-indol-3-ylmethyl)amine (60 mg, 0.34 mmol) were coupled to yield the title compound as a white powder and as a mixture of amide rotomers (40 mg, 35%). $^1$H NMR (300 MHz, DMSO-d$_6$) δ10.86 (s, 1H), 8.12 (bs, 1H), 7.77 (bs, 1H), 7.49-7.41 (m, 2H), 7.34-7.30 (m, 1H), 7.25-7.22 (m, 1H), 7.00-6.85 (m, 3H), 4.84-4.71 (m, 2H), 4.53 (s, 2H), 4.09-4.07 (m, 2H), 2.93-2.91 (m, 6H), 2.40 (bs, 3H); ESI MS m/z 404.

Example 306

Preparation of (E)-N-(3-Methoxy-2-propoxy-benzyl)-N-methyl-3-(2-oxo-2,3,4,5-tetrahydro-1H-pyrido[2,3-e][1,4]diazepin-7-yl)-acrylamide hydrochloride According to the method of Example 35g, 3-(2-oxo-2,3,4,5-tetrahydro-1H-pyrido[2,3-e][1,4]diazepin-7-yl)-acrylic acid (152 mg, 0.5 mmol) and (3-methoxy-2-propoxy-benzyl) methylamine (125 mg, 0.6 mmol) were coupled. The resulting free base was converted to the hydrochloride salt according the method of Example 35g to yield the title compound as a solid (56 mg, 24%). $^1$H NMR (300 MHz, DMSO-d$_6$) δ11.06-11.04 (m, 1H), 10.29 (bs, 1H), 8.75-8.69 (m, 1H), 8.32-8.24 (m, 1H), 7.60-7.53 (m, 1H), 7.37-7.32 (m, 1H), 7.04-6.93 (m, 2H), 6.69-6.60 (m, 1H), 4.79-4.64 (m, 2H), 4.27-4.22 (m, 2H), 3.91-3.81 (m, 4H), 3.78 (s, 3H), 2.88-2.72 (m, 3H), 1.73-1.66 (m, 2H), 1.00-0.93 (m, 3H); ESI MS m/z 425 [C$_{23}$H$_{28}$N$_4$O$_4$+H]$^+$.

Example 307

Preparation of (E)-N-Methyl-N-(2-methyl-1H-indol-3-ylmethyl)-3-(4-methyl-2-oxo-2,3,4,5-tetrahydro-1H-pyrido[2,3-e][1,4]diazepin-7-yl)-acrylamide According to the method of example 35g, methyl-(2-methyl-1H-indol-3-ylmethyl)amine (115 mg, 0.66 mmol) and 3-(4-Methyl-2-oxo-2,3,4,5-tetrahydro-1H-pyrido[2,3-e][1,4]diazepin-7-yl)-acrylic acid (192 mg, 0.6 mmol) were coupled to give crude product. Purification by column chromatography (silica gel, CH$_2$Cl$_2$/MeOH/NH$_3$, 9:4.55:0.05) gave title compound (24 mg, 9%) as a white solid and as a mixture of amide rotomers. $^1$H NMR (300 MHz, DMSO-d$_6$) δ 8.48 (s, 1H), 7.95-8.01 (m, 2H), 7.56-7.60 (m, 2H), 7.47-7.50 (m, 1H), 7.16-7.26 (m, 2H), 6.92-7.05 (m, 2H), 3.90 (s, 2H), 3.56 (s, 2H), 3.02 (s, 2H), 2.93 (s, 3H), 2.83 (s, 3H), 2.46 (s, 3H); MS (ESI) m/e 404 (C$_{23}$H$_{25}$N$_5$O$_2$+H)$^+$.

Example 308

Preparation of (E)-3-(6-Amino-pyridin-3-yl)-N-(3-chloro-benzofuran-2-ylmethyl)-N-methyl-acrylamide hydrochloride a) 2-Carboxymethoxybenzoic acid To a solution of salicylic acid (20 g, 145 mmol) in water (200 mL) is added carefully sodium hydroxide (60 g, 1.45 mol) followed by chloroacetic acid (27 g, 290 mmol). The mixture is refluxed for 5 d, cooled to room temperature and the precipitate is filtered and dried. Trituration with hexanes yielded the title compound (6.84 g, 24%) as a pink solid. $^1$H NMR (400 MHz, DMSO-$d_6$) δ 7.65-7.66 (dd, 1H, J=8.0, 2.0 Hz), 7.45-7.47 (dd, 1H, J=8.0, 2.0 Hz), 6.97-7.05 (m, 2H), 4.77 (s, 2H).

b) 3-Chlorobenzofuran-2-carboxaldehyde

To a cooled solution of phosphorus oxychloride (19 mL, 209 mmol) in DMF (40 mL) is slowly added 2-carboxymethoxybenzoic acid (6.84 g, 35 mmol) in portions. The mixture is warmed to room temperature for 30 min and then heated to 90° C. overnight. The mixture is cooled to room temperature and poured carefully into ice water, extracted with ethyl acetate (3×50 mL), dried with sodium sulfate and concentrated in vacuo. Purification by column chromatography (silica, hexanes/ethyl acetate, 4:1) gave title compound (1.62 g, 26%) as an orange solid. $^1$H NMR (400 MHz, DMSO-$d_6$) δ 9.98 (s, 1H), 7.82-7.88 (m, 2H), 7.69-7.73 (m, 1H), 5.51-7.56 (m, 1H).

c) (3-Chloro-benzofuran-2-ylmethyl)methylamine

To a solution of 3-chlorobenzofuran-2-carboxaldehyde (1.62 g, 8.9 mmol) in methanol (50 mL) is added N-methylamine (33% solution in ethanol, 1.11 g, 35.9 mmol) and stirred overnight at room temperature. The mixture is concentrated in vacuo, re-solvated in methanol (50 mL) and cooled in an ice bath. Sodium borohydride (407 mg, 10.8 mmol) is added in portions and the mixture stirred at room temperature for 4 h. The mixture is concentrated in vacuo, re-solvated in 1.3M sodium hydroxide solution, stirred for 20 min, extracted with ethyl acetate, dried with sodium sulfate and concentrated. Purification by column chromatography (silica, $CH_2Cl_2$/MeOH, 9/1) gave title compound (1.43 g, 82%) as a colorless oil. $^1$H NMR (300 MHz, DMSO-$d_6$) δ 7.55-7.63 (m, 2H), 7.33-7.42 (m, 2H), 3.93 (s, 2H), 2.27 (s, 3H).

d) (E)-3-(6-Amino-pyridin-3-yl)-N-(3-chloro-benzofuran-2-ylmethyl)-N-methyl-acrylamide hydrochloride EDC (0.21 g, 1.08 mmol) was added to a suspension of 3-(6-amino-pyridin-3-yl)-acrylic acid (148 mg, 0.9 mmol), HOBt (134 mg, 1 mmol), (3-chloro-benzofuran-2-ylmethyl)methylamine (194 mg, 0.99 mmol), and (i-Pr)$_2$EtN (0.75 mL, 4.46 mmol) in DMF (16 mL). The mixture was stirred overnight at room temperature then cooled to 0° C. and diluted with H$_2$O (32 mL) with rapid stirring. The resulting precipitate was collected by filtration, washed with H$_2$O (32 mL) and dried under high vacuum. The residue was re-solvated in methylene chloride (5 mL) and a solution of 2M HCl in ether (2 mL) was added to precipitate the hydrogen chloride salt. The precipitate was collected by filtration and dried to give the title compound (295 mg, 89%) as a white solid and as a mixture of amide rotamers. $^1$H NMR (300 MHz, DMSO-$d_6$) δ 8.40-8.42 (m, 3H), 7.57-7.65 (m, 2H), 7.38-7.46 (m, 3H), 6.98-7.03 (m, 1H), 4.86-5.05 (rotamers, 2s, 2H), 3.20 (s, 3H); MS (ESI) m/e 342 ($C_{18}H_{16}ClN_3O_2$+H)$^+$.

Example 309

Preparation of (E)-N-(3-Chloro-benzofuran-2-ylmethyl)-N-methyl-3-(7-oxo-5,6,7,8-tetrahydro-[1,8]naphthyridin-3-yl)-acrylamide According to the method of example 43d, 3-(7-Oxo-5,6,7,8-tetrahydro-[1,8]naphthyridin-3-yl)-acrylic acid (203 mg, 0.8 mmol) and (3-chloro-benzofuran-2-ylmethyl)methylamine (172 mg, 0.88 mmol) were coupled to yield the title compound (176, 56%) as a white solid and as a mixture of amide rotamers. $^1$H NMR (300 MHz, DMSO-$d_6$) δ 10.63 (s, 1H), 8.40 (s, 1H), 8.09 (s, 1H), 7.21-7.64 (m, 6H), 4.84-5.08 (rotamers, 2s, 2H), 3.22 (s, 3H), 2.91-2.96 (m, 2H), 2.52-2.59 (m, 2H); MS (ESI) m/e 396 ($C_{21}H_{18}ClN_3O_3$+H)$^+$.

Example 310

Preparation of (E)-N-(3-Chloro-benzofuran-2-ylmethyl)-N-methyl-3-(2-oxo-2,3,4,5-tetrahydro-1H-pyrido[2,3-e][1,4]diazepin-7-yl)-acrylamide hydrochloride According to the method of example 43d, 3-(2-oxo-2,3,4,5-tetrahydro-1H-pyrido[2,3-e][1,4]diazepin-7-yl)-acrylic acid hydrochloride (152 mg, 0.5 mmol) and (3-chloro-benzofuran-2-ylmethyl)methylamine (108 mg, 0.55 mmol) were coupled to yield crude product which was triturated with methanol and ether several times and dried. The residue was re-solvated in methylene chloride (5 mL) and a solution of 2M HCl in ether (2 mL) was added to precipitate the hydrogen chloride salt. The precipitate was collected by filtration and dried to give the title compound (42 mg, 19%) as a white solid and as a mixture of amide rotamers. $^1$H NMR (400 MHz, DMSO-$d_6$) δ 10.06 (s, 1H), 8.45 (s, 1H), 8.01 (s, 1H), 7.38-7.68 (m, 6H), 4.88-5.08 (rotamers, 2s, 2H), 3.90 (s, 2H), 3.63 (s, 2H), 3.31 (s, 3H); MS (ESI) m/e 411 ($C_{21}H_{19}ClN_4O_3$+H)$^+$.

Example 311

Preparation of (E)-N-(1H-Indol-5-ylmethyl)-N-methyl-3-(7-oxo-5,6,7,8-tetrahydro-[1,8]naphthyridin-3-yl)-acrylamide According to the procedure of Example 35g (1H-indol-5-yl-methyl)-methyl-amine (257 mg, 1.62 mmol) and (E)-3-(7-oxo-5,6,7,8-tetrahydro-[1,8]naphthyridin-3yl)acrylic acid hydrochloride (312 mg, 1.23 mmol), were coupled to give crude product. Purification by column chromatography (silica gel, 5% MeOH/$CH_2Cl_2$) gave the title compound (172 mg, 39%) as a white solid and a mixture of amide rotamers: $^1$H NMR (300 MHz, DMSO-$d_6$) δ 11.06-11.05 (m, 1H), 10.63-10.61 (m, 1H), 8.36-8.34 (m, 1H), 8.06 (s, 1H), 7.56-7.19 (m, 5H), 7.02-6.96 (m, 1H), 6.38 (s, 1H), 4.84-4.65 (m, 2H), 3.06-2.85 (m, 5H), 2.55-2.52 (m, 2H); ESI MS m/e 361 [$C_{21}H_{20}N_4O_2$+H]$^+$.

Example 311

Preparation of (E)-N-Methyl-N-(1-methyl-1H-indol-5-ylmethyl)-3-(7-oxo-5,6,7,8-tetrahydro-[1,8]naphthyridin-3-yl)-acrylamide a) Methyl-(1-methyl-1H-indol-5-ylmethyl)-amine 1-Methyl-1H-indole-5-carbaldehyde (338 mg, 2.13 mmol) was dissolved in anhydrous methanol (10 ml). Methylamine (0.80 ml of 33% solution in ethanol, 6.43 mmol) was added and the reaction was stirred for 3 h. The solution was concentrated to a brown oil and then dissolved in anhydrous methanol (10 ml). Sodium borohydride (83.0 mg, 2.19 mmol) was added and the mixture was stirred overnight at room temperature. Water (4 ml) was added and the solution was concentrated. Sodium hydroxide (8 ml, 1N) was added and the aqueous layer was extracted with ethyl acetate (3×20 ml). Combined organic layers were dried over $MgSO_4$, filtered and concentrated to afford methyl-(1-methyl-1H-indol-5-ylmethyl)-amine (167 mg, 45%) as an orange oil: $^1H$ NMR (400 MHz, DMSO-$d_6$) δ 7.44 (s, 1H), 7.34 (d, J=8.0 Hz, 1H), 7.261 (d, J=3.2 Hz, 1H), 7.11 (d, J=12.0 Hz, 1H), 6.345 (d, J=4.0 Hz, 1H), 3.75 (s, 3H), 3.70 (s, 2H), 2.25 (s, 3H).

b) Preparation of N-Methyl-N-(1-methyl-1H-indol-5-ylmethyl)-3-(7-oxo-5,6,7,8-tetrahydro-[1,8]naphthyridin-3-yl)-acrylamide According to the procedure of Example 35g, (methyl-(1-methyl-1H-indol-5-ylmethyl)-amine (155 mg, 0.89 mmol) and (E)-3-(7-oxo-5,6,7,8-tetrahydro-[1,8]naphthyridin-3yl) acrylic acid hydrochloride (229 mg, 0.90 mmol), were coupled to give crude product. Purification by column chromatography (silica gel, 5% MeOH/$CH_2Cl_2$) gave the title compound (217 mg, 65%) as a red solid and a mixture of amide rotamers: $^1H$ NMR (400 MHz, DMSO-$d_6$) δ 10.63-10.62 (m, 1H), 8.36-8.33 (m, 1H), 8.06 (s, 1H), 7.56-7.51 (m, 1H), 7.43-7.19 (m, 4H), 7.08-7.01 (m, 1H), 6.38 (s, 1H), 4.85-4.67 (m, 2H), 3.76 (s, 3H), 3.06-2.85 (m, 5H), 2.54-2.52 (m, 2H); ESI MS m/z 375 $[C_{22}H_{22}N_4O_2+H]^+$.

Example 312

Preparation of (E)-N-(3-tert-Butyl-2-propoxy-benzyl)-N-methyl-3-(7-oxo-5,6,7,8-tetrahydro-[1,8]naphthyridin-3-yl)-acrylamide a) 3-tert-Butyl-2-propoxy-benzaldehyde To a solution of 3-tert-butyl-2-hydroxy-benzaldehyde (2.04 g, 11.5 mmol) and $K_2CO_3$ (7.91 g, 57.3 mmol) in anhydrous DMF (23 ml) was added 1-iodopropane (2.34 ml, 24.0 mmol). The reaction mixture was left to stir for 48 h at room temperature. The reaction mixture was diluted with water (100 ml) and extracted with ethyl acetate (3×50 ml). Combined organic layers were washed with water (50 ml) and brine (50 ml), dried over $MgSO_4$, filtered and the solvent was removed in vacuo to give a yellow oil. Purification by column chromatography (silica gel, gradient elution of hexanes to 20% EtOAc/hxanes) gave 3-tert-butyl-2-propoxy-benzaldehyde (2.55 g, 99%) as a yellow oil: $^1H$ NMR (400 MHz, DMSO-$d_6$) δ 10.21 (s, 1H), 7.62 (s, 1H), 7.61 (s, 1H), 7.19 (t J=8.0, 1H), 3.89 (t, J=8.0 Hz, 2H), 1.91-1.82 (m, 2H), 1.37 (s, 9H), 1.03 (t, J=8.0 Hz, 3H).

b) (3-tert-Butyl-2-propoxy-benzyl)-methyl-amine 3-tert-Butyl-2-propoxy-benzaldehyde (1.15 g, 5.21 mmol) was dissolved in anhydrous methanol (25 ml). Methylamine (2.00 ml of 33% solution in ethanol, 16.1 mmol) was added and the reaction was stirred for 3 h. The solution was concentrated to a yellow oil and then dissolved in anhydrous methanol (25 ml). Sodium borohydride (198 mg, 5.23 mmol) was added and the mixture was stirred overnight at room temperature. Water (10 ml) was added and the solution was concentrated. Sodium hydroxide (30 ml, 1N) was added and the aqueous layer was extracted with ethyl acetate (3×50 ml). Combined organic layers were dried over $MgSO_4$, filtered and concentrated to afford (3-tert-butyl-2-propoxy-benzyl)-methyl-amine (1.18 g, 96%) as a clear oil: $^1H$ NMR (400 MHz, DMSO-$d_6$) δ 7.28 (d, J=8.0 Hz, 1H), 7.15 (d, J=8.0 Hz, 1H), 6.97 (y J=8.0, y1H), 3.79 (t, J=4.0 Hz, 2H), 3.61 (s, 2H), 2.28 (s, 3H), 1.80-1.75 (m, 2H), 1.33 (s, 9H), 1.03 (t, J=8.0 Hz, 3H).

c) N-(3-tert-Butyl-2-propoxy-benzyl)-N-methyl-3-(7-oxo-5,6,7,8-tetrahydro-[1,8]naphthyridin-3-yl)-acrylamide According to the procedure of Example 35g, 3-tert-butyl-2-propoxy-benzyl)-methyl-amine (368 mg, 1.56 mmol) and (E)-3-(7-oxo-5,6,7,8-tetrahydro-[1,8]naphthyridin-3yl) acrylic acid hydrochloride (402 mg, 1.58 mmol), were coupled to give crude product. Purification by column chromatography (silica gel, gradient elution of 50% EtOAc/Hexane to EtOAc) gave the title compound as an off-white solid (519 mg, 76%) as a mixture of amide rotomers: $^1H$ NMR (300 MHz, DMSO-$d_6$) δ 10.65-10.64 (m, 1H), 8.38-8.31 (m, 1H), 8.10-7.93 (m, 1H), 7.55-7.48 (m, 1H), 7.29-7.22 (m, 2H), 7.07-6.90 (m, 2H), 4.80-4.69 (m, 2H), 3.81-3.73 (m, 2H), 3.06-2.85 (m, 5H), 2.57-2.54 (m, 2H), 1.90-1.79 (m, 2H), 1.37 (s, 9H), 1.09-1.02 (m, 3H); ESI MS m/e 436 $[C_{26}H_{33}N_3O_3+H]^+$.

Example 313

Preparation of (E)-N-Methyl-N-(1-methyl-1H-indol-6-ylmethyl)-3-(7-oxo-5,6,7,8-tetrahydro-[1,8]naphthyridin-3-yl)-acrylamide a) 1-Methyl-1H-indole-6-carbaldehyde Dess-Martin periodane (2.56 g, 6.04 mmol) was dissolved into anhydrous $CH_2Cl_2$ (25 ml). (1H-Indol-6-yl)-methanol (883 mg, 6.04 mmol) in anhydrous $CH_2Cl_2$ (20 ml) was added and the mixture was stirred for 1 h. Aqueous sodium hydroxide (12 ml of 1N solution) was added and the reaction was stirred for 30 min. The organic layer was separated and washed with water (10 ml), brine (10 ml), dried over $MgSO_4$, filtered and concentrated to a thick brown oil. Purification by column chromatography (silica gel, gradient elution of 2% MeOH/$CH_2Cl_2$ to 5% MeOH/$CH_2Cl_2$) gave 1H-indole-6-carbaldehyde (212 mg, 24%) as a brown solid: $^1H$ NMR (300 MHz, DMSO-$d_6$) δ 11.67 (bs, 1H), 9.99 (s, 1H), 7.97 (s, 1H), 7.70-7.65 (m, 2H), 7.54-7.50 (m, 1H), 6.59-5.54 (m, 1H).

b) 1-Methyl-1H-indole-6-carbaldehyde

1-Methyl-1H-indole-6-carbaldehyde (146 mg, 0.91 mmol) was dissolved in anhydrous methanol (4 ml). Methylamine (0.35 ml of 33% solution in ethanol, 2.81 mmol) was added and the reaction was stirred for 3 h. The solution was concentrated to a yellow oil and then dissolved in anhydrous methanol (4 ml). Sodium borohydride (34.9 mg, 0.92 mmol) was added and the mixture was stirred overnight at room temperature. Water (10 ml) was added and the solution was concentrated. Sodium hydroxide (10 ml, 1N) was added and the aqueous layer was extracted with ethyl acetate (3×20 ml). Combined organic layers were dried over MgSO$_4$, filtered and concentrated to afford methyl-(1-methyl-1H-indol-6-yl-methyl)-amine (139 mg, 87%) as a yellow oil: $^1$H NMR (400 MHz, DMSO-d$_6$) δ 7.44 (d, J=8.0 Hz, 1H), 7.34 (s, 1H), 7.240 (d, J=3.6, 1H), 6.98 (d, J=8.0 Hz, 1H), 6.345 (d, J=4.0 Hz, 1H)), 3.75 (s, 3H), 3.73 (s, 2H), 2.27 (s, 3H).

c) Preparation of N-Methyl-N-(1-methyl-1H-indol-6-ylmethyl)-3-(7-oxo-5,6,7,8-tetrahydro-[1,8]naphthyridin-3-yl)-acrylamide According to the procedure of Example 35g methyl-(1-methyl-1H-indol-6-ylmethyl)-amine (129 mg, 0.74 mmol) and (E)-3-(7-oxo-5,6,7,8-tetrahydro-[1,8]naphthyridin-3yl) acrylic acid hydrochloride (190 mg, 0.75 mmol), were coupled to give crude product. Purification by column chromatography (silica gel, 5% MeOH/CH$_2$Cl$_2$) gave the title compound (180 mg, 65%) as a pink solid and a mixture of amide rotomers: $^1$H NMR (400 MHz, DMSO-d$_6$) δ 10.64-10.62 (m, 1H), 8.36-8.33 (m, 1H), 8.07-8.06 (m, 1H), 7.55-7.47 (m, 2H), 7.39-7.21 (m, 3H), 6.95-6.88 (m, 1H), 6.38-6.37 (m, 1H), 4.89-4.71 (m, 2H), 3.76-3.74 (m, 3H), 3.08-2.85 (m, 5H), 2.54-2.52 (m, 2H); ESI MS m/z 375 [C$_{22}$H$_{22}$N$_4$O$_2$+H]$^+$.

Example 314

Preparation of (E)-N-(3,4-Dihydro-2H-benzo[b][1,4]dioxepin-6-ylmethyl)-N-methyl-3-(7-oxo-5,6,7,8-tetrahydro-[1,8]naphthyridin-3-yl)-acrylamide a) (3,4-Dihydro-2H-benzo[b][1,4]dioxepin-6-ylmethyl)-methyl-amine 3,4-Dihydro-2H-benzo[b][1,4]dioxepine-6-carbaldehyde (269 mg, 1.51 mmol) was dissolved in anhydrous methanol (7 ml). Methylamine (0.60 ml of 33% solution in ethanol, 4.82 mmol) was added and the reaction was stirred for 3 hours. The solution was concentrated to a yellow oil and then dissolved in anhydrous methanol (7 ml). Sodium borohydride (58.3 mg, 1.54 mmol) was added and the mixture was stirred overnight at room temperature. Water (10 ml) was added and the solution was concentrated. Sodium hydroxide (20 ml, 1N) was added and the aqueous layer was extracted with ethyl acetate (3×40 ml). Combined organic layers were dried over MgSO$_4$, filtered and concentrated to afford (3,4-dihydro-2H-benzo[b][1,4]dioxepin-6-ylmethyl)-methyl-amine (251 mg, 86%) as a brown oil: $^1$H NMR (400 MHz, DMSO-d$_6$) δ 6.96 (dd, J=8.0, 4.0 Hz, 1H), 6.88-6.82 (m, 2H), 4.10-4.05 (m, 4H), 3.60 (s, 2H), 2.25 (s, 3H), 2.10-2.06 (m, 2H).

b) N-(3,4-Dihydro-2H-benzo[b][1,4]dioxepin-6-ylmethyl)-N-methyl-3-(7-oxo-5,6,7,8-tetrahydro-[1,8]naphthyridin-3-yl)-acrylamide According to the procedure of Example 35g (3,4-dihydro-2H-benzo[b][1,4]dioxepin-6-ylmethyl)-methyl-amine (239 mg, 1.24 mmol) and (E)-3-(7-oxo-5,6,7,8-tetrahydro-[1,8]naphthyridin-3yl)acrylic acid hydrochloride (318 mg, 1.25 mmol), were coupled to give crude product. Purification by column chromatography (silica gel, 5% MeOH/CH$_2$Cl$_2$) gave the title compound (385 mg, 79%) as a yellow solid and a mixture of amide rotomers: $^1$H NMR (400 MHz, DMSO-d$_6$) δ 10.66-10.63 (m, 1H), 8.36-8.32 (m, 1H), 8.07-8.03 (m, 1H), 7.51-7.46 (m, 1H), 7.30-721 (m, 1H), 6.93-6.88 (m, 2H), 6.78-6.76 (m, 1H), 4.76-4.59 (m, 2H), 4.13-4.06 (m, 4H), 3.11-2.84 (m, 5H), 2.54-2.52 (m, 2H), 2.11-2.07 (m, 2H); ESI MS m/e 394 [C$_{22}$H$_{23}$N$_3$O$_4$+H]$^+$.

Example 315

Preparation of (E)-N-(2,2-Dimethyl-2,3-dihydro-benzofuran-7-ylmethyl)-N-methyl-3-(7-oxo-5,6,7,8-tetrahydro-[1,8]naphthyridin-3-yl)-acrylamide a) (2,2-Dimethyl-2,3-dihydro-benzofuran-7-ylmethyl)-methyl-amine 2,2-Dimethyl-2,3-dihydro-benzofuran-7-carbaldehyde (281 mg, 1.59 mmol) was dissolved in anhydrous methanol (7 ml). Methylamine (0.63 ml of 33% solution in ethanol, 4.82 mmol) was added and the reaction was stirred for 3 h. The solution was concentrated to a yellow oil and then dissolved in anhydrous methanol (7 ml). Sodium borohydride (61.5 mg, 1.63 mmol) was added and the mixture was stirred overnight at room temperature. Water (5 ml) was added and the solution was concentrated. Sodium hydroxide (20 ml, 1N) was added and the aqueous layer was extracted with ethyl acetate (3×40 ml). Combined organic layers were dried over MgSO$_4$, filtered and concentrated to afford (2,2-Dimethyl-2,3-dihydro-benzofuran-7-ylmethyl)-methyl-amine (303 mg, 99%) as a yellow oil: $^1$H NMR (300 MHz, DMSO-d$_6$) δ 7.06-7.02 (m, 2H), 6.76-6.71 (m, 1H), 3.52 (s, 2H), 2.97 (s, 2H), 2.24 (s, 3H), 1.39 (s, 6H).

b) N-(2,2-Dimethyl-2,3-dihydro-benzofuran-7-ylmethyl)-N-methyl-3-(7-oxo-5,6,7,8-tetrahydro-[1,8]naphthyridin-3-yl)-acrylamide According to the procedure of Example 35g, (2,2-dimethyl-2,3-dihydro-benzofuran-7-ylmethyl)-methyl-amine (284 mg, 1.48 mmol) and (E)-3-(7-oxo-5,6,7,8-tetrahydro-[1,8]naphthyridin-3yl)acrylic acid hydrochloride (382 mg, 1.50 mmol), were coupled to give crude product. Purification by column chromatography (silica gel, 5% MeOH/CH$_2$Cl$_2$) gave the title compound (422 mg, 73%) as an orange solid and a mixture of amide rotomers. $^1$H NMR (300 MHz, DMSO-d$_6$) δ 10.65-10.64 (m, 1H), 8.35-8.34 (m, 1H), 8.06-8.01 (m, 1H), 7.51-7.44 (m, 1H), 7.37-7.07 (m, 2H), 6.92-6.89 (m, 1H), 6.81-6.73 (m, 1H), 4.65-4.49 (m, 2H), 3.11-2.87 (m, 7H), 2.55-2.53 (m, 2H), 1.42-1.39 (m, 6H); ESI MS m/e 392 [C$_{23}$H$_{25}$N$_3$O$_3$+H]$^+$.

Example 316

Preparation of (E)-N-(1H-Indol-4-ylmethyl)-N-methyl-3-(7-oxo-5,6,7,8-tetrahydro-[1,8]naphthyridin-3-yl)-acrylamide a) (1H-Indol-4-yl)-methanol 1H-Indole-6-carboxylic acid (1.00 g, 6.23 mmol) was dissolved into anhydrous THF (20 ml) under argon. The solution was cooled in an ice bath and lithium aluminum hydride (13.1 ml of 1M solution in THF, 13.1 mmol) was added dropwise. The reaction mixture was allowed to warm to room temperature and stir overnight. The reaction mixture was cooled to 0° C. and ethyl acetate (10 ml) was carefully added, followed by methanol (5 ml) and water (5 ml). The mixture was stirred for 30 min and filtered through celite. The solution was concentrated and dissolved in ethyl acetate (200 ml) and washed with brine (2×100 ml), dried over MgSO$_4$, filtered and concentrated to yield (1H-indol-4-yl)-methanol (471 mg, 52%) as an orange oil: $^1$H NMR (400 MHz, DMSO-d$_6$) δ 11.04 (bs, 1H), 7.30-7.26 (m, 2H), 7.05-6.98 (m, 2H), 6.48-6.47 (m, 1H), 5.04 (t, J=4.0 Hz, 1H), 4.74 (d, J=8.0 Hz, 2H).

b) 1H-Indole-4-carbaldehyde

Dess-Martin periodane (1.04 g, 2.46 mmol) was dissolved into anhydrous CH$_2$Cl$_2$ (10 ml). (1H-Indol-4-yl)-methanol (449 mg, 3.07 mmol) in anhydrous CH$_2$Cl$_2$ (10 ml) was added and the mixture was stirred for 1 h. Sodium hydroxide (50 ml of 1N solution) and ether (50 ml) were added and the reaction was stirred for 30 min. The organic layer was separated and washed with water (10 ml), brine (10 ml), dried over MgSO$_4$, filtered and concentrated to a thick brown oil. Purification by column chromatography (silica gel, gradient elution of 2% MeOH/CH$_2$Cl$_2$ to 5% MeOH/CH$_2$Cl$_2$) gave 1H-indole-4-carbaldehyde (235 mg, 53%) as a yellow solid: $^1$H NMR (300 MHz, DMSO-d$_6$) δ 11.59 (bs, 1H), 10.18 (s, 1H), 7.78-7.75 (m, 1H), 7.66-7.60 (m, 2H), 7.33-7.28 (m, 1H), 7.08 (d, J=3.0 Hz, 1H).

c) (1H-Indol-4-ylmethyl)-methyl-amine

1H-Indole-4-carbaldehyde (219 mg, 1.51 mmol) was dissolved in anhydrous methanol (7 ml). Methylamine (0.60 ml of 33% solution in ethanol, 4.82 mmol) was added and the reaction was stirred for 3 h. The solution was concentrated to an orange solid and then dissolved in anhydrous methanol (7 ml). Sodium borohydride (58.0 mg, 1.53 mmol) was added and the mixture was stirred overnight at room temperature. Water (10 ml) was added and the solution was concentrated. Sodium hydroxide (10 ml, 1N) was added and the aqueous layer was extracted with ethyl acetate (3×20 ml). Combined organic layers were dried over MgSO$_4$, filtered and concentrated to afford (1H-indol-4-ylmethyl)-methyl-amine (229 mg, 94%) as a brown solid: $^1$H NMR (400 MHz, DMSO-d$_6$) δ 11.03 (bs, 1H), 7.29-7.24 (m, 2H), 7.03-6.93 (m, 2H), 6.51-6.50 (m, 1H), 3.88 (s, 2H), 2.30 (s, 3H).

d) N-(1H-Indol-4-ylmethyl)-N-methyl-3-(7-oxo-5,6, 7,8-tetrahydro-[1,8]naphthyridin-3-yl)-acrylamide According to the procedure of Example 35g, (1H-indol-4-ylmethyl)-methyl-amine (223 mg, 1.39 mmol) and (E)-3-(7-oxo-5,6,7,8-tetrahydro-[1,8]naphthyridin-3yl)acrylic acid hydrochloride (359 mg, 1.41 mmol), were coupled to give crude product. Purification by column chromatography gave the title compound (369 mg, 73%) as a pink solid and a mixture of amide rotomers: $^1$H NMR (400 MHz, DMSO-d$_6$) δ 11.20-11.14 (m, 1H), 10.65-10.62 (m, 1H), 8.38-8.32 (m, 1H), 8.08-7.99 (m, 1H), 7.59-7.53 (m, 1H), 7.37-7.21 (m, 3H), 7.09-7.03 (m, 1H), 6.89-6.76 (m, 1H), 6.51 (s, 1H), 5.06-4.88 (m, 2H), 3.04-2.83 (m, 5H), 2.56-2.52 (m, 2H); ESI MS m/z 361 [C$_{21}$H$_{20}$N$_4$O$_2$+H]$^+$.

Example 317

Preparation of (E)-3-(2,2-Dimethyl-3-oxo-3,4-dihydro-2H-pyrido[3,2-b][1,4]oxazin-7-yl)-N-methyl-N-(1-methyl-1H-indol-2-ylmethyl)-acrylamide According to the procedure of Example 43d, methyl-(1-methyl-1H-indol-2-ylmethyl)-amine (124 mg, 0.71 mmol) and 3-(2,2-dimethyl-3-oxo-3,4-dihydro-2H-pyrido[3,2-b][1, 4]oxazin-7-yl)-acrylic acid (160 mg, 0.64 mmol), were coupled to yield the title compound (167 mg, 64%) as a white solid and as a mixture of amide rotomers. $^1$H NMR (400 MHz, DMSO-d$_6$) δ 11.03-11.04 (m, 1H), 8.15-8.20 (m, 1H), 7.89-7.94 (m, 1H), 7.41-7.56 (m, 3H), 7.39-7.41 (m, 1H), 7.00-7.12 (m, 1H), 6.14-6.99 (m, 1H), 4.87-5.05 (m, 2H), 3.68-3.72 (m, 3H), 2.99-3.10 (m, 3H), 1.39-1.44 (m, 6H); MS (ESI) m/e 405 (C$_{23}$H$_{24}$N$_4$O$_3$+H)$^+$.

Example 318

Preparation of (E)-3-(2,2-Dimethyl-3-oxo-3,4-dihydro-2H-pyrido[3,2-b][1,4]oxazin-7-yl)-N-methyl-N-(2-methyl-benzofuran-3-ylmethyl)-acrylamide According to the procedure of Example 43d, methyl-(2-methyl-benzofuran-3-ylmethyl)-amine (124 mg, 0.71 mmol) and 3-(2,2-dimethyl-3-oxo-3,4-dihydro-2H-pyrido[3,2-b][1, 4]oxazin-7-yl)-acrylic acid (160 mg, 0.64 mmol) were coupled to yield the title compound (211 mg, 81%) as a white solid and as a mixture of amide rotomers. $^1$H NMR (400 MHz, DMSO-d$_6$) δ 11.39 (is, 1H), 8.20 (1s, 1H), 7.92 (is, 1H), 7.54-7.58 (m, 2H), 7.46-7.48 (m, 1H), 7.17-7.25 (m, 3H), 4.72-4.93 (m, 2H), 3.32 (s, 3H), 3.04 (s, 2H), 2.47 (s, 3H), 1.43 (1s, 6H); MS (ESI) m/e 406 (C$_{23}$H$_{23}$N$_3$O$_4$+H)$^+$.

Example 319

Preparation of (E)-3-(2,2-Dimethyl-3-oxo-3,4-dihydro-2H-pyrido[3,2-b][1,4]oxazin-7-yl)-N-(3-methoxy-2-propoxy-benzyl)-N-methyl-acrylamide To a solution of (3-methoxy-2-propoxy-benzyl)-methyl-amine (115 mg, 0.55 mmol) in DMF (5 mL) were added in sequential order 3-(2,2-dimethyl-3-oxo-3,4-dihydro-2H-pyrido[3,2-b][1,4]oxazin-7-yl)-acrylic acid (181 mg, 0.5 mmol), 1-hydroxybenzotriazole (74 mg, 0.55 mmol), diisopropylethylamine (261 uL, 1.5 mmol), and N-(3-dimethylaminopropyl)-N'-ethylcarbodiimide (110 mg, 0.55 mmol). The reaction was placed in a microwave at 130° C. for 5 min. The solution was cooled in an ice bath and water was added with rapid stirring. The precipitate was filtered, dried and triturated with diethyl ether to yield the title compound (164 mg, 75%) as a white solid and as a mixture of amide rotomers: $^1$H NMR (400 MHz, DMSO-d$_6$) δ 11.37-11.39 (m, 1H), 8.14-8.18 (m, 1H), 7.87-7.93 (m, 1H), 7.47-7.53 (m, 1H), 7.27-7.34 (m, 1H), 6.92-7.09 (m, 3H), 6.60-6.66 (m, 1H), 4.62-4.79 (m, 2H), 3.84-3.90 (m, 2H), 3.78 (s, 3H), 2.88-3.09 (m, 3H), 1.70-1.74 (m, 2H), 1.40-1.49 (m 6H), 0.93-0.99 (m, 3H); MS (ESI) m/e 440 (C$_{24}$H$_{29}$N$_3$O$_5$+H)$^+$.

Example 320

Preparation of (E)-3-(3,4-Dihydro-2H-pyrido[3,2-b][1,4]oxazin-7-yl)-N-methyl-N-(2-methyl-benzofuran-3-ylmethyl)-acrylamide hydrochloride To a solution of methyl-(2-methyl-benzofuran-3-ylmethyl)-amine (159 mg, 0.91 mmol) in DMF (5 mL) were added in sequential order 3-(3,4-dihydro-2H-pyrido[3,2-b][1,4]oxazin-7-yl)-acrylic acid hydrochloride (171 mg, 0.83 mmol), 1-hydroxybenzotriazole (127 mg, 0.91 mmol), diisopropylethylamine (289 uL, 1.06 mmol), and N-(3-dimethylaminopropyl)-N'-ethylcarbodiimide (182 mg, 0.91 mmol). The mixture was stirred at room temperature overnight, cooled in an ice bath and treated with water under rapid stirring. The resulting precipitate was collected by filtration, dried and triturated with diethyl ether to yield a pale yellow solid. The solid was re-solvated in methylene chloride (5 mL) and a solution of 2M HCl in ether (2 mL) was added to precipitate an orange solid. The precipitated solid was collected by filtration, dried and triturated with diethyl ether to yield the title compound (118 mg, 39%) as a mixture of amide rotamers. $^1$H NMR (400 MHz, DMSO-d6) δ 8.76 (1s, 1H), 7.93-7.97 (m, 1H), 7.47-7.59 (m, 3H), 7.12-7.27 (m, 3H), 4.73-4.94 (m, 2H), 4.27 (m, 2H), 3.59 (m, 5H), 3.04 (s, 3H), 2.52 (s, 3H); MS (ESI) m/e 364 $(C_{21}H_{21}N_3O_3+H)^+$.

Example 321

Preparation of (E)-N-Methyl-N-(2-methyl-benzofuran-3-ylmethyl)-3-(3-oxo-3,4-dihydro-2H-pyrido[3,2-b][1,4]oxazin-7-yl)-acrylamide To a solution of methyl-(2-methyl-benzofuran-3-ylmethyl)-amine (152 mg, 0.87 mmol) in DMF (5 mL) were added in sequential order 3-(3-Oxo-3,4-dihydro-2H-pyrido[3,2-b][1,4]oxazin-7-yl)-acrylic acid (175 mg, 0.79 mmol), 1-hydroxybenzotriazole (121 mg, 0.87 mmol), diisopropylethylamine (412 uL, 2.37 mmol), and N-(3-dimethylaminopropyl)-N'-ethylcarbodiimide (174 mg, 0.87 mmol). The mixture was stirred at room temperature overnight, cooled in an ice bath and treated with water under rapid stirring. The precipitated product was filtered and dried, triturated with diethyl ether to yield the title compound (125 mg, 42%) as a light brown solid and as a mixture of amide rotamers. $^1$H NMR (400 MHz, DMSO-d6) δ 11.46 (s, 1H), 8.21 (s, 1H), 7.89 (s, 1H), 7.50-7.59 (m, 3H), 7.19-7.26 (m, 3H), 4.74 (s, 2H), 4.70 (s, 2H), 3.06 (s, 3H), 2.52 (s, 3H); MS (ESI) m/e 378 $(C_{21}H_{19}N_3O_4+H)^+$.

Example 322

Preparation of (E)-N-Methyl-N-(3-methyl-benzofuran-2-ylmethyl)-3-(3-oxo-3,4-dihydro-2H-pyrido[3,2-b][1,4]oxazin-7-yl)-acrylamide To a solution of methyl-(3-methyl-benzofuran-2-ylmethyl)-amine (152 mg, 0.87 mmol) in DMF (5 mL) were added in sequential order 3-(3-Oxo-3,4-dihydro-2H-pyrido[3,2-b][1,4]oxazin-7-yl)-acrylic acid (175 mg, 0.79 mmol), 1-hydroxybenzotriazole (121 mg, 0.87 mmol), diisopropylethylamine (412 uL, 2.37 mmol), and N-(3-dimethylaminopropyl)-N'-ethylcarbodiimide (174 mg, 0.87 mmol). The mixture was stirred at room temperature overnight, cooled in an ice bath and treated with water under rapid stirring. The precipitated product was filtered and dried, triturated with diethyl ether to yield the title compound (150 mg, 50%) as a light brown solid and as a mixtures of amide rotamers. $^1$H NMR (400 MHz, DMSO-d6) δ 11.46 (s, 1H), 8.19 (s, 1H), 7.89 (s, 1H), 7.5-7.59 (m, 3H), 7.24-7.32 (m, 3H), 4.8-5.02 (m, 2H), 4.70 (s, 2H), 2.95-3.19 (m, 3H), 2.28 (s, 3H); MS (ESI) m/e 378 $(C_{21}H_{19}N_3O_4+H)^+$.

Example 323

Preparation of (E)-N-(3-Chloro-benzofuran-2-ylmethyl)-3-(2,2-dimethyl-3-oxo-3,4-dihydro-2H-pyrido[3,2-b][1,4]oxazin-7-yl)-N-methyl-acrylamide To a solution of (3-chloro-benzofuran-2-ylmethyl)-methyl-amine (151 mg, 0.77 mmol) in DMF (5 mL) were added in sequential order 3-(2,2-dimethyl-3-oxo-3,4-dihydro-2H-pyrido[3,2-b][1,4]oxazin-7-yl)-acrylic acid (174 mg, 0.7 mmol), 1-hydroxybenzotriazole (107 mg, 0.77 mmol), diisopropylethylamine (366 uL, 2.1 mmol), and N-(3-dimethylaminopropyl)-N'-ethylcarbodiimide (154 mg, 0.77 mmol). The mixture was stirred at room temperature overnight, cooled in an ice bath and treated with water under rapid stirring. The precipitated product was filtered and dried, triturated with diethyl ether to yield the title compound (218 mg, 73%) as a light yellow solid. $^1$H NMR (400 MHz, DMSO-d6) δ 11.43 (s, 1H), 8.21 (s, 1H), 7.96 (s, 1H), 7.53-7.67 (m, 3H), 7.40-7.44 (m, 3H), 4.89-5.11 (m, 2H), 2.97-3.23 (m, 3H), 1.46 (s, 6H); MS (ESI) m/e 426 $(C_{22}H_{20}ClN_3O_4+H)^+$.

Example 324

Preparation of (E)-N-methyl-(1H-indol-2-ylmethyl)-3-(7-oxo-5,6,7,8-tetrahydro-[1,8]napthyridin-3-yl) acrylamide a) Preparation of 3-methyl-2-(methylaminomethyl)indole Methylamine (0.34 mL, 8.4 mmol, 33% in ethanol) was added to a solution of 3-methylindole-2-carboxaldehyde (447 mg, 2.8 mmol) in methanol (10 mL) and stirred for 5 hours. Sodium borohydride (104 mg, 2.8 mmol) was slowly added at 0° C. The resultant mixture was warmed to room temperature and stirred overnight. Water (2 mL) was added slowly at 0° C. and the mixture was evaporated to a paste. The paste was partitioned between water (2 mL) and dichloromethane (15 mL). The layers were separated and the aqueous layer was extracted with dichloromethane (2×15 mL). The combined organic phases were dried and evaporated to afford title compound (348 mg, 71%). $^1$H NMR (400 MHz, DMSO-d$_6$): 10.63 (s, 1H), 7.38 (d, J=7.7 Hz, 1H), 7.25 (d, J=8.0 Hz, 1H), 6.99 (t, J=8.0 Hz, 1H), 6.92 (t, J=6.6 Hz, 1H), 3.73 (s, 2H), 2.25 (s, 3H), 2.19 (s, 3H).

b) Preparation of N-methyl-(1H-indol-2-ylmethyl)-3-(7-oxo5,6,7,8-tetrahydro-[1,8]napthyridin-3-yl) acrylamide EDC (498 mg, 2.6 mmol) was added to a solution of 3-methyl-2-(methylaminomethyl)indole (348 mg, 2.0 mmol), 3-(7-oxo-5,6,7,8-tetrahydro-[1,8]naphthyridin-3-yl)-acrylic acid hydrochloride (533 mg, 2.1 mmol), HOBT.H$_2$O (270 mg, 2.0 mmol) and DIPEA (1.04 mL, 6 mmol) in DMF (5 mL). After stirring overnight, the mixture was slowly diluted with water (50 mL). The resulting precipitate was collected by filtration washed with water and dried. The precipitate was suspended in MeOH (10 mL), stirred for 60 hours, filtered and dried to afford title compound (203 mg, 27%). $^1$H NMR (300 MHz, DMSO-d$_6$, 8): 10.77 and 10.58 (rotamers, 2s, br, 1H), 10.64 (s, br, 1H), 8.37 (d, J=1.9 Hz, 1H), 8.08 (s, 1H), 7.58-

6.92 (m, 6H), 4.91 and 4.75 (rotamers, 2s, 2H), 3.09 and 2.91 (rotamers, 2s, 3H), 2.90 (m, 2H), 2.53, (m, 2H), 2.25 (s, 3H). MS (ESI): m/e 375 (M+H)$^+$.

Example 325

Preparation of (E)-3-(2,2-dimethyl-3,4-dihydro-2H-pyrido[3,2-b][1,4]oxazin-7-yl)-N-methyl-N-((3-methylbenzofuran-2-yl)methyl)acrylamide hydrochloride To a solution of methyl-(3-methyl-benzofuran-2-ylmethyl)-amine (88 mg, 0.5 mmol) in DMF (5 mL) were added in sequential order 3-(2,2-dimethyl-3,4-dihydro-2H-pyrido[3,2-b][1,4]oxazin-7-yl)acrylic acid hydrochloride (107 mg, 0.46 mmol), 1-hydroxybenzotriazole (68 mg, 0.5 mmol), diisopropylethylamine (240 uL, 1.38 mmol), and N-(3-dimethylaminopropyl)-N'-ethylcarbodiimide (100 mg, 0.5 mmol). The mixture was stirred at room temperature overnight, cooled in an ice bath and water added with rapid stirring. The product was extracted with ethyl acetate (3×10 mL), dried with sodium sulfate, filtered and concentrated. The free base was re-solvated in methylene chloride (5 mL) and a solution of 4M HCl in dioxane (1 mL) was added to precipitate the hydrogen chloride salt as a pale yellow solid (84 mg, 43%): $^1$H NMR (400 MHz, DMSO-d6) δ 8.94 (1s, 1H), 8.01-8.06 (m, 2H), 7.47-7.58 (m, 3H), 7.16-7.25 (m, 3H), 4.73-4.94 (rotamers, 2s, 2H), 3.42 (s, 2H), 3.04 (s, 3H), 2.42 (s, 3H), 1.34 (s, 6H); MS (ESI) m/e 392 ($C_{23}H_{25}N_3O_3$+H)$^+$.

Example 326

Preparation of (E)-3-(6-aminopyridin-3-yl)-N-((5-fluoro-3-methylbenzo[b]thiophen-2-yl)methyl)-N-methylacrylamide hydrochloride To a solution of (5-fluoro-1-methyl-1H-indol-2-yl)-N-methylmethanamine (168 mg, 0.8 mmol) in DMF (5 mL) were added in sequential order (E)-3-(6-aminopyridin-3-yl)acrylic acid (120 mg, 0.73 mmol), 1-hydroxybenzotriazole (111 mg, 0.8 mmol), diisopropylethylamine (391 uL, 2.19 mmol), and N-(3-dimethylaminopropyl)-N'-ethylcarbodiimide (160 mg, 0.8 mmol). The mixture was stirred at room temperature overnight, cooled in an ice bath and water added with rapid stirring. The product was extracted with ethyl acetate (3×10 mL), dried, filtered and concentrated. The crude free base was re-solvated in methylene chloride (10 mL) to which was added HCl (1 mL, 4M in dioxane), with the product precipitating out with the addition of ether. The title compound is triturated with ether (2×10 mL) to yield the product as a pale brown solid (76 mg, 25%): $^1$H NMR (300 MHz, DMSO-d6) δ 8.2-8.49 (m, 3H), 7.86-7.99 (m, 1H), 7.46-7.64 (m, 2H), 7.16-7.29 (m, 2H), 6.99 (d, J=12.0 Hz, 1H), 4.83-5.13 (rotamers, 2s, 2H), 2.95-3.16 (rotamers, 2s, 3H), 2.41 (s, 3H); MS (ESI) m/e 356 ($C_{19}H_{18}FN_3OS$+H)$^+$.

Example 327

Preparation of (E)-N-((3-chlorobenzofuran-2-yl)methyl)-N-methyl-3-(3-oxo-3,4-dihydro-2H-pyrido[3,2-b][1,4]oxazin-7-yl)acrylamide To a solution of (3-chlorobenzofuran-2-yl)-N-methylmethanamine (100 mg, 0.51 mmol) in DMF (5 mL) were added in sequential order (E)-3-(3-oxo-3,4-dihydro-2H-pyrido[3,2-b][1,4]oxazin-7-yl)acrylic acid (107 mg, 0.46 mmol), 1-hydroxybenzotriazole (71 mg, 0.51 mmol), diisopropylethylamine (243 uL, 1.39 mmol), and N-(3-dimethylaminopropyl)-N'-ethylcarbodiimide (102 mg, 0.51 mmol). The mixture was stirred at room temperature overnight, cooled in an ice bath and water was added with rapid stirring. The product precipitated and was filtered, triturated with ether and dried to yield title compound as a white solid (55 mg, 30%): $^1$H NMR (400 MHz, CDCl$_3$) δ 9.21 (s, 1H), 8.12-8.19 (m, 1H), 7.28-7.6 (m, 7H), 4.81-4.95 (rotamers, 2s, 2H), 4.714 (s, 2H); 3.21 (s, 3H); MS (ESI) m/e 398 ($C_{20}H_{16}ClN_3O_4$+H)$^+$.

Example 328

Preparation of (E)-N-(3-methoxy-2-propoxybenzyl)-N-methyl-3-(3-oxo-3,4-dihydro-2H-pyrido[3,2-b][1,4]oxazin-7-yl)acrylamide To a solution of (3-methoxy-2-propoxyphenyl)-N-methylmethanamine (75 mg, 0.36 mmol) in DMF (5 mL) were added in sequential order (E)-3-(3-oxo-3,4-dihydro-2H-pyrido[3,2-b][1,4]oxazin-7-yl)acrylic acid (75 mg, 0.26 mmol), 1-hydroxybenzotriazole (50 mg, 0.36 mmol), diisopropylethylamine (150 uL, 0.67 mmol), and N-(3-dimethylaminopropyl)-N'-ethylcarbodiimide (72 mg, 0.36 mmol). The mixture was placed in a microwave at a temperature of 140° C. for 8 minutes. The product precipitated with the addition of water and was filtered, triturated with ether and dried to yield title compound as a white solid (38 mg, 36%): $^1$H NMR (400 MHz, CDCl$_3$) δ 8.03-8.12 (rotamers, 2s, 1H), 7.63-7.69 (dd, J=15.2 Hz, J=11.2 Hz, 1H), 7.44-7.35 (rotamers, 2s, 1H), 7.02-7.04 (m, 1H), 6.80-6.91 (m, 2H), 6.72 (d, J=7.2 Hz, 1H), 4.67-4.81 (rotamers, 4s, 4H), 3.91-4.01 (m, 2H), 3.90 (2s, rotamers, 3H), 3.10 (s, 3H), 1.76-1.89 (m, 2H), 1.05 (t, J=7.2 Hz, 3H); MS (ESI) m/e 412 ($C_{22}H_{25}N_3O_5$+H)$^+$.

Example 329

Preparation of (E)-N-((3-isopropylbenzofuran-2-yl)methyl)-N-methyl-3-(3-oxo-3,4-dihydro-2H-pyrido[3,2-b][1,4]oxazin-7-yl)acrylamide a) 1-iodo-2-(3-methylbut-2-enyloxy)benzene To a solution of 2-iodophenol (3.69 g, 16.8 mmol) in THF (50 mL) is added NaH (804 mg, 33.5 mmol) portion wise and stirred for 30 min at room temperature. 3,3-Dimethylallyl-bromide (3.9 mL, 33.5 mmol) was added and the reaction was stirred over night at room temperature. The reaction is quenched with water (20 mL) and extracted with diethyl ether (3×25 mL), the organic layers are dried over magnesium sulfate, filtered and concentrated. The compound was purified on silica gel using 100% hexanes as the eluent to yield 4.78 g (98%) of the title compound as a pale yellow oil: $^1$H NMR (300 MHz, CDCl$_3$) δ 7.77 (d, J=6.0 Hz, 1H), 7.35 (t, J=9.0 Hz, 1H), 7.02 (d, J=9.0 Hz, 1H), 6.74 (t, J=9.0 Hz, 1H), 5.45 (m, 1H), 4.60 (d, J=6.0 Hz, 2H), 1.75 (2s, 6H)

b) 3-isopropylbenzofuran

A solution of 1-iodo-2-(3-methylbut-2-enyloxy)benzene (5 g, 17.3 mmol) in propionitrile (10 mL) and diisopropylethylamine (9 mL, 52 mmol) is degassed with argon for 15 min. To this solution is added palladium acetate (423 mg, 1.73 mmol) and the reaction is heated to 100° C. overnight. The reaction is then cooled to room temperature and passed through a pad of celite, washing the filter cake with ethyl acetate (50 mL). The ethyl acetate and amine base are then removed under vacuum. The crude reaction mixture is then chromatographed using 100% hexanes to yield title compound as a colorless oil in 52% yield (1.3 g): $^1$H NMR (300 MHz, CDCl$_3$) δ 7.7 (s, 1H), 7.68 (d, J=9.0 Hz, 1H,), 7.55 (d, J=9.0 Hz, 1H), 7.32-7.24 (m, 2H), 3.11-3.07 (m, 1H), 1.32 (2s, 6H).

c) 3-isopropylbenzofuran-2-carbaldehyde

To a cooled (0° C.) solution of 3-isopropylbenzofuran (250 mg, 1.56 mmol) in THF (1 mL) is added nBuLi (2 mL, 2 mmol) drop wise and the reaction is stirred for 30 minutes. DMF (1 mL) was added to the reaction and stirred at room temperature overnight. The solution is placed in an ice bath and carefully quenched with 5% aqueous HCl solution (2 mL), and extracted with ethyl acetate (3×5 mL), dried over sodium sulfate and concentrated. The product was purified on silica with 100% hexanes to yield title compound in as a colorless oil (250 mg, 85%): $^1$H NMR (400 MHz, CDCl$_3$) δ 10.10 (s, 1H), 7.78 (d, 1H, J=9.0 Hz), 7.55 (d, 1H, J=9.0 Hz), 7.32-7.24 (m, 2H), 3.11-3.07 (m, 1H), 1.33-1.31 (2s, 6H).

d) (3-isopropylbenzofuran-2-yl)-N-methylmethanamine

To a solution of 3-isopropylbenzofuran-2-carbaldehyde (250 mg, 1.33 mmol) in anhydrous methanol (8 mL) is added a solution of n-methylamine in ethanol (0.281 mL, 5.32 mmol) and the reaction is stirred at room temperature overnight under an atmosphere of argon. The solution is then concentrated, and re-solvated in methanol (8 mL) and cooled in an ice bath. Sodium borohydride (0.152 g, 4 mmol) was added portion wise and the reaction was stirred at room temperature under argon for 6 h. The solution is concentrated, and re-solvated in 1.3N NaOH (5 mL) and ether (5 mL) and stirred for 1 h. The ether layer was collected. The aqueous layer was washed with ether (2×10 mL), and the combined organic layers were dried over magnesium sulfate, filtered and concentrated in vacuo. Purification by chromatography (silica gel, 9:1 DCM:MeOH) yielded the title compound as a yellow oil (228 mg, 85%): $^1$H NMR (400 MHz, DMSO-d$_6$) δ 7.70 (d, J=4.0 Hz, 1H), 7.46 (d, J=8.0 Hz, 1H), 7.25-7.16 (m, 2H), 3.75 (s, 2H), 3.15-3.22 (m, 1H), 2.25 (s, 3H), 1.36-1.34 (2s, 6H).

Preparation of (E)-N-((3-isopropylbenzofuran-2-yl)methyl)-N-methyl-3-(3-oxo-3,4-dihydro-2H-pyrido[3,2-b][1,4]oxazin-7-yl)acrylamide To a solution of (3-isopropylbenzofuran-2-yl)-N-methylmethanamine (115 mg, 0.57 mmol) in DMF (5 mL) were added in sequential order 3-(2,2-dimethyl-3,4-dihydro-2H-pyrido[3,2-b][1,4]oxazin-7-yl)acrylic acid hydrochloride (118 mg, 0.51 mmol), 1-hydroxybenzotriazole (77 mg, 0.57 mmol), diisopropylethylamine (289 uL, 1.54 mmol), and N-(3-dimethylaminopropyl)-N'-ethylcarbodiimide (109 mg, 0.57 mmol). The mixture was stirred at room temperature overnight, cooled in an ice bath and water was added with rapid stirring. The product was extracted with ethyl acetate (3×10 mL), dried over sodium sulfate, filtered and concentrated to give a light brown solid (14 mg, 7%): $^1$H NMR (400 MHz, CD$_3$OD) δ 11.42 (s, 1H), 8.17-8.16 (m, 1H), 7.89-7.86 (m, 1H), 7.74-7.72 (m, 2H), 7.24-7.30 (m, 2H), 7.22-7.17 (m, 2H), 4.97 (s, 2H), 4.78 (s, 2H), 3.15 (s, 3H), 3.10-3.14 (m, 1H), 1.34 (s, 6H); MS (ESI) m/e 406 (C$_{23}$H$_{23}$N$_3$O$_4$+H)$^+$.

Example 330

Preparation of (E)-N-((3-ethylbenzofuran-2-yl)methyl)-N-methyl-3-(3-oxo-3,4-dihydro-2H-pyrido[3,2-b][1,4]oxazin-7-yl)acrylamide To a solution of (3-ethylbenzofuran-2-yl)-N-methylmethanamine (115 mg, 0.6 mmol) in DMF (5 mL) were added in sequential order (E)-3-(3-oxo-3,4-dihydro-2H-pyrido[3,2-b][1,4]oxazin-7-yl)acrylic acid (140 mg, 0.54 mmol), 1-hydroxybenzotriazole (84 mg, 0.6 mmol), diisopropylethylamine (282 uL, 1.62 mmol), and N-(3-dimethylaminopropyl)-N'-ethylcarbodiimide (120 mg, 0.6 mmol). The mixture was stirred at room temperature overnight, cooled in an ice bath and water added with rapid stirring. The product precipitated and was filtered, triturated with ether and dried to yield the title compound as a white solid (113 mg, 52%): $^1$H NMR (400 MHz, DMSO-d$_6$) δ 11.41 (s, 1H), 8.19 (s, 1H), 7.88 (d, J=6.4 Hz, 1H), 7.66 (d, J=7.6 Hz, 1H), 7.51-7.49 (m, 2H), 7.29-7.25 (m, 3H), 4.99-4.79 (rotamers, 2s, 2H), 4.68 (s, 2H), 3.39 (s, 3H), 2.79-2.73 (m, 2H), 1.23-1.20 (m, 3H); MS (ESI) m/e 392 (C$_{22}$H$_{21}$N$_3$O$_4$+H)$^+$.

Example 331

Preparation of (E)-N-((5-fluoro-3-methylbenzo[b]thiophen-2-yl)methyl)-N-methyl-3-(3-oxo-3,4-dihydro-2H-pyrido[3,2-b][1,4]oxazin-7-yl)acrylamide To a solution of (5-fluoro-3-methylbenzo[b]thiophen-2-yl)-N-methyl methanamine (200 mg, 0.96 mmol) in DMF (5 mL) were added in sequential order (E)-3-(3-oxo-3,4-dihydro-2H-pyrido[3,2-b][1,4]oxazin-7-yl)acrylic acid (185 mg, 0.87 mmol), 1-hydroxybenzotriazole (133 mg, 0.96 mmol), diisopropylethylamine (454 uL, 2.61 mmol), and N-(3-dimethylaminopropyl)-N'-ethylcarbodiimide (192 mg, 0.96 mmol). The mixture was stirred at room temperature overnight, cooled in an ice bath and water added with rapid stirring. The product was extracted with ethyl acetate (3×10 mL), dried with sodium sulfate, filtered and concentrated. The crude product was purified using preparative HPLC to give the title compound (45 mg, 13%): $^1$H NMR (400 MHz, DMSO-d$_6$) δ 11.42 (bs, 1H), 8.19 (s, 1H), 7.89-7.87 (m, 2H), 7.55-7.51 (m, 2H), 7.22-7.18 (m, 2H), 5.12-4.87 (2s, 2H, rotamers), 4.68 (s, 2H), 3.54 (s, 3H), 2.39 (s, 3H). MS (ESI) m/e 412 (C$_{21}$H$_{18}$FN$_3$O$_3$S+H)$^+$.

Example 332

Preparation of (E)-N-((5-fluoro-3-methylbenzo[b]thiophen-2-yl)methyl)-N-methyl-3-(7-oxo-5,6,7,8-tetrahydro-1,8-naphthyridin-3-yl)acrylamide To a solution of (5-fluoro-3-methylbenzo[b]thiophen-2-yl)-N-methylmethanamine (168 mg, 0.8 mmol) in DMF (5 mL) were added in sequential order (E)-3-(7-oxo-5,6,7,8-tetrahydro-1,8-naphthyridin-3-yl)acrylic acid (159 mg, 0.73 mmol), 1-hydroxybenzotriazole (111 mg, 0.8 mmol), diisopropylethylamine (381 uL, 2.19 mmol), and N-(3-dimethylaminopropyl)-N'-ethylcarbodiimide (160 mg, 0.8 mmol). The mixture was stirred at room temperature overnight, cooled in an ice bath and water added with rapid stirring. The product precipitated and was filtered, triturated with ether and dried to yield the title compound as a pale brown solid (224 mg, 75%): ¹H NMR (300 MHz, DMSO-d$_6$) δ 10.65 (s, 1H), 8.37 (s, 1H), 8.08 (s, 1H), 7.76-8.00 (m, 1H), 7.39-7.63 (m, 2H), 7.02-7.33 (m, 2H), 4.87-5.11 (rotamers, 2s, 2H), 3.16 (s, 3H), 2.56-2.89 (m, 2H), 2.49-2.51 (m, 2H), 2.39 (s, 3H); MS (ESI) m/e 410 (C$_{22}$H$_{20}$FN$_3$O$_2$S+H)⁺.

Example 333

Preparation of (E)-N-((5-fluoro-1-methyl-1H-indol-2-yl)methyl)-N-methyl-3-(7-oxo-5,6,7,8-tetrahydro-1,8-naphthyridin-3-yl)acrylamide To a solution of (5-fluoro-1-methyl-1H-indol-2-yl)-N-methylmethanamine (70 mg, 0.36 mmol) in DMF (5 mL) were added in sequential order (E)-3-(7-oxo-5,6,7,8-tetrahydro-1,8-naphthyridin-3-yl)acrylic acid (72 mg, 0.33 mmol), 1-hydroxybenzotriazole (49 mg, 0.36 mmol), diisopropylethylamine (191 uL, 1.1 mmol), and N-(3-dimethylaminopropyl)-N'-ethylcarbodiimide (72 mg, 0.36 mmol). The mixture was stirred at room temperature overnight, cooled in an ice bath and water added with rapid stirring. The product precipitated and was filtered, triturated with ether and dried to yield title compound as a pale brown solid (97 mg, 76%): ¹H NMR (300 MHz, DMSO-d$_6$) δ 10.68 (s, 1H), 8.40 (s, 1H), 8.08-8.18 (m, 1H), 7.91-8.08 (m, 1H), 7.52-7.68 (m, 1H), 7.37-7.52 (m, 1H), 7.13-7.36 (m, 2H), 6.42 (s, 1H), 4.86-5.06 (rotamers, 2s, 2H), 3.71 (s, 3H), 3.14 (m, 2H), 2.81-2.97 (m, 2H), 2.75 (s, 3H); MS (ESI) m/e 393 (C$_{22}$H$_{21}$FN$_4$O$_2$+H)⁺.

Example 334

Preparation of (E)-N-((3-ethylbenzofuran-2-yl)methyl)-N-methyl-3-(7-oxo-5,6,7,8-tetrahydro-1,8-naphthyridin-3-yl)acrylamide To a solution of (3-ethylbenzofuran-2-yl)-N-methylmethanamine (89 mg, 0.49 mmol) in DMF (5 mL) were added in sequential order (E)-3-(7-oxo-5,6,7,8-tetrahydro-1,8-naphthyridin-3-yl)acrylic acid (111 mg, 0.44 mmol), 1-hydroxybenzotriazole (68 mg, 0.49 mmol), diisopropylethylamine (232 uL, 1.34 mmol), and N-(3-dimethylaminopropyl)-N'-ethylcarbodiimide (98 mg, 0.49 mmol). The mixture was stirred at room temperature overnight, cooled in an ice bath and water added with rapid stirring. The product precipitated and was filtered, triturated with ether and dried to yield title compound as a pale brown solid (134 mg, 70%): ¹H NMR (300 MHz, DMSO-d$_6$) δ 10.67 (s, 1H), 8.37 (s, 1H), 8.09 (s, 1H), 7.96 (s, 1H), 7.18-7.64 (m, 5H), 4.81-5.01 (rotamers, 2s, 2H), 3.27-3.61 (m, 2H), 2.90 (d, J=9.0 Hz, 2H), 2.73-2.78 (m, 2H), 2.51-2.59 (m, 3H), 1.23 (t, J=9.0 Hz, 3H); MS (ESI) m/e 390 (C$_{23}$H$_{23}$N$_3$O$_3$+H)⁺.

Example 335

Preparation of (E)-N-((3-isopropylbenzofuran-2-yl)methyl)-N-methyl-3-(7-oxo-5,6,7,8-tetrahydro-1,8-naphthyridin-3-yl)acrylamide To a solution of (3-isopropylbenzofuran-2-yl)-N-methylmethanamine (115 mg, 0.57 mmol) in DMF (5 mL) were added in sequential order (E)-3-(7-oxo-5,6,7,8-tetrahydro-1,8-naphthyridin-3-yl)acrylic acid (111 mg, 0.51 mmol), 1-hydroxybenzotriazole (77 mg, 0.57 mmol), diisopropylethylamine (289 uL, 1.54 mmol), and N-(3-dimethylaminopropyl)-N'-ethylcarbodiimide (109 mg, 0.57 mmol). The mixture was stirred at room temperature overnight, cooled in an ice bath and water added with rapid stirring. The product precipitated and was filtered, triturated with ether and dried to yield the title compound as a white solid (38 mg, 17%): ¹H NMR (400 MHz, DMSO-d$_6$) δ 10.62 (s, 1H), 8.38 (s, 1H), 8.07 (s, 1H), 7.75-7.73 (d, J=7.6 Hz, 1H), 7.53-7.49 (m, 2H), 7.26-7.18 (m, 3H), 4.99-4.80 (rotamers, 2s, 2H), 3.40-3.35 (m, 1H), 3.32 (s, 3H), 2.91-2.89 (m, 2H), 2.55-2.53 (m, 2H), 1.37-1.36 (d, J=6.8 Hz, 6H); MS (ESI) m/e 404 (C$_{24}$H$_{25}$N$_3$O$_3$+H)⁺.

Example 336

Preparation of (E)-N-(benzofuran-5-ylmethyl)-N-methyl-3-(7-oxo-5,6,7,8-tetrahydro-1,8-naphthyridin-3-yl)acrylamide a) benzofuran-5-yl-N-methylmethanamine Benzofuran-5-carbaldehyde (315 mg, 2.16 mmol) was dissolved in anhydrous methanol (10 mL). Methylamine (0.86 mL of 33% solution in ethanol, 6.91 mmol) was added and the reaction was stirred for 3 h. The solution was concentrated to a brown oil and then dissolved in anhydrous methanol (10 mL). Sodium borohydride (83.2 mg, 2.20 mmol) was added and the mixture was stirred overnight at room temperature. Water (5 mL) was added and the solution was concentrated. Sodium hydroxide (10 mL, 1N) was added and the aqueous layer was extracted with ethyl acetate (3×20 mL). Combined organic layers were dried over MgSO$_4$, filtered and concentrated to afford benzofuran-5-yl-N-methylmethanamine (316 mg, 91%) as a light brown oil: ¹H NMR (400 MHz, DMSO-d$_6$) δ 7.93 (s, 1H), 7.56 (s, 1H), 7.50 (d, J=8.4 Hz, 1H), 7.25 (d, J=8.4 Hz, 1H), 6.90 (s, 1H), 3.70 (s, 2H), 3.17 (s, 3H).

(E)-N-(benzofuran-5-ylmethyl)-N-methyl-3-(7-oxo-5,6,7,8-tetrahydro-1,8-naphthyridin-3-yl)acrylamide To a solution of benzofuran-5-yl-N-methylmethanamine (297 mg, 1.84 mmol), 3-(7-oxo-5,6,7,8-tetrahydro-[1,8]naphthyridin-3-yl)-acrylic acid hydrochloride (474 mg, 1.86 mmol), HOBt (252 mg, 1.86 mmol) and DIPEA (1.32 mL, 7.58 mmol) in anhydrous DMF (30 mL) was added EDC hydrochloride (357 mg, 1.86 mmol). The mixture was stirred overnight at 40° C. Water (70 mL) was added and the solution was stirred for 1 h. The reaction mixture was extracted with ethyl acetate (3×100 mL). Combined organic layers were washed with water (50 mL) and brine (50 mL) and concentrated to give a red solid which was purified by column chromatography (silica gel, 5% MeOH/CH$_2$Cl$_2$) to afford (E)-N-(benzofuran-5-ylmethyl)-N-methyl-3-(7-oxo-5,6,7,8-tetrahydro-1,8-naphthyridin-3-yl)acrylamide (381 mg, 57%) as a red solid and a mixture of amide rotamers: ¹H NMR (400 MHz, DMSO-d$_6$) δ 10.64-10.62 (m, 1H), 8.36-8.33 (m, 1H), 8.07 (s, 1H), 7.97 (s, 1H), 7.59-7.49 (m, 3H), 7.38-7.17 (m, 2H), 6.94 (m, 1H), 4.89-4.69 (m, 2H), 3.10-2.85 (m, 5H), 2.54-2.52 (m, 2H); ESI MS m/z 362 [C$_{21}$H$_{19}$N$_3$O$_3$+H]⁺.

Example 337

Preparation of (E)-N-(benzo[b]thiophen-5-ylmethyl)-N-methyl-3-(7-oxo-5,6,7,8-tetrahydro-1,8-naphthyridin-3-yl)acrylamide a) benzo[b]thiophene-5-carbaldehyde Benzo[b]thiophen-5-ylmethanol (311 mg, 1.89 mmol) was dissolved in anhydrous benzene (20 mL). MnO$_2$ (1317 mg, 15.2 mmol) was added and the reaction was stirred for 12 h.

The solution was filtered through celite and the filter cake was washed with ethyl acetate (50 mL). The filtrate was concentrated under vacuum to give the product (284 mg, 92%) as an off-white solid: $^1$H NMR (400 MHz, DMSO-$d_6$) δ 10.09 (s, 1H), 8.46-8.45 (m, 1H), 8.21 (d, J=8.4 Hz, 1H), 7.94 (d, J=5.6 Hz, 1H), 7.81 (dd, J=8.4, 1.2 Hz, 1H), 7.66 (d, J=5.6 Hz, 1H).

b) benzo[b]thiophen-5-yl-N-methylmethanamine

Benzo[b]thiophene-5-carbaldehyde (276 mg, 1.70 mmol) was dissolved in anhydrous methanol (8.0 mL). Methylamine (0.68 mL of 33% solution in ethanol, 5.46 mmol) was added and the reaction was stirred for 3 h. The solution was concentrated to a white solid and then dissolved in anhydrous methanol (10 mL). Sodium borohydride (66.0 mg, 1.75 mmol) was added and the mixture was stirred overnight at room temperature. Water (8.0 mL) was added and the solution was concentrated. Sodium hydroxide (10 mL, 1N) was added and the aqueous layer was extracted with ethyl acetate (3×20 mL). Combined organic layers were dried over MgSO$_4$, filtered and concentrated to afford benzo[b]thiophen-5-yl-N-methylmethanamine (269 mg, 89%) as a yellow oil: $^1$H NMR (300 MHz, DMSO-$d_6$) δ 7.90 (d, J=8.7 Hz, 1H), 7.79 (s, 1H), 7.71 (d, J=5.7 Hz, 1H), 7.40 (d, J=5.4 Hz, 1H), 7.32 (d, J=8.1 Hz, 1H), 3.73 (s, 2H), 2.26 (s, 3H).

(E)-N-(benzo[b]thiophen-5-ylmethyl)-N-methyl-3-(7-oxo-5,6,7,8-tetrahydro-1,8-naphthyridin-3-yl)acrylamide To a solution of benzo[b]thiophen-5-yl-N-methylmethanamine (260 mg, 1.47 mmol), 3-(7-oxo-5,6,7,8-tetrahydro-[1,8]naphthyridin-3-yl)-acrylic acid hydrochloride (377 mg, 1.48 mmol), HOBt (200 mg, 1.48 mmol) and DIPEA (1.05 mL, 6.03 mmol) in anhydrous DMF (24 mL) was added EDC hydrochloride (284 mg, 1.48 mmol). The mixture was stirred overnight at 40° C. Water (50 mL) was added and the solution was stirred for 1 h. The reaction mixture was extracted with ethyl acetate (3×80 mL). Combined organic layers were washed with water (50 mL) and brine (50 mL) and concentrated to give an orange solid which was purified by column chromatography (silica gel, 5% MeOH/CH$_2$Cl$_2$) to afford (E)-N-(benzo[b]thiophen-5-ylmethyl)-N-methyl-3-(7-oxo-5,6,7,8-tetrahydro-1,8-naphthyridin-3-yl)acrylamide (430 mg, 78%) as a pink solid and a mixture of amide rotomers: $^1$H NMR (400 MHz, DMSO-$d_6$) δ 10.67-10.64 (m, 1H), 8.37-8.33 (m, 1H), 8.08-8.05 (m, 1H), 8.00-7.95 (m, 1H), 7.75-7.71 (m, 2H), 7.56-7.52 (m, 1H), 7.45-7.43 (m, 1H), 7.37-7.22 (m, 2H), 4.93-4.73 (m, 2H), 3.12-2.86 (m, 5H), 2.54-2.51 (m, 2H); ESI MS m/z 378 [$C_{21}H_{19}N_3O_2S$+H]$^+$.

Example 338

Preparation of (E)-N-methyl-N-((1-methyl-1H-indol-4-yl)methyl)-3-(7-oxo-5,6,7,8-tetrahydro-1,8-naphthyridin-3-yl)acrylamide a) 1-Methyl-1H-indole-4-carbaldehyde To a solution of 1H-indole-4-carbaldehyde (413 mg, 2.85 mmol) in anhydrous DMF (6.5 mL) was added sodium hydride (171 mg of 60% dispersion in oil, 4.27 mmol). The mixture was stirred for 40 min at room temperature. Methyl iodide (0.36 mL, 5.78 mmol) was then added and the reaction mixture was stirred for 12 h at room temperature. Water was added (25 mL) and the mixture was extracted with ethyl acetate (3×25 mL). Combined organic layers were washed with water (20 mL) and brine (20 mL), dried over Na$_2$SO$_4$, filtered and concentrated to a yellow oil. Purification by column chromatography (silica gel, CH$_2$Cl$_2$) gave 1-methyl-1H-indole-4-carbaldehyde (452 mg g, 99%) as a yellow oil: $^1$H NMR (400 MHz, DMSO-$d_6$) δ 10.20 (s, 1H), 7.84 (d, J=8.0 Hz, 1H), 7.68 (d, J=7.2 Hz, 1H), 7.58 (d, J=2.8 Hz, 1H), 7.38-7.34 (m, 1H), 7.08 (d, J=3.2 Hz, 1H), 3.87 (s, 3H).

b) N-methyl(1-methyl-1H-indol-4-yl)methanamine

1-Methyl-1H-indole-4-carbaldehyde (427 mg, 2.68 mmol) was dissolved in anhydrous methanol (12 mL). Methylamine (1.07 mL of 33% solution in ethanol, 8.59 mmol) was added and the reaction was stirred for 3 h. The solution was concentrated to a yellow oil and then dissolved in anhydrous methanol (12 mL). Sodium borohydride (104 mg, 2.74 mmol) was added and the mixture was stirred overnight at room temperature. Water (10 mL) was added and the solution was concentrated. Sodium hydroxide (20 mL, 1N) was added and the aqueous layer was extracted with ethyl acetate (3×30 mL). Combined organic layers were dried over Na$_2$SO$_4$, filtered and concentrated to afford N-methyl(1-methyl-1H-indol-4-yl)methanamine (432 mg, 92%) as a yellow oil: $^1$H NMR (400 MHz, DMSO-$d_6$) δ 7.29-7.26 (m, 2H), 7.10-7.06 (m, 1H), 7.00-6.98 (m, 1H), 6.51 (d, J=3.2 Hz, 1H), 3.87 (s, 2H), 3.76 (s, 3H), 2.29 (s, 3H).

(E)-N-methyl-N-((1-methyl-1H-indol-4-yl)methyl)-3-(7-oxo-5,6,7,8-tetrahydro-1,8-naphthyridin-3-yl)acrylamide To a solution of N-methyl(1-methyl-1H-indol-4-yl)methanamine (418 mg, 2.40 mmol), 3-(7-oxo-5,6,7,8-tetrahydro-[1,8]naphthyridin-3-yl)-acrylic acid hydrochloride (617 mg, 2.42 mmol), HOBt (327 mg, 2.42 mmol) and DIPEA (1.71 mL, 9.82 mmol) in anhydrous DMF (40 mL) was added EDC hydrochloride (460 mg, 2.40 mmol). The mixture was stirred overnight at 40° C. Water (60 mL) was added and the solution was stirred for 1 h. The reaction mixture was extracted with CH$_2$Cl$_2$ (3×100 mL). Combined organic layers were washed with water (50 mL) and brine (50 mL) and concentrated to give a red solid which was purified by column chromatography (silica gel, 5% MeOH/CH$_2$Cl$_2$) to afford (E)-N-methyl-N-((1-methyl-1H-indol-4-yl)methyl)-3-(7-oxo-5,6,7,8-tetrahydro-1,8-naphthyridin-3-yl)acrylamide (320 mg, 36%) as a pink solid and a mixture of amide rotomers: $^1$H NMR (400 MHz, DMSO-$d_6$) δ 10.64-10.61 (m, 1H), 8.36-8.32 (m, 1H), 8.07-7.98 (m, 1H), 7.56-7.51 (m, 1H), 7.37-7.23 (m, 3H), 7.19-7.09 (m, 1H), 6.92-6.79 (m, 1H), 6.49-6.48 (m, 1H), 5.05-4.87 (m, 2H); 3.78-3.77 (m, 3H), 3.01-2.82 (m, 5H), 2.54-2.52 (m, 2H); ESI MS m/z 375 [$C_{22}H_{22}N_4O_2$+H]$^+$.

Example 339

Preparation of (E)-N-((1-ethyl-1H-indol-4-yl)methyl)-N-methyl-3-(7-oxo-5,6,7,8-tetrahydro-1,8-naphthyridin-3-yl)acrylamide a) 1-ethyl-1H-indole-4-carbaldehyde To a solution of 1H-indole-4-carbaldehyde (2.00 g, 13.8 mmol) in anhydrous DMF (6.5 mL) was added sodium hydride (827 mg of 60% dispersion in oil, 20.7 mmol). The mixture was stirred for 30 min at room temperature. Ethyl iodide (2.22 mL, 27.5 mmol) was then added and the reaction mixture was stirred for 12 h at room temperature. Water was added (100 mL) and the mixture was extracted with ethyl acetate (3×100 mL). Combined organic layers were washed with brine (100 mL), dried over $Na_2SO_4$, filtered and concentrated to an orange oil. Purification by column chromatography (silica gel, gradient elution of $CH_2Cl_2$ to 5% MeOH/$CH_2Cl_2$) gave the title compound (1-ethyl-1H-indole-4-carbaldehyde) (2.43 g, 99%) as a yellow oil: $^1H$ NMR (300 MHz, DMSO-$d_6$) δ 10.19 (s, 1H), 7.88 (d, J=8.1 Hz, 1H), 7.68-7.64 (m, 2H), 7.37-7.32 (m, 1H), 7.08 (d, J=3.0, 1H), 4.28 (q, J=7.2 Hz, 2H), 1.36 (t, J=7.2 Hz, 3H).

b) ((1-ethyl-1H-indol-4-yl)-N-methylmethanamine)

1-Ethyl-1H-indole-4-carbaldehyde (2.40 mg, 13.8 mmol) was dissolved in anhydrous methanol (62 mL). Methylamine (6.00 mL of 33% solution in ethanol, 48.2 mmol) was added and the reaction was stirred for 3 h. The solution was concentrated to a greenish brown oil and then dissolved in anhydrous methanol (62 mL). Sodium borohydride (539 mg, 14.3 mmol) was added and the mixture was stirred overnight at room temperature. Water (90 mL) was added and the solution was concentrated. Sodium hydroxide (15 mL, 1N) was added and the aqueous layer was extracted with ethyl acetate (3×50 mL). Combined organic layers were dried over $Na_2SO_4$, filtered and concentrated to afford the title compound ((1-ethyl-1H-indol-4-yl)-N-methylmethanamine) (2.36 g, 91%) as a yellow oil: $^1H$ NMR (300 MHz, DMSO-$d_6$) δ 7.33-7.30 (m, 2H), 7.10-6.97 (m, 2H), 6.52 (d, J=3.0 Hz, 1H), 4.17 (q, J=7.2 Hz, 2H), 3.88 (s, 2H), 2.30 (s, 3H), 1.33 (t, J=7.2 Hz, 3H).

c) (N-((1-ethyl-1H-indol-4-yl)methyl)-N-methylacrylamide)

N-((1-ethyl-1H-indol-4-yl)methyl)-N-methylacrylamide was prepared according to the method of Preparation 47 except substituting ((1-ethyl-1H-indol-4-yl)-N-methylmethanamine) for methyl-(3-methyl-benzo[b]thiophen-2-ylmethyl)amine. The title compound (918 mg, 64%) was obtained as a yellow oil and a mixture of amide rotomers: $^1H$ NMR (400 MHz, DMSO-$d_6$) δ 7.41-7.35 (m, 2H), 7.13-7.07 (m, 1H), 6.88-6.72 (m, 2H), 6.48-6.45 (m, 1H), 6.22-6.16 (m, 1H), 5.73-5.62 (m, 1H), 4.89-4.81 (m, 2H), 4.23-4.15 (m, 2H), 2.91-2.90 (m, 3H), 1.34 (t, J=7.2 Hz, 3H).

(E)-N-((1-ethyl-1H-indol-4-yl)methyl)-N-methyl-3-(7-oxo-5,6,7,8-tetrahydro-1,8-naphthyridin-3-yl)acrylamide The title compound was prepared according to the procedure of Example 2, except substituting (N-((1-ethyl-1H-indol-4-yl)methyl)-N-methylacrylamide) for N-methyl-N-(3-methyl-benzo[b]thiophen-2-ylmethyl)acrylamide and 6-bromo-3,4-dihydro-1,8-naphthyridin-2(1H)-one for 7-bromo-3,3-dimethyl-1,3,4,5-tetrahydro-pyrido[2,3-e][1,4]diazepin-2-one. The title compound (329 mg, 46%) was obtained as an off-white solid and a mixture of amide rotomers: $^1H$ NMR (400 MHz, DMSO-$d_6$) δ 10.62-10.58 (m, 1H), 8.38-7.98 (m, 2H), 7.57-7.53 (m, 1H), 7.42-7.08 (m, 4H), 6.92-6.78 (m, 1H), 6.51 (s, 1H), 5.05-4.88 (m, 2H), 4.22-4.19 (m, 2H), 3.04-2.85 (m, 5H), 2.55-2.50 (m, 2H), 1.35 (t, J=7.2 Hz, 3H); ESI MS m/z 389 $[C_{23}H_{24}N_4O_2+H]^+$.

Example 340

Preparation of (E)-N-((1H-benzo[d]imidazol-5-yl)methyl)-N-methyl-3-(7-oxo-5,6,7,8-tetrahydro-1,8-naphthyridin-3-yl)acrylamide a) ((1H-benzo[d]imidazol-5-yl)methanol)

1H-benzo[d]imidazole-5-carboxylic acid (5.39 g, 33.3 mmol) was dissolved into anhydrous THF (100 ml) under argon. The solution was cooled in an ice bath and lithium aluminum hydride (70.0 ml of 1M solution in THF, 70.0 mmol) was added dropwise. The reaction mixture was allowed to warm to room temperature and stir overnight. The reaction mixture was cooled to 0° C. and ethyl acetate (90 ml) was carefully added, followed by methanol (15 ml) and water (15 ml). The mixture was stirred for 1 h and filtered through celite. The Solution was concentrated and dissolved in THF (200 ml) and washed with brine (2×100 ml), dried over $Na_2SO_4$, filtered and concentrated to yield the title compound ((1H-benzo[d]imidazol-5-yl)methanol) (1.26 g, 26%) as a yellow solid: $^1H$ NMR (400 MHz, DMSO-$d_6$) δ 8.15 (s, 1H), 7.54-7.47 (m, 2H), 7.13 (s, 1H), 5.14 (s, 1H), 4.58 (s, 2H).

b) (1H-benzo[d]imidazole-5-carbaldehyde)

To a stirring solution of (1H-benzo[d]imidazol-5-yl)methanol (501 mg, 3.38 mmol) in benzene (35 mL) was added $MnO_2$ (2.35, 27.0 mmol). After stirring at room temperature for 12 h the reaction was then filtered through celite and the filter cake was washed with THF (200 mL). The Filtrate was concentrated to give the title compound (1H-benzo[d]imidazole-5-carbaldehyde)(201 mg, 41%) as a white solid: $^1H$ NMR (400 MHz, DMSO-$d_6$) δ 12.90 (bs, 1H), 10.04 (s, 1H), 8.43 (s, 1H), 8.19 (s, 1H), 7.75 (s, 2H).

c) ((1H-benzo[d]imidazol-5-yl)-N-methylmethanamine)

Prepared according to the procedure of Preparation 1, except substituting (1H-benzo[d]imidazole-5-carbaldehyde) for the 1-propyl-naphthalene-2-carbaldehyde. The title compound (176 mg, 60%) was obtained as an off-white oil: $^1H$ NMR (400 MHz, DMSO-$d_6$) δ 8.13 (s, 1H), 7.49 (bs, 2H), 7.14 (d, J=7.2 Hz, 1H), 3.72 (s, 2H), 2.27 (s, 3H).

(E)-N-((1H-benzo[d]imidazol-5-yl)methyl)-N-methyl-3-(7-oxo-5,6,7,8-tetrahydro-1,8-naphthyridin-3-yl)acrylamide According to the procedure of Example 1 (a), except substituting ((1H-benzo[d]imidazol-5-yl)-N-methylmethanamine) for the methyl-(1-propyl-naphthalen-2-ylmethyl)amine, and substituting (E)-3-(7-oxo-5,6,7,8-tetrahydro-[1,8]naphthyridin-3yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride. Purification by preparative HPLC (water/acetonitrile/0.05% TFA mixture) gave the title compound ((E)-N-((1H-benzo[d]imidazol-5-yl)methyl)-N-methyl-3-(7-oxo-5,6,7,8-tetrahydro-1,8-naphthyridin-3-yl)acrylamide) (143 mg, 37%) as a white solid and a mixture of amide rotomers: $^1H$ NMR (400 MHz, DMSO-$d_6$) δ 10.60 (m, 1H), 8.36 (m, 1H), 8.21 (s, 1H), 8.07 (s, 1H), 7.59-7.21 (m, 4H), 7.12-7.08 (m, 1H), 4.91-4.72 (m, 2H), 3.10-2.86 (m, 5H), 2.55-2.49 (m, 2H); ESI MS m/z 362 $[C_{20}H_{19}N_5O_2+H]^+$.

Example 341

Preparation of (E)-N-methyl-N-((3-methylbenzofuran-2-yl)methyl)-3-(2-oxo-4-phenyl-2,3,4,5-tetrahydro-1H-pyrido[2,3-e][1,4]diazepin-7-yl)acrylamide hydrochloride a) ethyl 2-(((2-amino-5-bromopyridin-3-yl)methyl)(phenyl)amino)acetate

To a solution of phenyl glycine ethyl ester (4.94 g, 27.6 mmol) and $K_2CO_3$ (11.42 g, 82.7 mmol) in anhydrous DMF (300 mL) under argon was added 5-bromo-3-(bromomethyl)pyridin-2-amine hydrobromide (9.52 g, 27.6 mmol). The mixture was stirred for 12 h at 40° C. Water (500 mL) was added and the mixture was extracted with ethyl acetate (3×500 mL). Combined organic layers were washed with water (2×400 mL) and brine (400 mL), dried over $MgSO_4$, filtered and concentrated to a brown oil. Purification by column chromatography (silica gel, gradient elution of 30% ethyl acetate/hexanes to 80% ethyl acetate/hexanes) gave ethyl 2-(((2-amino-5-bromopyridin-3-yl)methyl)(phenyl)amino)acetate (3.41 g, 34%) as a yellow solid: $^1$H NMR (300 MHz, DMSO-d$_6$) δ 7.89-7.88 (m, 1H), 7.36-7.35 (m, 1H), 7.17-7.11 (m, 2H), 6.68-6.64 (m, 1H), 6.47-6.44 (m, 2H), 6.09 (s, 2H), 4.30-4.29 (m, 4H), 4.12 (q, J=6.9 Hz, 2H), 1.19 (t, J=6.9 Hz, 3H).

b) 7-bromo-4-phenyl-4,5-dihydro-1H-pyrido[2,3-e][1,4]diazepin-2(3H)-one

Ethyl 2-(((2-amino-5-bromopyridin-3-yl)methyl)(phenyl)amino)acetate (3.29 g, 9.0 mmol) was dissolved in anhydrous DMSO (105 mL) under Argon. NaH (361 mg of 60% dispersion in oil, 9.00 mmol) was added and the reaction was stirred for 12 h at room temperature. Water (200 mL) was added and the mixture was extracted with $CH_2Cl_2$ (4×100 mL). Combined organic layers were washed with water (200 mL) and brine (100 mL), dried over $Na_2SO_4$, filtered and concentrated to afford 7-bromo-4-phenyl-4,5-dihydro-1H-pyrido[2,3-e][1,4]diazepin-2(3H)-one (2.95 g, 99%) as an orange solid: $^1$H NMR (300 MHz, DMSO-d$_6$) δ 10.08 (s, 1H), 8.21 (d, J=2.4 Hz, 1H), 8.10 (d, J=2.4 Hz, 1H), 7.17-7.12 (m, 2H), 6.82-6.80 (m, 2H), 6.71-6.66 (m, 1H), 4.79 (s, 2H), 4.47 (s, 2H).

((E)-N-methyl-N-((3-methylbenzofuran-2-yl)methyl)-3-(2-oxo-4-phenyl-2,3,4,5-tetrahydro-1H-pyrido[2,3-e][1,4]diazepin-7-yl)acrylamide hydrochloride)

A solution of 7-bromo-4-phenyl-4,5-dihydro-1H-pyrido[2,3-e][1,4]diazepin-2(3H)-one (415 mg, 1.31 mmol), N-methyl-N-((3-methylbenzofuran-2-yl)methyl)acrylamide (473 mg, 2.06 mmol) and DIPEA (0.45 mL, 2.58 mmol) in anhydrous DMF (3.0 mL) and propionitrile (9.0 mL) was prepared in a pressure flask. Argon was bubbled into the mixture with stirring for 30 min. Next P(o-tol)$_3$ (79.4 mg, 0.261 mmol) and Pd(OAc)$_2$ (29.3 mg, 0.131 mmol) were added to the mixture and argon was bubbled into the reaction for an additional 5 min. The reaction was then sealed and was left to stir for 12 h at 110° C. The reaction was then allowed to cool to room temperature and was filtered through celite. The filter cake was washed with EtOAc (100 mL) and the filtrate was washed with water (50 mL) and brine (50 mL), dried over $Na_2SO_4$ and concentrated to give a brown oil. Purification by preparative HPLC (water/acetonitrile/0.05% TFA mixture) gave the desired product as a yellow solid which was dissolved in $CH_2Cl_2$ (6.0 mL). To the mixture was added HCl (142 μl of 1M solution in ether, 0.142 mmol) and the mixture was stirred for 5 minutes and then concentrated under high vacuum to give the title compound ((E)-N-methyl-N-((3-methylbenzofuran-2-yl)methyl)-3-(2-oxo-4-phenyl-2,3,4,5-tetrahydro-1H-pyrido[2,3-e][1,4]diazepin-7-yl)acrylamide hydrochloride) (41.2 mg, 6.0%) as a yellow solid and a mixture of amide rotamers: $^1$H NMR (300 MHz, DMSO-d$_6$) δ 10.10 (s, 1H), 8.44-8.40 (m, 1H), 8.27 (s, 1H), 7.55-7.47 (m, 3H), 7.30-7.21 (m, 3H), 7.7.16-7.10 (m, 2H), 6.82-6.79 (m, 2H), 6.69-6.63 (m, 1H), 5.00-4.80 (m, 4H), 4.49 (s, 2H), 3.19-2.93 (m, 3H), 2.26 (s, 3H); ESI MS m/z 467 $[C_{28}H_{26}N_4O_3+H]^+$.

Example 342

Preparation of (E)-3-((6-aminopyridin-3-yl)-N-methyl-N-((3-methyl-1H-indol-2-yl) methyl)acrylamide EDC (438 mg, 1.1 mmol) was added to a solution of N-methyl-(3-methyl-1H-indol-2-yl)methanamine (170 mg, 0.9 mmol), (E)-3-(6-aminopyrid-3-yl)acrylic acid hydrochloride (176 mg, 1.0 mmol), HOBT.H$_2$O (130 mg, 0.9 mmol) and DIPEA (0.58 mL, 2.7 mmol) in dry DMF (5 mL). After stirring overnight, water was added. The precipitate that formed was washed with ethyl acetate and dried to afford the title compound (65 mg, 23%). $^1$H NMR (300 MHz, DMSO-d$_6$) δ 10.75-0.54 (rotamers, s, 1H), 8.15 (d, J=7.2 Hz, 1H), 7.94 (s, 1H), 7.84 (d, J=7.7 Hz, 1H), 7.40 (d, J=7.0 Hz, 1H), 7.31 (d, J=7.9 Hz, 1H), 7.02-6.97 (m, 2H), 6.47-6.41 (m, 2H), 5.01-4.85 (rotamers, s, 2H), 4.72 (s, 3H), 2.23 (s, 3H); MS (ESI): m/e 321.3 $(C_{19}H_{20}N_4O+H)^+$.

Example 343

Preparation of (E)-N-methyl-N-((3-methyl-1H-indol-2-yl) methyl)-3-(3-oxo-3,4-dihydro-2H-pyrido[3,2-b][1,4]oxazin-7-yl)acrylamide EDC (149 mg, 1.3 mmol) was added to a solution of N-methyl(3-methyl-1H-indol-2-yl)methanamine (110 mg, 1.0 mmol), (E)-3-(3-oxo-3,4-dihydro-2H-pyrido[3,2-b][1,4]oxazin-7-yl)acrylic acid hydrochloride (220 mg, 1.1 mmol), HOBT.H$_2$O (81 mg, 1.0 mmol) and DIPEA (0.43 mL, 3.0 mmol) in dry DMF (5 mL). After stirring overnight, water was added. The precipitate that formed was washed with ethyl acetate and dried to afford the title compound (12 mg, 4%). $^1$H NMR (300 MHz, DMSO-d$_6$) δ 8.25 (s, 1H), 7.97 (s, 1H), 7.77 (d, J=7.1 Hz, 1H), 7.60 (s, 1H), 7.45 (d, J=7.4 Hz, 1H), 7.34 (m, 2H), 7.18 (s, 1H), 7.11 (m, 1H), 4.90-4.79 (rotamers, s, 2H), 4.72 (s, 2H), 4.60 (s, 3H), 2.31 (s, 3H); MS (ESI): mile 377.2 $(C_{21}H_{20}N_4O_3+H)^+$.

Example 344

Preparation of (E)-N-((3,7-dimethyl-1H-indol-2-yl) methyl)-N-methyl-3-(3-oxo-3,4-dihydro-2H-pyrido[3,2-b][1,4]oxazin-7-yl)acrylamide a) ethyl 3,7-dimethyl-1H-indole-2-carboxylate

A suspension of 1-o-tolylhydrazine (3.8 g, 30.9 mmol) in ethanol was warmed to 50° C. A solution of α-ketobutyric acid (3.16 g, 30.9 mmol) in ethanol was added and the mixture stirred at rt overnight. Hydrogen chloride was bubbled through the solution for 30 min and the mixture heated at reflux for 2 h then evaporated in vacuo. The crude reaction was chromatographed over silica gel eluting with ethyl acetate/hexane (5%) to afford the title compound (1.84 g, 27%). $^1$H NMR (400 MHz, CDCl$_3$) δ 8.55 (s, 1H), 7.50 (d, J=7.8 Hz, 1H), 7.09 (d, J=6.9 Hz, 1H), 7.03 (t, J=7.6 Hz, 1H), 4.41 (q, J=7.1 Hz, 2H), 2.59 (s, 3H), 2.48 (s, 3H), 1.44 (t, J=7.2 Hz, 3H).

b) (3,7-Dimethyl-1H-indol-2-yl)methanol

A solution of ethyl 3,7-dimethyl-1H-indole-2-carboxylate (1.84 g, 8.4 mmol) in THF (20 mL) was added to an ice-cooled solution of 1.0 M LAH in THF (17.8 mL 17.8 mmol) and stirred overnight. The reaction was quenched with ethyl acetate (5 mL) and 15% aqueous sodium hydroxide (5 mL), filtered through celite and evaporated in vacuo. The crude reaction was chromatographed over silica gel eluting with methanol/dichloromethane (1%) to afford the title compound (440 mg, 30%). $^1$H NMR (400 MHz, CDCl$_3$) δ 8.39 (s, 1H), 7.39 (d, J=7.7 Hz, 1H), 7.06 (t, J=7.2 Hz, 1H), 6.99 (d, J=7.1 Hz, 1H), 4.82 (s, 2H), 4.11 (q, J=7.1 Hz, 2H), 2.45 (s, 3H), 2.28 (s, 3H), 1.26 (t, J=7.1 Hz, 3H).

c) 3,7-Dimethyl-1H-indole-2-carbaldehyde

A mixture of (3,7-dimethyl-1H-indol-2-yl)methanol (440 mg, 2.5 mmol) and manganese dioxide (1.09 g, 12.5 mmol) in dichloromethane (15 mL) was stirred overnight at rt. The mixture was filtered and evaporated. The crude was chromatographed over silica gel eluting with ethyl acetate/hexane (5% and 7.5%) to afford the title compound (200 mg, 46%). $^1$H NMR (400 MHz, CDCl$_3$) δ 10.00 (s, 1H), 8.75 (s, 1H), 7.51 (d, J=7.2 Hz, 1H), 7.15 (d, J=7.4 Hz, 1H), 7.05 (t, J=7.3 Hz, 1H), 2.61 (s, 3H), 2.45 (s, 3H).

d) (3,7-Dimethyl-1H-indol-2-yl)-N-methanamine

Methylamine (0.43 mL, 3.4 mmol) was added to a solution of 3,7-dimethyl-1H-indole-2-carbaldehyde (200 mg, 1.1 mmol) in methanol (5 mL) and stirred for 5 h. The mixture was cooled to 0° C. and sodium borohydride (40.7 mg, 1.1 mmol) added slowly. The mixture was warmed to rt and stirred overnight. Water (3 mL) was added slowly at 0° C. and evaporated to a paste. Water was added and the mixture extracted with dichloromethane. The organic phase was washed with water, dried and evaporated to afford the title compound (120 mg, 57%). $^1$H NMR (400 MHz, CDCl$_3$) δ 8.40 (s, 1H), 7.36 (d, J=7.7 Hz, 1H), 7.00 (t, J=7.6 Hz, 1H), 6.94 (d, J=7.0 Hz, 1H), 3.89 (s, 2H), 2.48 (s, 3H), 2.45 (s, 3H), 2.27 (s, 3H).

(E)-N-((3,7-dimethyl-1H-indol-2-yl)methyl)-N-methyl-3-(3-oxo-3,4-dihydro-2H-pyrido[3,2-b][1,4]oxazin-7-yl)acrylamide EDC (157 mg, 0.8 mmol) was added to a solution of (3,7-dimethyl-1H-indol-2-yl)-N-methanamine (120 mg, 0.6 mmol), (E)-3-(3-oxo-3,4-dihydro-2H-pyrido[3,2-b][1,4]oxazin-7-yl)acrylic acid hydrochloride (177 mg, 0.7 mmol), HOBT.H$_2$O (85 mg, 0.6 mmol) and DIPEA (0.45 mL, 2.5 mmol) in dry DMF (5 mL). After stirring overnight, water was added. The precipitate that formed was washed with ethyl acetate and dried (14 mg, 6%). $^1$H NMR (400 MHz, DMSO-d$_6$) δ 11.41 (s, 1H), 10.60-10.52 (rotamers, s, 1H), 8.19 (s, 1H), 7.87 (s, 1H), 7.50 (d, J=7.6 Hz, 1H), 7.25 (d, J=6.8 Hz, 1H), 6.88 (m, 2H), 4.90-4.77 (rotamers, s, 2H), 4.68 (s, 3H), 3.05 (s, 2H), 2.84 (s, 1H), 2.44 (s, 3H), 2.21 (s, 3H); MS (ESI): m/e 391.1 (C$_{22}$H$_{22}$N$_4$O$_3$+H)$^+$.

Example 345

(E)-N-methyl-N-((3-methyl-7-(trifluoromethyl)-1H-indol-2-yl)methyl-3-(7-oxo-5,6,7,8-tetrahydro-1,8-naphthyridin-3-yl)acrylamide EDC (250 mg, 1.3 mmol) was added to a solution of (3,7-dimethyl-1H-indol-2-yl)-N-methanamine (174 mg, 1.0 mmol), (E)-3-(2-methylene-1,2,3,4-tetrahydroquinolin-6-yl)acrylic acid hydrochloride (369 mg, 1.1 mmol), HOBT.H$_2$O (136 mg, 1.0 mmol) and DIPEA (0.72 mL, 4.0 mmol) in dry DMF (5 mL). After stirring overnight, water was added. The precipitate that formed was washed with ethyl acetate and dried to afford the title compound (3 mg, 0.7%). $^1$H NMR (400 MHz, DMSO-d$_6$) δ 9.56 (s, 1H), 8.76 (s, 1H), 8.30 (s, 1H), 7.77 (s, 1H), 7.65 (d, J=7.8 Hz, 1H), 7.38 (d, J=7.2 Hz, 1H), 7.0 (m, 2H), 6.84 (d, J=7.2 Hz, 1H), 4.72 (s, 2H), 3.15 (s, 3H), 3.01 (t, J=6.8 Hz, 2H), 2.71 (t, J=6.9 Hz, 2H), 2.44 (s, 3H), 2.38 (s, 3H); MS (ESI): m/e 389.2 (C$_{23}$H$_{24}$N$_4$O$_2$+H)$^+$.

Example 346

Preparation of (E)-N-((3-ethyl-1H-indol-2-yl)methyl)-N-methyl-3-(7-oxo-5,6,7,8-tetrahydro-1,8-naphthyridin-3-yl)acrylamide a) N-methyl-1H-indole-2-carboxamide EDC (7.7 g, 40.3 mmol) was added to a solution of indole-2-carboxylic acid (5 g, 13.1 mmol), methylamine, 33% in ethanol (5.6 mL, 15.5 mmol), HOBT (4.1 g, 13.1 mmol) and DIPEA (2.1 mL, 12.4 mmol) in THF, anhydrous (45 mL) and stirred overnight. The crude mixture was evaporated in vacuo and chromatographed over silica eluting with methanol/dichloromethane (0-2%) to afford the title compound (3.51 g, 66%). $^1$H NMR (300 MHz, DMSO-d$_6$) δ 11.53 (s, 1H), 8.43 (s, 1H), 7.57 (d, J=7.9 Hz, 1H), 7.39 (d, J=8.2 Hz, 1H), 7.15 (t, J=8.2 Hz, 1H), 7.03 (s, 1H), 6.98 (t, J=7.9 Hz, 1H), 2.79 (d, J=4.7 Hz, 3H)

b) 3-formyl-N-methyl-1H-indole-2-carboxamide

Oxalyl chloride (2.6 mL, 30 mmol) was added drop-wise to an ice-cooled solution of dimethylformamide (34 mL) and dichloromethane (90 mL), then N-methyl-1H-indole-2-carboxamide (3.51 g, 20 mmol) was added and the mixture stirred at rt for 1 h. Water was added and the resulting precipitate filtered, washed with water and diethyl ether. The product was dried to afford the title compound (2.03 g, 50%). $^1$H NMR (300 MHz, DMSO-d$_6$) δ 12.58 (s, 1H), 10.2 (s, 1H), 9.51 (s, 1H), 8.26 (d, J=7.5 Hz, 1H), 7.66 (d, J=8.6 Hz, 1H), 7.47-7.10 (m, 2H), 2.73 (d, J=4.6 Hz, 3H).

c) N-methyl-3-vinyl-1H-indole-2-carboxamide n-Butyllithium (2.5M in hexanes) (48.6 mL, 121.7 mmol) was added dropwise to an ice-cooled solution of methyl triphenylphosphoniumbromide (43.5 g, 121.7 mmol) in THF (500 mL). The mixture was stirred at 0° C. for 1 h then at rt for 2 h. 3-Formyl-N-methyl-1H-indole-2-carboxamide (1.96 g, 9.7 mmol) in THF (100 mL) was added and the mixture stirred at rt for 2 h. The solvent was evaporated and the residue dissolved in ethyl acetate and washed twice with water. The organic phase was dried over magnesium bromide and evaporated in vacuo. The crude mixture was chromatographed over silica gel eluting with 40% ethyl acetate in hexanes to afford the title compound (730 mg (38%). $^1$H NMR (300 MHz, DMSO-$d_6$) δ 11.48 (s, 1H), 8.04 (s, 1H), 7.92 (d, J=8.0 Hz, 1H), 7.42 (d, J=7.9 Hz, 1H), 7.33 (d, J=18 Hz, 1H), 7.22 (t, J=7.6 Hz, 1H), 7.09 (t, J=7.2 Hz, 1H), 5.77 (d, J=18.4 Hz, 1H), 5.27 (d, J=11.6 Hz, 1H), 2.81 (s, 3H).

d) 3-ethyl-N-methyl-1H-indole-2-carboxamide

A mixture of N-methyl-3-vinyl-1H-indole-2-carboxamide (1.1 g, 5.4 mmol) and 10% Pd/C (55 mg) in ethyl acetate (150 mL) was stirred for 3 h under an atmosphere of hydrogen. The mixture was filtered through celite and evaporated to afford the title compound (970 mg 90%). $^1$H NMR (400 MHz, DMSO-$d_6$) δ 11.05 (s, 1H), 7.80 (s, 1H), 7.59 (d, J=7.6 Hz, 1H), 7.36 (d, J=8.4 Hz, 1H), 7.17 (t, J=6.8 Hz, 1H), 7.04 (t, J=6.0 Hz, 1H), 3.01 (q, J=7.4 Hz, 2H), 2.81 (d, J=4.6 Hz, 3H), 1.17 (t, J=7.4 Hz, 3H).

e) N-methyl(3-vinyl-1H-indol-2-yl)methanamine

A solution of N-methyl-3-vinyl-1H-indole-2-carboxamide (740 mg, 3.7 mmol) in dioxane was added slowly to an ice-cooled solution of lithium aluminium hydride (2.1 g, 55.5 mmol) in dioxane (100 mL). The mixture was stirred at reflux overnight. Excess lithium aluminium hydride was quenched with 15% NaOH (10 mL) and the mixture separated. The aqueous phase was washed twice with ethyl acetate and the combined organic phases dried to afford the title compound (430 mg 61%). $^1$H NMR (400 MHz, DMSO-$d_6$) δ 11.09 (s, 1H), 7.75 (d, J=8 Hz, 1H), 7.49 (d, J=6.4 Hz, 1H), 7.09-7.05 (m, 2H), 7.04-6.90 (m, 1H), 5.54 (d, J=16 Hz, 1H), 5.06 (d, J=10.0 Hz, 1H), 3.84 (s, 2H), 2.27 (s, 3H).

f) (3-ethyl-1H-indol-2-yl)-N-methylmethanamine

A solution of 3-ethyl-N-methyl-1H-indole-2-carboxamide (970 mg, 4.80 mmol) in dioxane was added slowly to an ice-cooled solution of lithium aluminium hydride (273 mg, 72 mmol) in dioxane (10 mL). The mixture was stirred at reflux overnight. Excess lithium aluminium hydride was quenched with 15% NaOH (2 mL) and the mixture separated. The aqueous phase was washed twice with ethyl acetate and the combined organic phases dried to afford the title compound (550 mg, 61%). $^1$H NMR (400 MHz, DMSO-$d_6$) δ 10.59 (s, 1H), 7.42 (d, J=8 Hz, 1H), 7.25 (d, J=7.6 Hz, 1H), 7.00 (t, J=7.2 Hz, 1H), 6.89 (t, J=7.2 Hz, 1H), 3.75 (s, 2H), 2.66 (q, J=7.5 Hz, 2H), 2.27 (s, 3H), 1.14 (t, J=7.6 Hz, 3H).

Preparation of (E)-N-((3-ethyl-1H-indol-2-yl)methyl)-N-methyl-3-(7-oxo-5,6,7,8-tetrahydro-1,8-naphthyridin-3-yl)acrylamide EDC (83 mg, 0.4 mmol) was added to a solution of (3-ethyl-1H-indol-2-yl)-N-methylmethanamine (62.7 mg, 0.3 mmol), (E)-3-(7-oxo-5,6,7,8-tetrahydro-1,8-naphthyridin-3-yl)acrylic acid hydrochloride (240 mg, 0.8 mmol), HOBT.H$_2$O (101 mg, 0.7 mmol) and DIPEA (0.58 mL, 2.7 mmol) in dry DMF (5 mL). After stirring overnight, water was added. The precipitate that formed was washed with ethyl acetate and dried to afford the title compound (77.8 mg, 67%). $^1$H NMR (400 MHz, DMSO-$d_6$) δ 10.61-10.59 (rotamers, s, 2H), 8.36 (s, 1H), 8.07 (s, 1H), 7.51-7.46 (m, 3H), 7.30 (d, J=7.8 Hz, 1H), 7.03 (t, J=7.6 Hz, 1H), 6.95 (t, J=7.2 Hz, 1H), 4.94 (s, 2H), 4.90-4.75 (rotamers, s, 3H), 3.29 (m, 2H), 3.08-2.91 (m, 4H), 1.13 (t, J=7.6 Hz, 3H); MS (ESI): m/e 389.2 ($C_{23}H_{24}N_4O_2$+H)$^+$.

Example 347

Preparation of (E)-N-((3-ethyl-1H-indol-2-yl)methyl)-N-methyl-3-(3-oxo-3,4-dihydro-2H-pyrido[3,2-b][1,4]oxazin-7-yl)acrylamide EDC (116 mg, 0.6 mmol) was added to a solution of (3-ethyl-1H-indol-2-yl)-N-methylmethanamine (87 mg, 0.46 mmol), (E)-3-(3-oxo-3,4-dihydro-2H-pyrido[3,2-b][1,4]oxazin-7-yl)acrylic acid hydrochloride (123.65 mg, 1.05 mmol), HOBT.H$_2$O (62 mg, 0.46 mmol) and DIPEA (0.33 mL, 1.8 mmol) in dry DMF (5 mL). After stirring overnight, water was added. The precipitate that formed was washed with ethyl acetate and dried to afford the title compound (76.2 mg, 42%). $^1$H NMR (400 MHz, DMSO-$d_6$) δ 11.41 (s, 1H), 8.18 (s, 1H), 7.88 (s, 1H), 7.46 (t, J=7.9 Hz, 2H), 7.25 (d, J=7.9 Hz, 1H), 7.03 (t, J=7.6 Hz, 1H), 6.95 (t, J=7.1 Hz, 2H), 4.92 (s, 2H), 4.90-4.74 (rotamers, s, 2H), 4.68 (s, 3H), 3.08 (m, 2H), 1.13 (t, J=7.4 Hz, 3H); MS (ESI): m/e 391.1 ($C_{22}H_{22}N_4O_3$+H)$^+$.

Example 348

Preparation of (E)-N-methyl-3-(3-oxo-3,4-dihydro-2H-pyrido[3,2-b][1,4]oxazin-7-yl)-N-((3-vinyl-1H-indol-2-yl)methyl)acrylamide EDC (73 mg, 0.3 mmol) was added to a solution of N-methyl(3-vinyl-1H-indol-2-yl)methanamine (54.7 mg, 0.29 mmol), (E)-3-(3-oxo-3,4-dihydro-2H-pyrido[3,2-b][1,4]oxazin-7-yl)acrylic acid hydrochloride (79 mg, 0.3 mmol), HOBT.H$_2$O (39 mg, 0.29 mmol) and DIPEA (0.21 mL, 1.1 mmol) in dry DMF (5 mL). After stirring overnight, water was added. The precipitate that formed was washed with ethyl acetate and dried to afford the title compound (26 mg, 23%). $^1$H NMR (400 MHz, DMSO-d6) δ 11.41 (s, 1H), 11.20-11.05 (rotamers, s, 1H), 8.18 (s, 1H), 7.87 (s, 1H), 7.80 (d, J=7.8 Hz, 1H), 7.51 (d, J=15.6 Hz, 1H), 7.38 (d, J=7.7 Hz, 1H), 7.22 (d, J=15.6 Hz, 1H), 7.10 (t, J=7.1 Hz, 1H), 7.07-6.98 (m, 2H), 5.62 (d, J=17.9 Hz, 1H), 5.12 (d, J=11.0 Hz, 1H), 5.03 (s, 2H), 4.68 (s, 3H), 3.09 (s, 2H); MS (ESI): m/e 389.1 ($C_{22}H_{20}N_4O_3$+H)$^+$.

Example 349

Preparation of (E)-N-((1,3-dimethyl-1H-indol-2-yl)methyl)-N-methyl-3-(3-oxo-3,4-dihydro-2H-pyrido[3,2-b][1,4]oxazin-7-yl)acrylamide a) 1,3-dimethyl-H indole Sodium hydride (600 mg, 16.6 mmol) was added to a solution of 3-methylindole (2 g, 15.2 mmol) in DMF (10 mL). The mixture was stirred for 30 min and iodomethane was added in one portion. The mixture was cooled in an icebath and left to warm to rt overnight. The mixture was evaporated and the residue dissolved in ethyl acetate. The solution was washed with water and brine, dried over magnesium sulfate and evaporated. The crude reaction was chromatographed over silica gel eluting with hexane and ethyl acetate/hexane (20 and 50%) to afford the title compound (1.3 g, 59%). $^1$H NMR (400 MHz, CDCl$_3$) δ 7.46 (d, J=8 Hz, 1H), 7.34 (d, J=8 Hz, 1H), 7.12 (t, J=7.8 Hz, 1H), 7.06 (s, 1H), 7.00 (t, J=7.6 Hz, 1H), 3.70 (s, 3H), 2.23 (s, 3H)

b) 1,3-dimethyl-1H indole-2-carbaldehyde

Phosphorous oxychloride (0.0.93 mL, 9.7 mmol) was added dropwise with stirring to DMF (5 mL) at 10° C. over 20 min. 1,3-dimethyl-1H indole (1.3 g mg, 8.9 mmol) in DMF (5 mL) was added slowly with stirring and the mixture was heated for 3 h at 98-100° C. Excess concentrated aqueous solution of sodium acetate was added. The mixture was stirred for 30 min at 28° C. and extracted with ethyl acetate, dried and evaporated. The crude mixture was chromatographed over silica gel eluting with hexane/ether to afford the title compound (1.5 g, 97%). $^1$H NMR (400 MHz, DMSO-$d_6$) δ 10.15 (s, 1H), 7.74 (d, J=7.6 Hz, 1H), 7.53 (d, J=7.8 Hz, 1H), 7.42 (t, J=8.0 Hz, 1H), 7.15 (t, J=7.6 Hz, 1H), 3.99 (s, 3H), 2.60 (s, 3H)

c) (1,3-dimethyl-1H-indol-2-yl)-N-methylmethanamine

Methylamine (0.53 mL, 13.1 mmol) was added to a solution of 1,3-dimethyl-1H indole-2-carbaldehyde (760 mg, 4.3 mmol) in methanol (15 mL) and stirred for 5 h. The mixture was cooled to 0° C. and sodium borohydride (159 mg, 4.3 mmol) added slowly. The mixture was warmed to rt and stirred overnight. Water (3 mL) was added slowly at 0° C. and evaporated to a paste. Water was added and the mixture extracted with dichloromethane. The organic phase was washed with water, dried and evaporated to afford the title compound (690 mg, 85%). $^1$H NMR (400 MHz, DMSO-$d_6$) δ 7.44 (d, J=7.8 Hz, 1H), 7.34 (d, J=8.1 Hz, 1H), 7.10 (t, J=7.6 Hz, 1H), 6.98 (t, J=8.0 Hz, 1H), 3.77 (s, 2H), 3.71 (s, 3H), 2.27 (s, 3H), 2.23 (s, 3H).

EDC (132.5 mg, 0.6 mmol) was added to a solution of (1,3-dimethyl-1H-indol-2-yl)-N-methylmethanamine (100 mg, 0.5 mmol), (E)-3-(3-oxo-3,4,dihydro-2H-pyrido[3,2-b][1,4]oxazin-7-yl)acrylic acid hydrochloride (143 mg, 0.55 mmol), HOBT.H$_2$O (72 mg, 0.5 mmol)) and DIPEA (0.38 mL, 2.1 mmol) in dry DMF (5 mL). After stirring overnight, water was added. The precipitate that formed was washed with ethyl acetate and dried to afford the title compound (144 mg, 74%). $^1$H NMR (400 MHz, DMSO-$d_6$) δ 11.51 (s, 1H), 8.24 (s, 1H), 7.94 (d, J=7.6 Hz, 1H), 7.60-7.48 (m, 2H), 7.38 (m, 1H), 7.20-7.28 (m, 1H), 7.14 (t, J=7.8 Hz, 1H), 7.07 (d, J=7.5 Hz, 1H), 5.11 (s, 2H), 5.01-4.98 (rotamers, s, 2H), 4.77 (s, 3H), 3.80 (s, 3H), 2.31 (s, 3H); MS (ESI): m/e 391.2 (C$_{22}$H$_{22}$N$_4$O$_3$+H)$^+$.

Example 350

(E)-N-((1,3-dimethyl-1H-indol-2-yl)methyl)-N-methyl-3-(2-oxo-4-phenyl-2,3,4,5-tetrahydro-1H-pyrido[2,3-e][1,4]diazepin-7-yl)acrylamide A solution of N-((1,3-dimethyl-1H-indol-2-yl)methyl)-N-methylacrylamide (92 mg, 0.3 mmol) and DIPEA (0.16 mL, 0.9 mmol) in DMF (5 mL) was purged with argon for 10 min. Pd(OAc)$_2$ (6 mg, 0.03 mmol) and P(o-Tol)$_3$ (18 mg, 0.06 mmol) were added and the mixture was purged with argon and heated to 100° C. The crude mixture was filtered and water was added. The precipitate that formed was washed with ethyl acetate and dried to afford the title compound (144 mg, 74%). $^1$H NMR (400 MHz, DMSO-$d_6$) δ 10.06-9.95 (rotamers, s, 1H), 8.32 (d, J=8.0 Hz, 2H), 7.57 (s, 1H), 7.50 (t, J=7.6 Hz, 2H), 7.38 (m, 3H), 7.12 (t, J=7.6 Hz, 2H), 7.03 (t, J=7.6 Hz, 1H), 6.84-6.35 (m, 2H), 4.90-4.80 (rotamers, s, 2H), 4.80 (s, 2H), 4.50 (s, 3H), 3.63 (s, 3H), 2.98 (s, 2H), 2.32 (s, 3H); MS (ESI): m/e 480.2 (C$_{29}$H$_{29}$N$_5$O$_2$+H)$^+$.

Example 351

Preparation of (E)-N-methyl-N-((3-methyl-7-(trifluoromethyl)-1H-indol-2-yl)methyl)-3-(3-oxo-3,4-dihydro-2H-pyrido[3,2-b][1,4]oxazin-7-yl)acrylamide a) Ethyl 3-methyl-7-(trifluoromethyl)-1H-indole-2-carboxylate

A solution of sodium nitrite (2.3 g, 34 mmol) was added dropwise to a mixture of trifluoromethyl aniline (3.85 mL, 31 mmol), HCl (7.5 mL) and water (15 mL) at −5° C. After the addition, the mixture was stirred at 0° C. for 15 min and brought to pH 3-4 by addition of sodium acetate. In a separate flask, a solution of ethyl α-ethylacetoacetate (5 mL, 31 mmol) in ethanol (25 mL) at 0° C. was treated with a solution of potassium hydroxide (1.74 g, 31 mmol) in water (10 mL) followed by addition of ice. The diazonium salt was immediately added to this alkaline solution. The mixture was adjusted to pH 5-6 by adding sodium acetate and stirred at 0° C. for 3 h. The solution was kept overnight at 4° C. and extracted with ethyl acetate, washed with brine, dried over magnesium sulfate and most of the solvent removed. The crude mixture was added dropwise to a solution of ethanolic HCl (25 mL) at 78° C. and stirred for 2 h at 78° C. The mixture was evaporated and chromatographed over silica gel eluting with ethyl acetate/hexane (3%) to afford the title compound (2.26 g, 26%). $^1$H NMR (400 MHz, CDCl$_3$) δ 8.92 (s, 1H), 7.79 (d, J=8 Hz, 1H), 7.55 (d, J=7.2 Hz, 1H), 7.15 (t, J=7.6 Hz, 1H), 4.41 (q, J=6.9 Hz, 2H), 2.60 (s, 3H), 1.42 (t, J=6.9 Hz, 3H)

b) (3-Methyl-7-(trifluoromethyl)-1H-indol-2-yl)methanol

A solution of ethyl 3-methyl-7-(trifluoromethyl)-1H-indole-2-carboxylate (2.2 g, 8.1 mmol) in THF (50 mL) was added to an ice cooled solution of 1M LAH in THF (16.2 mL, 16.2 mmol) and stirred overnight. The reaction was quenched with ethyl acetate and sodium hydroxide, filtered through celite and evaporated to afford the title compound (1.03 g, 57%). $^1$H NMR (400 MHz, CDCl$_3$) δ 8.74 (s, 1H), 7.66 (d, J=7.9 Hz, 1H), 7.40 (d, J=7.3 Hz, 1H), 7.12 (t, J=4.7 Hz, 1H), 4.81 (s, 2H), 2.26 (s, 3H)

c) 3-Methyl-7-(trifluoromethyl)-1H-indole-2-carbaldehyde

A mixture of (3-methyl-7-(trifluoromethyl)-1H-indol-2-yl)methanol (1.03 g, 4.4 mmol) and manganese (IV) oxide (1.95 g, 22.4 mmol) in dichloromethane (15 mL) was stirred overnight. The mixture was filtered through celite and evaporated to afford the title compound (510 mg, 51%). $^1$H NMR (400 MHz, CDCl$_3$) δ 10.08 (s, 1H), 8.95 (s, 1H), 7.87 (d, J=7.9 Hz, 1H), 7.62 (d, J=7.1 Hz, 1H), 7.20 (t, J=7.7 Hz, 1H), 2.65 (s, 3H)

d) N-methyl(3-methyl-7-trifluoromethyl)-1H-indol-2-yl)methanamine

Methylamine (0.28 mL, 6.7 mmol) was added to a solution of 3-methyl-7-(trifluoromethyl)-1H-indole-2-carbaldehyde (510 mg, 2.2 mmol) in methanol (5 mL) and stirred for 5 h. The mixture was cooled to 0° C. and sodium borohydride (83 mg, 2.2 mmol) added slowly. The mixture was warmed to rt and stirred overnight. Water (3 mL) was added slowly at 0° C.

and evaporated to a paste. Water was added and the mixture extracted with dichloromethane. The organic phase was washed with water, dried and evaporated to afford the title compound (310 mg, 58%). ¹H NMR (400 MHz, CDCl₃) δ 8.93 (s, 1H), 7.66 (d, J=7.8 Hz, 1H), 7.38 (d, J=7.4 Hz, 1H), 7.11 (t, J=7.5 Hz, 1H), 3.90 (s, 2H), 2.48 (s, 3H), 2.28 (s, 3H).

EDC (160 mg, 0.78 mmol) was added to a solution of N-methyl(3-methyl-7-trifluoromethyl)-1H-indol-2-yl)methanamine (155 mg, 0.6 mmol), (E)-3-(3-oxo-3,4,dihydro-2H-pyrido[3,2-b][1,4]oxazin-7-yl)acrylic acid hydrochloride (180 mg, 0.7 mmol), HOBT.H₂O (86 mg, 0.6 mmol) and DIPEA (0.46 mL, 2.5 mmol) in dry DMF (5 mL). After stirring overnight, water was added. The precipitate that formed was washed with ethyl acetate and dried to afford the title compound (72 mg, 27%). ¹H NMR (400 MHz, DMSO-d₆) δ 11.41 (s, 1H), 11.10-10.89 (rotamers, s, 1H), 8.20 (s, 1H), 7.80 (d, J=8.0 Hz, 1H), 7.76 (d, J=7.5 Hz, 1H), 7.54 (s, 1H), 7.41 (d, J=7.5 Hz, 1H), 7.31-7.20 (m, 2H), 5.05-4.81 (rotamers, s, 2H), 4.68 (s, 2H), 3.08 (s, 3H), 2.21 (s, 3H); MS (ESI): m/e 445.1 (C₂₂H₁₉F₃N₄O₃+H)⁺.

Example 352

(E)-N-methyl-N-((3-methyl-7-(trifluoromethyl)-1H-indol-2-yl)methyl)-3-(7-oxo-5,6,7,8-tetrahydro-1,8-naphthyridin-3-yl)acrylamide EDC (159 mg, 0.78 mmol) was added to a solution of N-methyl(3-methyl-7-trifluoromethyl)-1H-indol-2-yl)methanamine (155 mg, 0.6 mmol), (E)-3-(2-methylene-1,2,3,4-tetrahydroquinolin-6-yl)acrylic acid hydrochloride (172 mg, 0.67 mmol), HOBT.H₂O (86 mg, 0.6 mmol) and DIPEA (0.46 mL, 2.5 mmol) in dry DMF (5 mL). After stirring overnight, water was added. The precipitate that formed was washed with ethyl acetate and dried to afford the title compound (157 mg, 60%). ¹H NMR (400 MHz, DMSO-d₆) δ 11.05-10.90 (rotamers, s, 1H), 10.61 (s, 1H), 8.37 (s, 1H), 8.07 (s, 1H), 7.76 (d, J=7.7 Hz, 1H), 7.56-7.40 (m, 2H), 7.17-7.13 (m, 2H), 5.05-4.82 (rotamers, s, 2H), 3.10 (s, 2H), 2.84 (s, 3H), 2.32 (s, 3H); MS (ESI): m/e 443.1 (C₂₃H₂₁F₃N₄O₂+H)⁺.

Example 353

Preparation of (E)-N-((7-ethyl-3-methyl-1H-indol-2-yl)methyl)-N-methyl-3-(3-oxo-3,4-dihydro-2H-pyrido[3,2-b][1,4]oxazin-7-yl)acrylamide a) Ethyl 7-ethyl-3-methyl-1H-indole-2-carboxylate A solution of sodium nitrite (6.24 g, 90.64 mmol) was added dropwise to a mixture of 2-ethyl aniline (10.2 mL, 82.4 mmol), conc.HCl (20 mL) and water (30 mL) at −5° C. After the addition, the mixture was stirred at 0° C. for 15 min and brought to pH 34 by addition of sodium acetate. In a separate flask, a solution of ethyl α-ethylacetoacetate (14.6 mL, 90.64 mmol) in ethanol (50 mL) at 0° C. was treated with a solution of potassium hydroxide (5.08 g, 90.64 mmol) in water (20 mL) followed by addition of ice. The diazonium salt was immediately added to this alkaline solution. The mixture was adjusted to pH 5-6 by adding sodium acetate and stirred at 0° C. for 3 h. The solution was kept overnight at 4° C. and extracted with ethyl acetate, washed with brine, dried over magnesium sulfate and most of the solvent removed. The crude mixture was added dropwise to a solution of ethanolic HCl (50 mL) at 78° C. and stirred for 2 h at 78° C. The mixture was evaporated and chromatographed over silica gel eluting with ethyl acetate/hexane (3%) to afford the title compound (2.2 g, 11%). ¹H NMR (400 MHz, CDCl₃) δ 8.52 (s, 1H), 7.48 (d, J=8 Hz, 1H), 7.12 (d, J=6.8 Hz, 1H), 7.06 (t, J=7.2 Hz, 1H), 4.38 (q, J=7.3 Hz, 2H), 2.82 (q, J=7.6 Hz, 2H), 2.58 (s, 3H), 1.40 (t, J=7.2 Hz, 3H), 1.33 (t, J=7.6 Hz, 3H)

b) (7-Ethyl-3-methyl-1H-indol-2-yl)methanol

A solution of ethyl 7-ethyl-3-methyl-1H-indole-2-carboxylate (2.2 g, 9.5 mmol) in THF (50 mL) was added to an ice cooled solution of 1M LAH in THF (19 mL, 19.0 mmol) and stirred overnight. The reaction was quenched with ethyl acetate and sodium hydroxide, filtered through celite and evaporated to afford the title compound (1.6 g, 100%). ¹H NMR (400 MHz, CDCl₃) δ 8.45 (s, 1H), 7.39 (d, J=6.5 Hz, 1H), 7.04 (m, 2H), 4.80 (s, 2H), 2.83 (q, J=4.8 Hz, 2H), 2.28 (s, 3H), 1.34 (t, J=4.4 Hz, 3H)

c) 7-Ethyl-3-methyl-1H-indole-2-carbaldehyde

A mixture of (7-ethyl-3-methyl-1H-indol-2-yl)methanol (1.6 g, 9.1 mmol) and manganese (IV) oxide (3.97 g, 45.7 mmol) in dichloromethane (15 mL) was stirred overnight. The mixture was filtered through celite and evaporated to afford the title compound (1.1 mg, 65%). ¹H NMR (400 MHz, CDCl₃) δ 10.02 (s, 1H), 8.90 (s, 1H), 7.53 (d, J=8.0 Hz, 1H), 7.19 (d, J=7.6 Hz, 1H), 7.10 (t, J=7.7 Hz, 1H), 2.83 (q, J=7.5 Hz, 2H), 2.62 (s, 3H), 1.31 (t, J=7.5 Hz, 3H)

d) (7-Ethyl-3-methyl-1H-indol-2-yl)-N-methanamine

Methylamine (0.7 mL, 17.6 mmol) was added to a solution of 7-ethyl-3-methyl-1H-indole-2-carbaldehyde (1.1 mg, 5.8 mmol) in methanol (5 mL) and stirred for 5 h. The mixture was cooled to 0° C. and sodium borohydride (218 mg, 5.8 mmol) added slowly. The mixture was warmed to rt and stirred overnight. Water (3 mL) was added slowly at 0° C. and evaporated to a paste. Water was added and the mixture extracted with dichloromethane. The organic phase was washed with water, dried and evaporated to afford the title compound (826 mg, 75%). ¹H NMR (400 MHz, CDCl₃) δ 8.22 (s, 1H), 7.34 (d, J=7.7 Hz, 1H), 7.01 (t, J=7.6 Hz, 1H), 6.96 (d, J=6.8 Hz, 1H), 3.87 (s, 2H), 2.79 (q, J=7.5 Hz, 2H), 2.45 (s, 3H), 2.24 (s, 3H), 1.31 (t, J=7.6 Hz, 3H)

(E)-N-((7-ethyl-3-methyl-1H-indol-2-yl)methyl)-N-methyl-3-(3-oxo-3,4-dihydro-2H-pyrido[3,2-b][1,4]oxazin-7-yl)acrylamide EDC (147 mg, 0.7 mmol) was added to a solution of (7-ethyl-3-methyl-1H-indol-2-yl)-N-methanamine (108.7 mg, 0.5 mmol), (E)-3-(3-oxo-3,4,dihydro-2H-pyrido[3,2-b][1,4]oxazin-7-yl)acrylic acid hydrochloride (151 mg, 0.6 mmol), HOBT.H₂O (73 mg, 0.5 mmol) and DIPEA (0.39 mL, 2.1 mmol) in dry DMF (5 mL). After stirring overnight, water was added. The precipitate that formed was washed with ethyl acetate and dried to afford the title compound (25 mg, 0.001%). ¹H NMR (400 MHz, DMSO-d₆) δ 9.34 (s, 1H), 8.92 (s, 1H), 8.15 (s, 1H), 7.65 (d, J=7.6 Hz, 1H), 7.41 (s, 1H), 7.38 (d, J=7.2 Hz, 1H), 7.05 (m, 2H), 6.80 (d, J=7.5 Hz, 1H), 4.70 (s, 2H), 3.15 (s, 3H), 2.88 (q, J=7.0 Hz, 2H), 2.40 (s, 3H), 1.30 (t, J=7.2 Hz, 3H); MS (ESI): m/e 405.2 (C₂₃H₂₄N₄O₃+H)⁺.

Example 354

(E)-N-((7-ethyl-3-methyl-1H-indol-2-yl)methyl)-N-methyl-3-(7-oxo-5,6,7,8-tetrahydro-1,8-naphthyridin-3-yl)acrylamide EDC (138 mg, 0.7 mmol) was added to a solution of (7-ethyl-3-methyl-1H-indol-2-yl)-N-methanamine (112.2 mg, 0.5 mmol), (E)-3-(2-methylene-1,2,3,4-tetrahydroquinolin-6-yl)acrylic acid hydrochloride (155 mg, 0.6 mmol) HOBT.H$_2$O (75 mg, 0.5 mmol) and DIPEA (0.4 mL, 2.2 mmol) in dry DMF (5 mL). After stirring overnight, water was added. The precipitate that formed was washed with ethyl acetate and dried to afford the title compound (90 mg, 44.7%). $^1$H NMR (400 MHz, DMSO-d$_6$) δ 11.50 (s, 1H), 10.44 (s, 1H), 8.39 (s, 1H), 8.29 (s, 1H), 8.09 (m, 1H), 7.85 (d, J=7.6 Hz, 1H), 7.5 (d, J=7.0 Hz, 1H), 7.34 (d, J=7.8 Hz, 1H), 6.88 (m, 2H), 5.05-4.85 (rotamers, s, 2H), 3.22 (m, 2H), 3.15 (s, 3H), 2.88 (q, J=7.0 Hz, 2H), 2.70 (m, 2H), 2.40 (s, 3H), 1.30 (t, J=7.2 Hz, 3H); MS (ESI): m/e 419 (C$_{24}$H$_{26}$N$_4$O$_2$+H)$^+$.

Example 355 a) Ethyl 5-bromo-3,6-dimethyl-1H-indole-2-carboxylate

A solution of NaNO$_2$ (1.52 g, 22 mmol) in water (4 mL) was added to a vigorously stirred mixture of 4-bromo-3-methylaniline (3.72 g, 20 mmol) at −5° C. After 30 min stirring, the solution was adjusted to pH 5 with NaOAc (1.40 g). A cold solution of ethyl 2-ethyl-3-oxobutanoate (4.0 g, 22 mmol) and KOH (1.36 g, 22 mmol) in EtOH (16 mL) were added followed by crushed ice (30 g). NaOAc was added if necessary to adjust the pH to 5. The mixture was stirred for 5 h at 0° C. then kept at this temperature overnight. The solution was extracted with EtOAc, washed with brine, dried and evaporated to 8 mL. This solution was added to a solution of HCl (25 mL, 7M in EtOH). It was further refluxed for 3 h. Upon cooling in an ice bath, water (200 mL) was added slowly. The precipitate was filtered, washed with water and dried to afford 5.36 g (91%) as a 1:1 mixture of the title compound and its ethyl 5-bromo-3,4-dimethyl-1H-indole-2-carboxylate isomer. $^1$H NMR (300 MHz, CDCl$_3$), δ, mix 8.66 and 8.54 (2s, br, 1H), 7.83 and 7.23 (2s, 2×0.5H), 7.42 and 7.05 (2d, J=8.7 Hz, 2×0.5H), 4.41 (q, J=7.2 Hz, 2H), 2.81, 2.79, 2.53 and 2.49 (4s, 4×1.5H), 1.42 (t, J=7.2 Hz, 3H).

b) 5-Bromo-3,6-dimethyl-1H-indole-2-carboxylic acid

A 1:1 isomeric mixture of ethyl 5-bromo-3,6-dimethyl-1H-indole-2-carboxylate and 5-bromo-3,4-dimethyl-1H-indole-2-carboxylate (5.36 g, 18.1 mmol) was dissolved in EtOH (20 mL) and KOH (3.6 g, 54 mmol). The mixture was refluxed for 3 h and gave 4.67 g (99%) of a 1:1 isomeric mixture of the corresponding acids. The mixture was acidified and the precipitate that formed was filtered and dried at 120° C. to afford the title compound (4.39 g, 90.6%). $^1$H NMR (300 MHz, DMSO-d$_6$) δ, mix 12.96 (s, 1H), 11.50 and 11.40 (2s, 2×0.5H), 7.85 and 7.33 (2s, 2×0.5H), 7.34 and 7.16 (2d, J=8.7 Hz, 2×0.5H), 2.76, 2.73, 2.49 and 2.47 (4s, 4×1.5H).

c) 5-Bromo-3,6-dimethyl-1H-indole

A 1:1 mixture of 5-bromo-3,6-dimethyl-1H-indole-2-carboxylic acid and 5-bromo-3,4-dimethyl-1H-indole-2-carboxylic acid (4.39 g, 16.4 mmol) in quinoline (10 mL) with copper powder (250 mg) was stirred at 240° C. for 3 h to give the corresponding mixture of the decarboxylated products. Upon cooling, ether (200 mL) was added and the mixture acidified with 5N HCl. The layers were separated, the organics were washed with brine, dried and evaporated. Chromatography (silica, 15% CH$_2$Cl$_2$ in hexane) and crystallization from a CH$_2$Cl$_2$/hexane mixture afforded the title compound (1.35 g 37%). $^1$H NMR (300 MHz, CDCl$_3$) δ7.74 (s, 1H), 7.21 (is, 1H), 6.90 (s, 1H), 2.48 (s, 3H), 2.27 (s, 3H).

d) 3,6-Dimethyl-1H-indole-5-carbaldehyde tert-Butyl lithium (16.7 mL, 28.3 mmol, 1.7 M in pentanes) was added to a dry ether (20 mL) solution of 5-bromo-3,6-dimethyl-1H-indole (1.27 g, 5.67 mmol) at −78° C. under Argon. The mixture was stirred at 0° C. for 30 min then cooled to −78° C. DMF (18 mL) was added and the mixture was stirred at 0° C. for 1 h. The reaction was quenched with cold, saturated NH$_4$Cl solution at −78° C. The mixture was diluted with ether and hexane, washed with brine, dried and evaporated. Crystallization from a CH$_2$Cl$_2$/hexane mixture afforded the title compound (810 mg 82%). $^1$H NMR (300 MHz, CDCl$_3$) δ10.29 (s, 1H), 8.06 (s, 1H), 8.00 (s, br, 1H), 7.15 (1s, 1H), 6.97 (s, 1H), 2.76 (s, 3H), 2.36 (s, 3H).

e) 3,6-dimethyl-1H-indol-5-yl)-N-methylmethanamine

Methylamine (2.4 mL, 19 mmol, 33% in EtOH) was added to a MeOH (10 mL) solution of 3,6-dimethyl-1H-indole-5-carbaldehyde (810 mg, 4.7 mmol). The mixture was stirred for 5 h at 21° C. The mixture was cooled to 0° C. and NaBH$_4$ (180 mg, 4.7 mmol) was added slowly. The mixture was stirred at 21° C. for 16 h, water (1 mL) was added then it was evaporated to a paste. This was diluted with CH$_2$Cl$_2$, washed with water, dried over K$_2$CO$_3$ and evaporated to afford the title compound (848 mg 96%). (300 MHz, CDCl$_3$) δ7.77 (s, br, 1H), 7.47 (s, br, 1H), 7.26 (is, 1H), 6.87 (s, 1H), 3.83 (s, 2H), 2.54 (s, 3H), 2.45 (s, 3H), 2.31 (s, 3H).

Preparation of (E)-N-((3,6-dimethyl-1H-indol-5-yl)methyl)-N-methyl-3-(7-oxo-5,6,7,8-tetrahydro-1,8-naphthyridin-3-l)acrylamide EDC (132 mg, 0.69 mmol) was added to a solution of 3,6-dimethyl-1H-indol-5-yl)-N-methylmethanamine (100 mg, 0.5 mmol), (E)-3-(2-methylene-1,2,3,4-tetrahydroquinolin-6-yl)acrylic acid hydrochloride (148 mg, 0.6 mmol) HOBT.H$_2$O (71.8 mg, 0.5 mmol) and DIPEA (0.38 mL, 2.2 mmol) in dry DMF (5 mL). After heating overnight, water was added. The precipitate that formed was washed with ethyl acetate and dried to afford the title compound (33 mg, 17%). $^1$H NMR (300 MHz, DMSO-d$_6$) δ, 10.70-10.60 (m, 2H), 8.32-8.22 (rotamers, s, 1H), 8.00-7.95 (rotamers, s, 2H), 7.54 (d, J=7.6 Hz, 1H), 7.32 (m, 1H), 7.09 (m, 1H), 6.98 (s, 1H), 4.89-4.72 (rotamers, s, 2H), 3.32 (m, 2H), 3.02 (m, 2H), 2.84 (s, 3H), 2.46 (s, 3H), 2.31 (s, 3H); m/e 389.2 (C$_{23}$H$_{24}$N$_4$O$_2$+H)$^+$.

Example 356

Preparation of (E)-N-((3,6-dimethyl-1H-indol-5-yl)methyl)-N-methyl-3-(3-oxo-3,4-dihydro-2H-pyrido[3,2-b][1,4]oxazin-yl)acrylamide EDC (198 mg, 1.0 mmol) was added to a solution of (7-ethyl-3-methyl-1H-indol-2-yl)-N-methanamine (150 mg, 0.8 mmol), (E)-3-(3-oxo-3,4,dihydro-2H-pyrido[3,2-b][1,4]oxazin-7-yl)acrylic acid hydrochloride (224 mg, 0.87 mmol) HOBT.H$_2$O (107 mg, 0.8 mmol) and DIPEA (0.57 mL, 3.1 mmol) in dry DMF (5 mL). After heating overnight, water was added. The precipitate that formed was washed with ethyl acetate and dried (184 mg, 59%). $^1$H NMR (300 MHz, DMSO-d$_6$) δ, 11.42 (s, 1H), 10, 45 (s, 1H), 8.24-8.05 (rotamers, s, 1H), 7.98-7.80 (rotamers, s, 2H), 7.54 (d, J=7.4 Hz, 1H), 7.24 (m, 1H), 7.14 (m, 1H), 6.98 (s, 1H), 4.90-4.78 (rotamers, s, 2H), 3.05 (s, 2H), 2.84 (s, 3H), 2.45 (s, 3H), 2.31 (s, 3H); m/e 391.1 (C$_{22}$H$_{22}$N$_4$O$_3$+H)$^+$.

Example 357

Preparation of (E)-N-methyl-N-((3-methylbenzofuran-2-yl)methyl)-3-(7-oxo-7,8-dihydro-1,8-naphthyridin-3-yl)acrylamide a) (E)-tert-butyl 3-(2-amino-5-bromopyridin-3-yl)acrylate

A reaction vessel was charged with 5-bromo-3-iodopyridin-2-amine (1 g, 3.35 mmol), tert-butyl acrylate (0.97 mL, 6.69 mmol), and (i-Pr)$_2$EtN (1.75 mL, 10.01 mmol) followed by propionitrile (20 mL) and then DMF (5 mL). The solution was de-oxygenated with argon for 15 minutes. The mixture was treated with Pd(OAc)$_2$ (75 mg, 0.34 mmol) and P(o-tol)$_3$ (204 mg, 0.67 mmol) then heated to 90° C. for 16 h (overnight) then filtered through a pad of silica gel. The filtrate was concentrated and dried under reduced pressure to give a dark brown residue which was subjected to flash chromatography on silica gel using 20% ethyl acetate:hexanes to 40% ethyl acetate:hexanes. The appropriate fractions were collected and concentrated to give a yellow solid. Yield: 700 mg (70%); $^1$H NMR (300 MHz, DMSO-d$_6$) δ 8.06 (d, 1H, J=2.3 Hz), 8.03 (d, 1H, J=2.3 Hz), 7.61 (d, 1H, J=15.0 Hz), 6.58 (s, 2H), 6.50 (d, 1H, J=15.0 Hz), 1.50 (s, 9H); ESI MS m/z 299 (100%); 301 (100%)[C$_{12}$H$_{15}$N$_2$O$_2$Br+H]$^+$ b) 6-bromo-1,8-naphthyridin-2(1H)-one

A solution of (E)-tert-butyl 3-(2-amino-5-bromopyridin-3-yl)acrylate (2.5 g, 8.35 mmol) in anhydrous methanol (50 mL) was treated with sodium methoxide (8.5 mL of a 4.9 M solution, 41.75 mmol). The solution was heated at reflux for 2 h then cooled to room temperature. The mixture was cooled in an ice-H$_2$O bath and treated with H$_2$O (100 mL) under rapid stirring to give a precipitate. The solid was filtered and washed with H$_2$O (20 mL). The filtrate was neutralized with 1 M HCl(aq) to form a precipitate. The solid was filtered and washed with H$_2$O (20 mL). The solids were combined and dried under reduced pressure to give an off-white solid (1.75 g, 93%). $^1$H NMR (300 MHz, DMSO-d$_6$) δ 8.43 (d, 1H, J=2.5 Hz), 8.06 (d, 1H, J=2.5 Hz), 7.60 (d, 1H, J=9.1 Hz), 6.44 (d, 1H, J=9.1 Hz); ESI MS m/z 225 (100%); 227 (100%) [C$_8$H$_5$N$_2$OBr+H]$^+$ c) (E)-tert-butyl 3-(7-oxo-7,8-dihydro-1,8-naphthyridin-3-yl)acrylate

A reaction vessel was charged with 6-bromo-1,8-naphthyridin-2(1H)-one (1.5 g, 6.69 mmol), tert-butyl acrylate (4.86 mL, 33.45 mmol), and (i-Pr)$_2$EtN (3.5 mL, 20.07 mmol) followed by DMF (40 mL). The solution was de-oxygenated with argon for 20 min. The mixture was treated with Pd(OAc)$_2$ (150 mg, 0.67 mmol) and P(o-tol)$_3$ (407 mg, 1.34 mmol) then heated to 100° C. for 15 h (overnight). A TLC analysis indicated that only the starting arylhalide is present. At this time the mixture was a yellow suspension. To this mixture was added 20 DMSO (20 mL) and an additional 75 mg of Pd(OAc)$_2$. The mixture was heated at 100° C. for 24 h. After cooling, the dark mixture was filtered through celite and the filter cake was rinsed with EtOAc (100 mL). The filtrate was extracted with EtOAc (2×100 mL). The combined organic fractions were washed with brine (2×100 mL), H$_2$O (100 mL), dried over MgSO$_4$ and filtered through a pad of silica gel. The filtrate was concentrated to about 50 mL then treated with about 150 mL hexanes to form a precipitate. The precipitate was filtered to give the product as a light brown solid. Yield: 700 mg (39%); $^1$H-NMR (300 MHz, DMSO-d$_6$) δ 12.36 (s, 1H), 8.83 (d, 1H, J=2.3 Hz), 8.53 (d, 1H, J=2.3 Hz), 7.89 (d, 1H, J=9.0 Hz), 7.64 (d, 1H, J=18.0 Hz), 6.65 (d, 1H, J=18.0 Hz), 6.62 (m, 1H), 1.51 (s, 9H); ESI MS m/z 273 [C$_{15}$H$_{16}$N$_2$O$_3$+H]$^+$ d) (E)-3-(7-oxo-7,8-dihydro-1,8-naphthyridin-3-yl)acrylic acid Hydrochloride A suspension of (E)-tert-butyl 3-(7-oxo-7,8-dihydro-1,8-naphthyridin-3-yl)acrylate (500 mg, 1.84 mmol) in CH$_2$Cl$_2$ (7 mL) was treated with trifluoroacetic acid (7 mL). The mixture became homogeneous and it was stirred at room temperature for 1 h. The solution was concentrated to dryness and treated with 4M HCl in dioxane (5 mL). The suspension was sonicated for 20 min, diluted with Et$_2$O (50 mL) and sonicated for an additional 20 min. The solid was filtered and dried under reduced pressure overnight. Yield: 450 mg (96.8%) $^1$H-NMR (300 MHz, DMSO-d$_6$) δ 12.4 (br s, 1H), 8.82 (s, 1H), 8.52 (s, 1H), 7.91 (d, 1H, J=9.0 Hz), 7.67 (d, 1H, J=15.0 Hz), 6.67 (d, 1H, J=15.0 Hz), 6.61 (m, 1H); ESI MS m/z 217 [C$_{11}$H$_8$N$_2$O$_3$+H]$^+$

(E)-N-methyl-N-((3-methylbenzofuran-2-yl)methyl)-3-(7-oxo-7,8-dihydro-1,8-naphthyridin-3-yl)acrylamide EDC (0.18 g, 0.95 mmol) was added to a suspension of (E)-3-(7-oxo-7,8-dihydro-1,8-naphthyridin-3-yl)acrylic acid hydrochloride (0.20 g, 0.79 mmol), HOBt (0.12 g, 0.87 mmol), Methyl-(3-methyl-benzofuran-2-ylmethyl)-amine (0.15 g, 0.87 mmol) and (i-Pr)$_2$EtN (0.8 mL, 4.74 mmol) in DMF (10 mL). The mixture was heated at 40° C. overnight then diluted with H$_2$O (30 mL) with rapid stirring. The resulting precipitate was filtered, washed with H$_2$O (20 mL) and dried under high vacuum for 4 hours. The solid was suspended in 50% Et$_2$O:hexanes (20 mL), sonicated then filtered and dried under vacuum overnight. Yield: 0.13 g (44.1%) as a mixture of amide rotamers; $^1$H NMR (300 MHz, DMSO-d$_6$) δ 12.33 (s, 1H), 8.90 and 8.87 (2×s, 1H), 8.53 (s, 1H), 7.91 (d, 1H, J=9 Hz), 7.65-7.25 (m, 6H), 6.63 (d, 1H, J=9.0 Hz), 5.04 and 4.83 (2×s, 2H), 3.23 and 2.96 (2×s, 3H), 2.29 (s, 3H); ESI MS m/z 374 [C$_{22}$H$_{19}$N$_3$O$_3$+H]$^+$

Example 358

Preparation of (E)-3-(6,6-dimethyl-7-oxo-5,6,7,8-tetrahydro-1,8-naphthyridin-3-yl)-N-methyl-N-((3-methylbenzofuran-2-yl)methyl)acrylamide 6-bromo-3,3-dimethyl-3,4-dihydro-1,8-naphthyridin-2(1H)-one A mixture of activated Zn (1.0 g, 15 mmol) and ethyl 2-bromo-2-methylpropanoate (1.24 mL, 6.4 mmol) in THF (8 mL) were added together at 0° C. and stirred for 6 h while warming to room temperature. To this mixture a dropwise solution of 5-bromo-3-(bromomethyl)pyridin-2-amine in THF (5 mL) was added via canula and the reaction mixture was stirred for a further 19 h at rt. The mixture was diluted with ethyl acetate (25 mL) and washed with saturated aqueous $NH_4Cl$ (50 mL) and brine (50 mL), dried over magnesium sulphate, and concentrated in vacuo. The crude yellow solid product was triturated with diethyl ether and filtered to obtain the white solid product. Yield 158 mg (49%); $^1$H NMR (300 MHz, DMSO-$d_6$) δ 10.61 (s, 1H), 8.23 (s, 1H), 7.87 (s, 1H), 2.81 (s, 2H), 1.04 (s, 6H); ESI MS m/z 255, 257 $[C_{10}H_{11}N_2OBr+H]^+$ (E)-tert-butyl-3-(6,6-dimethyl-7-oxo-5,6,7,8-tetrahydro-1,8-naphthyridin-3-yl) acrylate A suspension of 6-bromo-3,3-dimethyl-3,4-dihydro-1,8-naphthyridin-2(1H)-one (434 mg, 1,7 mmol), tert-butyl acrylate (1.23 mL, 8.5 mmol) and (i-Pr)$_2$EtN (0.9 mL, 5.1 mmol) in DMF (25 mL) was de-oxygenated with Ar for 30 min. The mixture was treated with Pd(OAc)$_2$ (38 mg, 0.17 mmol) and P(o-tol)$_3$ (103 mg, 0.34 mmol) then heated to 110° C. for 22 h. The hot mixture was filtered through a pad of celite and washed with ethyl acetate (50 mL). The filtrate was diluted with H$_2$O (100 mL) and extracted with ethyl acetate (2×50 mL). The combined organic layers were washed with water, then brine, dried over magnesium sulphate, and concentrated in vacuo. The resulting brown solid was then triturated with a diethyl ether followed by filtration to yield the white solid product. Yield 178 mg (35%); $^1$H NMR (300 MHz, DMSO-$d_6$) δ 10.68 (s, 1H), 8.39 (s, 1H), 8.04 (s, 1H), 7.52 (d, J=16.1 Hz, 1H), 6.52 (d, J=15.8 Hz, 1H), 2.80 (s, 2H), 1.49 (s, 9H), 1.09 (s, 6H); ESI MS m/z 303 $[C_{17}H_{22}N_2O_3+H]^+$ (E)-3-(6,6-dimethyl-7-oxo-5,6,7,8-tetrahydro-1,8-naphthyridin-3-yl)acrylic acid hydrochloride A solution of (E)-tert-butyl 3-(6,6-dimethyl-7-oxo-5,6,7,8-tetrahydro-1,8-naphthyridin-3-yl)acrylate (165 mg, 0.55 mmol) in CH$_2$Cl$_2$ (10 mL) was treated with TFA (10 mL). After stirring at room temperature for 2 h, the solution was concentrated in vacuo. The resulting crude product was treated with anhydrous HCl in dioxane (4 mL, 4.0 M) and sonicated for 15 min. The off-white solid product was then isolated by filtration and dried under vacuum. Yield: 152 mg (quant); $^1$H NMR (300 MHz, DMSO-$d_6$) δ 10.71 (s, 1H), 8.38 (s, 1H), 8.04 (s, 1H), 7.56 (d, J=16.1 Hz, 1H), 6.54 (d, J=16.1 Hz, 1H), 2.81 (s, 2H), 1.09 (s, 6H); ESI MS m/z 247 $[C_{13}H_{14}N_3O_4+H]^+$ (E)-3-(6,6-dimethyl-7-oxo-5,6,7,8-tetrahydro-1,8-naphthyridin-3-yl)-N-methyl-N-((3-methylbenzofuran-2-yl)methyl)acrylamide EDC (102 mg, 0.53 mmol) was added to a suspension of (E)-3-(6,6-dimethyl-7-oxo-5,6,7,8-tetrahydro-1,8-naphthyridin-3-yl)acrylic acid hydrochloride (125 mg, 0.44 mmol), HOBt (66 mg, 0.49 mmol), N-methyl(3-methylbenzofuran-2-yl)methanamine (92 mg, 0.49 mmol) and (i-Pr)$_2$EtN (0.37 mL, 2.2 mmol) in DMF (5 mL). The mixture was allowed to stir for 23 h at 40° C. The mixture was cooled to room temperature and diluted with water (20 mL) at 0° C. to yield a brown precipitate, which was collected by suction filtration. The solid was then triturated with diethyl ether to obtain an off-white solid product. Yield: 137 mg (81%); $^1$H NMR (300 MHz, DMSO-d6) δ 10.64 (s, 1H), 8.40 (s, 1H), 8.09 (s, 1H), 7.59-7.19 (m, 6H), 4.91 (s, 2H), 3.09 (s, 3H), 2.81 (s, 2H), 2.28 (s, 3H), 1.09 (s, 6H); ESI MS m/z 404 $[C_{24}H_{25}N_3O_3+H]^+$.

Example 359 a) (S)-ethyl 2-(3-cyanopyridin-2-ylamino)propanoate

A solution of 2-chloro-3-cyanopyridine (2 g, 14.4 mmol), L-alanine ethyl ester hydrochloride (3.3 g, 21.6 mmol), sodium carbonate (5.9 g, 43 mmol) in pyridine (1.75 mL) and DMF (20 mL) was heated to 125° C. for 36 h. The reaction was quenched with water and extracted with ethyl acetate (3×15 mL). The product was purified using column chromatography (10% MeOH in CH$_2$Cl$_2$) to yield a pale yellow solid (720 mg, 23%): $^1$H NMR (400 MHz, CDCl$_3$) δ 8.26 (d, J=4.8 Hz, 1H), 7.69-7.67 (m, 1H), 6.67-6.64 (m, 1H), 4.77-4.74 (m, 1H), 4.23-4.19 (m, 2H), 1.54 (d, J=7.2 Hz, 3H), 1.30-1.26 (m, 3H).

b) (S)-2-methyl-1,2,4,5-tetrahydropyrido[2,3-e][1,4]diazepin-3-one

To a solution of (S)-ethyl 2-(3-cyanopyridin-2-ylamino)propanoate (720 mg, 3.28 mmol) in methanol (10 mL) and sodium methoxide (3.28 mmol) is added a pinch of Raney nickel and the reaction was stirred under hydrogen for 6 h. Once the reaction was complete, 1 eq of HCl was added and the solution filtered through celite, and washed with methanol. The solution was concentrated and re-solvated in ethyl acetate (10 mL) and washed with water (20 mL), the organic layers were combined, dried over sodium sulfate and concentrated. The residue was purified by preparative HPLC to yield a white solid (136 mg, 23%): $^1$H NMR (400 MHz, CD$_3$OD) δ 7.87 (s, 1H), 7.32 (s, 1H), 6.60-6.57 (m, 1H), 4.99 (d, J=16.4 Hz, 1H), 4.12-4.10 (m, 1H), 3.87 (d, J=16.4 Hz, 1H), 1.38 (d, J=6.8 Hz, 3H).

c) (S)-7-bromo-2-methyl-1,2,4,5-tetrahydropyrido[2,3-e][1,4]diazepin-3-one

Bromine (43 ul, 0.84 mmol) was added drop wise to a solution of (S)-2-methyl-1,2,4,5-tetrahydropyrido[2,3-e][1,4]diazepin-3-one (136 mg, 0.77 mmol) in acetic acid (10 mL). The reaction was stirred at room temperature for 3 h. The reaction was quenched with sat. NaHCO$_3$ (10 mL) and extracted with ethyl acetate (3×15 mL), dried over sodium sulfate and concentrated to give the title compound (140 mg, 71%): $^1$H NMR (400 MHz, CDCl$_3$) δ 7.93 (s, 1H), 7.31 (s, 1H), 7.20 (b, 1H), 5.95 (bs, 1H), 4.97-4.91 (m, 1H), 4.72-4.70 (m, 1H), 3.85-3.79 (m, 1H), 1.47 (d, J=6.4 Hz, 3H).

(S,E)-N-methyl-3-(2-methyl-3-oxo-2,3,4,5-tetrahydro-1H-pyrido[2,3-e][1,4]diazepin-7-yl)-N-((3-methylbenzofuran-2-yl)methyl)acrylamide trifluoroacetic acid salt To a solution of (S)-tert-butyl 7-bromo-3-methyl-2,3-dihydro-1H-pyrido[2,3-e][1,4]diazepine-4(5H)-carboxylate (70 mg, 0.27 mmol), tri(o-tolyl)phosphine (17 mg, 0.056 mmol), diisopropylethylamine (105 uL, 0.56 mmol), N-methyl-N-((3-methyl-3a,7a-dihydrobenzofuran-2-yl)methyl)acrylamide (125 mg, 0.55 mmol) in DMF (5 mL) was added palladium acetate (7 mg, 0.027 mmol) and the reaction heated to 90° C. overnight. The reaction was cooled to room temperature and passed through a pad of celite. The filter cake was washed with ethyl acetate (10 mL). The reaction was washed with water (10 mL) and extracted with ethyl acetate (2×15 mL), dried over sodium sulfate and concentrated. The residue was then re-dissolved in methylene chloride (5 mL) and cooled to 0° C. Trifluoroacetic acid (1 mL) was added and reaction stirred at room temperature for 1 h. The solution was concentrated and purified using preparative HPLC to yield a yellow solid (88 mg, 57%) as the TFA salt: $^1$H NMR (400 MHz, DMSO-d6) δ 8.29-8.01 (m, 2H), 7.57 (s, 1H), 7.55-7.42 (m, 3H), 7.30-7.22 (m, 2H), 4.96-4.90 (m, 3H), 4.78 (s, 1H), 3.98 (m, 1H), 3.16 (s, 2H), 2.90 (s, 1H), 2.26 (s, 3H), 1.26 (d, J=6.4 Hz, 3H). MS (ESI) m/e 405 $(C_{23}H_{24}N_4O_3+H)^+$.

Example 360

Combination Studies of Compound G and Commercial Antibodies

Checkerboard experiments were performed and analyzed according to standard procedures as outlined below.

As shown in FIG. 6, no antagonism was found with any of the combinations tested. Gentamicin and linezolid showed a synergistic effect with compound G against the *S. aureus* strains tested, and all other antibiotics showed an additive effect.

No antagonism was found for any of the compound G combinations shown in FIG. 7. In all cases where FabI does not exist in the test species or the commercial antibiotic had no activity (MIC>32 μg/ml) against a drug resistant strain, no change in MICs of the active component of the combination was observed (FIC<2). In cases where both compounds were active against the tested strain, the effect was highly additive (FIC values of 0.6-1). These results indicate that for all major pathogenic species tested compound G did not show antagonism against antibiotics active against these strains, and commercial antibiotics did not show any antagonism against compound G activities.

Combination time-kill studies were performed as follows. Bacterial inocula were prepared as for MIC determination according to CLSI guidelines. Log phase cells (~10$^6$ CFU/ml) were inoculated into 24 well plates and incubated with the indicated concentrations of compound G and commercial antibiotics for 24 hours at 35° C. At indicated time points samples were removed for determination of viable CFU counts. Results are plotted as log CFU/ml vs. time.

*S. pneumoniae* 22425, a penicillin and macrolide resistant clinical isolate, was tested with compound G and gatifloxacin (FIG. 8). Since *S. pneumoniae* does not posses the FabI target, compound G showed no activity against *S. pneumoniae* at both 0.03 μg/ml and 1 μg/ml. Gatifloxacin alone showed expected bactericidal activity of −3.5 log reduction in CFU at 24 hours. Addition of compound G at the above 2 concentrations had no effect on either the kill kinetics or kill extent of gatifloxacin, and the resulting time-kill curves were superimposable with the control curves. Similar results were obtained with compound G was tested in combination with azithromycin and cefuroxime. These results show that compound G has no effect on the bactericidal activity of gatifloxacin, azithromycin or cefuroxime against *S. pneumoniae*.

REFERENCES

All publications and patents mentioned herein, including those items listed below, are hereby incorporated by reference in their entirety as if each individual publication or patent was specifically and individually incorporated by reference. In case of conflict, the present application, including any definitions herein, will control.

Heath, et al. *Nature* 406: 145 (2000); Bergler, et al, (1994), *J. Biol. Chem.* 269, 5493-5496; Heath, et al, (1996), *J. Biol. Chem.* 271, 1833-1836; Grassberger, et al (1984) *J. Med Chem* 27 947-953; Turnowsky, et al, (1989), *J. Bacteriol.*, 171, 6555-6565; McMurry, et al, (1998) *Nature* 394, 531-532; Levy, et al, (1999) *Nature* 398, 383-384; Ward, et al ((1999) *Biochem.* 38, 12514-12525; Heck, *Org. Reactions* 1982, 27, 345; *J. Het. Chem.* 1978, 15, 249-251; U.S. patent application Ser. Nos. 08/790,043; 10/009,219, 10/089,019; 09/968,129; 09/968,123; 09/968,236; 09/959,172; 09/979,560; 09/980,369; 10/089,755; 10/089,739; 10/089,740; PCT Application Nos. WO 0027628; WO 0210332; U.S. Pat. Nos. 6,531,126; 6,527,759; 6,518,270; 6,518,239; 6,517,827; 6,461,829; 6,448,054; 6,423,341; 6,495,551; 6,486,149; 6,441,162; 6,436,980; 6,399,629; 6,518,263; 6,503,881; 6,503,881; 6,486,148; 6,465,429; 6,388,070; 6,531,649; 6,531,465; 6,528,089; 6,521,408; 6,518,487; 6,531,508; 6,514,962; 6,503,953; 6,492,351; 6,486,148; 6,461,607; 6,448,054; 6,495,161; 6,495,158; 6,492,351; 6,486,165; 6,531,465; 6,514,535; 6,489,318; 6,497,886; 6,503,953; 6,503,539; 6,500,459; 6,492,351; 6,500,463; 6,461,829; 6,448,238; 6,432,444; 6,333,045; 6,291,462; 6,221,859; 6,514,986; 6,340,689; 6,309,663; 6,303,572; 6,277,836; 6,367,985; 6,468,964; 6,461,607; 6,448,449; 6,436,980; 6,423,741; 6,406,880; 6,395,746; 6,346,391; 6,294,192; 6,267,985; 6,235,908; 6,515,113; 6,509,327; 6,503,955; 6,525,066; 6,531,291; 6,517,827; 6,514,953; 6,514,541; 6,428,579; 6,451,339; 6,461,607; 6,461,829; 6,503,906; 6,518,239; 6,133,260; 6,174,878; 6,184,380; 6,187,341; 6,194,429; 6,194,441; 6,198,000; 6,221,859; 6,221,864; 6,239,113; 6,239,141; 6,248,363; and U.S. Provisional Patent Application Nos. 60/455,189; 60/476,970, and 60/488,379.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A composition comprising:
   a) the compound (E)-N-methyl-N-(3-methylbenzofuran-2-ylmethyl)-3-(7-oxo-5,6,7,8-tetrahydro-1,8-naphthyridin-3-yl)acrylamide or pharmaceutically acceptable salts thereof; and
   b) gentamicin; wherein the combination of the compound and gentamicin has an fractional inhibitory concentration index value of 0.3 against S. aureus 29213.

2. The composition of claim 1, wherein the composition has an fractional inhibitory concentration index value of 0.4 against S. aureus 43300.

3. A composition comprising:
   a) the compound (E)-N-methyl-N-(3-methylbenzofuran-2-ylmethyl)-3-(7-oxo-5,6,7,8-tetrahydro-1,8-naphthyridin-3-yl)acrylamide or pharmaceutically acceptable salts thereof; and
   b) linezolid, wherein the combination of the compound and linezolid has an fractional inhibitory concentration index value of 0.5 against S. aureus 43300.

4. A composition comprising:
   a) the compound (E)-N-methyl-N-(3-methylbenzofuran-2-ylmethyl)-3-(7-oxo-5,6,7,8-tetrahydro-1,8-naphthyridin-3-yl)acrylamide or pharmaceutically acceptable salts thereof; and meropenem, wherein minimum inhibitory concentration of meropenem in combination with the compound has a 100-fold increase in killing at 24 hours as compared to meropenem alone against antibiotic resistant S. aureus.

* * * * *

SEQUENCE LISTING

<160> NUMBER OF SEQ ID NOS: 7

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgcctcgaga tgttaaatct tgaaaacaaa acatatgtc                              39

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgcggatcca atcaagtcag gttgaaatat cca                                    33

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
catgggctta aatcttgaaa acaaaaca                                          28

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tatgttttgt tttcaagatt taagcc                                            26

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcggtaccca tgcgcttggt tttcttagaa atattg                                 36

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

-continued

```
gcggccgctt attcttcgcc taattcgccc attgc                35
```

```
<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      His 10 tag

<400> SEQUENCE: 7

His His His His His His His His His His
1               5                   10
```